US011160870B2

(12) United States Patent
Yang et al.

(10) Patent No.: US 11,160,870 B2
(45) Date of Patent: Nov. 2, 2021

(54) EXTENDED RELEASE MICROPARTICLES AND SUSPENSIONS THEREOF FOR MEDICAL THERAPY

(71) Applicant: Graybug Vision, Inc., Redwood City, CA (US)

(72) Inventors: Ming Yang, Lutherville-Timonium, MD (US); Jeffrey L. Cleland, San Carlos, CA (US); Yun Yu, Baltimore, MD (US); Weiling Yu, Perry Hall, MD (US); Joshua Kays, Baltimore, MD (US)

(73) Assignee: Graybug Vision, Inc., Redwood City, CA (US)

( * ) Notice: Subject to any disclaimer, the term of this patent is extended or adjusted under 35 U.S.C. 154(b) by 0 days.

(21) Appl. No.: 15/976,847

(22) Filed: May 10, 2018

(65) Prior Publication Data

US 2018/0326078 A1  Nov. 15, 2018

Related U.S. Application Data

(60) Provisional application No. 62/508,355, filed on May 18, 2017, provisional application No. 62/504,366, filed on May 10, 2017.

(51) Int. Cl.
| | |
|---|---|
| *A61P 27/02* | (2006.01) |
| *A61K 31/542* | (2006.01) |
| *A61K 47/54* | (2017.01) |
| *A61K 9/50* | (2006.01) |
| *A61K 31/382* | (2006.01) |
| *A61K 31/404* | (2006.01) |
| *A61K 31/498* | (2006.01) |
| *A61K 31/5377* | (2006.01) |
| *A61K 31/4155* | (2006.01) |
| *A61K 31/216* | (2006.01) |
| *A61K 9/00* | (2006.01) |

(52) U.S. Cl.
CPC ............ *A61K 47/54* (2017.08); *A61K 9/0051* (2013.01); *A61K 9/5031* (2013.01); *A61K 31/216* (2013.01); *A61K 31/382* (2013.01); *A61K 31/404* (2013.01); *A61K 31/4155* (2013.01); *A61K 31/498* (2013.01); *A61K 31/5377* (2013.01); *A61K 31/542* (2013.01); *A61P 27/02* (2018.01)

(58) Field of Classification Search
CPC .. A61K 31/542; A61K 31/404; A61K 31/498; A61K 31/5377; A61K 9/0051; A61K 9/5031; A61K 47/54; A61P 27/02
See application file for complete search history.

(56) References Cited

U.S. PATENT DOCUMENTS

| | | | |
|---|---|---|---|
| 4,460,563 | A | 7/1984 | Calanchi |
| 4,760,057 | A * | 7/1988 | Alexander ........... C07D 215/56 514/187 |
| 4,794,000 | A | 12/1988 | Ecanow |
| 4,911,920 | A | 3/1990 | Jani et al. |
| 4,997,443 | A | 3/1991 | Walthall et al. |
| 4,997,652 | A | 3/1991 | Wong |
| 5,013,556 | A | 5/1991 | Woodle et al. |
| 5,019,400 | A | 5/1991 | Gombotz et al. |
| 5,286,495 | A | 2/1994 | Batich et al. |
| 5,344,701 | A | 9/1994 | Gagnon et al. |
| 5,441,722 | A | 8/1995 | Eng et al. |
| 5,502,092 | A | 3/1996 | Barrows et al. |
| 5,565,215 | A | 10/1996 | Gref et al. |
| 5,612,052 | A | 3/1997 | Shalaby |
| 5,612,053 | A | 3/1997 | Baichwal et al. |
| 5,624,677 | A | 4/1997 | El-Rashidy et al. |
| 5,650,541 | A | 7/1997 | May |
| 5,681,964 | A | 9/1997 | Ashton et al. |
| 5,855,615 | A | 1/1999 | Bley et al. |
| 5,866,155 | A | 2/1999 | Laurencin et al. |
| 5,869,103 | A | 2/1999 | Yeh et al. |
| 5,916,586 | A | 6/1999 | Villa et al. |
| 5,945,126 | A | 8/1999 | Thanoo et al. |
| 6,007,845 | A | 12/1999 | Domb et al. |
| 6,051,576 | A | 4/2000 | Ashton et al. |
| 6,129,761 | A | 10/2000 | Hubbell |
| 6,201,072 | B1 | 3/2001 | Rathi et al. |
| 6,270,802 | B1 | 8/2001 | Thanoo et al. |
| 6,287,588 | B1 | 9/2001 | Shih et al. |
| 6,290,729 | B1 | 9/2001 | Slepian et al. |
| 6,306,169 | B1 | 10/2001 | Lee et al. |
| 6,375,972 | B1 | 4/2002 | Guo et al. |
| 6,379,962 | B1 | 4/2002 | Holy et al. |
| 6,413,539 | B1 | 7/2002 | Shalaby |

(Continued)

FOREIGN PATENT DOCUMENTS

| | | |
|---|---|---|
| CN | 101081206 A | 12/2007 |
| CN | 103833998 B | 6/2014 |

(Continued)

OTHER PUBLICATIONS

Saralidze et al; title: Polymeric Microspheres for Medical Applications; Materials, vol. 3, pp. 3537-356; published Jun. 7, 2010. (Year: 2010).*

(Continued)

*Primary Examiner* — Yanzhi Zhang

(74) *Attorney, Agent, or Firm* — Knowles Intellectual Property Strategies, LLC

(57) ABSTRACT

An improved microparticle or lyophilized or otherwise reconstitutable microparticle composition thereof for medical therapy, including ocular therapy.

57 Claims, 32 Drawing Sheets

(56) References Cited

U.S. PATENT DOCUMENTS

| | | |
|---|---|---|
| 6,495,164 B1 | 12/2002 | Ramstack et al. |
| 6,534,084 B1 | 3/2003 | Vyakarnam et al. |
| 6,566,406 B1 | 5/2003 | Pathak et al. |
| 6,573,293 B2 | 6/2003 | Tang et al. |
| 6,589,549 B2 | 7/2003 | Shih et al. |
| 6,632,457 B1 | 11/2003 | Sawhney |
| 6,703,047 B2 | 3/2004 | Sawhney et al. |
| 6,706,289 B2 | 3/2004 | Lewis et al. |
| 6,765,019 B1 | 7/2004 | Crooks et al. |
| 6,818,018 B1 | 11/2004 | Sawhney |
| 6,841,097 B2 | 1/2005 | Andersson et al. |
| 6,841,617 B2 | 1/2005 | Jeong et al. |
| 7,030,250 B2 | 4/2006 | Losada et al. |
| 7,115,280 B2 | 10/2006 | Hanna et al. |
| 7,163,697 B2 | 1/2007 | Hanes et al. |
| 7,211,275 B2 | 5/2007 | Ying et al. |
| 7,211,600 B2 | 5/2007 | Lipson et al. |
| 7,470,717 B2 | 12/2008 | Ohta et al. |
| 7,501,179 B2 | 3/2009 | Song et al. |
| 7,585,075 B2 | 9/2009 | Marmo |
| 7,771,742 B2 | 8/2010 | Hughes et al. |
| 7,828,844 B2 | 11/2010 | Marmo et al. |
| 7,883,520 B2 | 2/2011 | Gaeckle et al. |
| 7,998,108 B2 | 8/2011 | Nazzaro et al. |
| 8,008,283 B2 | 8/2011 | Hochman et al. |
| 8,167,941 B2 | 5/2012 | Boyd et al. |
| 8,192,408 B2 | 6/2012 | Nazzaro et al. |
| 8,252,307 B2 | 8/2012 | Ashton |
| 8,268,342 B2 | 9/2012 | Panda |
| 8,277,830 B2 | 10/2012 | de Jean, Jr. et al. |
| 8,298,578 B2 | 10/2012 | de Jean, Jr. et al. |
| 8,399,006 B2 | 3/2013 | de Jean, Jr. et al. |
| 8,409,606 B2 | 4/2013 | Sawhney et al. |
| 8,409,607 B2 | 4/2013 | Hughes et al. |
| 8,414,646 B2 | 4/2013 | de Jean, Jr. et al. |
| 8,492,334 B2 | 7/2013 | Lavik et al. |
| 8,574,613 B2 | 11/2013 | Guo et al. |
| 8,574,659 B2 | 11/2013 | Guo et al. |
| 8,592,427 B2 | 11/2013 | Blumberg et al. |
| 8,623,395 B2 | 1/2014 | de Jean, Jr. et al. |
| 8,628,801 B2 | 1/2014 | Garreta et al. |
| 8,632,809 B2 | 1/2014 | Asgharian et al. |
| 8,663,674 B2 | 3/2014 | Wen et al. |
| 8,685,435 B2 | 4/2014 | Nivaggioli et al. |
| 8,710,069 B2 | 4/2014 | Holtman et al. |
| 8,710,070 B2 | 4/2014 | Holtman et al. |
| 8,715,346 B2 | 5/2014 | de Jean, Jr. et al. |
| 8,795,712 B2 | 8/2014 | de Jean, Jr. et al. |
| 8,808,727 B2 | 8/2014 | de Jean, Jr. et al. |
| 8,815,284 B2 | 8/2014 | Guo et al. |
| 8,871,241 B2 | 10/2014 | Chou et al. |
| 8,889,193 B2 | 11/2014 | McDonnell et al. |
| 8,905,963 B2 | 12/2014 | de Jean, Jr. et al. |
| 8,939,948 B2 | 1/2015 | de Jean, Jr. et al. |
| 8,957,034 B2 | 2/2015 | Hanes et al. |
| 8,962,577 B2 | 2/2015 | Hanes et al. |
| 8,993,615 B2 | 3/2015 | Zack et al. |
| 9,023,896 B2 | 5/2015 | Ashton et al. |
| 9,033,911 B2 | 5/2015 | de Jean, Jr. et al. |
| 9,044,319 B2 | 6/2015 | Matheny |
| 9,050,765 B2 | 6/2015 | Boyd et al. |
| 9,056,057 B2 | 6/2015 | Popov et al. |
| 9,066,779 B2 | 6/2015 | de Juan, Jr. et al. |
| 9,095,506 B2 | 8/2015 | Spada et al. |
| 9,107,748 B2 | 8/2015 | de Jean, Jr. et al. |
| 9,114,070 B2 | 8/2015 | Hara et al. |
| 9,125,735 B2 | 9/2015 | de Jean, Jr. et al. |
| 9,125,807 B2 | 9/2015 | Sawhney et al. |
| 9,161,903 B2 | 10/2015 | Drapeau et al. |
| 9,161,938 B2 | 10/2015 | Huang et al. |
| 9,162,981 B2 | 10/2015 | Zack et al. |
| 9,205,150 B2 | 12/2015 | Jarrett et al. |
| 9,222,060 B2 | 12/2015 | Barbe et al. |
| 9,327,037 B2 | 5/2016 | Suk et al. |
| 9,382,229 B2 | 7/2016 | Zack et al. |
| 9,399,636 B2 | 7/2016 | Cohen et al. |
| 9,415,020 B2 | 8/2016 | Ensign et al. |
| 9,533,068 B2 | 1/2017 | Kashiwabuchi et al. |
| 9,539,259 B2 | 1/2017 | Zack et al. |
| 9,669,136 B2 | 6/2017 | Friedman et al. |
| 9,682,928 B2 | 6/2017 | Partridge et al. |
| 9,775,906 B2 | 10/2017 | Sawhney et al. |
| 9,789,198 B2 | 10/2017 | Xu et al. |
| 9,868,720 B2 | 1/2018 | Cohen et al. |
| 9,968,708 B2 | 5/2018 | Spector et al. |
| 2002/0128224 A1 | 9/2002 | Boyer et al. |
| 2002/0183858 A1 | 12/2002 | Contiliano et al. |
| 2003/0118528 A1 | 6/2003 | Walters et al. |
| 2003/0220509 A1 | 11/2003 | Losada et al. |
| 2004/0175429 A1 | 9/2004 | Alavattam |
| 2004/0180036 A1 | 9/2004 | Ashton et al. |
| 2004/0209807 A1 | 10/2004 | Quay et al. |
| 2004/0234611 A1 | 11/2004 | Ahlheim et al. |
| 2004/0258763 A1 | 12/2004 | Bell |
| 2005/0048123 A1 | 3/2005 | Su et al. |
| 2005/0101676 A1 | 5/2005 | Fahl et al. |
| 2005/0164994 A1 | 7/2005 | Ashton et al. |
| 2005/0175709 A1 | 8/2005 | Baty et al. |
| 2005/0249773 A1 | 10/2005 | Maspero et al. |
| 2006/0083781 A1 | 4/2006 | Shastri et al. |
| 2006/0134221 A1 | 6/2006 | Geall |
| 2006/0135609 A1 | 6/2006 | Toone et al. |
| 2006/0246145 A1 | 11/2006 | Chang et al. |
| 2006/0260777 A1 | 11/2006 | Rashba-Step et al. |
| 2006/0263335 A1 | 11/2006 | France et al. |
| 2007/0112050 A1 | 5/2007 | Ashton et al. |
| 2007/0149593 A1 | 6/2007 | Ghosh et al. |
| 2008/0166411 A1 | 7/2008 | Shah et al. |
| 2008/0187568 A1 | 8/2008 | Sawhney et al. |
| 2008/0241248 A1 | 10/2008 | France et al. |
| 2008/0299205 A1 | 12/2008 | Mayer et al. |
| 2008/0305172 A1 | 12/2008 | Ahlheim et al. |
| 2008/0306041 A1 | 12/2008 | Garvey |
| 2009/0148487 A1 | 1/2009 | Siedler et al. |
| 2009/0163457 A1 | 6/2009 | Ashton et al. |
| 2009/0203709 A1 | 8/2009 | Steinberg et al. |
| 2010/0063035 A1 | 3/2010 | Benedini et al. |
| 2010/0063135 A1 | 3/2010 | Dande et al. |
| 2010/0063175 A1 | 3/2010 | Ginty et al. |
| 2010/0074957 A1 | 3/2010 | Robinson et al. |
| 2010/0124565 A1 | 5/2010 | Spada et al. |
| 2010/0152272 A1 | 5/2010 | Spada et al. |
| 2010/0143479 A1 | 7/2010 | Thanoo et al. |
| 2010/0215580 A1 | 8/2010 | Hanes et al. |
| 2010/0226985 A1 | 9/2010 | Van Tomme et al. |
| 2010/0227905 A1 | 9/2010 | Kabra et al. |
| 2010/0233277 A1* | 9/2010 | Panda .............. A61L 15/26 424/491 |
| 2010/0247669 A1 | 9/2010 | Eliasof et al. |
| 2010/0227865 A1 | 11/2010 | Riggs-Sauthier et al. |
| 2011/0123446 A1 | 5/2011 | DeSimone et al. |
| 2011/0142936 A1 | 6/2011 | Campbell et al. |
| 2012/0004225 A1 | 1/2012 | Wanaski et al. |
| 2012/0052041 A1 | 3/2012 | Basu et al. |
| 2012/0063997 A1 | 3/2012 | Hunter et al. |
| 2012/0071865 A1 | 3/2012 | Jarrett et al. |
| 2012/0121718 A1 | 5/2012 | Lai et al. |
| 2012/0259008 A1 | 10/2012 | Ueno |
| 2012/0263803 A1 | 10/2012 | Mashima et al. |
| 2012/0269894 A1 | 10/2012 | Ahlheim et al. |
| 2012/0321719 A1* | 12/2012 | McDonnell .......... A61K 9/0051 424/497 |
| 2013/0071349 A1 | 3/2013 | Robinson et al. |
| 2013/0071462 A1 | 3/2013 | Jarrett et al. |
| 2013/0122064 A1 | 5/2013 | Ahlheim et al. |
| 2013/0183244 A1 | 7/2013 | Hanes et al. |
| 2013/0272994 A1 | 10/2013 | Fu et al. |
| 2013/0281637 A1 | 10/2013 | Ueno et al. |
| 2013/0316006 A1 | 11/2013 | Popov et al. |
| 2013/0331425 A1 | 12/2013 | Culbertson et al. |
| 2014/0039030 A1 | 2/2014 | Kozlowski et al. |
| 2014/0107025 A1 | 4/2014 | Wirostko |
| 2014/0178475 A1 | 6/2014 | Figueiredo et al. |
| 2014/0248358 A1 | 9/2014 | Figueiredo et al. |

(56) References Cited

U.S. PATENT DOCUMENTS

| | | |
|---|---|---|
| 2014/0249158 A1 | 9/2014 | Figueiredo et al. |
| 2014/0276482 A1 | 9/2014 | Astafieva et al. |
| 2014/0294986 A1 | 10/2014 | Liu et al. |
| 2014/0323407 A1 | 10/2014 | Francois et al. |
| 2014/0329913 A1 | 11/2014 | Hanes et al. |
| 2015/0056300 A1 | 2/2015 | Dewitt et al. |
| 2015/0086484 A1 | 3/2015 | Hanes et al. |
| 2015/0099802 A1 | 4/2015 | Ueno et al. |
| 2015/0099805 A1 | 4/2015 | Hughes |
| 2015/0140106 A1 | 5/2015 | Mousa |
| 2015/0147406 A1 | 5/2015 | Robinson et al. |
| 2015/0157562 A1 | 6/2015 | Hughes |
| 2015/0174096 A1 | 6/2015 | Bottger et al. |
| 2016/0038407 A1 | 2/2016 | Drapeau et al. |
| 2016/0106587 A1 | 4/2016 | Jarrett et al. |
| 2016/0166504 A1 | 6/2016 | Jarrett et al. |
| 2016/0310417 A1 | 10/2016 | Prausnitz et al. |
| 2016/0324836 A1 | 11/2016 | Aston et al. |
| 2016/0331738 A1 | 11/2016 | Jarrett et al. |
| 2017/0020729 A1 | 1/2017 | Jarrett et al. |
| 2017/0143636 A1 | 5/2017 | Jaren et al. |
| 2017/0157147 A1 | 6/2017 | Hanes et al. |
| 2017/0273901 A1 | 9/2017 | Fu et al. |
| 2017/0360750 A1 | 12/2017 | Fu et al. |
| 2018/0008718 A1 | 1/2018 | Fu et al. |
| 2018/0333282 A1 | 11/2018 | Sawhney et al. |

FOREIGN PATENT DOCUMENTS

| | | |
|---|---|---|
| CN | 103897174 A | 7/2014 |
| EP | 2403335 B1 | 1/2012 |
| EP | 3006050 B1 | 2/2018 |
| GB | 929401 | 6/1963 |
| GB | 929406 | 6/1963 |
| JP | 2016-132616 A | 7/2016 |
| KR | 2015-10212015 A | 10/2015 |
| WO | WO 198807044 | 9/1988 |
| WO | WO 96/20698 * | 7/1996 |
| WO | WO 199620698 A2 | 7/1996 |
| WO | WO 199901498 A1 | 1/1999 |
| WO | WO 1999/025391 A2 | 5/1999 |
| WO | WO 200064953 A1 | 11/2000 |
| WO | WO 200064977 A1 | 11/2000 |
| WO | WO 2001/040767 A1 | 6/2001 |
| WO | WO 2002/038127 A2 | 5/2002 |
| WO | WO 2002/053189 A2 | 7/2002 |
| WO | WO 2002/080910 A1 | 10/2002 |
| WO | WO 2003/000237 A2 | 1/2003 |
| WO | WO 2004/028583 A2 | 4/2004 |
| WO | WO 2004/084968 A1 | 10/2004 |
| WO | WO 2005/112884 A1 | 12/2005 |
| WO | WO 2006/044660 A2 | 4/2006 |
| WO | WO 2006/116107 A2 | 11/2006 |
| WO | WO 2006/133519 A1 | 12/2006 |
| WO | WO 2007/062266 A2 | 5/2007 |
| WO | WO 2007/065933 A1 | 6/2007 |
| WO | WO 2007/068489 A2 | 6/2007 |
| WO | WO 2007/090793 A1 | 8/2007 |
| WO | WO 2008/030557 A2 | 3/2008 |
| WO | WO 2008/041001 A2 | 4/2008 |
| WO | WO 2008041001 A1 | 4/2008 |
| WO | WO 2008/093095 A2 | 8/2008 |
| WO | WO 2009030270 A1 | 3/2009 |
| WO | WO 2009035565 A1 | 3/2009 |
| WO | WO 2009/089070 A2 | 7/2009 |
| WO | WO 2009089070 A2 | 7/2009 |
| WO | WO 2009/109501 A1 | 9/2009 |
| WO | WO 2010/100506 A2 | 9/2010 |
| WO | WO 2011/119777 A2 | 9/2011 |
| WO | WO 2012/054923 A2 | 4/2012 |
| WO | WO 2012/061703 A1 | 5/2012 |
| WO | WO 2012/112674 A2 | 8/2012 |
| WO | WO 2013/112434 A1 | 8/2013 |
| WO | WO 2013/166385 A1 | 11/2013 |
| WO | WO 2013/177367 A2 | 11/2013 |
| WO | WO 2013/188283 A1 | 12/2013 |
| WO | WO 2014146486 A1 | 9/2014 |
| WO | WO 2015/035974 A1 | 3/2015 |
| WO | WO 2015172149 A1 | 11/2015 |
| WO | WO 2016/025215 A1 | 2/2016 |
| WO | WO 2016/100380 A1 | 6/2016 |
| WO | WO 2016/100392 A1 | 6/2016 |
| WO | WO 2016/118506 A1 | 7/2016 |
| WO | WO 2018/175922 A1 | 9/2018 |
| WO | WO 2019/118924 A1 | 6/2019 |
| WO | WO 2019/209883 A1 | 10/2019 |
| WO | WO 2019/210215 A1 | 10/2019 |
| WO | WO 2020069353 A1 | 4/2020 |
| WO | WO 2020102758 A1 | 5/2020 |

OTHER PUBLICATIONS

Qiang Huang, et al; title: Prodrug AST-003 Improves the Therapeutic Index of the Multi-Targeted Tyrosine Kinase Inhibitor Sunitinib; PLoS One; 2015; vol. 10(10); pp. 1-14; Published online Oct. 29, 2015. (Year: 2015).*

Makadia, et al; title: Poly Lactic-co-Glycolic Acid (PLGA) as Biodegradable Controlled Drug Delivery Carrier; Polymers (Basel). Sep. 1, 2011; 3(3): 1377-1397; published online Aug. 26, 2011. (Year: 2011).*

Chang SC, et al; title: Improved corneal penetration of timolol by prodrugs as a means to reduce systemic drug load; Invest Ophthalmol Vis Sci.; vol. 28(3); pp. 487-491; Mar. 1987 (Year: 1987).*

Signa-Aldrich, title: hydrophilic polymers, product information downloaded from website of Signa-Aldrich on Feb. 5, 2020. (Year: 2020).*

Signa-Aldrich, title: hydrophobic polymers, product information downloaded from website of Signa-Aldrich on Feb. 5, 2020. (Year: 2020).*

Barot et al; title: Prodrug Strategies in Ocular Drug Delivery, Med Chem. Jul. 2012; vol. 8(4); pp. 753-768. (Year: 2012).*

Tam, et al. Oligo(lactic acid)n-Paclitaxel Prodrugs for Polyethylene glycol)-block-poly(lactic acid) Micelles: Loading, Release, and Backbiting Conversion for Anti cancer Activity, Supplemtal information. J. Am. Chem. Soc. 2016, 138, 28, 8674-8677 Publication Date:Jul. 3, 2016 (Year: 2016).*

Shahzard et at, title: Aggregation and clogging phenomena of rigid microparticles in microfluidics, Microfluidics and Nanofluidics; vol. 22, issue 104; pp. 1-17; Aug. 2018. (Year: 2018).*

U.S. Pat. No. 9,808,531, B2, U.S. Appl. No. 15/273,686, Cleland et al., Nov. 7, 2017.

U.S. Pat. No. 9,956,302, B2, U.S. Appl. No. 15/782,755, Cleland et al., May 1, 2018.

U.S. Pat. No. 10,098,965, B2, U.S. Appl. No. 15/782,744, Cleland et al., Oct. 6, 2018.

U.S. Pat. No. 10,111,964, B2, U.S. Appl. No. 15/842,712, Cleland et al., Oct. 30, 2018.

U.S. Pat. No. 10,117,950, B2, U.S. Appl. No. 15/782,749, Cleland et al., Nov. 6, 2018.

US 2017/0135960, A1, U.S. Appl. No. 15/349,985, Yu et al., May 18, 2017.

US 2018/0110864, A1, U.S. Appl. No. 15/842,684, Cleland et al., Apr. 26, 2018.

WO 2018/175922, A1, PCT/US18/24080, Cleland et al., Sep. 27, 2018.

US 2019-0060474 A1, U.S. Appl. No. 16/162,158, Cleland et al., Feb. 28, 2019.

Bundhaard, H., "Communications to the Editor" J. Med. Chem. 1988, 31, 2066-2069.

Herrero-Vanrell et al. "The potential of using biodegradable microspheres in retinal diseases and othe rintraocular pathologies" Progress in Retinal and Eye Research 42, 27-43 (2014).

Van De Ven et al. Journal of Controlled Release, 158, 148-155, 2012.

Wagh, et al. "Polymers used in ocular dosage form and drug delivery systems" Asian Journal of Pharmaceutics—Jan. 2008.

Ayalasomayajula, S.P. and Kompella, U.B., "Subconjunctivally administered celecoxib-PLGA microparticles sustain retinal drug

(56) References Cited

OTHER PUBLICATIONS levels and alleviate diabetes-induced oxidative stress in a rat model", *Eur. J. Pharm.*, 511, 191-198 (2005).

Cynkowski et al. (2005). "Novel antiglaucoma prodrugs and codrugs of ethacrynic acid" Bioorganic & Medicinal Chemistry Letters 15: 3524-3527.

Fuchs et al. "Sunitinib-eluting beads for chemoembolization: methods for in vitro evaluation of drug release" International Journal of Pharmaceutics 482, 68-74 (2015).

Hutmacher D.W. "Scaffolds in tissue engineering bone and cartilage." Biomaterials, 21, 2529-2543 (2000).

International Search Report and Written Opinion for International Application PCT/US2016/053210; International Filing Date: Sep. 22, 2016; dated Feb. 3, 2017; 11 pages.

International Search Report and Written Opinion for International Application PCT/US2016/061706; International Filing Date: Nov. 11, 2016; dated Mar. 16, 2017; 12 pages.

International Search Report and Written Opinion for International Application PCT/US2018/24080; International Filing Date: Mar. 23, 2018; dated Jul. 30, 2018; 12 pages.

International Search Report and Written Opinion for International Application PCT/US2018/32167; International Filing Date: May 10, 2018; dated Aug. 1, 2018; 9 pages.

Jacobs et al. Polymer Delivery Systems Concepts in Polymeric Delivery Systems; El-Nokaly, M., et al.; ACS Symposium Series; American Chemical Society: Washington, DC, 1993.

Jeyanthi et al. "Effect of solvent removal technique on the matrix characteristics of polylactide/glycolide microspheres for peptide delivery" Journal of Controlled Release 1996; 38, 235-244.

Kirby, G. et al. "PLGA-Based Microparticles for the Sustained Release of BMP-2" Polymers 2011; 3(1), 571-586.

Li et al. (2008). "Microencapsulation by solvent evaporation: State of the art for process engineering approaches" International Journal of Pharmaceutics 363: 26-39.

Luan X et al. "Key parameters affecting the initial release (burst) and encapsulation efficiency of peptide-containing poly(lactide-co-glycolide) microparticles," International Journal of Pharmaceutics, 2006; 324(2), 168-175.

Makadia et al. "Poly Lactic-co-Glycolic Acid (PLGA) as Biodegradable Controlled Drug Delivery Carrier" Polymers (Basel). 3, 1377-1397 (2011).

Prajapati et al. "Current knowledge on biodegradable microspheres in drug delivery," Expert Opinion on Drug Delivery, 12, 1238-1299 (2015).

Qutachi et al. "Injectable and porous PLGA microspheres that form highly porous scaffolds at body temperature", *Acta Biomaterialia*, 10, 5080-5098, (2014).

Rahman et al. "PLGA/PEG-hydrogel composite scaffolds with controllable mechanical properties" *J. of Biomedical Materials Research*, 101, 648-655, (2013).

Ramazani et al. (2015) "Sunitinib microspheres based on [PDLLA-PEG-PDLLA]-b-PLLA multi-block copolymers for ocular drug delivery" Eur J Pharm Biopharm. 95(Pt B):368-77.

Rao et al. (1989). "Zur Acylierung von Hydroxy- and Mercapto-carbonsaureestern nach dem Carbodiimid/Acylierungskatalysator—Verfahren" Arch. Pharm. (Weinheim) 322:523-530, Table 3, compound 18.

Welsbie et al. (2013). "Functional genomic screening identifies dual leucine zipper kinase as a key mediator of retinal ganglion cell death" PNAS 110:4045-4050.

Yang et al. "The Design of Scaffolds for Use in Tissue Engineering. Part I. Traditional Factors" Tissue Engineering, 7, 679-689 (2001).

Yang et al. "Effect of preparation conditions on morphology and release profiles of biodegradable polymeric microspheres containing protein fabricated by double-emulsion method" Chemical Engineering Science 2000; 55, 2223-2236.

US, US 2020-0000734, A1, U.S. Appl. No. 16/566,721, Yu et al., Jan. 20, 2020.

US, US 2020-0000735, A1, U.S. Appl. No. 16/566,724, Yu et al., Jan. 20, 2020.

Amparo F. et al. "Safety and efficacy of the multitargeted receptor kinase inhibitor pazopanib in the treatment of corneal neovascularization" Invest Ophthalmol Vis Sci. 2013; 54(1), 537-44.

Anderson et al. "Biodegradation and biocompatibility of PLA and PLGA microspheres" Advanced Drug Delivery Reviews, 28, 5-24 (1997).

Benny, O. "Local Delivery of Poly Lactic-co-glycolic Acid Microspheres Containing Imatinib Mesylate Inhibits Intracranial Xenograft Glioma Growth" Clin Cancer Res 2009; 15(4), 1222-1231.

Hou, et al. "In Situ Gelling Hydrogels Incorporating Microparticles as Drug Delivery Carriers for Regenerative Medicine" Journal of Pharmaceutical Sciences, 97, 3972-3980 (2008).

Kempen et al. "Controlled drug release from a novel injectable biodegradable microsphere/scaffold composite based on poly(propylene funarate)" J Biomed Mater Res A. 2006, 77, 103-111.

Kim et al. "Biodegradable polymeric microspheres with "open/closed" pores for sustained release of human growth hormone" *J. of Controlled Release*, 112, 167-174, (2006).

Ungaro et al. "Microsphere-integrated collagen scaffolds for tissue engineering: effect of microspheres formulation and scaffold properties on protein release kinetics" J Control Release, 113(2):128-136 (2006).

Lai et al. "Rapid transport of large polymeric nanoparticles in fresh undiluted human mucus" PNAS, 2007, 104, 1482-1487.

Sahoo et al. "Residual polyvinyl alcohol associated with poly(D,L-lactide-co-glycolide) nanoparticles affects their physical properties and cellular uptake" Journal of Controlled Release 2002, 82, 105-114.

Suh et al. "PEGylation of nanoparticles improves their cytoplasmic transport" International Journal of Nanomedicine 2007, 2, 735-741.

US, US 2020-0031783, A1, U.S. Appl. No. 16/578,003, Yang et al., Jan. 30, 2020.

Bouligand, et al., "The lyotropic polymorphism of two pharmacologically active molecules", Liquid Crystals, vol. 26, No. 9, Dec. 1293, 1999.

Chang, et al., "Synthesis and Characterization of Novel PGA and PLA Prodrug with Sulfadiazine and 5-Fluorouracil Terminal Groups", Journal of Macromolecular Science, Part A: Pure and Applied Chemistry, (2007) 44, 887-892.

Chien, et al., "Role of Enzymatic Lability in the Corneal and Conjunctival Penetration of Timolol Ester Prodrugs in the Pigmented Rabbit", Pharmaceutical Research, vol. 8, No. 6, 1991.

Luo, et al., "One-pot preparation of polylactic acid-ibuprofen conjugates and their performance characterization", Polymer Chemistry; Issue 45, 2017.

Pech, et al., "Preliminary Evaluation of a Series of Amphiphilic Timolol Prodrugs: Possible Evidence for Transcleral Absorption" Journal of Ocular Pharmacology, vol. 9, No. 2, 1993.

Pubchem CID 33624 (Create Date: Jun. 24, 2005).

Tam, et al. Oligo(lactic acid)n-Paclitaxel Prodrugs for Poly(ethylene glycol)-block-poly(lactic acid) Micelles: Loading, Release, and Backbiting Conversion for Anticancer Activity.

US, 2020-0230246, A1, U.S. Appl. No. 16/821,738, Yang et al., Jul. 23, 2020.

Alexander et al. (Acyloxy)alkyl Carbamates as Novel Bioreversible Prodrugs for Amines: Increased Permeation through Biological Membranes; J. Med. Chem. 1988, 31, 318-322; American Chemical Society (1988).

Baiardo et al. "Thermal and Mechanical Properties of Plasticized Poly(L-lactic acid)" Journal of Applied Polymer Science, 90, 1731-1738 (2003).

Bible et al. "Attachment of stem cells to scaffold particles for intra-cerebral transplantation", Nat. Protoc., 10, 1440-1453, (2009).

Cattel et al. From conventional to stealth liposomes a new frontier in cancer chemotherapy, Tumori, 83(3):237-249 (2003).

Chang et al., "Improved Corneal Penetration of Timolol by Prodrugs as a Means to Reduce Systemic Drug Load", Investigative Ophthalmology & Visual Science, Mar. 1987 vol. 28.

Gaudana, R. et al. "Recent Perspectives in Ocular Drug Delivery" Pharm Res. 2009; 26(5), 1197-1216.

Garbuzenko et al. Effect of grafted PEG on liposome size on compressibility and packing of lipid bilayer, Chem Phys Lipids, 135:117-129 (2005).

(56) References Cited

OTHER PUBLICATIONS

Hedberg, et al. "Controlled release of an osteogenic peptide from injectable biodegradable polymeric composites" Journal of Controlled Release, 84, 137-150 (2002).

Huang et al., "Prodrug AST-003 Improves the Therapeutic Index of the Multi-Targeted Tyrosine Kinase Inhibitor Sunitinib", PLOS ONE DOI:10.1371-/journal.pones.0141395, Oct. 20, 2015.

Immordino et al. "Stealth liposomes: review of the basic science, rationale, and clinical applications, existing and potential," Int J Naomed., 1(3):297-315 (2006).

Peeters, et al. "Can ultrasound solve the transport barrier of the neural retina," Pharma Res., 25(11):2657-65 (2008).

Saralidze et al. "Polymeric Microspheres for Medical Applications", Materials 2010, 3, 3537-3564; doi:10.3390/ma3063537.

Sawhney et al. "Bioerodible Hydogels Based on Photopolymerized Poly(ethyleneglycol)-co-poly($\alpha$-hydroxy acid) Diacrylate Macromers" Macromolecules, 26, 581-587 (1993).

Sigma-Aldrich, title: Hydrophilic polymers, product information downloaded from website of Sigma-Aldrich on Feb. 5, 2020. (Year 2020).

Sun, et al., "Control of encapsulation efficiency and drug loading in PLGA microsphere", Journal of Guangdong Pharmaceutical University, 2011, 27(6), 643-647; publication date Dec. 31, 2011—Machine Translation.

Sun, et al., "Control of encapsulation efficiency and drug loading in PLGA microsphere", Journal of Guangdong Pharmaceutical University, 2011, 27(6), 643-647; publication date Dec. 31, 2011.

Takahashi, H. et al. "A Novel Vascular Endothelial Growth Factor Receptor 2 Inhibitor, SU11248, Suppresses Choroidal Neovascularization In Vitro" Journal of Ocular Pharmacology and Therapeutics, 22, 213-219, (2006).

Wang et al. "Combination of hyaluronic acid hydrogel scaffold and PLGA microspheres for supporting survival of neural stem cells." Pharm Res. 28(6): 1406-1414 (2011).

Xingguo, M. "Microcanier Drug Delivery System", Huazhong University of Science & Technology Press; p. 50 (Nov. 30, 2009).

Xingguo, M. "Microcanier Drug Delivery System", Huazhong University of Science & Technology Press; p. 50 (Nov. 30, 2009)—Machine Translation.

Zhao, Z. "Preparation and characterization of sunitinib-loaded microspheres for arterial embolization" Journal of Chinese Pharmaceutical Sciences 23, 558-564 (2014).

US, 2020/0308162, A1, U.S. Appl. No. 16/899,422, Cleland et al., Oct. 1, 2020.

US, 2021/0040111, A1, U.S. Appl. No. 17/077,853, Yang et al., Feb. 11, 2021.

US, 2021/0085607, A1, U.S. Appl. No. 17/077,856, Saragnese et al., Mar. 25, 2021.

U.S. Appl. No. 17/212,873, Bauman et al., filed Mar. 25, 2021.

* cited by examiner

S-21

   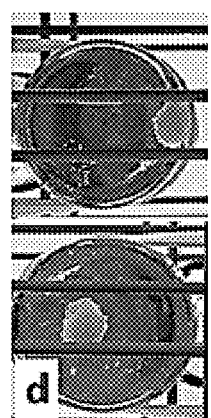
FIG. 8A  FIG. 8B  FIG. 8C  FIG. 8D
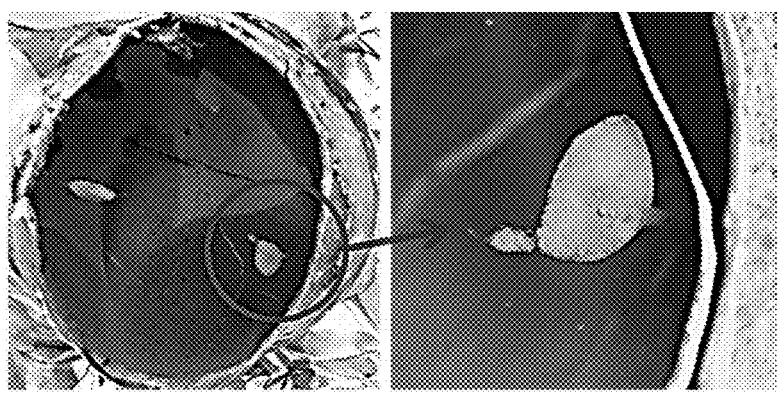
FIG. 9

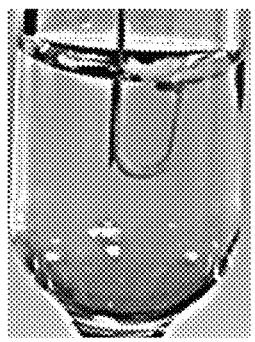 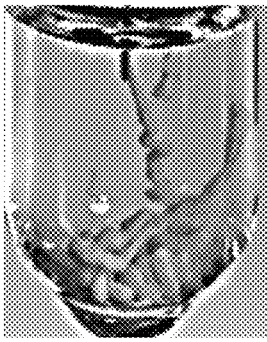 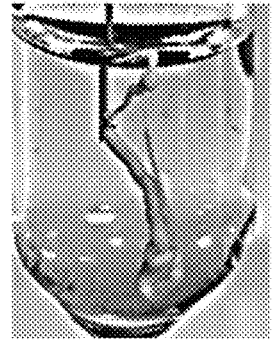 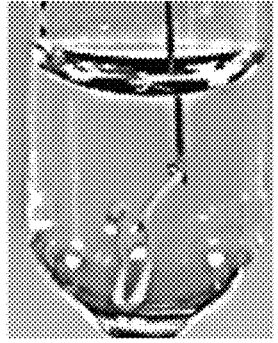
FIG. 23A     FIG. 23B     FIG. 23C     FIG. 23D
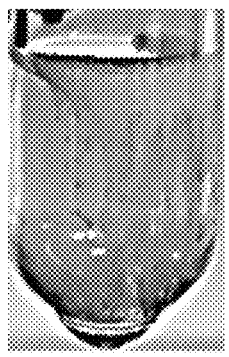 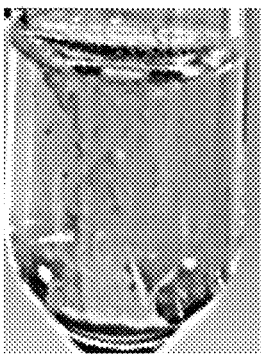  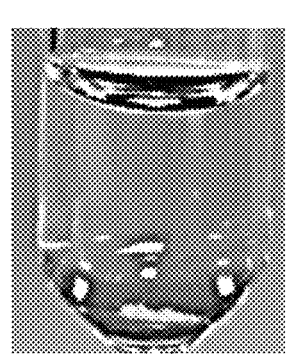
FIG. 23E     FIG. 23F     FIG. 23G     FIG. 23H
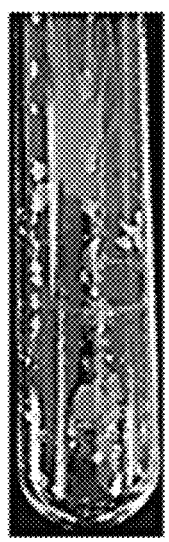 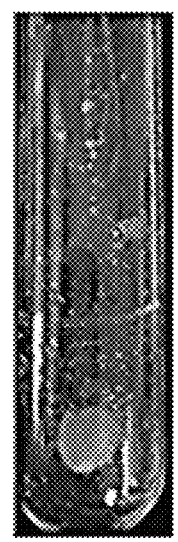 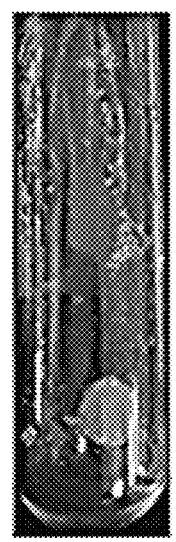 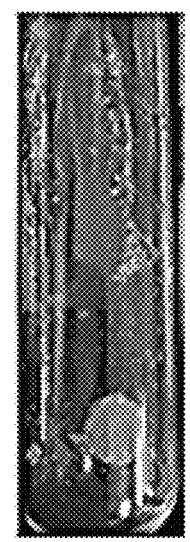
FIG. 23I     FIG. 23J     FIG. 23K     FIG. 23L

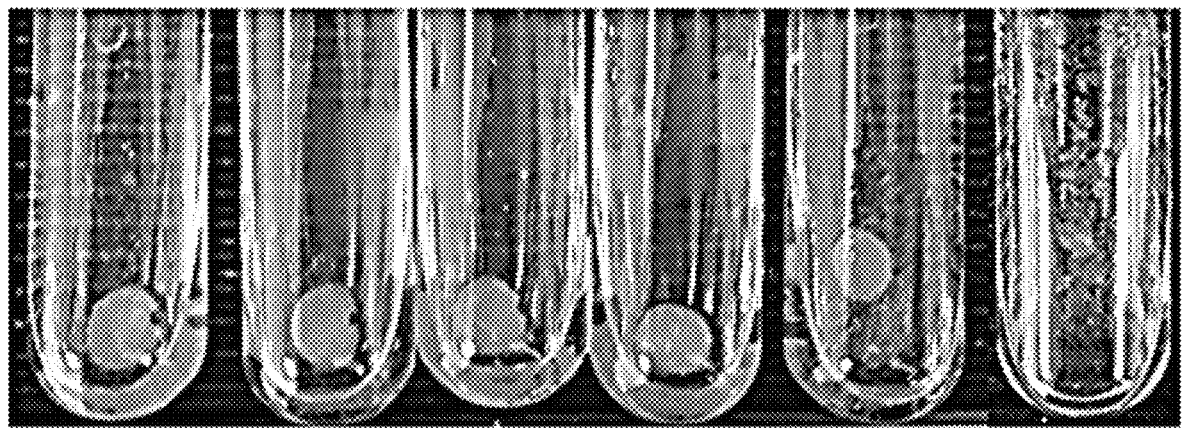
FIG. 28
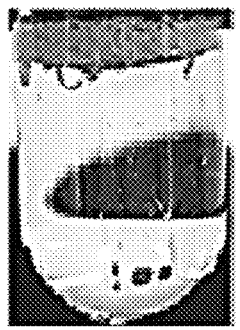   
FIG. 29A   FIG. 29B
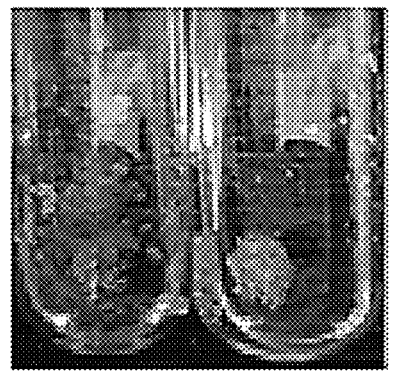
FIG. 30

EXTENDED RELEASE MICROPARTICLES AND SUSPENSIONS THEREOF FOR MEDICAL THERAPY

CROSS-REFERENCE TO RELATED APPLICATIONS

This application claims the benefit of provisional U.S. Application Nos. 62/504,366 filed May 10, 2017 and 62/508,355 filed May 18, 2017. The entirety of these applications is hereby incorporated by reference for all purposes.

FIELD OF THE INVENTION

This invention is in the area of improved microparticles, lyophilized or otherwise solidified microparticles, or microparticle suspensions, and processes thereof, which can, optimally, be loaded with an active drug or a prodrug of an active drug, for use in medical drug delivery, including for ocular drug delivery.

BACKGROUND

The structure of the eye can be divided into two segments referred to as the anterior and posterior. The anterior segment comprises the front third of the eye and includes the structures in front of the vitreous humor: the cornea, iris, ciliary body, and lens. The posterior segment includes the back two-thirds of the eye and includes the sclera, choroid, retinal pigment epithelium, neural retina, optic nerve, and vitreous humor.

Important diseases affecting the anterior segment of the eye include glaucoma, allergic conjunctivitis, anterior uveitis, and cataracts. Diseases affecting the posterior segment of the eye include dry and wet age-related macular degeneration (AMD), cytomegalovirus (CMV) infection, diabetic retinopathy, choroidal neovascularization, acute macular neuroretinopathy, macular edema (such as cystoid macular edema and diabetic macular edema), Behcet's disease, retinal disorders, diabetic retinopathy (including proliferative diabetic retinopathy), retinal arterial occlusive disease, central retinal vein occlusion, uveitis retinal disease, retinal detachment, ocular trauma, damage caused by ocular laser treatment or photodynamic therapy, photocoagulation, radiation retinopathy, epiretinal membrane disorders, branch retinal vein occlusion, anterior ischemic optic neuropathy, non-retinopathy diabetic retinal dysfunction and retinitis pigmentosa. Glaucoma is sometimes also considered a posterior ocular condition because a therapeutic goal of glaucoma treatment is to prevent or reduce the loss of vision due to damage or loss of retinal cells or optic nerve cells.

Typical routes of drug administration to the eye include topical, systemic, intravitreal, intraocular, intracameral, sub-conjunctival, sub-tenon, retrobulbar, and posterior juxtascleral. (Gaudana, R., et al., "Ocular Drug Delivery", *The American Association of Pharmaceutical Scientist Journal*, 12(3)348-360, 2010).

A number of types of delivery systems have been developed to deliver therapeutic agents to the eye. Such delivery systems include conventional (solution, suspension, emulsion, ointment, inserts, and gels), vesicular (liposomes, niosomes, discomes, and pharmacosomes), advanced materials (scleral plugs, gene delivery, siRNA, and stem cells), and controlled-release systems (implants, hydrogels, dendrimers, iontophoresis, collagen shields, polymeric solutions, therapeutic contact lenses, cyclodextrin carriers, microneedles, microemulsions, and particulates (microparticles and nanoparticles)).

Treatment of posterior segment diseases remains a daunting challenge for formulation scientists. Drug delivery to the posterior segment of the eye is typically achieved via an intravitreal injection, the periocular route, implant, or by systemic administration. Drug delivery to the posterior segment by way of the periocular route can involve the application of a drug solution to the close proximity of the sclera, resulting in high retinal and vitreal concentrations.

Intravitreal injection is often carried out with a 30 gauge or less needle. While intravitreal injections offer high concentrations of drug to the vitreous chamber and retina, they can be associated with various short-term complications such as retinal detachment, endophthalmitis, and intravitreal hemorrhages. Experience shows that injection of small particles can lead to the rapid dispersal of the particles that can obstruct vision (experienced by the patient as "floaties" or "floaters") and the rapid removal of the particles from the injection site (which can occur via the lymphatic drainage system or by phagocytosis). In addition, immunogenicity can occur upon recognition of the microspheres by macrophages and other cells and mediators of the immune system.

Complications in periocular injections include increased intraocular pressure, cataract, lur, strabismus, and corneal decompensation. Transscleral delivery with periocular administration is seen as an alternative to intravitreal injections. However, ocular barriers such as the sclera, choroid, retinal pigment epithelium, lymphatic flow, and general blood flow can compromise efficacy. Systemic administration, which is not advantageous given the ratio of the volume of the eye to the entire body, can lead to potential systemic toxicity.

A number of companies have developed microparticles for treatment of eye disorders. For example, Allergan has disclosed a biodegradable microsphere to deliver a therapeutic agent that is formulated in a high viscosity carrier suitable for intraocular injection or to treat a non-ocular disorder (U.S. publication 2010/0074957 and U.S. publication 2015/0147406 claiming priority to a series of applications back to Dec. 16, 2003). In one embodiment, the '957 application describes a biocompatible, intraocular drug delivery system that includes a plurality of biodegradable microspheres, a therapeutic agent, and a viscous carrier, wherein the carrier has a viscosity of at least about 10 cps at a shear rate of 0.1/second at 25° C.

Allergan has also disclosed a composite drug delivery material that can be injected into the eye of a patient that includes a plurality of microparticles dispersed in a media, wherein the microparticles contain a drug and a biodegradable or bioerodible coating and the media includes the drug dispersed in a depot-forming material, wherein the media composition may gel or solidify on injection into the eye (WO 2013/112434 A1, claiming priority to Jan. 23, 2012). Allergan states that this invention can be used to provide a depot means to implant a solid sustained drug delivery system into the eye without an incision. In general, the depot on injection transforms to a material that has a viscosity that may be difficult or impossible to administer by injection.

In addition, Allergan has disclosed biodegradable microspheres between 40 and 200 μm in diameter, with a mean diameter between 60 and 150 μm that are effectively retained in the anterior chamber of the eye without producing hyperemia (US 2014/0294986). The microspheres contain a drug effective for an ocular condition with greater than seven-day release following administration to the anterior chamber of the eye. The administration of these large particles is intended to overcome the disadvantages of injecting 1-30 µm particles which are generally poorly tolerated.

Regentec Limited has filed a series of patent applications on the preparation of porous particles that can be used as tissue scaffolding (WO 2004/084,968 and U.S. publication 2006/0263335 (filed Mar. 27, 2003) and U.S. publication 2008/0241248 (filed Sep. 20, 2005) and WO 2008/041,001 (filed Oct. 7, 2006)). The porosity of the particles must be sufficient to receive cells to be held in the particle. The cells can be added to the matrix at, or prior to, implantation of the matrix or afterward in the case of recruitment from endogenous cells in situ. Regentec also published an article on tissue scaffolding with porous particles (Qutachi et al. "Injectable and porous PLGA microspheres that form highly porous scaffolds at body temperature", *Acta Biomaterialia*, 10, 5080-5098, (2014)).

In addition, Regentec Limited also filed patent applications on the preparation of large porous particles that can be used in drug delivery (WO 2010/100,506 and U.S. publication 2012/0063997 (filed Mar. 5, 2009)). The porosity of the particles allows for quick delivery of the therapeutic agent. The particles are intended to form a scaffold that fills the space in which they are injected by a trigger such as a change in temperature.

Additional references pertaining to highly porous microparticles include publications by Rahman and Kim. Rahman et al. "PLGA/PEG-hydrogel composite scaffolds with controllable mechanical properties" *J. of Biomedical Materials Research*, 101, 648-655, (2013) describes hydrogels of approximately 50 percent porosity and their corresponding mechanical properties. Kim et al. "Biodegradable polymeric microspheres with "open/closed" pores for sustained release of human growth hormone" *J. of Controlled Release*, 112, 167-174, (2006) describes PLGA polymers with pores for the delivery of human growth hormone.

EP 2125048 filed by Locate Therapeutics Limited (filed Feb. 1, 2007) as well as WO 2008/093094, U.S. publication 2010/0063175 (filed Feb. 1, 2007), and WO 2008/093095 (filed Feb. 1, 2007) filed by Regentec Limited disclose the preparation of particles that are not necessarily porous but that when exposed to a trigger (such as temperature) form a tissue scaffold useful in the repair of damaged or missing tissue in a host.

U.S. Pat. No. 9,161,903 issued on Oct. 20, 2015 to Warsaw Orthopedic and U.S. publication 2016/0038407 filed by Warsaw Orthopedic Inc. disclose a flowable composition for injection at a target tissue site beneath the skin that includes a flowable composition that hardens at or near the target tissue site.

Bible et al. "Attachment of stem cells to scaffold particles for intra-cerebral transplantation", *Nat. Protoc.*, 10, 1440-1453, (2009) describes a detailed process to make microparticles of PLGA that do not clump or aggregate.

U.S. Patent Application Publication 2011/0123446 filed by Liquidia Technologies titled "Degradable compounds and methods of use thereof, particularly with particle replication in non-wetting templates" describes degradable polymers that utilize a silyl core and can form rapidly degrading matrixes.

Additional references pertaining to particles for ocular delivery include the following. Ayalasomayajula, S. P. and Kompella, U. B. have disclosed the subconjunctival administration of celecoxib-poly(lactide co-glycolide) (PLGA) microparticles in rats (Ayalasomayajula, S. P. and Kompella, U. B., "Subconjunctivally administered celecoxib-PLGA microparticles sustain retinal drug levels and alleviate diabetes-induced oxidative stress in a rat model", *Eur. J. Pharm.*, 511, 191-198 (2005)). Danbiosyst UK Ltd., has disclosed a microparticle comprising a mixture of a biodegradable polymer, a water soluble polymer of 8,000 Daltons or higher and an active agent (U.S. Pat. No. 5,869,103). Poly-Med, Inc. has disclosed compositions comprising a hydrogel mass and a carrier having a biological active agent deposited on the carrier (U.S. Pat. No. 6,413,539). MacroMed Inc. has disclosed the use of an agent delivery system comprising a microparticle and a biodegradable gel (U.S. Pat. Nos. 6,287,588 and 6,589,549). Novartis has disclosed ophthalmic depot formulations for periocular or subconjunctival administration where the pharmacologically acceptable polymer is a polylactide-co-glycolide ester of a polyol (U.S. publication 2004/0234611, U.S. publication 2008/0305172, U.S. publication 2012/0269894, and U.S. publication 2013/0122064). The Universidad De Navarra has disclosed oral pegylated nanoparticles for carrying biologically active molecules comprising a pegylated biodegradable polymer (U.S. Pat. No. 8,628,801). Surmodics, Inc. has disclosed microparticles containing matrices for drug delivery (U.S. Pat. No. 8,663,674). Minu, L.L.C., has disclosed the use of an agent in microparticle of nanoparticle form to facilitate transmembrane transport. Emory University and Georgia Tech Research Corporation have disclosed particles dispersed in a non-Newtonian fluid that facilitates the migration of the therapeutic particles from the insertion site in the suprachoroidal space to the treatment site (U.S. 2016/0310417). Pfizer has disclosed nanoparticles as injectable depot formulations (U.S. publication 2008/0166411). Abbott has disclosed a pharmaceutical dosage form that comprises a pharmaceutically acceptable polymer for the delivery of a tyrosine kinase inhibitor (U.S. publication 2009/0203709). The Brigham and Woman's Hospital, Inc. has disclosed modified poly(lactic-co-glycolic) polymers having therapeutic agents covalently bound to the polymer (U.S. 2012/0052041). BIND Therapeutics, Inc. has disclosed therapeutic nanoparticles comprising about 50 to 99.75 weight percent of a diblock poly (lactic) acid-poly(ethylene)glycol copolymer or a diblock poly (lactic acid-co-glycolic acid)-poly(ethylene)glycol copolymer wherein the therapeutic nanoparticle comprises 10 to about 30 weight percent poly (ethylene)glycol (U.S. publication 2014/0178475). Additional publications assigned to BIND Therapeutics, Inc. include U.S. publication 2014/0248358 and U.S. publication 2014/0249158. Allergan has disclosed the use of biodegradable microspheres containing a drug to treat an ocular condition (U.S. publication 2010/0074957, U.S. publication 2014/0294986, U.S. publication 2015/0147406, EP 1742610, and WO 2013/112434). Allergan has also disclosed a biocompatible implant containing a prostamide component, which can exist in particle form, and a biodegradable polymer that allows for slow release of the drug over the course of 1 week to 6 months for the treatment of an ocular condition, such as glaucoma (U.S. application 2015/0157562 and U.S. application 2015/0099805). Jade Therapeutics has disclosed formulations containing an active agent and a polymer matrix that can be delivered directly to the target tissue or placed in a suitable delivery device (U.S. publication 2014/0107025). Bayer Healthcare has disclosed a topical ophthalmological pharmaceutical composition comprising sunitinib and at least one pharmaceutically acceptable vehicle (WO 2013/188,283). pSivida Us, Inc. has disclosed biodegradable drug eluting particles comprising a microporous or mesoporous silicon body for intraocular use (U.S. Pat. No. 9,023,896). Additional patents assigned to pSivida Us, Inc. include: U.S. Pat. Nos. 8,871, 241; 8,815,284; 8,574,659; 8,574,613; 8,252,307; 8,192,408 and 7,998,108. ForSight Vision4, Inc. has disclosed therapeutic devices for implantation in the eye (U.S. Pat. No. 8,808,727). Additional patents assigned to ForSight Vision4, Inc. include: U.S. Pat. Nos. 9,125,735; 9,107,748; 9,066,779; 9,050,765; 9,033,911; 8,939,948; 9,905,963; 8,795,712; 8,715,346; 8,623,395; 8,414,646; 8,399,006; 8,298,578; 8,277,830; 8,167,941; 7,883,520; 7,828,844 and 7,585,075. The Nagoya Industrial Science Research Institute has recently disclosed the use to liposomes to deliver a drug to the posterior segment of the eye (U.S. Pat. No. 9,114,070).

Johns Hopkins University has filed a number of patents claiming formulations for ocular injections including WO2013/138,343 titled "Controlled Release Formulations for the Delivery of HIF-1 Inhibitors", WO2013/138,346 titled "Non-linear Multiblock Copolymer-drug Conjugates for the Delivery of Active Agents", WO2011/106,702 titled "Sustained Delivery of Therapeutic Agents to an Eye Compartment", WO2016/025,215 titled "Glucorticoid-loaded Nanoparticles for Prevention of Corneal Allograft Rejection and Neovascularization", WO2016/100392 titled "Sunitinib Formulations and Methods for Use Thereof in Treatment of Ocular Disorders", WO2016/100,380 titled "Sunitinib Formulation and Methods for Use Thereof in Treatment of Glaucoma", WO2016/118,506 titled "Compositions for the Sustained Release of Anti-Glaucoma Agents to Control Intraocular Pressure", WO2013/166,385 titled "Nanocrystals, Compositions, and Methods that Aid Particle Transport in Mucus", WO2005/072,710 titled "Drug and Gene Carrier Particles that Rapidly move Through Mucus Barriers," WO2008/030,557 titled "Compositions and Methods for Enhancing Transport through Mucus", WO2012/061,703 titled "Compositions and Methods Relating to Reduced Mucoadhesion," WO2012/039,979 titled "Large Nanoparticles that Penetrate Tissue," WO2012/109,363 titled "Mucus Penetrating Gene Carriers", WO2013/090,804 titled "Biodegradable Stealth Nanoparticles Prepared by a Novel Self-Assembly Emulsification Method," WO2013/110,028 titled "Nanoparticles Formulations with Enhanced Mucosal Penetration", and WO2013/166,498 titled "Lipid-based Drug Carriers for Rapid Penetration through Mucus Linings".

GrayBug Vision, Inc. discloses prodrugs for the treatment of ocular therapy in US 2018-0036416, US 2018-0064823, US 2018-0110865, US 2018-0104350, granted U.S. Pat. Nos. 9,808,531 and 9,956,302 and PCT application WO2017/053,638. Aggregating microparticles for ocular therapy are described in US 2017-0135960 and WO2017/083,779.

In order to treat ocular diseases, and in particular diseases of the posterior segment, the drug must be delivered in therapeutic levels and for a sufficient duration to achieve efficacy. This seemingly straightforward goal is difficult to achieve in practice.

The object of this invention is to provide compositions and methods to treat ocular disorders.

SUMMARY

The present invention has at least the following aspects:
(i) A lyophilized microparticle solid material that has less propensity to result in floating microparticles than the same microparticle solid material that has not been processed as described herein, when resuspended in fluid for example buffered aqueous solution or aqueous hyaluronic acid, for in vivo delivery. The process as described herein is based on the discovery that very small air bubbles or gas or a thin layer of air adhered to microparticles can adversely affect the quality of the resuspended microparticle of the present invention, and that improved microparticles for lyophilization can be provided by removing adhered air or gas by treating the microparticles with a vacuum, sonication, or excipient addition or other method that removes or decreases the adhered air or gas prior to lyophilization, or by doing so after resuspending the lyophilized microparticle material. It has been discovered that the issue of air adhered to the microparticle can be more pronounced if the microparticle has been surface treated even under mild conditions to remove or decrease surface surfactant, such as those described in U.S. Ser. No. 15/349,985 and PCT/US16/61706 (see nonlimiting Example 2 below).

(ii) An improved lyophilized microparticle, microparticle suspension, and method for manufacture thereof, processed as described in (i) that is loaded with a pharmaceutically active agent, including those listed below, which can be active in the form delivered or is a prodrug, with non-limiting examples provided herein, for in vivo treatment of a patient in need thereof.

(iii) Microparticles as described herein, and lyophilized or suspended materials thereof, whether treated to remove adhered air or gas, and which include any of the active drugs, including prodrugs, described herein.

For example, it has been identified that for certain applications, the processes and materials in U.S. Ser. No. 15/349,985 and PCT/US16/61706 provide acceptable aggregating microparticles in vivo, however, there are occasions when if surface-treated microparticles are overtreated (e.g., treated under strong chemical conditions or for an extended period of time), they may have a tendency to float upon injection into an aqueous solution with low viscosity (e.g., PBS buffer solution or sometimes vitreal fluid, wherein the viscosity may decrease with age of the patient), which is disadvantageous for forming a pellet that remains out of the visual axis. Since ocular disorders increase with age, it is important to provide a particle suspension that still aggregates to a pellet in lower viscosity vitreous fluid. Certain aspects of this invention address those certain situations, where a thin layer of air, air bubbles or gas generally can adhere to the surface of some microparticles and prevent the particles from being completely wetted. If this tiny layer of air or bubbles is high enough to create buoyancy, the microparticles will be less likely to aggregate to the desired pellet.

Thus, according to the present invention, microparticles and microparticle suspensions are provided that have improved aggregation to a pellet for medical therapy due to enhanced wettability in vivo. Examples of processes that provide improved aggregation of particles to the desired ocular pellet include, but are not limited to, one or a combination of 1) applying a vacuum to the particle suspension to facilitate the disassociation of air from particles; 2) adding one or more excipients to reduce surface hydrophobicity of particles and thus reduce the amount of air adhering to the particles; and, 3) sonication to facilitate the disassociation of air from the particles, either prior to lyophilization or other drying means to make a solid reconstitutable microparticle material, or by carrying out one or more of these processes after reconstitution. These processes are described in more detail below.

In the third independent aspect of the invention, solid microparticles that aggregate in vivo to a pellet and provide release of a therapeutic agent in vivo are provided. In certain embodiments, the therapeutic agent is a lipophilic prodrug as described herein. In certain embodiments, the lipophilic prodrug releases a prostaglandin, carbonic anhydrase inhibitor, receptor tyrosine kinase inhibitor (RTKIs), Rho kinase (ROCK) inhibitor, beta-blocker, alpha-adrenergic agonist, or loop diuretic. In certain embodiments, the therapeutic agent is the active agent itself not in prodrug form, such as a prostaglandin, a carbonic anhydrase inhibitor, a receptor tyrosine kinase inhibitor (RTKIs), a Rho kinase (ROCK) inhibitor, a beta-blocker, an alpha-adrenergic agonists, or a loop diuretic. Nonlimiting examples of prodrugs and active agents that can be used in the present invention are provided herein. For example, one or more of the processes can be used at the time the particles are being prepared to produce the powder or material that is stored and then later resuspended (for example, prior to lyophilization) for injection. In one example, the vessel with the dried microparticles can be placed under pressure for storage before use. In another non-limiting example, the container storing the surface-treated microparticles can be placed under vacuum directly before administration. In other embodiments, it is not necessary to remove air or gas from the active-loaded microparticle at any stage of manufacture to achieve a suitable therapeutic effect.

In typical embodiments of invention (i) above, the process to prepare the improved suspension for medical use, including for administration into low viscosity fluids, is conducted following mild surface treatment, isolation, and reconstitution in an appropriate diluent. Non-limiting illustrations in Examples 32-37 establish that treatments to provide an improved suspension of microparticles upon injection in an aqueous solution result in less floatation and better aggregation compared to microparticles that have not been treated for enhanced wettability. FIGS. 22A-22C and 23A-23L illustrate the effect of vacuum strength on particle floatation and aggregation, and FIGS. 27A-27L illustrate the effect of excipient addition on particle floatation and aggregation. FIGS. 29A, 29B and 30 depict the effect of sonication on particle floatation and aggregation.

In one embodiment of a selected aspect of the invention, the microparticles are mildly surface treated prior to treatments for enhanced wettability. In one embodiment, the solid biodegradable microparticles are suitable for ocular injection, at which point the particles aggregate to form a pellet that remains outside the visual axis so as not to significantly impair vision. The particles can aggregate into one or several pellets. The size of the aggregate depends on the concentration and volume of the microparticle suspensions injected and the diluent in which the microparticles are suspended.

In one aspect of the invention, the improved process of (i) for preparing a microparticle or lyophilized or otherwise solidified material thereof or a suspension thereof, leading to an aggregated pellet in vivo, can be used in combination with a selected method and for forming aggregating microparticles described in U.S. Ser. No. 15/349,985 and PCT/US16/61706 (and the resulting materials thereof). For example, methods include providing solid aggregating microparticles that include at least one biodegradable polymer, wherein the solid aggregating microparticles have a solid core, include a therapeutic agent, have a modified surface which has been treated under mild conditions at a temperature, that may optionally be at or less than about 18° C., to remove surface surfactant, are sufficiently small to be injected in vivo, and are capable of aggregating in vivo to form at least one pellet of at least 500 µm in vivo to provide sustained drug delivery in vivo for at least three months, four months, five months, six months seven months, eight months, nine months or more. In certain embodiments, sustained drug deliver in vivo is provided for up to one year. The solid aggregating microparticles are suitable, for example, for an intravitreal injection, implant, including an ocular implant, periocular delivery, or delivery in vivo outside of the eye. In certain embodiments, the therapeutic agent is a prodrug as described herein.

As an illustration, the present invention includes a process for the preparation of surface-modified solid aggregating microparticles that are advantageous for pellet formation in vivo, and microparticle materials made thereby, that includes:

A. a first step of preparing microparticles comprising one or more biodegradable polymers by dissolving or dispersing the polymer(s) and a therapeutic agent in one or more solvents to form a polymer and therapeutic agent solution or dispersion, mixing the polymer and the therapeutic agent solution or dispersion with an aqueous phase containing a surfactant to produce solvent-laden microparticles and then removing the solvent(s) to produce polymer microparticles that contain the therapeutic agent, polymer and surfactant; and B. a second step of mildly treating the surface of microparticles of step (i) at a temperature at or below about 18, 15, 10, 8 or 5° C. optionally up to about 1, 2, 3, 4, 5, 10, 30, 40, 50, 60, 70, 80, 90 100, 11, 120 or 140 minutes with an agent that removes surface surfactant, surface polymer, or surface oligomer in a manner that does not significantly produce internal pores; and C. isolating the surface treated microparticles; and D. subjecting the microparticles to at least one process selected from 1) vacuum treatment prior to lyophilization or other form of reconstitutable solidification, or after the step of reconstitution wherein the microparticles are suspended in a diluent and the suspension is placed under vacuum prior to use; 2) excipient addition, wherein an excipient is added prior to lyophilization; and 3) sonication, prior to lyophilization or other form of reconstitutable solidification, or after the step of reconstitution; 4) sealing the vial containing the dry powder of particles under vacuum, including but not limited to high vacuum; or 5) pre-wetting (i.e., resuspending) the surface-treated microparticles in a diluent for 2-24 hours before injecting into the eye, for example in a hyaluronic acid solution or other sterile solution suitable for ocular injection.

The process of these steps can be achieved in a continuous manufacturing line or via one step or in step-wise fashion as appropriate. The process of step D. above can be carried out following isolation of the microparticles and/or upon reconstitution prior to injection. In one embodiment, the surface treated solid biodegradable microparticles do not significantly aggregate during the manufacturing process. In another embodiment, the surface treated solid biodegradable microparticles do not significantly aggregate when resuspended and loaded into a syringe. In some embodiments, the syringe is approximately 30, 29, 28, 27, 26 or 25 gauge, with either normal or thin wall.

In another nonlimiting embodiment, a process for preparing a suspension comprising a microparticle and a pharmaceutically active compound encapsulated in the microparticle and the resulting materials thereof; which process comprises:

(a) preparing a solution or suspension (organic phase) comprising: (i) PLGA or PLA or PLA and PLGA, (ii) PLGA-PEG or PLA-PEG (iii) a pharmaceutically active compound, for example, as described herein and (iv) one or more organic solvents;

(b) preparing an emulsion in an aqueous polyvinyl alcohol (PVA) solution (aqueous phase) by adding the organic phase into the aqueous phase and mixing them until particle formation (for example at about 3,000 to about 10,000 rpm for about 1 to about 30 minutes);

(c) removing additional solvent as necessary using known techniques;

(d) centrifuging or causing the sedimentation of the microparticle that is loaded with a pharmaceutically active compound or prodrug thereof;

(e) optionally removing additional solvent and/or washing the microparticle loaded with the pharmaceutically active compound or prodrug thereof with water;

(f) filtering the microparticle loaded with pharmaceutically active compound or prodrug thereof to remove aggregates or particles larger than the desired size;

(g) optionally lyophilizing the microparticle comprising the pharmaceutically active compound and storing the microparticle as a dry powder in a manner that maintains stability for up to about 6, 8, 10, 12, 20, 22, or 24 months or more; and (h) optionally improving the aggregation potential of the particles by subjecting the particles to at least one process selected from 1) vacuum treatment prior to step (g), or after reconstitution wherein the microparticles are suspended in a diluent and the suspension is placed under vacuum; 2) excipient addition, wherein an excipient is added prior to lyophilization; and 3) sonication prior to step (g), or during reconstitution wherein the microparticles are suspended in a diluent and sonicated; 4) sealing the vial containing the dry powder of particles under vacuum, including but not limited to high vacuum; or 5) pre-wetting (i.e., resuspending) the surface-treated microparticles in a diluent for 2-24 hours before injecting into the eye, for example in a hyaluronic acid solution or other sterile solution suitable for ocular injection.

In one embodiment, a process for preparing an improved lyophilized material or a suspension of microparticles following reconstitution includes suspending the particles in a diluent and subjecting the particles to vacuum treatment at a pressure of about less than about 500, 400, 300, 200, 150, 100, 75, 50, 40, 35, 34, 33, 32, 31, 30, 29, 28 or 25 Torr for a suitable amount of time to substantially remove air attached to the particles, which in some embodiments can be up to 3, 5, 8, 10, 20, 30, 40, 50, 60, 70, 80, or 90 minutes or up to 2, 3, 4, 5, or 6, 10, 15 or 24 or more hours. In one embodiment, the vacuum treatment is conducted with a VacLock syringe in a size of up to at least 10, 20, 30, or 60 mL.

In certain non-limiting embodiments, the microparticles are vacuumed at a strength of less than 40 Torr for about 3, 5, 8, 10, 20, 30, 45, 60, 75, or 90 minutes. In certain non-limiting embodiments, the microparticles are vacuumed at a strength less than 40 Torr from about 1 to 90 minutes, from about 1 to 60 minutes, from about 1 to 45 minutes, from about 1 to 30 minutes, from about 1 to 15 minutes, or from about 1 to 5 minutes.

In certain embodiments, the diluent for suspending particles is ProVisc. In some embodiments, the microparticles are diluted from about 10-fold to about 40-fold, from about 15-fold to about 35-fold, or from about 20-fold to about 25-fold. In some embodiments, the diluent for suspending particles is a 10×-diluted ProVisc (0.1% HA in PBS) solution, a 20×-diluted ProVisc (0.05% HA in PBS) solution, or a 40×-diluted ProVisc (0.025% HA in PBS) solution. In some embodiment, the particles are suspended in the diluent at a concentration of at least about 100 mg/mL, 200 mg/mL, 300 mg/mL, 400 mg/mL, or 500 mg/mL.

BRIEF DESCRIPTION OF THE FIGURES

FIG. 8A illustrates the in vitro aggregation of surface treated microparticles (STMP) in 5-fold diluted ProVisc at a concentration of 100 mg/mL into 4 mL of PBS after incubation at 37° C. for 2 hours (top) and after incubation at 37° C. for 2 hours followed by shaking at 250 rpm for 2 minutes on an orbital shaker (bottom) (Example 17).

FIG. 8B illustrates the in vitro aggregation of surface treated microparticles (STMP) in 5-fold diluted ProVisc at a concentration of 100 mg/mL into 4 mL of HA (5 mg/mL solution) after incubation at 37° C. for 2 hours (top) and after incubation at 37° C. for 2 hours followed by shaking at 250 rpm for 2 minutes on an orbital shaker (bottom) (Example 17).

FIG. 8C illustrates the in vitro aggregation of surface treated microparticles (STMP) in 5-fold diluted ProVisc at a concentration of 200 mg/mL into 4 mL of PBS after incubation at 37° C. for 2 hours followed by shaking at 250 rpm for 2 minutes on an orbital shaker (bottom) (Example 17).

FIG. 8D illustrates the in vitro aggregation of surface treated microparticles (STMP) in 5-fold diluted ProVisc at a concentration of 200 mg/mL into 4 mL of HA (5 mg/mL solution) after incubation at 37° C. for 2 hours followed by shaking at 250 rpm for 2 minutes on an orbital shaker (bottom) (Example 17).

FIG. 9 illustrates photos of aggregates of particles in an ex vivo cow eye 2 hours after injection (Example 18).

FIG. 23A is an image depicting the effect of vacuum treatment as described in Example 32 on particle floatation during injection. The image was taken during the injection of particles into a glass tube containing 37° C. phosphate buffered saline solution (PBS).

FIG. 23B is an image depicting the effect of vacuum treatment as described in Example 32 on particle floatation during injection. The image was taken during the injection of particles into a glass tube containing 37° C. phosphate buffered saline solution (PBS). The particles had been subjected to vacuum treatment for 10 minutes at 143 Torr prior to injection.

FIG. 23C is an image depicting the effect of vacuum treatment as described in Example 32 on particle floatation during injection. The image was taken during the injection of particles into a glass tube containing 37° C. phosphate buffered saline solution (PBS). The particles had been subjected to vacuum treatment for 10 minutes at 87 Torr prior to injection.

FIG. 23D is an image depicting the effect of vacuum treatment as described in Example 32 on particle floatation during injection. The image was taken during the injection of particles into a glass tube containing 37° C. phosphate buffered saline solution (PBS). The particles had been subjected to vacuum treatment for 10 minutes at 32 Torr prior to injection.

FIG. 23E is an image depicting the effect of vacuum treatment as described in Example 32 on particle floatation 10 seconds after injection. The image was taken after the injection of particles into a glass tube containing 37° C. phosphate buffered saline solution (PBS). The particles had not been subjected to vacuum treatment prior to injection (no vacuum was pulled, but the pressure in the vial attached to the VacLock syringe was approximately 550 Torr due to the slight vacuum introduced before vial capping).

FIG. 23F is an image depicting the effect of vacuum treatment as described in Example 32 on particle floatation 10 seconds after injection. The image was taken after the injection of particles into a glass tube containing 37° C. phosphate buffered saline solution (PBS). The particles had been subjected to vacuum treatment for 10 minutes at 143 Torr prior to injection.

FIG. 23G is an image depicting the effect of vacuum treatment as described in Example 32 on particle floatation 10 seconds after injection. The image was taken after the injection of particles into a glass tube containing 37° C. phosphate buffered saline solution (PBS). The particles had been subjected to vacuum treatment for 10 minutes at 87 Torr prior to injection.

FIG. 23H is an image depicting the effect of vacuum treatment as described in Example 32 on particle floatation 10 seconds after injection. The image was taken after the injection of particles into a glass tube containing 37° C. phosphate buffered saline solution (PBS). The particles had been subjected to vacuum treatment for 10 minutes at 32 Torr prior to injection.

FIG. 23I is an image depicting the effect of vacuum treatment as described in Example 32 on particle aggregation. The image was taken after particles were allowed to incubate for 2 hours in a glass tube containing 37° C. phosphate buffered saline solution (PBS) and the particles were detached from the bottom of the glass by gently tapping. The particles had not been subjected to vacuum treatment prior to injection (no vacuum was pulled, but the pressure in the vial attached to the VacLock syringe was approximately 550 Torr due to the slight vacuum introduced before vial capping).

FIG. 23J is an image depicting the effect of vacuum treatment as described in Example 32 on particle aggregation. The image was taken after particles were allowed to incubate for 2 hours in a glass tube containing 37° C. phosphate buffered saline solution (PBS) and the particles were detached from the bottom of the glass by gently tapping. The particles had been subjected to vacuum treatment for 10 minutes at 143 Torr prior to injection.

FIG. 23K is an image depicting the effect of vacuum treatment as described in Example 32 on particle aggregation. The image was taken after particles were allowed to incubate for 2 hours in a glass tube containing 37° C. phosphate buffered saline solution (PBS) and the particles were detached from the bottom of the glass by gently tapping. The particles had been subjected to vacuum treatment for 10 minutes at 87 Torr prior to injection.

FIG. 23L is an image depicting the effect of vacuum treatment as described in Example 32 on particle aggregation. The image was taken after particles were allowed to incubate for 2 hours in a glass tube containing 37° C. phosphate buffered saline solution (PBS) and the particles were detached from the bottom of the glass by gently tapping. The particles had been subjected to vacuum treatment for 10 minutes at 32 Torr prior to injection.

FIG. 28 is an image depicting the effects of excipient type and concentration on particle aggregation as described in Example 36. The image was taken after particles were allowed to incubate for 2 hours in a glass tube containing phosphate buffered saline solution (PBS) and the particles were detached from the bottom of the glass by gently tapping. Prior to injection, the particles were subjected to lyophilization in mannitol, sucrose, or trehalose solution. Particles with excipients aggregated, while the control had poor aggregation. Excipient solutions for lyophilization (in order from left to right) included 10% mannitol, 10% sucrose, 10% trehalose, 1% sucrose, 10% sucrose, and control.

FIG. 29A is an image depicting the effect of sonication on particle floatation as described in Example 37. The image was taken after particles suspended in HA were injected into a glass tube containing PBS solution before the particles were sonicated.

FIG. 29B is an image depicting the effect of sonication on particle floatation as described in Example 37. The image was taken after particles suspended in HA were injected into a glass tube containing PBS solution after the particles were sonicated.

FIG. 30 is an image depicting the effect of sonication on particle aggregation as described in Example 37. The image was taken after particles suspended in HA were allowed to incubate for 2 hours in a glass tube containing phosphate buffered saline solution (PBS) and the particles were detached from the bottom of the glass by gently tapping. Sample 1 in an image of particle aggregation when the particles were not subjected to sonication prior to incubation in PBS. Sample 2 is an image of particle aggregation when the particles were subjected to sonication prior to incubation in PBS. Aggregation was improved when particles were pre-treated with sonication.

DETAILED DESCRIPTION

Figure 1:
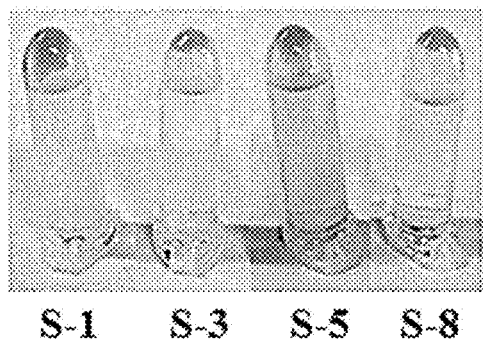
FIG. 1 illustrates the aggregation of non-surface treated microparticles (NSTMP) (S-1 and S-5) and surface treated microparticles (STMP) (S-3 and S-8) after injection into PBS and incubation at 37° C. for 2 hours. The NSTMP, S-1 and S-5, started to disperse immediately when the tubes were inverted after the 2 hour-incubation, while the STMP, S-3 and S-8, remained aggregated at the bottom of the tubes without dispersion throughout the entire period of observation (about 10 minutes). Samples from left to right are S-1, S-3, S-5 and S-8 (Example 5).
Figure 2:
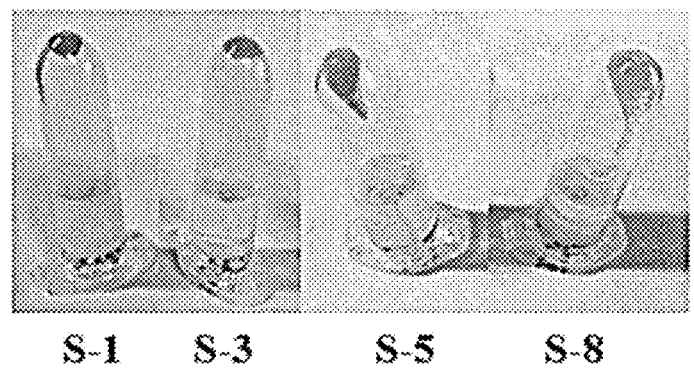
FIG. 2 illustrates the aggregation of surface treated microparticles (STMP) (S-3 and S-8) after injection into HA and incubation at 37° C. for 2 hours. Samples left to right are S-1, S-3, S-5 and S-8 (Example 5).

The present invention has at least the following aspects:
(i) A lyophilized or otherwise reconstitutable microparticle composition that has less propensity to result in floating microparticles than the same microparticle composition that has not been processed as described herein, when resuspended in fluid, such as including but not limited to buffered aqueous solution or aqueous hyaluronic acid, for in vivo delivery. The process as described herein is based on the discovery that very small air bubbles or gas or a thin layer of air adhered to microparticles can adversely affect the quality of the resuspended microparticle of the present invention, and that improved microparticles for lyophilization can be provided by removing adhered air or gas by treating the microparticles with a vacuum, sonication, or excipient addition or other method that removes or decreases the adhered air or gas prior to lyophilization, or by doing so after resuspending the lyophilized microparticle material. It has been discovered that the issue of air adhered to the microparticle can be more pronounced if the microparticle has been surface treated even under mild conditions to remove or decrease surface surfactant, such as those described in U.S. Ser. No. 15/349, 985 and PCT/US16/61706 (see nonlimiting Example 2 below).
(ii) An improved lyophilized microparticle, microparticle suspension, and method for manufacture thereof, processed as described in (i) that is loaded with a pharmaceutically active agent, including those listed below, which can be active in the form delivered or is a prodrug, with non-limiting examples provided herein, for in vivo treatment of a patient in need thereof.
(iii) Microparticles as described herein, and lyophilized or suspended materials thereof, whether treated to remove adhered air or gas, and which include any of the active drugs, including prodrugs, described herein.

For example, it has been identified that for certain applications, the processes and materials in U.S. Ser. No. 15/349, 985 and PCT/US16/61706 provide acceptable aggregating microparticles in vivo, however, there are occasions when if surface-treated microparticles are overtreated (e.g., treated under strong chemical conditions or for an extended period of time), they may have a tendency to float upon injection into an aqueous solution with low viscosity (e.g., PBS buffer solution or sometimes vitreal fluid, wherein the viscosity may decrease with age of the patient), which can be disadvantageous for forming a pellet that remains out of the visual axis. Since ocular disorders increase with age, it is important to provide a particle suspension that still aggregates to a pellet in lower viscosity vitreous fluid. Certain aspects of this invention address those certain situations, where a thin layer of air, air bubbles or gas generally can adhere to the surface of some microparticles and prevent the particles from being completely wetted. If this tiny layer of air or bubbles is high enough to create buoyancy, the microparticles will be less likely to aggregate to the desired pellet.

Thus, according to the present invention, microparticles and microparticle suspensions are provided that have improved aggregation to a pellet for medical therapy due to enhanced wettability in vivo. Examples of processes that provide improved aggregation of particles to the desired ocular pellet include, but are not limited to, one or a combination of 1) applying a vacuum to the particle suspension to facilitate the disassociation of air from particles; 2) adding one or more excipients to reduce surface hydrophobicity of particles and thus reduce the amount of air adhering to the particles; and, 3) sonication to facilitate the disassociation of air from the particles, either prior to lyophilization or other drying means to make a solid reconstitutable microparticle material, or by carrying out one or more of these processes after reconstitution. These processes are described in more detail below.

In the third independent aspect of the invention, solid microparticles that aggregate in vivo to a pellet and provide release of a therapeutic agent in vivo are provided. In certain embodiments, the therapeutic agent is a lipophilic prodrug as described herein. In certain embodiments, the lipophilic prodrug releases a prostaglandin, carbonic anhydrase inhibitor, receptor tyrosine kinase inhibitor (RTKIs), Rho kinase (ROCK) inhibitor, beta-blocker, alpha-adrenergic agonist, or loop diuretic. In certain embodiments, the therapeutic agent is the active agent itself not in prodrug form, such as a prostaglandin, a carbonic anhydrase inhibitor, a receptor tyrosine kinase inhibitor (RTKIs), a Rho kinase (ROCK) inhibitor, a beta-blocker, an alpha-adrenergic agonists, or a loop diuretic. Nonlimiting examples of prodrugs and active agents that can be used in the present invention are provided herein. For example, one or more of the processes can be used at the time the particles are being prepared to produce the powder or material that is stored and then later resuspended (for example, prior to lyophilization) for injection. In one example, the vessel with the dried microparticles can be placed under pressure for storage before use. In another non-limiting example, the container storing the surface-treated microparticles can be placed under vacuum directly before administration. In other embodiments, it is not necessary to remove air or gas from the active-loaded microparticle at any stage of manufacture to achieve a suitable therapeutic effect.

In typical embodiments of invention (i) above, the process to prepare the improved suspension for medical use, including for administration into low viscosity fluids, is conducted following mild surface treatment, isolation, and reconstitution in an appropriate diluent. Non-limiting illustrations in Examples 32-37 establish that treatments to provide an improved suspension of microparticles upon injection in an aqueous solution result in less floatation and better aggregation compared to microparticles that have not been treated for enhanced wettability.

FIGS. 22A-22C and 23A-23L illustrate the effect of vacuum strength on particle floatation and aggregation, and FIGS. 27A-27L illustrate the effect of excipient addition on particle floatation and aggregation. FIGS. 29A, 29B and 30 depict the effect of sonication on particle floatation and aggregation.

In one embodiment of a selected aspect of the invention, the microparticles are mildly surface treated prior to treatments for enhanced wettability. In one embodiment, the solid biodegradable microparticles are suitable for ocular injection, at which point the particles aggregate to form a pellet that remains outside the visual axis so as not to significantly impair vision. The particles can aggregate into one or several pellets. The size of the aggregate depends on the concentration and volume of the microparticle suspensions injected and the diluent in which the microparticles are suspended.

In one aspect of the invention, the improved process of (i) for preparing a microparticle or lyophilized or otherwise solidified material thereof or a suspension thereof, leading to an aggregated pellet in vivo, can be used in combination with a selected method and for forming aggregating microparticles described in U.S. Ser. No. 15/349,985 and PCT/US16/61706 (and the resulting materials thereof). For example, methods include providing solid aggregating microparticles that include at least one biodegradable polymer, wherein the solid aggregating microparticles have a solid core, include a therapeutic agent, have a modified surface which has been treated under mild conditions at a temperature, that may optionally be at or less than about 18° C., to remove surface surfactant, are sufficiently small to be injected in vivo, and are capable of aggregating in vivo to form at least one pellet of at least 500 µm in vivo to provide sustained drug delivery in vivo for at least three months, four months, five months, six months seven months, eight months, nine months or more. In certain embodiments, sustained drug deliver in vivo is provided for up to one year. The solid aggregating microparticles are suitable, for example, for an intravitreal injection, implant, including an ocular implant, periocular delivery, or delivery in vivo outside of the eye. In certain embodiments, the therapeutic agent is a prodrug as described herein.

As an illustration, the present invention includes a process for the preparation of surface-modified solid aggregating microparticles that are advantageous for pellet formation in vivo, and microparticle materials made thereby, that includes:

A. a first step of preparing microparticles comprising one or more biodegradable polymers by dissolving or dispersing the polymer(s) and a therapeutic agent in one or more solvents to form a polymer and therapeutic agent solution or dispersion, mixing the polymer and the therapeutic agent solution or dispersion with an aqueous phase containing a surfactant to produce solvent-laden microparticles and then removing the solvent(s) to produce polymer microparticles that contain the therapeutic agent, polymer and surfactant; and B. a second step of mildly treating the surface of microparticles of step (i) at a temperature at or below about 18, 15, 10, 8 or 5° C. optionally up to about 1, 2, 3, 4, 5, 10, 30, 40, 50, 60, 70, 80, 90 100, 11, 120 or 140 minutes with an agent that removes surface surfactant, surface polymer, or surface oligomer in a manner that does not significantly produce internal pores; and C. isolating the surface treated microparticles; and D. subjecting the microparticles to at least one process selected from 1) vacuum treatment prior to lyophilization or other form of reconstitutable solidification, or after the step of reconstitution wherein the microparticles are suspended in a diluent and the suspension is placed under vacuum prior to use; 2) excipient addition, wherein an excipient is added prior to lyophilization; and 3) sonication, prior to lyophilization or other form of reconstitutable solidification, or after the step of reconstitution; 4) sealing the vial containing the dry powder of particles under vacuum, including but not limited to high vacuum; or 5) pre-wetting (i.e., resuspending) the surface-treated microparticles in a diluent for 2-24 hours before injecting into the eye, for example in a hyaluronic acid solution or other sterile solution suitable for ocular injection.

The process of these steps can be achieved in a continuous manufacturing line or via one step or in step-wise fashion as appropriate. The process of step D. above can be carried out following isolation of the microparticles and/or upon reconstitution prior to injection. In one embodiment, the surface treated solid biodegradable microparticles do not significantly aggregate during the manufacturing process. In another embodiment, the surface treated solid biodegradable microparticles do not significantly aggregate when resuspended and loaded into a syringe. In some embodiments, the syringe is approximately 30, 29, 28, 27, 26 or 25 gauge, with either normal or thin wall.

In another nonlimiting embodiment, a process for preparing a suspension comprising a microparticle and a pharmaceutically active compound encapsulated in the microparticle and the resulting materials thereof; which process comprises:

(i) preparing a solution or suspension (organic phase) comprising: (i) PLGA or PLA or PLA and PLGA, (ii) PLGA-PEG or PLA-PEG (iii) a pharmaceutically active compound, for example, as described herein and (iv) one or more organic solvents;

(j) preparing an emulsion in an aqueous polyvinyl alcohol (PVA) solution (aqueous phase) by adding the organic phase into the aqueous phase and mixing them until particle formation (for example at about 3,000 to about 10,000 rpm for about 1 to about 30 minutes);

(k) removing additional solvent as necessary using known techniques;

(l) centrifuging or causing the sedimentation of the microparticle that is loaded with a pharmaceutically active compound or prodrug thereof;

(m) optionally removing additional solvent and/or washing the microparticle loaded with the pharmaceutically active compound or prodrug thereof with water;

(n) filtering the microparticle loaded with pharmaceutically active compound or prodrug thereof to remove aggregates or particles larger than the desired size;

(o) optionally lyophilizing the microparticle comprising the pharmaceutically active compound and storing the microparticle as a dry powder in a manner that maintains stability for up to about 6, 8, 10, 12, 20, 22, or 24 months or more; and (p) optionally improving the aggregation potential of the particles by subjecting the particles to at least one process selected from 1) vacuum treatment prior to step (g), or after reconstitution wherein the microparticles are suspended in a diluent and the suspension is placed under vacuum; 2) excipient addition, wherein an excipient is added prior to lyophilization; and 3) sonication prior to step (g), or during reconstitution wherein the microparticles are suspended in a diluent and sonicated; 4) sealing the vial containing the dry powder of particles under vacuum, including but not limited to high vacuum; or 5) pre-wetting (i.e., resuspending) the surface-treated microparticles in a diluent for 2-24 hours before injecting into the eye, for example in a hyaluronic acid solution or other sterile solution suitable for ocular injection.

In one embodiment, a process for preparing an improved lyophilized material or a suspension of microparticles following reconstitution includes suspending the particles in a diluent and subjecting the particles to vacuum treatment at a pressure of about less than about 500, 400, 300, 200, 150, 100, 75, 50, 40, 35, 34, 33, 32, 31, 30, 29, 28 or 25 Torr for a suitable amount of time to substantially remove air attached to the particles, which in some embodiments can be up to 3, 5, 8, 10, 20, 30, 40, 50, 60, 70, 80, or 90 minutes or up to 2, 3, 4, 5, or 6, 10, 15 or 24 or more hours. In one embodiment, the vacuum treatment is conducted with a VacLock syringe in a size of up to at least 10, 20, 30, or 60 mL.

In certain non-limiting embodiments, the microparticles are vacuumed at a strength of less than 40 Torr for about 3, 5, 8, 10, 20, 30, 45, 60, 75, or 90 minutes. In certain non-limiting embodiments, the microparticles are vacuumed at a strength less than 40 Torr from about 1 to 90 minutes, from about 1 to 60 minutes, from about 1 to 45 minutes, from about 1 to 30 minutes, from about 1 to 15 minutes, or from about 1 to 5 minutes.

In certain embodiments, the diluent for suspending particles is ProVisc. In some embodiments, the microparticles are diluted from about 10-fold to about 40-fold, from about 15-fold to about 35-fold, or from about 20-fold to about 25-fold. In some embodiments, the diluent for suspending particles is a 10×-diluted ProVisc (0.1% HA in PBS) solution, a 20×-diluted ProVisc (0.05% HA in PBS) solution, or a 40×-diluted ProVisc (0.025% HA in PBS) solution. In some embodiment, the particles are suspended in the diluent at a concentration of at least about 100 mg/mL, 200 mg/mL, 300 mg/mL, 400 mg/mL, or 500 mg/mL.

I. Terminology

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Compounds are described using standard nomenclature. Unless defined otherwise, all technical and scientific terms used herein have the same meaning as is commonly understood by one of skill in the art to which this invention belongs.

The terms "a" and "an" do not denote a limitation of quantity, but rather denote the presence of at least one of the referenced items.

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and are independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed.

The term "carrier" refers to a diluent, excipient, or vehicle.

A "dosage form" means a unit of administration of a composition that includes a surface treated microparticle and a therapeutically active compound. Examples of dosage forms include injections, suspensions, liquids, emulsions, implants, particles, spheres, creams, ointments, inhalable forms, transdermal forms, buccal, sublingual, topical, gel, mucosal, and the like. A "dosage form" can also include, for example, a surface treated microparticle comprising a pharmaceutically active compound in a carrier.

The term "microparticle" means a particle whose size is measured in micrometers (m). Typically, the microparticle has an average diameter of from about 1 μm to 100 μm. In some embodiments, the microparticle has an average diameter of from about 1 μm to 60 μm, for instance from about 1 μm to 40 μm; from about 10 μm to 40 μm; from about 20 μm to 40 μm; from about 25 μm to 40 μm; from about 25 μm to about 30 μm; from about 20 μm to 35 μm. For example, the microparticle may have an average diameter of from 20 μm to 40 μm, and in certain embodiments, 20, 21, 22, 23, 24, 25, 26, 27, 28, 29, 30, 31, 32 or 33. As used herein, the term "microsphere" means a substantially spherical microparticle.

A "patient" or "host" or "subject" is typically a human, however, may be more generally a mammal. In an alternative embodiment it can refer to, for example, a cow, sheep, goat, horse, dog, cat, rabbit, rat, mouse, bird and the like.

The term "mild" or "mildly" when used to describe the surface modification of the microparticles means that the modification (typically the removal of surfactant from the surface, as opposed to the inner core, of the particle) is less severe, pronounced or extensive than when carried out at room temperature with the otherwise same conditions. In general, the surface modification of the solid microparticles of the present invention is carried out in a manner that does not create significant channels or large pores that would significantly accelerate the degradation of the microparticle in vivo, yet serves to soften and decrease the hydrophilicity of the surface to facilitate in vivo aggregation.

The term "solid" as used to characterize the mildly surface treated microparticle means that the particle is substantially continuous in material structure as opposed to heterogeneous with significant channels and large pores that would undesirably shorten the time of biodegradation.

The term "sonicate" means to subject the microparticle suspension to ultrasonic vibration, or high frequency sound waves.

II. Processes for Producing Improved Suspensions of Surface-Treated Aggregating Microparticles for Therapeutic Purposes In one embodiment, the present invention provides processes for producing suspensions of surface-treated aggregating microparticles for therapeutic purposes that aggregate in vivo to form pellet(s). The processes include improving the wettability of surface-treated microparticles by removing air or air bubbles from the surface of the microparticle. The treatment for enhanced wettability is conducted following mild surface treatment, isolation, and reconstitution in an appropriate diluent.

In one embodiment, the invention is thus solid aggregating microparticles treated for improved wettability that include at least one biodegradable polymer, wherein the surface-modified solid aggregating microparticles have a solid core, include a therapeutic agent, have a modified surface which has been treated under mild conditions at a temperature at or less than about 18° C. to remove surface surfactant or cause surface polymer to partially degrade, have been treated by at least one or more processes selected from vacuum treatment, the addition of an excipient, and sonication to improve wettability upon injection, are sufficiently small to be injected in vivo, and aggregate in vivo to form at least one pellet of at least 500 μm in vivo in a manner that provides sustained drug delivery in vivo for at least one, two, three, four, five, six or seven months or more. The surface modified solid aggregating microparticles are suitable, for example, for an intravitreal injection, implant, including an ocular implant, periocular delivery or delivery in vivo outside of the eye.

The present invention further includes a process for the preparation of surface-modified solid aggregating microparticles that have also been treated for enhanced wettability that includes
  (i) a first step of preparing microparticles comprising one or more biodegradable polymers by dissolving or dispersing the polymer(s) and a therapeutic agent in one or more solvents to form a polymer and therapeutic agent solution or dispersion, mixing the polymer and the therapeutic agent solution or dispersion with an aqueous phase containing a surfactant to produce microparticles that contain the therapeutic agent, polymer and surfactant; and
  (ii) a second step of mildly treating the surface of microparticles of step (i) at a temperature at or below about 18, 15, 10, 8 or 5° C. optionally up to about 1, 2, 3, 4, 5, 10, 30, 40, 50, 60, 70, 80, 90 100, 11, 120 or 140 minutes with an agent that removes surface surfactant, surface polymer, or surface oligomer in a manner that does not significantly produce internal pores; and
  (iii) isolating the surface treated microparticles; and
  (iv) improving the aggregation potential of the particles by subjecting the particles to at least one process selected from 1) vacuum treatment, wherein the microparticles are suspended in a diluent and the suspension is placed under vacuum prior to use; 2) excipient addition, wherein an excipient is added prior to lyophilization; and 3) sonication, wherein the microparticles are suspended in a diluent and sonicated; 4) sealing the vial containing the dry powder of particles under vacuum, including but not limited to high vacuum; or 5) pre-wetting (i.e., resuspending) the surface-treated microparticles in a diluent for 2-24 hours before injecting into the eye, for example in a hyaluronic acid solution or other sterile solution suitable for ocular injection.

In one embodiment, the surface treatment includes treating microparticles with aqueous base, for example, sodium hydroxide and a solvent (such as an alcohol, for example ethanol or methanol, or an organic solvent such as DMF, DMSO or ethyl acetate) as otherwise described above. More generally, a hydroxide base is used, for example, potassium hydroxide. An organic base can also be used. In other embodiments, the surface treatment as described above is carried out in aqueous acid, for example hydrochloric acid. In one embodiment, the surface treatment includes treating microparticles with phosphate buffered saline and ethanol.

In some embodiments, the surface treatment is carried out at a temperature of not more than 5, 6, 7, 8, 9, 10, 11, 12, 13, 14, 15, 16, 17 or 18° C., at a reduced temperature of about 5 to about 18° C., about 5 to about 16° C., about 5 to about 15° C., about 0 to about 10° C., about 0 to about 8° C., or about 1 to about 5° C., about 5 to about 20° C., about 1 to about 10° C., about 0 to about 15° C., about 0 to about 10° C., about 1 to about 8° C., or about 1 to about 5° C. Each combination of each of these conditions is considered independently disclosed as if each combination were separately listed.

The pH of the surface treatment will of course vary based on whether the treatment is carried out in basic, neutral or acidic conditions. When carrying out the treatment in base, the pH may range from about 7.5 to about 14, including not more than about 8, 9, 10, 11, 12, 13 or 14. When carrying out the treatment in acid, the pH may range from about 6.5 to about 1, including not less than 1, 2, 3, 4, 5, or 6. When carrying out under neutral conditions, the pH may typically range from about 6.4 or 6.5 to about 7.4 or 7.5.

A key aspect of the present invention is that the treatment, whether done in basic, neutral or acidic conditions, includes a selection of the combination of the time, temperature, pH agent and solvent that causes a mild treatment that does not significantly damage the particle in a manner that forms pores, holes or channels. Each combination of each of these conditions is considered independently disclosed as if each combination were separately listed.

The treatment conditions should simply mildly treat the surface in a manner that allows the particles to remain as solid particles, be injectable without undue aggregation or clumping, and form at least one aggregate particle of at least 500 μm.

In one embodiment, the surface treatment includes treating microparticles with an aqueous solution of pH=6.6 to 7.4 or 7.5 and ethanol at a reduced temperature of about 1 to about 10° C., about 1 to about 15° C., about 5 to about 15° C., or about 0 to about 5° C. In one embodiment, the surface treatment includes treating microparticles with an aqueous solution of pH=6.6 to 7.4 or 7.5 and an organic solvent at a reduced temperature of about 0 to about 10° C., about 5 to about 8° C., or about 0 to about 5° C. In one embodiment, the surface treatment includes treating microparticles with an aqueous solution of pH=1 to 6.6 and ethanol at a reduced temperature of about 0 to about 10° C., about 0 to about 8° C., or about 0 to about 5° C. In one embodiment, the surface treatment includes treating microparticles with an organic solvent at a reduced temperature of about 0 to about 18° C., about 0 to about 16° C., about 0 to about 15° C., about 0 to about 10° C., about 0 to about 8° C., or about 0 to about 5° C. The decreased temperature of processing (less than room temperature, and typically less than 18° C.) assists to ensure that the particles are only "mildly" surface treated.

In yet another embodiment, a method for the treatment of an ocular disorder is provided that includes administering to a host in need thereof solid aggregating microparticles described herein that include an effective amount of a therapeutic agent, wherein the solid aggregating microparticles are injected into the eye and aggregate in vivo to form at least one pellet of at least 500 μm that provides sustained drug delivery for at least approximately one, two, three, four, five, six, seven, eight, nine, ten, eleven, twelve or more months in such a manner that the pellet stays substantially outside the visual axis so as not to significantly impair vision. In one embodiment, the solid biodegradable microparticles release about 1 to about 20 percent, about 1 to about 15 percent, about 1 to about 10 percent, or about 5 to 20 percent, for example, up to about 1, 5, 10, 15 or 20 percent, of the therapeutic agent over the first twenty-four-hour period.

Vacuum Treatment

In one embodiment, the process for providing an improved microparticle suspension prior to injection includes vacuum treatment wherein the particles are suspended in a diluent and subjected to negative pressure to remove unwanted air at the surface of the microparticles. Nonlimiting examples of the negative pressure can be about or less than 300, 200, 100, 150, 145, 143, 90, 89, 88, 87, 86, 85, 75, 50, 35, 34, 33, 32, 31, or 30 Torr for any appropriate time to achieve the desired results, including but not limited to 120, 110, 100, 90, 80, 70, 60, 50, 40, 30, 20, 10, 8, 5, or 3 minutes.

In one embodiment, microparticles are stored under negative pressure following the manufacturing and isolation process, wherein negative pressure is defined as any pressure lower than the pressure of ambient room temperature (approximately 760 Torr). In one embodiment, the microparticles are stored at a pressure of less than about 700 Torr, 550 Torr, 500 Torr, 450 Torr, 400 Torr, 350 Torr, 300 Torr, 250 Torr, 200 Torr, 150 Torr, 100 Torr, 90 Torr, 80 Torr, 60 Torr, 40 Torr, 35 Torr, 32 Torr, 30 Torr, or 25 Torr following the manufacturing and isolation process. In one embodiment, the microparticles are stored at a pressure of about 500 Torr to about 25 Torr following the manufacturing and isolation process. In one embodiment, the microparticles are stored at a pressure of about 300 Torr to about 25 Torr following the manufacturing and isolation process. In one embodiment, the microparticles are stored at a pressure of about 100 Torr to about 25 Torr following the manufacturing and isolation process. In one embodiment, the microparticles are stored at a pressure of about 90 Torr to about 25 Torr following the manufacturing and isolation process. In one embodiment, the microparticles are stored at a pressure of about 50 Torr to about 25 Torr following the manufacturing and isolation process. In one embodiment, the microparticles are stored at a pressure of about 40 Torr to about 25 Torr following the manufacturing and isolation process. In one embodiment, the microparticles are stored at a pressure of about 35 Torr to about 25 Torr following the manufacturing and isolation process. In a further embodiment, the microparticles are stored at a temperature of between about 2-8° C. at a pressure that is less than about 700, 550, 500, 450, 400, 350, 300, 250, 200, 150, 100, 80, 60, 50, 40, 35, 32, 30, or 25 Torr.

In one embodiment, the microparticles are stored at pressure for up to 1 week, 2 weeks, 3 weeks, 4 weeks, 1 month, 2 months, 3 months, 4 months, or more following the manufacture and isolation process. In one embodiment, the microparticles are stored for up to 1 week to up to 4 weeks at a pressure that is less than 700, 550, 500, 450, 400, 350, 300, 250, 200, 150, 100, 80, 60, 50, 40, 35, 32, or 30 Torr. In one embodiment, the microparticles are stored for up to 1 month to up to 2 months at a pressure that is less than 700, 550, 500, 450, 400, 350, 300, 250, 200, 150, 100, 80, 60, 50, 40, 35, 32, or 30 Torr. In one embodiment, the microparticles are stored for up to 3 months at a pressure that is less than 700, 550, 500, 450, 400, 350, 300, 250, 200, 150, 100, 80, 60, 50, 40, 35, 32, or 30 Torr In one embodiment, the microparticles are stored at a temperature of between about 2-8° C. following the manufacturing and isolation process and the microparticles are vacuumed less than about 2 hours, 1 hour, 30 minutes, 15 minutes, or 10 minutes prior to in vivo injection. In one embodiment, the microparticles are stored at a temperature of between about 2-8° C. following the manufacturing and isolation process and the microparticles are vacuumed 1 hour to 30 minutes prior to in vivo injection. In one embodiment, the microparticles are stored at a temperature of between about 2-8° C. following the manufacturing and isolation process and the microparticles are vacuumed 30 minutes to 10 minutes prior to in vivo injection. In one embodiment, the microparticles are stored at a temperature of between about 2-8° C. following the manufacturing and isolation process and the microparticles are vacuumed immediately prior to in vivo injection.

In one embodiment, the microparticles are stored at a temperature of between about 2-8° C. and the microparticles are vacuumed for less than 1 hour, 30 minutes, 20 minutes, 15 minutes, or 10 minutes at a strength of less than about 35 Torr immediately prior to in vivo injection. In one embodiment, the microparticles are stored at a temperature of between about 2-8° C. and the microparticles are vacuumed for 1 hour to 30 minutes at a strength of less than about 35 Torr immediately prior to in vivo injection. In one embodiment, the microparticles are stored at a temperature of between about 2-8° C. and the microparticles are vacuumed for 30 minutes to 10 minutes at a strength of less than about 35 Torr immediately prior to in vivo injection.

Figure 20A:
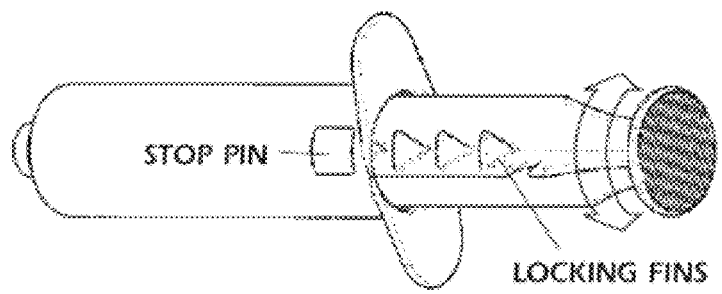
FIG. 20A is a schematic representation of the locking mechanism of the VacLock syringe highlighting the locking fins and stopping pin as described in Example 31A.
Figure 20B:
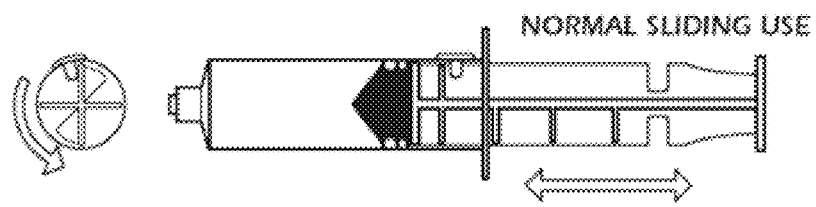
FIG. 20B is a schematic representation of the VacLock syringe when the apparatus is being used for normal sliding use. The stopping pin is positioned in such a way that the pin does not make contact with a locking fin as described in Example 31A.
Figure 20C:
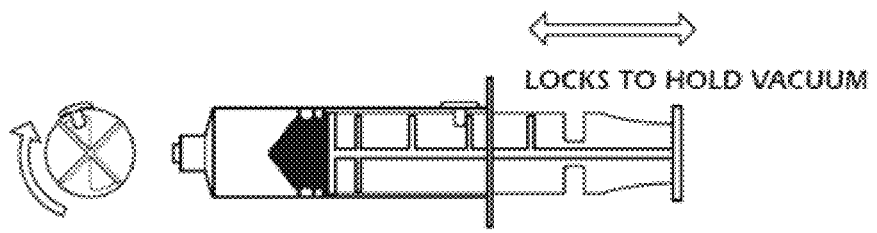
FIG. 20C is a schematic representation of the VacLock syringe when the apparatus is capable of being locked to hold vacuum. The stopping pin is positioned to make contact with the locking fins as described in Example 31A.
Figure 21:
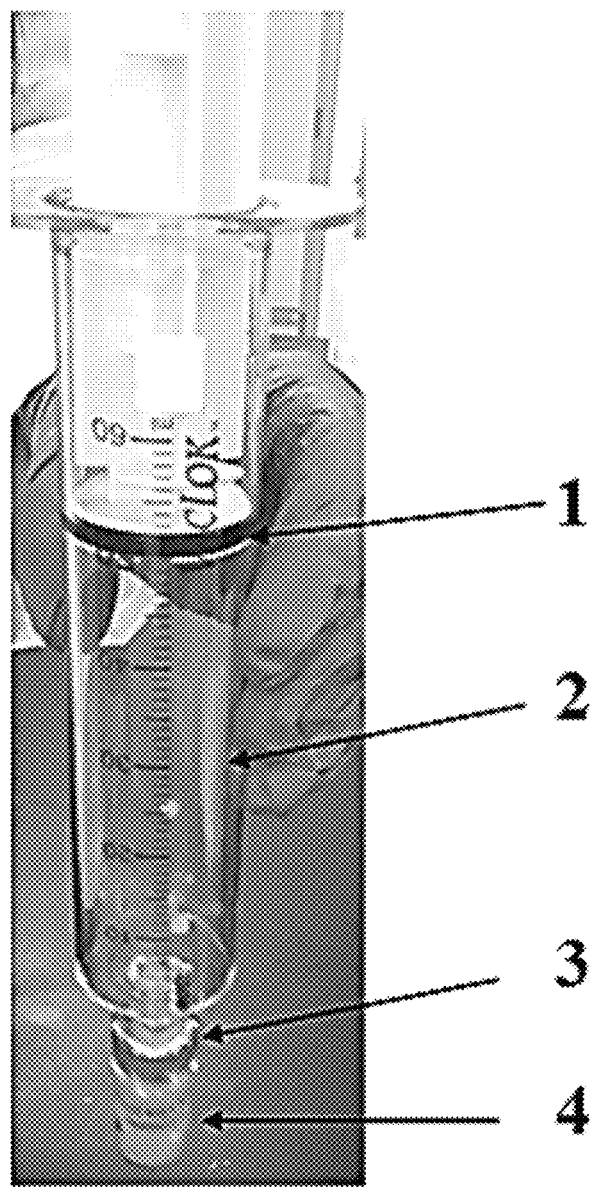
FIG. 21 is an image of a 60 mL VacLok syringe attached to a suspension vial through a vial adapter as described in Example 31A. The syringe plunger is locked at 50 mL to create a pressure of approximately 40 Torr inside the vial. The parts of the apparatus are as follows: 1) syringe plunger, which can be locked in different positions to create different pressures inside the glass vial; 2) 60 mL lockable syringe; 3) vial adapter; and, 4) 2 mL glass vial containing the particle suspension.

In one embodiment, the particles are suspended in a glass vial that is attached to a vial adapter and the vial adapter is in turn attached to a VacLok syringe (FIG. 21). A negative pressure is created in the vial by pulling the plunger of the syringe into a locking position as shown in FIG. 20C. In one embodiment, the vacuum treatment is conducted in a syringe of the 60 mL, 30 mL, 20 mL, or 10 mL size. The vacuum is then held in the syringe with the vial facing up and the large syringe attached for up to at least 10 minutes, 20 minutes, 30 minutes, 40 minutes, 50 minutes, 60 minutes, 70 minutes, 90 minutes, 100 minutes, or 129 minutes. The vacuum is released, the large syringe is detached, and a syringe is attached for in vivo injection.

In one embodiment, the particles are subjected to vacuum treatment at a strength of about 143 Torr for about at least 10 minutes, 20 minutes, 30 minutes, 40 minutes, 50 minutes, 60 minutes, 70 minutes, 80 minutes, 90 minutes, 100 minutes, or 120 minutes. In one embodiment, the particles are subjected to vacuum treatment at a strength of at least about 90, 89, 88, 87, 86, or 85 Torr for at least about at 10 minutes, 20 minutes, 30 minutes, or 40 minutes. In one embodiment, the particles are subjected to vacuum treatment at a strength of at least about 87 Torr for at least about 10 minutes, 20 minutes, 30 minutes, 40 minutes, 60 minutes, 90 minutes, or 120 minutes. In one embodiment, the particles are subjected to vacuum treatment at a strength of at least about 35, 34, 33, 32, 31, or 30 Torr for at least 5 minutes. In one embodiment, the particles are subjected to vacuum treatment at a strength of at least about 35, 34, 33, 32, 31, or 30 Torr for at least 8 minutes. In one embodiment, the particles are subjected to vacuum treatment at a strength of at least about 35, 34, 33, 32, 31, or 30 Torr for at least 10 minutes. In one embodiment, the particles are subjected to vacuum treatment at a strength of at least about 35, 34, 33, 32, 31, or 30 Torr for at least 20 minutes. In one embodiment, the particles are subjected to vacuum treatment at a strength of at least about 35, 34, 33, 32, 31, or 30 Torr for at least 30 minutes. In one embodiment, the particles are subjected to vacuum treatment at a strength of at least about 35, 34, 33, 32, 31, or 30 Torr for at least 40 minutes. In one embodiment, the particles are subjected to 30 Torr for at least 5, 10, 15, 20, 25, 30, 35, 40, 45, 50, 55, 60, 65, 70, 75, 80, 85, or 90 minutes. In one embodiment, the particles are subjected to vacuum treatment at a strength of about 35 Torr for at least 90 minutes. In one embodiment, the particles are subjected to vacuum treatment at a strength of about 35 Torr for at least 60 minutes. In one embodiment, the particles are subjected to vacuum treatment at a strength of about 35 Torr for at least 30 minutes. In one embodiment, the particles are subjected to vacuum treatment at a strength of about 35 Torr for at least 15 minutes. In one embodiment, the particles are subjected to vacuum treatment at a strength of about 35 Torr for at least 5 minutes. In one embodiment, the particles are subjected to vacuum treatment at a strength of about 32 Torr for at least 30 minutes. In one embodiment, the particles are subjected to vacuum treatment at a strength of about 32 Torr for at least 15 minutes. In one embodiment, the particles are subjected to vacuum treatment at a strength of about 32 Torr for at least 5 minutes. In one embodiment, the particles are subjected to vacuum treatment at a strength of about 30 Torr for at least 30 minutes. In one embodiment, the particles are subjected to vacuum treatment at a strength of about 30 Torr for at least 15 minutes. In one embodiment, the particles are subjected to vacuum treatment at a strength of about 30 Torr for at least 5 minutes.

In an alternative embodiment, the particles are suspended in a diluent in a vial attached to a vial adapter that is further attached to a 60 mL VacLok syringe containing a plunger (as shown in FIG. 21) wherein the plunger is pulled to the 50 mL mark and locked to create a negative pressure of approximately 30 Torr and the pressure is held for at least about 3, 5, 8, 10, 15, 20, 25, 30, or 35 minutes. In an alternative embodiment, the particles are suspended in a diluent in a vial attached to a vial adapter that is further attached to a 60 mL VacLok syringe containing a plunger wherein the plunger is pulled to the 45 mL mark, locked, and held for at least about 3, 5, 8, 10, 15, 20, 25, 30, 35, 40, 45, 50, 55, 60, 65, 70, 75, 80, 85, or 90 minutes. In an alternative embodiment, the particles are suspended in a diluent in a vial attached to a vial adapter that is further attached to a 60 mL VacLok syringe containing a plunger wherein the plunger is pulled to the 40 mL mark, locked, and the pressure is held for at least about 3, 5, 8, 10, 15, 20, 25, 30, or 35 minutes. In an alternative embodiment, the particles are suspended in a diluent in a vial attached to a vial adapter that is further attached to a 60 mL VacLok syringe containing a plunger wherein the plunger is pulled to the 35 mL mark, locked, and held for about at least 3, 5, 8, 10, 15, 20, 25, 30, or 35 minutes. In an alternative embodiment, the particles are suspended in a diluent in a vial attached to a vial adapter that is further attached to a 60 mL VacLok syringe containing a plunger wherein the plunger is pulled to the 30 mL mark, locked, and held for at least about 3, 5, 8, 10, 15, 20, 25, 30, or 35 minutes. In an alternative embodiment, the particles are suspended in a diluent in a vial attached to a vial adapter that is further attached to a 60 mL VacLok syringe containing a plunger wherein the plunger is pulled to the 25 mL mark, locked, and held for at least about 3, 5, 8, 10, 15, 20, 25, 30, or 35 minutes.

In certain embodiments, the particles are suspended in a diluent and the suspension is exposed to a pressure of less than 40 Torr for between about 90 minutes and 1 minute, between about 60 minutes and 1 minute, between about 45 minutes and 1 minute, between about 30 minutes and 1 minute, between about 15 minutes and 1 minute, or between about 5 minutes and 1 minute.

In certain embodiments, the particles are suspended in a diluent and the suspension is exposed to a pressure of less than 30 Torr for between about 90 minutes and 1 minute, between about 60 minutes and 1 minute, between about 45 minutes and 1 minute, between about 30 minutes and 1 minute, between about 15 minutes and 1 minute, or between about 5 minutes and 1 minute.

In one embodiment, the microparticles are suspended in a diluent of 10×ProVisc-diluted (0.1% HA in PBS) solution. In one embodiment, the microparticles are suspended in a diluent of 20×-diluted ProVisc (0.05% HA in PBS). In one embodiment, the microparticles are suspended in a diluent of 40×-diluted ProVisc (0.025% HA in PBS).

In one embodiment, the particles are suspended in the diluent at a concentration of 100 mg/mL, 150 mg/mL, 200 mg/mL, 250 mg/mL, 300 mg/mL, 350 mg/mL, 400 mg/mL, 450 mg/mL or 500 mg/mL. In one embodiment, the particles are suspended in 10×-diluted ProVisc (0.1% HA in PBS) solution and the suspension has a final concentration of 200 mg/mL. In one embodiment, the particles are suspended in 10×-diluted ProVisc (0.1% HA in PBS) solution and the suspension has a final concentration of 400 mg/mL. In one embodiment, the particles are suspended in a 20×-diluted ProVisc (0.05% HA in PBS) and the suspension has a final concentration of 200 mg/mL. In one embodiment, the particles are suspended in a 20×-diluted ProVisc (0.05% HA in PBS) and the suspension has a final concentration of 400 mg/mL. In one embodiment, the particles are suspended in a 40×-diluted ProVisc (0.025% HA in PBS) and the suspension has a concentration of 200 mg/mL. In one embodiment, the particles are suspended in a 40×-diluted ProVisc (0.025% HA in PBS) and the suspension has a concentration of 400 mg/mL.

The Addition of an Excipient

In one embodiment, the process for preparing an improved microparticle suspension prior to injection is the addition of at least one excipient, typically prior to lyophilization that reduces the amount of air adhering to the particles. Particles are suspended in an aqueous solution and sonicated before being flash frozen in −80° C. ethanol and lyophilized overnight. In one embodiment, the particles are suspended in an aqueous sugar solution that is 1%, 2%, 3%, 4%, 5%, 6%, 7%, 8%, 9%, 10%, 11%, 12%, 13%, 14%, or 15% sugar. In one embodiment, the sugar is sucrose. In one embodiment, the sugar is mannitol. In one embodiment, the sugar is trehalose. In one embodiment, the sugar is glucose. In one embodiment, the sugar is selected from arabinose, fucose, mannose, rhamnose, xylose, D-xylose, glucose, fructose, ribose, D-ribose, galactose, dextrose, dextran, lactose, maltodextrin, maltose, glycerol, erythritol, threitol, arabitol, xylitol, ribitol, sorbitol, galactitol, fucitol, iditol, inositol, volemitol, isomalt, maltitol, lactitol, maltotriitol, maltotetraitol, and polyglycitol. In an alternative embodiment, the sugar is selected from aspartame, saccharin, stevia, sucralose, acesulfame potassium, advantame, alitame, neotame, and sucralose. In one embodiment, the particles are suspended in an aqueous sugar solution that is 1%, 2%, 3%, 4%, 5%, 6%, 7%, 8%, 9%, 10%, 11%, 12%, 13%, 14%, or 15% sucrose. In one embodiment, the particles are suspended in a 1% sucrose solution. In one embodiment, the particles are suspended in a 10% sucrose solution. In one embodiment, the particles are suspended in an aqueous sugar solution that is 1%, 2%, 3%, 4%, 5%, 6%, 7%, 8%, 9%, 10%, 11%, 12%, 13%, 14%, or 15% mannitol. In one embodiment, the particles are suspended in a 1% mannitol solution. In one embodiment, the particles are suspended in a 10% mannitol solution. In one embodiment, the particles are suspended in a 1% trehalose solution. In one embodiment, the particles are suspended in a 10% trehalose solution. In one embodiment, the particles are suspended in an aqueous sugar solution that is 1%, 2%, 3%, 4%, 5%, 6%, 7%, 8%, 9%, 10%, 11%, 12%, 13%, 14%, or 15% trehalose. In an alternative embodiment, the particles are suspended in a small surfactant molecule, including, but not limited to tween 20 or tween 80. In an alternative embodiment, the particles are flash frozen in −80° C. methanol or isopropanol.

Sonication

In one embodiment, a process for providing an improved microparticle suspension prior to injection is sonication wherein particles are suspended in a diluent and the suspension of microparticles is sonicated for at least 30 minutes, at least 25 minutes, at least 20 minutes, at least 15 minutes, at least 10 minutes, at least 8 minutes, at least 5 minutes, or at least 3 minutes. In one embodiment, the particle solutions are sonicated at a frequency of 40 kHz. In one embodiment, the particles are suspended in the diluent at a concentration of 100 mg/mL, 150 mg/mL, 200 mg/mL, 250 mg/mL, 300 mg/mL, 350 mg/mL, 400 mg/mL, 450 mg/mL or 500 mg/mL. In one embodiment, the diluent is hyaluronic acid. In an alternative embodiment, the diluent is selected from hyaluronic acid, hydroxypropyl methylcellulose, chondroitin sulfate, or a blend of at least two diluents selected from hyaluronic acid, hydroxypropyl methylcellulose, and chondroitin sulfate. In an alternative embodiment, the diluent is selected from aacia, tragacanth, alginic acid, carrageenan, locust bean gum, gellan gum, guar gum, gelatin, starch, methylcellulose, sodium carboxymethylcellulose, hydroxyethylcellulose, hydroxypropyl cellulose, Carbopol® homopolymers (acrylic acid crosslinked with allyl sucrose or allyl pentaerythritol), and Carbopol® copolymers (acrylic acid and $C_{10}$-$C_{30}$ alkyl acrylate crosslinked with allyl pentaerythritol).

In certain embodiments, a combination of vacuum treatment, the addition of excipients, and sonication can be used following isolation and reconstitution of the microparticles. In certain embodiments, the methods for enhancing wettability are conducted at least 1 hour prior to in vivo injection, at least 45 minutes prior to in vivo injection, at least 30 minutes prior to in vivo injection, at least 25 minutes prior to in vivo injection, at least 20 minutes prior to injection, at least 15 minutes prior to in vivo injection, at least 10 minutes prior to in vivo injection, or at least 5 minutes prior to in vivo injection. In one embodiment, the vacuum treatment, addition of an excipient, and/or sonication is conducted immediately before in vivo injection. In one embodiment, the particles are vacuumed at a strength of less than 35 Torr for less than 30 minutes and are immediately injected in vivo. In an alternative embodiment, the particles are vacuumed at a strength of less than 35 Torr for less than 20 minutes and are immediately injected in vivo. In an alternative embodiment, the particles are vacuumed at a strength of less than 35 Torr for less than 15 minutes and are immediately injected in vivo. In an alternative embodiment, the particles are vacuumed at a strength of less than 35 Torr for less than 10 minutes and are immediately injected in vivo.

In one embodiment, the microparticles are stored at a temperature of between about 2-8° C. following the manufacturing and isolation process and the microparticles are held under negative pressure for about 24, 12, 8, 6, 2 hours, 1 hour, 30 minutes, 15 minutes, or 10 minutes or less prior to in vivo injection. In one embodiment, the microparticles are stored at a temperature of between about 2-8° C. following the manufacturing and isolation process and the microparticles are held under negative pressure 1 hour to 30 minutes prior to in vivo injection. In one embodiment, the microparticles are stored at a temperature of between about 2-8° C. following the manufacturing and isolation process and the microparticles are vacuumed 30 minutes to 10 minutes prior to in vivo injection. In one embodiment, the microparticles are stored at a temperature of between about 2-8° C. following the manufacturing and isolation process and the microparticles are vacuumed immediately prior to in vivo injection.

In one embodiment, the microparticles are stored at a temperature of between about 2-8° C. and the microparticles are vacuumed for less than 1 hour, 30 minutes, 20 minutes, 15 minutes, or 10 minutes at a strength of less than about 35 Torr immediately prior to in vivo injection. In one embodiment, the microparticles are stored at a temperature of between about 2-8° C. and the microparticles are vacuumed for 1 hour to 30 minutes at a strength of less than about 35 Torr immediately prior to in vivo injection. In one embodiment, the microparticles are stored at a temperature of between about 2-8° C. and the microparticles are vacuumed for 30 minutes to 10 minutes at a strength of less than about 35 Torr immediately prior to in vivo injection.

In one embodiment, the microparticles are stored at negative pressure for up to 1 week, 2 weeks, 3 weeks, 4 weeks, 1 month, 2 months, 3 months, 4 months, or more following the manufacture and isolation process. In one embodiment, the microparticles are stored for up to 1 week to up to 4 weeks at a negative pressure that is less than 700, 550, 500, 450, 400, 350, 300, 250, 200, 150, 100, 80, 60, 50, 40, 35, 32, or 30 Torr. In one embodiment, the microparticles are stored for up to 1 month to up to 2 months at a negative pressure that is less than 700, 550, 500, 450, 400, 350, 300, 250, 200, 150, 100, 80, 60, 50, 40, 35, 32, or 30 Torr. In one embodiment, the microparticles are stored for up to 3 months at a negative pressure that is less than 700, 550, 500, 450, 400, 350, 300, 250, 200, 150, 100, 80, 60, 50, 40, 35, 32, or 30 Torr.

III. Mildly Surface Treated Aggregating Microparticles and Methods

In one aspect, the improved microparticles and microparticle suspensions are made from mildly surface treated solid biodegradable microparticles that upon injection in vivo, aggregate to a larger particle (pellet) in a manner that reduces unwanted side effects of the smaller particles and are suitable for long term (for example, up to or at least three month, up to four month, up to five month, up to six months, up to seven months, up to eight months, up to nine months or longer) sustained delivery of a therapeutic agent. In one embodiment, the lightly surface treated solid biodegradable microparticles are suitable for ocular injection, at which point the particles aggregate to form a pellet and thus remains outside the visual axis as not to significantly impair vision. The particles can aggregate into one or several pellets. The size of the aggregate depends on the mass (weight) of the particles injected.

The mildly surface treated biodegradable microparticles provided herein are distinguished from "scaffold" microparticles, which are used for tissue regrowth via pores that cells or tissue material can occupy. In contrast, the present microparticles are designed to be solid materials of sufficiently low porosity so that they can aggregate to form a larger combined particle that erodes primarily by surface erosion for long-term controlled drug delivery.

The surface modified solid aggregating microparticles of the present invention are suitable, for example, for intravitreal injection, implant, periocular delivery, or delivery in vivo outside the eye.

The surface modified solid aggregating microparticles of the present invention are also suitable for systemic, parenteral, transmembrane, transdermal, buccal, subcutaneous, endosinusial, intra-abdominal, intra-articular, intracartilaginous, intracerebral, intracoronal, dental, intradiscal, intramuscular, intratumor, topical, or vaginal delivery in any manner useful for in vivo delivery.

In one embodiment, the invention is thus surface-modified solid aggregating microparticles that include at least one biodegradable polymer, wherein the surface-modified solid aggregating microparticles have a solid core, include a therapeutic agent, have a modified surface which has been treated under mild conditions at a temperature at or less than about 18° C. to remove surface surfactant or cause surface polymer to partially degrade, are sufficiently small to be injected in vivo, and aggregate in vivo to form at least one pellet of at least 500 µm in vivo in a manner that provides sustained drug delivery in vivo for at least one, two, three, four, five, six seven, eight, nine, ten, eleven, twelve months or more. The surface modified solid aggregating microparticles are suitable, for example, for an intravitreal injection, implant, including an ocular implant, periocular delivery or delivery in vivo outside of the eye. In certain embodiments, the therapeutic agent is a prodrug as described herein. In certain embodiments, microparticles have also been treated for enhanced wettability.

Alternatively, the surface treatment is conducted at a temperature at or less than about 10° C., 8° C. or 5° C.

The surface treatment can be carried out at any pH that achieves the desired purpose. Nonlimiting examples of the pH are between about 6 and about 8, 6.5 and about 7.5, about 1 and about 4; about 4 and about 6; and 6 and about 8. In one embodiment, the surface treatment can be conducted at a pH between about 8 and about 10. In one embodiment, the surface treatment can be conducted at a pH between about 10.0 and about 13.0. In one embodiment, the surface treatment can be conducted at a pH between about 10.0 and about 12.0. In one embodiment, the surface treatment can be conducted at a pH between about 12 and about 14. In one embodiment, the surface treatment can be conducted with an organic solvent. In one embodiment, the surface treatment can be conducted with ethanol. In other various embodiments, the surface treatment is carried out in a solvent selected from methanol, ethyl acetate and ethanol. Nonlimiting examples are ethanol with an aqueous organic base; ethanol and aqueous inorganic base; ethanol and sodium hydroxide; ethanol and potassium hydroxide; an aqueous acidic solution in ethanol; aqueous hydrochloric acid in ethanol; and aqueous potassium chloride in ethanol.

Examples of solid cores included in the present invention include solid cores comprising a biodegradable polymer with less than 10 percent porosity, 8 percent porosity, 7 percent porosity, 6 percent porosity, 5 percent porosity, 4 percent porosity, 3 percent porosity, or 2 percent porosity. Porosity as used herein is defined by ratio of void space to total volume of the surface-modified solid aggregating microparticle.

The surface-modified solid aggregating microparticles of the present invention provides sustained delivery for at least one month, or at least two months, or at least three months, or at least four months, or at least five months, or at least six months, or at least seven months, or at least eight months, or at least nine months, or at least ten months, or at least eleven months, or at least twelve months.

The therapeutic agent delivered by the surface-modified solid aggregating microparticle is in one embodiment a pharmaceutical drug or a biologic. In nonlimiting examples, the pharmaceutical drugs include sunitinib, another tyrosine kinase inhibitor, an anti-inflammatory drug, an antibiotic, an immunosuppressing agent, an anti-VEGF agent, an anti-PDGF agent, or other therapeutic agents as described below. In one embodiment, the tyrosine kinase inhibitor is selected from Tivosinib, Imatinib, Gefitinib, Erlotinib, Lapatinib, Canertinib, Semaxinib, Vatalaninib, Sorafenib, Axitinib, Pazopanib, Dasatinib, Nilotinib, Crizotinib, Ruxolitinib, Vandetanib, Vemurafenib, Bosutinib, Cabozantinib, Regorafenib, Vismodegib, and Ponatinib.

In one embodiment the surface-modified solid aggregating microparticle has a mean diameter between 10 and 60 µm, 20 and 50 µm, 20 and 40 µm, 20 and 30 µm, 25 and 40 µm, or 25 and 35 µm.

Further, the surface-modified solid aggregating microparticles of the disclosed invention can aggregate to produce at least one pellet when administered in vivo that has a diameter of at least about 300 µm, 400 µm, 500 µm, 600 µm, 700 µm, 1 µm, 1.5 mm, 2 mm, 3 mm, 4 mm, or 5 mm.

In one embodiment, the surface-modified solid aggregating microparticles of the present invention produces a pellet in vivo that releases the therapeutic agent without a burst of more than about 10 percent or 15 percent of the total payload of the therapeutic agent over a one week, or a five, four, three, two day or one day period.

In some embodiments, the long-term controlled drug delivery is accomplished by a combination of surface erosion of an aggregated microparticle over several months (for example, one, two, three, or four months or more) followed by erosion of remaining parts of the aggregated microparticle, followed by slow release of active material from in vivo proteins to which it has bound over the period of long term release from the aggregated particle. In another embodiment, the microparticle degrades substantially by surface erosion over a period of at least about one, two, three, four, five or six months or more.

In another embodiment, the surface-modified solid aggregating microparticles of the present invention have a drug loading of 1-40 percent, 5-25 percent, or 5-15 percent weight/weight.

Examples of polymeric compositions included in surface-modified solid aggregating microparticles of the present invention include, but are not limited to: poly(lactide co-glycolide); poly(lactide-co-glycolide) covalently linked to polyethylene glycol; more than one biodegradable polymer or copolymer mixed together, for example, a mixture of poly(lactide-co-glycolide) and poly(lactide-co-glycolide) covalently linked to polyethylene glycol, a mixture of poly(lactic acid) and poly(lactide-co-glycolide) covalently linked to polyethylene glycol, or a mixture of poly(lactic acid), poly(lactide-co-glycolide) and poly(lactide-co-glycolide) covalently linked to polyethylene glycol; poly(lactic acid); a surfactant, such as polyvinyl alcohol (which can be hydrolyzed polyvinyl acetate).

In another embodiment, the invention is an injectable material that includes the microparticles of the present invention in a pharmaceutically acceptable carrier for administration in vivo. The injectable material may include a compound that inhibits aggregation of microparticles prior to injection and/or a viscosity enhancer and/or a salt. In one embodiment, the injectable material has a range of concentration of the surface-modified solid aggregating microparticles of about 50-700 mg/ml, 500 or less mg/ml, 400 or less mg/ml, 300 or less mg/ml, 200 or less mg/ml, or 150 or less mg/ml.

The present invention further includes a process for the preparation of surface-modified solid aggregating microparticles that includes (i) a first step of preparing microparticles comprising one or more biodegradable polymers by dissolving or dispersing the polymer(s) and a therapeutic agent in one or more solvents to form a polymer and therapeutic agent solution or dispersion, mixing the polymer and the therapeutic agent solution or dispersion with an aqueous phase containing a surfactant to produce microparticles that contain the therapeutic agent, polymer and surfactant; and (ii) a second step of mildly surface-only treating the microparticles of step (i) at a temperature at or below about 18° C. for optionally up to about 140, 120, 110, 100, 90, 80, 70, 60, 50, 40, 30, 10, 8, 5, 4, 3, 2, or 1 minutes with an agent that removes surface surfactant, surface polymers, or surface oligomers in a manner that does not significantly produce internal pores; and (iii) isolating the surface treated microparticles.

In one embodiment, the process for the preparation of surface-treated solid aggregating microparticles includes a fourth step for improving the aggregation potential of the particles by subjecting the particles to at least one process selected from 1) vacuum treatment, wherein the microparticles are suspended in a diluent and the suspension is placed under vacuum prior to use; 2) excipient addition, wherein an excipient is added prior to lyophilization; and 3) sonication, wherein the microparticles are suspended in a diluent and sonicated; 4) sealing the vial containing the dry powder of particles under vacuum, including but not limited to high vacuum; or 5) pre-wetting (i.e., resuspending) the surface-treated microparticles in a diluent for 2-24 hours before injecting into the eye, for example in a hyaluronic acid solution or other sterile solution suitable for ocular injection.

In certain embodiments step (ii) above is carried out at a temperature below 17° C., 15° C., 10° C., or 5° C. Further, step (iii) is optionally carried out at a temperature below 25° C., below 17° C., 15° C., 10° C., 8° C. or 5° C. Step (ii), for example, can be carried out for less than 8, less than 6, less than 4, less than 3, less than 2, or less than 1 minutes. In one embodiment, step (ii) is carried out for less than 60, 50, 40, 30, 20, or 10 minutes.

In one embodiment, the process of manufacturing surface-modified solid aggregating microparticles includes using an agent that removes surface surfactant. Nonlimiting examples include for example, those selected from: aqueous acid, phosphate buffered saline, water, aqueous NaOH, aqueous hydrochloric acid, aqueous potassium chloride, alcohol or ethanol.

In one embodiment, the process of manufacturing surface-modified solid aggregating microparticles includes using an agent that removes surface surfactant which comprises, for example, a solvent selected from an alcohol, for example, ethanol; ether, acetone, acetonitrile, DMSO, DMF, THF, dimethylacetamide, carbon disulfide, chloroform, 1,1-dichloroethane, dichloromethane, ethyl acetate, heptane, hexane, methanol, methyl acetate, methyl t-butyl ether (MTBE), pentane, propanol, 2-propanol, toluene, N-methyl pyrrolidinone (NMP), acetamide, piperazine, triethylenediamine, diols, and $CO_2$.

The agent that removes the surface surfactant can comprise a basic buffer solution. Further, the agent that removes surface surfactant can comprise a base selected from sodium hydroxide, lithium hydroxide, potassium hydroxide, calcium hydroxide, magnesium hydroxide, lithium amide, sodium amide, barium carbonate, barium hydroxide, barium hydroxide hydrate, calcium carbonate, cesium carbonate, cesium hydroxide, lithium carbonate, magnesium carbonate, potassium carbonate, sodium carbonate, strontium carbonate, ammonia, methylamine, ethylamine, propylamine, isopropylamine, dimethylamine, diethylamine, dipropylamine, diisopropylamine, trimethylamine, triethylamine, tripropylamine, triisopropylamine, aniline, methylaniline, dimethylaniline, pyridine, azajulolidine, benzylamine, methylbenzylamine, dimethylbenzylamine, DABCO, 1,5-diazabicyclo[4.3.0]non-5-ene, 1,8-diazabicyclo[5.4.0]non-7-ene, 2,6-lutidine, morpholine, piperidine, piperazine, Proton-sponge, 1,5,7-Triazabicyclo[4.4.0]dec-5-ene, tripelennamine, ammonium hydroxide, triethanolamine, ethanolamine, and Trizma.

In one embodiment, the process of manufacturing surface-modified solid aggregating microparticles includes using an agent that removes surface surfactant, for example, those selected from the following: aqueous acid, phosphate buffered saline, water, or NaOH in the presence of a solvent such as an alcohol, for example, ethanol, ether, acetone, acetonitrile, DMSO, DMF, THF, dimethylacetamide, carbon disulfide, chloroform, 1,1-dichloroethane, dichloromethane, ethyl acetate, heptane, hexane, methanol, methyl acetate, methyl t-butyl ether (MTBE), pentane, ethanol, propanol, 2-propanol, toluene, N-methyl pyrrolidinone (NMP), acetamide, piperazine, triethylenediamine, diols, and $CO_2$.

In one embodiment, the agent that removes the surface surfactant can comprise an aqueous acid. The agent that removes the surface surfactant can comprise an acid derived from inorganic acids including, but not limited to, hydrochloric, hydrobromic, sulfuric, sulfamic, phosphoric, nitric and the like; or organic acids including, but not limited to, acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like.

In one embodiment, the agent that removes surface surfactant is not a degrading agent of the biodegradable polymer under the conditions of the reaction. The hydrophilicity of the microparticles can be decreased by removing surfactant.

In one embodiment, the process of manufacturing surface-modified solid aggregating microparticles comprises using an agent that removes surface surfactant that comprises a solvent selected from an alcohol, for example, ethanol, ether, acetone, acetonitrile, DMSO, DMF, THF, dimethylacetamide, carbon disulfide, chloroform, 1,1-dichloroethane, dichloromethane, ethyl acetate, heptane, hexane, methanol, methyl acetate, methyl t-butyl ether (MTBE), pentane, ethanol, propanol, 2-propanol, toluene, N-methyl pyrrolidinone (NMP), acetamide, piperazine, triethylenediamine, diols, and $CO_2$. In a typical embodiment the process of surface treating, comprises an agent that removes surface surfactant that comprises ethanol.

The encapsulation efficiency of the process of manufacturing surface-modified solid aggregating microparticles depends on the microparticle forming conditions and the properties of the therapeutic agent. In certain embodiments, the encapsulation efficiency can be greater than about 50 percent, greater than about 75 percent, greater than about 80 percent, or greater than about 90 percent.

In one embodiment, the process of manufacturing surface-modified solid aggregating microparticles includes 5/95, 10/90, 15/85, 20/80, 25/75, 30/70, 35/65, 40/60, 45/55, 50/50, 55/45, 60/40, 65/35, 70/30, 75/25, 80/20, 85/15, 90/10, 95/5 PLGA as a biodegradable polymer. In one embodiment, the process of manufacturing surface-modified solid aggregating microparticles includes 50/50 PLGA as a biodegradable polymer.

In one embodiment, the process of manufacturing surface-modified solid aggregating microparticles includes PLA as a biodegradable polymer. In one embodiment, the process of manufacturing surface-modified solid aggregating microparticles includes PLA and PLGA as a biodegradable polymer. In one embodiment, the process of manufacturing surface-modified solid aggregating microparticles includes PLA and 75/25 PLGA as a biodegradable polymer. In one embodiment, the process of manufacturing surface-modified solid aggregating microparticles includes PLA and 50/50 PLGA as a biodegradable polymer. In one embodiment, the process of manufacturing surface-modified solid aggregating microparticles includes PLGA as a biodegradable polymer.

In one embodiment, the process of manufacturing surface-modified solid aggregating microparticles is carried out below about a pH of 14 and above a pH of 12, below a pH of 12 and above a pH of 10, below a pH of about 10 and above a pH of 8, below about a pH of 8 and above a pH of about 6, neutral pH, below about a pH of 7 and above a pH of 4, below about a pH of 4 and above a pH of about 1.0.

In one embodiment, step (ii) above is carried out for a time of about less than 140, 120, 110, 100, 90, 60, 40, 30, 20, 10, 3, 2, or 1 minutes.

In yet another embodiment, a method for the treatment of an ocular disorder is provided that includes administering to a host in need thereof surface-modified solid aggregating microparticles that include an effective amount of a therapeutic agent, wherein the therapeutic agent containing surface-modified solid aggregating microparticles are injected into the eye and in vivo aggregate to form at least one pellet of at least 500 µm that provides sustained drug delivery for at least one, two, or three, four, five, six, seven, eight, nine, ten, eleven, twelve or more months in such a manner that the pellet stays substantially outside the visual axis as not to significantly impair vision. In one embodiment, the therapeutic agent is a prodrug as described herein.

In an alternative embodiment, the weight percent of surface-modified solid aggregating microparticles that are not aggregated into a larger pellet in vivo is about 10 percent or less, 7 percent or less, 5 percent or less, or 2 percent or less by total weight administered.

In one embodiment, the surface-modified solid aggregating microparticles do not cause substantial inflammation in the eye.

In another embodiment, the surface-modified solid aggregating microparticles do not cause an immune response in the eye.

In one embodiment, the surface-modified microparticles of the present invention, as described herein, are used to treat a medical disorder which is glaucoma, a disorder mediated by carbonic anhydrase, a disorder or abnormality related to an increase in intraocular pressure (IOP), a disorder mediated by nitric oxide synthase (NOS), or a disorder requiring neuroprotection such as to regenerate/repair optic nerves. In another embodiment more generally, the disorder treated is allergic conjunctivitis, anterior uveitis, cataracts, dry or wet age-related macular degeneration (AMD), or diabetic retinopathy.

Another embodiment is provided that includes the administration of a surface treated microparticle comprising an effective amount of a pharmaceutically active compound or a pharmaceutically acceptable salt thereof, optionally in a pharmaceutically acceptable carrier, to a host to treat an ocular or other disorder that can benefit from topical or local delivery. The therapy can be delivered to the anterior or posterior chamber of the eye. In specific aspects, a surface treated microparticle comprising an effective amount of a pharmaceutically active compound is administered to treat a disorder of the cornea, conjunctiva, aqueous humor, iris, ciliary body, lens sclera, choroid, retinal pigment epithelium, neural retina, optic nerve, or vitreous humor.

Any of the compositions described can be administered to the eye as described further herein in any desired form of administration, including via intravitreal, intrastromal, intracameral, subtenon, sub-retinal, retrobulbar, peribulbar, suprachoroidal, subchoroidal, conjunctival, subconjunctival, episcleral, posterior juxtascleral, circumcorneal, tear duct injections, or through a mucus, mucin, or a mucosal barrier, in an immediate or controlled release fashion.

In one embodiment, the disclosure provides a beta-adrenergic antagonist for ocular therapy, which can be released from a surface treated microparticle while maintaining efficacy over an extended time such as up to at least 1, 2, 3, 4, 5, 6, 7, 8, 9, 10, 11, or 12 months.

In one embodiment, the disclosure provides a prostaglandin or a prodrug thereof for ocular therapy, which can be released from a surface treated microparticle while maintaining efficacy over an extended time such as up to at least 1, 2, 3, 4, 5, 6, 7, 8, 9, 10, 11, or 12 months.

In one embodiment, the disclosure provides an adrenergic agonist for ocular therapy, which can be released from a surface treated microparticle while maintaining efficacy over an extended time such as up to at least 1, 2, 3, 4, 5, 6, 7, 8, 9, 10, 11, or 12 months.

In one embodiment, the disclosure provides a carbonic anhydrase inhibitor for ocular therapy, which can be released from a surface treated microparticle while maintaining efficacy over an extended time such as up to at least 1, 2, 3, 4, 5, 6, 7, 8, 9, 10, 11, or 12 months.

In one embodiment, the disclosure provides a parasympathomimetic agent for ocular therapy, which can be released from a surface treated microparticle while maintaining efficacy over an extended time such as up to at least 1, 2, 3, 4, 5, 6, 7, 8, 9, 10, 11, or 12 months.

In one embodiment, the disclosure provides a dual anti-VEGF/anti-PDGF agent for ocular therapy, which can be released from a surface treated microparticle while maintaining efficacy over an extended time such as up to at least 1, 2, 3, 4, 5, 6, 7, 8, 9, 10, 11, or 12 months.

In one embodiment, the disclosure provides a loop diuretic for ocular therapy, which can be released from a surface treated microparticle while maintaining efficacy over an extended time such as up to at least 1, 2, 3, 4, 5, 6, 7, 8, 9, 10, 11, or 12 months.

In one embodiment, the disclosure provides a Rho kinase (ROCK) inhibitor for ocular therapy, which can be released from a surface treated microparticle while maintaining efficacy over an extended time such as up to at least 1, 2, 3, 4, 5, 6, 7, 8, 9, 10, 11, or 12 months.

In one embodiment, the disclosure provides a prodrug as described herein for ocular therapy, which can be released from a surface treated microparticle while maintaining efficacy over an extended time such as up to at least 1, 2, 3, 4, 5, 6, 7, 8, 9, 10, 11, or 12 months.

Methods of treating or preventing ocular disorders, including glaucoma, a disorder mediated by carbonic anhydrase, a disorder or abnormality related to an increase in intraocular pressure (IOP), a disorder mediated by nitric oxide synthase (NOS), a disorder requiring neuroprotection such as to regenerate/repair optic nerves, allergic conjunctivitis, anterior uveitis, cataracts, dry or wet age-related macular degeneration (AMD) or diabetic retinopathy are disclosed comprising administering a therapeutically effective amount of a surface treated microparticle comprising a pharmaceutically active compound to a host, including a human, in need of such treatment. In one embodiment, the host is a human.

In another embodiment, an effective amount of a surface treated microparticle comprising a pharmaceutically active compound is provided to decrease intraocular pressure (IOP) caused by glaucoma. In an alternative embodiment, the surface treated microparticle comprising a pharmaceutically active compound can be used to decrease intraocular pressure (IOP), regardless of whether it is associated with glaucoma.

In one embodiment, the disorder is associated with an increase in intraocular pressure (IOP) caused by potential or previously poor patient compliance to glaucoma treatment. In yet another embodiment, the disorder is associated with potential or poor neuroprotection through neuronal nitric oxide synthase (NOS). The surface treated microparticle comprising a pharmaceutically active compound provided herein may thus dampen or inhibit glaucoma in a host, by administration of an effective amount in a suitable manner to a host, typically a human, in need thereof.

Methods for the treatment of a disorder associated with glaucoma, increased intraocular pressure (IOP), optic nerve damage caused by either high intraocular pressure (IOP) or neuronal nitric oxide synthase (NOS) are provided that includes the administration of an effective amount of a surface treated microparticle comprising a pharmaceutically active compound are also disclosed.

In one aspect of the present invention, an effective amount of a pharmaceutically active compound as described herein is incorporated into a surface treated microparticle, e.g., for convenience of delivery and/or sustained release delivery. The use of materials in micrometer scale provides one the ability to modify fundamental physical properties such as solubility, diffusivity, and drug release characteristics. These micrometer scale agents may provide more effective and/or more convenient routes of administration, lower therapeutic toxicity, extend the product life cycle, and ultimately reduce healthcare costs. As therapeutic delivery systems, surface treated microparticles can allow targeted delivery and sustained release.

In another aspect of the present invention, the surface treated microparticle is coated with a surface agent. The present invention further comprises a method of producing surface treated microparticles comprising a pharmaceutically active compound. The present invention further comprises methods of using the surface treated microparticles comprising a pharmaceutically active compound to treat a patient.

In one embodiment, surface treated microparticles including a pharmaceutically active compound are obtained by forming an emulsion and using a bead column as described in, for example, U.S. Pat. No. 8,916,196.

In one embodiment, surface treated microparticles including a pharmaceutically active compound are obtained by using a vibrating mesh or microsieve.

In one embodiment, surface treated microparticles including a pharmaceutically active compound are obtained by using slurry sieving.

The processes of producing microspheres described herein are amenable to methods of manufacture that narrow the size distribution of the resultant particles. In one embodiment, the particles are manufactured by a method of spraying the material through a nozzle with acoustic excitation (vibrations) to produce uniform droplets. A carrier stream can also be utilized through the nozzle to allow further control of droplet size. Such methods are described in detail in: Berkland, C., K. Kim, et al. (2001). "Fabrication of PLG microspheres with precisely controlled and monodisperse size distributions." *J Control Release* 73(1): 59-74; Berkland, C., M. King, et al. (2002). "Precise control of PLG microsphere size provides enhanced control of drug release rate." *J Control Release* 82(1): 137-147; Berkland, C., E. Pollauf, et al. (2004). "Uniform double-walled polymer microspheres of controllable shell thickness." *J Control Release* 96(1): 101-111.

In another embodiment, microparticles of uniform size can be manufactured by methods that utilize microsieves of the desired size. The microsieves can either be used directly during production to influence the size of microparticles formed, or alternatively post production to purify the microparticles to a uniform size. The microsieves can either be mechanical (inorganic material) or biological in nature (organic material such as a membrane). One such method is described in detail in U.S. Pat. No. 8,100,348.

In one embodiment, the surface treated microparticles comprise a therapeutically active compound and have a particle size of 25<Dv50<40 µm, Dv90<45 µm.

In one embodiment, the surface treated microparticles comprise a therapeutically active compound and have a particle size of Dv10>10 µm.

In one embodiment, the surface treated microparticles comprise a therapeutically active compound and have only residual solvents that are pharmaceutically acceptable.

In one embodiment, the surface treated microparticles comprise a therapeutically active compound and afford a total release of greater than eighty percent by day 14.

In one embodiment, the surface treated microparticles comprise a therapeutically active agent and have syringeability with a regular-walled 26-, 27-, 28-, 29- or 30-gauge needle of 200 mg/ml with no clogging of the syringe.

In one embodiment, the surface treated microparticles comprise a therapeutically active agent and have syringeability with a thin-walled 26-, 27-, 28-, 29- or 30-gauge needle of 200 mg/ml with no clogging of the syringe.

In one embodiment, the surface treated microparticles comprises sunitinib have a particle size of 25<Dv50<40 µm, Dv90<45 µm.

In one embodiment, the surface treated microparticles comprising sunitinib have a particle size of Dv10>10 µm.

In one embodiment, the surface treated microparticles comprising sunitinib have only residual solvents that are pharmaceutically acceptable.

In one embodiment, the surface treated microparticles comprising sunitinib afford a total release of greater than eighty percent by day 14.

In one embodiment, the surface treated microparticles comprising sunitinib have syringeability with a regular-walled 26-, 27-, 28-, 29- or 30-gauge needle of 200 mg/ml with no clogging of the syringe.

In one embodiment, the surface treated microparticles comprising sunitinib have syringeability with a thin-walled 26-, 27-, 28-, 29- or 30-gauge needle of 200 mg/ml with no clogging of the syringe.

In one embodiment, the surface treated microparticles comprising sunitinib have an endotoxin level of less than 0.02 EU/mg.

In one embodiment, the surface treated microparticles comprising sunitinib have a bioburden level of less than 10 CFU/g.

Biodegradable Polymers

The surface treated microparticles can include one or more biodegradable polymers or copolymers. The polymers should be biocompatible in that they can be administered to a patient without an unacceptable adverse effect. Biodegradable polymers are well known to those in the art and are the subject of extensive literature and patents. The biodegradable polymer or combination of polymers can be selected to provide the target characteristics of the microparticles, including the appropriate mix of hydrophobic and hydrophilic qualities, half-life and degradation kinetics in vivo, compatibility with the therapeutic agent to be delivered, appropriate behavior at the site of injection, etc.

For example, it should be understood by one skilled in the art that by manufacturing a microparticle from multiple polymers with varied ratios of hydrophobic, hydrophilic, and biodegradable characteristics that the properties of the microparticle can be designed for the target use. As an illustration, a microparticle manufactured with 90 percent PLGA and 10 percent PEG is more hydrophilic than a microparticle manufactured with 95 percent PLGA and 5 percent PEG. Further, a microparticle manufactured with a higher content of a less biodegradable polymer will in general degrade more slowly. This flexibility allows microparticles of the present invention to be tailored to the desired level of solubility, rate of release of pharmaceutical agent, and rate of degradation.

In certain embodiments, the microparticle includes a poly($\alpha$-hydroxyacid). Examples of poly($\alpha$-hydroxyacids) include poly lactic acid (PLA), polyglycolic acid (PGA), poly(D,L-lactide-co-glycolide)(PLGA), and poly D,L-lactic acid (PDLLA). polyesters, poly ($\epsilon$-caprolactone), poly (3-hydroxy-butyrate), poly (s-caproic acid), poly (p-dioxanone), poly (propylene fumarate), poly (ortho esters), polyol/diketene acetals, polyanhydrides, poly (sebacic anhydride) (PSA), poly (carboxybis-carboxyphenoxyphosphazene) (PCPP), poly [bis (p-carboxyphenoxy) methane] (PCPM), copolymers of SA, CPP and CPM (as described in Tamat and Langer in *Journal of Biomaterials Science Polymer* Edition, 3, 315-353, 1992 and by Domb in Chapter 8 of *The Handbook of Biodegradable Polymers*, Editors Domb A J and Wiseman R M, Harwood Academic Publishers), and poly (amino acids).

In one embodiment, the microparticle includes about at least 90 percent hydrophobic polymer and about not more than 10 percent hydrophilic polymer. Examples of hydrophobic polymers include polyesters such as poly lactic acid (PLA), polyglycolic acid (PGA), poly(D,L-lactide-co-glycolide)(PLGA), and poly D,L-lactic acid (PDLLA); polycaprolactone; polyanhydrides, such as polysebacic anhydride, poly(maleic anhydride); and copolymers thereof. Examples of hydrophilic polymers include poly(alkylene glycols) such as polyethylene glycol (PEG), polyethylene oxide (PEO), and poly(ethylene glycol) amine; polysaccharides; poly(vinyl alcohol) (PVA); polypyrrolidone; polyacrylamide (PAM); polyethylenimine (PEI); poly(acrylic acid); poly(vinylpyrolidone) (PVP); or a copolymer thereof.

In one embodiment, the microparticle includes about at least 85 percent hydrophobic polymer and at most 15 percent hydrophilic polymer.

In one embodiment, the microparticle includes about at least 80 percent hydrophobic polymer and at most 20 percent hydrophilic polymer.

In one embodiment, the microparticle includes PLA. In one embodiment, the PLA is acid-capped. In one embodiment, the PLA is ester-capped.

In one embodiment, the microparticle includes PLA and PLGA-PEG.

In one embodiment, the microparticle includes PLA and PLGA-PEG and PVA.

In one embodiment, the microparticle includes PLA, PLGA, and PLGA-PEG.

In one embodiment, the microparticle includes PLA, PLGA, and PLGA-PEG and PVA.

In one embodiment, the microparticle includes PLGA.

In one embodiment, the microparticle includes a copolymer of PLGA and PEG.

In one embodiment, the microparticle includes a copolymer of PLA and PEG.

In one embodiment, the microparticle comprises PLGA and PLGA-PEG, and combinations thereof.

In one embodiment, the microparticle comprises PLA and PLA-PEG.

In one embodiment, the microparticle includes PVA.

In one embodiment, the microparticles include PLGA, PLGA-PEG, PVA, or combinations thereof.

In one embodiment, the microparticles include the biocompatible polymers PLA, PLA-PEG, PVA, or combinations thereof.

In one embodiment, the microparticles have a mean size of about 20 μm to about 50 μm, m to about 45 μm, 25 μm to about 30 μm and a median size of about 29 μm to about 31 μm before surface treatment.

In one embodiment, the microparticles after surface treatment have about the same mean size and median size. In another embodiment, the microparticles after surface treatment have a mean size which is larger than the median size. In another embodiment, the microparticles after surface treatment have a mean size which is smaller than the median size.

In one embodiment, the microparticles have a mean size of about 20 μm to about 50 μm, m to about 45 rpm, 25 μm to about 30 μm, or 30 to 33 μm and a median size of about 31 μm to about 33 μm after surface treatment with approximately 0.0075 M NaOH/ethanol to 0.75 M NaOH/ethanol (30:70, v:v).

In one embodiment, the microparticles have a mean size of about 20 μm to about 50 μm, m to about 45 μm, 25 μm to about 30 μm or 30 to 33 μm and a median size of about 31 μm to about 33 μm after surface treatment with approximately 0.75 M NaOH/ethanol to 2.5 M NaOH/ethanol (30:70, v:v).

In one embodiment, the microparticles have a mean size of about 20 μm to about 50 μm, about 25 μm to about 45 μm, about 25 μm to about 30 μm or 30 to 33 μm and a median size of about 31 μm to about 33 μm after surface treatment with approximately 0.0075 M HCl/ethanol to 0.75 M NaOH/ethanol (30:70, v:v).

In one embodiment, the microparticles have a mean size of about 20 μm to about 50 μm, about 25 μm to about 45 μm, about 25 µm to about 30 µm or 30 to 33 µm and a median size of about 31 µm to about 33 µm after surface treatment with approximately 0.75 M NaOH/ethanol to 2.5 M HCl/ethanol (30:70, v:v).

In one embodiment, a surface-modified solid aggregating microparticle is manufactured using a wet microparticle.

In one embodiment, the surface-modified solid aggregating microparticle can release a therapeutic agent over a longer period of time when compared to a non-surface treated microparticle.

In one embodiment, a surface-modified solid aggregating microparticle contains less surfactant than a microparticle prior to the surface modification.

In one embodiment, a surface-modified solid aggregating microparticle is more hydrophobic than a microparticle prior to the surface modification.

In one embodiment, a surface-modified solid aggregating microparticle is less inflammatory than a non-surface treated microparticle.

In one embodiment, the agent that removes the surface surfactant of a surface-modified solid aggregating microparticle comprises a solvent that partially dissolves or swells the surface-modified solid aggregating microparticle.

In one aspect of the present invention, an effective amount of a pharmaceutically active compound as described herein is incorporated into a surface treated microparticle, e.g., for convenience of delivery and/or sustained release delivery. The use of materials provides the ability to modify fundamental physical properties such as solubility, diffusivity, and drug release characteristics. These micrometer scale agents may provide more effective and/or more convenient routes of administration, lower therapeutic toxicity, extend the product life cycle, and ultimately reduce healthcare costs. As therapeutic delivery systems, surface treated microparticles can allow targeted delivery and sustained release.

Surfactants

In one embodiment, the manufacture of the microparticle includes a surfactant. Examples of surfactants include, for example, polyoxyethylene glycol, polyoxypropylene glycol, decyl glucoside, lauryl glucoside, octyl glucoside, polyoxyethylene glycol octylphenol, Triton X-100, glycerol alkyl ester, glyceryl laurate, cocamide MEA, cocamide DEA, dodecyldimethylamine oxide, and poloxamers. Examples of poloxamers include, poloxamers 188, 237, 338 and 407. These poloxamers are available under the trade name Pluronic® (available from BASF, Mount Olive, N.J.) and correspond to Pluronic® F-68, F-87, F-108 and F-127, respectively. Poloxamer 188 (corresponding to Pluronic® F-68) is a block copolymer with an average molecular mass of about 7,000 to about 10,000 Da, or about 8,000 to about 9,000 Da, or about 8,400 Da. Poloxamer 237 (corresponding to Pluronic® F-87) is a block copolymer with an average molecular mass of about 6,000 to about 9,000 Da, or about 6,500 to about 8,000 Da, or about 7,700 Da. Poloxamer 338 (corresponding to Pluronic® F-108) is a block copolymer with an average molecular mass of about 12,000 to about 18,000 Da, or about 13,000 to about 15,000 Da, or about 14,600 Da. Poloxamer 407 (corresponding to Pluronic® F-127) is a polyoxyethylene-polyoxypropylene triblock copolymer in a ratio of between about E101 P56 E101 to about E106 P70 E106, or about E101 P56E101, or about E106 P70 E106, with an average molecular mass of about 10,000 to about 15,000 Da, or about 12,000 to about 14,000 Da, or about 12,000 to about 13,000 Da, or about 12,600 Da.

Additional examples of surfactants that can be used in the invention include, but are not limited to, polyvinyl alcohol (which can be hydrolyzed polyvinyl acetate), polyvinyl acetate, Vitamin E-TPGS, poloxamers, cholic acid sodium salt, dioctyl sulfosuccinate sodium, hexadecyltrimethyl ammonium bromide, saponin, TWEEN® 20, TWEEN® 80, sugar esters, Triton X series, L-a-phosphatidylcholine (PC), 1,2-dipalmitoylphosphatidylcholine (DPPC), oleic acid, sorbitan trioleate, sorbitan mono-oleate, sorbitan monolaurate, polyoxyethylene (20) sorbitan monolaurate, polyoxyethylene (20) sorbitan monooleate, natural lecithin, oleyl polyoxyethylene (2) ether, stearyl polyoxyethylene (2) ether, lauryl polyoxyethylene (4) ether, block copolymers of oxyethylene and oxypropylene, synthetic lecithin, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, cetylpyridinium chloride, benzalkonium chloride, olive oil, glyceryl monolaurate, corn oil, cotton seed oil, sunflower seed oil, lecithin, oleic acid, and sorbitan trioleate.

It should be recognized by one skilled in the art that some surfactants can be used as polymers in the manufacture of the microparticle. It should also be recognized by one skilled in the art that in some manufacture the microparticle may retain a small amount of surfactant which allows further modification of properties as desired.

IV. Biodegradable Polymeric-Containing Microparticles

In certain aspects, solid aggregating microparticles are provided that include a poly(α-hydroxyacid) biodegradable polymer, for example poly-lactic acid (PLA) biodegradable polymer, and a hydrophobic polymer covalently bound to a hydrophilic polymer, for example PLGA-PEG biodegradable polymer, wherein the solid aggregating microparticles have a solid core, include a therapeutic agent, are sufficiently small to be injected in vivo, and are capable of aggregating in vivo. In one embodiment, the microparticles aggregate in vivo to form at least one pellet of at least 500 µm in vivo to provide sustained drug delivery in vivo for at least one month, two months, three months, four months, five months, six months, seven months, eight months, nine months, or more. In one embodiment, the microparticles are about 10 µm to about 50 µm, from about 20 µm to about 45 µm, from about 25 µm to about 35 µm.

It has been discovered that the inclusion of PLA in certain microparticle formulations allows for the achievement of long-term slow substantially surface erosion for example, 9 months, 10 months, 11 months, 12 months or greater. In some embodiments, nearly zero-order or linear release drug delivery in vivo, can be achieved.

As contemplated herein, PLA for use in the present invention can include any known variant, for example, but not limited to, PLLA (Poly-L-lactic Acid), racemic PLLA (Poly-L-lactic Acid), PDLA (Poly-D-lactic Acid), and PDLLA (Poly-DL-lactic Acid), or a mixture thereof. In one embodiment, the PLA is Poly-L-lactic Acid. The PLA can be ester end-capped or acid end-capped.

In one embodiment, the PLA comprises at least about 40%, 45%, 50%, 55%, 60%, 65%, 70%, 75%, 80%, 85%, 90%, 95%, 96%, 97%, 98%, 99%, 99.5%, or 99.9% of the microparticle. In one embodiment, the PLA has a molecular weight between about 30 and 60 kD, about 35 and 55 kD, or about 40 and 50 kD. The microparticle further includes a hydrophobic polymer covalently bound to a hydrophilic biodegradable polymer. Hydrophobic degradable polymers are known in the art, and include, but are not limited to, polyglycolic acid (PGA), poly(D,L-lactide-co-glycolide) (PLGA), and poly D,L-lactic acid (PDLLA); polycaprolactone; polyanhydrides, such as polysebacic anhydride, poly (maleic anhydride); and copolymers thereof. Hydrophilic polymers are known in the art and include, for example poly(alkylene glycols) such as polyethylene glycol (PEG), polyethylene oxide (PEO), and poly(ethylene glycol) amine; polysaccharides; poly(vinyl alcohol) (PVA); polypyrrolidone; polyacrylamide (PAM); polyethylenimine (PEI); poly (acrylic acid); poly(vinylpyrolidone) (PVP); or a copolymer thereof. Hydrophobic polymers covalently bound to hydrophilic polymers include, for example, PLGA-PEG, PLA-PEG, PCL-PEG in an amount from about 0.5 percent to about 10 percent, about 0.5 percent to about 5 percent, about 0.5 percent to about 4 percent, about 0.5 percent to about 3 percent, or about 0.1 percent to about 1, 2, 5, or 10 percent. In one embodiment, the hydrophobic polymer covalently bound to the hydrophilic polymer is PLGA-PEG.

In one embodiment, the ratio of PLA/hydrophobic polymer covalently bound to a hydrophilic polymer in the microparticle is between about 40/1 to about 120/1. In one embodiment, the ratio of PLA/hydrophobic polymer covalently bound to hydrophilic polymer in the microparticle is about 45/1, 50/1, 55/1, 60/1, 65/1, 70/1, 75/1, 80/1, 85/1, 90/1, 95/1, 96/1, 97/1, 98/1, 99/1, 99.5/1, 99.9/1, 100/1, 101/1, 102/1, 103/1, 104/1, 105/1, or greater than 105/1. In one embodiment, the hydrophobic polymer covalently bound to a hydrophilic polymer is PLGA-PEG.

In one embodiment, the PLA/hydrophobic polymer covalently bound to hydrophilic polymer microparticle further comprises an additional hydrophobic biodegradable polymer, for example polyglycolic acid (PGA), poly(D,L-lactide-co-glycolide)(PLGA), and poly D,L-lactic acid (PDLLA); polycaprolactone; polyanhydrides, such as polysebacic anhydride, poly(maleic anhydride); and copolymers thereof. In one embodiment, the additional hydrophobic biodegradable polymer comprises about 1%, 5%, 10%, 15%, 20%, 25%, 30%, 35%, 40%, 45%, 50%, or 55% of the microparticle. In one embodiment, the additional hydrophobic polymer is PLGA. In one embodiment, the ratio of lactide/glycolide in the PLGA is about 5/95, 10/90, 15/85, 20/80, 25/75, 30/70, 35/65, 40/60, 45/55, 50/50, 55/45, 60/40, 65/35, 70/30, 75/25, 80/20, 85/15, 90/10, or 95/5. The PLGA can be acid end-capped or ester end-capped. The PLA can be acid end-capped or ester end-capped.

In one embodiment, the microparticle contains PLA, PLGA, and PLGA-PEG. In one embodiment, the ratio of PLA/PLGA/PLGA-PEG in the microparticle is about 5/95/1, 10/90/1, 15/85/1, 20/80/1, 25/75/1, 30/70/1, 35/65/1, 40/60/1, 45/55/1, 40/60/1, 45/55/1, 50/50/1, 55/45/1, 60/40/1, 65/35/1, 70/30/1, 75/25/1, 80/20/1, 85/15/1, 90/10/1, 95/5/1, or 100/1/1. In one embodiment, PLA-PEG or PLC-PEG is substituted for PLGA-PEG.

In one embodiment, the microparticles comprise PLA/PLGA45k-PEG5k. The PLA can be ester or acid end-capped. In one embodiment, the PLA is acid end-capped. In one embodiment, the microparticles comprise PLA/PLGA45k-PEG5k in a ratio of between about 100/1 to 80/20, about 100/1, 95/5, 90/10, 85/15, or 80/20. In one embodiment, the microparticles comprise PLA/PLGA7525/PLGA45k-PEG5k in a ratio of between about 99/1/1 to 1/99/1, about 99/1/1, 95/5/1, 90/10/1, 85/15/1, 80/20/1, 75/25/1, 70/30/1, 65/35/1, 60/40/1, 55/45/1, 50/50/1, 45/55/1, 40/60/1, 35/65/1, 30/70/1, 25/75/1, 20/80/1, 15/85/1, 10/90/1, 5/95/1, or 1/99/1. The PLGA7525 and PLA can be acid or ester end capped. In one embodiment, both the PLGA7525 and PLA are acid end-capped. In one embodiment, the microparticles comprise PLA/PLGA5050/PLGA45k-PEG5k. In one embodiment, the microparticles comprise PLA/PLGA5050/PLGA45k-PEG5k in a ratio of about 99/1/1, 95/5/1, 90/10/1, 85/15/1, 80/20/1, 75/25/1, 70/30/1, 65/35/1, 60/40/1, 55/45/1, 50/50/1, 45/55/1, 40/60/1, 35/65/1, 30/70/1, 25/75/1, 20/80/1, 15/85/1, 10/90/1, 5/95/1, or 1/99/1. The PLA and PLGA5050 can be acid or ester end-capped. In one embodiment, both the PLA and PLGA are acid end-capped.

In one embodiment, the PLA microparticles described herein is surface modified. In one embodiment, the microparticles have a modified surface which has been treated under mild conditions at a temperature at or less than about 18° C. to remove surface surfactant or cause surface polymer to partially degrade. The solid aggregating microparticles are suitable, for example, for an intravitreal injection, implant, including an ocular implant, periocular delivery, or delivery in vivo outside of the eye.

In one embodiment, the aggregate formed in vivo is a blend or mix of microparticles, wherein at least one of the microparticles includes a poly-lactic acid (PLA) biodegradable polymer and a hydrophobic biodegradable polymer covalently linked to a hydrophilic polymer, for example PLGA-PEG biodegradable polymer. In one embodiment, the mix or blend includes one or more microparticles comprised of a non-PLA polymer. In one embodiment, the mix or blend includes PLA/PLGA-PEG microparticles and PLGA/PLGA-PEG microparticles. In one embodiment, the mix or blend comprises a ratio of PLA/PLGA-PEG to PLGA/PLGA-PEG of about 1/99, 5/95, 10/90, 15/85, 20/80, 25/75, 30/70, 35/65, 40/60, 45/55, 50/50, 55/45, 60/40, 65/35, 70/30, 75/25, 80/20, 85/15, 90/10, 95/5, or 99/1. In one embodiment, the ratio of lactide/glycolide in the PLGA or PLGA-PEG is about 5/95, 10/90, 15/85, 20/80, 25/75, 30/70, 35/65, 40/60, 45/55, 50/50, 55/45, 60/40, 65/35, 70/30, 75/25, 80/20, 85/15, 90/10, or 95/5. The PLGA can be acid end capped or ester end capped. In one embodiment, the PLGA is a block co-polymer, for example, diblock, triblock, multiblock, or star-shaped block. In one embodiment, the PLGA is a random co-polymer.

In one embodiment, the mix or blend includes PLA/PLGA-PEG microparticles and PLA/PLGA/PLGA-PEG microparticles. In one embodiment, the mix or blend comprises a ratio of PLA/PLGA-PEG to PLA/PLGA/PLGA-PEG of about 1/99, 5/95, 10/90, 15/85, 20/80, 25/75, 30/70, 35/65, 40/60, 45/55, 50/50, 55/45, 60/40, 65/35, 70/30, 75/25, 80/20, 85/15, 90/10, 95/5, or 99/1. In one embodiment, the ratio of lactide/glycolide in the PLGA or PLGA-PEG is about 5/95, 10/90, 15/85, 20/80, 25/75, 30/70, 35/65, 40/60, 45/55, 50/50, 55/45, 60/40, 65/35, 70/30, 75/25, 80/20, 85/15, 90/10, or 95/5. In one embodiment, the PLGA is in a lactide/glycolide ratio of 95/5, 90/10, 85/15, 80/20, 75/25, 70/30, 65/35, 60/40, 55/45, 50/50, 45/55, 40/60, 35/65, 30/70, 25/75, 20/80, 15/85, 10/90, 5/95. The PLGA can be acid end capped or ester end capped. In one embodiment, the PLGA is a block co-polymer, for example, diblock, triblock, multiblock, or star-shaped block. In one embodiment, the PLGA is a random co-polymer.

In one embodiment, the blend or mix of microparticles is comprised of a PLA/PLGA-PEG microparticle, wherein the PLA comprises from about 80% to 99.9% of the microparticle, and a PLGA/PLGA-PEG microparticle, wherein the PLGA comprises from about 80% to 99.9% of the microparticle. In one embodiment, the blend or mix of microparticles is comprised of a PLA/PLGA45k-PEG5k microparticle and a PLGA7525/PLGA45k-PEG5k microparticle in a ratio of from about 1/99 to about 99/1, about 1.99, 5/95, 10/90, 15/85, 20/80, 25/75, 30/70, 35/65, 40/60, 45/55, 50/50, 55/45, 60/40, 65/35, 70/30, 75/25, 80/20, 85/15, 90/10, 95/5, or 99/1. In one embodiment, the ratio of PLA/PLGA45k-PEG5k microparticle to PLGA7525/PLGA45k-PEG5k microparticles is between about 20/80 to 40/60, about 20/80, 25/75, 30/70, 35/65, or 40/60. The PLA and PLGA can be ester or acid end capped. In one embodiment, the blend or mix of microparticles is comprised of a PLA 4A/PLGA45k-PEG5k microparticle and a PLGA7525 4A/PLGA45k-PEG5k microparticle in a ratio of from about 1/99 to about 99/1, about 1.99, 5/95, 10/90, 15/85, 20/80, 25/75, 30/70, 35/65, 40/60, 45/55, 50/50, 55/45, 60/40, 65/35, 70/30, 75/25, 80/20, 85/15, 90/10, 95/5, or 99/1. In one embodiment, the ratio of PLA 4A/PLGA45k-PEG5k microparticle to PLGA7525 4A/PLGA45k-PEG5k microparticles is between about 20/80 to 40/60, about 20/80, 25/75, 30/70, 35/65, or 40/60.

In one embodiment, the blend or mix of microparticles is comprised of a PLA/PLGA45k-PEG5k microparticle and a PLGA5050/PLGA45k-PEG5k microparticle in a ratio of from about 1/99 to about 99/1, about 1.99, 5/95, 10/90, 15/85, 20/80, 25/75, 30/70, 35/65, 40/60, 45/55, 50/50, 55/45, 60/40, 65/35, 70/30, 75/25, 80/20, 85/15, 90/10, 95/5, or 99/1. In one embodiment, the ratio of PLA/PLGA45k-PEG5k microparticle to PLGA5050/PLGA45k-PEG5k microparticles is between about 20/80 to 40/60, about 20/80, 25/75, 30/70, 35/65, or 40/60. The PLA and PLGA can be ester or acid end capped. In one embodiment, the blend or mix of microparticles is comprised of a PLA 4A/PLGA45k-PEG5k microparticle and a PLGA5050 4A/PLGA45k-PEG5k microparticle in a ratio of from about 1/99 to about 99/1, about 1.99, 5/95, 10/90, 15/85, 20/80, 25/75, 30/70, 35/65, 40/60, 45/55, 50/50, 55/45, 60/40, 65/35, 70/30, 75/25, 80/20, 85/15, 90/10, 95/5, or 99/1. In one embodiment, the ratio of PLA 4A/PLGA45k-PEG5k microparticle to PLGA5050 4A/PLGA45k-PEG5k microparticles is between about 20/80 to 40/60, about 20/80, 25/75, 30/70, 35/65, or 40/60.

In one embodiment, the blend or mix of microparticles is comprised of a PLA/PLGA/PLGA-PEG microparticle and a PLGA/PLGA-PEG microparticle, In one embodiment, the blend or mix of microparticles is comprised of a PLA/PLGA/PLGA45k-PEG5k microparticle and a PLGA/PLGA45k-PEG5k microparticle in a ratio of from about 1/99 to about 99/1, about 1.99, 5/95, 10/90, 15/85, 20/80, 25/75, 30/70, 35/65, 40/60, 45/55, 50/50, 55/45, 60/40, 65/35, 70/30, 75/25, 80/20, 85/15, 90/10, 95/5, or 99/1. In one embodiment, the blend or mix of microparticles is comprised of a PLA/PLGA7525/PLGA45k-PEG5k microparticle and a PLGA7525/PLGA45k-PEG5k microparticle in a ratio of from about 1/99 to about 99/1, about 1.99, 5/95, 10/90, 15/85, 20/80, 25/75, 30/70, 35/65, 40/60, 45/55, 50/50, 55/45, 60/40, 65/35, 70/30, 75/25, 80/20, 85/15, 90/10, 95/5, or 99/1. In one embodiment, the blend or mix of microparticles is comprised of a PLA/PLGA7525/PLGA45k-PEG5k microparticle and a PLGA5050/PLGA45k-PEG5k microparticle in a ratio of from about 1/99 to about 99/1, about 1.99, 5/95, 10/90, 15/85, 20/80, 25/75, 30/70, 35/65, 40/60, 45/55, 50/50, 55/45, 60/40, 65/35, 70/30, 75/25, 80/20, 85/15, 90/10, 95/5, or 99/1. In one embodiment, the blend or mix of microparticles is comprised of a PLA/PLGA5050/PLGA45k-PEG5k microparticle and a PLGA7525/PLGA45k-PEG5k microparticle in a ratio of from about 1/99 to about 99/1, about 1.99, 5/95, 10/90, 15/85, 20/80, 25/75, 30/70, 35/65, 40/60, 45/55, 50/50, 55/45, 60/40, 65/35, 70/30, 75/25, 80/20, 85/15, 90/10, 95/5, or 99/1. The PLA and PLGA can be acid end capped or ester end capped.

In one embodiment, the microparticle comprises a blend or mix of ratio of PLA4A/PLGA45k-PEG5k and PLGA7525 4A/PLGA45k-PEG5k. In one embodiment, the blend or mix of microparticles comprise a ratio of PLA 4A/PLGA45k-PEG5k microparticle to PLGA7525 4A/PLGA45k-PEG5k microparticles is between about 20/80 to 40/60, about 20/80, 25/75, 30/70, 35/65, or 40/60. In one embodiment, the blend or mix of microparticles is comprised of a PLA 4A/PLGA45k-PEG5k microparticle and a PLGA5050 4A/PLGA45k-PEG5k microparticle in a ratio of from about 1/99 to about 99/1, about 1.99, 5/95, 10/90, 15/85, 20/80, 25/75, 30/70, 35/65, 40/60, 45/55, 50/50, 55/45, 60/40, 65/35, 70/30, 75/25, 80/20, 85/15, 90/10, 95/5, or 99/1. In one embodiment, the ratio of PLA 4A/PLGA45k-PEG5k microparticle to PLGA5050 4A/PLGA45k-PEG5k microparticles is between about 20/80 to 50/50, about 20/80, 25/75, 30/70, 35/65, 40/60, or 50/50.

As contemplated herein, PLA, as utilized herein, can be replaced with a different poly($\alpha$-hydroxyacid) biodegradable polymer, for example, polyglycolic acid (PGA), poly (D,L-lactide-co-glycolide)(PLGA), and poly D,L-lactic acid (PDLLA). polyesters, poly ($\varepsilon$-caprolactone), poly (3-hydroxy-butyrate), poly (s-caproic acid), poly (p-dioxanone), poly (propylene fumarate), poly (ortho esters), polyol/diketene acetals, polyanhydrides, poly (sebacic anhydride) (PSA), poly (carboxybis-carboxyphenoxyphosphazene) (PCPP), poly [bis (p-carboxyphenoxy) methane](PCPM), copolymers of SA, CPP, CPM, and poly(amino acids).

Non-limiting embodiments of solid aggregating microparticles, injections, and suspensions include:

(I) A solid aggregating microparticle comprising surface surfactant and a prodrug disclosed herein encapsulated in at least one biodegradable polymer selected from PLA and PLGA and at least one hydrophobic polymer covalently bound to a hydrophillic polymer, wherein the microparticle has a mean diameter between 10 µm and 60 µm that:
   (i) has a solid core with less than 10% porosity by ratio of void space to total volume;
   (ii) has a modified surface which has been treated under mild conditions at a temperature less than about 18° C. to remove surface surfactant; and
   (iii) is capable of aggregating in vivo to form at least one pellet of at least 500 µm in vivo capable of sustained drug delivery in vivo for at least three months.

(II) A solid aggregating microparticle comprising surface surfactant and a tyrosine kinase inhibitor selected from Tivosinib, Imatinib, Gefitinib, Erlotinib, Lapatinib, Canertinib, Semaxinib, Vatalaninib, Sorafenib, Axitinib, Pazopanib, Dasatinib, Nilotinib, Crizotinib, Ruxolitinib, Vandetanib, Vemurafenib, Bosutinib, Cabozantinib, Regorafenib, Vismodegib, and Ponatinib encapsulated in at least one biodegradable polymer selected from PLA and PLGA and at least one hydrophobic polymer covalently bound to a hydrophillic polymer, wherein the microparticle has a mean diameter between 10 µm and 60 µm that:
   (i) has a solid core with less than 10% porosity by ratio of void space to total volume;
   (ii) has a modified surface which has been treated under mild conditions at a temperature less than about 18° C. to remove surface surfactant; and
   (iii) is capable of aggregating in vivo to form at least one pellet of at least 500 µm in vivo capable of sustained drug delivery in vivo for at least three months.

(III) A solid aggregating microparticle comprising surface surfactant and a loop diuretic selected from furosemide, bumetanide, piretanide, ethacrynic acid, etozolin, and ozolinone, encapsulated in at least one biodegradable polymer selected from PLA and PLGA and at least one hydrophobic polymer covalently bound to a hydrophillic polymer, wherein the microparticle has a mean diameter between 10 μm and 60 μm that:
  (i) has a solid core with less than 10% porosity by ratio of void space to total volume;
  (ii) has a modified surface which has been treated under mild conditions at a temperature less than about 18° C. to remove surface surfactant; and
  (iii) is capable of aggregating in vivo to form at least one pellet of at least 500 μm in vivo capable of sustained drug delivery in vivo for at least three months.

(IV) An injectable material that comprises the microparticles of (I), (II), or (III) in a pharmaceutically acceptable carrier for administration in vivo.

(V) A composition comprising a mixture or blend of solid aggregating microparticles wherein the microparticles are capable of aggregating in vivo to form at least one pellet of at least 500 μm in vivo capable of sustained drug delivery in vivo for at least four months wherein the composition comprises:
  (i) a first microparticle with a solid core comprising surface surfactant and a therapeutic agent encapsulated in PLA and PLGA-PEG; and
  (ii) a second microparticle with a solid core comprising surface surfactant and a therapeutic agent encapsulated in PLGA and PLGA-PEG; and (VI) A composition comprising a mixture or blend of solid aggregating microparticles wherein the microparticles are capable of aggregating in vivo to form at least one pellet of at least 500 μm in vivo capable of sustained drug delivery in vivo for at least four months wherein the composition comprises:
  (i) a first microparticle with a solid core comprising surface surfactant and a therapeutic agent encapsulated in PLA and PLGA-PEG; and
  (ii) a second microparticle with a solid core comprising surface surfactant and a therapeutic agent encapsulated in PLA/PLGA and PLGA-PEG.

(VII) A composition comprising a mixture or blend of solid aggregating microparticles wherein the microparticles are capable of aggregating in vivo to form at least one pellet of at least 500 μm in vivo capable of sustained drug delivery in vivo for at least four months wherein the composition comprises:
  (i) a first microparticle with a solid core comprising surface surfactant and a therapeutic agent encapsulated in PLGA and PLGA-PEG; and
  (ii) a second microparticle with a solid core comprising surface surfactant and a therapeutic agent encapsulated in PLA/PLGA and PLGA-PEG.

(VIII) An injectable material that comprises the composition of (V), (VI), or (VII) in a pharmaceutically acceptable carrier for administration in vivo.

Particular Embodiments Include:

The solid aggregating microparticles of (I), (II), or (III), suitable for a delivery route selected from the group consisting of intravitreal, intrastromal, intracameral, subtenon, sub-retinal, retrobulbar, peribulbar, suprachoroidal, subchoroidal, conjunctival, subconjunctival, episcleral, posterior juxtascleral, circumcorneal, and tear duct injections.

The solid aggregating microparticles of (I), (II), or (III), wherein the at least one pellet is capable of sustained delivery for at least four months, at least five months, at least six months, at least seven months, at least eight months, at least nine months, or at least ten months.

The solid aggregating microparticles of (I), (II), or (III), wherein the surface modification is carried out at a pH between about 14 and about 12.

The solid aggregating microparticles of (I), (II), or (III), wherein the surface modification is carried out at a pH between about 12 and about 10.

The solid aggregating microparticles of (I), (II), or (III), wherein the surface modification is carried out at a pH between about 10 and about 8.

The solid aggregating microparticles of (I), (II), or (III), wherein the surface modification is carried out at a pH between about 6.5 and about 7.5.

The solid aggregating microparticles of (I), (II), or (III), wherein the surface modification is carried out at a pH between about 1 and about 6.

The solid aggregating microparticles of (I), (II), or (III), wherein the surface modification is carried out at a temperature of less than about 16° C.

The solid aggregating microparticles of (I), (II), or (III), wherein the surface modification is carried out at a temperature of less than about 10° C.

The solid aggregating microparticles of (I), (II), or (III), wherein the surface modification is carried out at a temperature of less than about 8° C.

The solid aggregating microparticles of (I), (II), or (III), wherein the surface modification is carried out at a temperature of less than about 5° C.

The solid aggregating microparticles of (I), (II), or (III), wherein the surface modification is carried out at a temperature of less than about 2° C.

The solid aggregating microparticles of (I), (II), or (III), wherein the hydrophobic polymer covalently bound to a hydrophilic polymer is poly(D,L-lactide-co-glycolide) covalently bound to polyethylene glycol (PLGA-PEG).

The solid aggregating microparticles of (I), (II), or (III), wherein the microparticles comprise PLA and PLGA-PEG.

The solid aggregating microparticles of (I), (II), or (III), wherein the microparticles comprise PLA PLGA-PEG the ratio of PLA to PLGA-PEG is between about 99/1.

The solid aggregating microparticles of (I), (II), or (III), wherein the microparticles comprise PLGA PLGA-PEG.

The solid aggregating microparticles of (I), (II), or (III), wherein the microparticles comprise PLGA and PLGA-PEG the ratio of PLA to PLGA-PEG is between about 99/1.

The solid aggregating microparticles of (I), (II), or (III), wherein the microparticles comprise PLA/PLGA PLGA-PEG.

The solid aggregating microparticles of (I), (II), or (III), wherein the microparticles comprise PLA/PLGA PLGA-PEG and the ratio of PLA/PLGA/PLGA-PEG is about 5/95/1, 10/90/1, 15/85/1, 20/80/1, 25/75/1, 30/70/1, 35/65/1, 40/60/1, 45/55/1, 50/50/1, 55/45/1, 60/40/1, 65/35/1, 70/30/1, 75/25/1, 80/20/1, 85/15/1, 90/10/1, 95/5/1, or 100/1/1.

The solid aggregating microparticles of (I), (II), or (III), wherein the microparticles comprise PLA/PLGA PLGA-PEG and the ratio of PLA/PLGA/PLGA-PEG is about 95/5/1.

The solid aggregating microparticles of (I), (II), or (III), wherein the microparticles comprise PLA/PLGA PLGA-PEG and the ratio of PLA/PLGA/PLGA-PEG is about 90/10/1.

The solid aggregating microparticles of (I), (II), or (III), wherein the microparticles comprise PLA/PLGA PLGA-PEG and the ratio of PLA/PLGA/PLGA-PEG is about 70/30/1.

The solid aggregating microparticles of (I), (II), or (III), wherein the microparticles comprise (i) PLGA; (ii) PLGA wherein the PLGA in (ii) has a different ratio of lactide to glycolide than the PLGA in (i); and, PLGA-PEG.

The solid aggregating microparticles of (I), (II), or (III), wherein the microparticles comprise PLGA50:50, PLGA75:25, and PLGA-PEG.

The solid aggregating microparticles of (I), (II), or (III), wherein the microparticles comprise PLGA50:50, PLGA85:15, and PLGA-PEG.

The solid aggregating microparticles of (I), (II), or (III), wherein the microparticles comprise PLGA85:15, PLGA75:25, and PLGA-PEG.

The solid aggregating microparticles of (I), (II), or (III), wherein the PLA is ester end-capped.

The solid aggregating microparticles of (I), (II), or (III), wherein the PLA is acid end-capped.

The solid aggregating microparticles of (I), (II), or (III), wherein the microparticles have a mean diameter between about 20 and 30 μm.

The solid aggregating microparticles of (I), (II), or (III), wherein the microparticles have a mean diameter between about 20 and 50 μm.

The solid aggregating microparticles of (I), (II), or (III), wherein the microparticles have a mean diameter between about 25 and 35 μm.

The solid aggregating microparticles of (I), (II), or (III), wherein the microparticles have a mean diameter between about 20 and 40 μm.

The solid aggregating microparticles of (I), (II), or (III), wherein the microparticles have a mean diameter between about 25 and 40 μm.

The injectable material of (IV), wherein the injectable material comprises a compound that inhibits aggregation of the microparticles prior to injection.

The injectable material of (IV), wherein the injectable material comprises a sugar.

The injectable material of (IV), wherein the injectable material comprises mannitol, sucrose, trehalose, glucose, or lactose.

The injectable material of (IV), wherein the injectable material comprises a viscosity enhancer.

The injectable material of (IV), wherein the injectable material comprises hyaluronic acid.

The injectable material of (IV), wherein the injectable material comprises sodium hyaluronate.

The injectable material of (IV), wherein the injectable material has a range of concentration of the solid aggregating microparticles of about 100-600 mg/ml.

The injectable material of (IV), wherein the injectable material has a range of concentration of the solid aggregating microparticles of about 500 or less mg/ml.

The injectable material of (IV), wherein the injectable material has a range of concentration of the solid aggregating microparticles of about 300 or less mg/ml.

The injectable material of (IV), wherein the injectable material has a range of concentration of the solid aggregating microparticles of about 200 or less mg/ml.

The injectable material of (IV), wherein the injectable material has a range of concentration of the solid aggregating microparticles of about 150 or less mg/ml.

The composition of (V) or (VI), wherein the ratio of PLA to PLGA-PEG in the first microparticle is between about 105/1 to about 80/10.

The composition of (V) or (VI), wherein the ratio of PLA to PLGA-PEG in the first microparticle is between about 100/1.

The composition of (V), wherein the ratio of PLGA to PLGA-PEG in the second microparticle is between about 105/1 to about 80/10.

The composition of (V), wherein the ratio of PLGA to PLGA-PEG in the second microparticle is between about 100/1.

The composition of (V), (VI), or (VII), wherein the PLGA-PEG is PLGA45k-PEG5k.

The composition of (V), (VI), or (VII), wherein the ratio of first microparticles to second microparticles is between about 1/99 to 99/1.

The composition of (V), (VI), or (VII), wherein the ratio of first microparticles to second microparticles is about 99/1.

The composition of (V), (VI), or (VII), wherein the ratio of first microparticles to second microparticles is about 95/5.

The composition of (V), (VI), or (VII), wherein the ratio of first microparticles to second microparticles is about 90/10.

The composition of (V), (VI), or (VII), wherein the ratio of first microparticles to second microparticles is about 85/15.

The composition of (V), (VI), or (VII), wherein the ratio of first microparticles to second microparticles is about 80/20.

The composition of (V), (VI), or (VII), wherein the ratio of first microparticles to second microparticles is about 75/25.

The composition of (V), (VI), or (VII), wherein the ratio of first microparticles to second microparticles is about 70/30.

The composition of (V), (VI), or (VII), wherein the ratio of first microparticles to second microparticles is about 65/35.

The composition of (V), (VI), or (VII), wherein the ratio of first microparticles to second microparticles is about 60/40.

The composition of (V), (VI), or (VII), wherein the ratio of first microparticles to second microparticles is about 55/45.

The composition of (V), (VI), or (VII), wherein the ratio of first microparticles to second microparticles is about 50/50.

The composition of (V), (VI), or (VII), wherein the ratio of first microparticles to second microparticles is about 45/55.

The composition of (V), (VI), or (VII), wherein the ratio of first microparticles to second microparticles is about 40/60.

The composition of (V), (VI), or (VII), wherein the ratio of first microparticles to second microparticles is about 1/99.

The composition of (VI) or (VII), wherein the ratio of PLA/PLGA/PLGA-PEG in the second microparticle is 90/10/1.

The composition of (VI) or (VII), wherein the ratio of PLA/PLGA/PLGA-PEG in the second microparticle is 85/15/1.

The composition of (VI) or (VII), wherein the ratio of PLA/PLGA/PLGA-PEG in the second microparticle is 80/20/1.

The composition of (VI) or (VII), wherein the ratio of PLA/PLGA/PLGA-PEG in the second microparticle is 75/25/1.

The composition of (VI) or (VII), wherein the ratio of PLA/PLGA/PLGA-PEG in the second microparticle is 70/30/1.

The composition of (VI) or (VII), wherein the ratio of PLA/PLGA/PLGA-PEG in the second microparticle is 65/35/1.

The composition of (VI) or (VII), wherein the ratio of PLA/PLGA/PLGA-PEG in the second microparticle is 60/40/1.

The composition of (VI) or (VII), wherein the ratio of PLA/PLGA/PLGA-PEG in the second microparticle is 55/45/1.

The composition of (VI) or (VII), wherein the ratio of PLA/PLGA/PLGA-PEG in the second microparticle is 50/50/1.

The composition of (VI) or (VII), wherein the ratio of PLA/PLGA/PLGA-PEG in the second microparticle is 45/55/1.

The composition of (VI) or (VII), wherein the ratio of PLA/PLGA/PLGA-PEG in the second microparticle is 40/60/1.

The composition of (VI) or (VII), wherein the ratio of PLA/PLGA/PLGA-PEG in the second microparticle is 35/65/1.

The composition of (VI) or (VII), wherein the ratio of PLA/PLGA/PLGA-PEG in the second microparticle is 30/70/1.

The composition of (VI) or (VII), wherein the ratio of PLA/PLGA/PLGA-PEG in the second microparticle is 25/75/1.

The composition of (VI) or (VII), wherein the ratio of PLA/PLGA/PLGA-PEG in the second microparticle is 20/80/1.

The composition of (VI) or (VII), wherein the ratio of PLA/PLGA/PLGA-PEG in the second microparticle is 15/85/1.

The composition of (VI) or (VII), wherein the ratio of PLA/PLGA/PLGA-PEG in the second microparticle is 10/90/1.

The composition of (V), (VI) or (VII), wherein the PLGA is acid end-capped.

The composition of (V), (VI) or (VII), wherein the PLGA is ester end-capped.

The composition of (V), (VI) or (VII), wherein the PLA is acid end-capped.

The composition of (V), (VI) or (VII), wherein the PLA is ester end-capped.

The composition of (V), (VI) or (VII), wherein the microparticles are surface-modified.

The composition of (V), (VI) or (VII), wherein the therapeutic agent is a pharmaceutical drug.

The composition of (V), (VI) or (VII), wherein the therapeutic agent is an prodrug as described herein.

The composition of (V), (VI) or (VII), wherein the therapeutic agent is sunitinib or a pharmaceutically acceptable salt thereof.

The composition of (V), (VI) or (VII), wherein the therapeutic agent is sunitinib malate.

The composition of (V), (VI) or (VII), wherein the therapeutic agent is selected from Tivosinib, Imatinib, Gefitinib, and Erlotinib.

The composition of (V), (VI) or (VII), wherein the therapeutic agent is selected from Lapatinib, Canertinib, Semaxinib, and Vatalaninib, The composition of (V), (VI) or (VII), wherein the therapeutic agent is selected from Sorafenib, Axitinib, Pazopanib, and Dasatinib.

The composition of (V), (VI) or (VII), wherein the therapeutic agent is selected from Nilotinib, Crizotinib, Ruxolitinib, Vandetanib, and Vemurafenib.

The composition of (V), (VI) or (VII), wherein the therapeutic agent is selected from Bosutinib, Cabozantinib, Regorafenib, Vismodegib, and Ponatinib.

The composition of (V), (VI) or (VII), wherein the therapeutic agent is selected furosemide, bumetanide, piretanide, ethacrynic acid, etozolin, and ozolinone.

The composition of (V), (VI) or (VII), wherein the microparticles have a mean diameter between about 20 and 30 µm.

The composition of (V), (VI) or (VII), wherein the microparticles have a mean diameter between about 20 and 50 µm.

The composition of (V), (VI) or (VII), wherein the microparticles have a mean diameter between about 25 and 35 µm.

The composition of (V), (VI) or (VII), wherein the microparticles have a mean diameter between about 20 and 40 µm.

The composition of (V), (VI) or (VII), wherein the microparticles have a mean diameter between about 25 and 40 µm.

The injectable material of (VIII), wherein the injectable material comprises a compound that inhibits aggregation of the microparticles prior to injection.

The injectable material of (VIII), wherein the injectable material comprises a sugar.

The injectable material of (VIII), wherein the injectable material comprises mannitol, sucrose, trehalose, glucose, or lactose.

The injectable material of (VIII), wherein the injectable material comprises a viscosity enhancer.

The injectable material of (VIII), wherein the injectable material comprises hyaluronic acid.

The injectable material of (VIII), wherein the injectable material comprises sodium hyaluronate.

The injectable material of (VIII), wherein the injectable material has a range of concentration of the solid aggregating microparticles of about 100-600 mg/ml.

The injectable material of (VIII), wherein the injectable material has a range of concentration of the solid aggregating microparticles of about 500 or less mg/ml.

The injectable material of (VIII), wherein the injectable material has a range of concentration of the solid aggregating microparticles of about 300 or less mg/ml.

The injectable material of (VIII), wherein the injectable material has a range of concentration of the solid aggregating microparticles of about 200 or less mg/ml.

The injectable material of (VIII), wherein the injectable material has a range of concentration of the solid aggregating microparticles of about 150 or less mg/ml.

V. Examples of Disorders to be Treated

In one embodiment, the microparticles described herein and a pharmaceutically active compound encapsulated in the microparticle optionally in combination with a pharmaceutically acceptable carrier, excipient, or diluent are used for the treatment of a disorder, including a human disorder. In one embodiment, the composition is a pharmaceutical composition for treating an eye disorder or eye disease.

Non-limiting exemplary eye disorders or diseases treatable with the composition include age related macular degeneration, alkaline erosive keratoconjunctivitis, allergic conjunctivitis, allergic keratitis, anterior uveitis, Behcet's disease, blepharitis, blood-aqueous barrier disruption, choroiditis, chronic uveitis, conjunctivitis, contact lens-induced keratoconjunctivitis, corneal abrasion, corneal trauma, corneal ulcer, crystalline retinopathy, cystoid macular edema, dacryocystitis, diabetic keratopathy, diabetic macular edema, diabetic retinopathy, dry eye disease, dry age-related macular degeneration, eosinophilic granuloma, episcleritis, exudative macular edema, Fuchs' Dystrophy, giant cell arteritis, giant papillary conjunctivitis, glaucoma, glaucoma surgery failure, graft rejection, herpes zoster, inflammation after cataract surgery, iridocorneal endothelial syndrome, iritis, keratoconjunctivitis sicca, keratoconjunctivitis inflammatory disease, keratoconus, lattice dystrophy, map-dot-fingerprint dystrophy, necrotic keratitis, neovascular diseases involving the retina, uveal tract or cornea, for example, neovascular glaucoma, corneal neovascularization, neovascularization resulting following a combined vitrectomy and lensectomy, neovascularization of the optic nerve, and neovascularization due to penetration of the eye or contusive ocular injury, neuroparalytic keratitis, non-infectious uveitis ocular herpes, ocular lymphoma, ocular rosacea, ophthalmic infections, ophthalmic pemphigoid, optic neuritis, panuveitis, papillitis, pars planitis, persistent macular edema, phacoanaphylaxis, posterior uveitis, post-operative inflammation, proliferative diabetic retinopathy, proliferative sickle cell retinopathy, proliferative vitreoretinopathy, retinal artery occlusion, retinal detachment, retinal vein occlusion, retinitis pigmentosa, retinopathy of prematurity, rubeosis iritis, scleritis, Stevens-Johnson syndrome, sympathetic ophthalmia, temporal arteritis, thyroid associated ophthalmopathy, uveitis, vernal conjunctivitis, vitamin A insufficiency-induced keratomalacia, vitritis, and wet age-related macular degeneration.

VI. Therapeutically Active Agents to be Delivered

A wide variety of therapeutic agents can be delivered in a long term sustained manner in vivo using the present invention.

A "therapeutically effective amount" of a pharmaceutical composition/combination of this invention means an amount effective, when administered to a patient, to provide a therapeutic benefit such as an amelioration of symptoms of the selected disorder, typically an ocular disorder. In certain aspects, the disorder is glaucoma, a disorder mediated by carbonic anhydrase, a disorder or abnormality related to an increase in intraocular pressure (IOP), a disorder mediated by nitric oxide synthase (NOS), a disorder requiring neuroprotection such as to regenerate/repair optic nerves, allergic conjunctivitis, anterior uveitis, cataracts, dry or wet age-related macular degeneration (AMD), or diabetic retinopathy.

A "pharmaceutically acceptable salt" is formed when a therapeutically active compound is modified by making an inorganic or organic, non-toxic, acid or base addition salt thereof. Salts can be synthesized from a parent compound that contains a basic or acidic moiety by conventional chemical methods. Generally, such a salt can be prepared by reacting a free acid form of the compound with a stoichiometric amount of the appropriate base (such as Na, Ca, Mg, or K hydroxide, carbonate, bicarbonate, or the like), or by reacting a free base form of the compound with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC\text{---}(CH_2)_n\text{---}COOH$ where n is 0-4, and the like. Lists of additional suitable salts may be found, e.g., in *Remington's Pharmaceutical Sciences,* 17th ed., Mack Publishing Company, Easton, Pa., p. 1418 (1985).

In one embodiment, the microparticles of the present invention can comprise a compound for the treatment of glaucoma, for instance a beta-adrenergic antagonists, a prostaglandin analog, an adrenergic agonist, a carbonic anhydrase inhibitor, a parasympathomimetic agent, a dual anti-VEGF/Anti-PDGF therapeutic or a dual leucine zipper kinase (DLK) inhibitor. In another embodiment, the microparticles of the present invention can comprise a compound for the treatment of diabetic retinopathy. Such compounds may be administered in lower doses according to the invention as they may be administered at the site of the ocular disease.

Examples of loop diuretics include furosemide, bumetanide, piretanide, ethacrynic acid, etozolin, and ozolinone.

Examples of beta-adrenergic antagonists include, but are not limited to, timolol (Timoptic®), levobunolol (Betagan®), carteolol (Ocupress®), Betaxolol (Betoptic), and metipranolol (OptiPranolol®).

Examples of prostaglandin analogs include, but are not limited to, latanoprost (Xalatan®), travoprost (Travatan®), bimatoprost (Lumigan®) and tafluprost (Zioptan®).

Examples of adrenergic agonists include, but are not limited to, brimonidine (Alphagan®), epinephrine, dipivefrin (Propine®) and apraclonidine (Lopidine®).

Examples of carbonic anhydrase inhibitors include, but are not limited to, dorzolamide (Trusopt®), brinzolamide (Azopt®), acetazolamide (Diamox®) and methazolamide (Neptazane®), see structures below:

Examples of tyrosine kinase inhibitors include Tivosinib, Imatinib, Gefitinib, Erlotinib, Lapatinib, Canertinib, Semaxinib, Vatalaninib, Sorafenib, Axitinib, Pazopanib, Dasatinib, Nilotinib, Crizotinib, Ruxolitinib, Vandetanib, Vemurafenib, Bosutinib, Cabozantinib, Regorafenib, Vismodegib, and Ponatinib. In one embodiment, the tyrosine kinase inhibitor is selected from Tivosinib, Imatinib, Gefitinib, and Erlotinib. In one embodiment, the tyrosine kinase inhibitor is selected from Lapatinib, Canertinib, Semaxinib, and Vatalaninib. In one embodiment, the tyrosine kinase inhibitor is selected from Sorafenib, Axitinib, Pazopanib, and Dasatinib. In one embodiment, the tyrosine kinase inhibitor is selected from Nilotinib, Crizotinib, Ruxolitinib, Vandetanib, and Vemurafenib. In one embodiment, the tyrosine kinase inhibitor is selected from Bosutinib, Cabozantinib, Regorafenib, Vismodegib, and Ponatinib.

An example of a parasympathomimetic includes, but is not limited to, pilocarpine.

DLK inhibitors include, but are not limited to, Crizotinib, KW-2449 and Tozasertib, see structure below.

Drugs used to treat diabetic retinopathy include, but are not limited to, ranibizumab (Lucentis®).

In one embodiment, the dual anti-VEGF/Anti-PDGF therapeutic is sunitinib malate (Sutent®).

In one embodiment, the compound is a treatment for glaucoma and can be used as an effective amount to treat a host in need of glaucoma treatment.

In another embodiment, the compound acts through a mechanism other than those associated with glaucoma to treat a disorder described herein in a host, typically a human.

In one embodiment, the therapeutic agent is selected from a phosphoinositide 3-kinase (PI3K) inhibitor, a Bruton's tyrosine kinase (BTK) inhibitor, or a spleen tyrosine kinase (Syk) inhibitor, or a combination thereof.

PI3K inhibitors that may be used in the present invention are well known. Examples of PI3 kinase inhibitors include but are not limited to Wortmannin, demethoxyviridin, perifosine, idelalisib, Pictilisib, Palomid 529, ZSTK474, PWT33597, CUDC-907, and AEZS-136, duvelisib, GS-9820, BKM120, GDC-0032 (Taselisib) (2-[4-[2-(2-Isopropyl-5-methyl-1,2,4-triazol-3-yl)-5,6-dihydroimidazo[1,2-d][1,4]benzoxazepin-9-yl]pyrazol-1-yl]-2-methylpropanamide), MLN-1117 ((2R)-1-Phenoxy-2-butanyl hydrogen (S)-methylphosphonate; or Methyl(oxo) {[(2R)-1-phenoxy-2-butanyl]oxy}phosphonium)), BYL-719 ((2S)—N1-[4-Methyl-5-[2-(2,2,2-trifluoro-1,1-dimethylethyl)-4-pyridinyl]-2-thiazolyl]-1,2-pyrrolidinedicarboxamide), GSK2126458 (2,4-Difluoro-N-{2-(methyloxy)-5-[4-(4-pyridazinyl)-6-quinolinyl]-3-pyridinyl}benzenesulfonamide) (omipalisib), TGX-221 ((+)-7-Methyl-2-(morpholin-4-yl)-9-(1-phenylaminoethyl)-pyrido[1,2-a]-pyrimidin-4-one), GSK2636771 (2-Methyl-1-(2-methyl-3-(trifluoromethyl)benzyl)-6-morpholino-1H-benzo[d]imidazole-4-carboxylic acid dihydrochloride), KIN-193 ((R)-2-((1-(7-methyl-2-morpholino-4-oxo-4H-pyrido[1,2-a]pyrimidin-9-yl)ethyl)amino)benzoic acid), TGR-1202/RP5264, GS-9820 ((S)-1-(4-((2-(2-aminopyrimidin-5-yl)-7-methyl-4-mohydroxypropan-1-one), GS-1101 (5-fluoro-3-phenyl-2-([S)]-1-[9H-purin-6-ylamino]-propyl)-3H-quinazolin-4-one), AMG-319, GSK-2269557, SAR245409 (N-(4-(N-(3-((3,5-dimethoxyphenyl)amino)quinoxalin-2-yl)sulfamoyl)phenyl)-3-methoxy-4 methylbenzamide), BAY80-6946 (2-amino-N-(7-methoxy-8-(3-morpholinopropoxy)-2,3-dihydroimidazo[1,2-c]quinaz), AS 252424 (5-[1-[5-(4-Fluoro-2-hydroxy-phenyl)-furan-2-yl]-meth-(Z)-ylidene]-thiazolidine-2,4-dione), CZ 24832 (5-(2-amino-8-fluoro-[1,2,4]triazolo[1,5-a]pyridin-6-yl)-N-tert-butylpyridine-3-sulfonamide), Buparlisib (5-[2,6-Di(4-morpholinyl)-4-pyrimidinyl]-4-(trifluoromethyl)-2-pyridinamine), GDC-0941 (2-(1H-Indazol-4-yl)-6-[[4-(methylsulfonyl)-1-piperazinyl]methyl]-4-(4-morpholinyl)thieno[3,2-d] pyrimidine), GDC-0980 ((S)-1-(4-((2-(2-aminopyrimidin-5-yl)-7-methyl-4- morpholinothieno[3,2-d]pyrimidin-6-yl)methyl)piperazin-1-yl)-2-hydroxypropan-1-one (also known as RG7422)), SF1126 ((8S,14S,17S)-14-(carboxymethyl)-8-(3-guanidinopropyl)-17-(hydroxymethyl)-3,6,9,12,15-pentaoxo-1-(4-(4-oxo-8-phenyl-4H-chromen-2-yl)morpholino-4-ium)-2-oxa-7,10,13,16-tetraazaoctadecan-18-oate), PF-05212384 (N-[4-[[4-(Dimethylamino)-1-piperidinyl]carbonyl]phenyl]-N-[4-(4,6-di-4-morpholinyl-1,3,5-triazin-2-yl)phenyl]urea) (gedatolisib), LY3023414, BEZ235 (2-Methyl-2-{4-[3-methyl-2-oxo-8-(quinolin-3-yl)-2,3-dihydro-1H-imidazo[4,5-c]quinolin-1-yl]phenyl} propanenitrile) (dactolisib), XL-765 (N-(3-(N-(3-(3,5-dimethoxyphenylamino)quinoxalin-2-yl)sulfamoyl)phenyl)-3-methoxy-4-methylbenzamide), and GSK1059615 (5-[[4-(4-Pyridinyl)-6-quinolinyl]methylene]-2,4-thiazolidenedione), PX886 ([(3aR,6E,9S,9aR,10R,11aS)-6-[[bis(prop-2-enyl) amino]methylidene]-5-hydroxy-9-(methoxymethyl)-9a,11a-dimethyl-1,4,7-trioxo-2,3,3a,9,10,11-hexahydroindeno[4,5h]isochromen-10-yl]acetate (also known as sonolisib)), LY294002, AZD8186, PF-4989216, pilaralisib, GNE-317, PI-3065, PI-103, NU7441 (KU-57788), HS 173, VS-5584 (SB2343), CZC24832, TG100-115, A66, YM201636, CAY10505, PIK-75, PIK-93, AS-605240, BGT226 (NVP-BGT226), AZD6482, voxtalisib, alpelisib, IC-87114, TGI100713, CH5132799, PKI-402, copanlisib (BAY 80-6946), XL 147, PIK-90, PIK-293, PIK-294, 3-MA (3-methyladenine), AS-252424, AS-604850, apitolisib (GDC-0980; RG7422), and the structure described in WO2014/071109 having the formula:

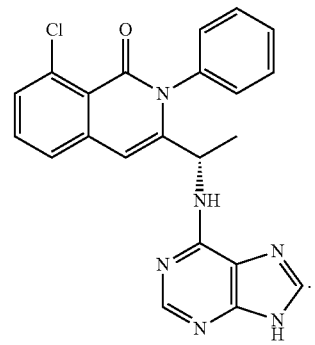

Compound 292

BTK inhibitors for use in the present invention are well known. Examples of BTK inhibitors include ibrutinib (also known as PCI-32765)(Imbmvica™)(1-[(3R)-3-[4-amino-3-(4-phenoxy-phenyl)pyrazolo[3,4-d]pyrimidin-1-yl]piperidin-1-yl]prop-2-en-1-one), dianilinopyrimidine-based inhibitors such as AVL-101 and AVL-291/292 (N-(3-((5-fluoro-2-((4-(2-methoxyethoxy)phenyl)amino)pyrimidin-4-yl)amino)phenyl)acrylamide) (Avila Therapeutics) (US Patent publication No 2011/0117073, incorporated herein in its entirety), Dasatinib ([N-(2-chloro-6-methylphenyl)-2-(6-(4-(2-hydroxyethyl)piperazin-1-yl)-2-methylpyrimidin-4-ylamino)thiazole-5-carboxamide], LFM-A13 (alpha-cyano-beta-hydroxy-beta-methyl-N-(2,5-ibromophenyl) propenamide), GDC-0834 ([R—N-(3-(6-(4-(1,4-dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide], CGI-560 4-(tert-butyl)-N-(3-(8-(phenylamino)imidazo[1,2-a]pyrazin-6-yl) phenyl)benzamide, CGI-1746 (4-(tert-butyl)-N-(2-methyl-3-(4-methyl-6-((4-(morpholine-4-carbonyl)phenyl)amino)-5-oxo-4,5-dihydropyrazin-2-yl)phenyl)benzamide), CNX-774 (4-(4-((4-((3-acrylamidophenyl)amino)-5-fluoropyrimidin-2-yl)amino)phenoxy)-N-methylpicolinamide), CTA056 (7-benzyl-1-(3-(piperidin-1-yl)propyl)-2-(4-(pyridin-4-yl)phenyl)-1H-imidazo[4,5-g]quinoxalin-6(5H)-one), GDC-0834 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b] thiophene-2-carboxamide), GDC-0837 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), HM-71224, ACP-196, ONO-4059 (Ono Pharmaceuticals), PRT062607 (4-((3-(2H-1,2,3-triazol-2-yl)phenyl)amino)-2-(((1R,2S)-2-aminocyclohexyl)amino)pyrimidine-5-carboxamide hydrochloride), QL-47 (1-(1-acryloylindolin-6-yl)-9-(1-methyl-1H-pyrazol-4-yl)benzo[h][1,6]naphthyridin-2 (1H)-one), and RN486 (6-cyclopropyl-8-fluoro-2-(2- hydroxymethyl-3-{1-methyl-5-[5-(4-methyl-piperazin-1-yl)-pyridin-2-ylamino]-6-oxo-1,6-dihydro-pyridin-3-yl}-phenyl)-2H-isoquinolin-1-one), and other molecules capable of inhibiting BTK activity, for example those BTK inhibitors disclosed in Akinleye et ah, Journal of Hematology & Oncology, 2013, 6:59, the entirety of which is incorporated herein by reference.

Syk inhibitors for use in the present invention are well known, and include, for example, Cerdulatinib (4-(cyclopropylamino)-2-((4-(4-(ethylsulfonyl)piperazin-1-yl)phenyl)amino)pyrimidine-5-carboxamide), entospletinib (6-(1H-indazol-6-yl)-N-(4-morpholinophenyl)imidazo[1,2-a]pyrazin-8-amine), fostamatinib ([6-({5-Fluoro-2-[(3,4,5-trimethoxyphenyl)amino]-4-pyrimidinyl}amino)-2,2-dimethyl-3-oxo-2,3-dihydro-4H-pyrido[3,2-b][1,4]oxazin-4-yl]methyl dihydrogen phosphate), fostamatinib disodium salt (sodium (6-((5-fluoro-2-((3,4,5-trimethoxyphenyl)amino)pyrimidin-4-yl)amino)-2,2-dimethyl-3-oxo-2H-pyrido[3,2-b][1,4]oxazin-4(3H)-yl)methyl phosphate), BAY 61-3606 (2-(7-(3,4-Dimethoxyphenyl)-imidazo[1,2-c]pyrimidin-5-ylamino)-nicotinamide HCl), RO9021 (6-[(1R,2S)-2-Amino-cyclohexylamino]-4-(5,6-dimethyl-pyridin-2-ylamino)-pyridazine-3-carboxylic acid amide), imatinib (Gleevac; 4-[(4-methylpiperazin-1-yl)methyl]-N-(4-methyl-3-{[4-(pyridin-3-yl)pyrimidin-2-yl]amino}phenyl)benzamide), staurosporine, GSK143 (2-(((3R,4R)-3-aminotetrahydro-2H-pyran-4-yl)amino)-4-(p-tolylamino)pyrimidine-5-carboxamide), PP2 (1-(tert-butyl)-3-(4-chlorophenyl)-1H-pyrazolo[3,4-d]pyrimidin-4-amine), PRT-060318 (2-(((1R,2S)-2-aminocyclohexyl)amino)-4-(m-tolylamino)pyrimidine-5-carboxamide), PRT-062607 (4-((3-(2H-1,2,3-triazol-2-yl)phenyl)amino)-2-(((1R,2S)-2-aminocyclohexyl)amino)pyrimidine-5-carboxamide hydrochloride), R112 (3,3'-((5-fluoropyrimidine-2,4-diyl)bis(azanediyl))diphenol), R348 (3-Ethyl-4-methylpyridine), R406 (6-((5-fluoro-2-((3,4,5-trimethoxyphenyl)amino)pyrimidin-4-yl)amino)-2,2-dimethyl-2H-pyrido[3,2-b][1,4]oxazin-3(4H)-one), piceatannol (3-Hydroxyresveratol), YM193306 (Singh et al. Discovery and Development of Spleen Tyrosine Kinase (SYK) Inhibitors, J. Med. Chem. 2012, 55, 3614-3643), 7-azaindole, piceatannol, ER-27319 (Singh et al. Discovery and Development of Spleen Tyrosine Kinase (SYK) Inhibitors, J. Med. Chem. 2012, 55, 3614-3643 incorporated in its entirety herein), Compound D (Singh et al. Discovery and Development of Spleen Tyrosine Kinase (SYK) Inhibitors, J. Med. Chem. 2012, 55, 3614-3643 incorporated in its entirety herein), PRT060318 (Singh et al. Discovery and Development of Spleen Tyrosine Kinase (SYK) Inhibitors, J. Med. Chem. 2012, 55, 3614-3643 incorporated in its entirety herein), luteolin (Singh et al. Discovery and Development of Spleen Tyrosine Kinase (SYK) Inhibitors, J. Med. Chem. 2012, 55, 3614-3643 incorporated in its entirety herein), apigenin (Singh et al. Discovery and Development of Spleen Tyrosine Kinase (SYK) Inhibitors, J. Med. Chem. 2012, 55, 3614-3643 incorporated in its entirety herein), quercetin (Singh et al. Discovery and Development of Spleen Tyrosine Kinase (SYK) Inhibitors, J. Med. Chem. 2012, 55, 3614-3643 incorporated in its entirety herein), fisetin (Singh et al. Discovery and Development of Spleen Tyrosine Kinase (SYK) Inhibitors, J. Med. Chem. 2012, 55, 3614-3643 incorporated in its entirety herein), myricetin (Singh et al. Discovery and Development of Spleen Tyrosine Kinase (SYK) Inhibitors, J. Med. Chem. 2012, 55, 3614-3643 incorporated in its entirety herein), morin (Singh et al. Discovery and Development of Spleen Tyrosine Kinase (SYK) Inhibitors, J. Med. Chem. 2012, 55, 3614-3643 incorporated in its entirety herein).

In one embodiment, the therapeutic agent is a MEK inhibitor. MEK inhibitors for use in the present invention are well known, and include, for example, trametinib/GSK1120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1(2H-yl}phenyl)acetamide), selumetinib (6-(4-bromo-2-chloroanilino)-7-fluoro-N-(2-hydroxyethoxy)-3-methylbenzimidazole-5-carboxamide), pimasertib/AS703026/MSC 1935369 ((S)—N-(2,3-dihydroxypropyl)-3-((2-fluoro-4-iodophenyl)amino)isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol), refametinib/BAY869766/RDEA1 19 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3-d]pyrimidine-4,7(3H,8H)-dione), MEK162/ARRY438162 (5-[(4-Bromo-2-fluorophenyl)amino]-4-fluoro-N-(2-hydroxyethoxy)-1-methyl-1H-benzimidazole-6-carboxamide), RO5126766 (3-[[3-Fluoro-2-(methyl sulfamoylamino)-4-pyridyl]methyl]-4-methyl-7-pyrimidin-2-yloxychromen-2-one), WX-554, R04987655/CH4987655 (3,4-difluoro-2-((2-fluoro-4-iodophenyl)amino)-N-(2-hydroxyethoxy)-5-((3-oxo-1,2-oxazinan-2yl)methyl)benzamide), or AZD8330 (2-((2-fluoro-4-iodophenyl)amino)-N-(2 hydroxyethoxy)-1,5-dimethyl-6-oxo-1,6-dihydropyridine-3-carboxamide), U0126-EtOH, PD184352 (CI-1040), GDC-0623, BI-847325, cobimetinib, PD98059, BIX 02189, BIX 02188, binimetinib, SL-327, TAK-733, PD318088, and additional MEK inhibitors as described below.

In one embodiment, the therapeutic agent is a Raf inhibitor. Raf inhibitors for use in the present invention are well known, and include, for example, Vemurafinib (N-[3-[[5-(4-Chlorophenyl)-1H-pyrrolo[2,3-b]pyridin-3-yl]carbonyl]-2,4-difluorophenyl]-1-propanesulfonamide), sorafenib tosylate (4-[4-[[4-chloro-3-(trifluoromethyl)phenyl]carbamoylamino]phenoxy]-N-methylpyridine-2-carboxamide; 4-methylbenzenesulfonate), AZ628 (3-(2-cyanopropan-2-yl)-N-(4-methyl-3-(3-methyl-4-oxo-3,4-dihydroquinazolin-6-ylamino)phenyl)benzamide), NVP-BHG712 (4-methyl-3-(1-methyl-6-(pyridin-3-yl)-1H-pyrazolo[3,4-d]pyrimidin-4-ylamino)-N-(3-(trifluoromethyl)phenyl)benzamide), RAF-265 (1-methyl-5-[2-[5-(trifluoromethyl)-1H-imidazol-2-yl]pyridin-4-yl]oxy-N-[4-(trifluoromethyl)phenyl]benzimidazol-2-amine), 2-Bromoaldisine (2-Bromo-6,7-dihydro-1H,5H-pyrrolo[2,3-c]azepine-4,8-dione), Raf Kinase Inhibitor IV (2-chloro-5-(2-phenyl-5-(pyridin-4-yl)-1H-imidazol-4-yl)phenol), Sorafenib N-Oxide (4-[4-[[[[4-Chloro-3(trifluoroMethyl)phenyl]aMino]carbonyl]aMino]phenoxy]-N-Methyl-2pyridinecarboxaMide 1-Oxide), PLX-4720, dabrafenib (GSK2118436), GDC-0879, RAF265, AZ 628, SB590885, ZM336372, GW5074, TAK-632, CEP-32496, LY3009120, and GX818 (Encorafenib).

In one embodiment, the therapeutic agent is a programmed death protein 1 (PD-1) inhibitor, a programmed death protein ligand 1 (PDL1) inhibitor, or a programmed death protein ligand 2 (PDL2) inhibitor. PD-1, PDL1, and PDL2 inhibitors are known in the art, and include, for example, nivolumab (BMS), pembrolizumab (Merck), pidilizumab (CureTech/Teva), AMP-244 (Amplimmune/

GSK), BMS-936559 (BMS), and MEDI4736 (Roche/Genentech), and MPDL3280A (Genentech).

In one embodiment, a therapeutic agent can be administered in a sustained fashion.

In one embodiment, the therapeutic agent is a monoclonal antibody (MAb). Some MAbs stimulate an immune response that destroys cancer cells. Similar to the antibodies produced naturally by B cells, these MAbs "coat" the cancer cell surface, triggering its destruction by the immune system. For example, bevacizumab targets vascular endothelial growth factor (VEGF), a protein secreted by tumor cells and other cells in the tumor's microenvironment that promotes the development of tumor blood vessels. When bound to bevacizumab, VEGF cannot interact with its cellular receptor, preventing the signaling that leads to the growth of new blood vessels. Similarly, cetuximab and panitumumab target the epidermal growth factor receptor (EGFR), and trastuzumab targets the human epidermal growth factor receptor 2 (HER-2). MAbs that bind to cell surface growth factor receptors prevent the targeted receptors from sending their normal growth-promoting signals. They may also trigger apoptosis and activate the immune system to destroy tumor cells.

Other agents may include, but are not limited to, at least one of tamoxifen, midazolam, letrozole, bortezomib, anastrozole, goserelin, an mTOR inhibitor, a PI3 kinase inhibitor as described above, a dual mTOR-PI3K inhibitor, a MEK inhibitor, a RAS inhibitor, ALK inhibitor, an HSP inhibitor (for example, HSP70 and HSP 90 inhibitor, or a combination thereof), a BCL-2 inhibitor as described above, apopototic inducing compounds, an AKT inhibitor, including but not limited to, MK-2206, GSK690693, Perifosine, (KRX-0401), GDC-0068, Triciribine, AZD5363, Honokiol, PF-04691502, and Miltefosine, a PD-1 inhibitor as described above including but not limited to, Nivolumab, CT-011, MK-3475, BMS936558, and AMP-514 or a FLT-3 inhibitor, including but not limited to, P406, Dovitinib, Quizartinib (AC220), Amuvatinib (MP-470), Tandutinib (MLN518), ENMD-2076, and KW-2449, or a combination thereof. Examples of mTOR inhibitors include but are not limited to rapamycin and its analogs, everolimus (Afinitor), temsirolimus, ridaforolimus, sirolimus, and deforolimus. Examples of MEK inhibitors include but are not limited to tametinib/GSK1120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1(2H-yl}phenyl)acetamide), selumetinob (6-(4-bromo-2-chloroanilino)-7-fluoro-N-(2-hydroxyethoxy)-3-methylbenzimidazole-5-carboxamide), pimasertib/AS703026/MSC1935369 ((S)—N-(2,3-dihydroxypropyl)-3-((2-fluoro-4-iodophenyl)amino)isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol) (cobimetinib), refametinib/BAY869766/RDEA119 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3d]pyrimidine-4,7(3H,8H)-dione), MEK162/ARRY438162 (5-[(4-Bromo-2-fluorophenyl)amino]-4-fluoro-N-(2-hydroxyethoxy)-1-methyl-1H-benzimidazole-6 carboxamide), R05126766 (3-[[3-Fluoro-2-(methylsulfamoylamino)-4-pyridyl]methyl]-4-methyl-7-pyrimidin-2-yloxychromen-2-one), WX-554, R04987655/CH4987655 (3,4-difluoro-2-((2-fluoro-4-iodophenyl)amino)-N-(2-hydroxyethoxy)-5-((3-oxo-1,2-oxazinan-2 yl)methyl)benz-amide), or AZD8330 (2-((2-fluoro-4-iodophenyl)amino)-N-(2-hydroxyethoxy)-1,5-dimethyl-6-oxo-1,6-dihydropyridine-3-carboxamide). Examples of RAS inhibitors include but are not limited to Reolysin and siGl2D LODER. Examples of ALK inhibitors include but are not limited to Crizotinib, Ceritinib (Zykadia), AP26113, and LDK378. HSP inhibitors include but are not limited to Geldanamycin or 17-N-Allylamino-17-demethoxygeldanamycin (17AAG), and Radicicol.

In certain aspects, the therapeutic agent is an anti-inflammatory agent, a chemotherapeutic agent, a radiotherapeutic, an additional therapeutic agent, or an immunosuppressive agent.

In one embodiment, a chemotherapeutic is selected from, but not limited to, imatinib mesylate (Gleevac®), dasatinib (Sprycel®), nilotinib (Tasigna®), bosutinib (Bosulif®), trastuzumab (Herceptin®), trastuzumab-DM1, pertuzumab (Perjeta™), lapatinib (Tykerb®), gefitinib (Iressa®), erlotinib (Tarceva®), cetuximab (Erbitux®), panitumumab (Vectibix®), vandetanib (Caprelsa®), vemurafenib (Zelboraf®), vorinostat (Zolinza®), romidepsin (Istodax®), bexarotene (Tagretin®), alitretinoin (Panretin®), tretinoin (Vesanoid®), carfilizomib (Kyprolis™), pralatrexate (Folotyn®), bevacizumab (Avastin®), ziv-aflibercept (Zaltrap®), sorafenib (Nexavar®), sunitinib (Sutent®), pazopanib (Votrient®), regorafenib (Stivarga®), and cabozantinib (Cometriq™).

Additional chemotherapeutic agents include, but are not limited to, a radioactive molecule, a toxin, also referred to as cytotoxin or cytotoxic agent, which includes any agent that is detrimental to the viability of cells, and liposomes or other vesicles containing chemotherapeutic compounds. General anticancer pharmaceutical agents include: vincristine (Oncovin®) or liposomal vincristine (Marqibo®), daunorubicin (daunomycin or Cerubidine®) or doxorubicin (Adriamycin®), cytarabine (cytosine arabinoside, ara-C, or Cytosar®), L-asparaginase (Elspar®) or PEG-L-asparaginase (pegaspargase or Oncaspar®), etoposide (VP-16), teniposide (Vumon®), 6-mercaptopurine (6-MP or Purinethol®), Methotrexate, cyclophosphamide (Cytoxan®), Prednisone, dexamethasone (Decadron), imatinib (Gleevec®), dasatinib (Sprycel®), nilotinib (Tasigna®), bosutinib (Bosulif®), and ponatinib (Iclusig™). Examples of additional suitable chemotherapeutic agents include but are not limited to 1-dehydrotestosterone, 5-fluorouracil decarbazine, 6-mercaptopurine, 6-thioguanine, actinomycin D, adriamycin, aldesleukin, an alkylating agent, allopurinol sodium, altretamine, amifostine, anastrozole, anthramycin (AMC)), an anti-mitotic agent, cis-dichlorodiamine platinum (II) (DDP) cisplatin), diamino dichloro platinum, anthracycline, an antibiotic, an antimetabolite, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), chlorambucil, cisplatin, cladribine, colchicin, conjugated estrogens, cyclophosphamide, cyclothosphamide, cytarabine, cytarabine, cytochalasin B, cytoxan, dacarbazine, dactinomycin, dactinomycin (formerly actinomycin), daunirubicin HCL, daunorucbicin citrate, denileukin diftitox, Dexrazoxane, Dibromomannitol, dihydroxy anthracin dione, docetaxel, dolasetron mesylate, doxorubicin HCL, dronabinol, E. coli L-asparaginase, emetine, epoetin-α, Erwinia L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon α-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

Additional therapeutic agents can include bevacizumab, sutinib, sorafenib, 2-methoxyestradiol or 2ME2, finasunate, vatalanib, vandetanib, aflibercept, volociximab, etaracizumab (MEDI-522), cilengitide, erlotinib, cetuximab, panitumumab, gefitinib, trastuzumab, dovitinib, figitumumab, atacicept, rituximab, alemtuzumab, aldesleukine, atlizumab, tocilizumab, temsirolimus, everolimus, lucatumumab, dacetuzumab, HLL1, huN901-DM1, atiprimod, natalizumab, bortezomib, carfilzomib, marizomib, tanespimycin, saquinavir mesylate, ritonavir, nelfinavir mesylate, indinavir sulfate, belinostat, panobinostat, mapatumumab, lexatumumab, dulanermin, ABT-737, oblimersen, plitidepsin, talmapimod, P276-00, enzastaurin, tipifarnib, perifosine, imatinib, dasatinib, lenalidomide, thalidomide, simvastatin, celecoxib, bazedoxifene, AZD4547, rilotumumab, oxaliplatin (Eloxatin), PD0332991 (palbociclib), ribociclib (LEE011), amebaciclib (LY2835219), HDM201, fulvestrant (Faslodex), exemestane (Aromasin), PIM447, ruxolitinib (INC424), BGJ398, necitumumab, pemetrexed (Alimta), and ramucirumab (IMC-1121B).

In one aspect of the present invention, an immunosuppressive agent is used, preferably selected from the group consisting of a calcineurin inhibitor, e.g. a cyclosporin or an ascomycin, e.g. Cyclosporin A (NEORAL®), FK506 (tacrolimus), pimecrolimus, a mTOR inhibitor, e.g. rapamycin or a derivative thereof, e.g. Sirolimus (RAPAMUNE®), Everolimus (Certican®), temsirolimus, zotarolimus, biolimus-7, biolimus-9, a rapalog, e.g. ridaforolimus, azathioprine, campath 1H, a S1P receptor modulator, e.g. fingolimod or an analogue thereof, an anti-IL-8 antibody, mycophenolic acid or a salt thereof, e.g. sodium salt, or a prodrug thereof, e.g. Mycophenolate Mofetil (CELLCEPT®), OKT3 (ORTHOCLONE OKT3®), Prednisone, ATGAM®, THYMOGLOBULIN®, Brequinar Sodium, OKT4, T10B9.A-3A, 33B3.1, 15-deoxyspergualin, tresperimus, Leflunomide ARAVA®, CTLAI-Ig, anti-CD25, anti-IL2R, Basiliximab (SIMULECT®), Daclizumab (ZENAPAX®), mizorbine, methotrexate, dexamethasone, ISAtx-247, SDZ ASM 981 (pimecrolimus, Elidel®), CTLA4lg (Abatacept), belatacept, LFA3lg, etanercept (sold as Enbrel® by Immunex), adalimumab (Humira®), infliximab (Remicade®), an anti-LFA-1 antibody, natalizumab (Antegren®), Enlimomab, gavilimomab, antithymocyte immunoglobulin, siplizumab, Alefacept efalizumab, pentasa, mesalazine, asacol, codeine phosphate, benorylate, fenbufen, naprosyn, diclofenac, etodolac and indomethacin, aspirin and ibuprofen.

Examples of types of therapeutic agents that can be eluted from the microparticles include anti-inflammatory drugs, antimicrobial agents, anti-angiogenesis agents, immunosuppressants, antibodies, steroids, ocular antihypertensive drugs and combinations thereof. Examples of therapeutic agents include amikacin, anecortane acetate, anthracenedione, anthracycline, an azole, amphotericin B, bevacizumab, camptothecin, cefuroxime, chloramphenicol, chlorhexidine, chlorhexidine digluconate, clortrimazole, a clotrimazole cephalosporin, corticosteroids, dexamethasone, desamethazone, econazole, eftazidime, epipodophyllotoxin, fluconazole, flucytosine, fluoropyrimidines, fluoroquinolines, gatifloxacin, glycopeptides, imidazoles, itraconazole, ivermectin, ketoconazole, levofloxacin, macrolides, miconazole, miconazole nitrate, moxifloxacin, natamycin, neomycin, nystatin, ofloxacin, polyhexamethylene biguanide, prednisolone, prednisolone acetate, pegaptanib, platinum analogues, polymicin B, propamidine isethionate, pyrimidine nucleoside, ranibizumab, squalamine lactate, sulfonamides, triamcinolone, triamcinolone acetonide, triazoles, vancomycin, anti-vascular endothelial growth factor (VEGF) agents, VEGF antibodies, VEGF antibody fragments, vinca alkaloid, timolol, betaxolol, travoprost, latanoprost, bimatoprost, brimonidine, dorzolamide, acetazolamide, pilocarpine, ciprofloxacin, azithromycin, gentamycin, tobramycin, cefazolin, voriconazole, gancyclovir, cidofovir, foscarnet, diclofenac, nepafenac, ketorolac, ibuprofen, indomethacin, fluoromethalone, rimexolone, anecortave, cyclosporine, methotrexate, tacrolimus and combinations thereof.

Examples of immunosuppressive agents are calcineurin inhibitor, e.g., a cyclosporin or an ascomycin, e.g., Cyclosporin A (NEORAL®), FK506 (tacrolimus), pimecrolimus, a mTOR inhibitor, e.g., rapamycin or a derivative thereof, e.g., Sirolimus (RAPAMUNE®), Everolimus (Certican®), temsirolimus, zotarolimus, biolimus-7, biolimus-9, a rapalog, e.g., ridaforolimus, azathioprine, campath 1H, a S1P receptor modulator, e.g., fingolimod or an analogue thereof, an anti IL-8 antibody, mycophenolic acid or a salt thereof, e.g., sodium salt, or a prodrug thereof, e.g., Mycophenolate Mofetil (CELLCEPT®), OKT3 (ORTHOCLONE OKT3®), Prednisone, ATGAM®, THYMOGLOBULIN®, Brequinar Sodium, OKT4, T10B9.A-3A, 33B3.1, 15-deoxyspergualin, tresperimus, Leflunomide ARAVA®, CTLAI-Ig, anti-CD25, anti-IL2R, Basiliximab (SIMULECT®), Daclizumab (ZENAPAX®), mizorbine, methotrexate, dexamethasone, ISAtx-247, SDZ ASM 981 (pimecrolimus, Elidel®), CTLA4lg (Abatacept), belatacept, LFA3lg, etanercept (sold as Enbrel® by Immunex), adalimumab (Humira®), infliximab (Remicade®), an anti-LFA-1 antibody, natalizumab (Antegren®), Enlimomab, gavilimomab, antithymocyte immunoglobulin, siplizumab, Alefacept efalizumab, pentasa, mesalazine, asacol, codeine phosphate, benorylate, fenbufen, naprosyn, diclofenac, etodolac and indomethacin, aspirin and ibuprofen.

In certain embodiments, the surface-treated microparticles of the present invention can comprise a prodrug as disclosed below. In all of the polymer moieties described in this specification, where the structures are depicted as block copolymers (for example, blocks of "x" followed by blocks of "y") it is intended that the polymer can alternately be a random or alternating copolymer (for example, "x" and "y", are either randomly distributed or alternate). Unless stereochemistry is specifically indicated, each individual moiety of each oligomer that has a chiral center can be presented at the chiral carbon in (R) or (S) configuration or a mixture thereof, including a racemic mixture.

In addition, prodrug moieties that have repetitive units of the same or varying monomers, for example including but not limited to an oligomer of polylactic acid, polylactide-coglycolide, or polypropylene oxide, that has a chiral carbon can be used with the chiral carbons all having the same stereochemistry, random stereochemistry (by either monomer or oligomer), racemic (by either monomer or oligomer) or ordered but different stereochemistry such as a block of S enantiomer units followed by a block of R enantiomer units in each oligomeric unit. In some embodiments lactic acid is used in its naturally occurring S enantiomeric form.

Prostaglandin Prodrugs

The disclosure provides prostaglandin prodrugs of Formula IA:

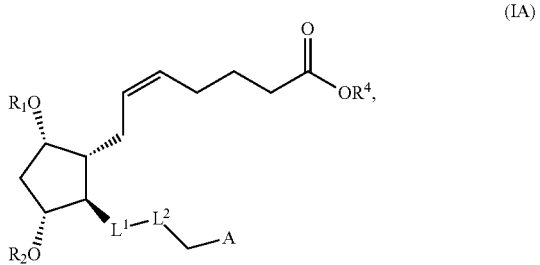

(IA)

or a pharmaceutically acceptable composition, salt, or isotopic derivative thereof wherein $L^1$ is selected from:

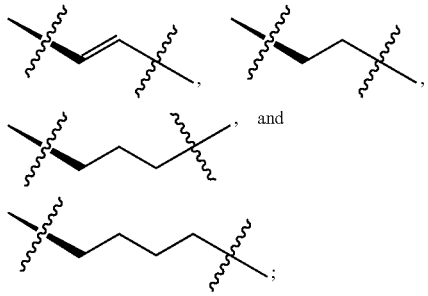

, and

;

$L^2$ is selected from:

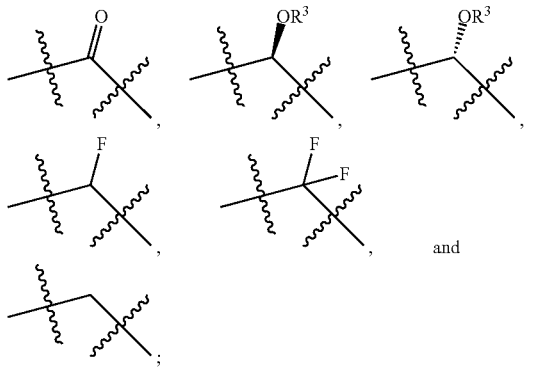

, and

;

A is selected from: H, alkyl, cycloalkyl, cycloalkylalkyl, heterocycle, heterocycloalkyl, aryl, arylalkyl, heteroaryl, heteroarylalkyl, aryloxy, and alkyloxy wherein each group can be optionally substituted with another desired substituent group which is pharmaceutically acceptable and sufficiently stable under the conditions of use, for example selected from $R^5$;

$R^1$, $R^2$, and $R^3$ are selected from: —C(O)$R^4$, C(O)A, and hydrogen wherein in Formula IA either $R^1$ or $R^2$ cannot be hydrogen and wherein $R^1$, $R^2$, and $R^3$ can be further optionally substituted with $R^5$;

$R^4$ is selected from:

(i) —$C_{10}$-$C_{30}$alkyl$R^5$, —$C_{10}$-$C_{30}$alkenyl$R^5$, —$C_{10}$-$C_{30}$alkynyl$R^5$, —$C_{10}$-$C_{30}$alkenylalkynyl$R^5$, —$C_{10}$-$C_{30}$alkyl, —$C_{10}$-$C_{30}$alkenyl, —$C_{10}$-$C_{30}$alkynyl, —$C_{10}$-$C_{30}$alkenylalkynyl; and (ii) an unsaturated fatty acid residue including but not limited to the carbon chains from linoleic acid (—(CH$_2$)$_8$(CH)$_2$CH$_2$(CH)$_2$(CH$_2$)$_4$CH$_3$)), docosahexaenoic acid (—(CH$_2$)$_3$(CHCHCH$_2$)$_6$CH$_3$)), eicosapentaenoic acid (—(CH$_2$)$_4$(CHCHCH$_2$)$_5$CH$_3$)), alpha-linolenic acid (—(CH$_2$)$_8$(CHCHCH$_2$)$_3$CH$_3$)), stearidonic acid, γ-linolenic acid, arachidonic acid, docosatetraenoic acid, palmitoleic acid, vaccenic acid, paullinic acid, oleic acid, elaidic acid, gondoic acid, euric acid, nervonic acid and mead acid, and wherein, if desired, each of which can be substituted with $R^5$; and $R^5$ is selected from: halogen, hydroxyl, cyano, mercapto, amino, alkyl, alkoxy, alkenyl, alkynyl, cycloalkyl, cycloalkylalkyl, heterocyclyl, heterocycloalkyl, aryl, arylalkyl, heteroaryl, heteroarylalkyl, aryloxy, —S(O)$_2$alkyl, —S(O)alkyl, —P(O)(Oalkyl)$_2$, B(OH)$_2$, —Si(CH$_3$)$_3$, —COOH, —COOalkyl, and —CONH$_2$, each of which except halogen, cyano, and —Si(CH$_3$)$_3$ may be optionally substituted, for example with halogen, alkyl, aryl, heterocycle or heteroaryl if desired and if the resulting compound achieves the desired purpose, wherein the group cannot be substituted with itself, for example alkyl would not be substituted with alkyl.

Non-limiting examples of $R^4$ include:

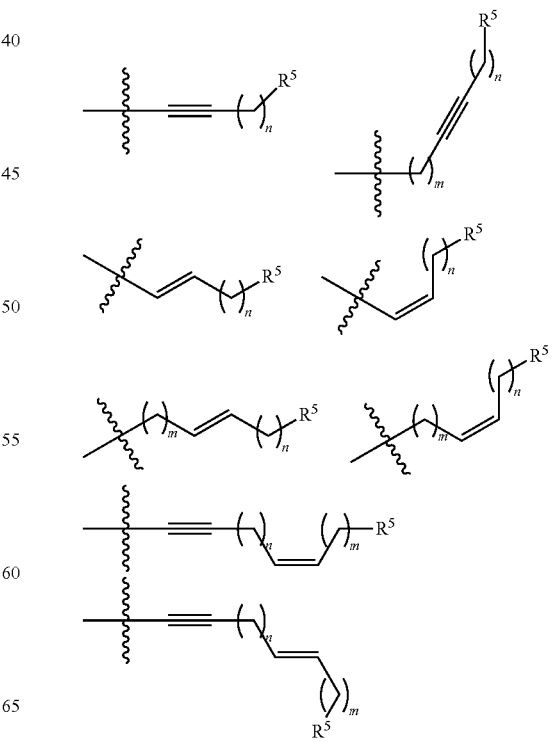

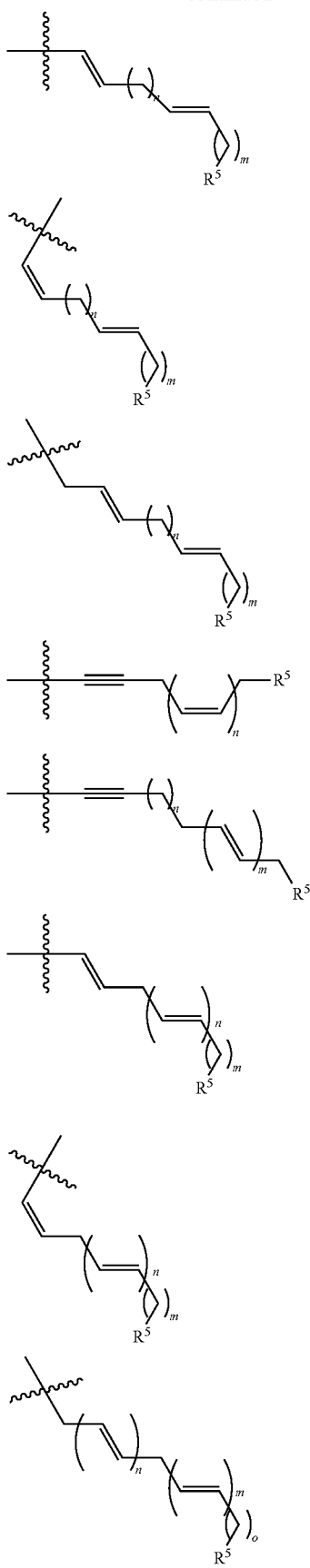
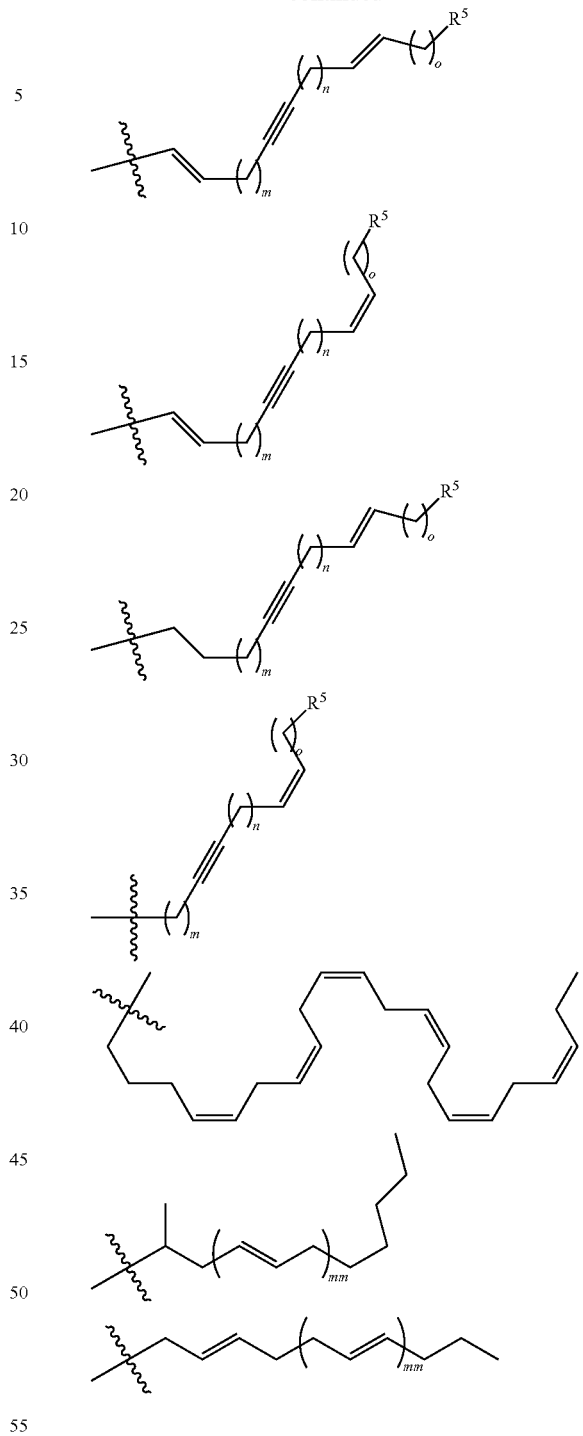
wherein n, m, and o are independently selected from any integer between 0 and 29 (1, 2, 3, 4, 5, 6, 7, 8, 9, 10, 11, 12, 13, 14, 15, 16, 17, 18, 19, 20, 21, 22, 23, 24, 25, 26, 27, 28 or 29) wherein n+m+o is 7 to 30 carbons and wherein mm is any integer between 1 and 30 (1, 2, 3, 4, 5, 6, 7, 8, 9, 10, 11, 12, 13, 14, 15, 16, 17, 18, 19, 20, 21, 22, 23, 24, 25, 26, 27, 28, 29 or 30). In one embodiment mm is independently selected from the following ranges: 1 to 5, 6 to 11, 12 to 17, 18 to 23, and 24 to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30).

In one embodiment, —C₁₀-C₃₀ as used in the definition of R⁴ is —C₁₀-C₂₈, —C₁₀-C₂₆, —C₁₀-C₂₄, —C₁₀-C₂₂, —C₁₀-C₂₀, —C₁₀-C₁₈, —C₁₀-C₁₆, —C₁₀-C₁₄, or —C₁₀-C₁₂.

Non-limiting examples of Formula IA include:

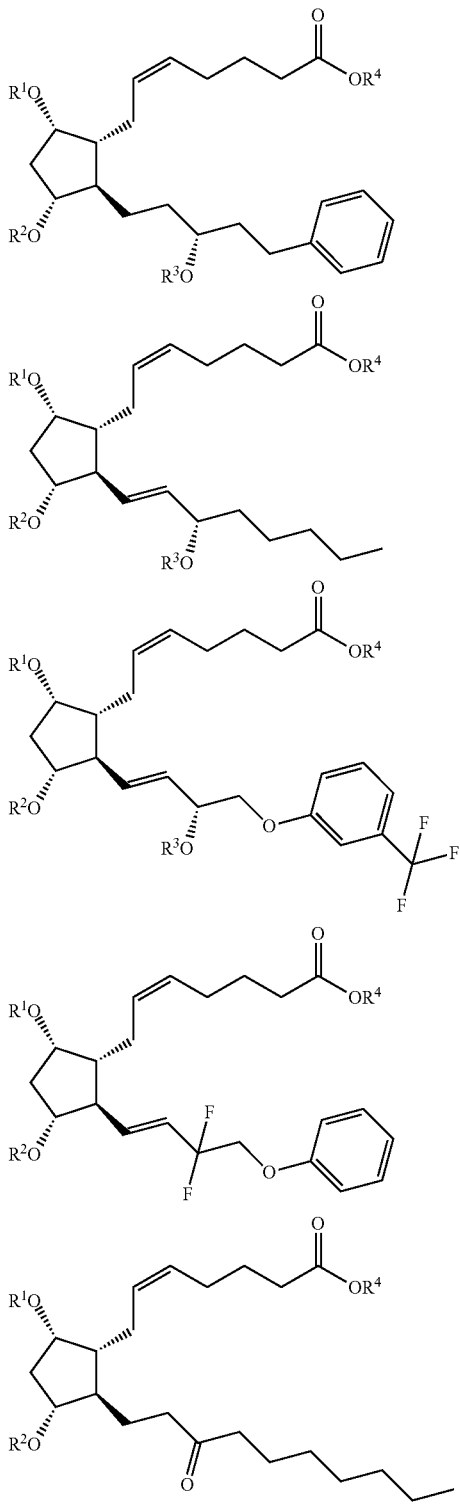

The disclosure provides prostaglandin prodrugs of Formula IIA:

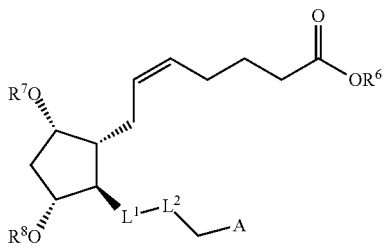

or a pharmaceutically acceptable composition, salt, or isotopic derivative thereof wherein R⁶ is selected from:

(i) polyethylene glycol, polypropylene glycol, polypropylene oxide, polylactic acid, and poly(lactic-co-glycolic acid) including:

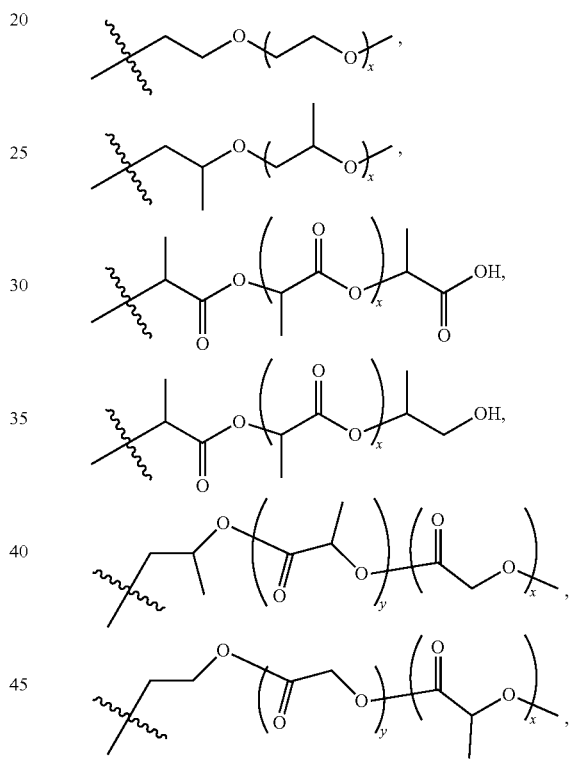

or polyglycolic acid, or a polyester, polyamide, or other biodegradable polymer, each of which can be capped to complete the terminal valence. In some embodiments, the compound can be capped with hydrogen, or can be capped to create a terminal ester or ether. For example, the moiety can be capped with a terminal hydroxyl or carboxy which can be further derivatized to an ether or ester;

(ii) —C₁₀-C₃₀alkylR⁵, —C₁₀-C₃₀alkenylR⁵, —C₁₀-C₃₀alkynylR⁵, —C₁₀-C₃₀alkenylalkynylR⁵, —C₁₀-C₃₀alkyl, —C₁₀-C₃₀alkenyl, —C₁₀-C₃₀alkynyl, —C₁₀-C₃₀alkenylalkynyl;

(iii) an unsaturated fatty acid residue including but not limited the carbon fragment taken from linoleic acid (—(CH₂)₈(CH)₂CH₂(CH)₂(CH₂)₄CH₃)), docosahexaenoic acid (—(CH₂)₃(CHCHCH₂)₆CH₃)), eicosapentaenoic acid (—(CH₂)₄(CHCHCH₂)₅CH₃)), alpha-linolenic acid (—(CH₂)₈(CHCHCH₂)₃CH₃)) stearidonic acid, γ-linolenic acid, arachidonic acid, docosatetraenoic acid, palmitoleic acid, vaccenic acid, paullinic acid, oleic acid, elaidic acid, gondoic acid, euric acid, nervonic acid or mead acid;

(iv) alkyl, cycloalkyl, cycloalkylalkyl, heterocycle, heterocycloalkyl, arylalkyl, heteroarylalkyl;

wherein $R^6$ can only be selected from (ii), (iii), and (iv) in Formula IIA if at least one of $R^7$ and $R^8$ is selected to be $R^{50}$;

$R^7$ and $R^8$ are independently selected from: —C(O)$R^4$, —C(O)A, hydrogen, and $R^{50}$;

$R^{50}$ is selected from carbonyl derivatives of polyethylene glycol, polypropylene glycol, polypropylene oxide, polylactic acid, and poly(lactic-co-glycolic acid) including:

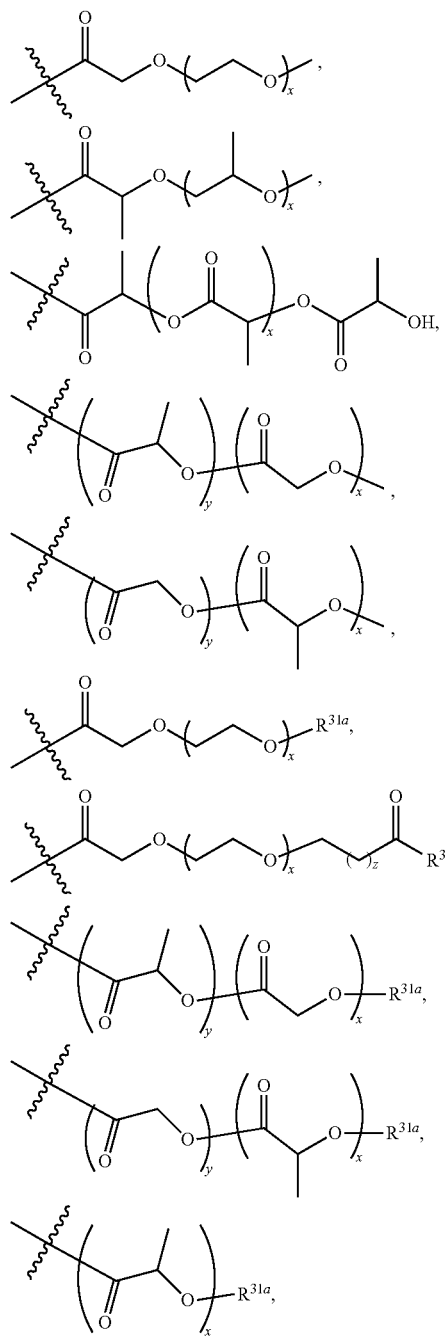

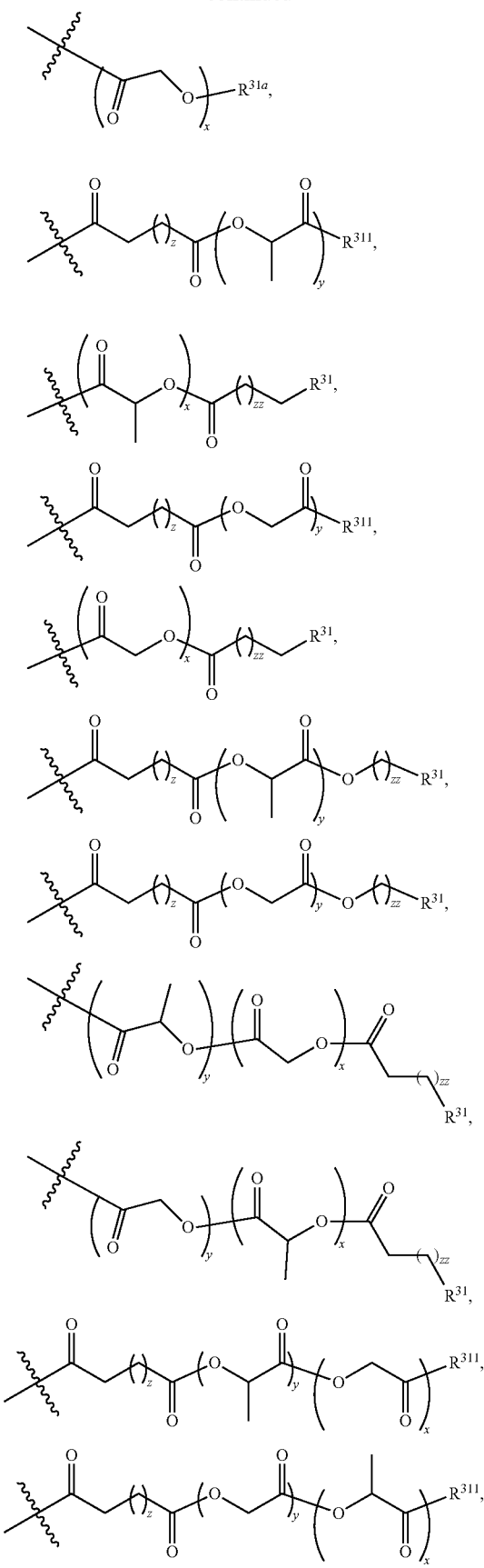

-continued

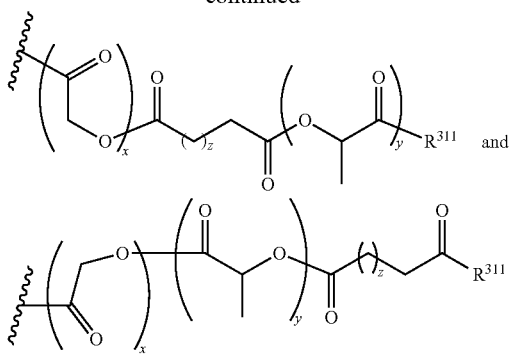
and or polyglycolic acid, or a polyester, polyamide, or other biodegradable polymer, each of which can be capped to complete the terminal valence. In some embodiments, the compound can be capped with hydrogen, or can be capped to create a terminal ester or ether. For example, the moiety can be capped with a terminal hydroxyl or carboxy which can be further derivatized to an ether or ester; and $R^{311}$ is hydroxy, amino, A, alkyl, alkoxy, alkenyl, alkynyl, cycloalkyl, cycloalkylalkyl, heterocyclyl, heterocycloalkyl, aryl, arylalkyl, heteroaryl, heteroarylalkyl, aryloxy, or polyethylene glycol;

$R^{31}$ is hydrogen, A, —COOH, —C(O)A, alkyl, alkoxy, alkenyl, alkynyl cycloalkyl, cycloalkylalkyl, heterocyclyl, heterocycloalkyl, aryl, arylalkyl, heteroaryl, heteroarylalkyl, aryloxy, hydroxy, and polyethylene glycol; and $R^{31a}$ is hydrogen, —C(O)alkyl, aryl, alkyl, cycloalkyl, cycloalkylalkyl, heterocyclyl, heterocycloalkyl, arylalkyl, heteroaryl, heteroarylalkyl, polylactic acid, polygylcolic acid, polyethylene glycol, stearoyl, or

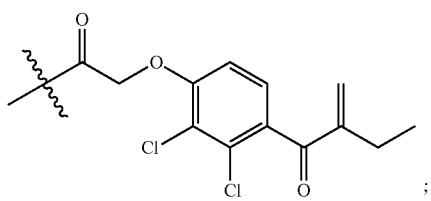 [SMILES: *C(=O)COc1ccc(C(=O)C(=C)CC)c(Cl)c1Cl]
;

x and y are independently selected from any integer between 1 and 30 (1, 2, 3, 4, 5, 6, 7, 8, 9, 10, 11, 12, 13, 14, 15, 16, 17, 18, 19, 20, 21, 22, 23, 24, 25, 26, 27, 28, 29 or 30). In one embodiment x and y are independently selected from the following ranges: 1 to 5, 6 to 11, 12 to 17, 18 to 23, and 24 to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30) and in a preferred embodiment, x and y are independently selected form an integer between 1 and 12 (1, 2, 3, 4, 5, 6, 7, 8, 9, 10, 11, and 12);

z is independently selected from any integer between 0 and 20 (0, 1, 2, 3, 4, 5, 6, 7, 8, 9, 10, 11, 12, 13, 14, 15, 16, 17, 18, 19, or 20) and in a preferred embodiment, z is an integer between 0 and 12 (0, 1, 2, 3, 4, 5, 6, 7, 8, 9, 10, 11, or 12) or between 0 and 6 (0, 1, 2, 3, 4, 5, or 6);

zz is independently selected from any integer between 1 and 20 (1, 2, 3, 4, 5, 6, 7, 8, 9, 10, 11, 12, 13, 14, 15, 16, 17, 18, 19, or 20) and in a preferred embodiment, z is an integer between 1 and 12 (1, 2, 3, 4, 5, 6, 7, 8, 9, 10, 11, or 12) or between 1 and 6 (1, 2, 3, 4, 5, or 6); and wherein all other variables are defined herein.

Non-limiting examples of $R^{50}$ include:

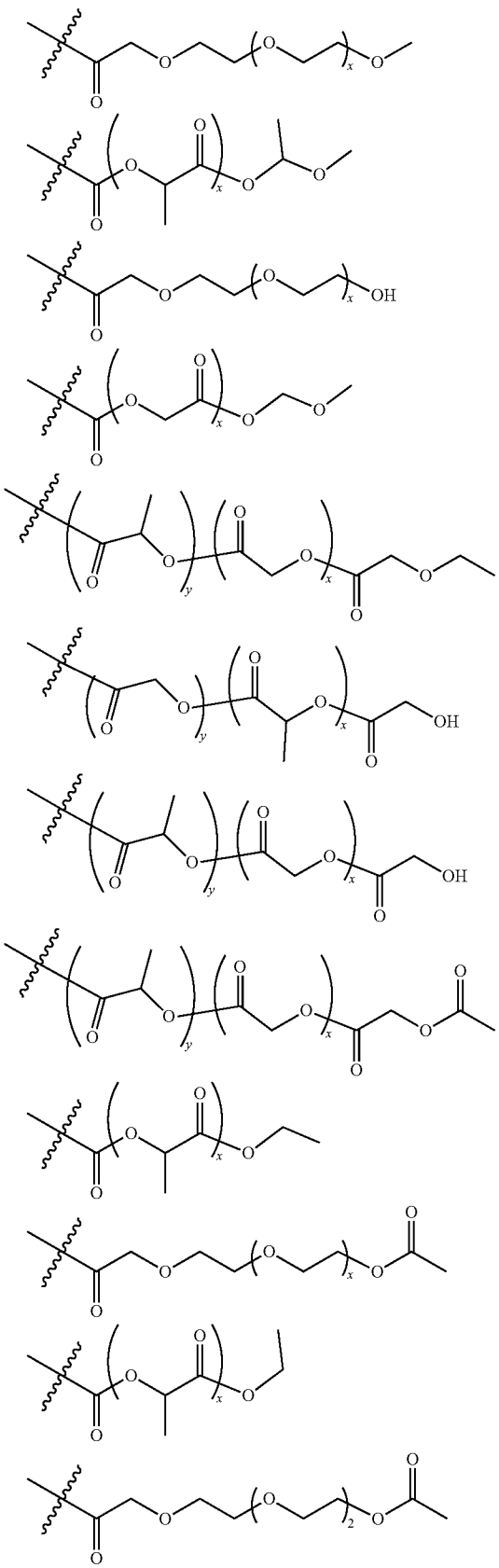

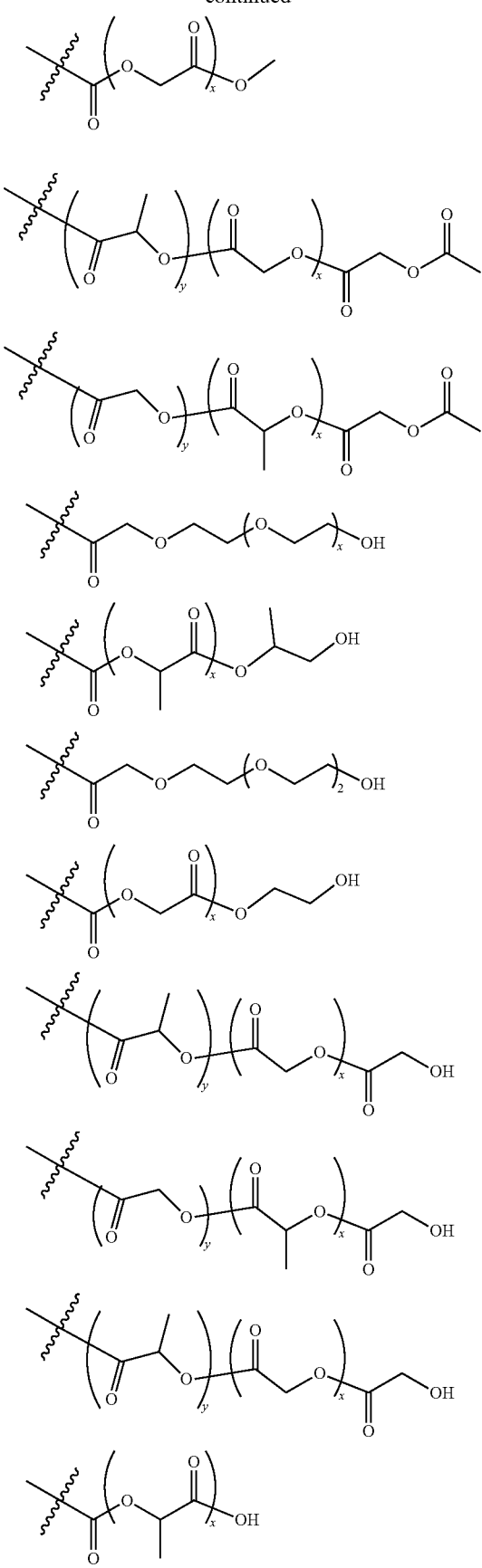
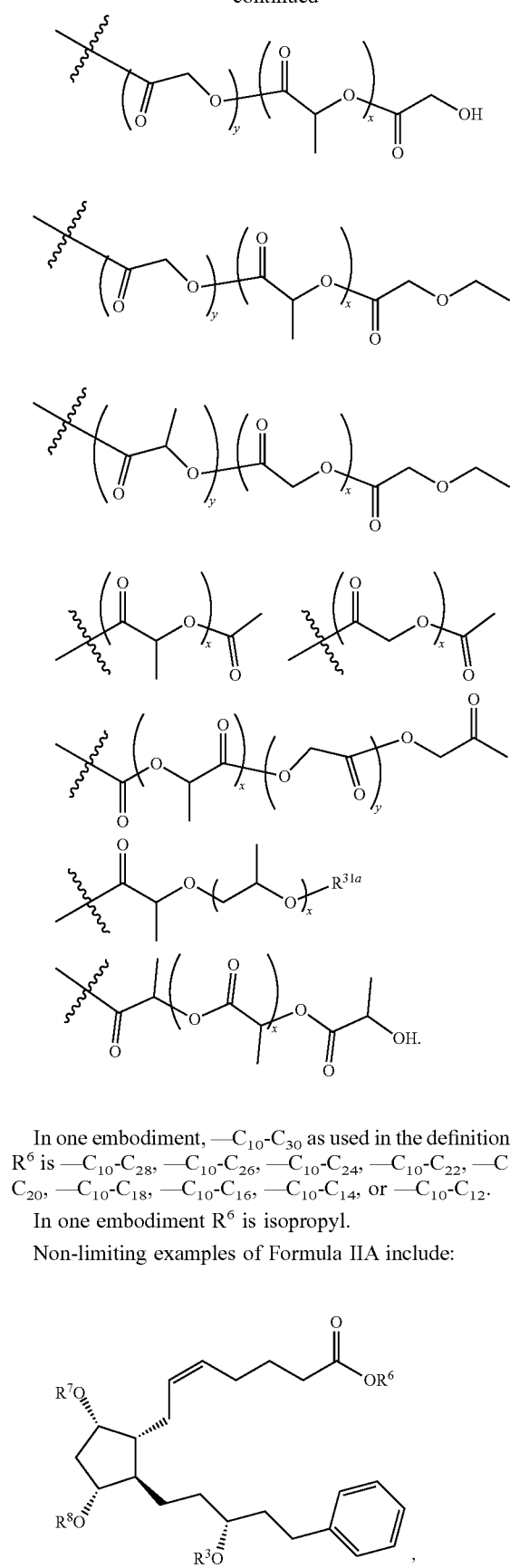
In one embodiment, —$C_{10}$-$C_{30}$ as used in the definition of $R^6$ is —$C_{10}$-$C_{28}$, —$C_{10}$-$C_{26}$, —$C_{10}$-$C_{24}$, —$C_{10}$-$C_{22}$, —$C_{10}$-$C_{20}$, —$C_{10}$-$C_{18}$, —$C_{10}$-$C_{16}$, —$C_{10}$-$C_{14}$, or —$C_{10}$-$C_{12}$.
In one embodiment $R^6$ is isopropyl.
Non-limiting examples of Formula IIA include:
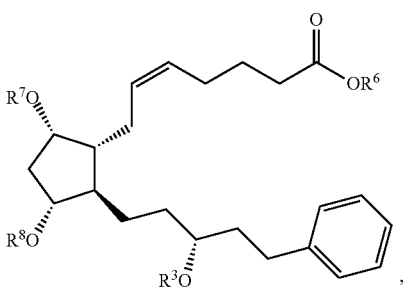

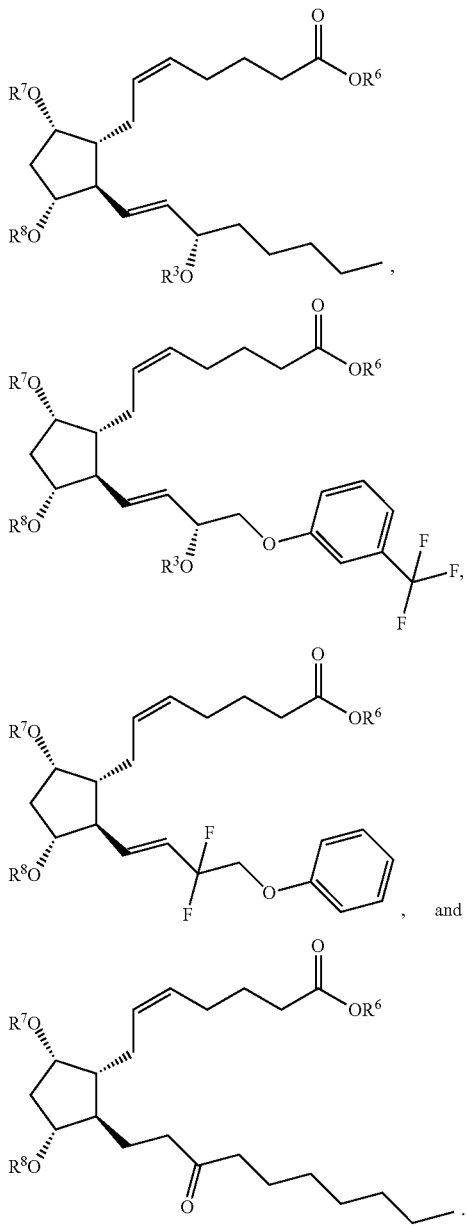

The disclosure provides prostaglandin prodrugs of Formula IIIA:

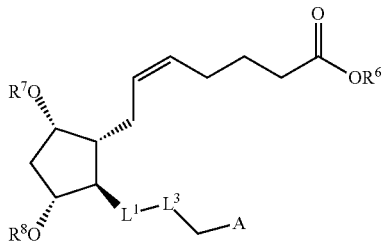
(IIIA)

or a pharmaceutically acceptable composition, salt, or isotopic derivative thereof wherein $L^3$ is selected from:

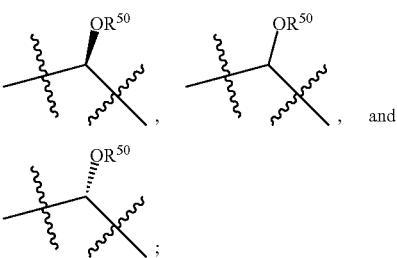

wherein all other variables are defined herein.

In one embodiment, —$C_{10}$-$C_{30}$ as used in the definition of $R^6$ is —$C_{12}$-$C_{28}$, —$C_{12}$-$C_{26}$, —$C_{12}$-$C_{24}$, —$C_{14}$-$C_{22}$, —$C_{14}$-$C_{20}$, —$C_{14}$-$C_{18}$, —$C_{14}$-$C_{16}$, or —$C_{12}$-$C_{14}$.

Non-limiting examples of Formula IIIA include:

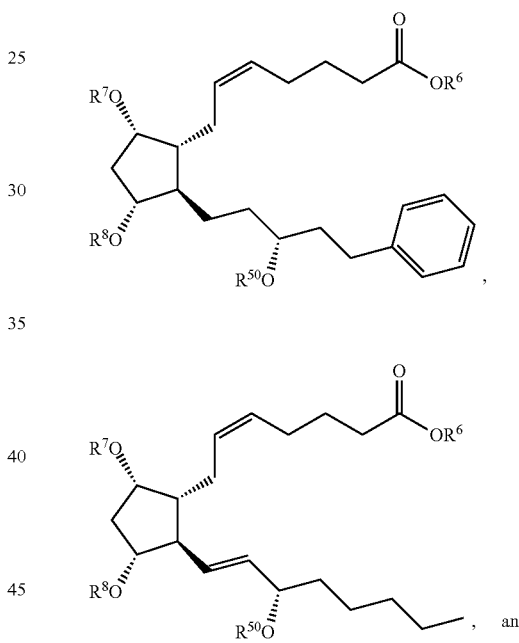

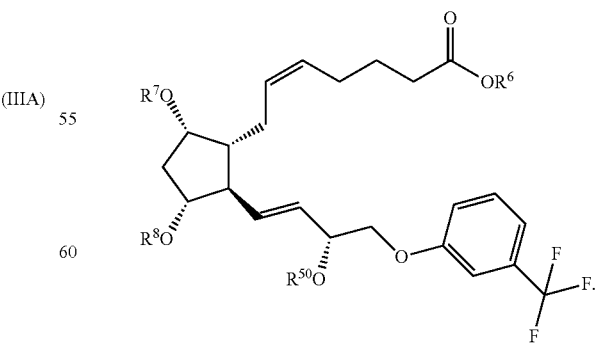

The disclosure provides prostaglandin prodrugs of Formula IVA:

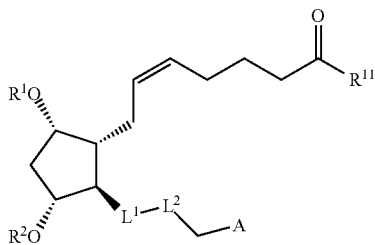

(IVA)

or a pharmaceutically acceptable composition, salt, or isotopic derivative thereof wherein $R^{11}$ is selected from:

(i) $R^{12}$;

(ii) $-NH-C_4-C_{30}$alkenyl-$C(O)R^{12}$, $-NH-C_4-C_{30}$alkynyl-$C(O)R^{12}$, $-NH-C_4-C_{30}$alkenylalkynyl-$C(O)R^{12}$, $-NH-C_2-C_{30}$alkyl-$C(O)R^{12}$, $-O-C_4-C_{30}$alkenyl-$C(O)R^{12}$, $-O-C_4-C_{30}$alkynyl-$C(O)R^{12}$, $-O-C_4-C_{30}$alkenylalkynyl-$C(O)R^{12}$, and $-O-C_2-C_{30}$alkyl-$C(O)R^{12}$;

(iii) $-NH-C_4-C_{30}$alkenyl=$R^{13}$, $-NH-C_4-C_{30}$alkynyl=$R^{13}$, $-NH-C_4-C_{30}$alkenylalkynyl=$R^{13}$, $-NH-C_2-C_{30}$alkyl=$R^{13}$, $-O-C_4-C_{30}$alkenyl=$R^{13}$, $-O-C_4-C_{30}$alkynyl=$R^{13}$, $-O-C_4-C_{30}$alkenylalkynyl=$R^{13}$, $-O-C_2-C_{30}$alkyl=$R^{13}$;

(iv) polyethylene glycol, polypropylene glycol, polypropylene oxide, polylactic acid, and poly(lactic-co-glycolic acid), polyglycolic acid, or a polyester, polyamide, or other biodegradable polymer, each of which is substituted with at least one $L^4$-$R^{12}$ including:

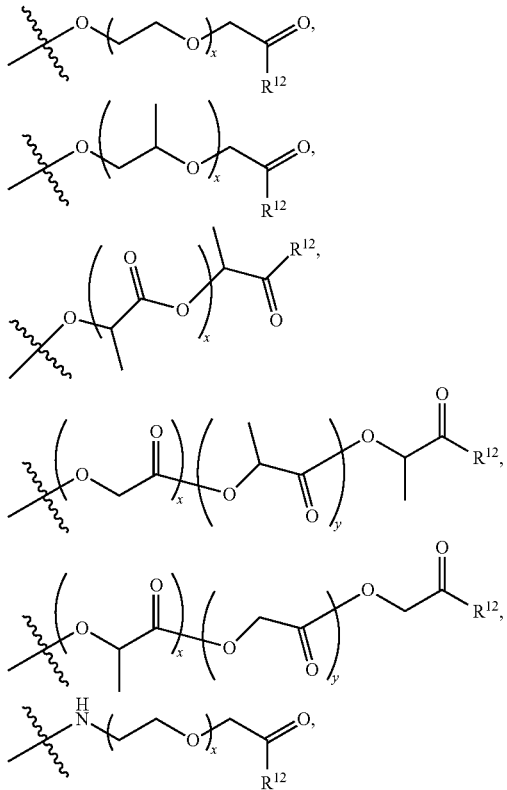

and (v) polyethylene glycol, polypropylene glycol, polypropylene oxide, polylactic acid, and poly(lactic-co-glycolic acid), polyglycolic acid, or a polyester, polyamide, or other biodegradable polymer, each of which is substituted with at least one moiety of L=$R^{13}$ including

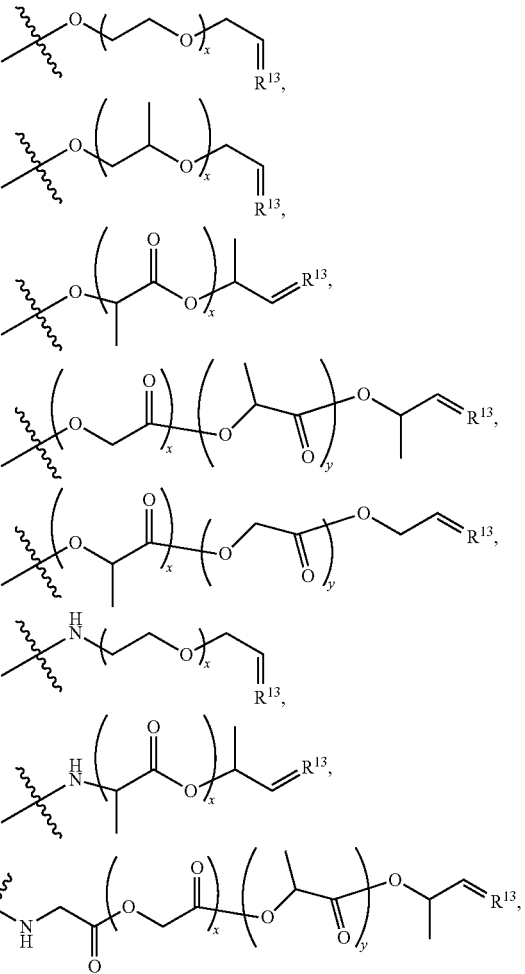

-continued

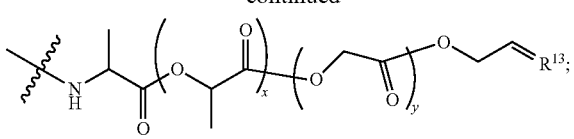

wherein $R^{11}$ can be further substituted with $R^5$ if valence permits, a stable compound is formed, and the resulting compound is pharmaceutically acceptable;

$R^{12}$ is selected from:

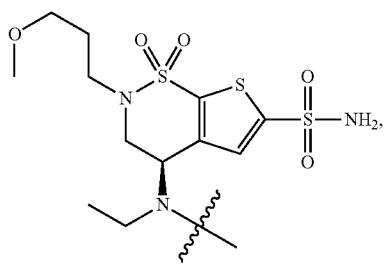

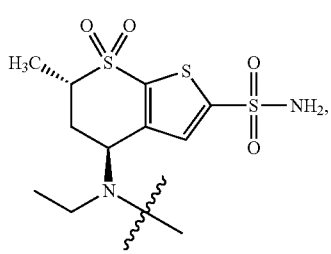

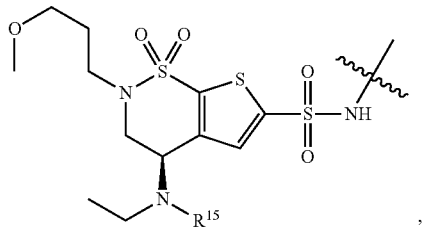

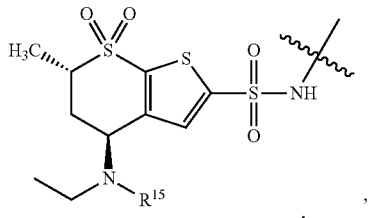

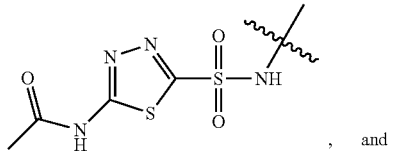

, and

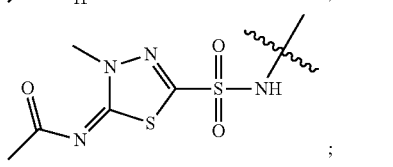

;

$R^{13}$ is selected from:

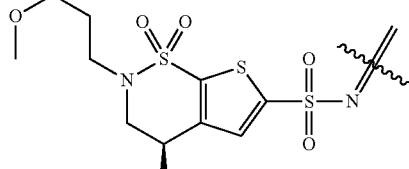

,

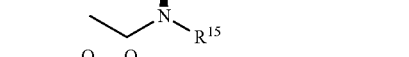

,

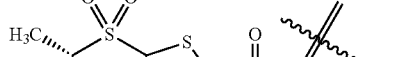

, and

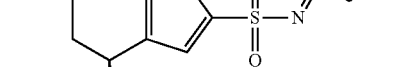

;

and
$R^{15}$ is selected from $R^{16}$ and $R^{17}$;
$R^{16}$ is selected from:
(i) —C(O)C$_3$-C$_{30}$alkylR$^5$, —C(O)C$_3$-C$_{30}$alkenylR$^5$, —C(O)C$_3$-C$_{30}$alkynylR$^5$, —C(O)C$_3$-C$_{30}$alkenylalkynylR$^5$, —C(O)C$_3$-C$_{30}$alkyl, —C(O)C$_3$-C$_{30}$alkenyl, —C(O)C$_3$-C$_{30}$alkynyl, and —C(O)C$_3$-C$_{30}$alkenylalkynyl;
(ii) an unsaturated fatty acid residue including but not limited the carbonyl fragment taken from linoleic acid (—C(O)(CH$_2$)$_7$(CH)$_2$CH$_2$(CH)$_2$(CH$_2$)$_4$CH$_3$)), docosahexaenoic acid (—C(O)(CH$_2$)$_2$(CHCHCH$_2$)$_6$CH$_3$)), eicosapentaenoic acid (—C(O)(CH$_2$)$_3$(CHCHCH$_2$)$_5$CH$_3$)), alpha-linolenic acid (—C(O)(CH$_2$)$_7$(CHCHCH$_2$)$_3$CH$_3$)) stearidonic acid, y-linolenic acid, arachidonic acid, docosatetraenoic acid, palmitoleic acid, vaccenic acid, paullinic acid, oleic acid, elaidic acid, gondoic acid, euric acid, nervonic acid and mead acid;
(iii) polyethylene glycol, polypropylene glycol, polypropylene oxide, polylactic acid, and poly(lactic-co-glycolic acid) including:

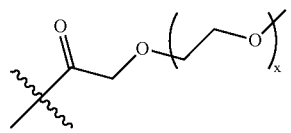

,

,

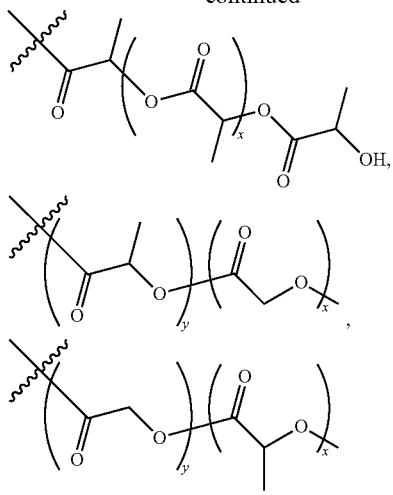

or polyglycolic acid, or a polyester, polyamide, or other biodegradable polymer, each of which can be capped to complete the terminal valence. In some embodiments, the compound can be capped with hydrogen, or can be capped to create a terminal ester or ether. For example, the moiety can be capped with a terminal hydroxyl or carboxy which can be further derivatized to an ether or ester;

$R^{17}$ is selected from: H and —C(O)A;

$L^4$ is bond, alkyl, alkenyl, alkynyl, —C(O)—, —C(S)—, —NH—, —N(alkyl)-, —O—, or alkyl-C(O)—;

$L^5$ is double bond, alkyl, or alkenyl; and wherein all other variables are defined herein.

In one embodiment $R^{11}$ is selected from: —NH—$C_4$-$C_{29}$alkenyl-CH=$R^{13}$, —NH—$C_4$-$C_{29}$alkynyl-CH=$R^{13}$, —NH—$C_4$-$C_{29}$alkenylalkynyl-CH=$R^{13}$, —NH—$C_2$-$C_{29}$alkyl-CH=$R^{13}$, —O—$C_4$-$C_{29}$alkenyl-CH=$R^{13}$, —O—$C_4$-$C_{29}$alkynyl-CH=$R^{13}$, —O—$C_4$-$C_{29}$alkenylalkynyl-CH=$R^{13}$, and —O—$C_2$-$C_{29}$alkyl-CH=$R^{13}$.

In various different embodiments, —$C_4$-$C_{29}$ as used in the definition of $R^{11}$ may be —$C_4$-$C_{28}$, —$C_4$-$C_{26}$, —$C_4$-$C_{24}$, —$C_6$-$C_{22}$, —$C_6$-$C_{20}$, —$C_8$-$C_{18}$, —$C_8$-$C_{16}$, —$C_8$-$C_{14}$, —$C_8$-$C_{12}$, —$C_8$-$C_{20}$, or —$C_6$-$C_{24}$.

Non-limiting examples of $R^{11}$ include:

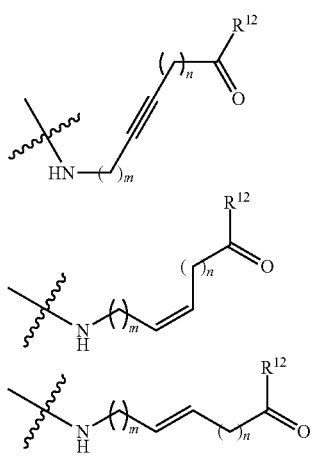

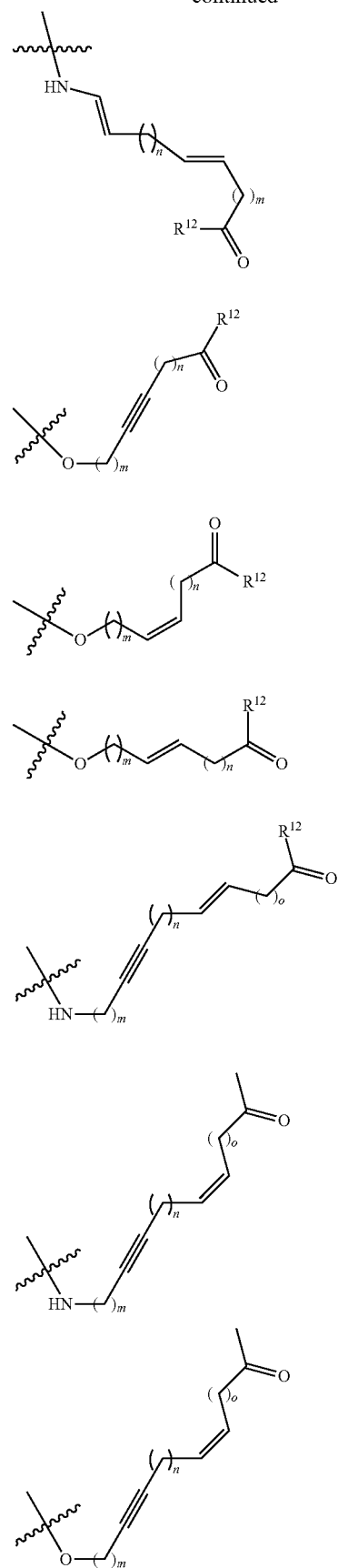

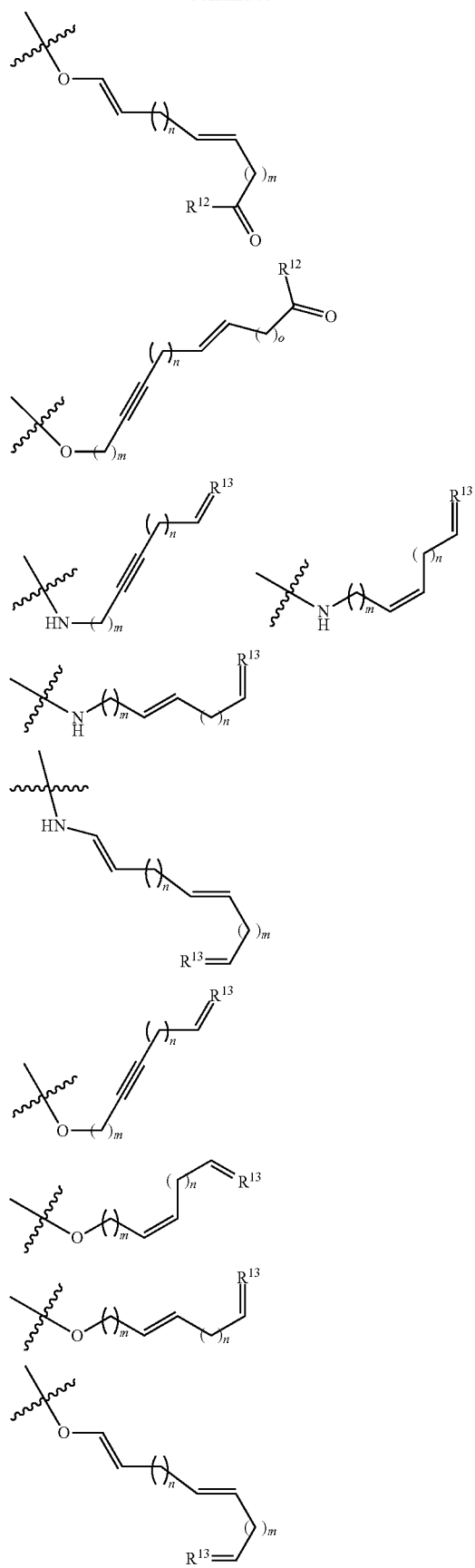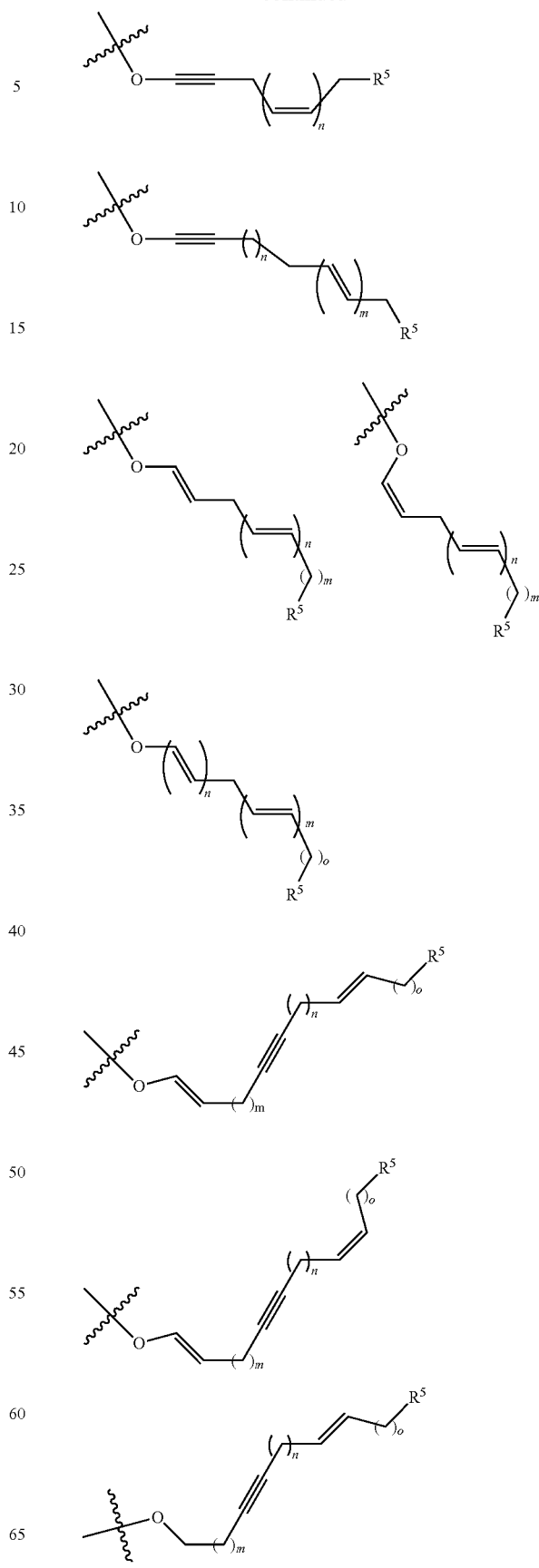

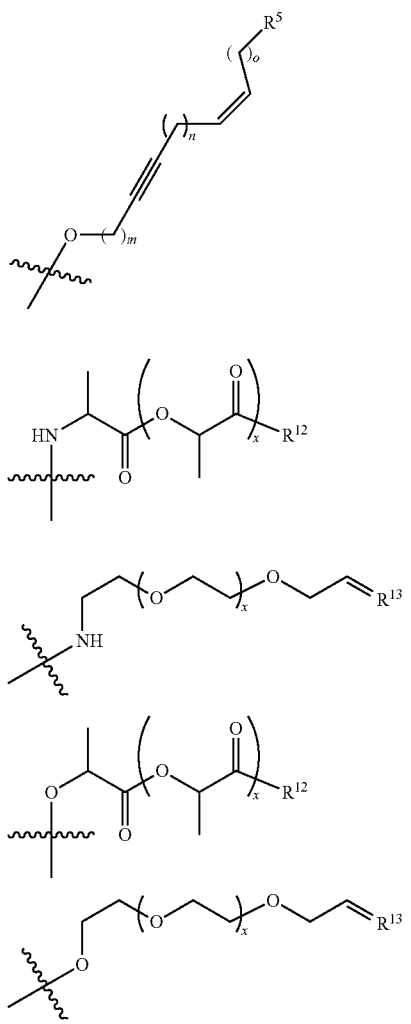
wherein n, m, o, x, and y are as defined above.
Non-limiting examples of $R^{16}$ include:
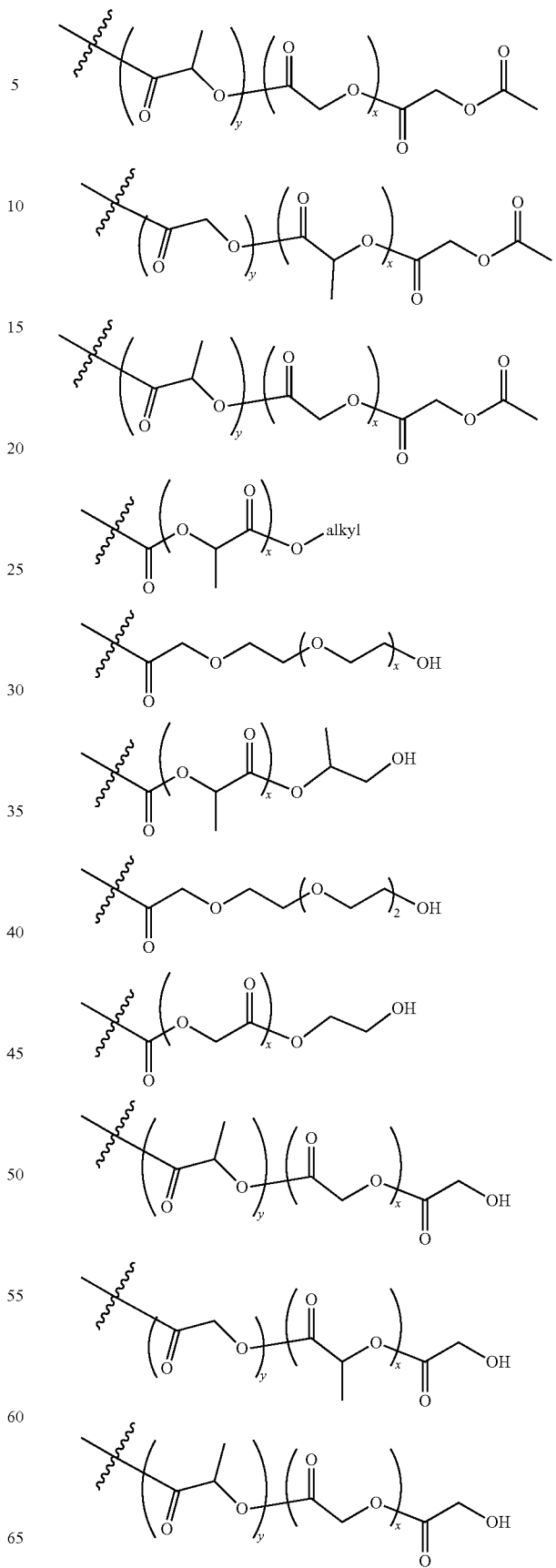

87
-continued
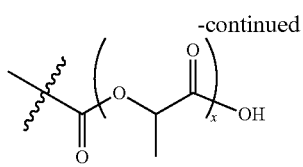
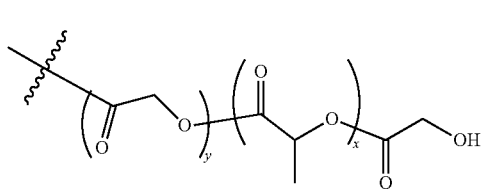
88
-continued
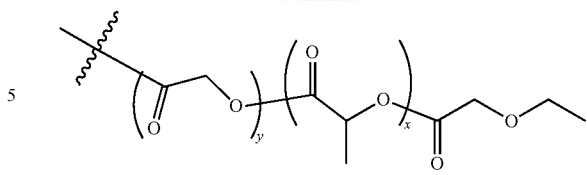
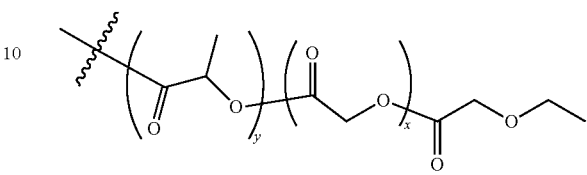
Non-limiting examples of Formula IVA include:
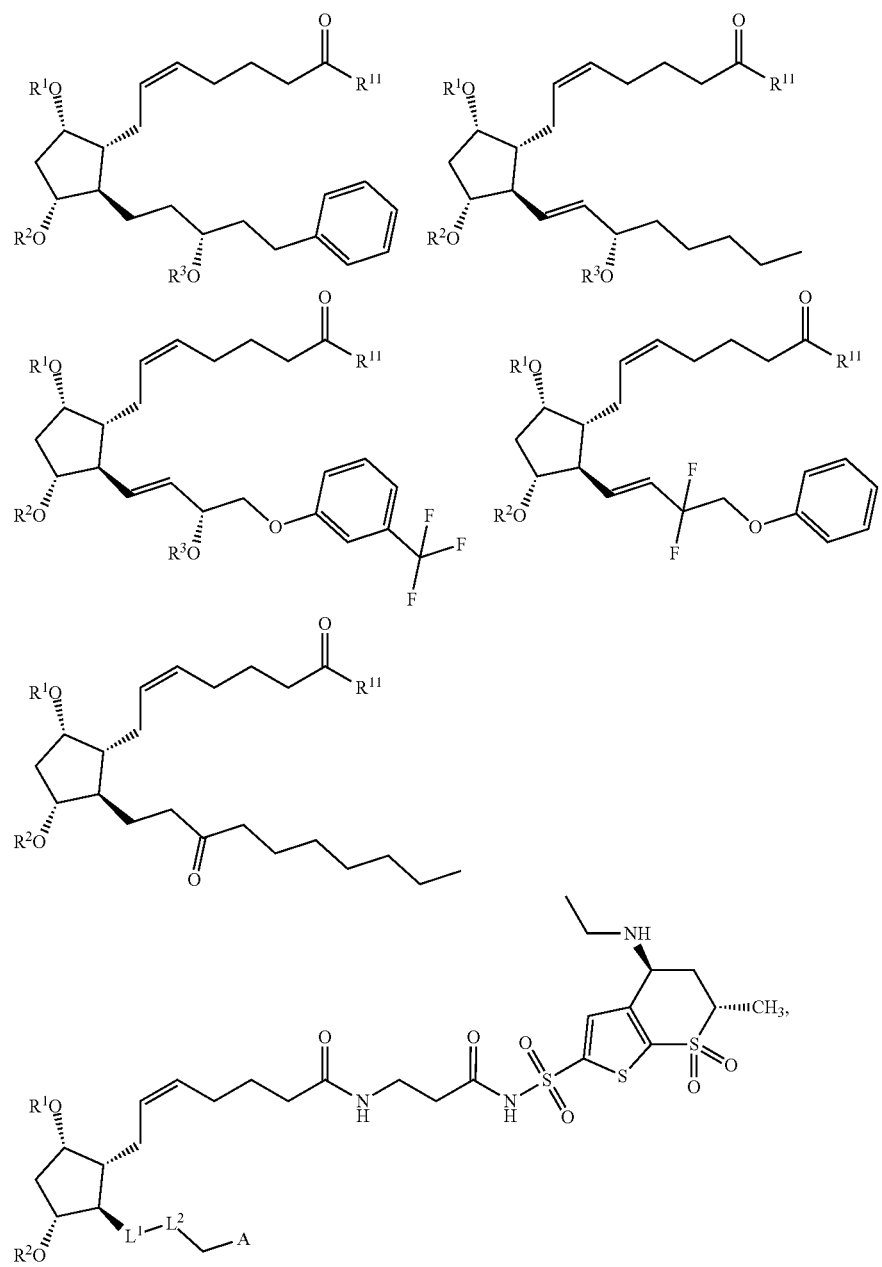

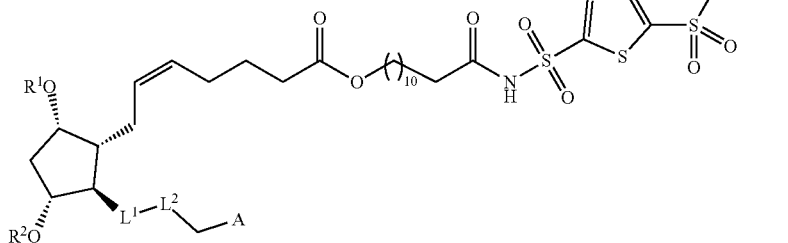
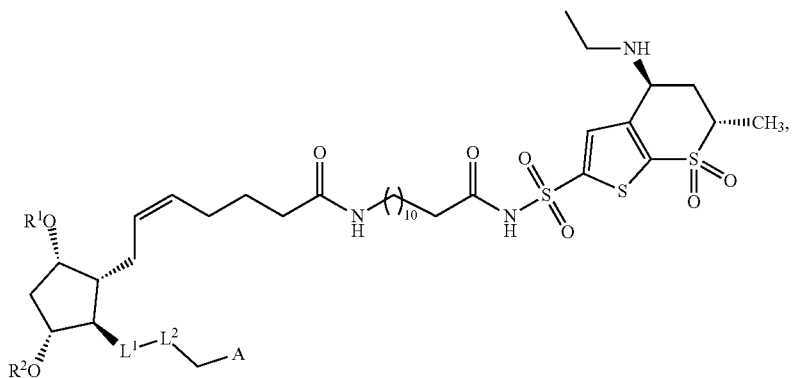
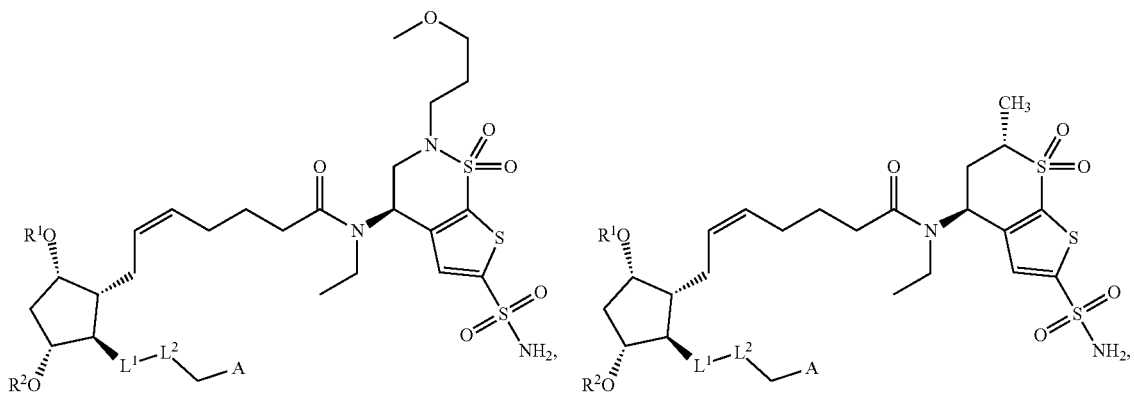
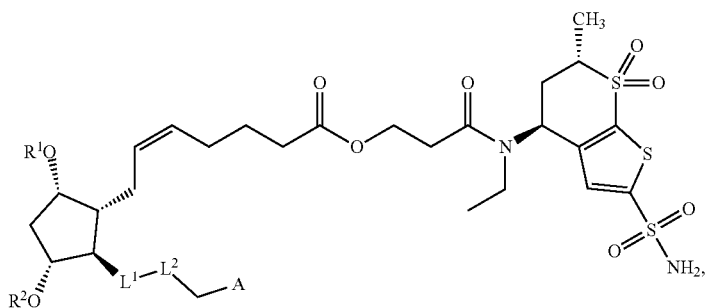

-continued
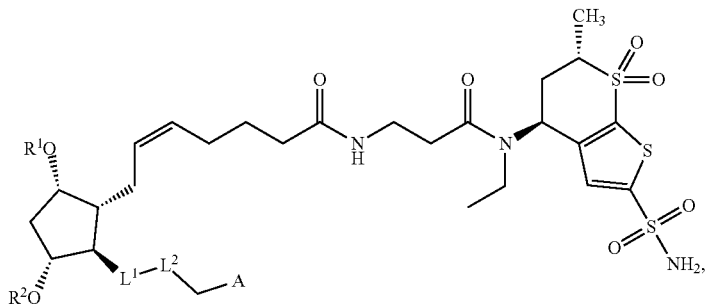
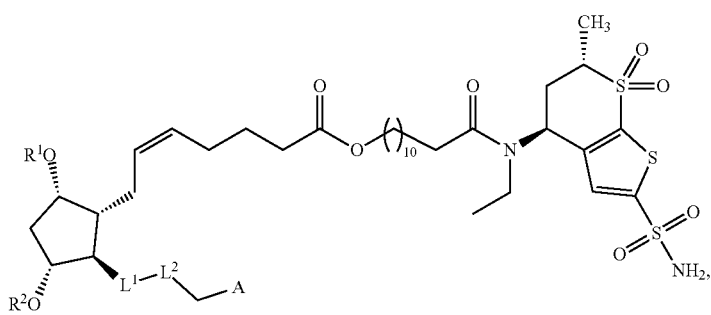
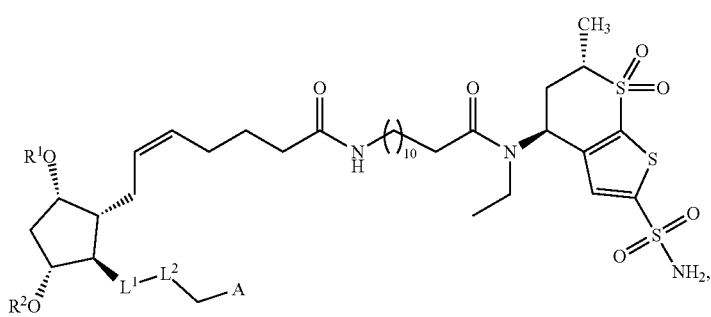
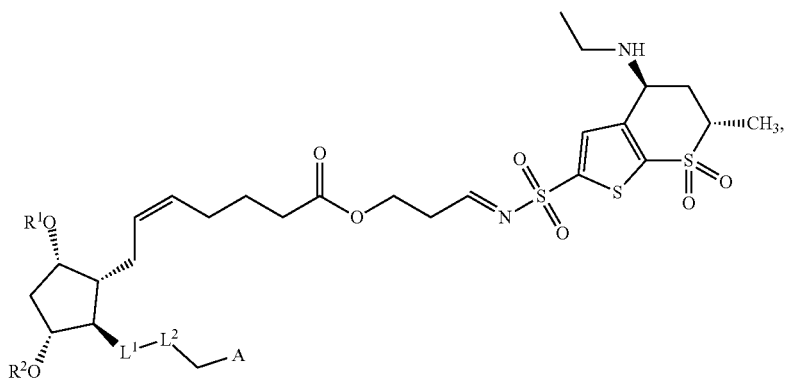
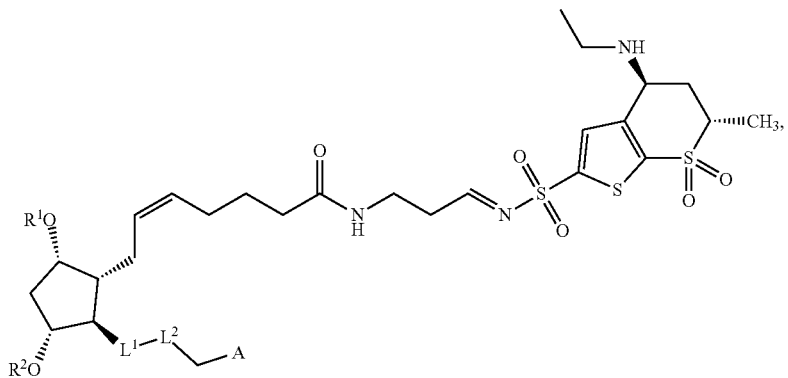

-continued

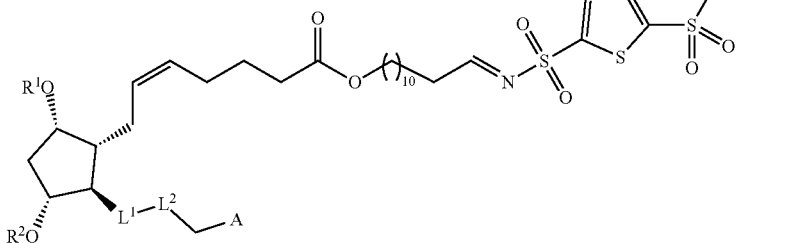

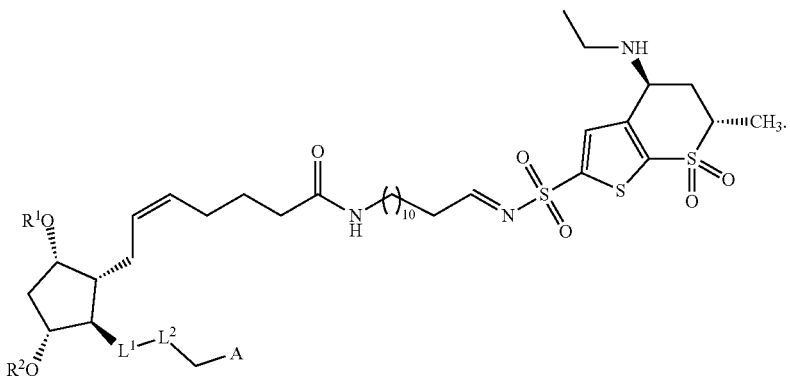

The disclosure provides prostaglandin prodrugs of Formula VA:

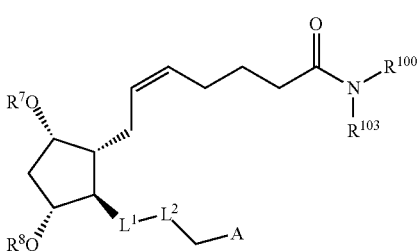

(VA)

or a pharmaceutically acceptable composition, salt, or isotopic derivative thereof wherein $R^{103}$ is selected from: H, alkyl, cycloalkyl, cycloalkylalkyl, heterocycle, heterocycloalkyl, aryl, arylalkyl, heteroaryl, and heteroarylalkyl wherein each group other than hydrogen can be optionally substituted with another desired substituent group which is pharmaceutically acceptable and sufficiently stable under the conditions of use, for example selected from $R^5$;

$R^{100}$ is selected from:

(i) $C_1$-$C_{10}$alkyl, —$C_0$-$C_{10}$alkyl($C_3$-$C_7$cycloalkyl), heterocycle, —$C_0$-$C_{10}$alkyl($C_3$-$C_7$heterocycloalkyl), -aryl$C_0$-$C_{10}$alkyl, -heteroarylalkyl, —$C_0$-$C_{10}$alkyl$C_2$-$C_{10}$alkenyl, and $C_2$-$C_{10}$alkynyl;

(ii) an unsaturated fatty acid residue including but not limited the carbon fragment taken from linoleic acid (—$(CH_2)_8(CH)_2CH_2(CH)_2(CH_2)_4CH_3$)), docosahexaenoic acid (—$(CH_2)_3(CHCHCH_2)_6CH_3$)), eicosapentaenoic acid (—$(CH_2)_4(CHCHCH_2)_5CH_3$)), alpha-linolenic acid (—$(CH_2)_8(CHCHCH_2)_3CH_3$)) stearidonic acid, y-linolenic acid, arachidonic acid, docosatetraenoic acid, palmitoleic acid, vaccenic acid, paullinic acid, oleic acid, elaidic acid, gondoic acid, euric acid, nervonic acid and mead acid;

(iii) —$C_{10}$-$C_{30}$alkyl$R^5$, —$C_{10}$-$C_{30}$alkenyl$R^5$, —$C_{10}$-$C_{30}$alkynyl$R^5$, —$C_{10}$-$C_{30}$alkenylalkynyl$R^5$, —$C_{10}$-$C_{30}$alkyl, —$C_{10}$-$C_{30}$alkenyl, —$C_{10}$-$C_{30}$alkynyl, —$C_{10}$-$C_{30}$alkenylalkynyl; and (iv) $R^{50}$;

wherein $R^{100}$ in Formula VA can only be selected from (i), (ii), and (iii) above if at least one of $R^7$ and $R^8$ is selected to be $R^{50}$; and wherein all other variables are defined herein.

In one embodiment, —$C_0$-$C_{30}$ as used in the definition of $R^{100}$ is —$C_{12}$-$C_{28}$, —$C_{12}$-$C_{26}$, —$C_{12}$-$C_{24}$, —$C_{14}$-$C_{22}$, —$C_{14}$-$C_{20}$, —$C_{14}$-$C_{18}$, —$C_{14}$-$C_{16}$, or —$C_{12}$-$C_{14}$.

Non-limiting examples of Formula VA include:

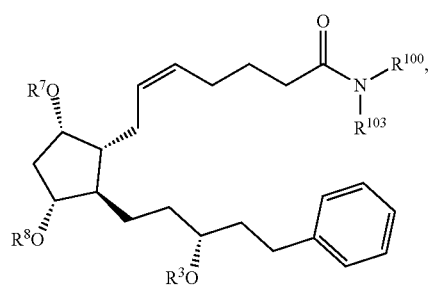

-continued

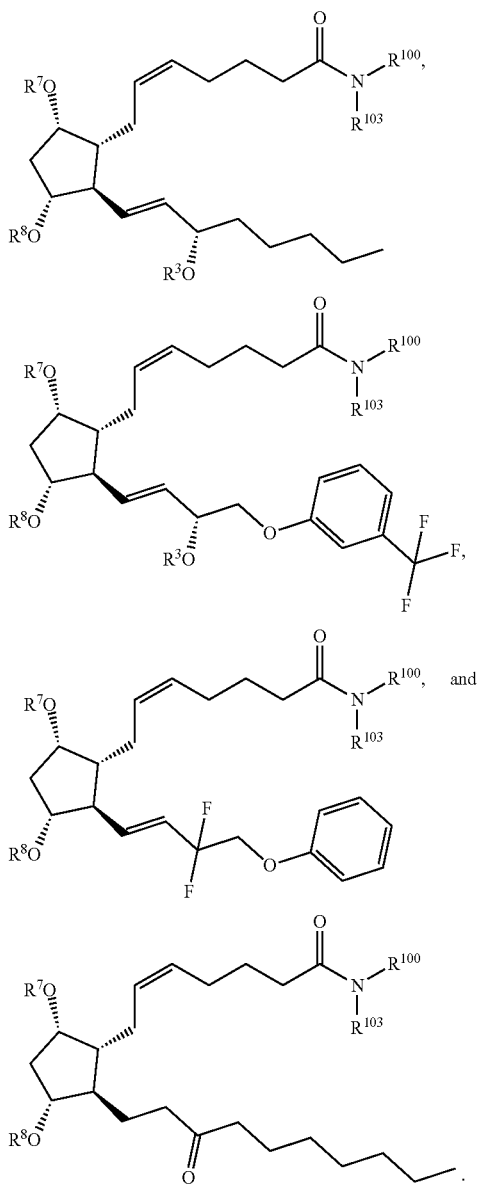

The disclosure provides prostaglandin prodrugs of Formula VIA:

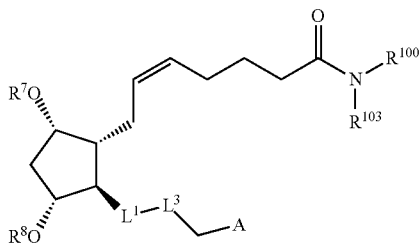

(VIA)

or a pharmaceutically acceptable composition, salt, or isotopic derivative thereof wherein all variables are as defined herein.

Non-limiting examples of Formula VIA include:

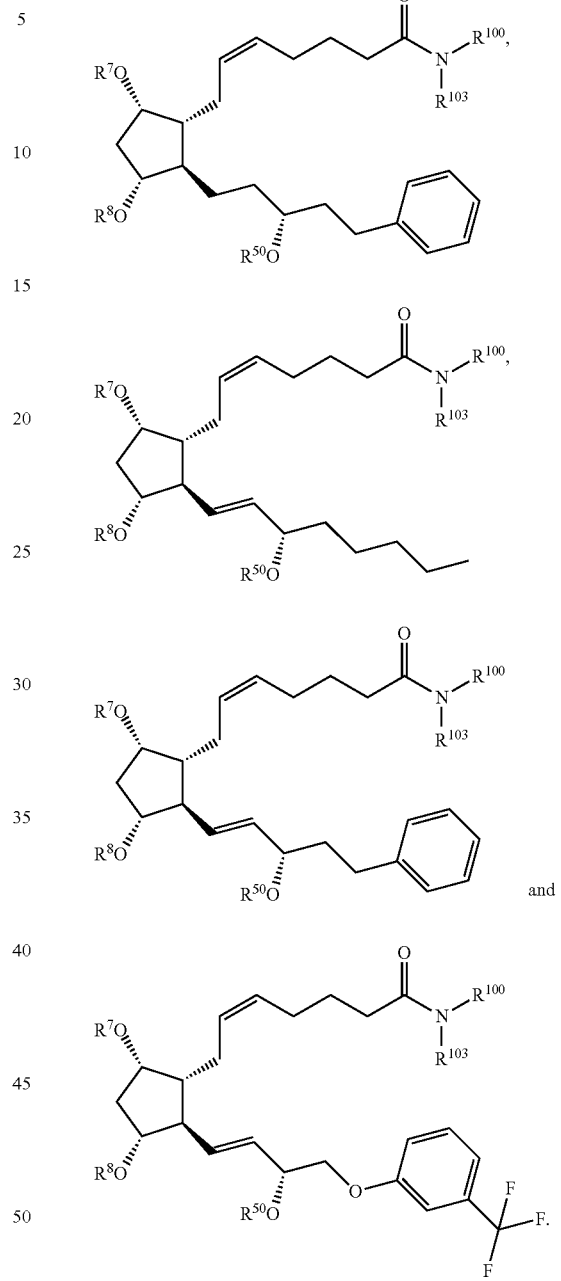

In one embodiment, $R^{100}$ is ethyl and $R^{103}$ is hydrogen.

In one embodiment, $R^{50}$ is

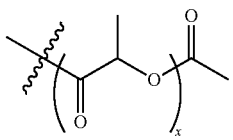

.

The disclosure provides prostaglandin prodrugs of Formula VIIA:

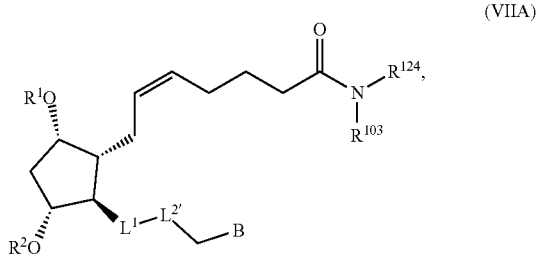

(VIIA)

or a pharmaceutically acceptable composition, salt, or isotopic derivative thereof.

$L^{2'}$ is selected from:

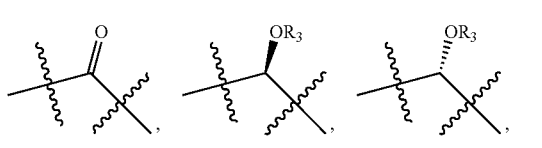

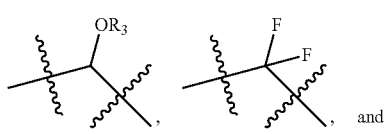

, and

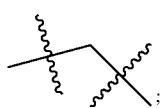

;

B is selected from: heterocycle, heterocycloalkyl, aryl, arylalkyl, heteroaryl, heteroarylalkyl, aryloxy, and alkyloxy wherein each group can be optionally substituted with another desired substituent group which is pharmaceutically acceptable and sufficiently stable under the conditions of use, for example selected from $R^5$; and $R^1$, $R^2$, and $R^3$ are independently selected from: —C(O)$R^4$, C(O)A, and hydrogen, wherein in Formula VIIA, $R^1$ or $R^2$ is —C(O)$R^4$;

$R^{124}$ is selected from:

(i) an unsaturated fatty acid residue containing at least 22 carbon atoms including but not limited to the carbon chains from docosahexaenoic acid (—(CH$_2$)$_3$(CHCHCH$_2$)$_6$CH$_3$)), alpha-linolenic acid (—(CH$_2$)$_8$(CHCHCH$_2$)$_3$CH$_3$)), docosatetraenoic acid, and nervonic acid, (ii) —C$_{22}$-C$_{30}$alkylR$^5$, —C$_{22}$-C$_{30}$alkenylR$^5$, —C$_{22}$-C$_{30}$alkynylR$^5$, —C$_{22}$-C$_{30}$alkenylalkynylR$^5$, —C$_{22}$-C$_{30}$alkyl, —C$_{22}$-C$_{30}$alkenyl, —C$_{22}$-C$_{30}$alkynyl, —C$_{22}$-C$_{30}$alkenylalkynyl;

and wherein, if desired, each $R^{124}$ can be substituted with $R^5$; and wherein all other variables are defined herein.

Non-limiting examples of Formula VIIA include:

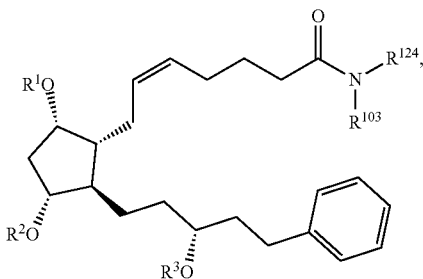

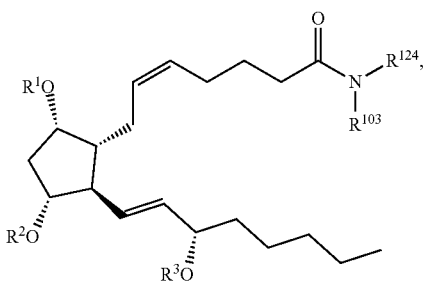

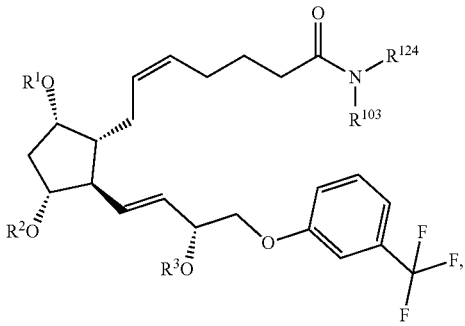

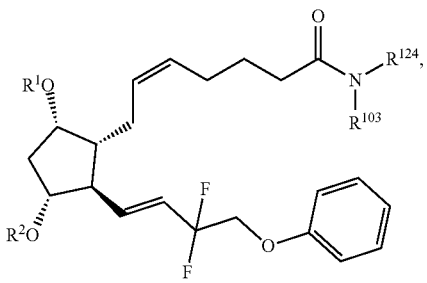

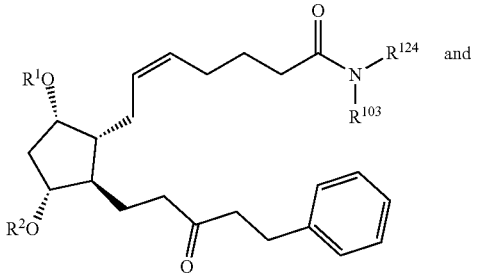

and

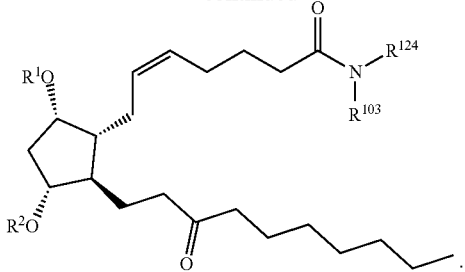

In one embodiment, —C$_{22}$-C$_{30}$ as used in the definition of R$^4$ is —C$_{22}$-C$_{28}$, —C$_{22}$-C$_{26}$, or —C$_{22}$-C$_{24}$.

The disclosure provides prostaglandin prodrugs of Formula VIIIA:

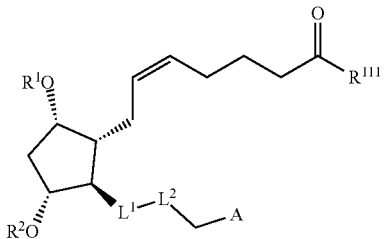

(VIIIA)

or a pharmaceutically acceptable composition, salt, or isotopic derivative thereof.

R$^{111}$ is selected from:

(i) R$^{102}$;

(ii) —NH—C$_2$-C$_{30}$alkenyl-C(O)R$^{102}$, —NH—C$_2$-C$_{30}$alkynyl-C(O)R$^{102}$, —NH—C$_2$-C$_{30}$alkenylalkynyl-C(O)R$^{102}$, —NH—C$_1$-C$_{30}$alkyl-C(O)R$^{102}$, —O—C$_2$-C$_{30}$alkenyl-C(O)R$^{102}$, —O—C$_2$-C$_{30}$alkynyl-C(O)R$^{102}$, —O—C$_2$-C$_{30}$alkenylalkynyl-C(O)R$^{102}$, and —O—C$_1$-C$_{30}$alkyl-C(O)R$^{102}$;

(iii)

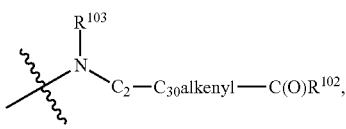

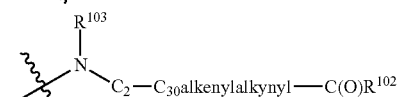

and

(iv) polyethylene glycol, polypropylene glycol, polypropylene oxide, polylactic acid, and poly(lactic-co-glycolic acid) capped with R$^{102}$,

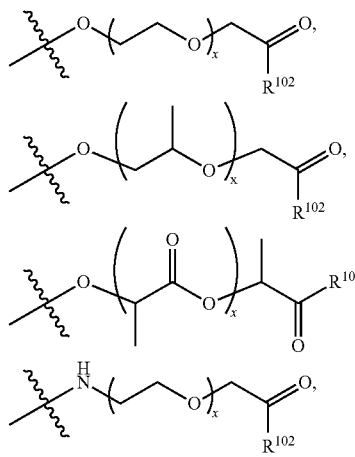

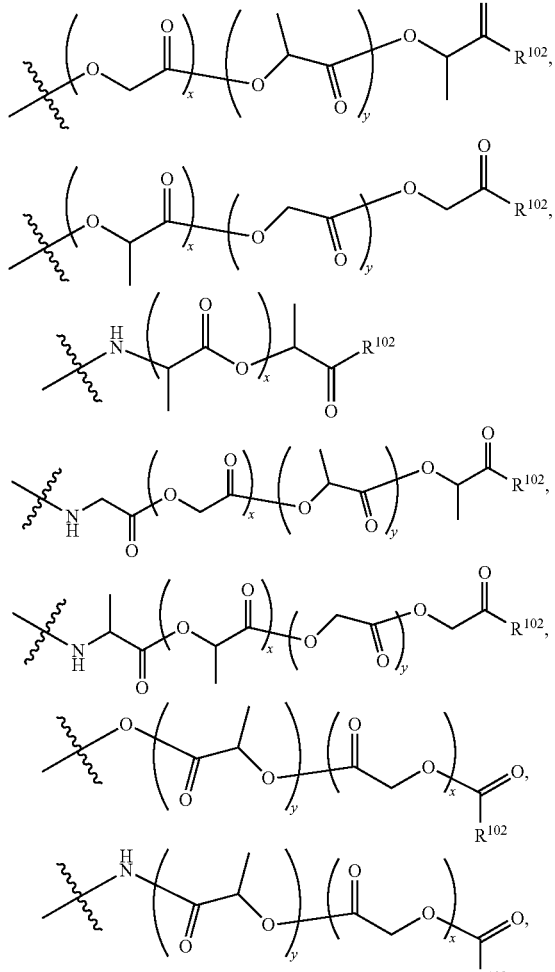

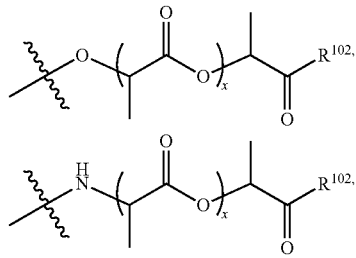

-continued

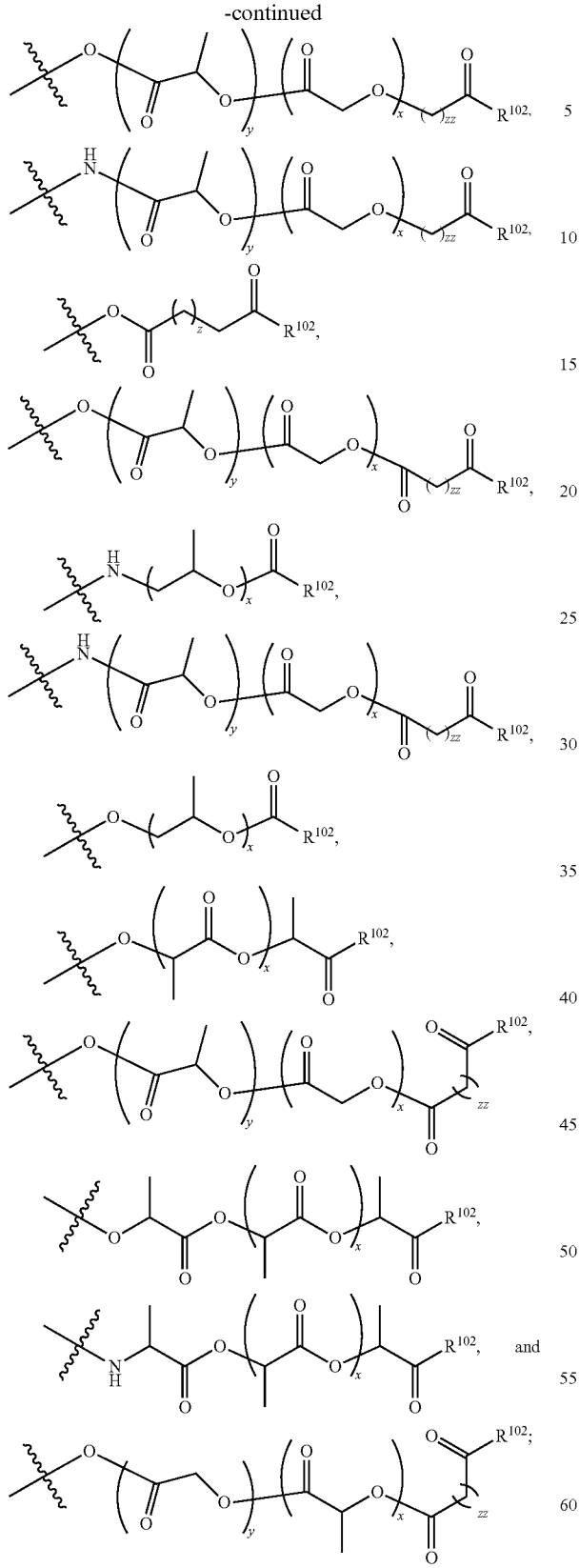

wherein R¹¹¹ can be further substituted with R⁵ if valence permits, a stable compound is formed, and the resulting compound is pharmaceutically acceptable;

R¹⁰² is

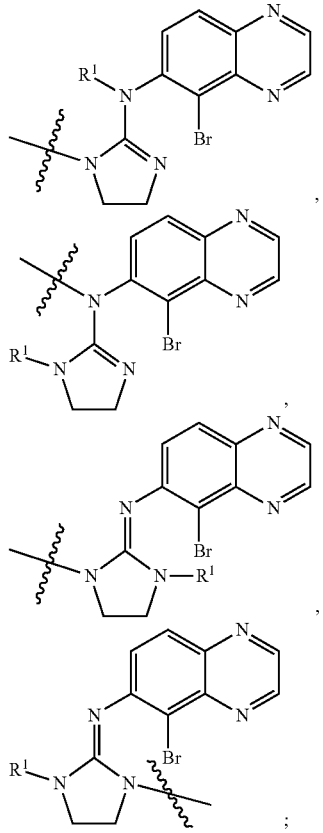

and
wherein all other variables are as defined herein.

In various different embodiments, —$C_2$-$C_{30}$ as used in the definition of R¹¹¹ may be —$C_2$-$C_{28}$, —$C_4$-$C_{26}$, —$C_4$-$C_{24}$, —$C_6$-$C_{22}$, —$C_6$-$C_{20}$, —$C_5$-$C_{18}$, —$C_5$-$C_{16}$, —$C_5$-$C_{14}$, —$C_5$-$C_{12}$, —$C_8$-$C_{20}$, or —$C_6$-$C_{24}$ Non-limiting examples of Formula VIIIA include:

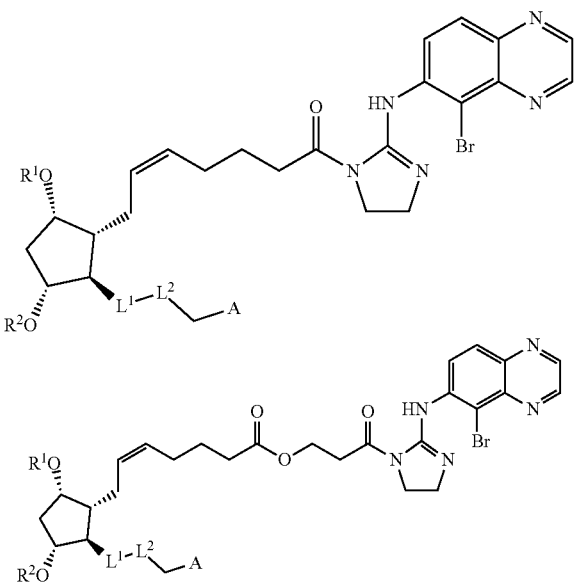

-continued

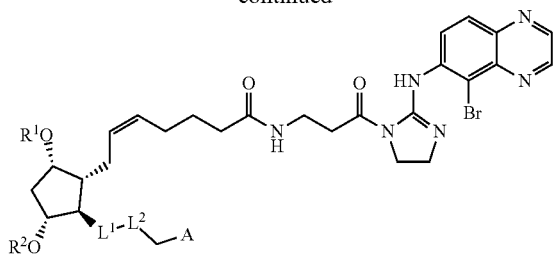

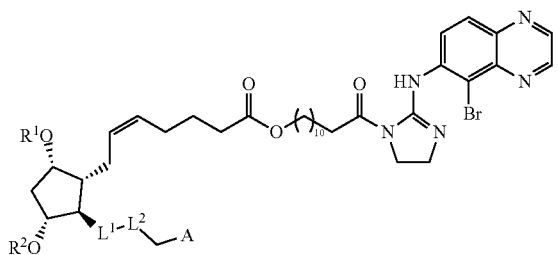

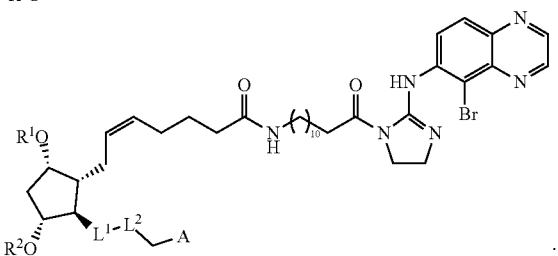

The disclosure also provides prostaglandin prodrugs of Formula IXA, Formula XA, Formula XIA, and Formula XIIA:

(IXA)

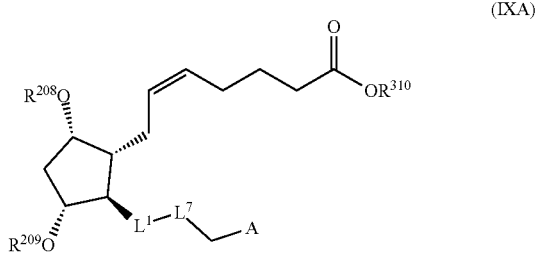

(XA)

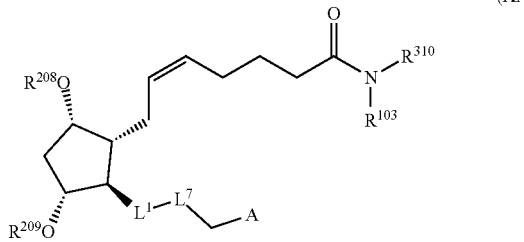

(XIA)

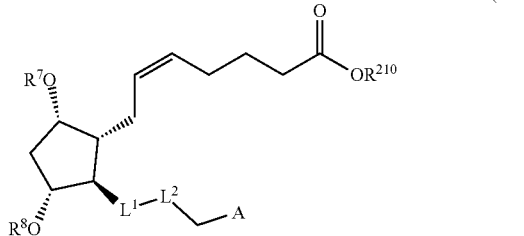

(XIIA)

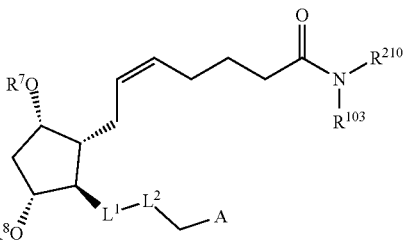

or a pharmaceutically acceptable composition, salt, or isotopic derivative thereof wherein $R^{310}$ is alkyl or hydrogen;

$L^7$ is selected from:

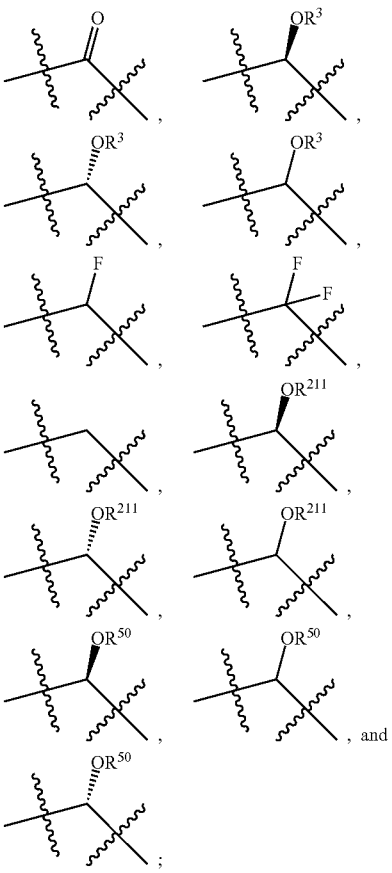

$R^{208}$ and $R^{209}$ are independently selected from: —C(O)$R^{4b}$, —C(O)A, hydrogen, $R^{211}$, and $L^8$-$R^{212}$;

$R^{4b}$ is selected from:
(i) —$C_{10}$-$C_{30}$alkyl$R^5$, —$C_{10}$-$C_{30}$alkenyl$R^5$, —$C_{10}$-$C_{30}$alkynyl$R^5$, —$C_{10}$-$C_{30}$alkenylalkynyl$R^5$, —$C_{10}$-$C_{30}$alkyl, —$C_{10}$-$C_{30}$alkenyl, —$C_{10}$-$C_{30}$alkynyl, —$C_{10}$-$C_{30}$alkenylalkynyl;
(ii) an unsaturated fatty acid residue including but not limited to the carbon chains from linoleic acid (—$(CH_2)_8(CH)_2CH_2(CH)_2(CH_2)_4CH_3$), docosahexaenoic acid (—$(CH_2)_3(CHCHCH_2)_6CH_3$), eicosapentaenoic acid (—$(CH_2)_4(CHCHCH_2)_5CH_3$), alpha-linolenic acid (—$(CH_2)_8(CHCHCH_2)_3CH_3$) stearidonic acid, γ-linolenic acid, arachidonic acid, docosatetraenoic acid, palmitoleic acid, vaccenic acid, paullinic acid, oleic acid, elaidic acid, gondoic acid, euric acid, nervonic acid or mead acid, and wherein, if desired, each of which can be substituted with $R^5$.

wherein either at least one of $R^{208}$ and $R^{209}$ is $R^{211}$ or L-$R^{212}$; or $L^7$ is selected from

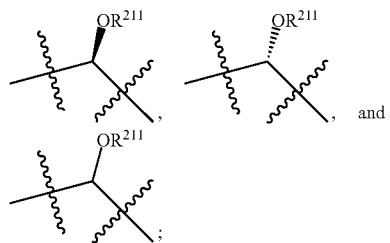

$L^8$ is —C(O)-alkyl-C(O)—, and —C(O)-alkenyl-C(O)—; $R^{210}$ is

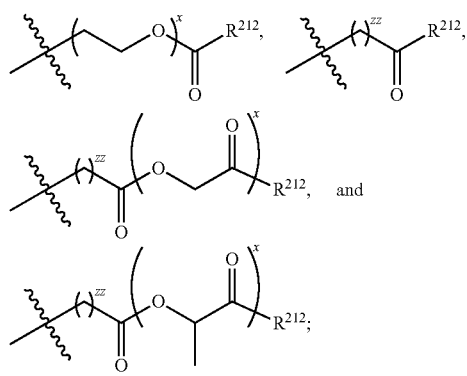

$R^{211}$ is selected from:

polyethylene glycol, polypropylene glycol, polypropylene oxide, polylactic acid, a biodegradable polymer and poly(lactic-co-glycolic acid) each of which is optionally linked by a carbonyl and each is capped with $R^{212}$ including:

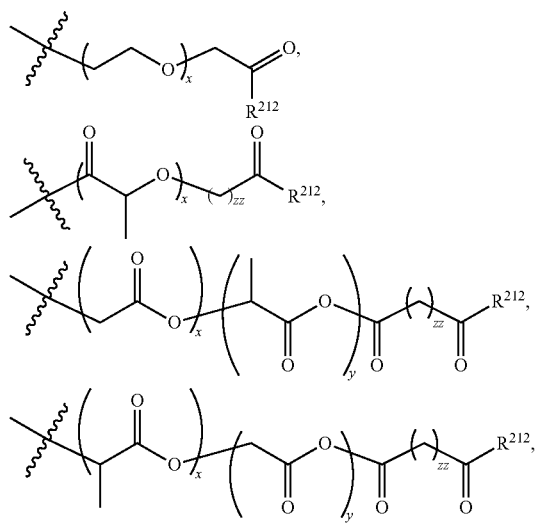

-continued

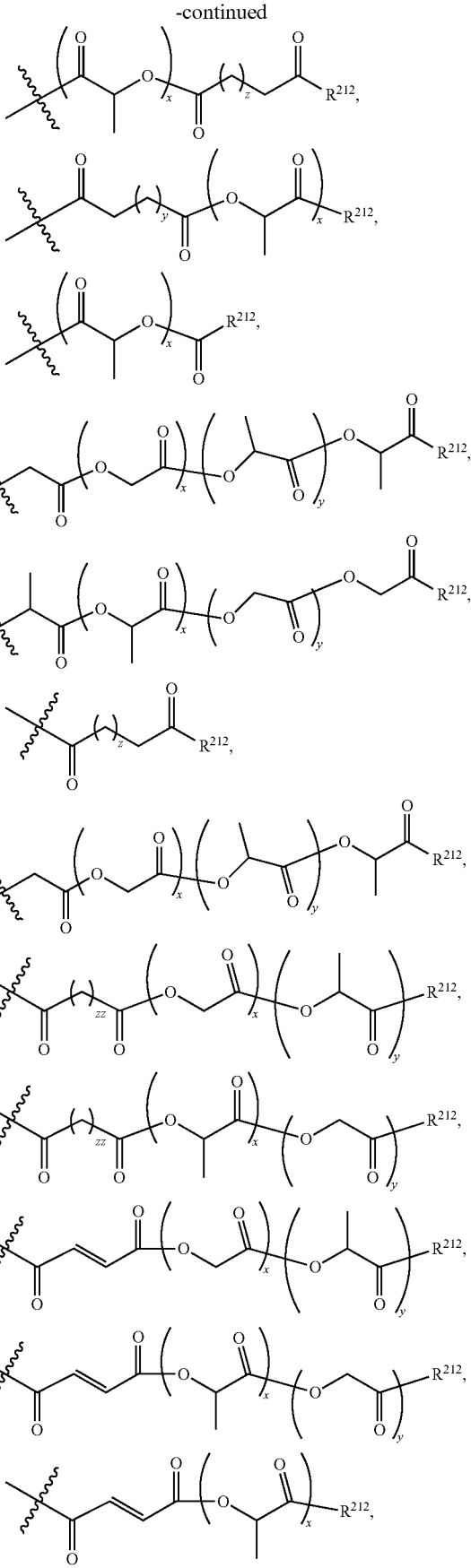

107
-continued
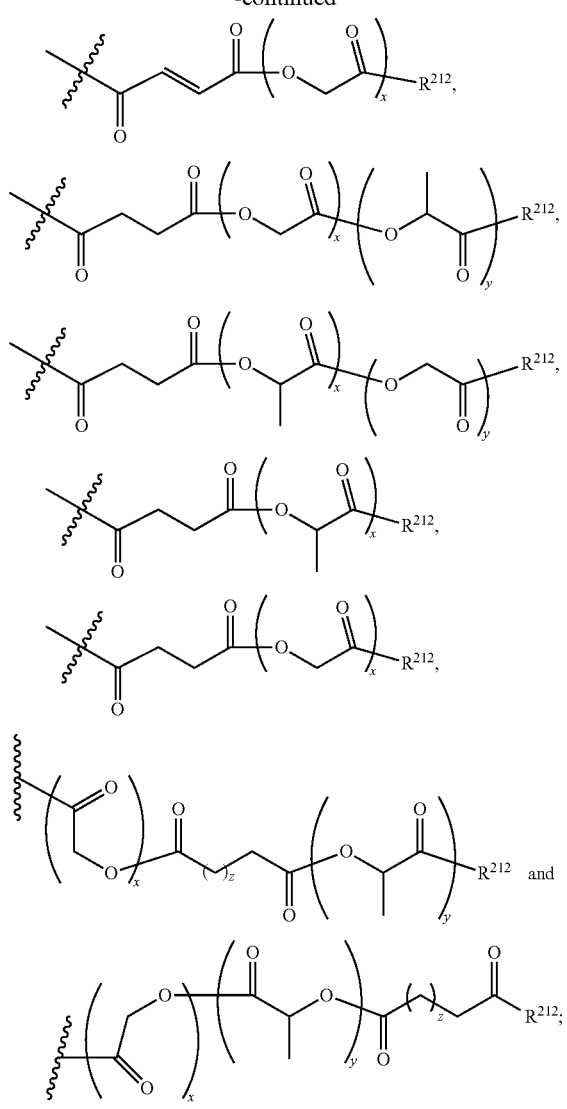
$R^{212}$ is selected from:
108
-continued
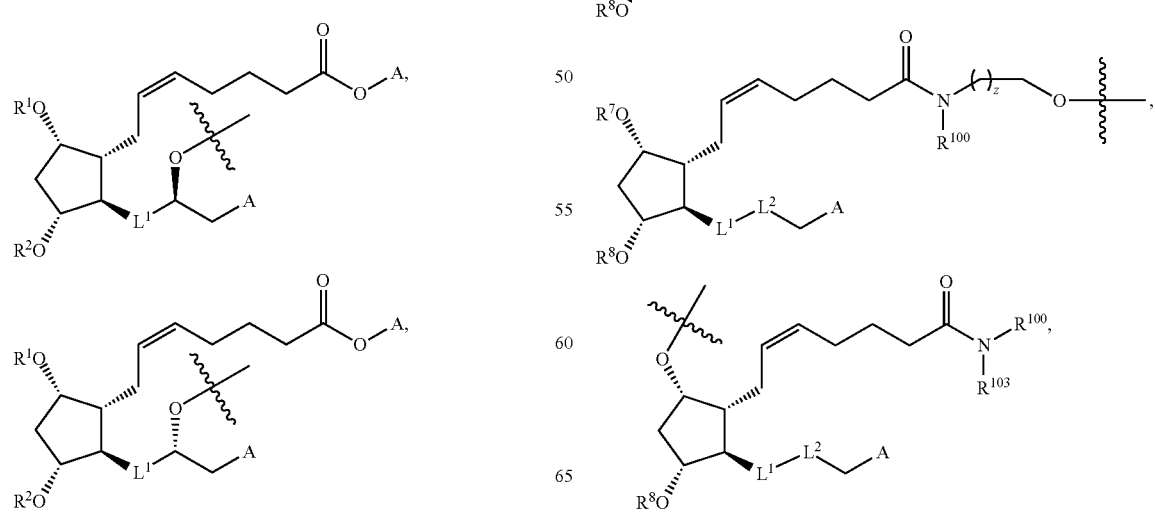

-continued

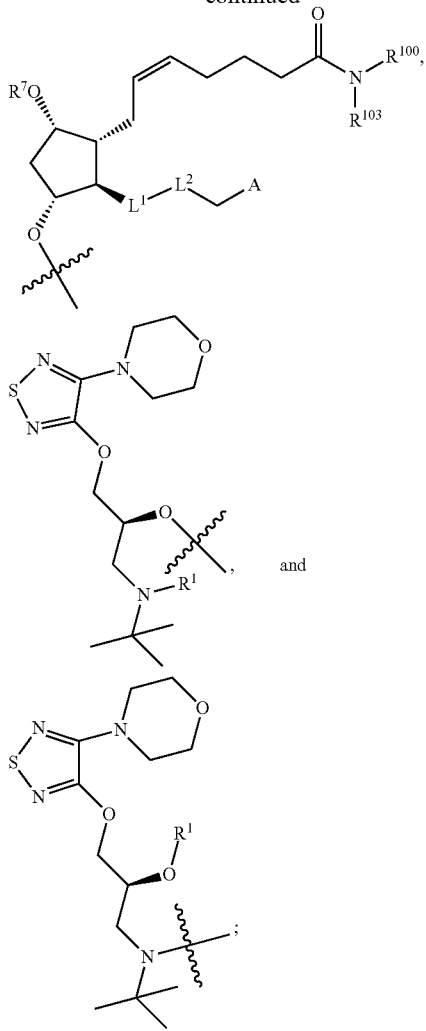

and
wherein all other variables are defined herein.
In one embodiment $R^{212}$ is

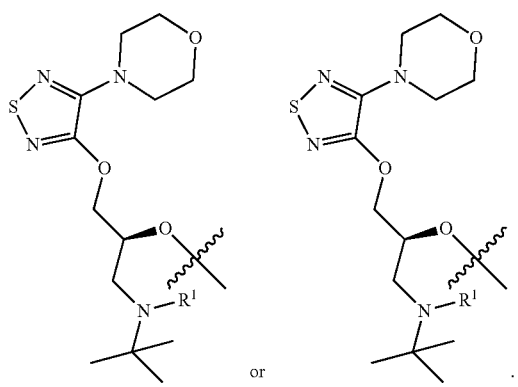

Carbonic Anhydrase Inhibitor Prodrugs

The disclosure provides carbonic anhydrase inhibitor prodrugs of Formula IB, Formula IIB, Formula IIIB and Formula IVB:

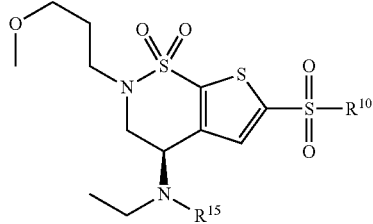

(IB)

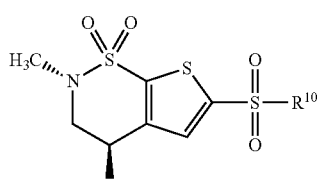

(IIB)

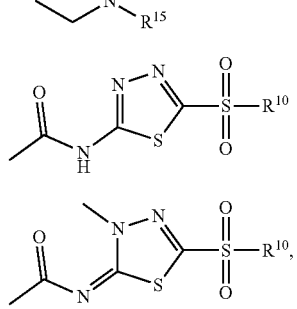

(IIIB)

(IVB)

or a pharmaceutically acceptable composition, salt, or isotopic derivative thereof wherein $R^{10}$ is selected from:

(i) $-N=C_4-C_{30}$alkenyl$R^5$, $-N=C_4-C_{30}$alkynyl$R^5$, $-N=C_4-C_{30}$alkenylalkynyl$R^5$, $-N=C_1-C_{30}$alkyl$R^5$, $-N=C_4-C_{30}$alkenyl, $-N=C_4-C_{30}$alkynyl, $-N=C_4-C_{30}$alkenylalkynyl, $-N=C_1-C_{30}$alkyl, $-N=CH-C_3-C_{30}$alkenyl$R^5$, $-N=CH-C_3-C_{30}$alkynyl$R^5$, $-N=CH-C_3-C_{30}$alkenylalkynyl$R^5$, $-N=C_1-C_{30}$alkyl$R^5$, $-N=CH-C_3-C_{30}$alkenyl, $-N=CH-C_3-C_{30}$alkynyl, $-N=CH-C_3-C_{30}$alkenylalkynyl, $-N=C_1-C_{30}$alkyl, $-NHC_3-C_{30}$alkenyl$R^5$, $-NH-C_3-C_{30}$alkynyl$R^5$, $-NH-C_5-C_{30}$alkenylalkynyl$R^5$, $-NHC_0-C_{30}$alkyl$R^5$, $-NHC_3-C_{30}$alkenyl$R^{16}$, $-NH-C_3-C_{30}$alkynyl$R^{16}$, $-NH-C_5-C_{30}$alkenylalkynyl$R^{16}$, $-NHC_0-C_{30}$alkyl$R^{16}$;

(ii) an imine-, amine- or amide-linked unsaturated fatty acid residue including but not limited to derivatives of linoleic acid ($-N=CH(CH_2)_7(CH)_2CH_2(CH)_2(CH_2)_4CH_3$, $-NHCH_2(CH_2)_7(CH)_2CH_2(CH)_2(CH_2)_4CH_3$, or $-NHC(O)(CH_2)_7(CH)_2CH_2(CH)_2(CH_2)_4CH_3$), docosahexaenoic acid ($-N=CH(CH_2)_2(CHCHCH_2)_6CH_3$, $-NH(CH_2)_3(CHCHCH_2)_6CH_3$, or $-NHC(O)(CH_2)_2(CHCHCH_2)_6CH_3$), eicosapentaenoic acid ($-N=CH(CH_2)_3(CHCHCH_2)_5CH_3$, $-NH(CH_2)_4(CHCHCH_2)_5CH_3$, or $-NHC(O)(CH_2)_3(CHCHCH_2)_5CH_3$), alpha-linolenic acid ($-N=CH(CH_2)_7(CHCHCH_2)_3CH_3$, $-NH(CH_2)_4(CHCHCH_2)_5CH_3$, or $-NHC(O)(CH_2)_3(CHCHCH_2)_5CH_3$), stearidonic acid, γ-linolenic acid, arachidonic acid, docosatetraenoic acid, palmitoleic acid, vaccenic acid, paullinic acid, oleic acid, elaidic acid, gondoic acid, euric acid, nervonic acid or mead acid, each of which can be further substituted with $R^5$ (including for example a second $R^5$) if valence permits, a stable compound is formed, and the resulting compound is pharmaceutically acceptable;

(iii) an imine-, amine- or amide-linked polypropylene glycol, polypropylene oxide, polylactic acid, or poly(lactic-co-glycolic acid) including:

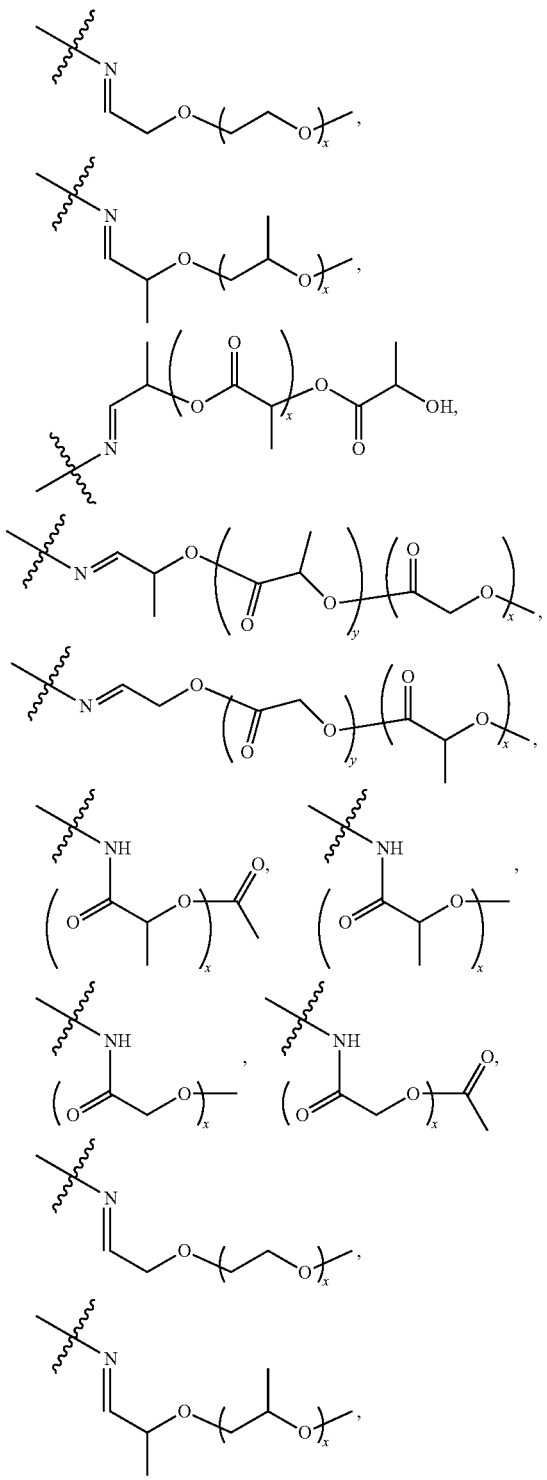

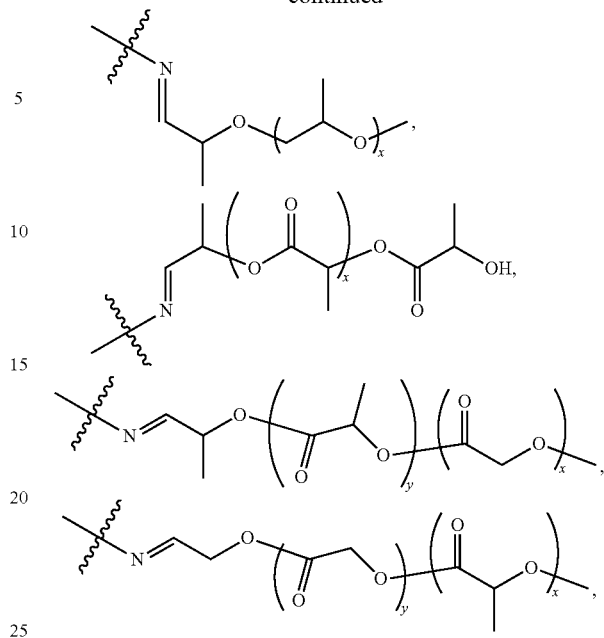

or polyglycolic acid, or a polyester, polyamide, or other biodegradable polymer, each of which can be capped to complete the terminal valence. In some embodiments, the compound can be capped with hydrogen, or can be capped to create a terminal ester or ether. For example, the moiety can be capped with a terminal hydroxyl or carboxy which can be further derivatized to an ether or ester. And wherein each of which can be further substituted with $R^5$ if valence permits, a stable compound is formed, and the resulting compound is pharmaceutically acceptable; and wherein in some embodiments a terminal hydroxy or carboxy group can be substituted to create an ether or ester, respectively;

(iv) —NHC(O)C$_{1-20}$alkyl, —NHC(O)C$_{1-20}$alkenyl, —NHC$_{1-20}$alkynyl, —NHC(O)(C$_{1-20}$alkyl with at least one $R^5$ substituent on the alkyl chain), —NHC(O)(C$_{1-20}$alkenyl with at least one $R^5$ substituent on the alkenyl chain), —NHC(O)(C$_{1-20}$alkynyl with at least one $R^5$ substituent on the alkynyl chain), —NH(lactic acid)$_{2-20}$ C(O)C$_{1-20}$alkyl, —NH(lactic acid)$_{2-10}$C(O)C$_{1-20}$alkyl, —NH(lactic acid)$_{4-20}$C(O)C$_{1-20}$alkyl, —NH(lactic acid)$_{2-20}$C(O)C$_{1-10}$alkyl, —NH(lactic acid)$_{2-20}$C(O)C$_{4-10}$alkyl, —NH(lactic acid)$_{2-20}$C(O)OH, —NH(lactic acid)$_{2-10}$C(O)OH, —NH(lactic acid)$_{4-20}$C(O)OH, —NH(lactic acid)$_{2-10}$C(O)OH, —NH(lactic acid)$_{4-10}$C(O)OH, —NH(lactide-co-glycolide)$_{2-10}$C(O)C$_{1-20}$alkyl, —NH(lactide-co-glycolide)$_{4-10}$C(O)C$_{1-20}$alkyl, —NH(lactide-co-glycolide)$_{2-10}$C(O)C$_{1-10}$alkyl, —NH(lactide-co-glycolide)$_{2-10}$C(O)C$_{4-20}$alkyl, —NH(glycolic acid)$_{2-10}$ C(O)C$_{1-10}$alkyl, —NH(glycolic acid)$_{4-10}$ C(O)C$_{1-10}$alkyl, —NH(lactic acid)$_{4-10}$C(O)C$_{1-10}$alkyl, —NH(lactic acid)$_{2-10}$C(O)C$_{1-10}$alkyl, NH(lactic acid)$_{2-10}$C(O)C$_{4-10}$alkyl, —NH(lactic acid)$_{2-10}$C(O)C$_{4-10}$alkyl, or —NH(lactic acid)$_{2-10}$C(O)C$_{4-10}$alkyl;

(v)

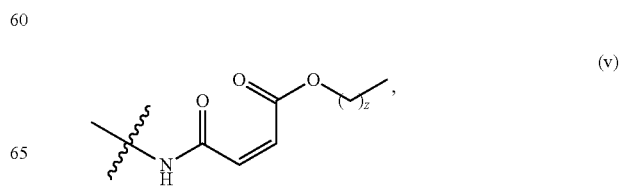

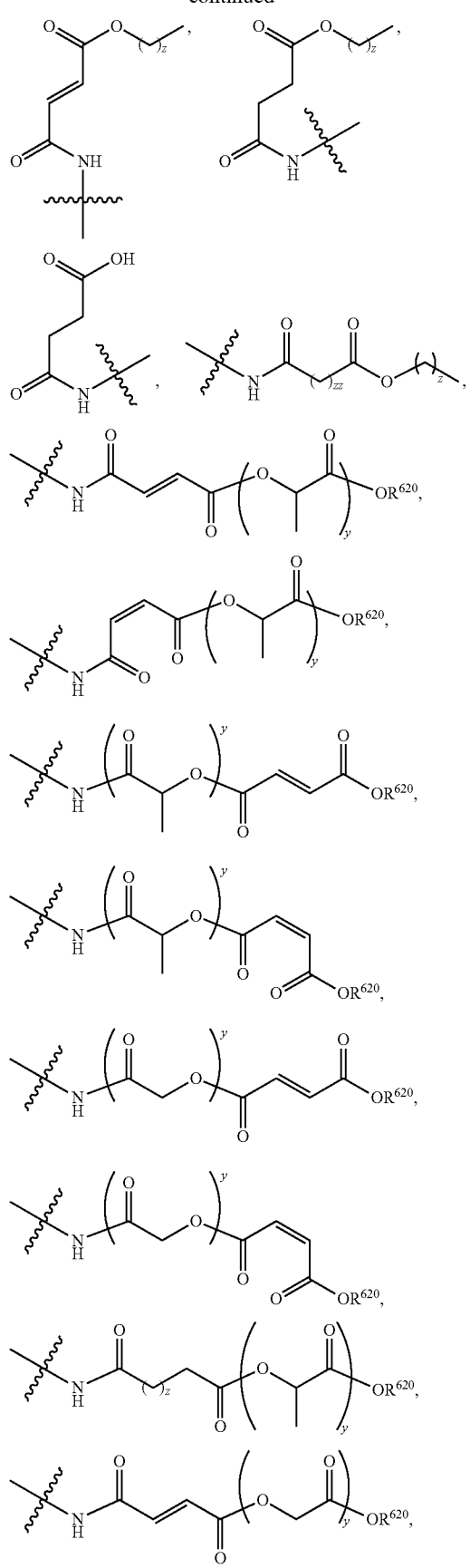
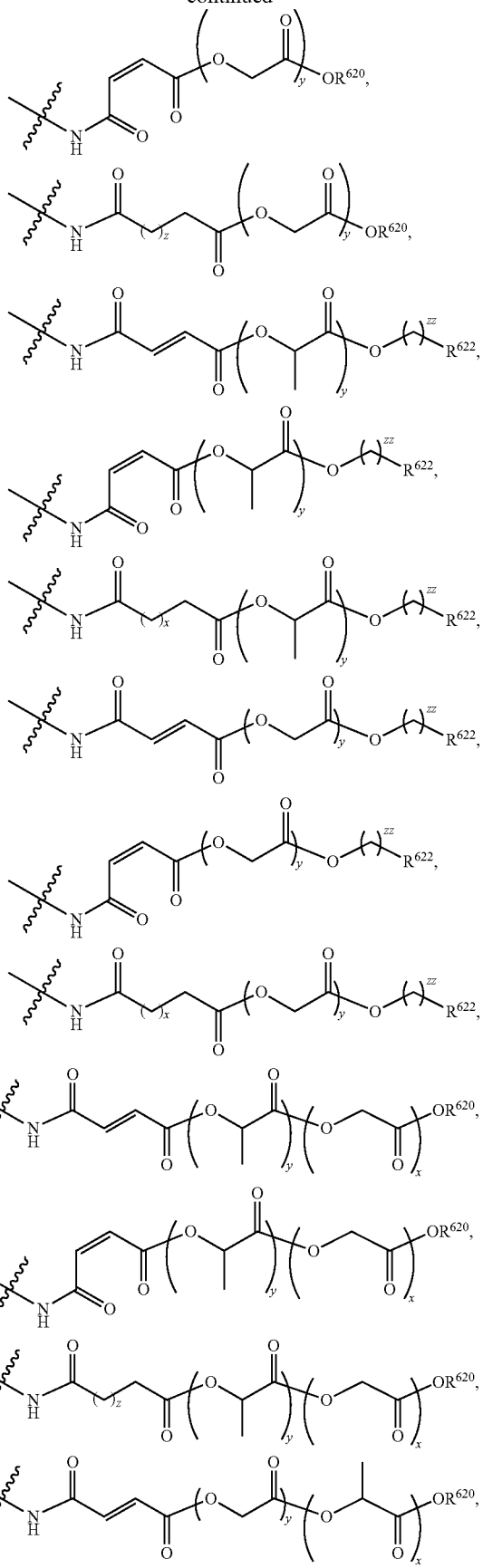

-continued

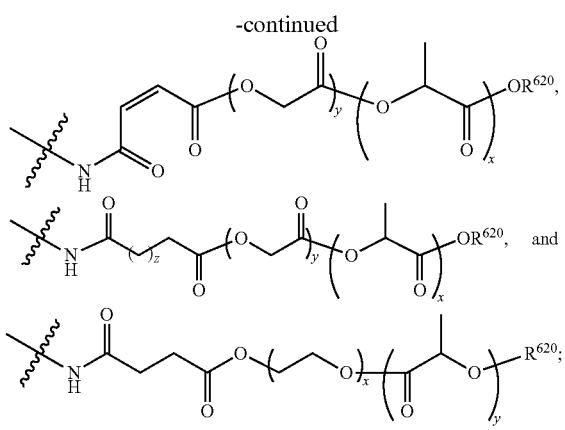

(vi) NH$_2$ wherein R$^{15}$ is R$^{16}$;

R$^{620}$ is selected at each instance from hydrogen, alkyl, alkenyl, alkynyl cycloalkyl, cycloalkylalkyl, heterocyclyl, heterocycloalkyl, aryl, arylalkyl, heteroaryl, or heteroarylalkyl, each of which except hydrogen may be optionally substituted with R$^5$ if the resulting compound is stable and achieves the desired purpose and wherein the group cannot be substituted with itself, for example alkyl would not be substituted with alkyl;

R$^{622}$ is hydrogen, hydroxy, amino, A, alkyl, alkoxy, alkenyl, alkynyl cycloalkyl, cycloalkylalkyl, heterocyclyl, heterocycloalkyl, aryl, arylalkyl, heteroaryl, heteroarylalkyl, aryloxy, or stearoyl; In one embodiment, —C$_3$-C$_{30}$ as used in the definition of R$^{10}$ is —C$_3$-C$_{28}$, —C$_3$-C$_{26}$, —C$_3$-C$_{24}$, —C$_3$-C$_{22}$, —C$_3$-C$_{20}$, —C$_3$-C$_{18}$, —C$_3$-C$_{16}$, —C$_3$-C$_{14}$, —C$_3$-C$_{12}$, —C$_5$-C$_{12}$, —C$_7$-C$_{12}$, or —C$_7$-C$_{10}$.

In one embodiment R$^{10}$ is selected from —N=CH—C$_3$-C$_{30}$alkenylR$^5$, —N=CH—C$_3$-C$_{30}$alkynylR$^5$, —N=CH—C$_3$-C$_{30}$alkenylalkynylR$^5$, —N=C$_1$-C$_{30}$alkylR$^5$, —N=CH—C$_3$-C$_{30}$alkenyl, —N=CH—C$_3$-C$_{30}$alkynyl, —N=CH—C$_3$-C$_{30}$alkenylalkynyl, —N=C$_1$-C$_{30}$alkyl;

In one embodiment, R$^{10}$ is selected from

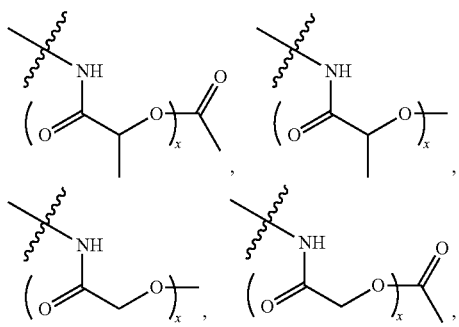

and x and R$^{15}$ is hydrogen.

In one embodiment of Formula IIB, R$^{10}$ is

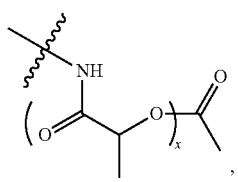

x is an integer selected from 1, 2, 3, 4, 5, 6, 7, or 8, and R$^{15}$ is hydrogen. In a further embodiment, x is 2, 4, or 6.

In one embodiment of Formula IIB, R$^{10}$ is selected from —NH(lactide-co-glycolide)$_{2-10}$C(O)C$_{1-20}$alkyl, —NH(lactide-co-glycolide)$_{4-10}$C(O)C$_{1-20}$alkyl, —NH(lactide-co-glycolide)$_{2-10}$C(O)C$_{1-10}$alkyl, and —NH(lactide-co-glycolide)$_{2-10}$C(O)C$_{4-20}$alkyl and R$^{15}$ is hydrogen.

Non-limiting examples of R$^{10}$ include:

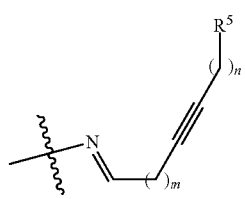

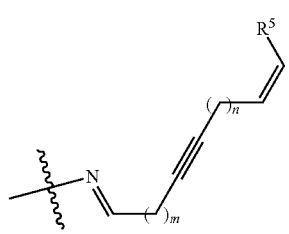

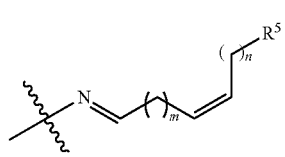

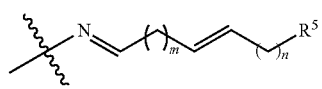

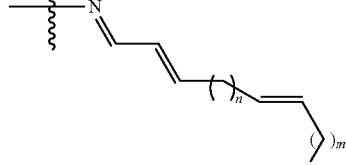

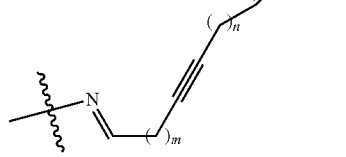

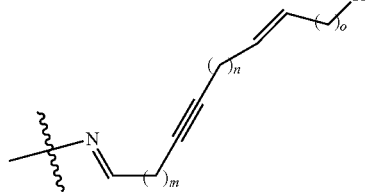

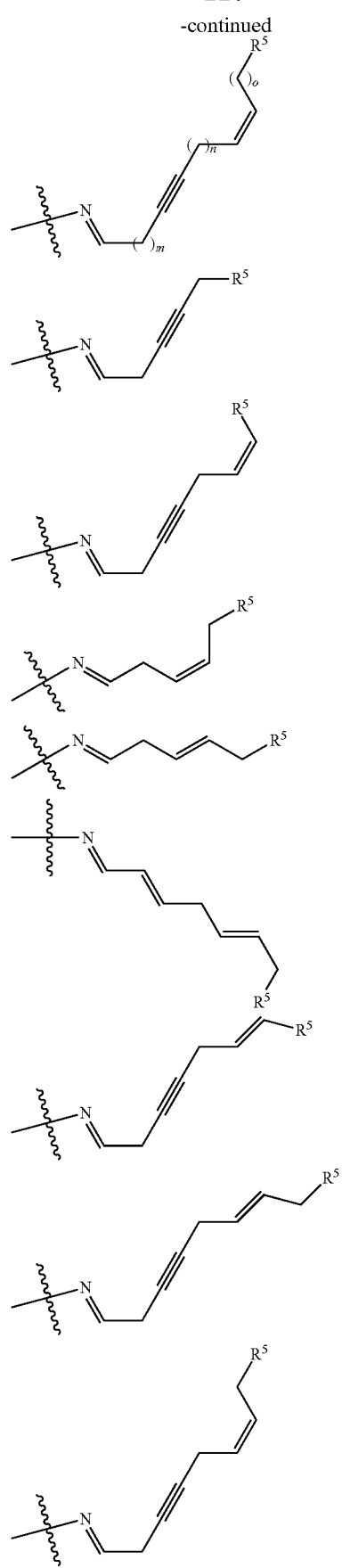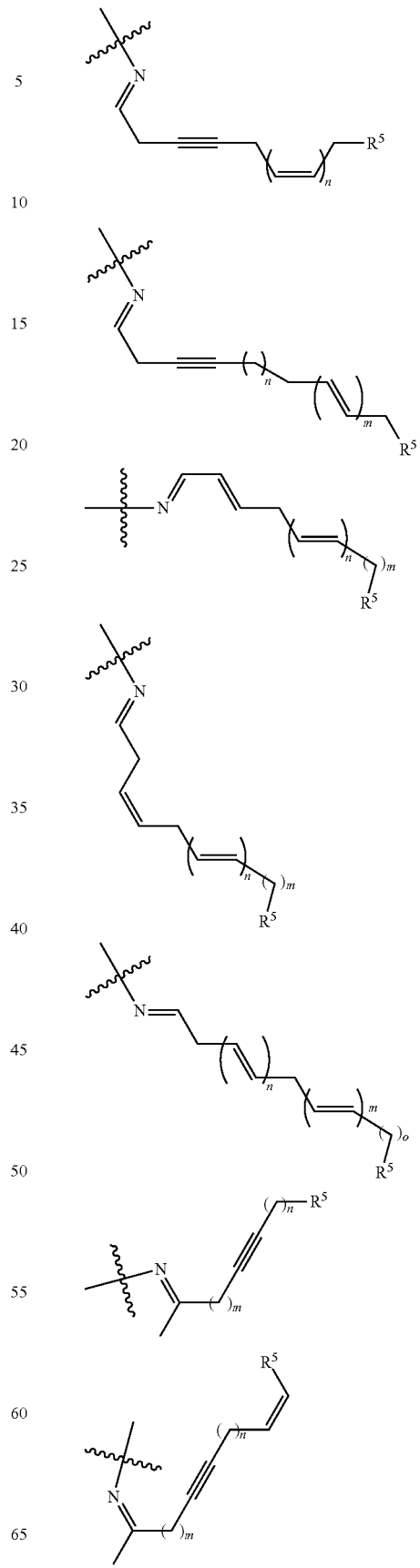

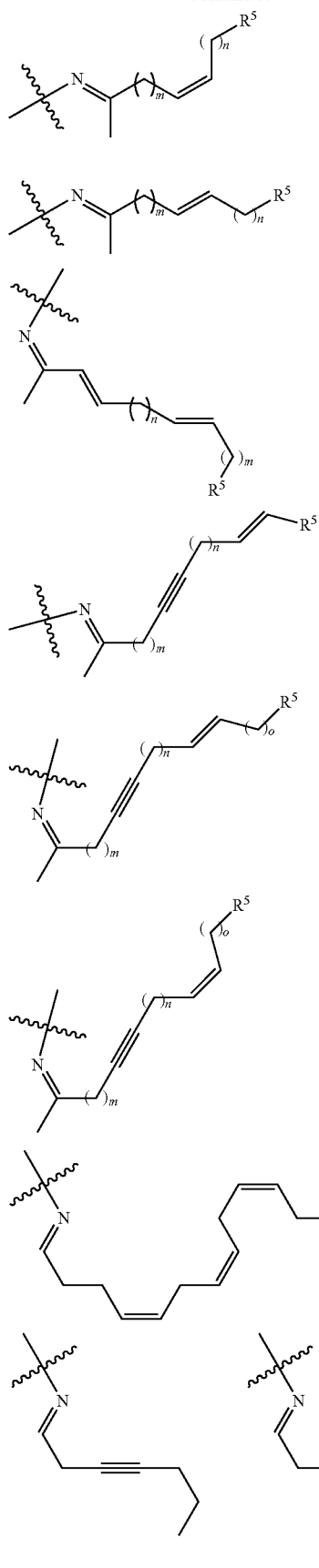
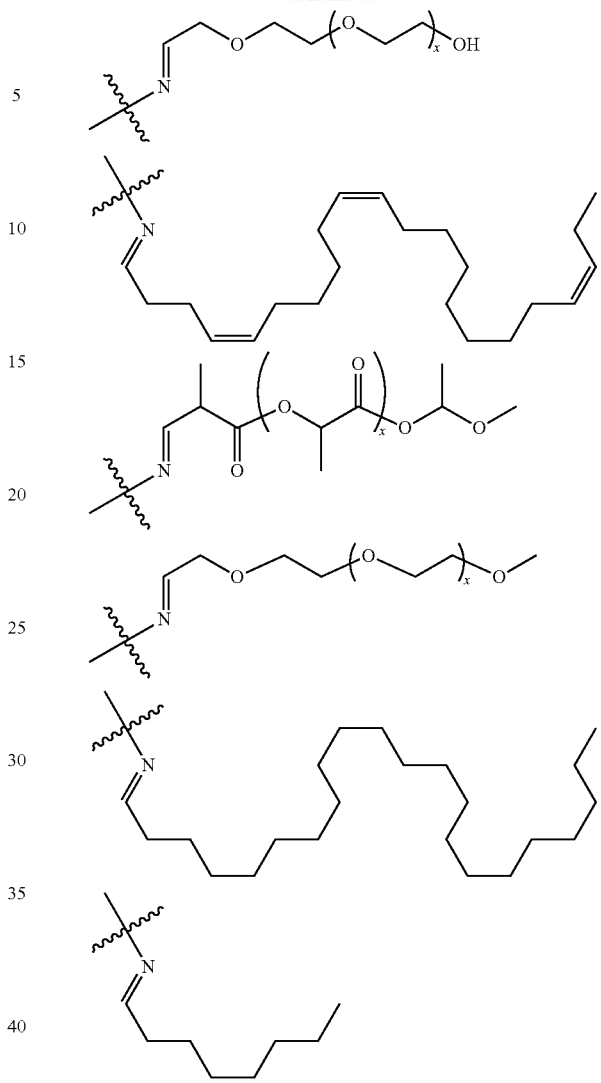
wherein all other variables are as defined herein.
Non-limiting Examples of Formula IIB include
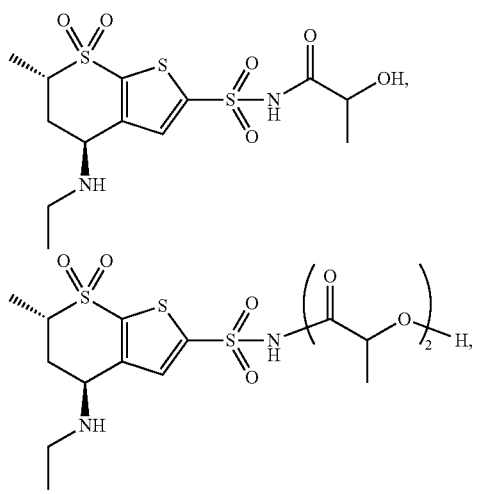

121
-continued
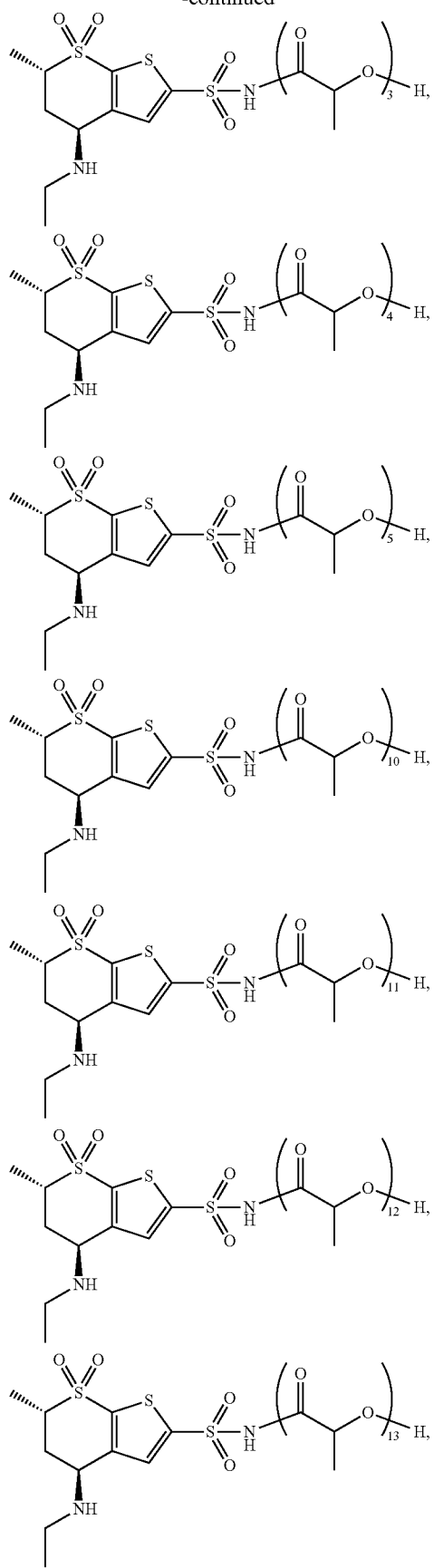
122
-continued
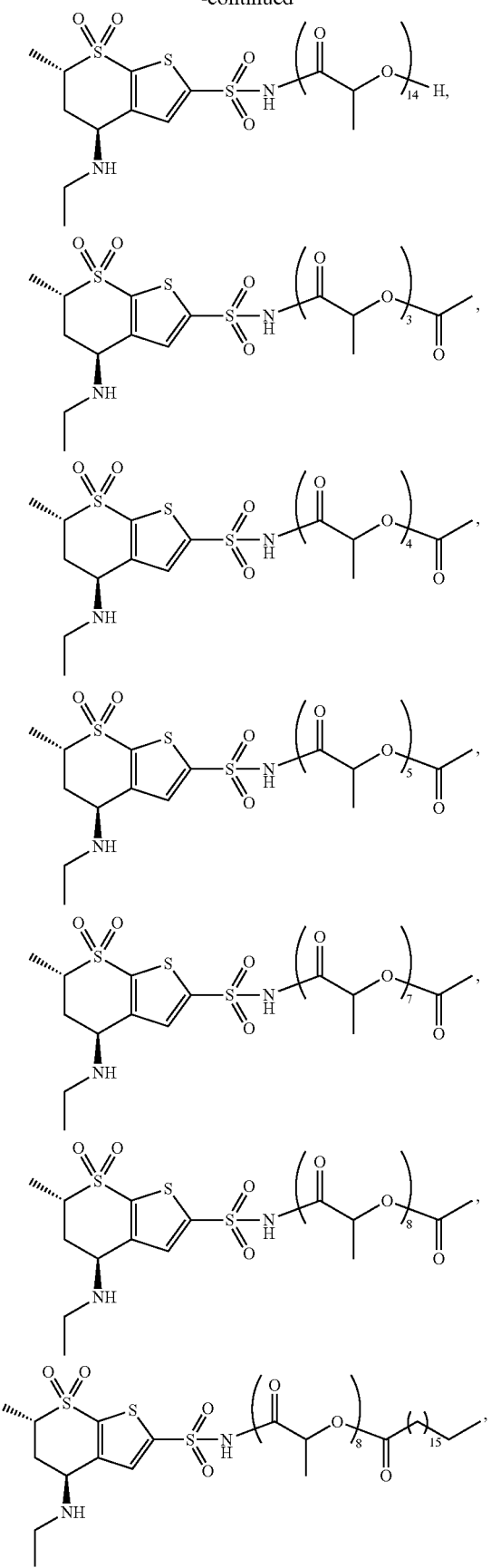

-continued

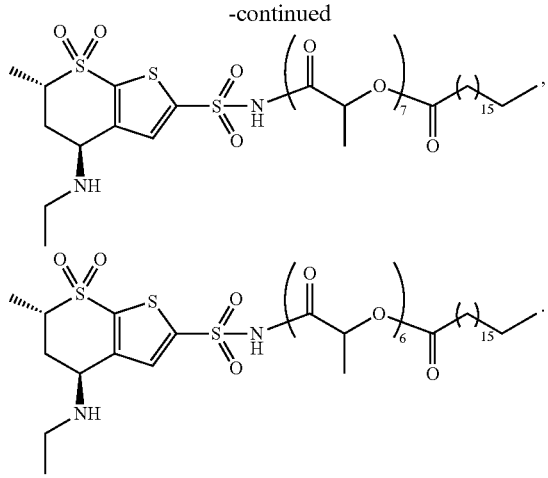

In one embodiment, the compound of Formula IIB is

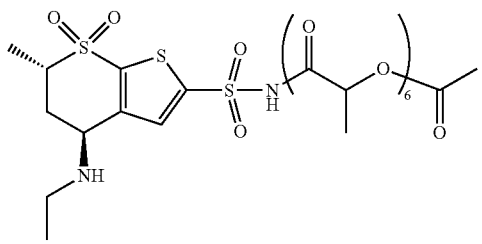

The disclosure provides carbonic anhydrase inhibitor prodrugs of Formula VB, Formula VIB, and Formula VIIB:

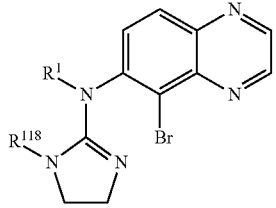

(VB)

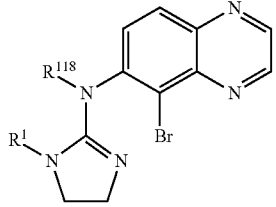

(VIB)

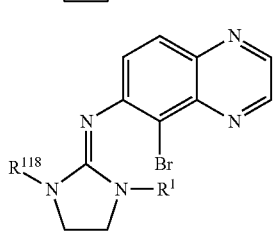

(VIIB)

or a pharmaceutically acceptable composition, salt, or isotopic derivative thereof wherein $R^{118}$ is selected from:

(i) —C(O)C$_5$-C$_{30}$alkylR$^5$, —C(O)C$_2$-C$_{30}$alkenylR$^5$, —C(O)C$_2$-C$_{30}$alkynylR$^5$, —C(O)C$_4$-C$_{30}$alkenylalkynylR$^5$, —C(O)C$_5$-C$_{30}$alkyl, —C(O)C$_2$-C$_{30}$alkenyl, —C(O)C$_2$-C$_{30}$alkynyl, and —C(O)C$_4$-C$_{30}$alkenylalkynyl;

(ii) —C(O)(C$_{1-30}$alkyl with at least one R$^5$ substituent on the alkyl chain), —C(O)(C$_{1-30}$alkenyl with at least one R$^5$ substituent on the alkenyl chain), —C(O)(C$_{1-30}$alkynyl with at least one R$^5$ substituent on the alkynyl chain), -(lactic acid)$_{1-20}$C(O)C$_{1-30}$alkyl, -(lactic acid)$_{1-10}$C(O)C$_{1-30}$alkyl, -(lactic acid)$_{4-20}$C(O)C$_{1-30}$alkyl, -(lactic acid)$_{1-20}$C(O)C$_{1-10}$alkyl, -(lactic acid)$_{1-20}$C(O)C$_{4-10}$alkyl, -(lactic acid)$_{1-20}$C(O)OH, -(lactic acid)$_{1-10}$C(O)OH, -(lactic acid)$_{4-20}$C(O)OH, -(lactic acid)$_{1-10}$C(O)OH, -(lactic acid)$_{4-10}$C(O)OH, -(lactide-co-glycolide)$_{1-10}$C(O)C$_{1-30}$alkyl, -(lactide-co-glycolide)$_{4-10}$C(O)C$_{1-30}$alkyl, -(lactide-co-glycolide)$_{1-10}$C(O)C$_{1-12}$alkyl, -(lactide-co-glycolide)$_{1-10}$C(O)C$_{4-22}$alkyl, -(glycolic acid)$_{1-10}$C(O)C$_{1-10}$alkyl, -(glycolic acid)$_{4-10}$C(O)C$_{1-10}$alkyl, -(lactic acid)$_{4-10}$C(O)C$_{1-10}$alkyl, -(lactic acid)$_{1-10}$C(O)C$_{1-10}$alkyl, -(lactic acid)$_{1-10}$C(O)C$_{4-10}$alkyl, -(lactic acid)$_{1-10}$C(O)C$_{4-10}$alkyl, and —(lactic acid)$_{1-10}$C(O)C$_{4-10}$alkyl;

(iii) an unsaturated fatty acid residue including but not limited to the carbonyl fragment taken from linoleic acid (—(CH$_2$)$_8$(CH)$_2$CH$_2$(CH)$_2$(CH$_2$)$_4$CH$_3$)), docosahexaenoic acid (—(CH$_2$)$_3$(CHCHCH$_2$)$_6$CH$_3$)), eicosapentaenoic acid (—(CH$_2$)$_4$(CHCHCH$_2$)$_5$CH$_3$)), alpha-linolenic acid (—(CH$_2$)$_8$(CHCHCH$_2$)$_3$CH$_3$)), stearidonic acid, y-linolenic acid, arachidonic acid, docosatetraenoic acid, palmitoleic acid, vaccenic acid, paullinic acid, oleic acid, elaidic acid, gondoic acid, euric acid, nervonic acid and mead acid, each of which can be further optionally further substituted with R$^5$ (including for example a second R$^5$) if valence permits, a stable compound is formed, and the resulting compound is pharmaceutically acceptable;

(iv) polyethylene glycol, polypropylene glycol, polypropylene oxide, polylactic acid, poly(lactic-co-glycolic acid), polyglycolic acid, polyester, polyamide, and other biodegradable polymers, each of which can be capped to complete the terminal valence or to create a terminal ether or ester;

(v)

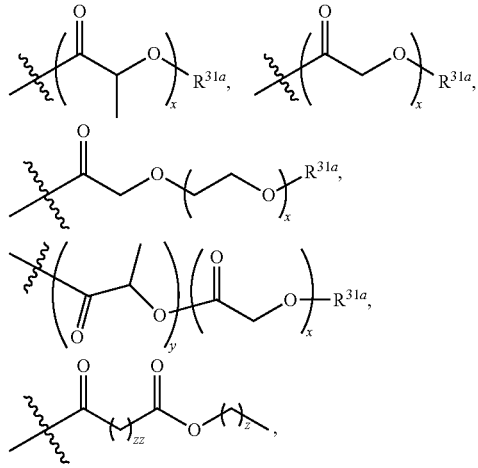

-continued

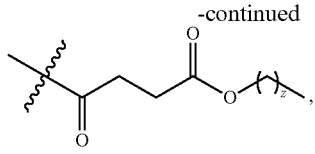

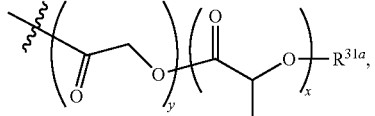

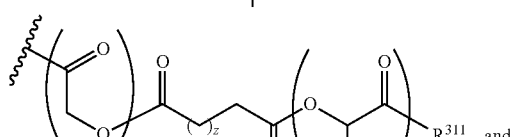

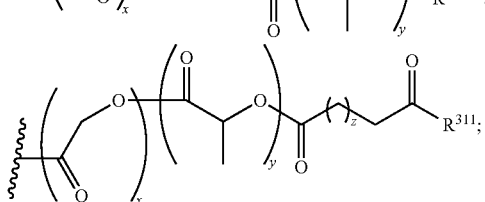

(vi) —(C(O)CH$_2$O)$_{1-20}$C(O)C$_{1-30}$alkyl, —(C(O)CH(CH$_3$)O)$_{1-20}$C(O)C$_{1-30}$alkyl, —(C(O)CH$_2$O)$_{1-10}$C(O)C$_{1-30}$alkyl, —(C(O)CH(CH$_3$)O)$_{1-10}$C(O)C$_{1-30}$alkyl, —(C(O)CH$_2$O)$_{4-20}$C(O)C$_{1-30}$alkyl, —(C(O)CH(CH$_3$)O)$_{4-20}$C(O)C$_{1-30}$alkyl, —(C(O)CH$_2$O)$_{1-20}$C(O)C$_{1-10}$alkyl, —(C(O)CH(CH$_3$)O)$_{1-20}$C(O)C$_{1-10}$alkyl, —(C(O)CH$_2$O)$_{1-20}$C(O)C$_{4-10}$alkyl, —(C(O)CH(CH$_3$)O)$_{1-20}$C(O)C$_{4-10}$alkyl, —(C(O)CH(CH$_3$)O)$_{4-10}$C(O)C$_{1-10}$alkyl, —(C(O)CH$_2$O)$_{4-10}$C(O)C$_{1-10}$alkyl, —(C(O)CH(CH$_3$)O)$_{1-10}$C(O)C$_{1-10}$alkyl, —(C(O)CH$_2$O)$_{1-10}$C(O)C$_{1-10}$alkyl, —(C(O)CH(CH$_3$)O)$_{1-10}$C(O)C$_{4-10}$alkyl, (C(O)CH$_2$O)$_{1-10}$C(O)C$_{4-10}$alkyl, —(C(O)CH$_2$O)$_{1-10}$C(O)C$_{4-10}$alkyl, —(C(O)CH(CH$_3$)O)$_{1-10}$C(O)C$_{4-10}$alkyl, —(C(O)CH$_2$O)$_{1-10}$C(O)C$_{4-10}$alkyl, —(C(O)CH(CH$_3$)O)$_{1-10}$C(O)C$_{4-10}$alkyl, —(C(O)CH$_2$O)$_{1-10}$C(O)CH(CH$_3$)O)$_{1-10}$C(O)C$_{1-30}$alkyl, —(C(O)CH$_2$O)$_{2-10}$(C(O)CH(CH$_3$)O)$_{2-10}$C(O)C$_{1-30}$alkyl, —(C(O)CH$_2$O)$_{1-10}$(C(O)CH(CH$_3$)O)$_{1-10}$C(O)C$_{1-12}$alkyl, —(C(O)CH$_2$O)$_{1-10}$(C(O)CH(CH$_3$)O)$_{1-10}$C(O)C$_{4-22}$alkyl, —(C(O)CH(CH$_3$)O)$_{1-10}$(C(O)CH$_2$O)$_{1-10}$C(O)C$_{1-30}$alkyl, —(C(O)CH(CH$_3$)O)$_{2-10}$(C(O)CH$_2$O)$_{2-10}$C(O)C$_{1-30}$alkyl, —(C(O)CH(CH$_3$)O)$_{1-10}$(C(O)CH$_2$O)$_{1-10}$C(O)C$_{1-12}$alkyl, and —(C(O)CH(CH$_3$)O)$_{1-10}$(C(O)CH$_2$O)$_{1-10}$C(O)C$_{4-22}$alkyl; and wherein all other variables are as defined herein.

In various different embodiments, —C$_{10}$-C$_{30}$ as used in the definition of R$^{118}$ is —C$_{10}$-C$_{18}$, —C$_{10}$-C$_{16}$, —C$_{10}$-C$_{14}$, —C$_{10}$-C$_{12}$, —C$_{19}$-C$_{28}$, —C$_{19}$-C$_{26}$, —C$_{19}$-C$_{24}$, —C$_{19}$-C$_{22}$, —C$_{19}$-C$_{20}$, —C$_{20}$-C$_{28}$, —C$_{20}$-C$_{26}$, —C$_{20}$-C$_{24}$, —C$_{20}$-C$_{22}$, —C$_{22}$-C$_{28}$, —C$_{22}$-C$_{26}$, —C$_{22}$-C$_{24}$, or —C$_{26}$-C$_{28}$.

Non-limiting examples of Formula VB include:

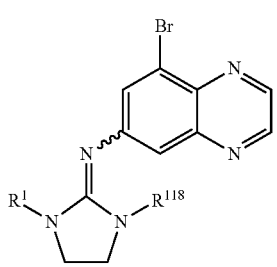

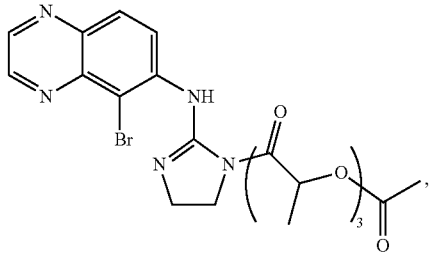

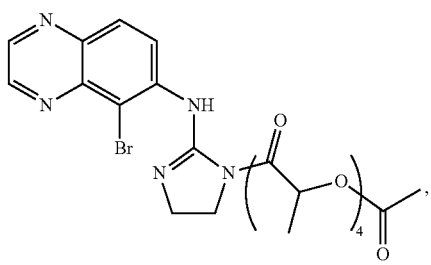

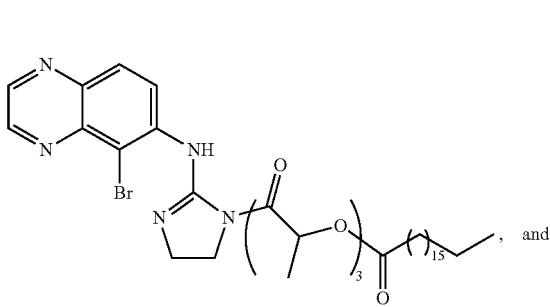

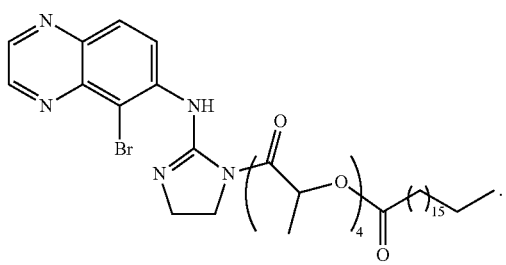

Compounds of Formula VIIB are drawn as where the bond between the aromatic ring and the imidazole ring is drawn as a wavy line. In one embodiment, compounds of Formula VIIB are the Z isomer. In one embodiment, compounds of Formula VIIB are the E isomer. For example, in one embodiment,

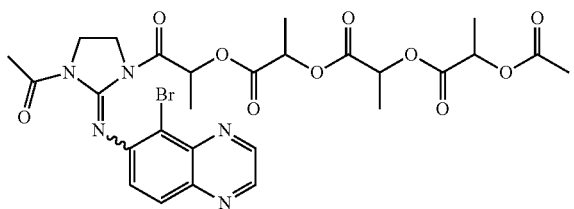 [SMILES: CC(=O)OC(C)C(=O)OC(C)C(=O)OC(C)C(=O)OC(C)C(=O)N1CCN(C(C)=O)C1=Nc1ccc2nccnc2c1Br]

is the Z isomer:

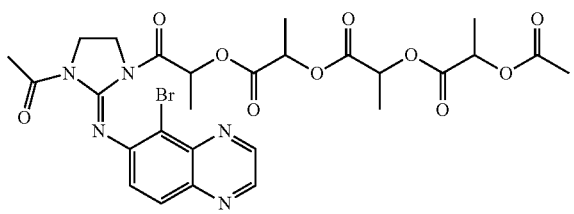 [SMILES: CC(=O)OC(C)C(=O)OC(C)C(=O)OC(C)C(=O)OC(C)C(=O)N1CCN(C(C)=O)/C1=N/c1ccc2nccnc2c1Br]

and
in an alternative embodiment, is the E isomer:

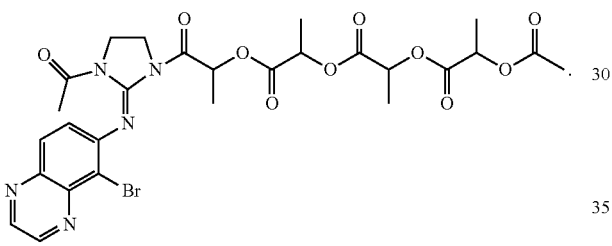

The disclosure provides carbonic anhydrase inhibitor prodrugs of Formula VIIIB and Formula IXB:

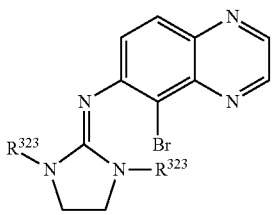

(VIIIB)

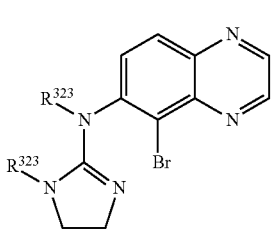

(IXB)

or a pharmaceutically acceptable composition, salt, or isotopic derivative thereof wherein wherein $R^{323}$ is independently selected from polyethylene glycol, polypropylene glycol, polypropylene oxide, polylactic acid, poly(lactic-co-glycolic acid), polyglycolic acid, polyester, polyamide,

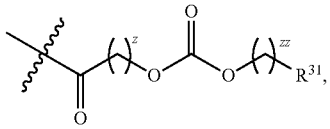

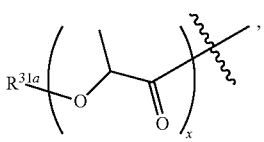

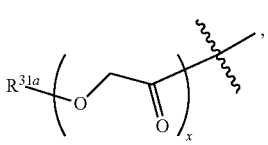

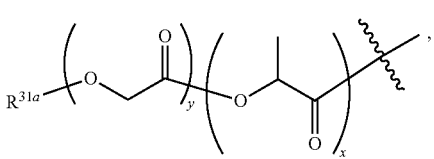

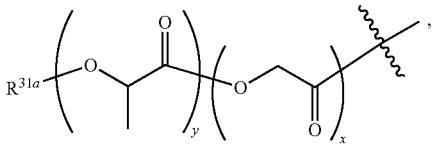

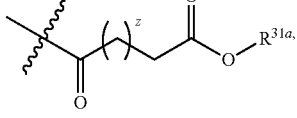

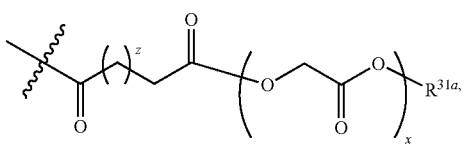

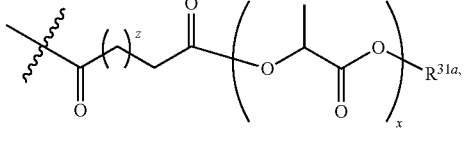

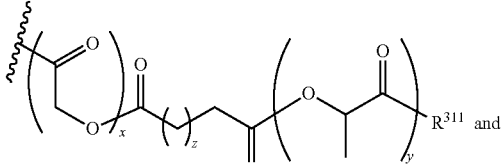

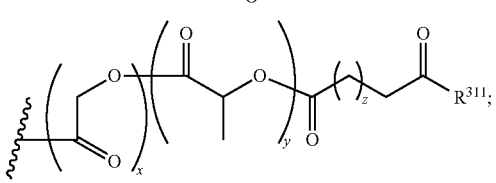

In certain embodiments of Formula VIIIB or Formula IXB, $R^{323}$ is

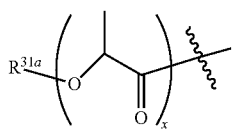

and R$^{31a}$ is —C(O)alkyl.

In certain embodiments of Formula VIIIB or Formula IXB, R$^{323}$ is

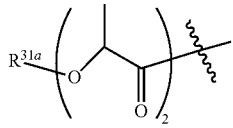

and R$^{31a}$ is —C(O)alkyl.

In certain embodiments of Formula VIIIB or Formula IXB, R$^{323}$ is

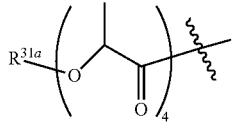

and R$^{31a}$ is —C(O)alkyl.

Non-limiting Examples of Formula VIIIB include

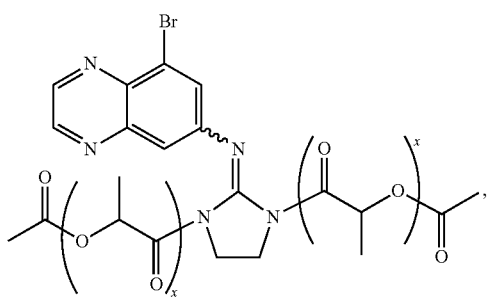

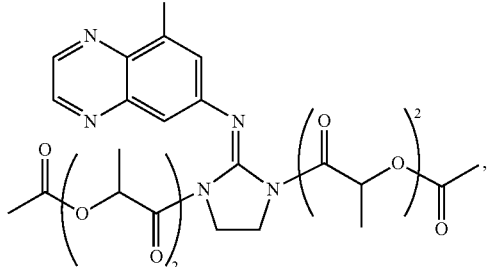

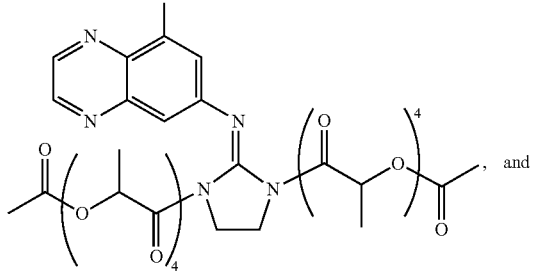

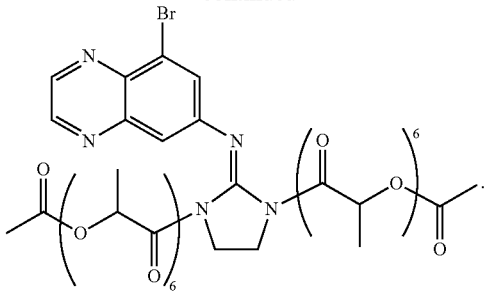

Compounds of Formula VIIIB are drawn as

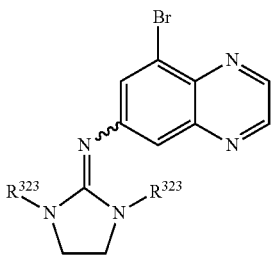

where the bond between the aromatic ring and the imidazole ring is drawn as a wavy line. In one embodiment, compounds of Formula VIIIB are the Z isomer. In one embodiment, compounds of Formula VIIIB are the E isomer.

The disclosure provides carbonic anhydrase inhibitor prodrugs of Formula XB, Formula XIB, Formula XIIB, Formula XIIIB, Formula XIVB, and Formula XVB:

(XB)

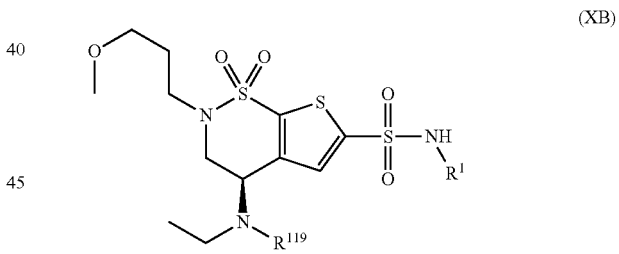

(XIB)

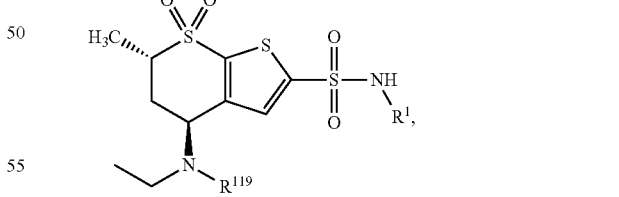

(XIIB)

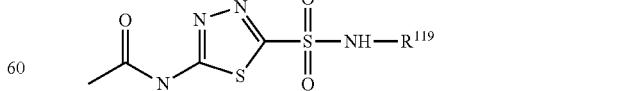

(XIIIB)

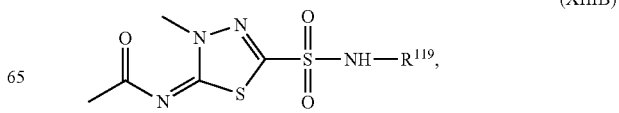

(XIVB)

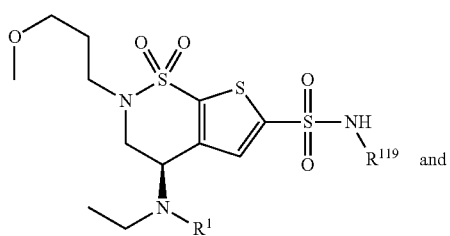

and (XVB)

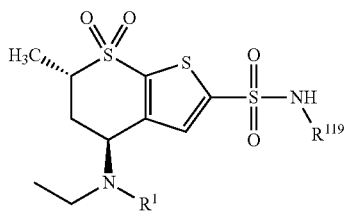

or a pharmaceutically acceptable composition, salt, or isotopic derivative thereof wherein R[119] is selected from: acyl, R[120], polyethylene glycol, polypropylene glycol, polypropylene oxide, polylactic acid, poly(lactic-co-glycolic acid), a polyglycolic acid, a polyester, polyamide, or other biodegradable polymer, wherein each R[119] other than R[120] is substituted with at least one L[4]-R[121].

R[120] is selected from:

(i)

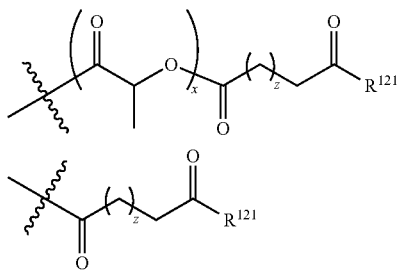

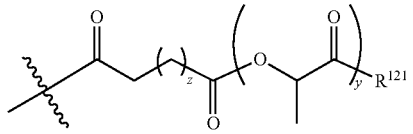

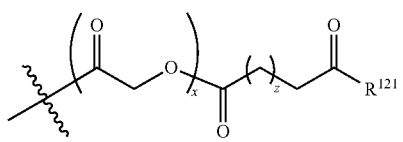

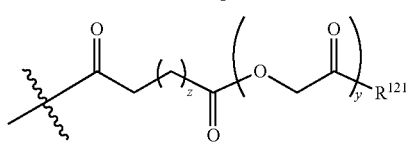

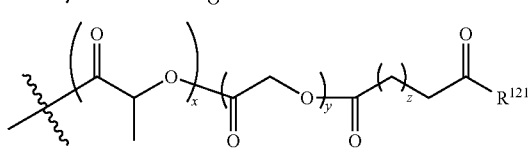

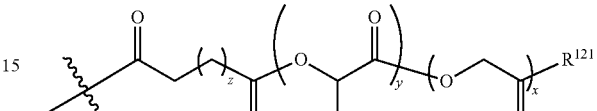

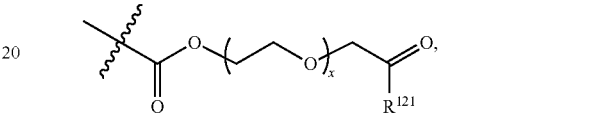

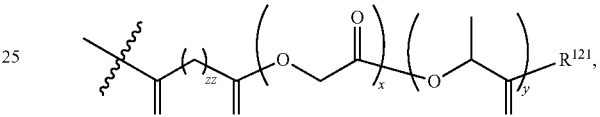

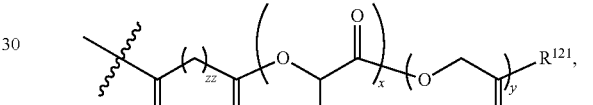

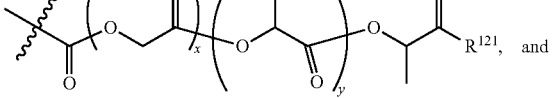

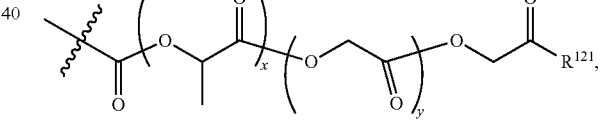

,

 and

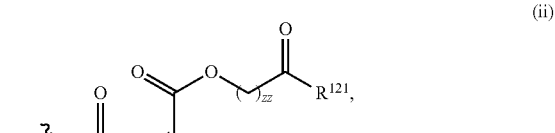; and (ii)

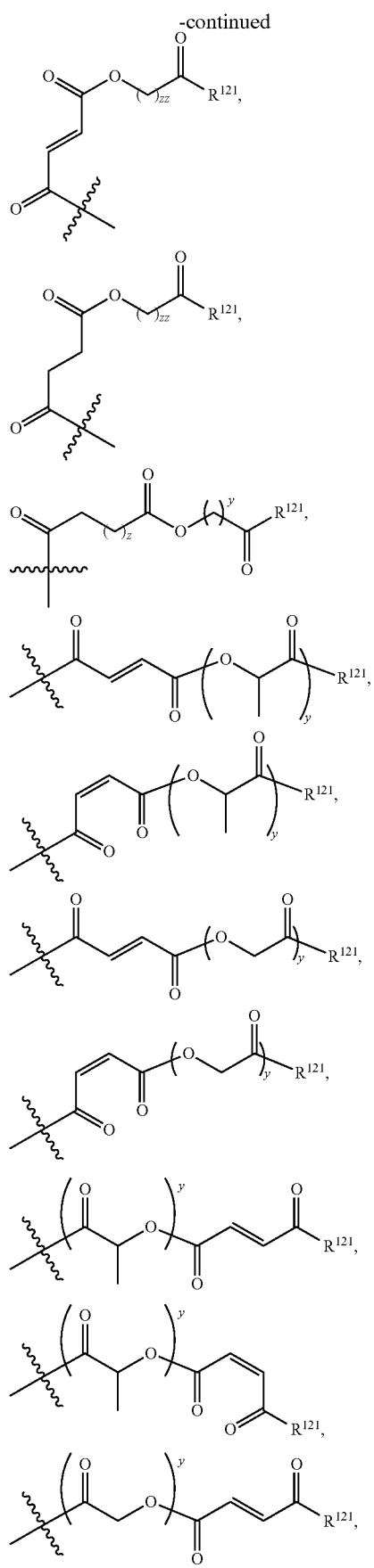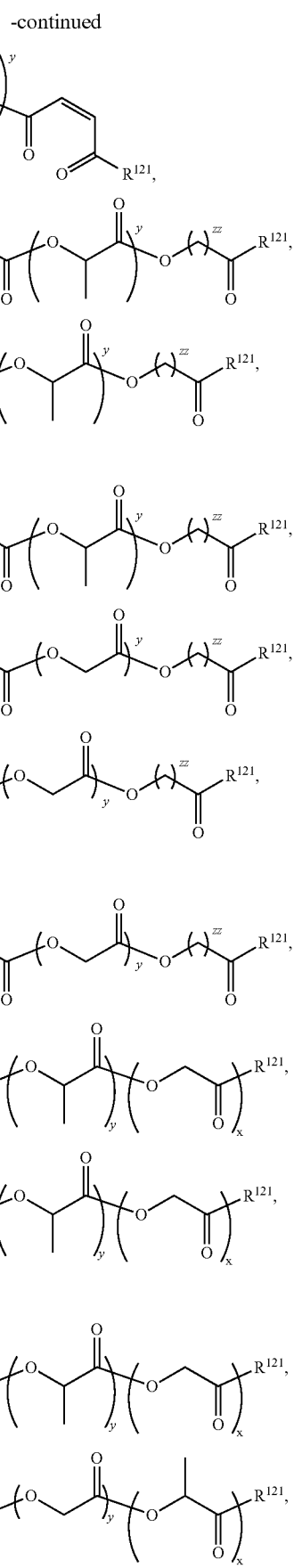

135
-continued
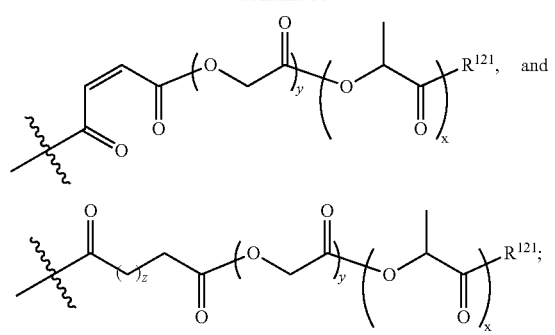
$R^{121}$ is selected from:
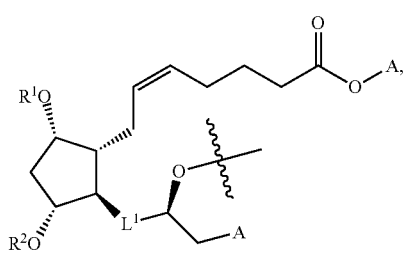
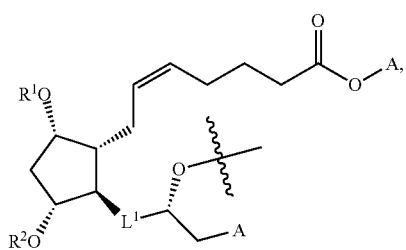
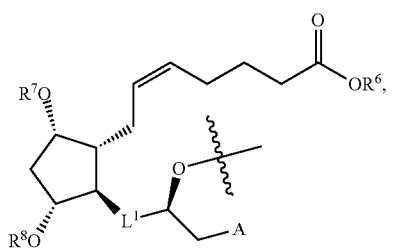
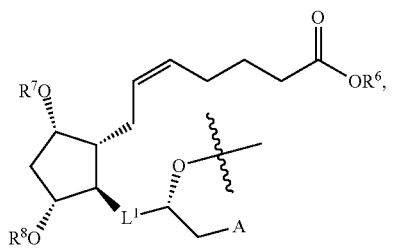
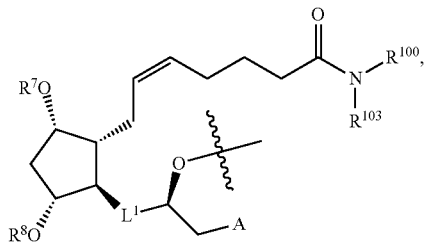
136
-continued
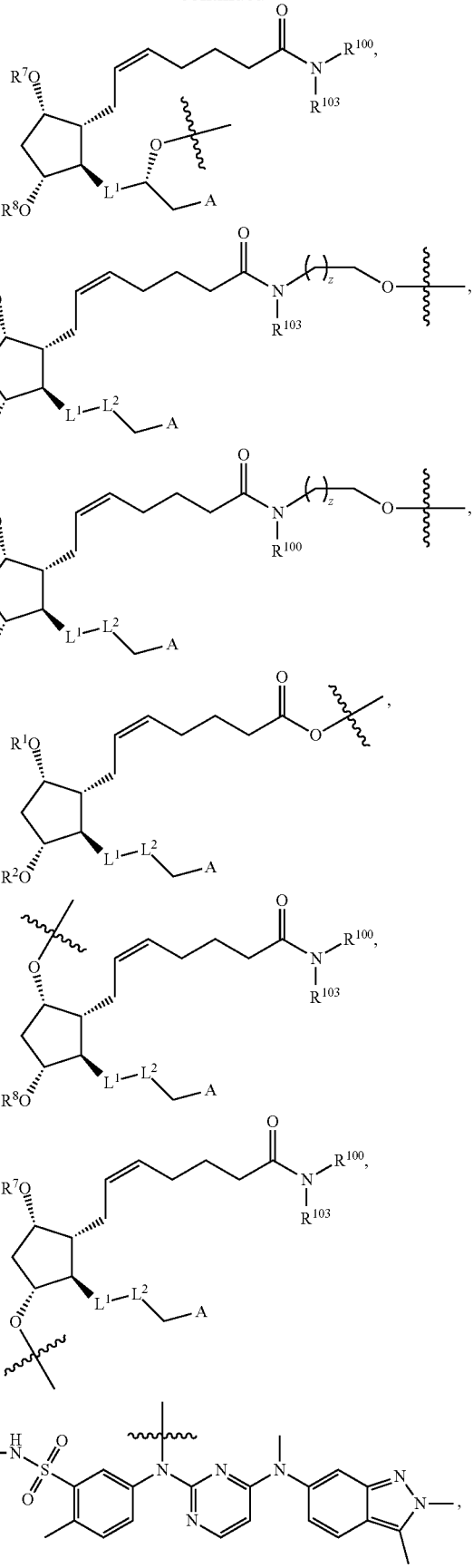

137
-continued
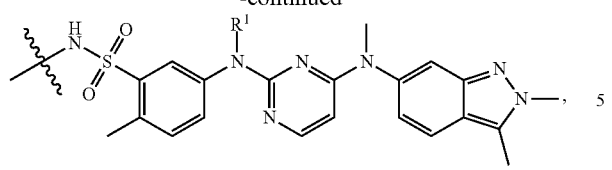
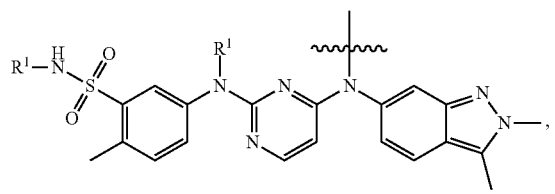
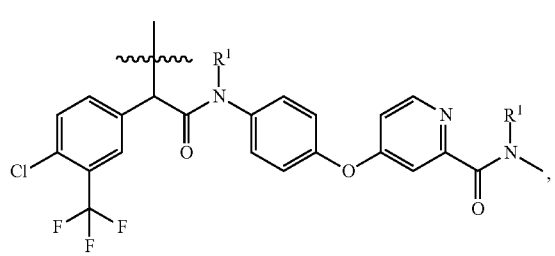
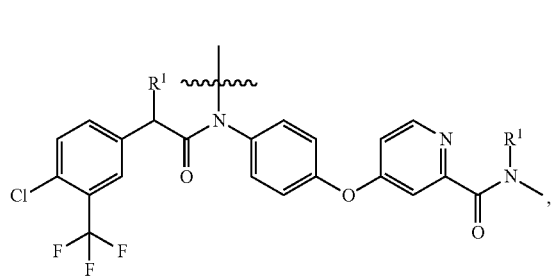
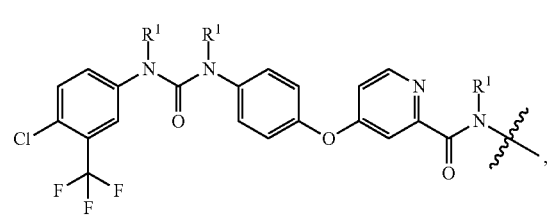
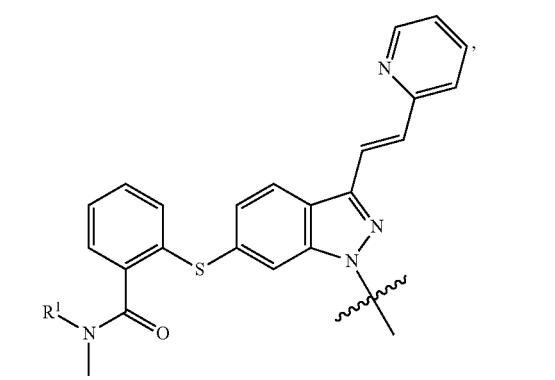
138
-continued
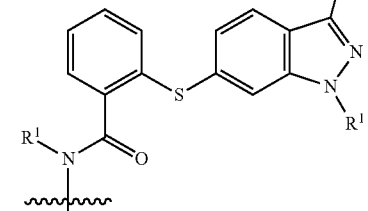
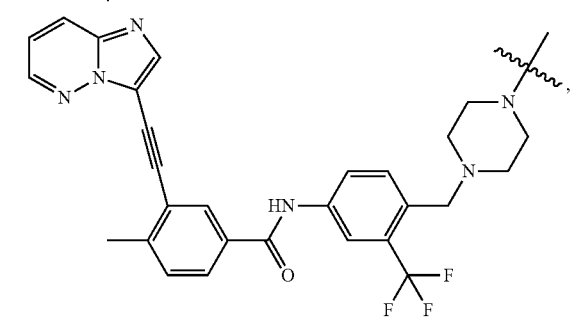
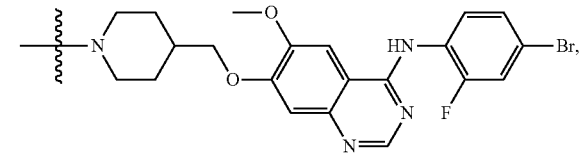
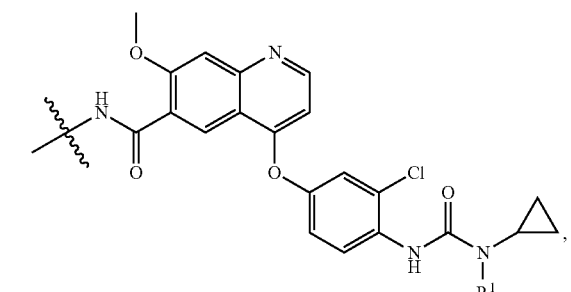
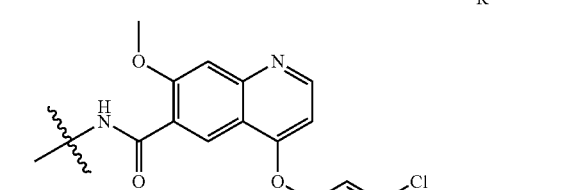
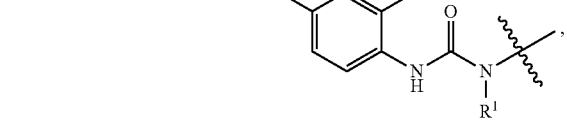
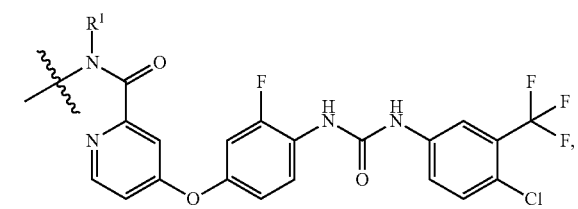

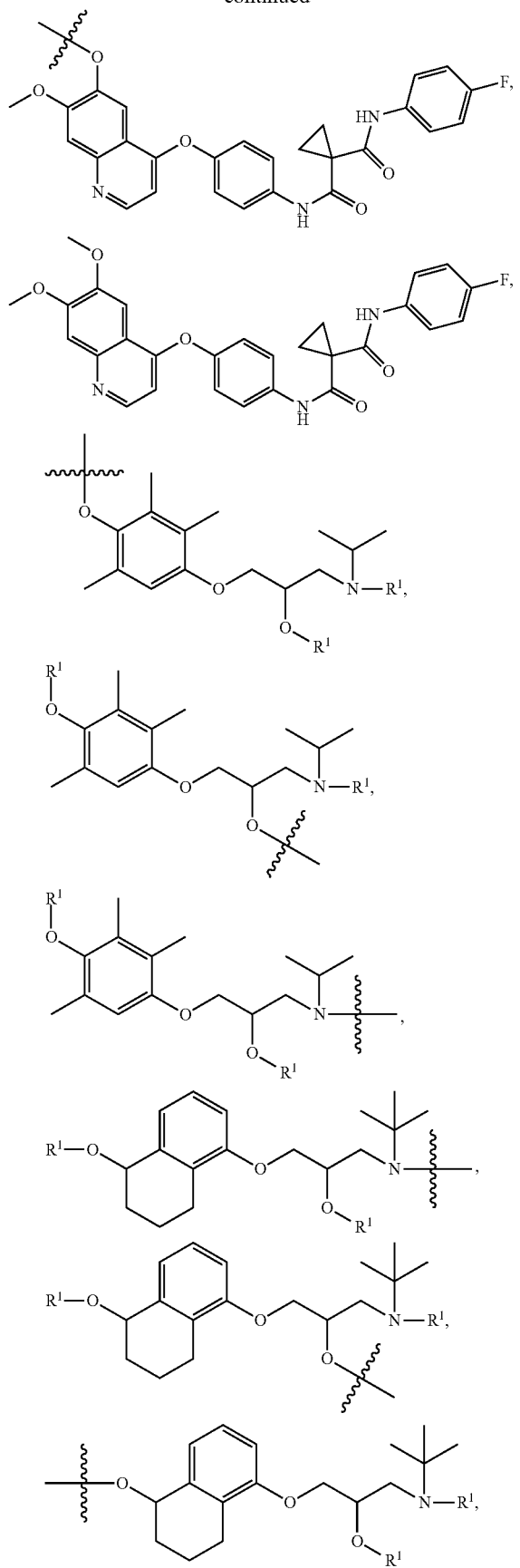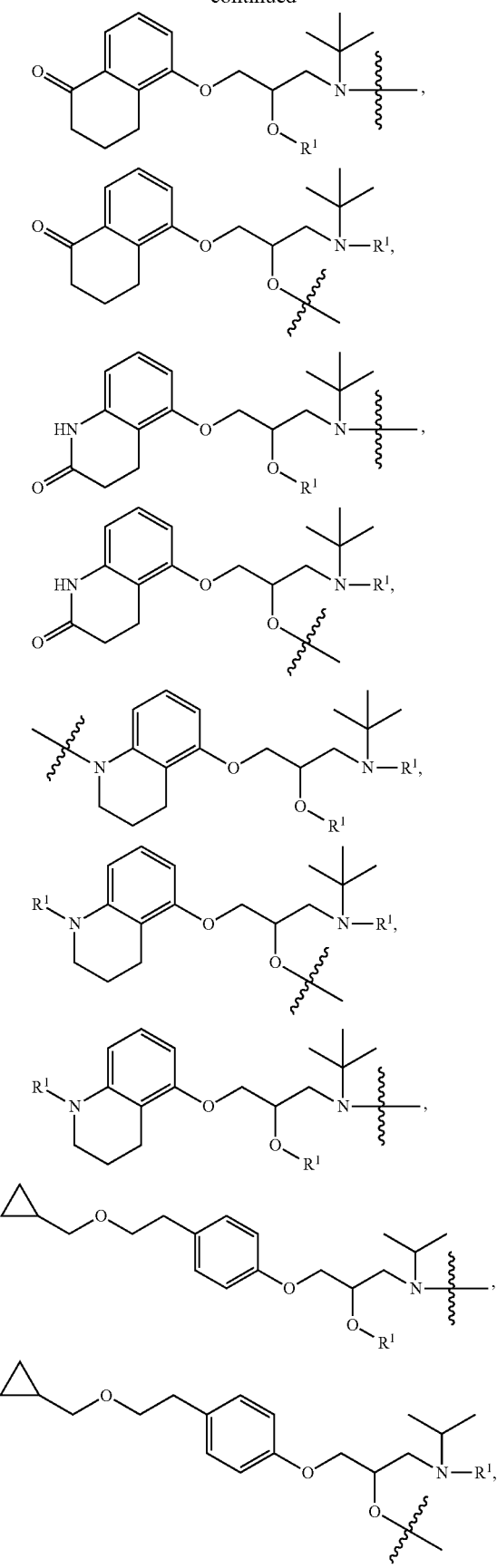

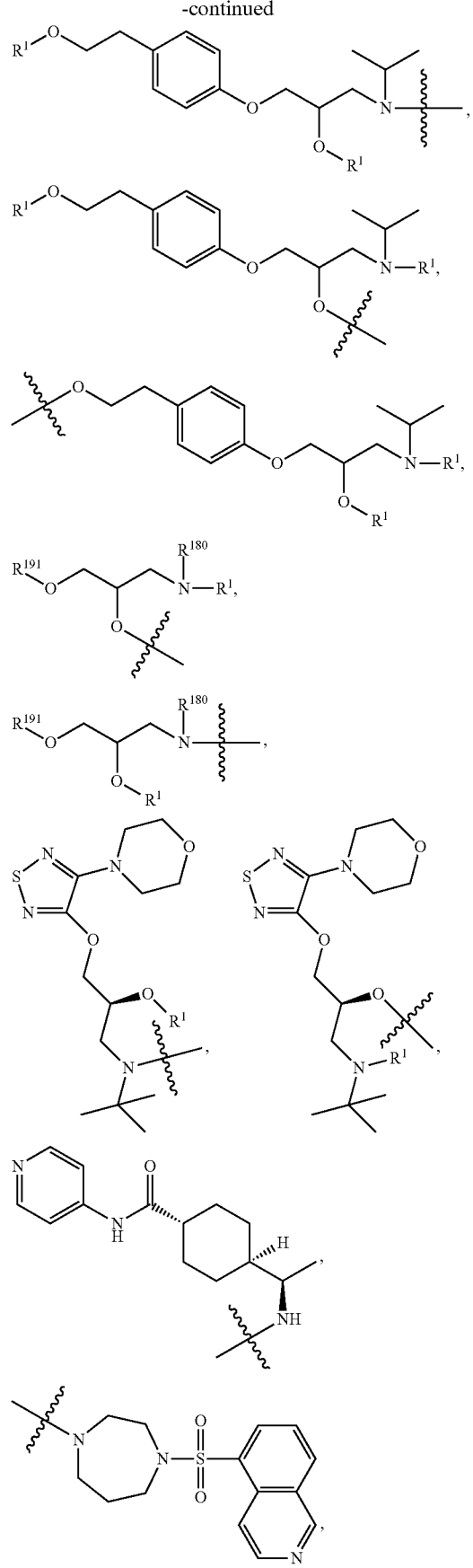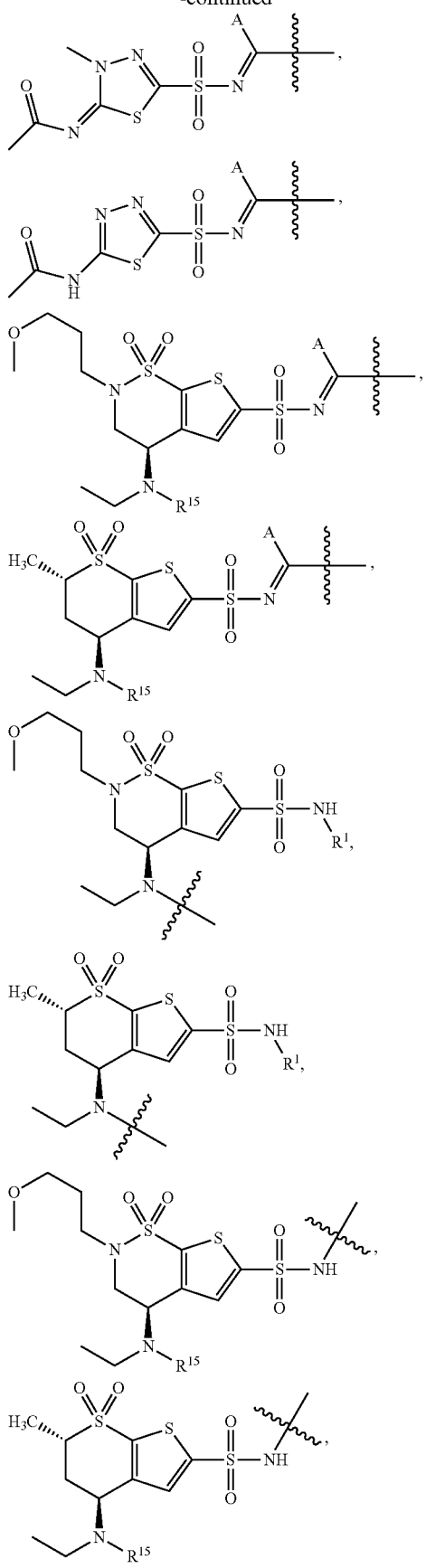

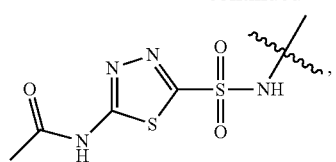
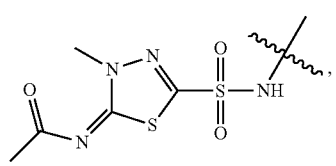
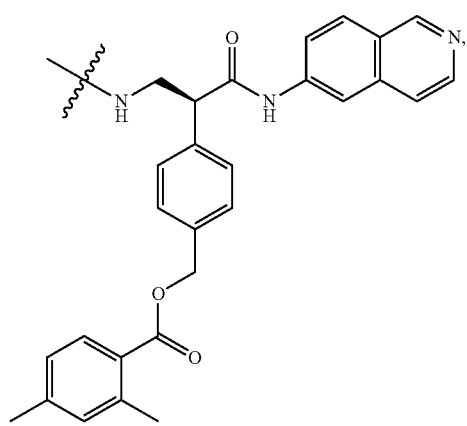
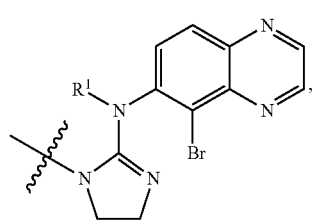
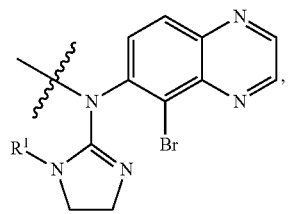
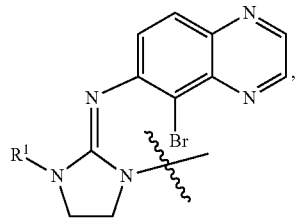
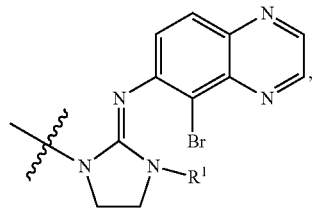
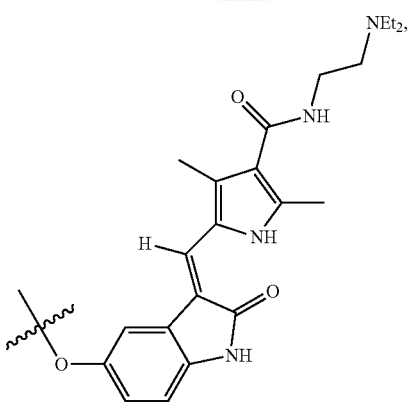
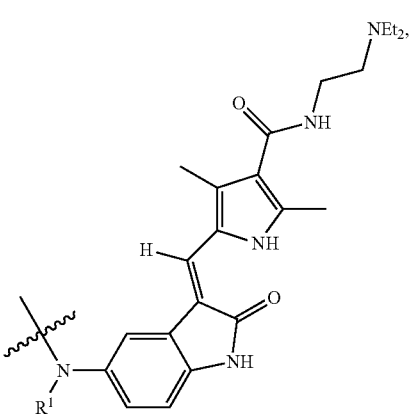
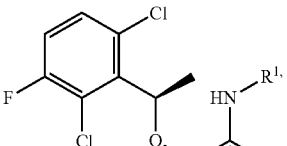
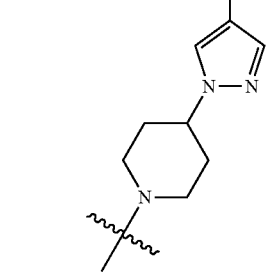

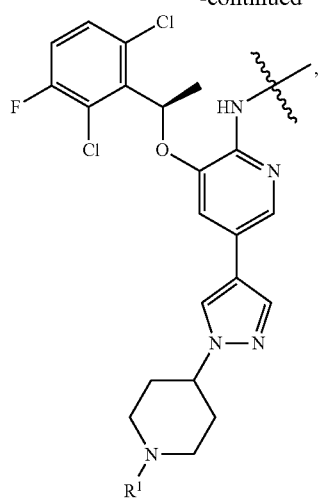
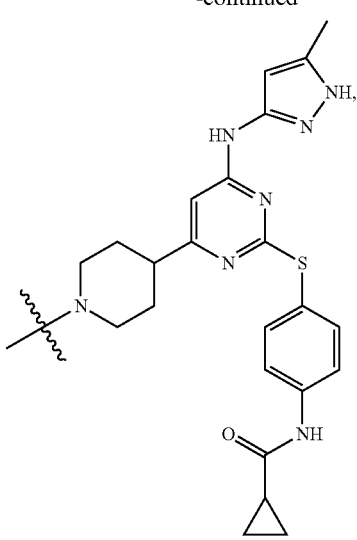
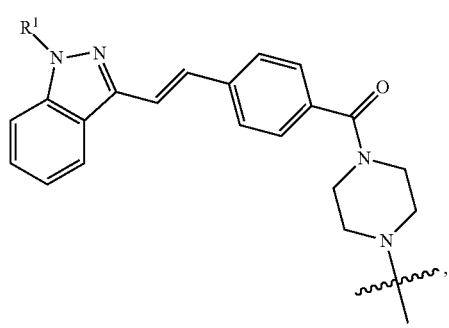
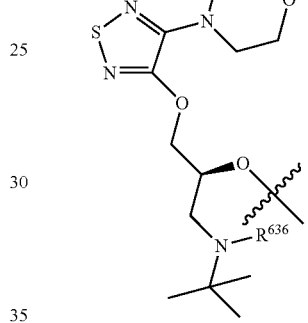
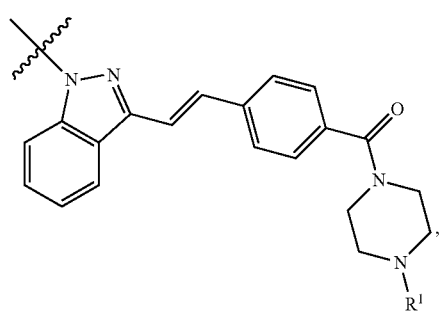
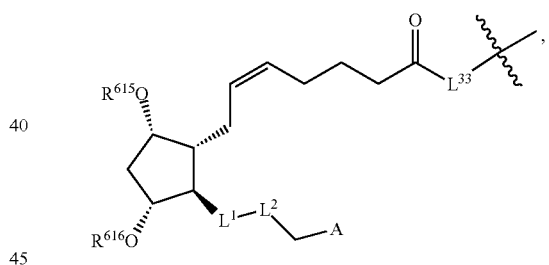
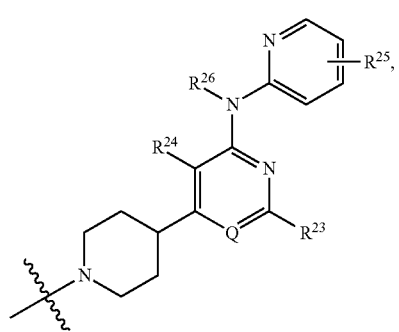
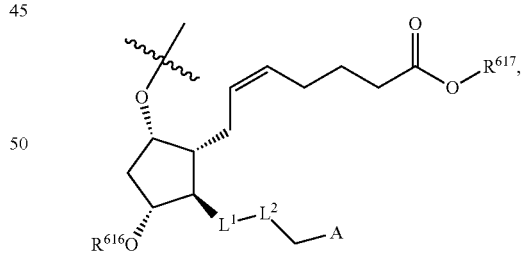
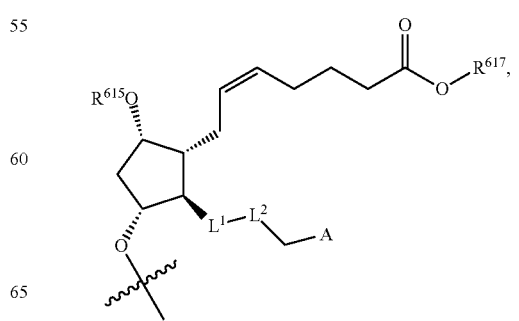

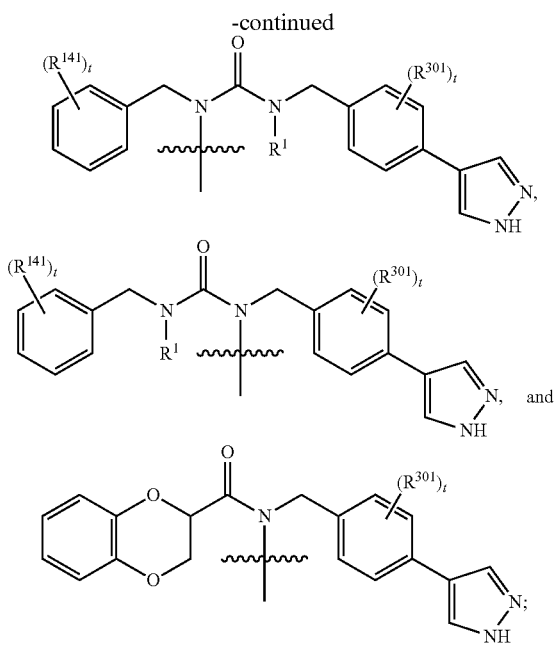

Q is selected from: N, CH, and CR²³;

R²³, R²⁴, and R²⁵ are independently selected from: hydrogen, halogen, hydroxyl, cyano, mercapto, nitro, amino, aryl, alkyl, alkoxy, alkenyl, alkynyl cycloalkyl, cycloalkylalkyl, heterocyclyl, heterocycloalkyl, aryl, arylalkyl, heteroaryl, heteroarylalkyl, aryloxy, —S(O)₂alkyl, —S(O)alkyl, —P(O)(Oalkyl)₂, B(OH)₂, —Si(CH₃)₃, —COOH, —COOalkyl, —CONH₂,

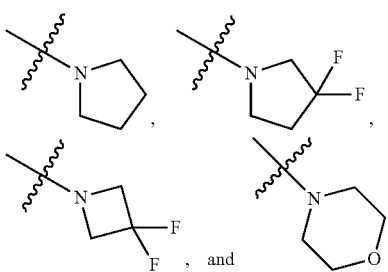

each of which except halogen, nitro, and cyano, may be optionally substituted, for example with halogen, alkyl, aryl, heterocycle or heteroaryl.

R²⁶ is selected from H, C(O)A, —C₀-C₁₀alkylR⁵, —C₂-C₁₀alkenylR⁵, —C₂-C₁₀alkynylR⁵, —C₂-C₁₀alkenyl, and —C₂-C₁₀alkynyl.

R¹⁴¹ is selected from hydrogen, —C(O)NR¹⁶¹R¹⁶², —C(O)R¹⁶¹, —C(O)OR¹⁶¹, nitro, amino, —NR¹³⁴R¹³⁵, alkyl, alkoxy, alkylalkoxy, alkoxyalkoxy, haloalkoxy, cycloalkyl, heterocycloalkyl, heteroaryl, aryl, and halogen;

R¹³⁴ and R¹³⁵ are independently selected from H, alkyl, —SO₂CH₃, —C(O)CH₃, and —C(O)NH₂;

R¹⁶¹ and R¹⁶² are independently selected from hydrogen, aryl, alkyl, cycloalkyl, arylalkyl, heteroaryl, heteroarylalkyl, and heterocyclyl;

R³⁰¹ is selected from hydrogen, —C(O)NR¹⁶¹R¹⁶², —C(O)R¹⁶¹, —C(O)OR¹⁶¹, nitro, amino, —NR¹³⁴R¹³⁵, alkyl, alkoxy, alkylalkoxy, alkoxyalkoxy, haloalkoxy, cycloalkyl, heterocycloalkyl, heteroaryl, aryl, halogen, —O(CH₂)₂NR¹³⁴R¹³⁵, and —N(CH₃)(CH₂)₂NR¹³⁴R¹³⁵;

or R¹³⁴ and R¹³⁵ can together form a heterocycloalkyl;

R¹⁸⁰ is C₁-C₆ alkyl, acyl, or hydrogen;

R¹⁹¹ is selected from:

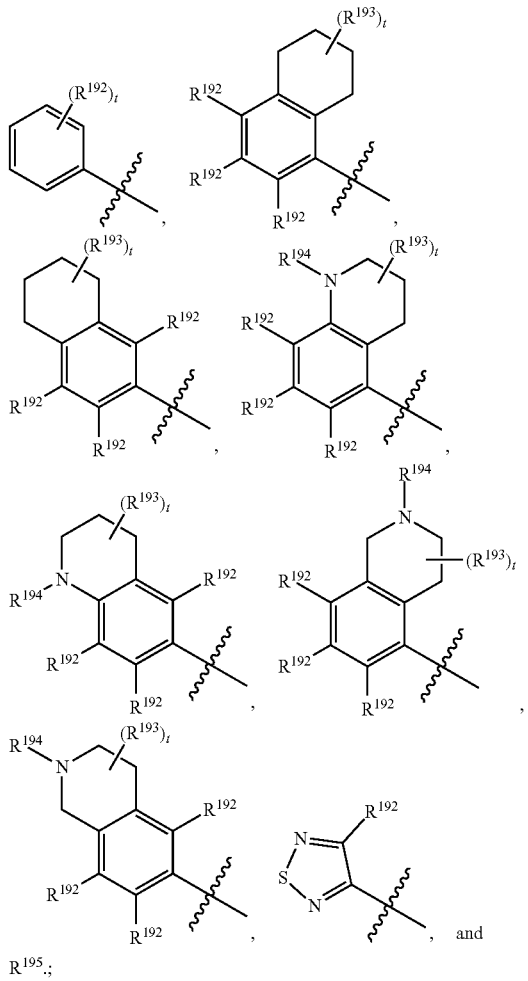

t is independently selected from 0, 1, 2, 3, and 4;

R¹⁹² is independently selected from alkyl, cycloalkyl, aryl, heteroaryl, heterocycle, cyano, amino, hydroxyl, and acyl, each of which R¹⁹² is optionally substituted with a R¹⁷⁵ group;

R¹⁹³ is independently selected from alkyl, cycloalkyl, aryl, heteroaryl, heterocycle, amino, hydroxyl, and acyl;

or two R¹⁹³ groups with the carbon to which they are linked form a carbonyl group;

or two R¹⁹³ groups with the carbon(s) to which they are linked form a fused or spirocyclic ring;

R¹⁹⁴ is selected from alkyl, cycloalkyl, R¹⁷⁵, and acyl; and

R¹⁹⁵ is selected from aryl, heteroaryl, cycloalkyl, and heterocycle, wherein each R¹⁹⁵ is optionally substituted with 1, 2, 3, or 4 R¹⁹² groups;

R¹⁷⁵ is selected from: C(O)A, C(O)R⁴, and R¹⁷⁸;

R¹⁷⁸ is selected from:

(i) carbonyl linked polyethylene glycol, carbonyl linked polypropylene glycol, carbonyl linked polypropylene oxide, polylactic acid, poly(lactic-co-glycolic acid), polyglycolic acid, polyester, polyamide,

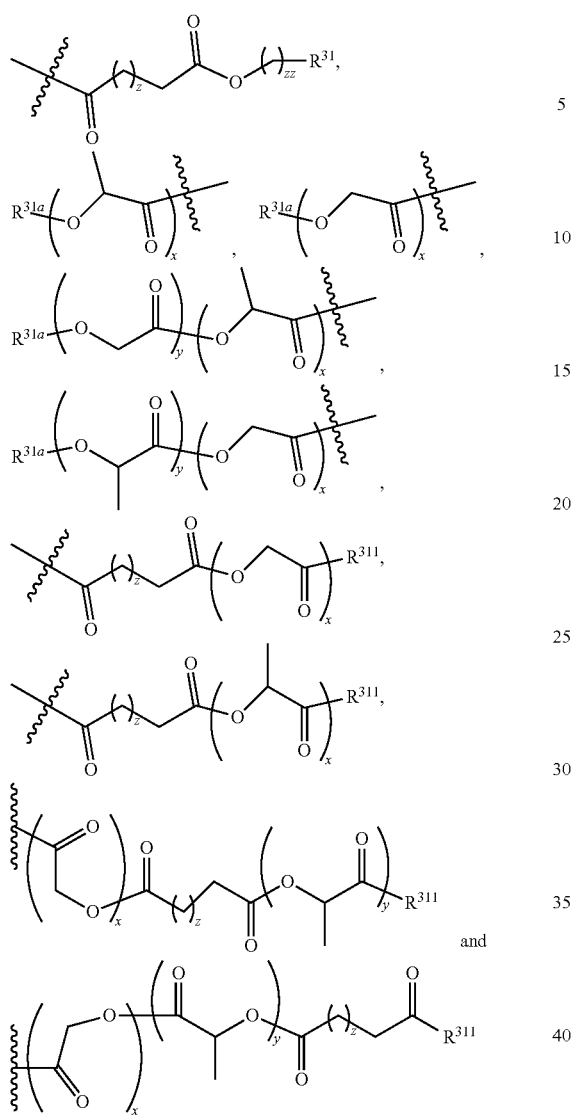

and other biodegradable polymers, wherein each $R^{178}$ is optionally substituted with $R^{31a}$ or $R^{311}$, and wherein each of $R^{178}$ with a terminal hydroxy or carboxy group can be substituted to create an ether or ester;

(ii) —(lactic acid)$_{1-20}$C(O)C$_{1-22}$alkyl, -(lactic acid)$_{1-10}$C(O)C$_{1-22}$alkyl, -(lactic acid)$_{4-20}$C(O)C$_{1-22}$alkyl, -(lactic acid)$_{1-20}$C(O)C$_{1-10}$alkyl, -(lactic acid)$_{1-20}$C(O)$_{C4-10}$alkyl, -(lactic acid)$_{1-20}$C(O)OH, -(lactic acid)$_{1-10}$C(O)OH, -(lactic acid)$_{4-20}$C(O)OH, -(lactic acid)$_{1-10}$C(O)OH, -(lactic acid)$_{4-10}$C(O)OH, -(lactide-co-glycolide)$_{1-10}$C(O)C$_{1-22}$alkyl, -(lactide-co-glycolide)$_{4-10}$C(O)C$_{1-22}$alkyl, -(lactide-co-glycolide)$_{1-10}$C(O)C$_{1-12}$alkyl, -(lactide-co-glycolide)$_{1-10}$C(O)C$_{4-22}$alkyl, -(glycolic acid)$_{1-10}$C(O)C$_{1-10}$alkyl, -(glycolic acid)$_{4-10}$C(O)C$_{1-10}$alkyl, -(lactic acid)$_{4-10}$C(O)C$_{1-10}$alkyl, -(lactic acid)$_{1-10}$C(O)C$_{1-10}$alkyl, -(lactic acid)$_{1-10}$C(O)C$_{4-10}$alkyl, -(lactic acid)$_{1-10}$C(O)C$_{4-10}$alkyl, or —(lactic acid)$_{1-10}$C(O)C$_{4-10}$alkyl;

(iii) —(C(O)CH$_2$O)$_{1-20}$C(O)C$_{1-30}$alkyl, —(C(O)CH(CH$_3$)O)$_{1-20}$C(O)C$_{1-30}$alkyl, —(C(O)CH$_2$O)$_{1-10}$C(O)C$_{1-30}$alkyl, —(C(O)CH(CH$_3$)O)$_{1-10}$C(O)C$_{1-30}$alkyl, —(C(O)CH$_2$O)$_{4-20}$C(O)C$_{1-30}$alkyl, —(C(O)CH(CH$_3$)O)$_{4-20}$C(O)C$_{1-30}$alkyl, —(C(O)CH$_2$O)$_{1-20}$C(O)C$_{1-10}$alkyl, —(C(O)CH(CH$_3$)O)$_{1-20}$C(O)C$_{1-10}$alkyl, —(C(O)CH$_2$O)$_{1-20}$C(O)C$_{4-10}$alkyl, —(C(O)CH(CH$_3$)O)$_{1-20}$C(O)C$_{4-10}$alkyl, —(C(O)CH(CH$_3$)O)$_{4-10}$C(O)C$_{1-10}$alkyl, —(C(O)CH$_2$O)$_{4-10}$C(O)C$_{1-10}$alkyl, —(C(O)CH(CH$_3$)O)$_{1-10}$C(O)C$_{1-10}$alkyl, —(C(O)CH$_2$O)$_{1-10}$C(O)C$_{1-10}$alkyl, —(C(O)CH(CH$_3$)O)$_{1-10}$C(O)C$_{4-10}$alkyl, (C(O)CH$_2$O)$_{1-10}$C(O)C$_{4-10}$alkyl, —(C(O)CH$_2$O)$_{1-10}$C(O)C$_{4-10}$alkyl, —(C(O)CH(CH$_3$)O)$_{1-10}$C(O)C$_{4-10}$alkyl, —(C(O)CH$_2$O)$_{1-10}$C(O)C$_{4-10}$alkyl, —(C(O)CH(CH$_3$)O)$_{1-10}$C(O)C$_{4-10}$alkyl, —(C(O)CH$_2$O)$_{1-10}$(C(O)CH(CH$_3$)O)$_{1-10}$C(O)C$_{1-30}$alkyl, —(C(O)CH$_2$O)$_{2-10}$(C(O)CH(CH$_3$)O)$_{2-10}$C(O)C$_{1-30}$alkyl, —(C(O)CH$_2$O)$_{1-10}$(C(O)CH(CH$_3$)O)$_{1-10}$C(O)C$_{1-12}$alkyl, —(C(O)CH$_2$O)$_{1-10}$(C(O)CH(CH$_3$)O)$_{1-10}$C(O)C$_{4-22}$alkyl, —(C(O)CH(CH$_3$)O)$_{1-10}$(C(O)CH$_2$O)$_{1-10}$C(O)C$_{1-30}$alkyl, —(C(O)CH(CH$_3$)O)$_{2-10}$(C(O)CH$_2$O)$_{2-10}$C(O)C$_{1-30}$alkyl, —(C(O)CH(CH$_3$)O)$_{1-10}$(C(O)CH$_2$O)$_{1-10}$C(O)C$_{1-12}$alkyl, and —(C(O)CH(CH$_3$)O)$_{1-10}$(C(O)CH$_2$O)$_{1-10}$C(O)C$_{4-22}$alkyl;

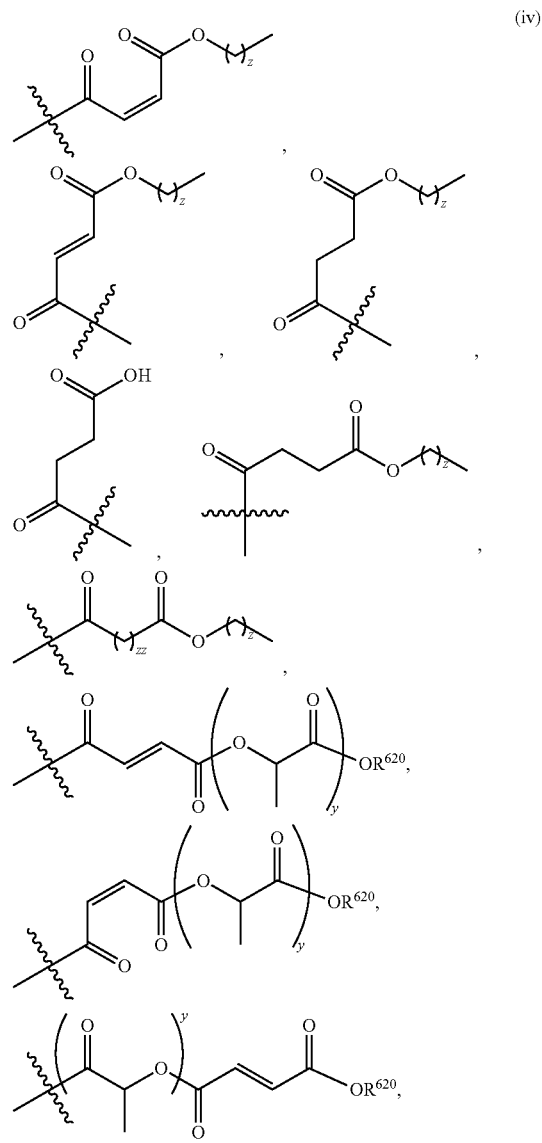

(iv)

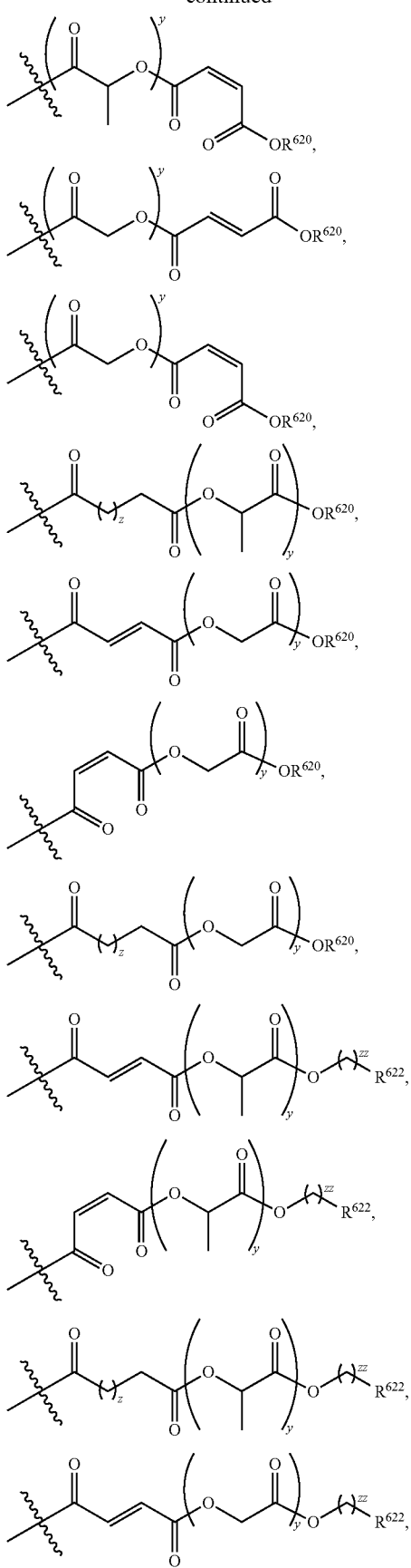

$R^{615}$ and $R^{616}$ are independently selected from: —C(O)$R^{618}$, C(O)A, and hydrogen, each of which except hydrogen can be optionally substituted with $R^5$;

$R^{617}$ is selected from:

(i) polyethylene glycol, polypropylene glycol, polypropylene oxide, polylactic acid, and poly(lactic-co-glycolic acid), polyglycolic acid, or a polyester, a polyamide, or other biodegradable polymers, wherein a terminal hydroxy or carboxy group can be substituted to create an ether or ester, respectively;

(ii) —C$_{10}$-C$_{30}$alkylR$^5$, —C$_{10}$-C$_{30}$alkenylR$^5$, —C$_{10}$-C$_{30}$alkynylR$^5$, —C$_{10}$-C$_{30}$alkenylalkynylR$^5$, —C$_{10}$-C$_{30}$alkyl, —C$_{10}$-C$_{30}$alkenyl, —C$_{10}$-C$_{30}$alkynyl, —C$_{10}$-C$_{30}$alkenylalkynyl;

(iii) an unsaturated fatty acid residue including but not limited the carbon fragment taken from linoleic acid (—(CH$_2$)$_8$(CH)$_2$CH$_2$(CH)$_2$(CH$_2$)$_4$CH$_3$)), docosahexaenoic acid (—(CH$_2$)$_3$(CHCHCH$_2$)$_6$CH$_3$)), eicosapentaenoic acid (—(CH$_2$)$_4$(CHCHCH$_2$)$_5$CH$_3$)), alpha-linolenic acid (—(CH$_2$)$_8$(CHCHCH$_2$)$_3$CH$_3$)) stearidonic acid, γ-linolenic acid, arachidonic acid, docosatetraenoic acid, palmitoleic acid, vaccenic acid, paullinic acid, oleic acid, elaidic acid, gondoic acid, euric acid, nervonic acid or mead acid; and (iv) alkyl, cycloalkyl, cycloalkylalkyl, heterocycle, heterocycloalkyl, arylalkyl, heteroarylalkyl;

R$^{618}$ is selected from:

(iii) —C$_{10}$-C$_{30}$alkylR$^5$, —C$_{10}$-C$_{30}$alkenylR$^5$, —C$_{10}$-C$_{30}$alkynylR$^5$, —C$_{10}$-C$_{30}$alkenylalkynylR$^5$, —C$_{10}$-C$_{30}$alkyl, —C$_{10}$-C$_{30}$alkenyl, —C$_{10}$-C$_{30}$alkynyl, —C$_{10}$-C$_{30}$alkenylalkynyl; and (iv) an unsaturated fatty acid residue including but not limited to the carbon chains from linoleic acid (—(CH$_2$)$_8$(CH)$_2$CH$_2$(CH)$_2$(CH$_2$)$_4$CH$_3$)), docosahexaenoic acid (—(CH$_2$)$_3$(CHCHCH$_2$)$_6$CH$_3$)), eicosapentaenoic acid (—(CH$_2$)$_4$(CHCHCH$_2$)$_5$CH$_3$)), alpha-linolenic acid (—(CH$_2$)$_8$(CHCHCH$_2$)$_3$CH$_3$)), stearidonic acid, γ-linolenic acid, arachidonic acid, docosatetraenoic acid, palmitoleic acid, vaccenic acid, paullinic acid, oleic acid, elaidic acid, gondoic acid, euric acid, nervonic acid and mead acid, and wherein, if desired, each of which can be substituted with R$^5$;

R$^{636}$ is selected from C(O)A,

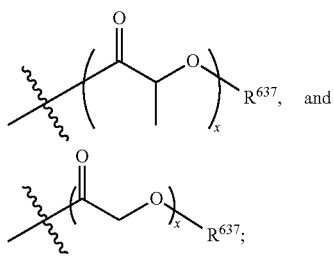
R$^{637}$, and

R$^{637}$ is selected from hydrogen, —C(O)A, —C(O)alkyl, aryl, alkyl, cycloalkyl, cycloalkylalkyl, heterocyclyl, heterocycloalkyl, arylalkyl, heteroaryl, and heteroarylalkyl; and L$^{33}$ is selected from: bond, —OC$_1$-C$_{30}$alkyl-O—, —NHC$_1$-C$_{30}$alkyl-O—, N(alkyl)C$_1$-C$_{30}$alkyl-O—, —NHC$_1$-C$_{30}$alkyl-NH—, N(alkyl)C$_1$-C$_{30}$alkyl-NH—, —NHC$_1$-C$_{30}$alkyl-N(alkyl)-, —N(alkyl)C$_1$-C$_{30}$alkyl-N-(alkyl)-, —OC$_1$-C$_{30}$alkenyl-O—, —NHC$_1$-C$_{30}$alkenyl-O—, N(alkyl)C$_1$-C$_{30}$alkenyl-O—, —NHC$_1$-C$_{30}$alkenyl-NH—, N(alkyl)C$_1$-C$_{30}$alkenyl-NH—, —NHC$_1$-C$_{30}$alkenyl-N(alkyl)-, —N(alkyl)C$_1$-C$_{30}$alkenyl-N-(alkyl)-, —OC$_1$-C$_{30}$alkynyl-O—, —NHC$_1$-C$_{30}$alkynyl-O—, N(alkyl)C$_1$-C$_{30}$alkynyl-O—, —NHC$_1$-C$_{30}$alkynyl-NH—, N(alkyl)C$_1$-C$_{30}$alkynyl-NH—, —NHC$_1$-C$_{30}$alkynyl-N(alkyl)-, and —N(alkyl)C$_1$-C$_{30}$alkynyl-N-(alkyl)-; and wherein all other variables are as defined herein.

The disclosure provides carbonic anhydrase inhibitor prodrugs of Formula XVIB, Formula XVIIB, and Formula XVIIIB:

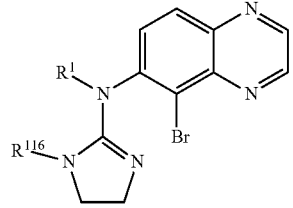
(XVIB)

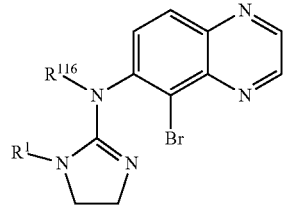
(XVIIB)

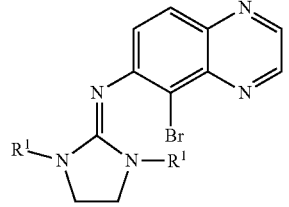
(XVIIIB)

or a pharmaceutically acceptable composition, salt, or isotopic derivative thereof wherein R$^{116}$ is selected from: R$^{117}$, alkyl, alkyloxy, acyl, polyethylene glycol, polypropylene glycol, polypropylene oxide, polylactic acid, poly(lactic-co-glycolic acid), a polyglycolic acid, a polyester, polyamide, or other biodegradable polymer, wherein each R$^{116}$ other than R$^{117}$ is substituted with at least one L$^4$-R$^{121}$;

wherein R$^{116}$ can be further substituted with R$^5$ if valence permits, a stable compound is formed, and the resulting compound is pharmaceutically acceptable.

R$^{117}$ is selected from:

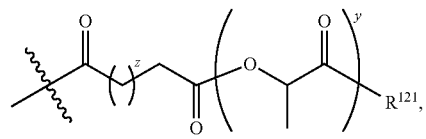

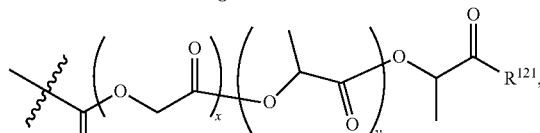

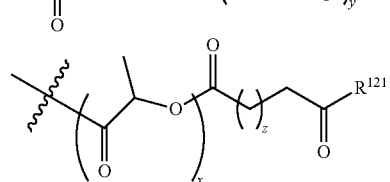

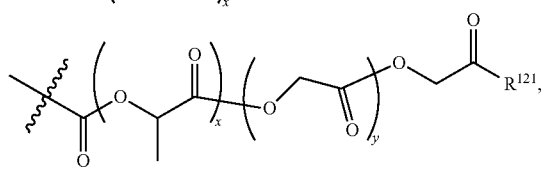

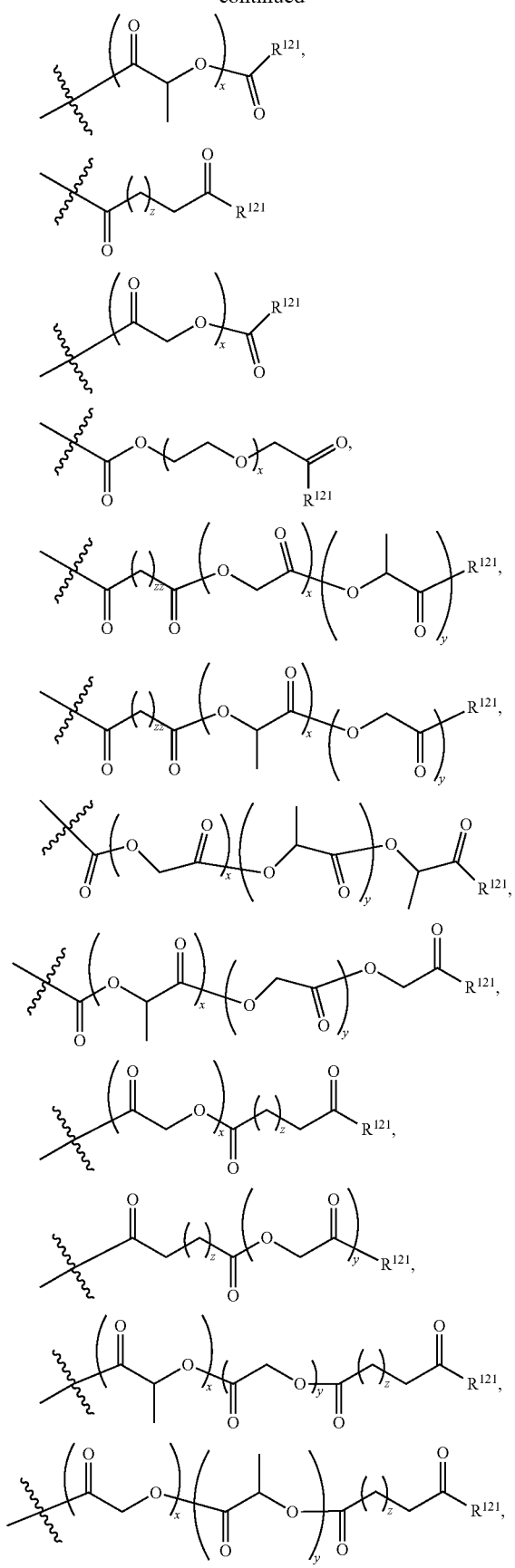

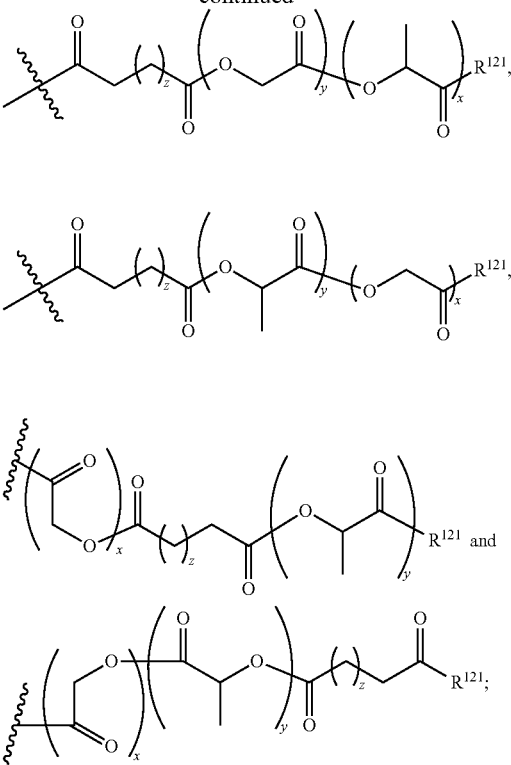

and wherein all other variables are as defined herein.

The disclosure provides carbonic anhydrase inhibitor prodrugs of Formula XIXB:

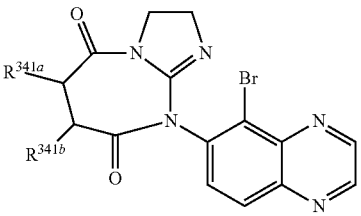

(XIXB)

or a pharmaceutically acceptable composition, salt, or isotopic derivative thereof wherein $R^{341a}$ and $R^{341b}$ are independently selected from hydrogen and alkyl.

In one embodiment of Formula XIXB, $R^{341a}$ and $R^{341b}$ are hydrogen.

In one embodiment of Formula XIXB, $R^{341a}$ is hydrogen and $R^{341b}$ is methyl.

In one embodiment of Formula XIXB, $R^{341a}$ is methyl and $R^{341b}$ is hydrogen.

In one embodiment of Formula XIXB is the malic salt.

In one embodiment of Formula XIXB is the maleate salt.

Sunitinib Prodrugs

The disclosure provides Sunitinib prodrugs of Formula IC and Formula IIC:

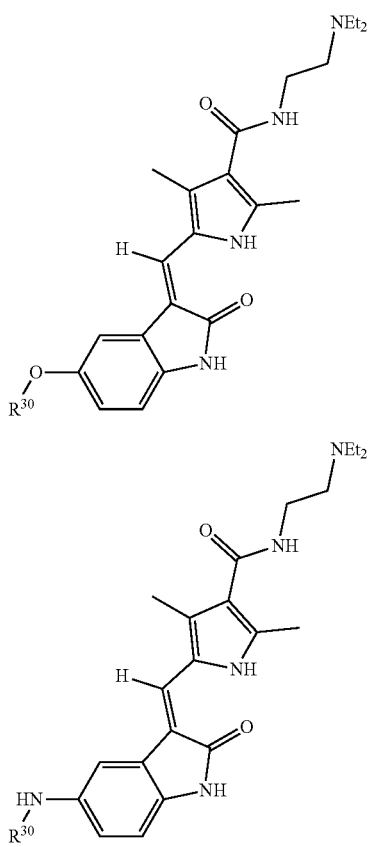

(IC)

(IIC)

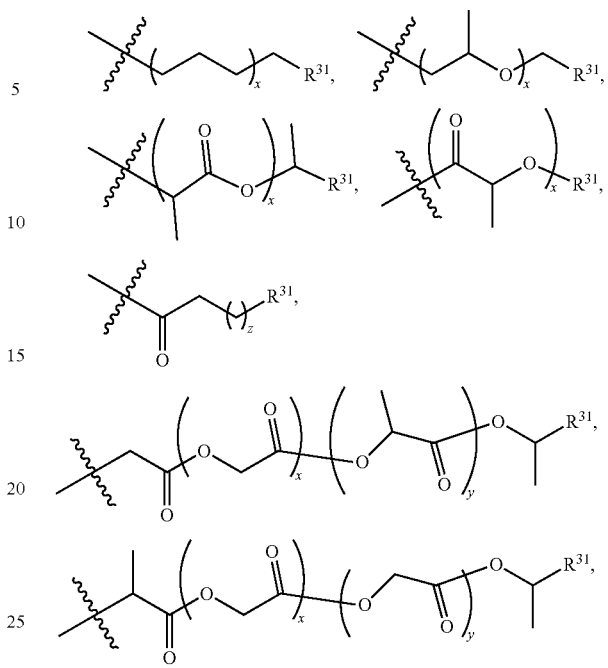

-continued wherein $R^{30}$ is optionally substituted with $R^{31}$, and wherein each $R^{30}$ with a terminal hydroxy or carboxy group can be substituted to create an ether or ester, respectively;

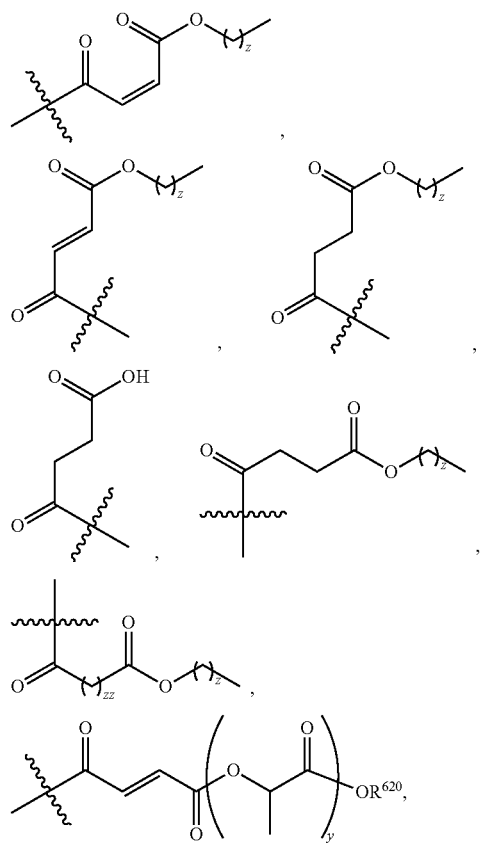

(iii)

or a pharmaceutically acceptable composition, salt, or isotopic derivative thereof. This structure is related to Sunitinib (marketed in the form of the (−)-malic acid salt as SUTENT® by Pfizer, and previously known as SU11248), which is an oral, small-molecule, multi-targeted receptor tyrosine kinase (RTK) inhibitor that was approved by the FDA for the treatment of renal cell carcinoma (RCC) and imatinib-resistant gastrointestinal stromal tumor (GIST) on Jan. 26, 2006. Sunitinib was the first cancer drug simultaneously approved for two different indications. Sunitinib inhibits cellular signaling by targeting multiple receptor tyrosine kinases (RTKs). These include all receptors for platelet-derived growth factor (PDGF-Rs) and vascular endothelial growth factor receptors (VEGFRs), which play a role in both tumor angiogenesis and tumor cell proliferation. The simultaneous inhibition of these targets leads to both reduced tumor vascularization and cancer cell death, and, ultimately, tumor shrinkage. Sunitinib and derivatives thereof are described in U.S. Pat. Nos. 7,211,600; 6,573,293; and 7,125,905.

$R^{30}$ is selected from:
(i) polyethylene glycol, polypropylene glycol, polypropylene oxide, polylactic acid, poly(lactic-co-glycolic acid), a polyglycolic acid, a polyester, and a polyamide

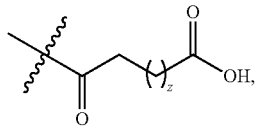

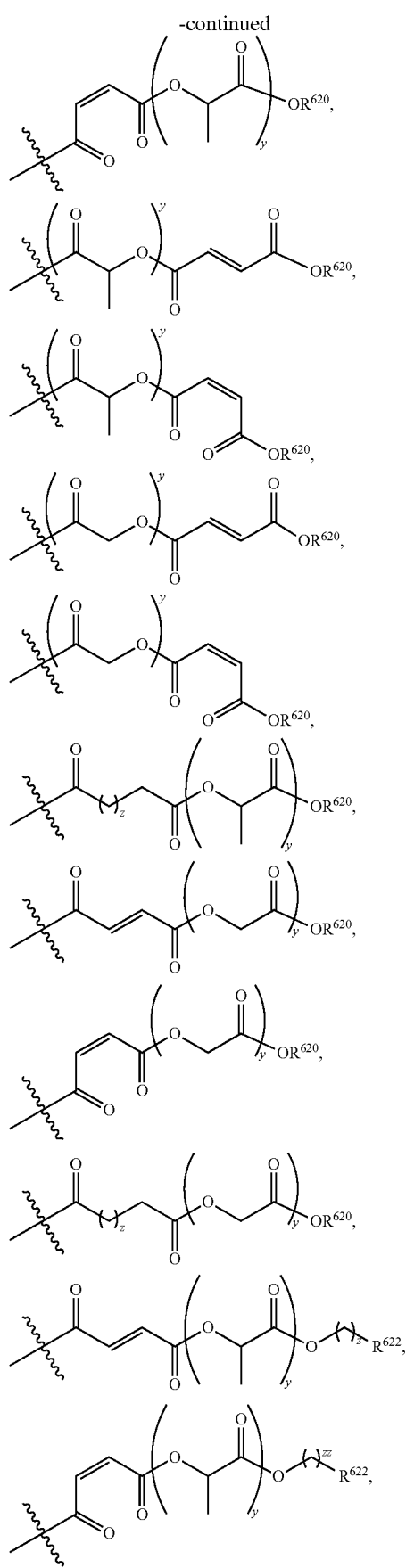
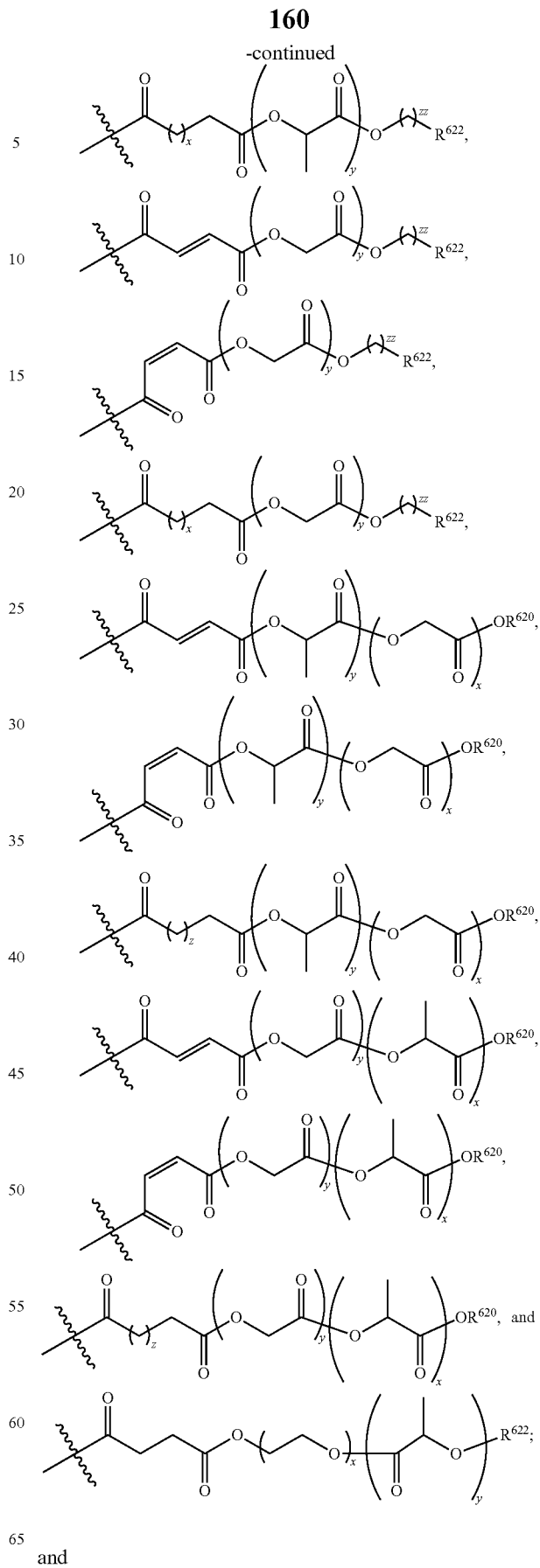
and
wherein all other variables are defined herein.

The disclosure provides Sunitinib prodrugs of Formula IIIC:

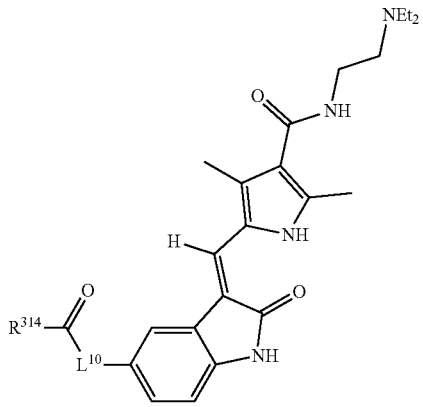
(IIIC)

or a pharmaceutically acceptable composition, salt, or isotopic derivative thereof wherein $L^{10}$ is —O—, —NH—, or —N(alkyl)-;

$R^{314}$ is an unsaturated fatty acid residue including but not limited to the carbon chains from linoleic acid (—$(CH_2)_8$ $(CH)_2CH_2(CH)_2(CH_2)_4CH_3$)), docosahexaenoic acid (—$(CH_2)_3(CHCHCH_2)_6CH_3$)), eicosapentaenoic acid (—$(CH_2)_4(CHCHCH_2)_5CH_3$)), alphalinolenic acid (—$(CH_2)_8(CHCHCH_2)_3CH_3$)), stearidonic acid, γ-linolenic acid, arachidonic acid, docosatetraenoic acid, palmitoleic acid, vaccenic acid, paullinic acid, oleic acid, elaidic acid, gondoic acid, euric acid, nervonic acid and mead acid, and wherein, if desired, each of which can be substituted with $R^5$; and $R^5$ is defined above.

In one embodiment, $R^{314}$ is

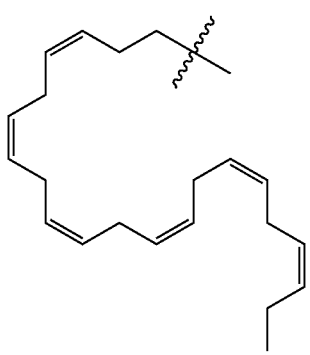

The disclosure provides Sunitinib prodrugs of Formula IVC:

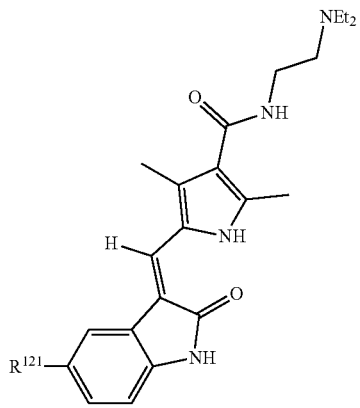
(IVC)

or a pharmaceutically acceptable composition, salt, or isotopic derivative thereof wherein $R^{121}$ is as defined herein.

The disclosure provides Sunitinib prodrugs of Formula VIC:

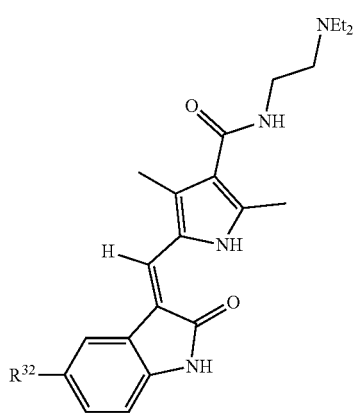
(VC)

or a pharmaceutically acceptable composition, salt, or isotopic derivative thereof wherein $R^{32}$ is selected from: $R^{35}$, $R^{121}$, alkyl, alkyloxy, polyethylene glycol, polypropylene glycol, polypropylene oxide, polylactic acid, poly(lactic-co-glycolic acid), a polyglycolic acid, a polyester, polyamide, or other biodegradable polymer, wherein each $R^{32}$ other than $R^{35}$ and $R^{121}$ is substituted with at least one $L^4$-$R^{121}$;

wherein $R^{32}$ can be further substituted with $R^5$ if valence permits, a stable compound is formed, and the resulting compound is pharmaceutically acceptable.

$R^{35}$ is selected from:

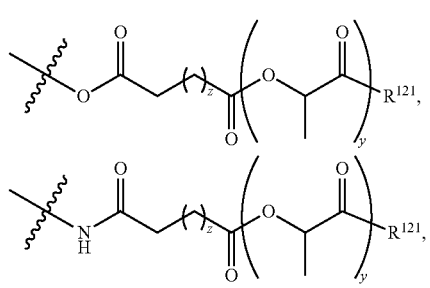

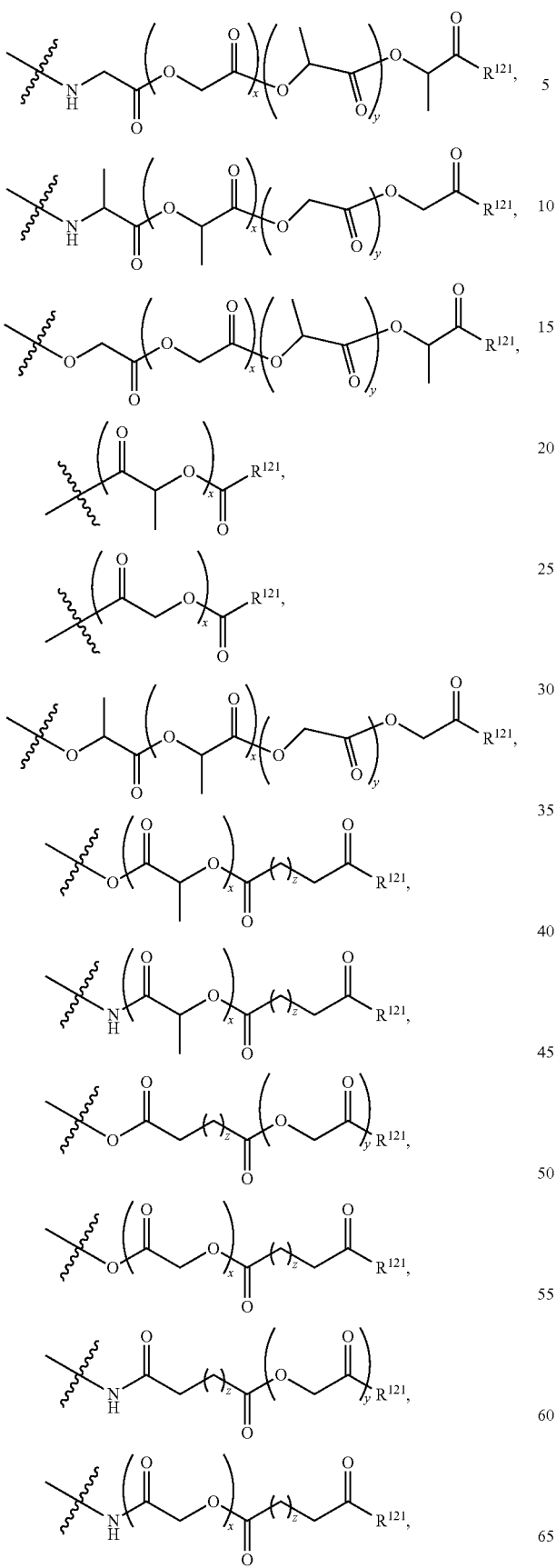
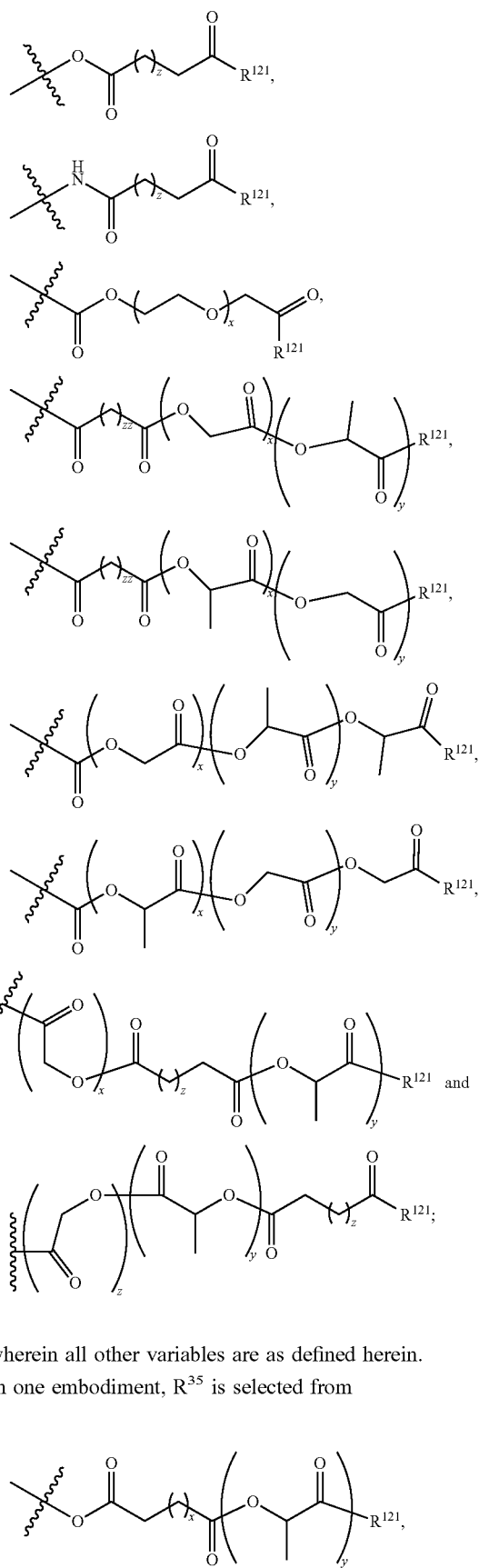
wherein all other variables are as defined herein.
In one embodiment, $R^{35}$ is selected from
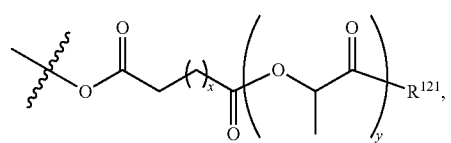

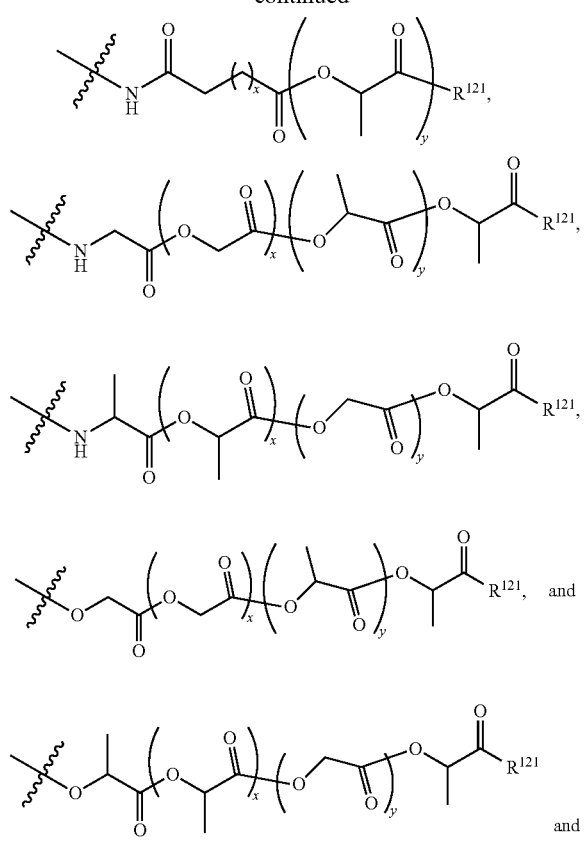
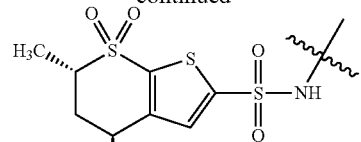
$R^{121}$ is $R^{15}$, and $R^{15}$ is hydrogen.
In a further embodiment, x and y are independently selected from 1, 2, 3, 4, 5, and 6.
In one embodiment, $R^{35}$ is
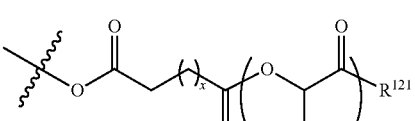
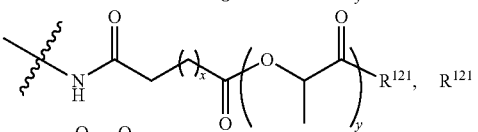, $R^{121}$
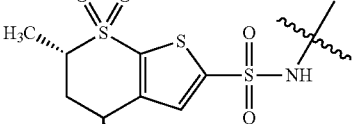
and $R^{15}$ is hydrogen.
Non-limiting examples of Formula VC include
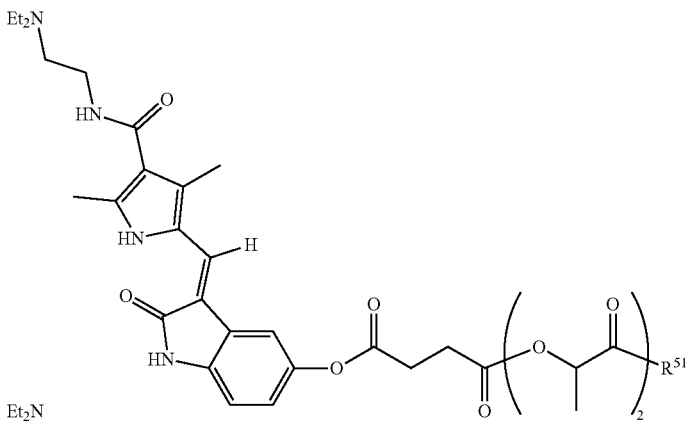
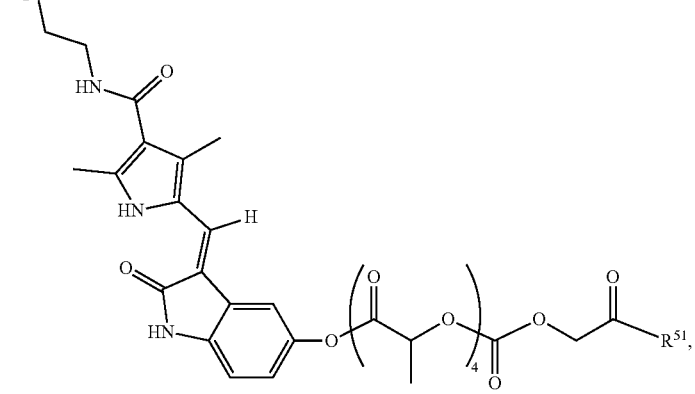

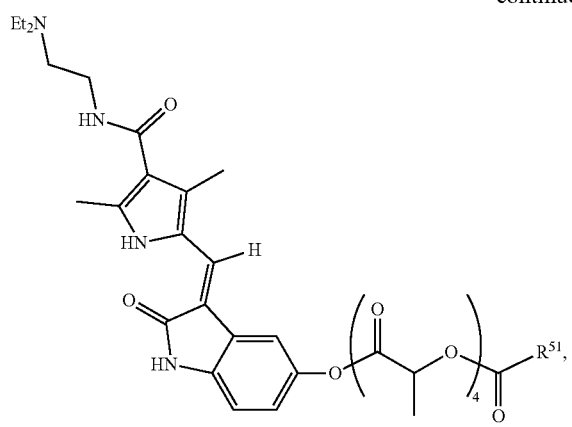
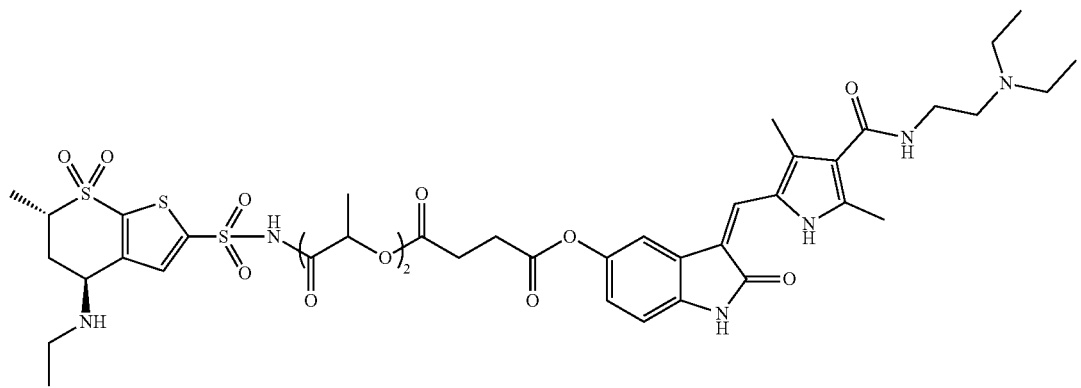
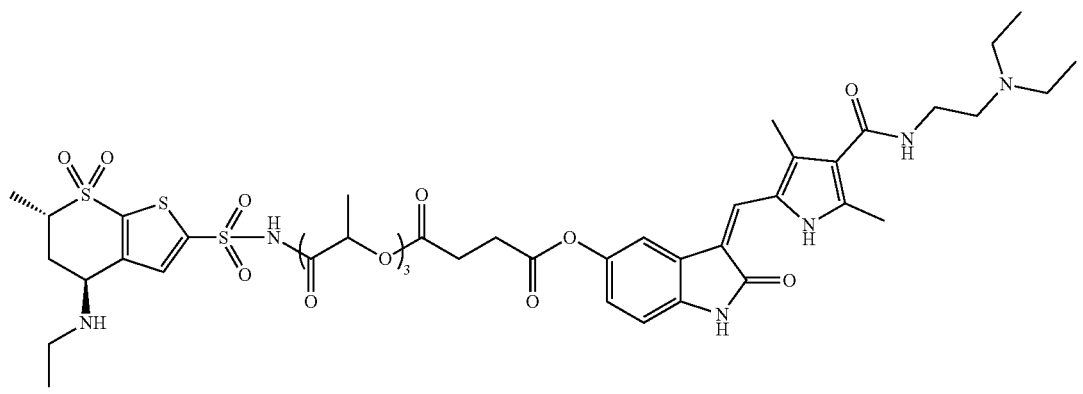
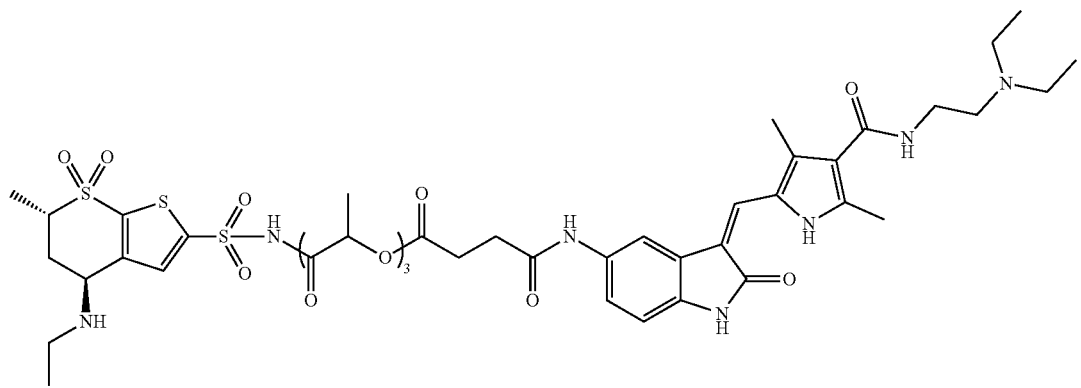

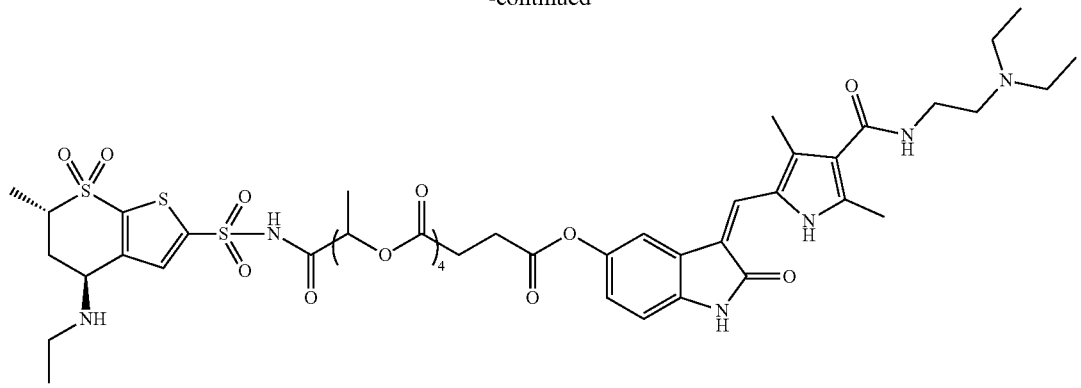

The disclosure provides Sunitinib prodrugs of Formula VIC:

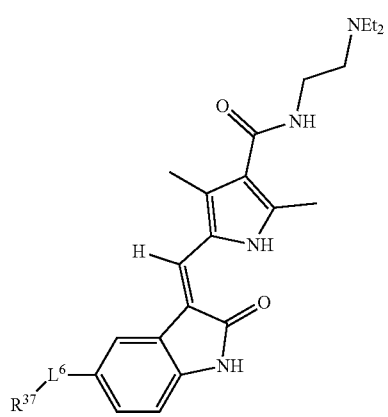

or a pharmaceutically acceptable composition, salt, or isotopic derivative thereof wherein $L^6$ is selected from —O—, —NH—, —N(alkyl)$_{1-4}$-, —C(O)O—, —S—, —C(O)— and —OC(O)—;

$R^{37}$ is selected from: $R^{121}$, polyethylene glycol, polypropylene glycol, polypropylene oxide, polylactic acid, poly(lactic-co-glycolic acid), a polyglycolic acid, a polyester, a polyamide, or other biodegradable polymer, wherein each $R^{37}$ other than $R^{38}$ and $R^{121}$ is substituted with at least one $L^6$-$R^{121}$ $R^{38}$ is selected from:

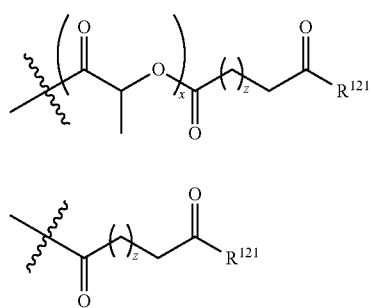

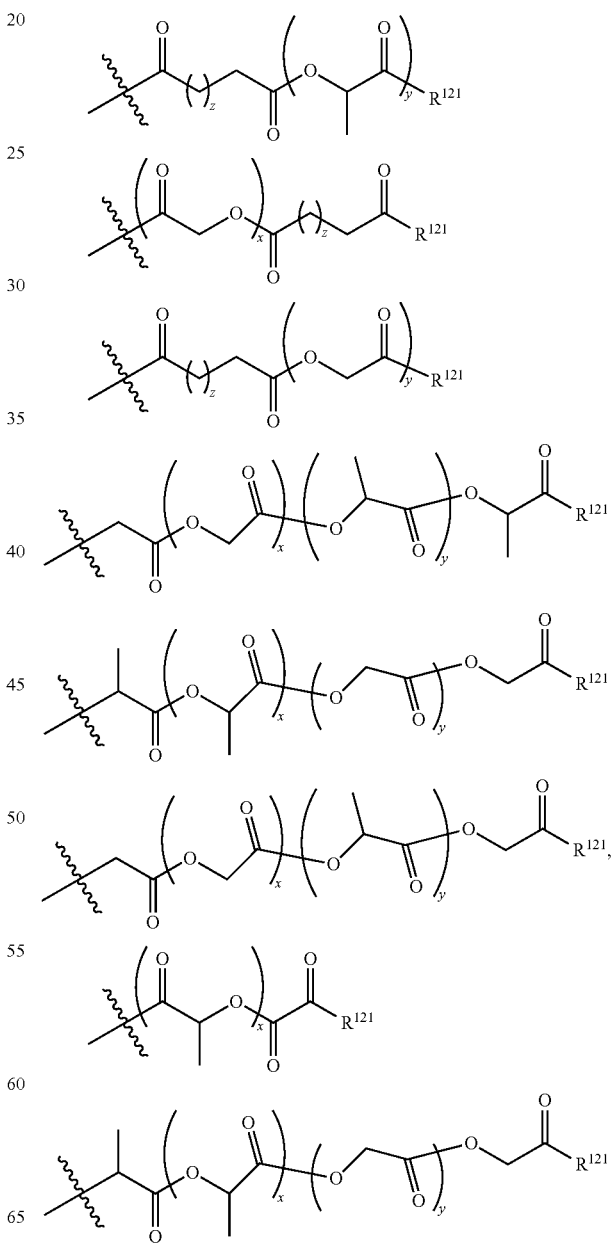

171

-continued

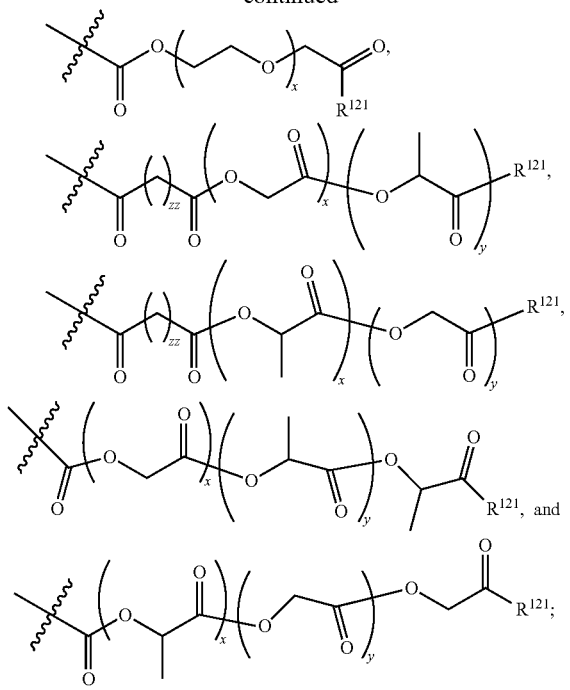

wherein all other variables are as defined herein.

Timolol Prodrugs

The disclosure provides Timolol prodrugs of Formula ID:

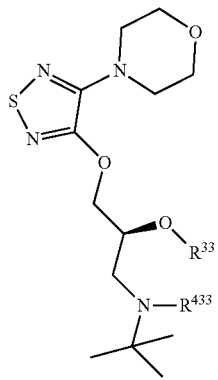

(ID)

or a pharmaceutically acceptable composition, salt, or isotopic derivative thereof wherein $R^{33}$ is selected from:

(i) carbonyl linked polyethylene glycol, carbonyl linked polypropylene glycol, carbonyl linked polypropylene oxide, polylactic acid, poly(lactic-co-glycolic acid), a polyglycolic acid, a polyester, and a polyamide;

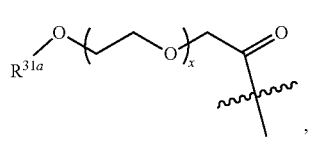

(i)

172

-continued

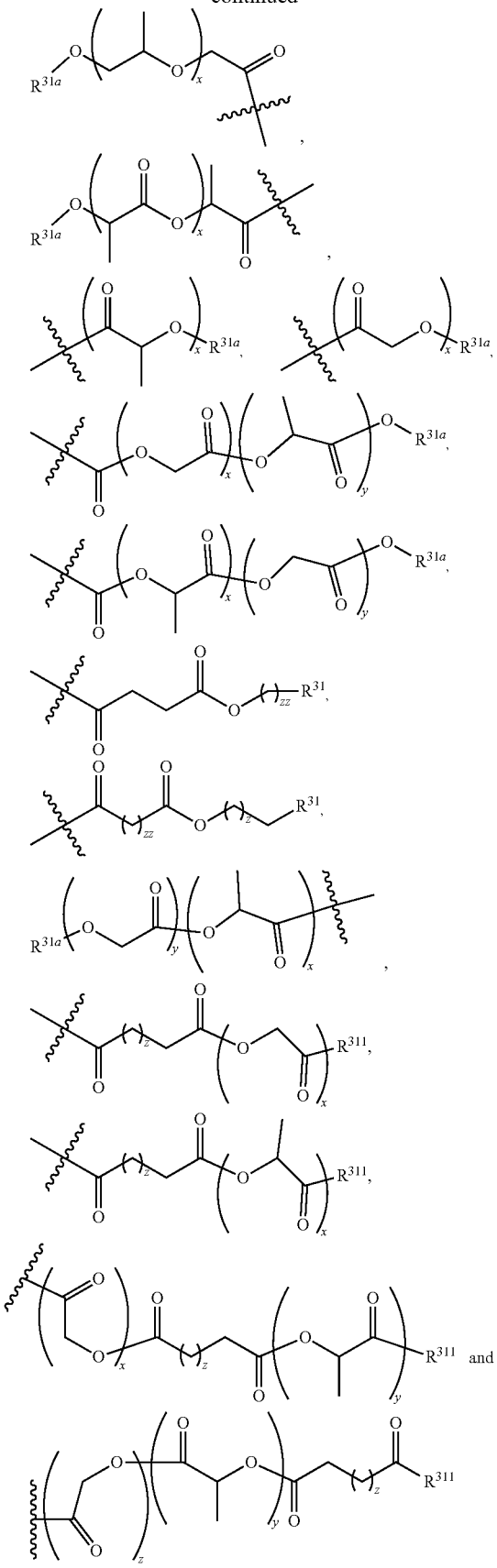

or other biodegradable polymer, wherein each $R^{33}$ is optionally substituted with $R^{31a}$ or $R^{311}$, and wherein each of $R^{33}$ with a terminal hydroxy or carboxy group can be substituted to create an ether or ester, respectively; and (iii) —C(O)C$_{17-30}$alkyl, —C(O)C$_{10-30}$alkenyl, —C(O)C$_{10-30}$alkynyl, —C(O)(C$_{10-30}$alkyl with at least one $R^5$ substituent on the alkyl chain), —C(O)(C$_{10-30}$alkenyl, with at least one $R^5$ substituent on the alkenyl chain), and —C(O)(C$_{10-30}$alkynyl, with at least one $R^5$ substituent on the alkynyl chain);

(iv) —(lactic acid)$_{1-20}$C(O)C$_{1-30}$alkyl, —(lactic acid)$_{1-10}$C(O)C$_{1-30}$alkyl, -(lactic acid)$_{4-20}$C(O)C$_{1-30}$alkyl, —(lactic acid)$_{1-20}$C(O)C$_{1-10}$alkyl, -(lactic acid)$_{1-20}$C(O)C$_{4-10}$alkyl, —(lactic acid)$_{1-20}$C(O)OH, -(lactic acid)$_{1-10}$C(O)OH, -(lactic acid)$_{4-20}$C(O)OH, —(lactic acid)$_{1-10}$C(O)OH, -(lactic acid)$_{4-10}$C(O)OH, —(lactide-co-glycolide)$_{1-10}$C(O)C$_{1-22}$alkyl, -(lactide-co-glycolide)$_{4-10}$C(O)C$_{1-22}$alkyl, -(lactide-co-glycolide)$_{1-10}$C(O)C$_{1-12}$alkyl, -(lactide-co-glycolide)$_{1-10}$C(O)C$_{4-22}$alkyl, -(glycolic acid)$_{1-10}$C(O)C$_{1-10}$alkyl, -(glycolic acid)$_{4-10}$C(O)C$_{1-10}$alkyl, -(lactic acid)$_{4-10}$C(O)C$_{1-10}$alkyl, -(lactic acid)$_{1-10}$C(O)C$_{1-10}$alkyl, —(lactic acid)$_{1-10}$C(O)C$_{4-10}$alkyl, -(lactic acid)$_{1-10}$C(O)C$_{4-10}$alkyl, or —(lactic acid)$_{1-10}$C(O)C$_{4-10}$alkyl;

(v) —(C(O)CH$_2$O)$_{1-20}$C(O)C$_{1-30}$alkyl, —(C(O)CH(CH$_3$)O)$_{1-20}$C(O)C$_{1-30}$alkyl, —(C(O)CH$_2$O)$_{1-10}$C(O)C$_{1-30}$alkyl, —(C(O)CH(CH$_3$)O)$_{1-10}$C(O)C$_{1-30}$alkyl, —(C(O)CH$_2$O)$_{4-20}$C(O)C$_{1-30}$alkyl, —(C(O)CH(CH$_3$)O)$_{4-20}$C(O)C$_{1-30}$alkyl, —(C(O)CH$_2$O)$_{1-20}$C(O)C$_{1-10}$alkyl, —(C(O)CH(CH$_3$)O)$_{1-20}$C(O)C$_{1-10}$alkyl, —(C(O)CH$_2$O)$_{1-20}$C(O)C$_{4-10}$alkyl, —(C(O)CH(CH$_3$)O)$_{1-20}$C(O)C$_{4-10}$alkyl, —(C(O)CH(CH$_3$)O)$_{4-10}$C(O)C$_{1-10}$alkyl, —(C(O)CH$_2$O)$_{4-10}$C(O)C$_{1-10}$alkyl, —(C(O)CH(CH$_3$)O)$_{1-10}$C(O)C$_{1-10}$alkyl, —(C(O)CH$_2$O)$_{1-10}$C(O)C$_{1-10}$alkyl, —(C(O)CH(CH$_3$)O)$_{1-10}$C(O)C$_{4-10}$alkyl, (C(O)CH$_2$O)$_{1-10}$C(O)C$_{4-10}$alkyl, —(C(O)CH$_2$O)$_{1-10}$C(O)C$_{4-10}$alkyl, —(C(O)CH(CH$_3$)O)$_{1-10}$C(O)C$_{4-10}$alkyl, —(C(O)CH$_2$O)$_{1-10}$C(O)C$_{4-10}$alkyl, —(C(O)CH(CH$_3$)O)$_{1-10}$C(O)C$_{4-10}$alkyl, —(C(O)CH$_2$O)$_{1-10}$(C(O)CH(CH$_3$)O)$_{1-10}$C(O)C$_{1-30}$alkyl, —(C(O)CH$_2$O)$_{2-10}$(C(O)CH(CH$_3$)O)$_{2-10}$C(O)C$_{1-30}$alkyl, —(C(O)CH$_2$O)$_{1-10}$(C(O)CH(CH$_3$)O)$_{1-10}$C(O)C$_{1-12}$alkyl, —(C(O)CH$_2$O)$_{1-10}$(C(O)CH(CH$_3$)O)$_{1-10}$C(O)C$_{4-22}$alkyl, —(C(O)CH(CH$_3$)O)$_{1-10}$(C(O)CH$_2$O)$_{1-10}$C(O)C$_{1-30}$alkyl, —(C(O)CH(CH$_3$)O)$_{2-10}$(C(O)CH$_2$O)$_{2-10}$C(O)C$_{1-30}$alkyl, —(C(O)CH(CH$_3$)O)$_{1-10}$(C(O)CH$_2$O)$_{1-10}$C(O)C$_{1-12}$alkyl, and —(C(O)CH(CH$_3$)O)$_{1-10}$(C(O)CH$_2$O)$_{1-10}$C(O)C$_{4-22}$alkyl;

(iv)

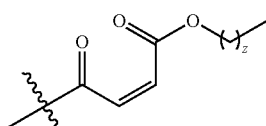

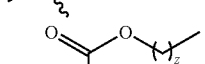 , 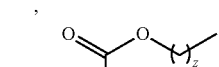 ,

-continued

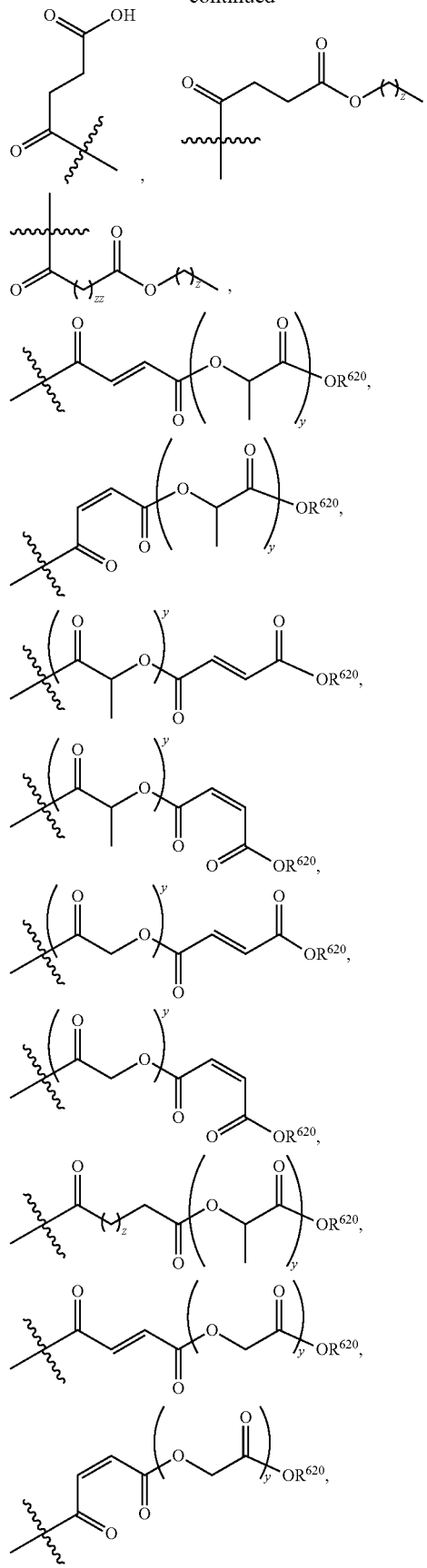

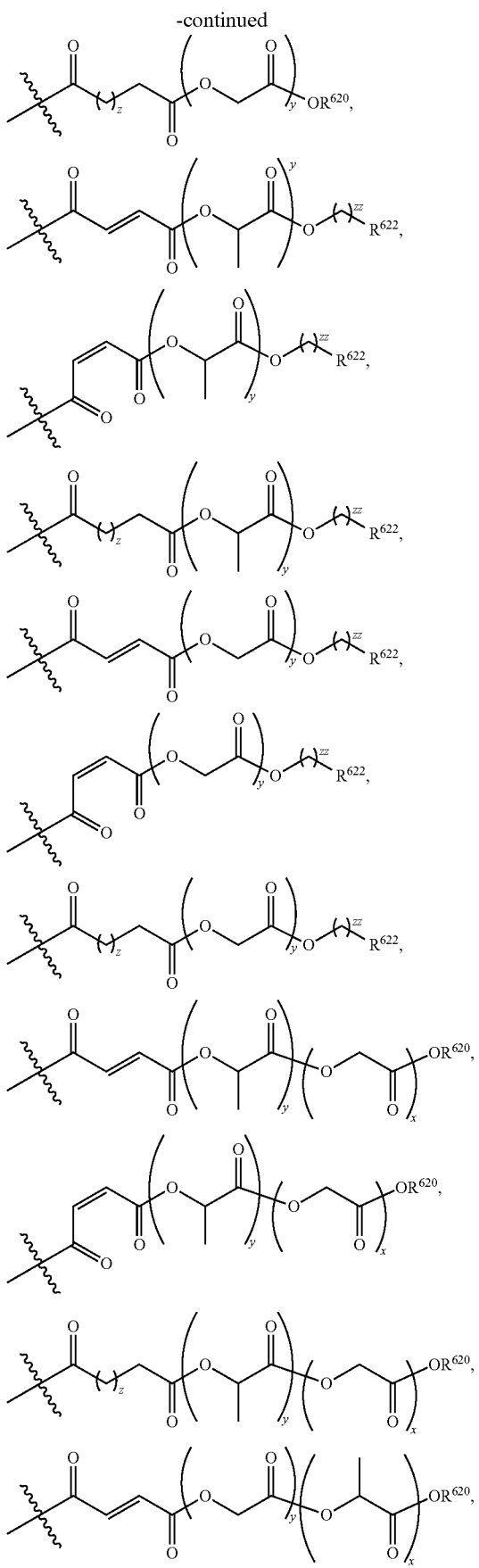

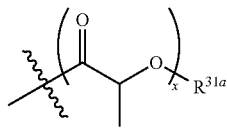

$R^{433}$ is selected from hydrogen, —C(O)A, acyl, aryl, alkyl, alkenyl, alkynyl cycloalkyl, cycloalkylalkyl, heterocyclyl, heterocycloalkyl, aryl, arylalkyl, heteroaryl, and heteroarylalkyl; and wherein all other variables are as defined herein.

In one embodiment $R^{31}$ is —C(O)A, alkyl, or PEG.

In one embodiment $R^{31}$ is —C(O)A, wherein A is methyl.

In one embodiment $R^{33}$ is

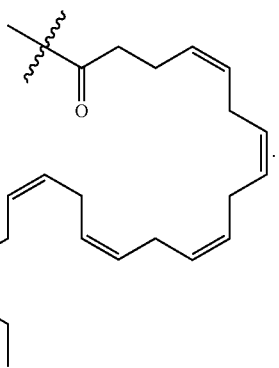

and $R^{43}$ is hydrogen.

In one embodiment, $R^{33}$ is —C(O)(CH$_2$)$_{16}$CH$_3$ and $R^{433}$ is hydrogen.

In one embodiment, $R^{433}$ is hydrogen and $R^{33}$ is

In one embodiment, $R^{33}$ is

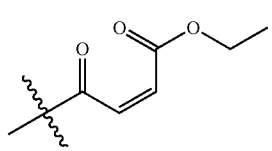 [SMILES: *C(=O)/C=C\C(=O)OCC]

and $R^{433}$ is hydrogen.

In one embodiment, $R^{33}$ is

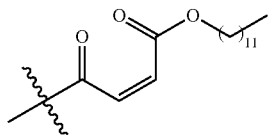

and $R^{433}$ is hydrogen.

In one embodiment, $R^{33}$ is

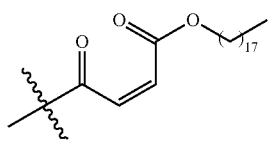

and $R^{433}$ is hydrogen.

In one embodiment, $R^{33}$ is

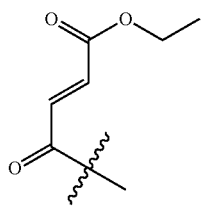 [SMILES: *C(=O)/C=C/C(=O)OCC]

and $R^{433}$ is hydrogen.

In one embodiment, $R^{33}$ is

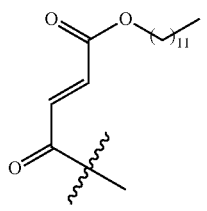

and $R^{433}$ is hydrogen.

In one embodiment, $R^{33}$ is

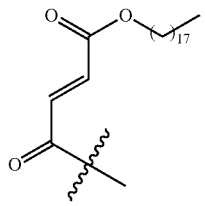

and $R^{433}$ is hydrogen.

In one embodiment, $R^{33}$ is

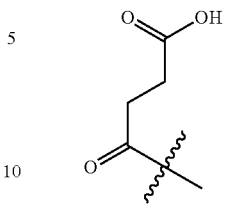

and $R^{433}$ is hydrogen.

In one embodiment, $R^{33}$ is

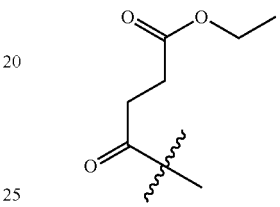

and $R^{433}$ is hydrogen.

In one embodiment, $R^{33}$ is

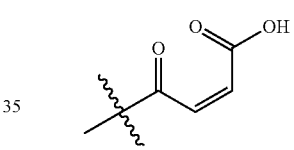

and $R^{433}$ is hydrogen.

In one embodiment, $R^{33}$ is

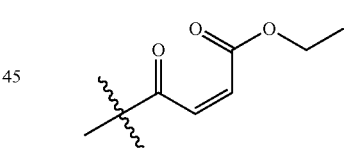

and $R^{433}$ is hydrogen.

In one embodiment, $R^{33}$ is

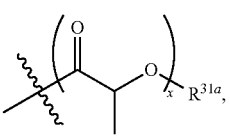

$R^{433}$ is hydrogen, x is selected from 1, 2, 3, 4, 5, and 6, and $R^{31}$ is —C(O)Me.

In one embodiment, a compound of Formula ID is the pharmaceutically acceptable HCl salt.

In one embodiment, a compound of Formula ID is the pharmaceutically acceptable maleic salt.

Non-limiting Examples of ID include
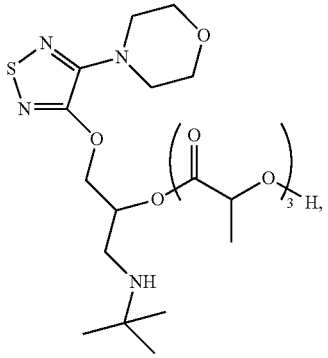
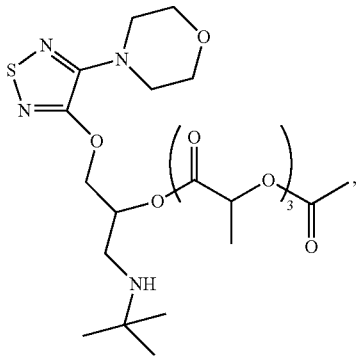
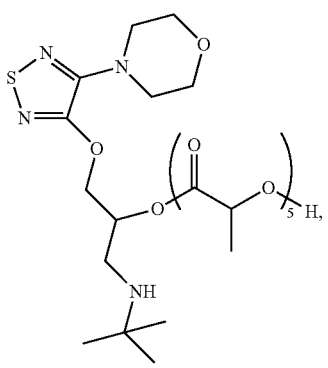
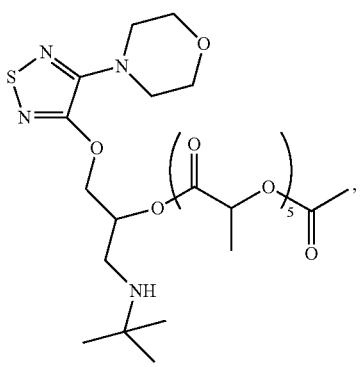
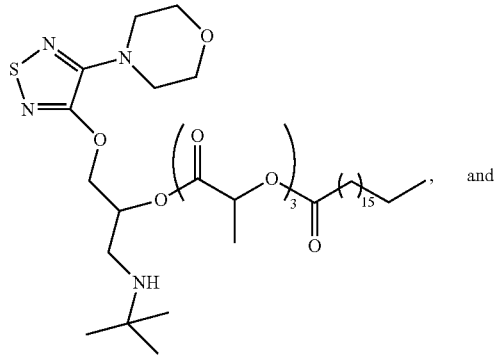
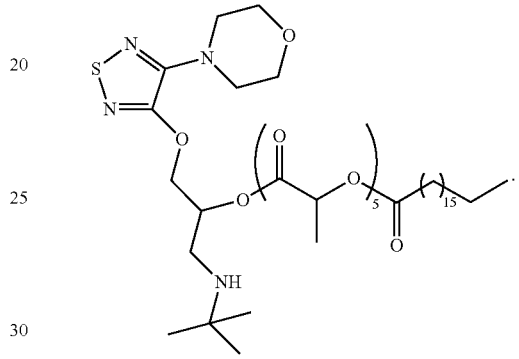
The disclosure provides Timolol prodrugs of Formula IID:
(IID)
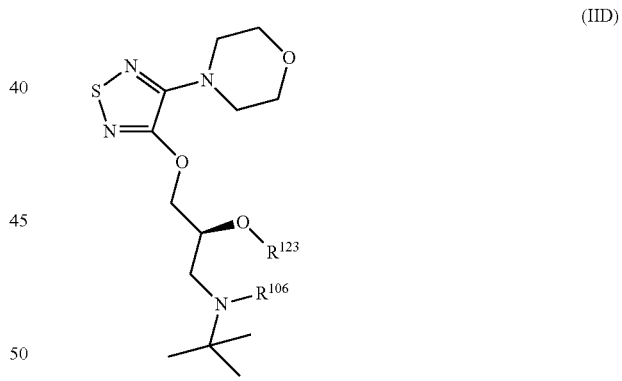
or a pharmaceutically acceptable composition, salt, or isotopic derivative thereof.
$R^{123}$ is selected from:
(ii) polyethylene glycol, polypropylene glycol, polypropylene oxide, polylactic acid, poly(lactic-co-glycolic acid), polyglycolic acid, polyester, polyamide,
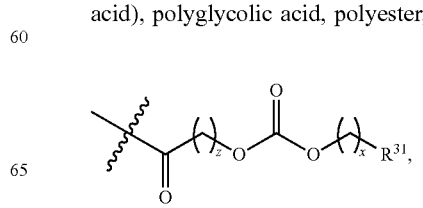

-continued wherein each $R^{123}$ is optionally substituted with $R^{311}$ or $R^{31a}$, and wherein each of $R^{123}$ with a terminal hydroxy or carboxy group can be substituted to create an ether or ester;

(ii) —C(O)C$_{17-30}$alkyl, —C(O)C$_{10-30}$alkenyl, —C(O)C$_{10-30}$alkynyl, —C(O)C$_{10-30}$alkyl with at least one $R^5$ substituent on the alkyl chain), —C(O)(C$_{10-30}$alkenyl, with at least one $R^5$ substituent on the alkenyl chain) —C(O)(C$_{10-30}$alkynyl, with at least one $R^5$ substituent on the alkynyl chain), -(lactic acid)$_{1-20}$C(O)C$_{1-30}$alkyl, —(lactic acid)$_{1-10}$C(O)C$_{1-30}$alkyl, -(lactic acid)$_{4-20}$C(O)C$_{1-30}$alkyl, —(lactic acid)$_{1-20}$C(O)C$_{1-10}$alkyl, -(lactic acid)$_{1-20}$C(O)C$_{4-10}$alkyl, —(lactic acid)$_{1-20}$C(O)OH, -(lactic acid)$_{1-10}$C(O)OH, -(lactic acid)$_{4-20}$C(O)OH, —(lactic acid)$_{1-10}$C(O)OH, -(lactic acid)$_{4-10}$C(O)OH, —(lactide-co-glycolide)$_{1-10}$C(O)C$_{1-22}$alkyl, -(lactide-co-glycolide)$_{4-10}$C(O)C$_{1-22}$alkyl, -(lactide-co-glycolide)$_{1-10}$C(O)C$_{1-12}$alkyl, -(lactide-co-glycolide)$_{1-10}$C(O)C$_{4-22}$alkyl, -(glycolic acid)$_{1-10}$C(O)C$_{1-10}$alkyl, -(glycolic acid)$_{4-10}$C(O)C$_{1-10}$alkyl, -(lactic acid)$_{4-10}$C(O)C$_{1-10}$alkyl, -(lactic acid)$_{1-10}$C(O)C$_{1-10}$alkyl, —(lactic acid)$_{1-10}$C(O)C$_{4-10}$alkyl, -(lactic acid)$_{1-10}$C(O)C$_{4-10}$alkyl, or —(lactic acid)$_{1-10}$C(O)C$_{4-10}$alkyl;

(iii) —C(O)CH$_2$O)$_{1-20}$C(O)C$_{1-30}$alkyl, —C(O)CH(CH$_3$)O)$_{1-20}$C(O)C$_{1-30}$alkyl, —C(O)CH$_2$O)$_{1-10}$C(O)C$_{1-30}$alkyl, —C(O)CH(CH$_3$)O)$_{1-10}$C(O)C$_{1-30}$alkyl, —C(O)CH$_2$O)$_{4-20}$C(O)C$_{1-30}$alkyl, —C(O)CH(CH$_3$)O)$_{4-20}$C(O)C$_{1-30}$alkyl, —C(O)CH$_2$O)$_{1-20}$C(O)C$_{1-10}$alkyl, —C(O)CH(CH$_3$)O)$_{1-20}$C(O)C$_{1-10}$alkyl, —C(O)CH$_2$O)$_{1-20}$C(O)C$_{4-10}$alkyl, —C(O)CH(CH$_3$)O)$_{1-20}$C(O)C$_{4-10}$alkyl, —C(O)CH(CH$_3$)O)$_{4-10}$C(O)C$_{1-10}$alkyl, —C(O)CH$_2$O)$_{4-10}$C(O)C$_{1-10}$alkyl, —C(O)CH(CH$_3$)O)$_{1-10}$C(O)C$_{1-10}$alkyl, —C(O)CH$_2$O)$_{1-10}$C(O)C$_{1-10}$alkyl, —C(O)CH(CH$_3$)O)$_{1-10}$C(O)C$_{4-10}$alkyl, (C(O)CH$_2$O)$_{1-10}$C(O)C$_{4-10}$alkyl, —C(O)CH$_2$O)$_{1-10}$C(O)C$_{4-10}$alkyl, —C(O)CH(CH$_3$)O)$_{1-10}$C(O)C$_{4-10}$alkyl, —C(O)CH$_2$O)$_{1-10}$C(O)C$_{4-10}$alkyl, —C(O)CH(CH$_3$)O)$_{1-10}$C(O)C$_{4-10}$alkyl, —C(O)CH$_2$O)$_{1-10}$(C(O)CH(CH$_3$)O)$_{1-10}$C(O)C$_{1-30}$alkyl, —C(O)CH$_2$O)$_{2-10}$(C(O)CH(CH$_3$)O)$_{2-10}$C(O)C$_{1-30}$alkyl, —C(O)CH$_2$O)$_{1-10}$(C(O)CH(CH$_3$)O)$_{1-10}$C(O)C$_{1-12}$alkyl, —C(O)CH$_2$O)$_{1-10}$(C(O)CH(CH$_3$)O)$_{1-10}$C(O)C$_{4-22}$alkyl, —C(O)CH(CH$_3$)O)$_{1-10}$(C(O)CH$_2$O)$_{1-10}$C(O)C$_{1-30}$alkyl, —C(O)CH(CH$_3$)O)$_{2-10}$(C(O)CH$_2$O)$_{2-10}$C(O)C$_{1-30}$alkyl, —C(O)CH(CH$_3$)O)$_{1-10}$(C(O)CH$_2$O)$_{1-10}$C(O)C$_{1-12}$alkyl, and —C(O)CH(CH$_3$)O)$_{1-10}$(C(O)CH$_2$O)$_{1-10}$C(O)C$_{4-22}$alkyl;

(iv) hydrogen, —C(O)A, aryl, alkyl, alkenyl, alkynyl cycloalkyl, cycloalkylalkyl, heterocyclyl, heterocycloalkyl, aryl, arylalkyl, heteroaryl, and heteroarylalkyl;

$R^{106}$ is selected from:

(i)

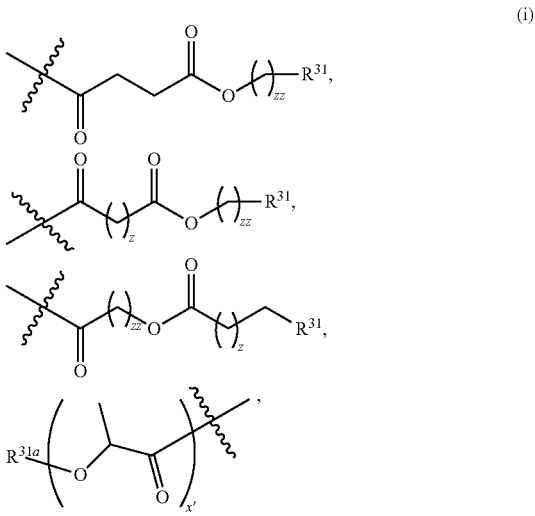

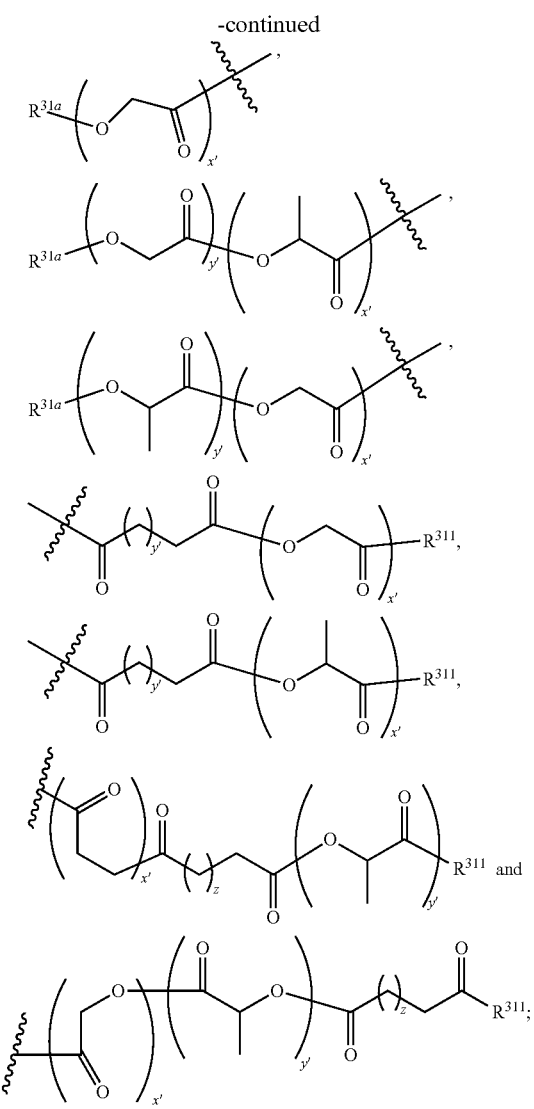

(ii) —C(O)C$_{10-30}$alkyl, —C(O)C$_{10-30}$alkenyl, —C(O)C$_{10-30}$alkynyl, —C(O)(C$_{10-30}$alkyl with at least one R$^5$ substituent on the alkyl chain), —C(O)(C$_{10-30}$alkenyl, with at least one R$^5$ substituent on the alkenyl chain) —C(O)(C$_{10-30}$alkynyl, with at least one R$^5$ substituent on the alkynyl chain), -(lactic acid)$_{1-20}$C(O)C$_{1-30}$alkyl, —(lactic acid)$_{1-10}$C(O)C$_{1-30}$alkyl, -(lactic acid)$_{4-20}$C(O)C$_{1-30}$alkyl, —(lactic acid)$_{1-20}$C(O)C$_{1-10}$alkyl, -(lactic acid)$_{1-20}$C(O)C$_{4-10}$alkyl, —(lactic acid)$_{1-20}$C(O)OH, -(lactic acid)$_{1-10}$C(O)OH, -(lactic acid)$_{4-20}$C(O)OH, —(lactic acid)$_{1-10}$C(O)OH, -(lactic acid)$_{4-10}$C(O)OH, —(lactide-co-glycolide)$_{1-10}$C(O)$_{C1-22}$alkyl, -(lactide-co-glycolide)$_{4-10}$C(O)$_{C1-22}$alkyl, —(lactide-co-glycolide)$_{1-10}$C(O)$_{C1-12}$alkyl, -(lactide-co-glycolide)$_{1-10}$C(O)$_{C4-22}$alkyl, —(glycolic acid)$_{1-10}$C(O)$_{C1-10}$alkyl, -(glycolic acid)$_{4-10}$C(O)$_{C1-10}$alkyl, —(lactic acid)$_{4-10}$C(O)C$_{1-10}$alkyl, -(lactic acid)$_{1-10}$C(O)C$_{1-10}$alkyl, —(lactic acid)$_{1-10}$C(O)C$_{4-10}$alkyl, -(lactic acid)$_{1-10}$C(O)C$_{4-10}$alkyl, and —(lactic acid)$_{1-10}$C(O)C$_{4-10}$alkyl;

(iii) —(C(O)CH$_2$O)$_{1-20}$C(O)C$_{1-30}$alkyl, —(C(O)CH(CH$_3$)O)$_{1-20}$C(O)C$_{1-30}$alkyl, —(C(O)CH$_2$O)$_{1-10}$C(O)C$_{1-30}$alkyl, —(C(O)CH(CH$_3$)O)$_{1-10}$C(O)C$_{1-30}$alkyl, —(C(O)CH$_2$O)$_{4-20}$C(O)C$_{1-30}$alkyl, —(C(O)CH(CH$_3$)O)$_{4-20}$C(O)C$_{1-30}$alkyl, —(C(O)CH$_2$O)$_{1-20}$C(O)C$_{1-10}$alkyl, —(C(O)CH(CH$_3$)O)$_{1-20}$C(O)C$_{1-10}$alkyl, —(C(O)CH$_2$O)$_{1-20}$C(O)C$_{4-10}$alkyl, —(C(O)CH(CH$_3$)O)$_{1-20}$C(O)C$_{4-10}$alkyl, —(C(O)CH(CH$_3$)O)$_{4-10}$C(O)C$_{1-10}$alkyl, —(C(O)CH$_2$O)$_{4-10}$C(O)C$_{1-10}$alkyl, —(C(O)CH(CH$_3$)O)$_{1-10}$C(O)C$_{1-10}$alkyl, —(C(O)CH$_2$O)$_{1-10}$C(O)C$_{1-10}$alkyl, —(C(O)CH(CH$_3$)O)$_{1-10}$C(O)C$_{4-10}$alkyl, (C(O)CH$_2$O)$_{1-10}$C(O)C$_{4-10}$alkyl, —(C(O)CH$_2$O)$_{1-10}$C(O)C$_{4-10}$alkyl, —(C(O)CH(CH$_3$)O)$_{1-10}$C(O)C$_{4-10}$alkyl, —(C(O)CH$_2$O)$_{1-10}$C(O)C$_{4-10}$alkyl, —(C(O)CH(CH$_3$)O)$_{1-10}$C(O)C$_{4-10}$alkyl, —(C(O)CH$_2$O)$_{1-10}$(C(O)CH(CH$_3$)O)$_{1-10}$C(O)C$_{1-30}$alkyl, —(C(O)CH$_2$O)$_{2-10}$(C(O)CH(CH$_3$)O)$_{2-10}$C(O)C$_{1-30}$alkyl, —(C(O)CH$_2$O)$_{1-10}$(C(O)CH(CH$_3$)O)$_{1-10}$C(O)C$_{1-12}$alkyl, —(C(O)CH$_2$O)$_{1-10}$(C(O)CH(CH$_3$)O)$_{1-10}$C$_{4-22}$alkyl, —(C(O)CH(CH$_3$)O)$_{1-10}$(C(O)CH$_2$O)$_{1-10}$C(O)C$_{1-30}$alkyl, —(C(O)CH(CH$_3$)O)$_{2-10}$(C(O)CH$_2$O)$_{2-10}$C(O)C$_{1-30}$alkyl, —(C(O)CH(CH$_3$)O)$_{1-10}$(C(O)CH$_2$O)$_{1-10}$C(O)C$_{1-12}$alkyl, and —(C(O)CH(CH$_3$)O)$_{1-10}$(C(O)CH$_2$O)$_{1-10}$C(O)C$_{4-22}$alkyl;

x' and y' are independently selected from any integer between 1 and 30 (1, 2, 3, 4, 5, 6, 7, 8, 9, 10, 11, 12, 13, 14, 15, 16, 17, 18, 19, 20, 21, 22, 23, 24, 25, 26, 27, 28, 29 or 30). In one embodiment x' and y' are independently selected from the following ranges: 1 to 5, 6 to 11, 12 to 17, 18 to 23, and 24 to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30). In a preferred embodiment, x and y are independently selected from any integer between 1 and 10 (1, 2, 3, 4, 5, 6, 7, 8, 9, or 10); and wherein all other integers are as defined herein.

In one embodiment, R$^{106}$ is —C(O)(CH$_2$)$_{16}$CH$_3$ and R$^{123}$ is hydrogen.

In one embodiment, R$^{123}$ is hydrogen and R$^{106}$ is

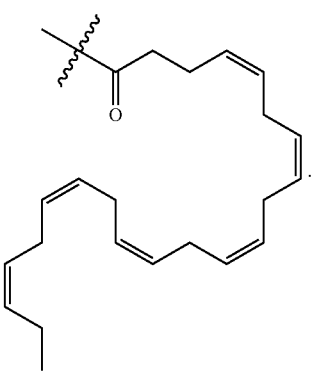 [SMILES: *C(=O)CC/C=C\C/C=C\C/C=C\C/C=C\C/C=C\C/C=C\CC]

In one embodiment, R$^{123}$ is

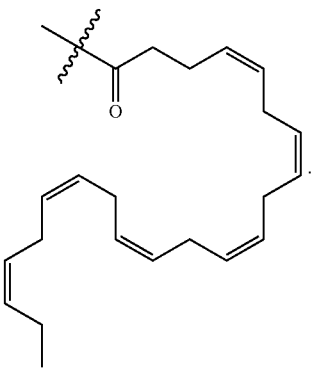 [SMILES: *C(=O)CC/C=C\C/C=C\C/C=C\C/C=C\C/C=C\C/C=C\CC]

In one embodiment, $R^{123}$ is

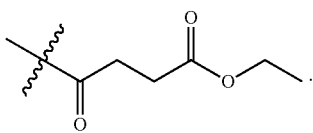 [SMILES: *C(=O)CCC(=O)OCC]

In one embodiment, $R^{123}$ is

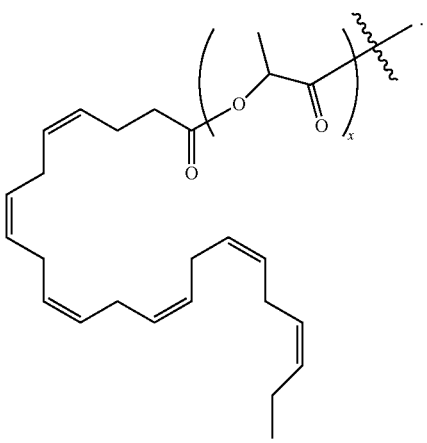

In one embodiment, $R^{106}$ is

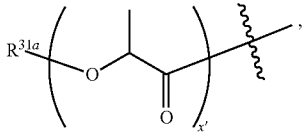

x is 1, and $R^{123}$ is —C(O)A.

In one embodiment, $R^{106}$ is

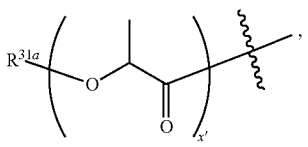

and $R^{31a}$ is —C(O)alkyl.

In one embodiment, $R^{106}$ is

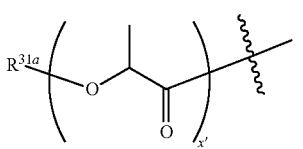

and $R^{31a}$ is —C(O)alkyl wherein alkyl is methyl.

In one embodiment $R^{123}$ is selected from

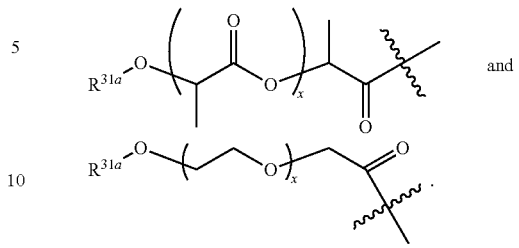

and

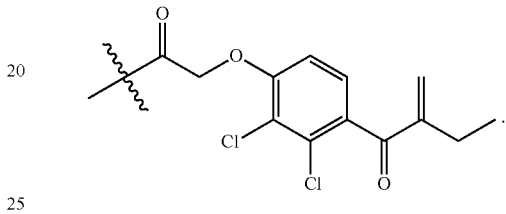

In one embodiment $R^{31a}$ is selected from —C(O)alkyl, stearoyl, and

Non-limiting Examples of Formula IID include

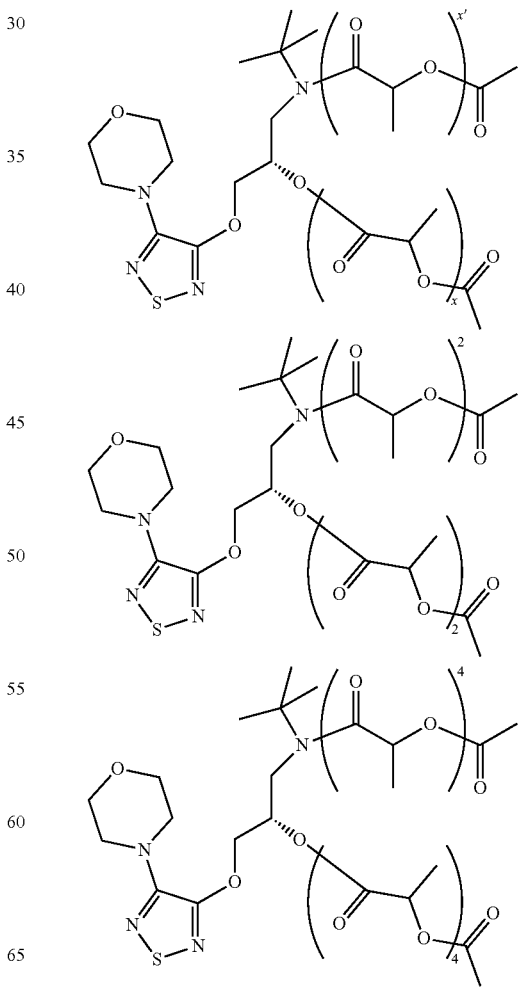

187
-continued
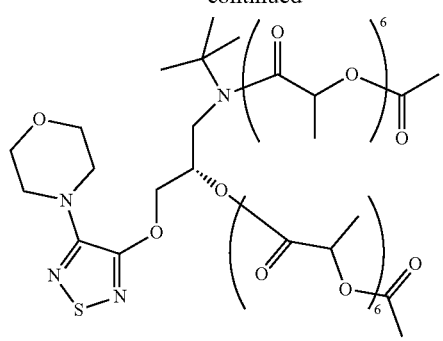
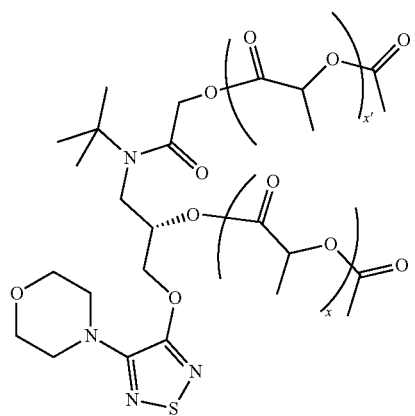
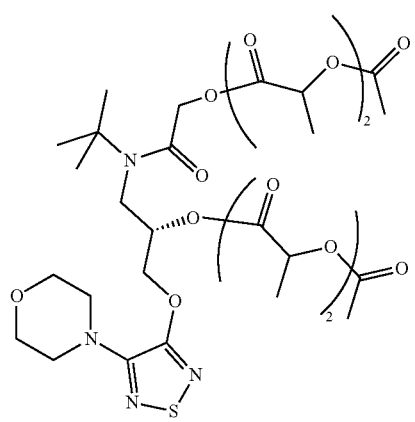
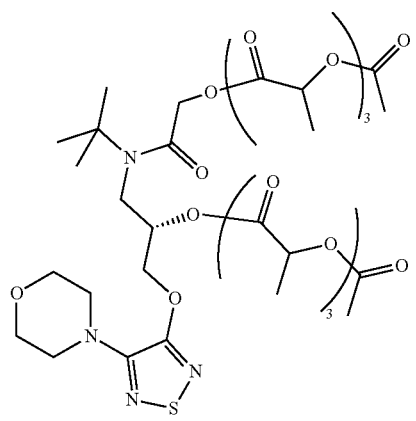
188
-continued
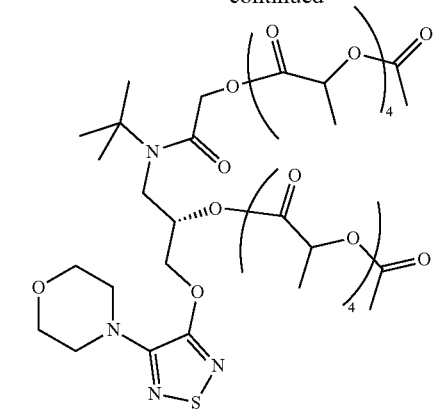
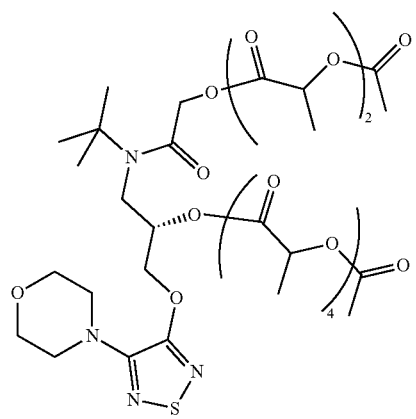
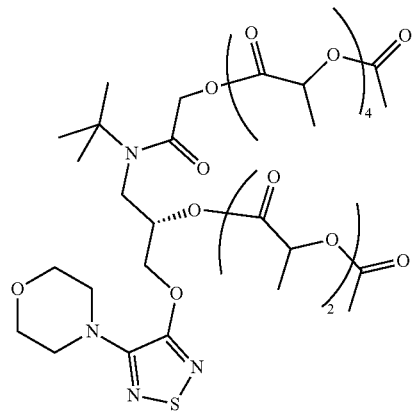
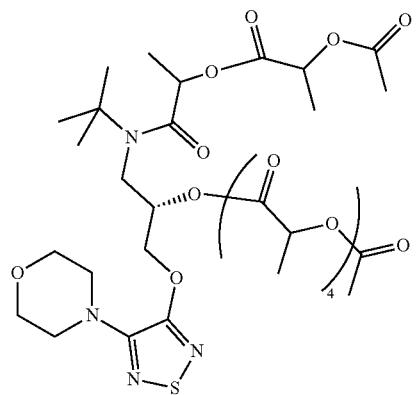

189
-continued
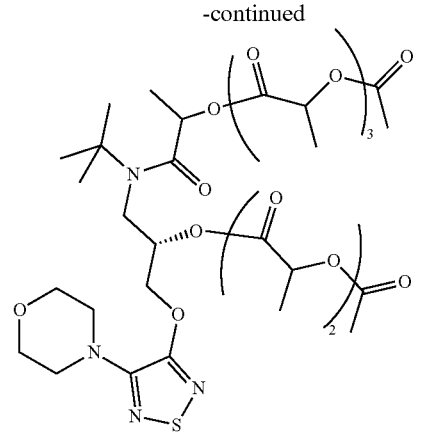
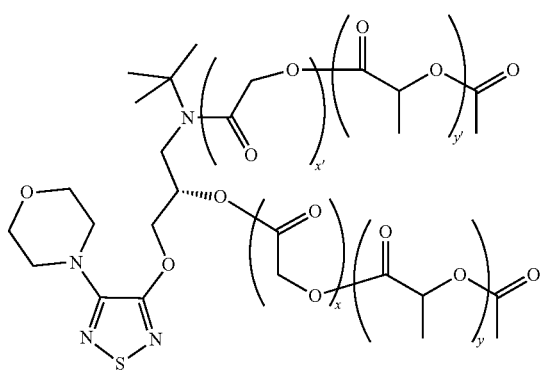
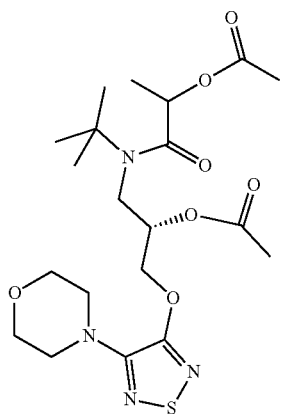
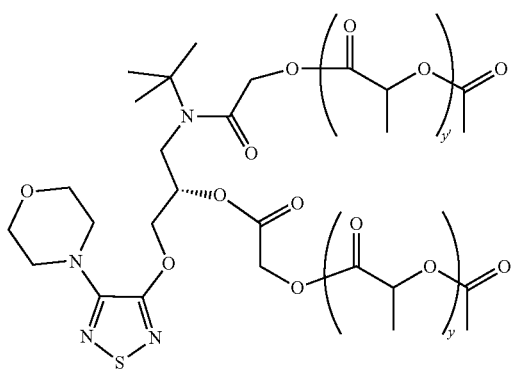
190
-continued
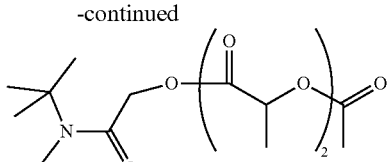
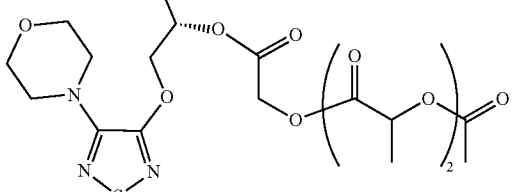
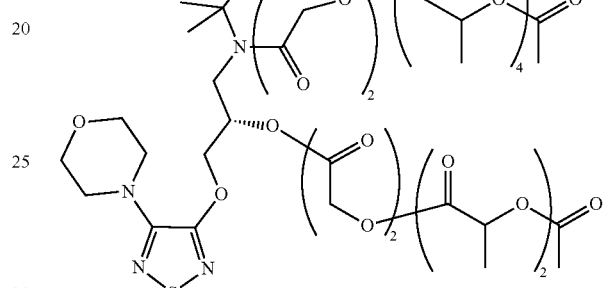
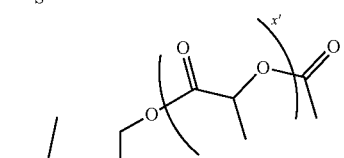
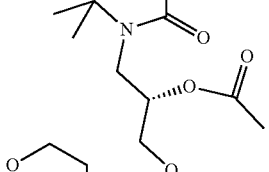
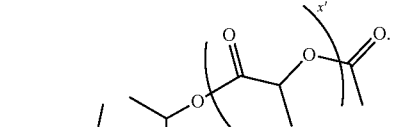
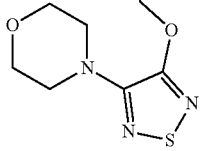
The disclosure provides Timolol prodrugs of Formula IIID and Formula IVD:

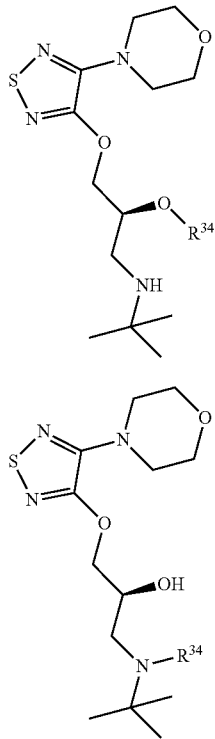

or a pharmaceutically acceptable composition, salt, or isotopic derivative thereof.

$R^{34}$ is selected from: $R^{381}$, carbonyl linked polyethylene glycol, carbonyl linked polypropylene glycol, carbonyl linked polypropylene oxide, polylactic acid, and poly(lactic-co-glycolic acid), a polyglycolic acid, a polyester, polyamide,

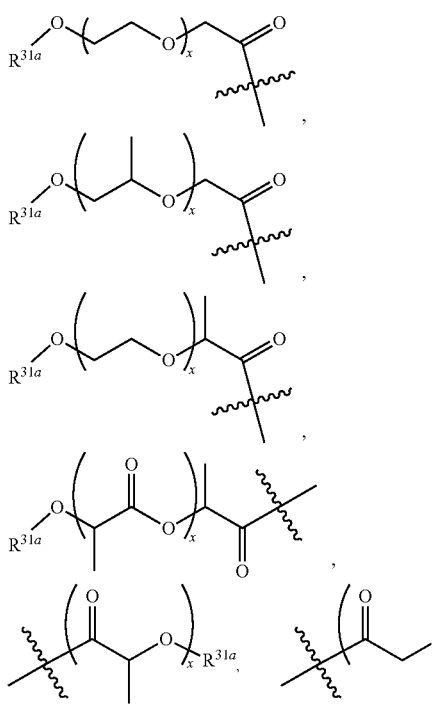

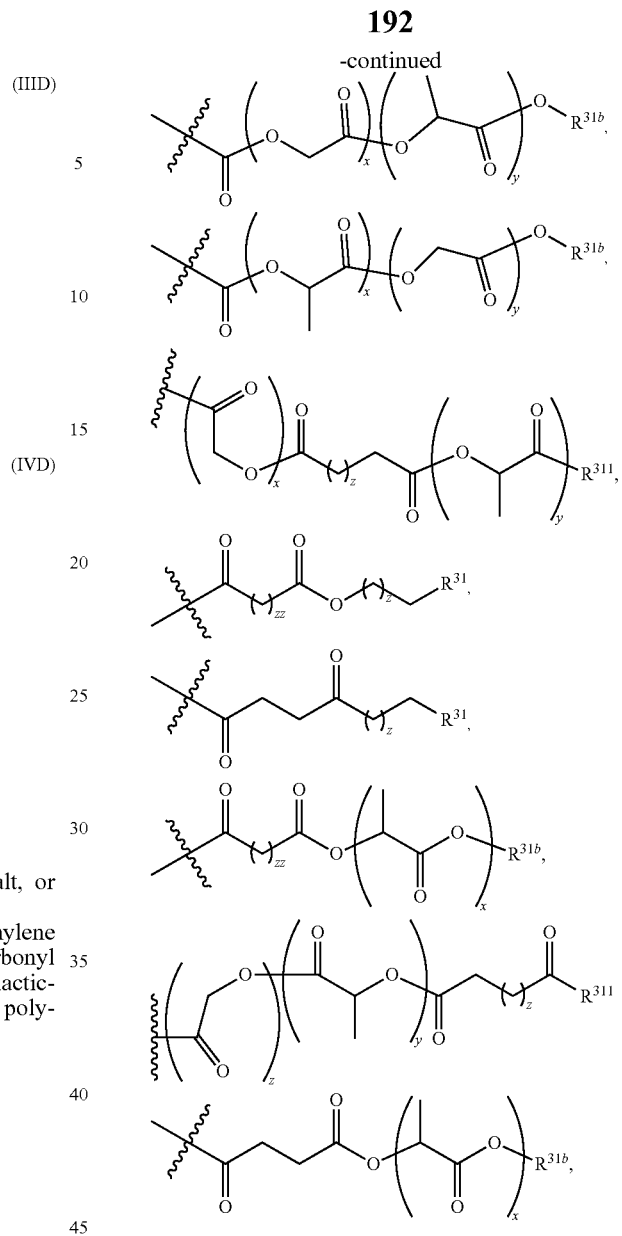

or other biodegradable polymer, wherein each $R^{34}$ other than $R^{381}$ is substituted with at least one $L^4$-$R^{121}$.

$R^{31b}$ is hydrogen, aryl, alkyl, cycloalky, cycloalkyl, cycloalkylalkyl, heterocyclyl, heterocycloalkyl, arylalkyl, heteroaryl, heteroarylalkyl, and polyethylene glycol;

$R^{381}$ is selected from:

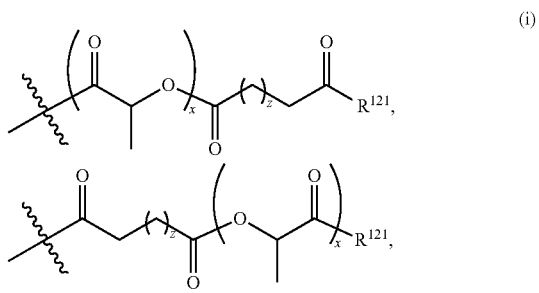

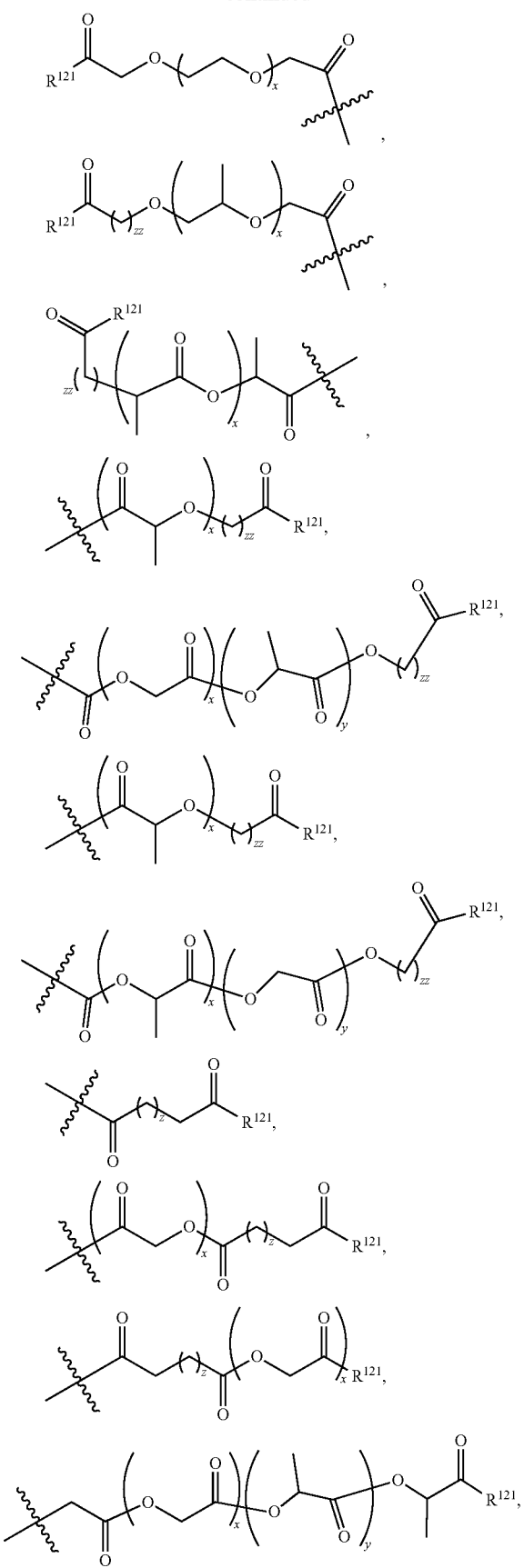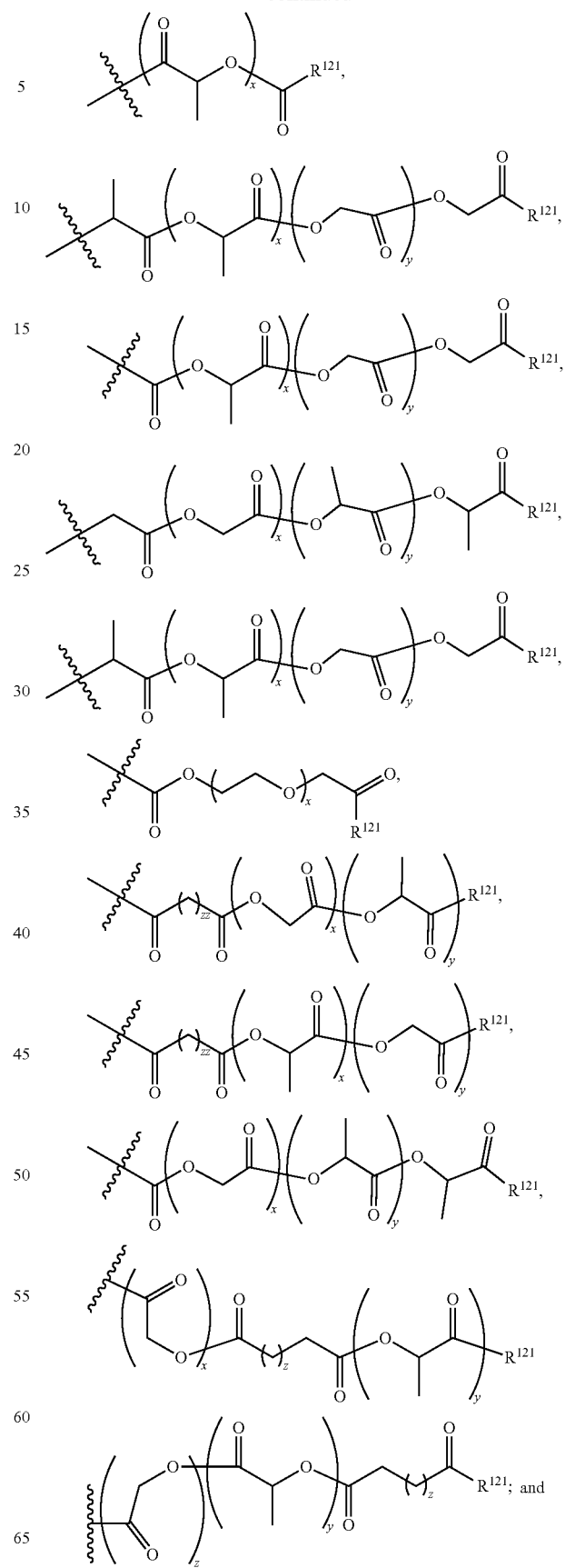

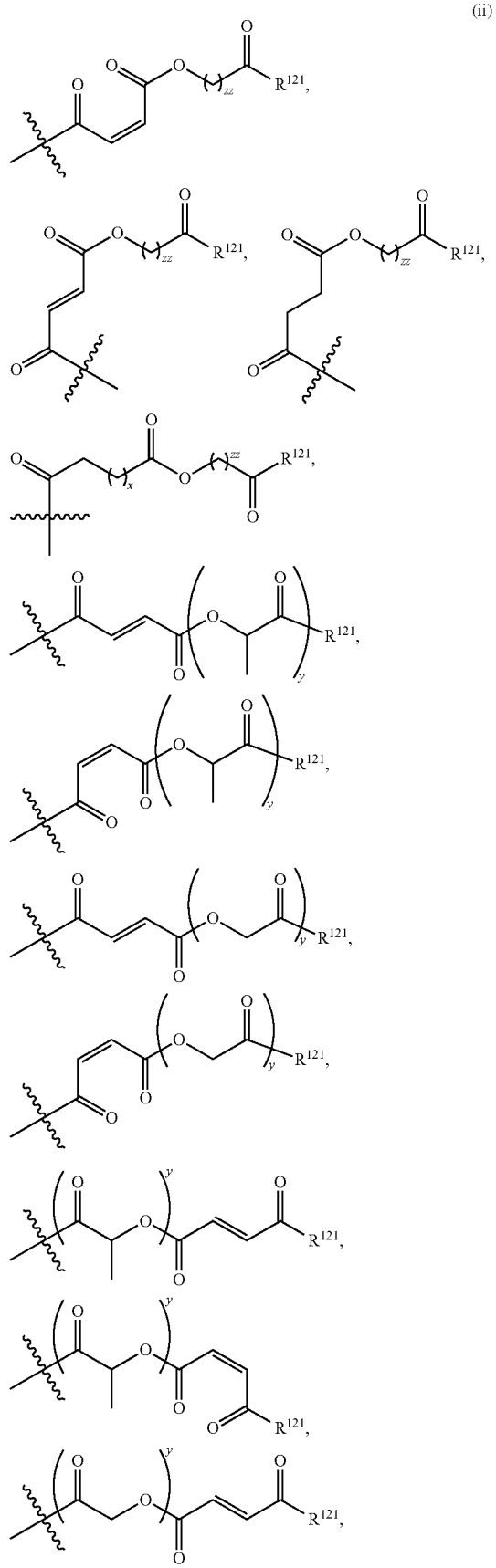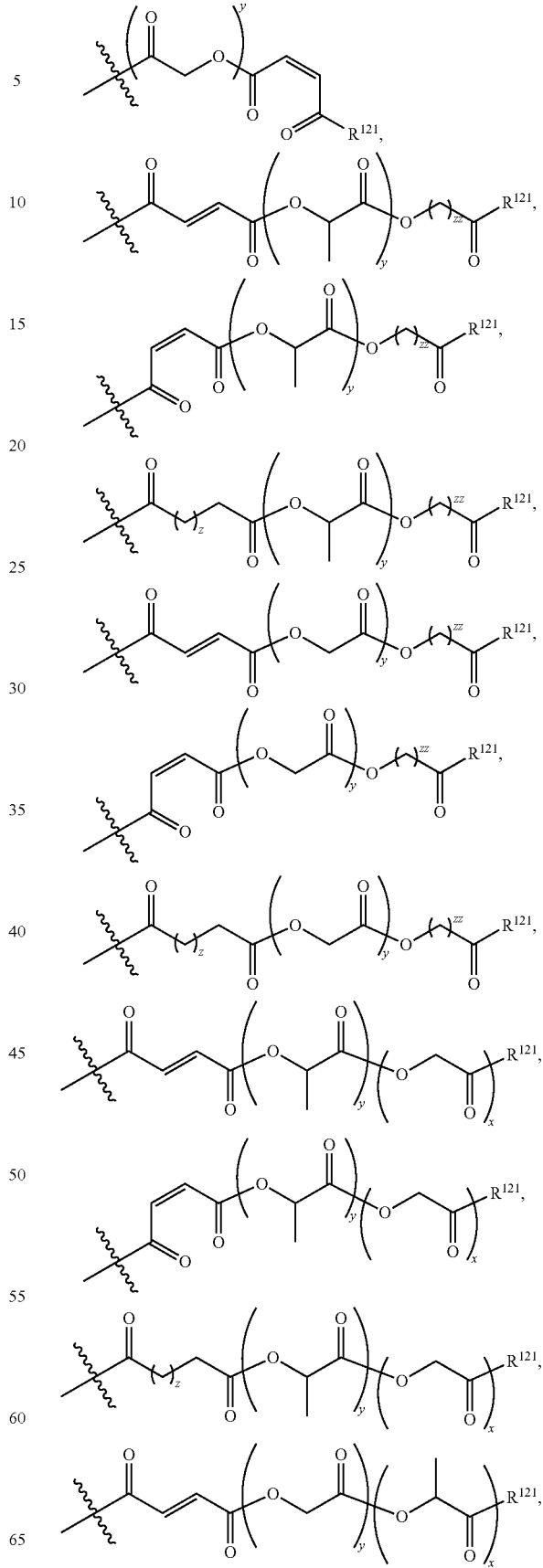

-continued

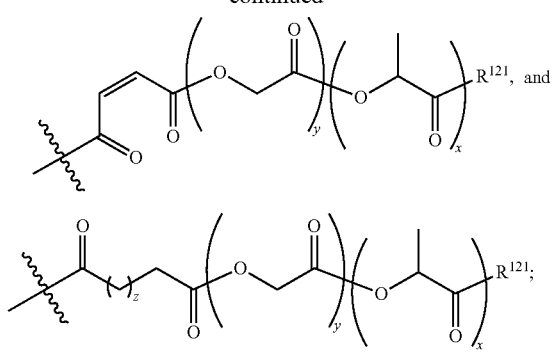

and wherein all other variables are as defined herein.

The disclosure provides Timolol prodrugs of Formula VD and Formula VID:

(VD)

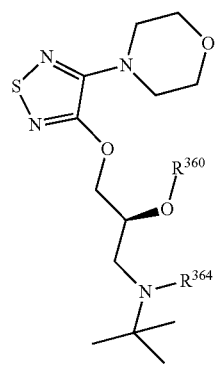

(VID)

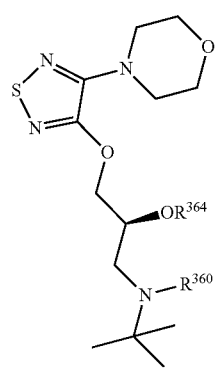

or a pharmaceutically acceptable composition, salt, or isotopic derivative thereof.

$R^{364}$ is selected from: acyl, carbonyl linked polyethylene glycol, carbonyl linked polypropylene glycol, carbonyl linked polypropylene oxide, polylactic acid, poly(lactic-co-glycolic acid), polyglycolic acid, polyester, polyamide,

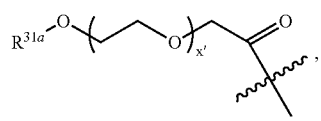

-continued

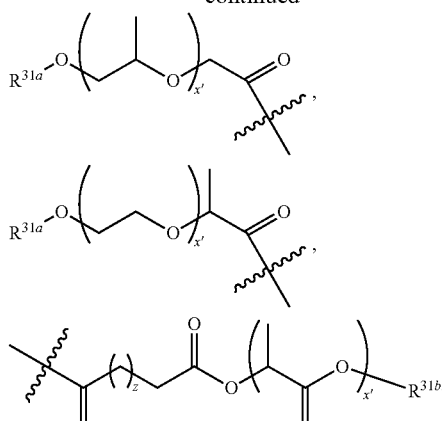

$R^{360}$ is selected from

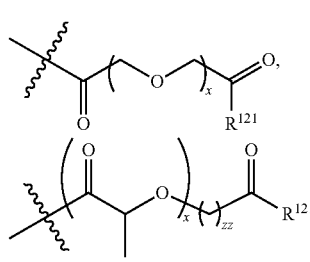

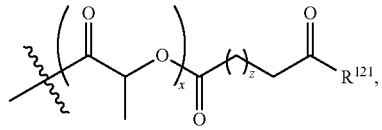

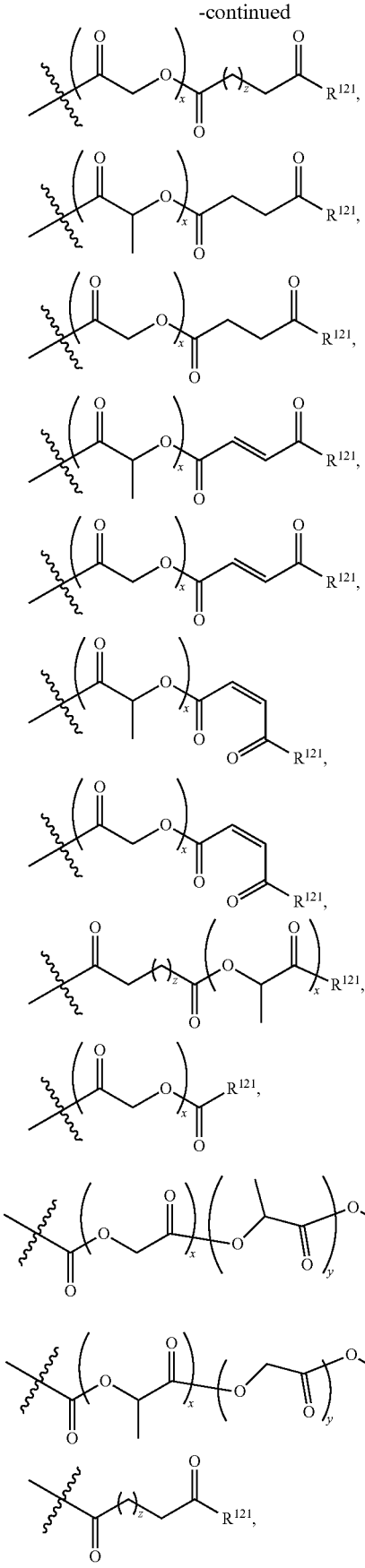
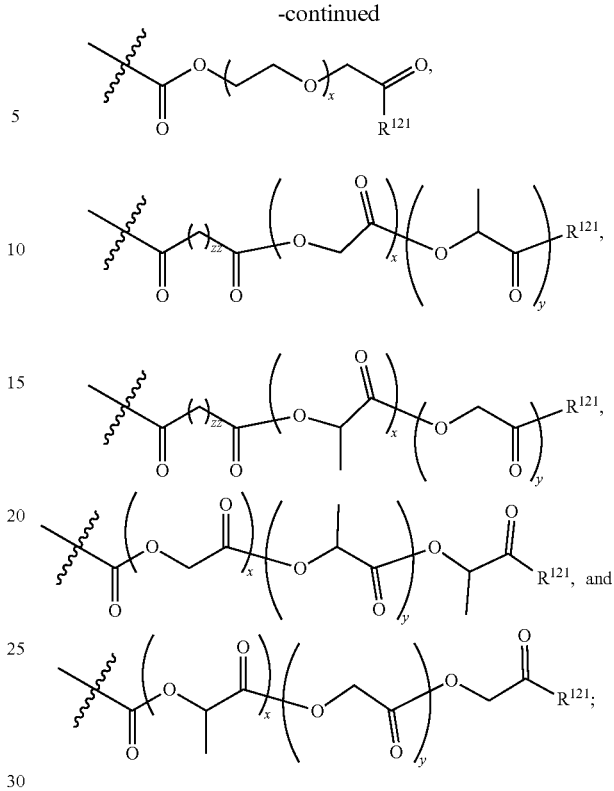
and
wherein all other variables are as defined herein.
In one embodiment, $R^{364}$ is
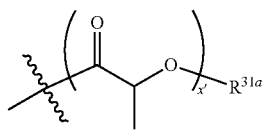
and $R^{31a}$ is —C(O)alkyl.
In one embodiment, $R^{364}$ is
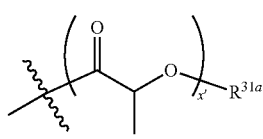
and $R^{31a}$ is —C(O)Me.
In one embodiment, $R^{364}$ is
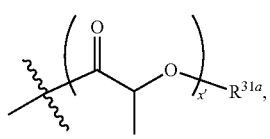
$R^{31a}$ is —C(O)Me, and x' is an integer between 1 and 6 (1, 2, 3, 4, 5, or 6);

In one embodiment, $R^{364}$ is
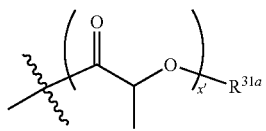
and $R^{31a}$ is stearoyl;
In one embodiment, $R^{364}$ is
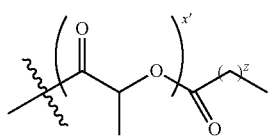
x' is an integer between 1 and 6 (1, 2, 3, 4, 5, or 6), and y is 11 or 17, or in an alternative embodiment, y is 10 or 16.
In one embodiment, $R^{360}$ is
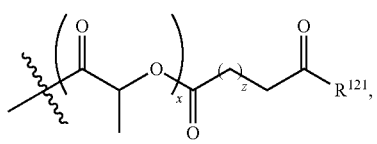
$R^{121}$ is
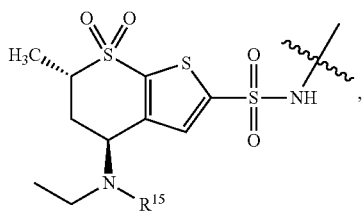
and $R^{15}$ is hydrogen.
In one embodiment, $R^{360}$ is
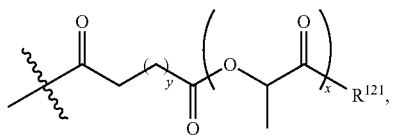
$R^{121}$ is
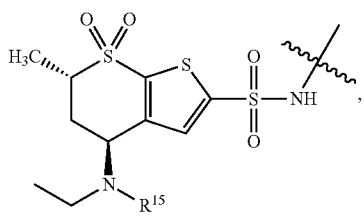
and $R^{15}$ is hydrogen.
In one embodiment, $R^{360}$ is
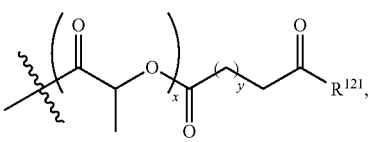
$R^{121}$ is
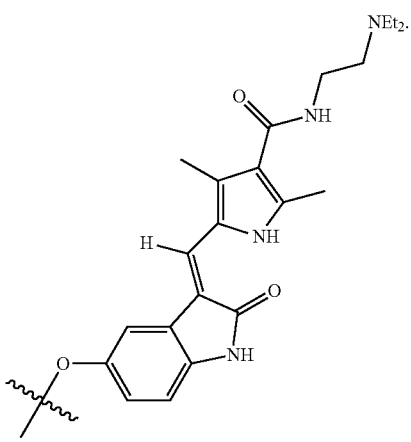
In one embodiment, $R^{360}$ is
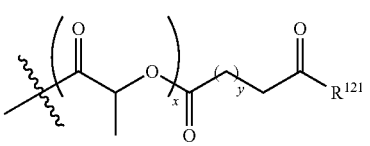
and $R^{121}$ is
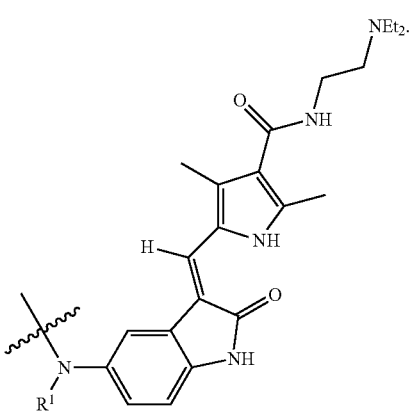

In certain embodiments, $R^{360}$ is

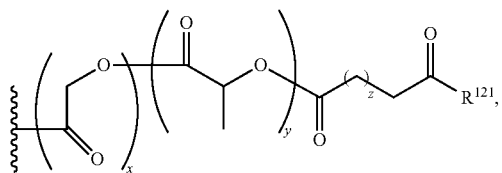

x and y are independently selected from 1, 2, 3, 4, 5, and 6, and z is 1, 2, or 3.

In certain embodiments, $R^{360}$ is

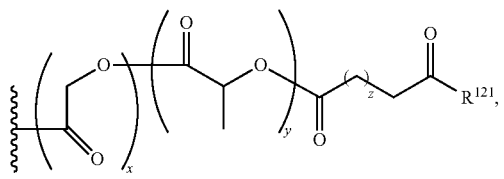

x and y are independently selected from 1, 2, and 3, and z is 1, 2, or 3.

In certain embodiments, $R^{360}$ is

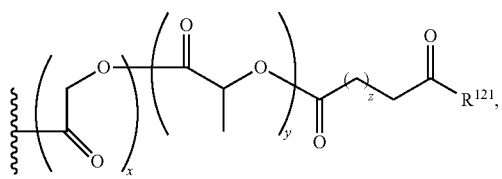

x and y are independently selected from 1, 2, and 3, z is 1, 2, or 3, and $R^{364}$ is

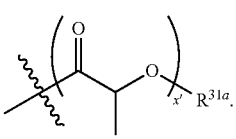

In certain embodiments, x' and x are 1 and y and y' are independently selected from 1, 2, 3, 4, 5, and 6.

In certain embodiments, x' and x are 2 and y and y' are independently selected from 1, 2, 3, 4, 5, and 6.

In certain embodiments, x' and x are 3 and y and y' are independently selected from 1, 2, 3, 4, 5, and 6.

In certain embodiments, x' and x are 1 and y and y' are independently selected from 1, 2, or 3.

In certain embodiments, x' and x are 2 and y and y' are independently selected from 1, 2, or 3.

In certain embodiments, y' and y are 1 and x and x' are independently selected from 1, 2, 3, 4, 5, and 6.

In certain embodiments, y' and y are 2 and x and x' are independently selected from 1, 2, 3, 4, 5, and 6.

In certain embodiments, y' and y are 3 and x and x' are independently selected from 1, 2, 3, 4, 5, and 6.

In certain embodiments, y' and y are 1 and x and x' are independently selected from 1, 2, and 3.

In certain embodiments, y' and y are 2 and x and x' are independently selected from 1, 2, and 3.

Non-limiting examples of compounds of Formula VD include

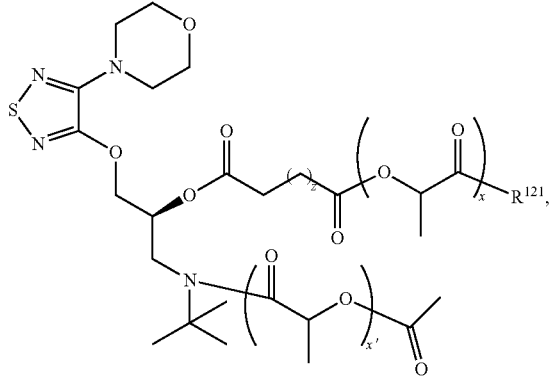

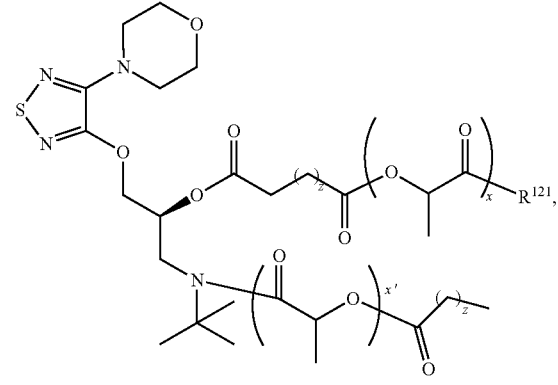

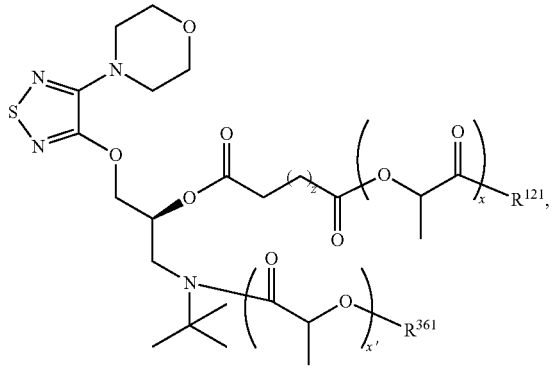

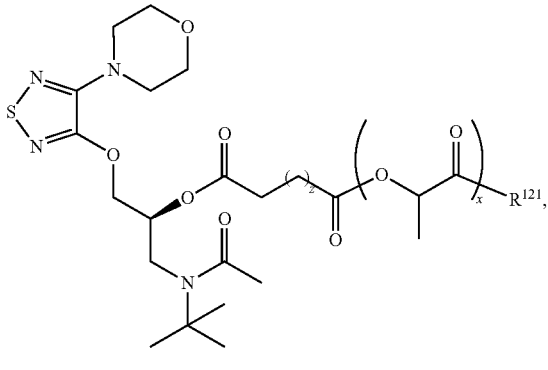

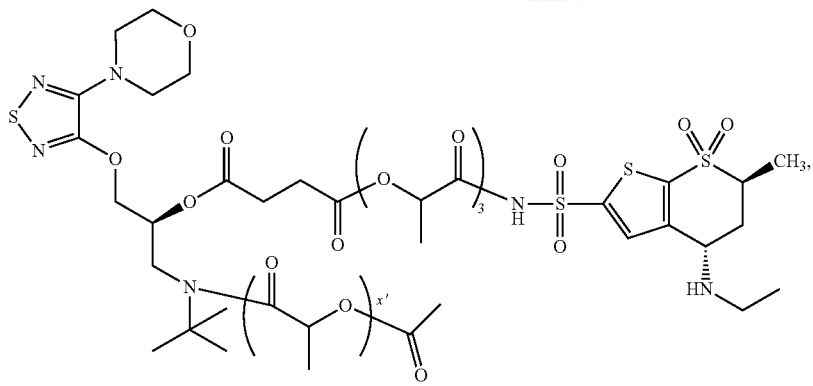
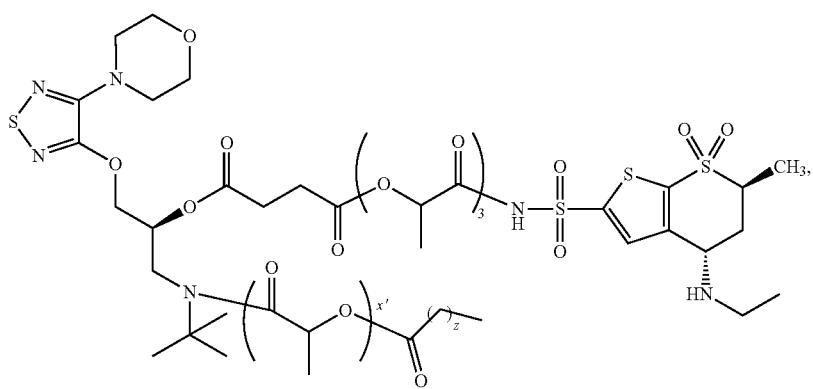
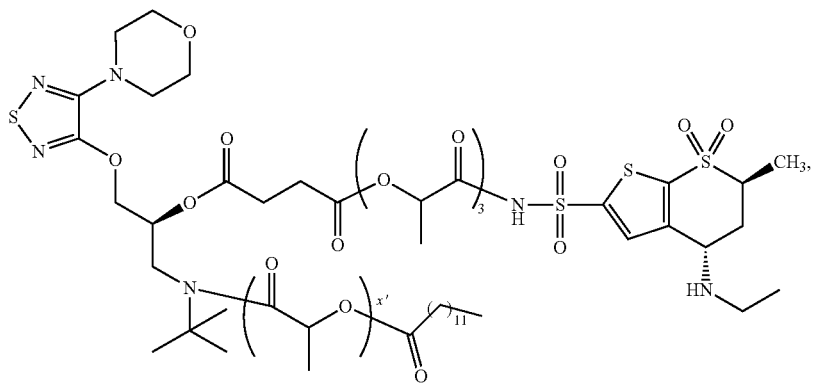
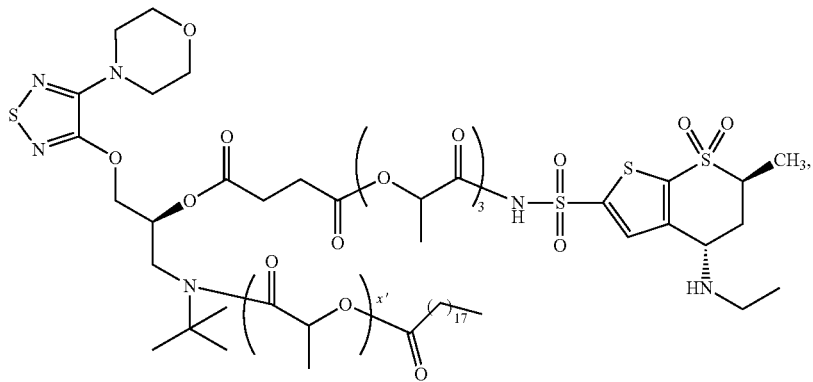

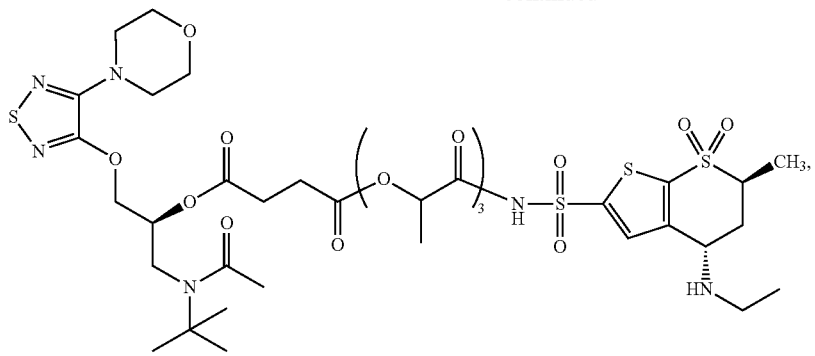
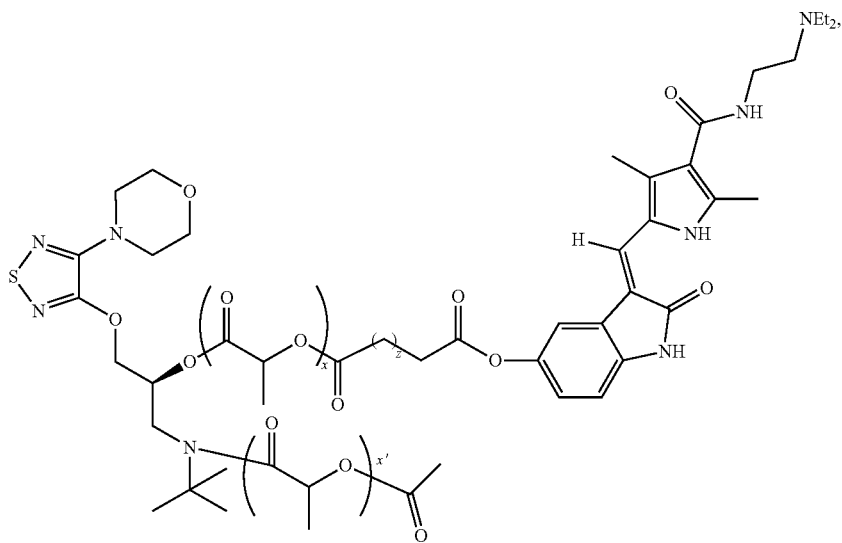
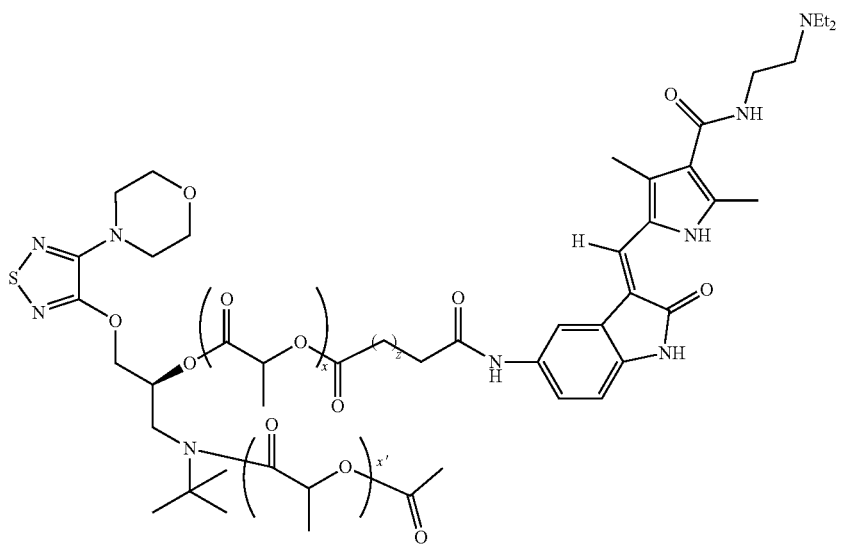

-continued
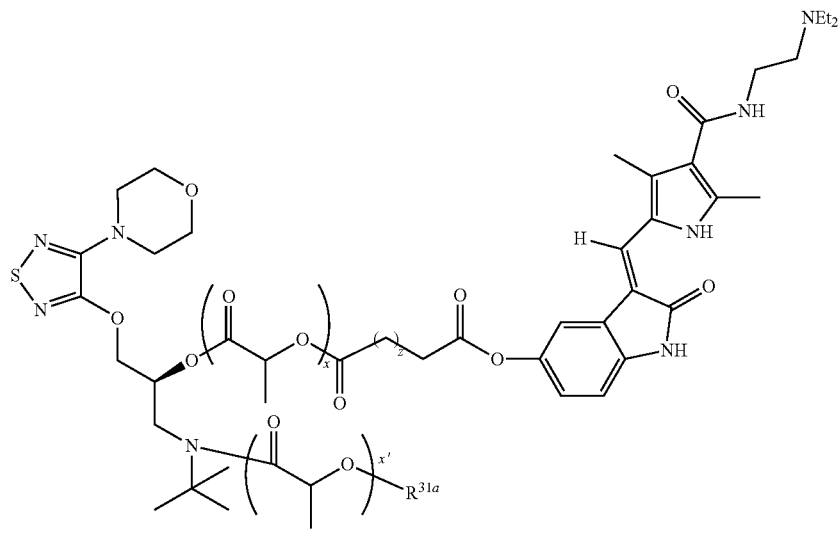
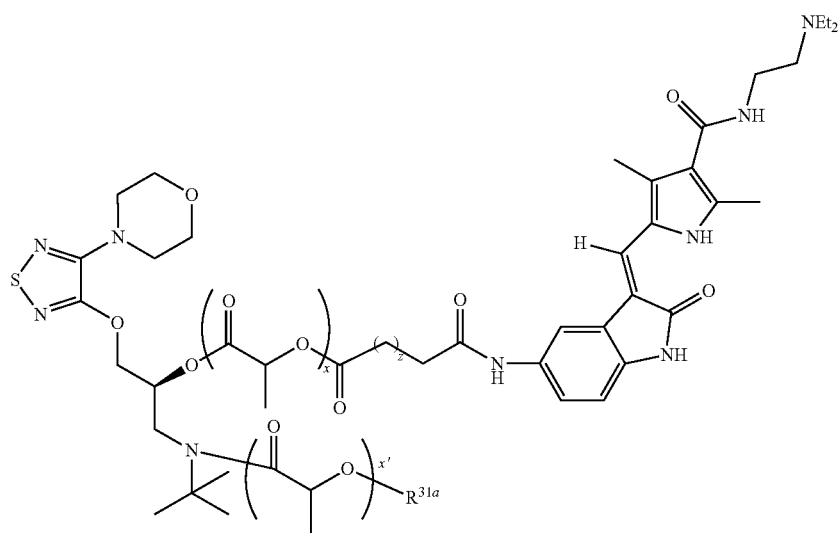
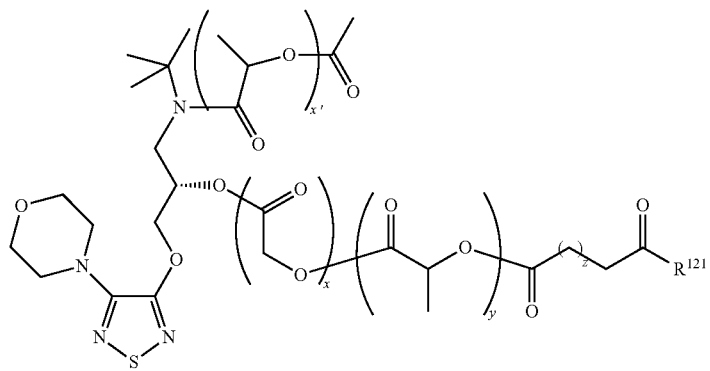

211
-continued
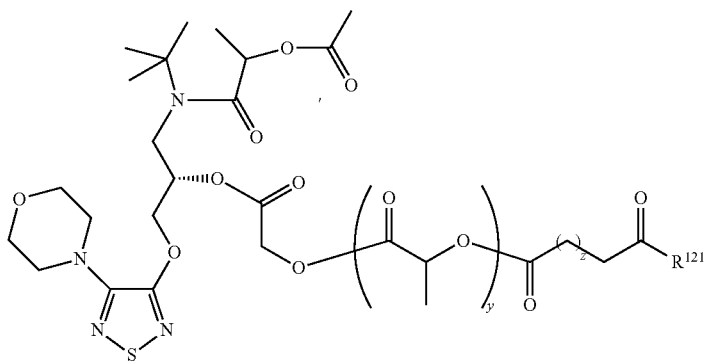
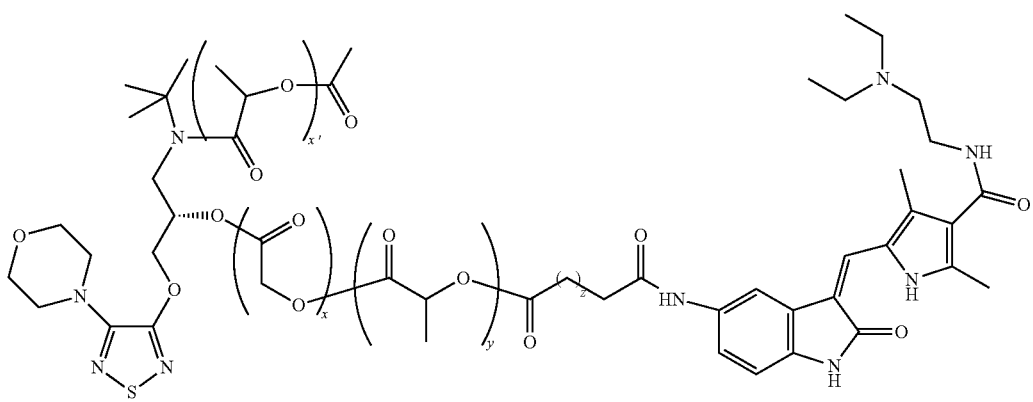
212
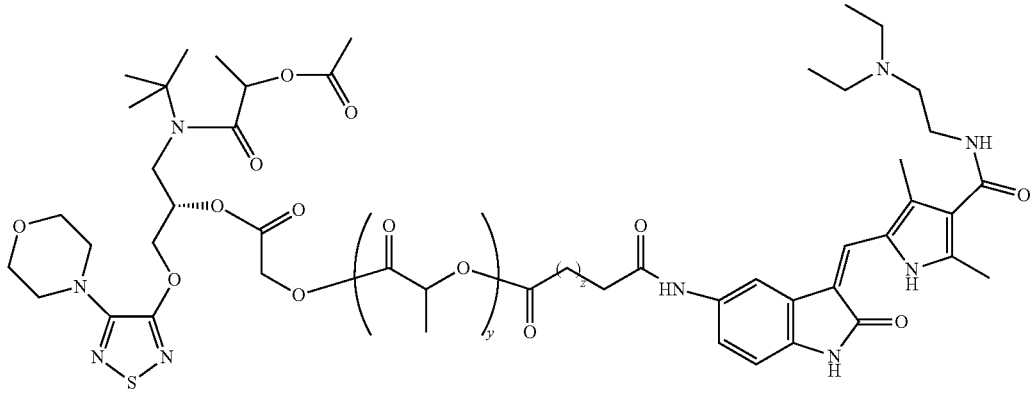

Non-limiting Examples of Compound of Formula VID include:
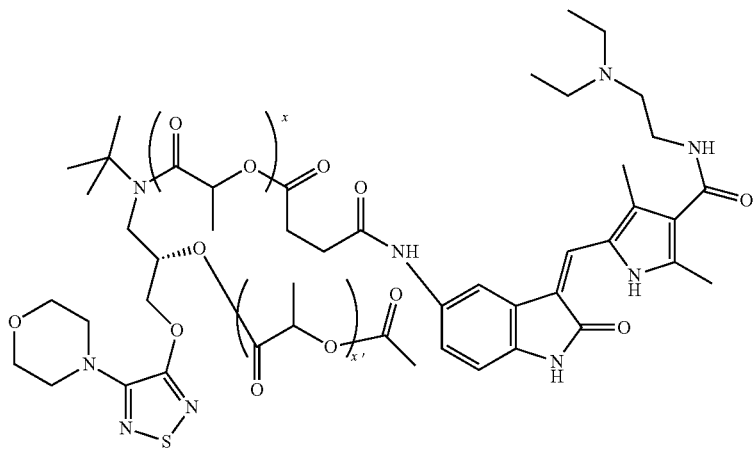
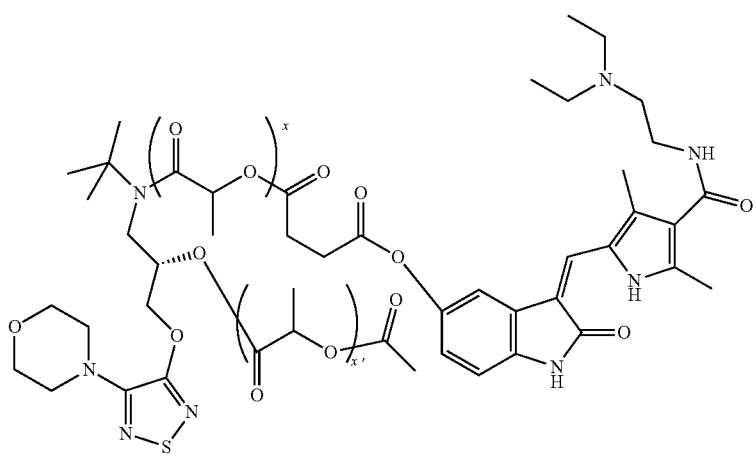
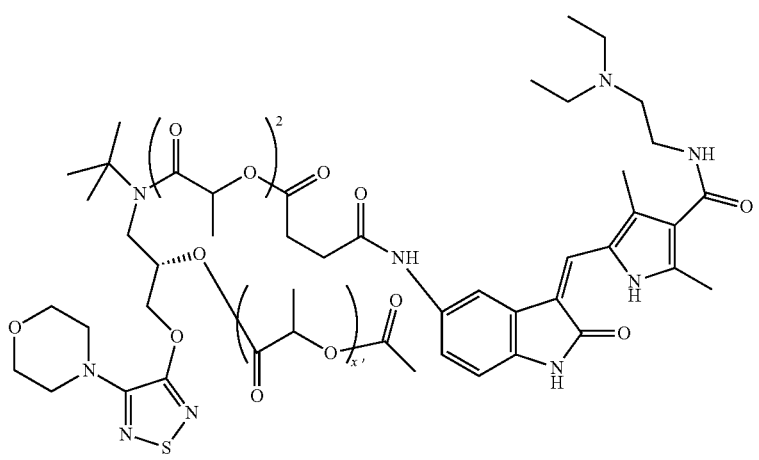

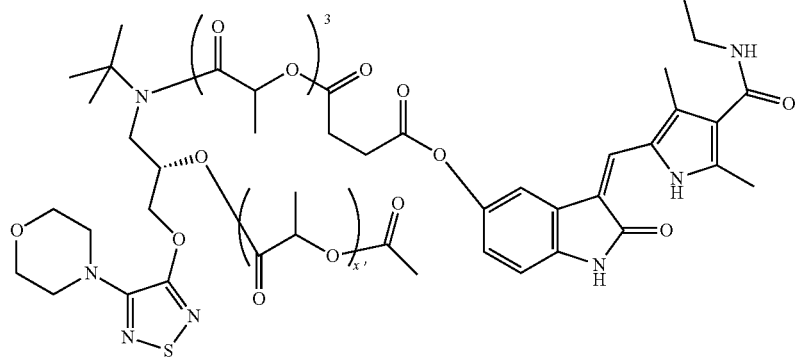
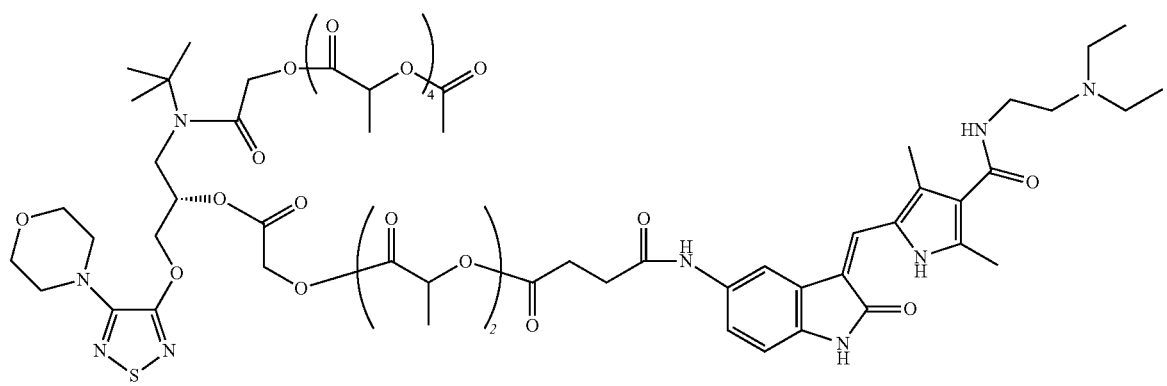
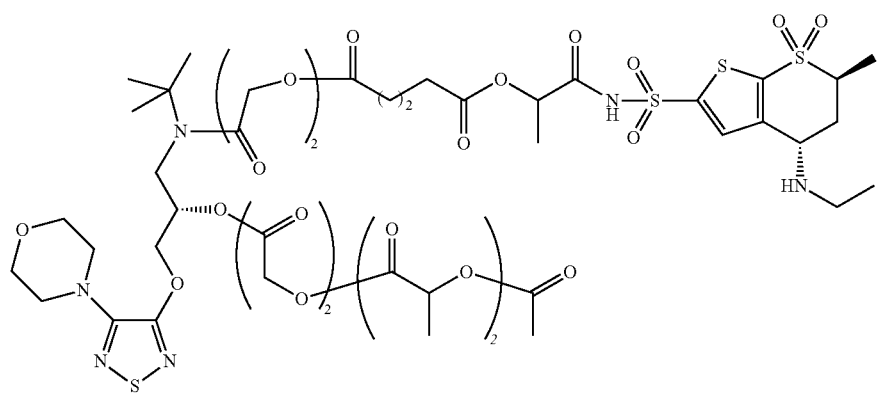

The disclosure provides Timolol prodrugs of Formula VIID:
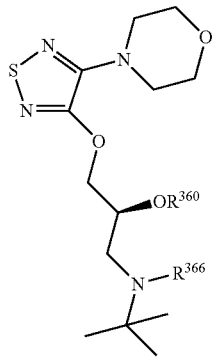
(VIID)
or a pharmaceutically acceptable composition, salt, or isotopic derivative thereof
wherein
R$^{366}$ is selected from
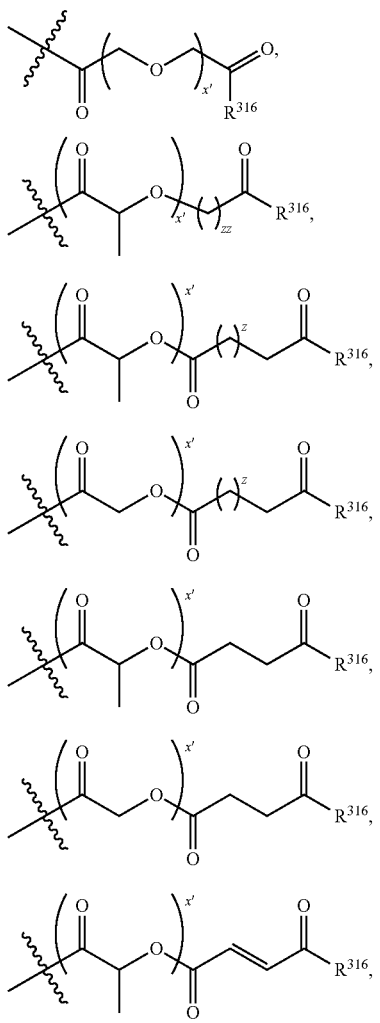
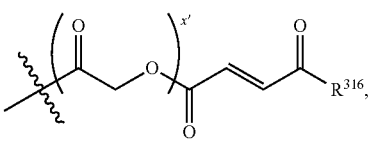
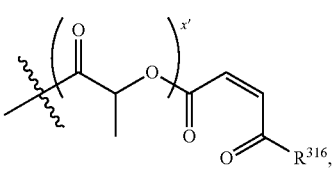
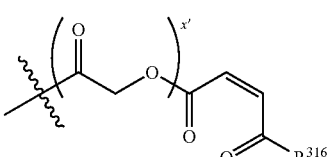
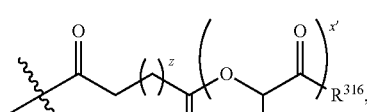
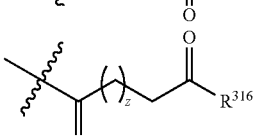
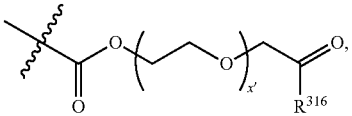
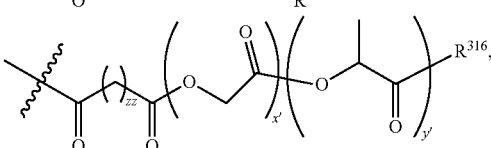
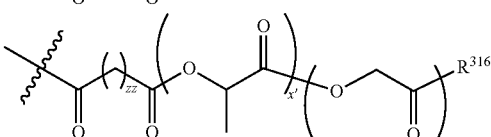
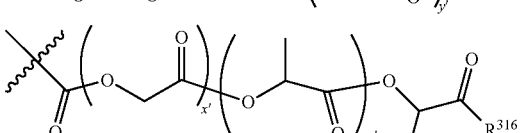
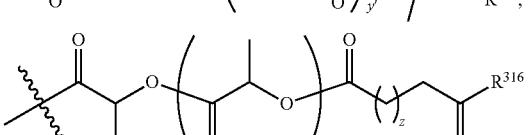
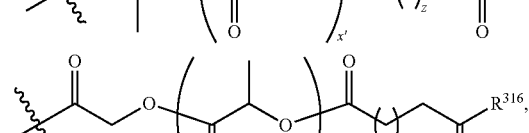
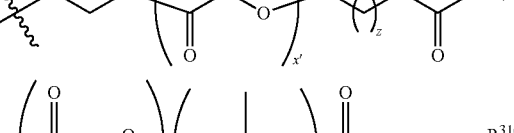
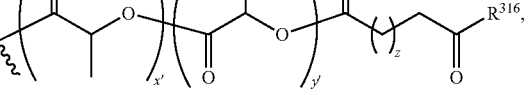

-continued
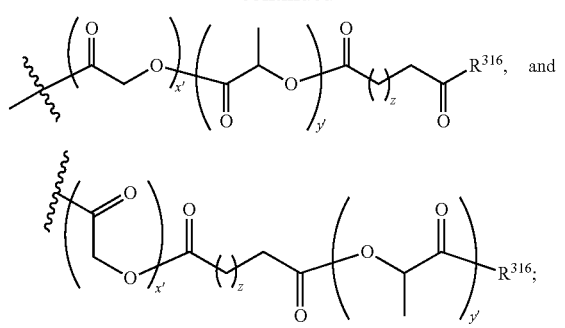
$R^{316}$ is selected from
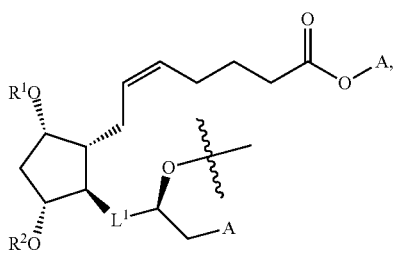
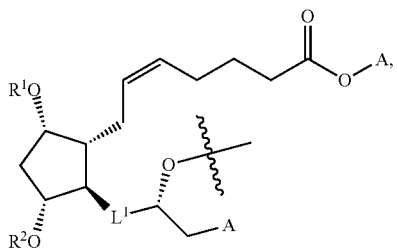
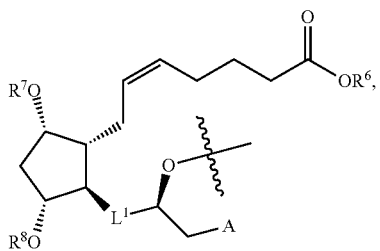
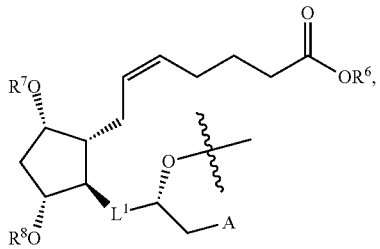
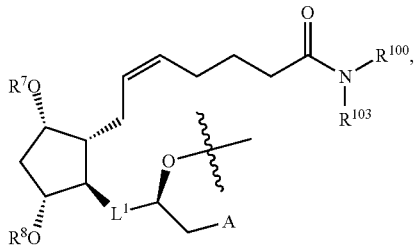
-continued
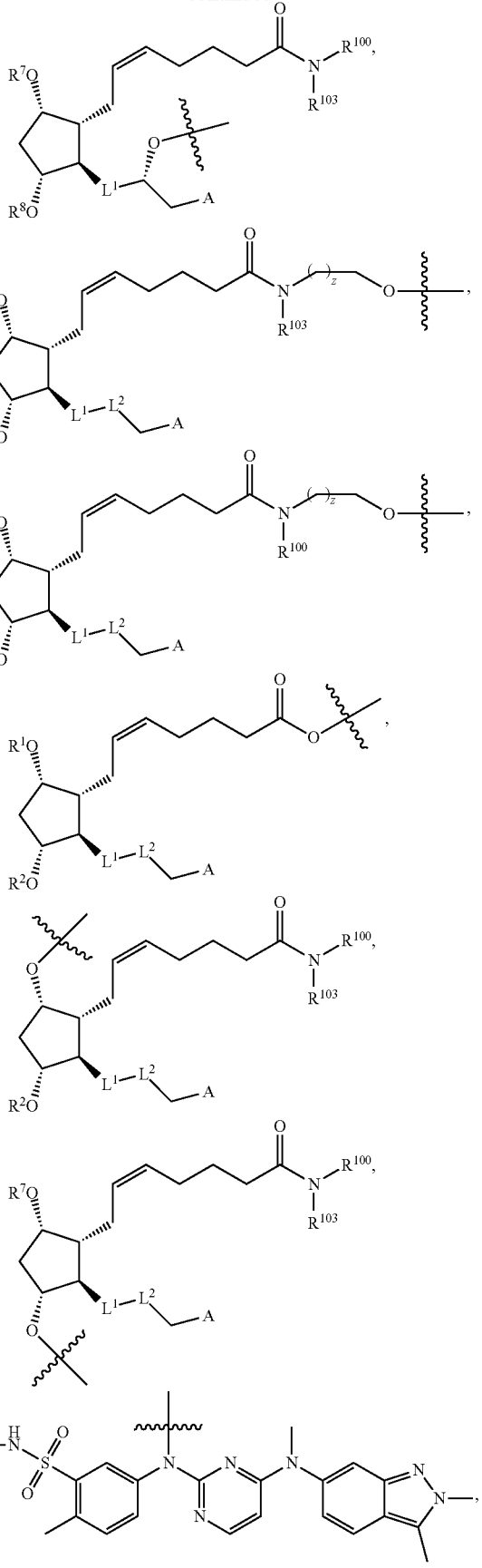

221
-continued
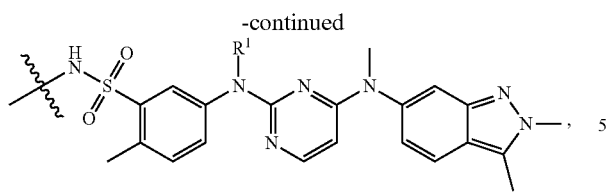
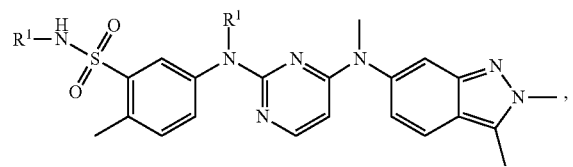
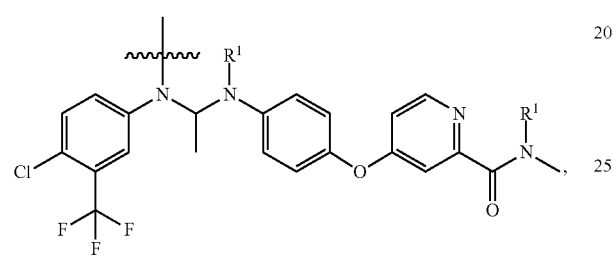
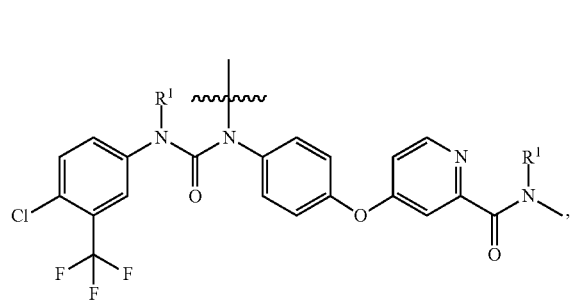
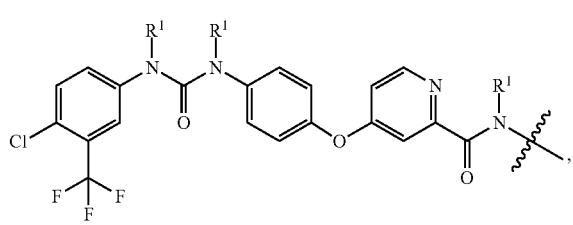
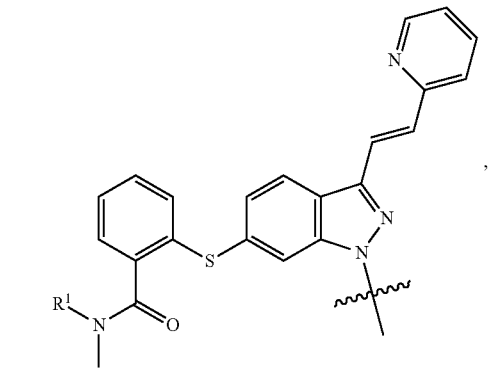
222
-continued
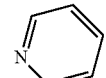
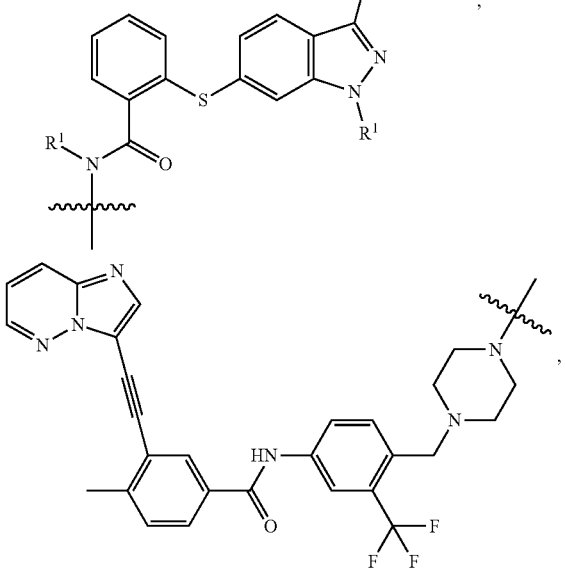
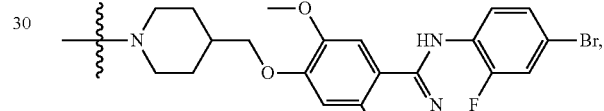
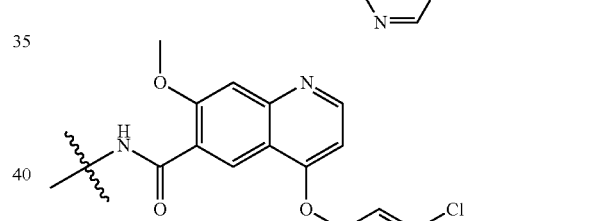
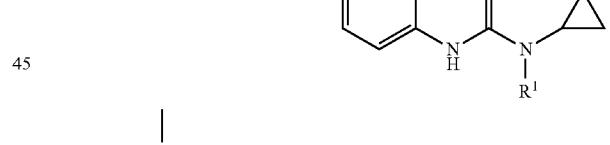
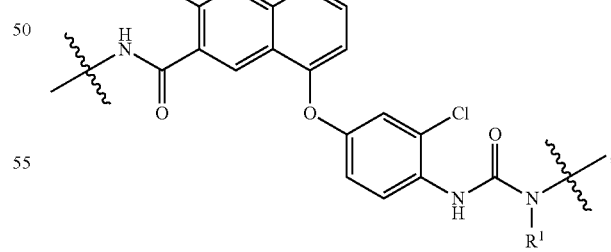
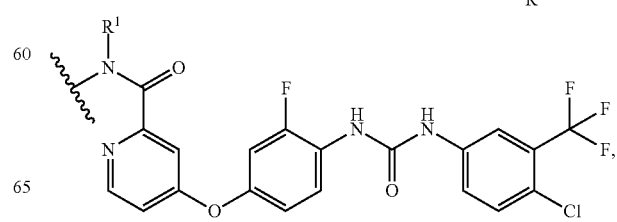

-continued
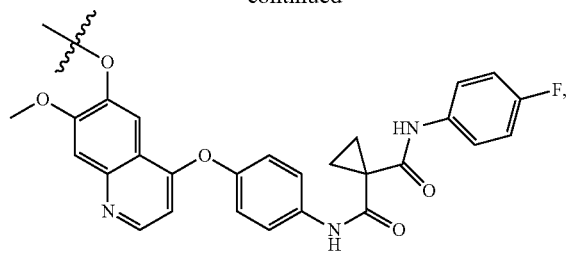
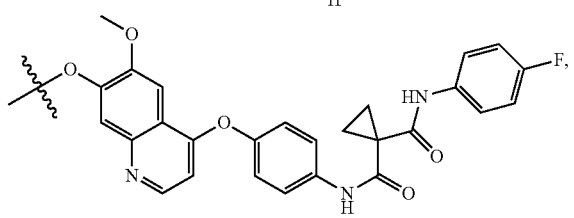
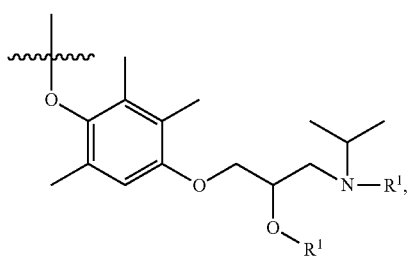
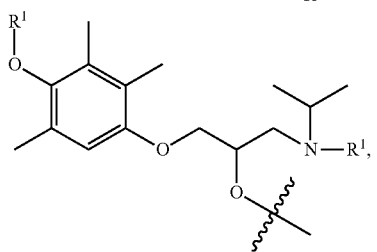
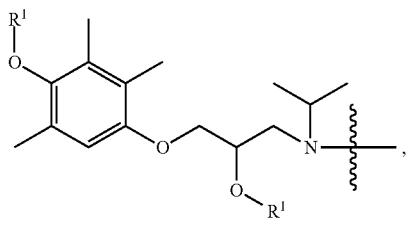
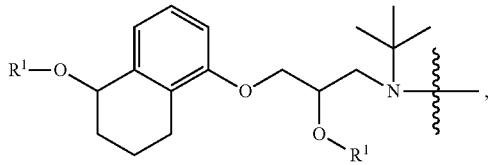
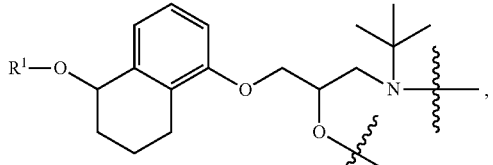
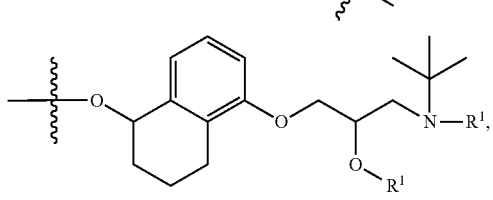
-continued
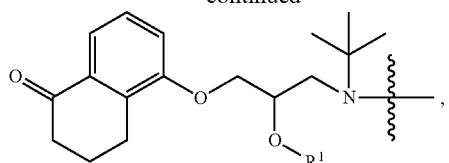
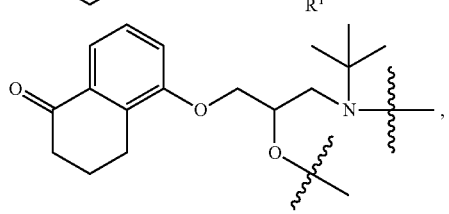
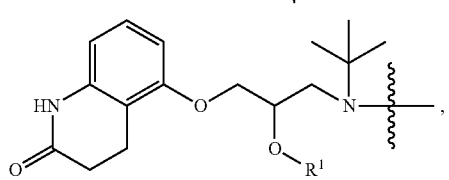
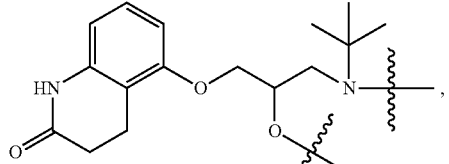
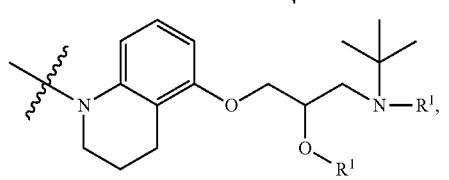
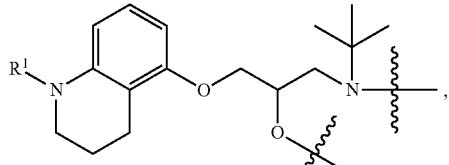
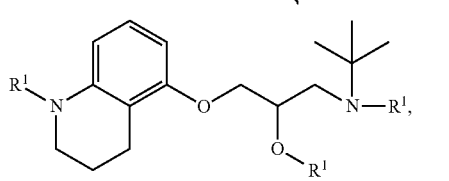
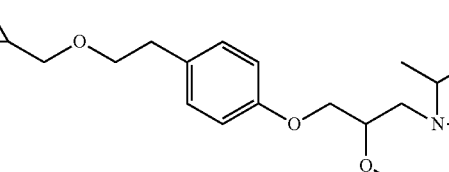
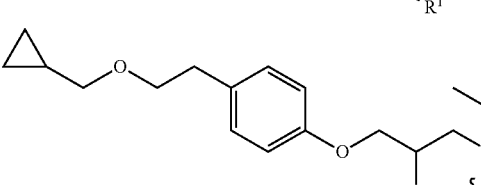

225
-continued
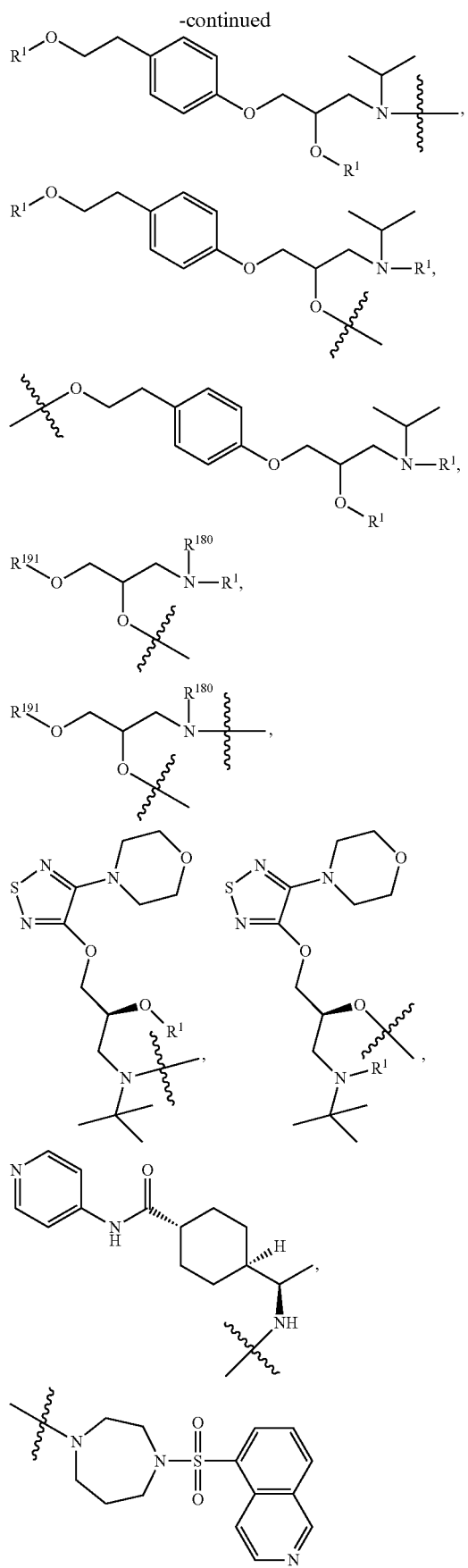
226
-continued
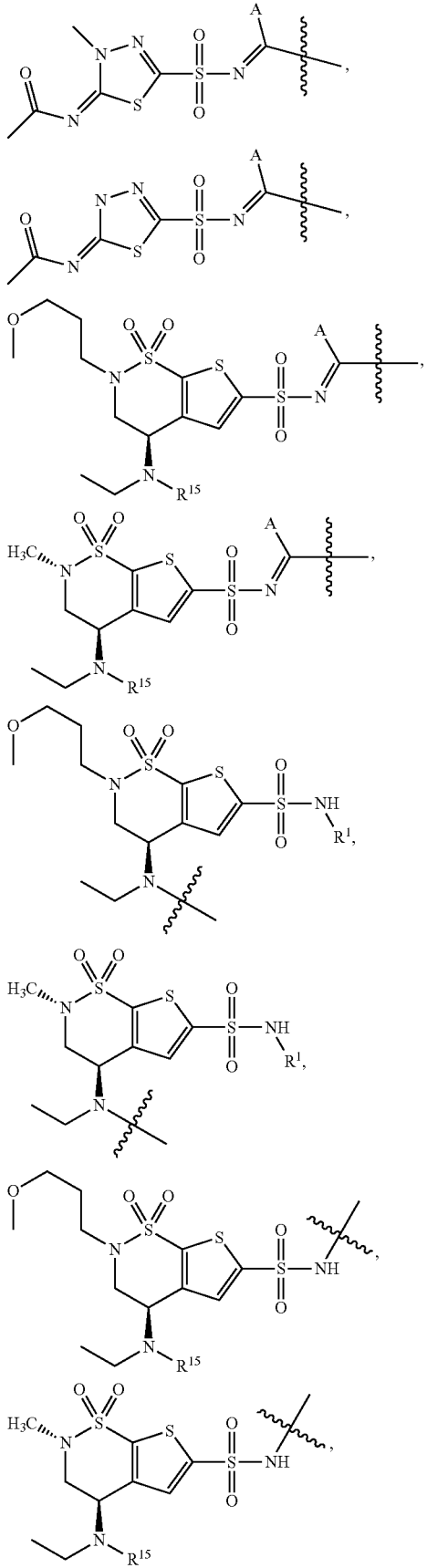

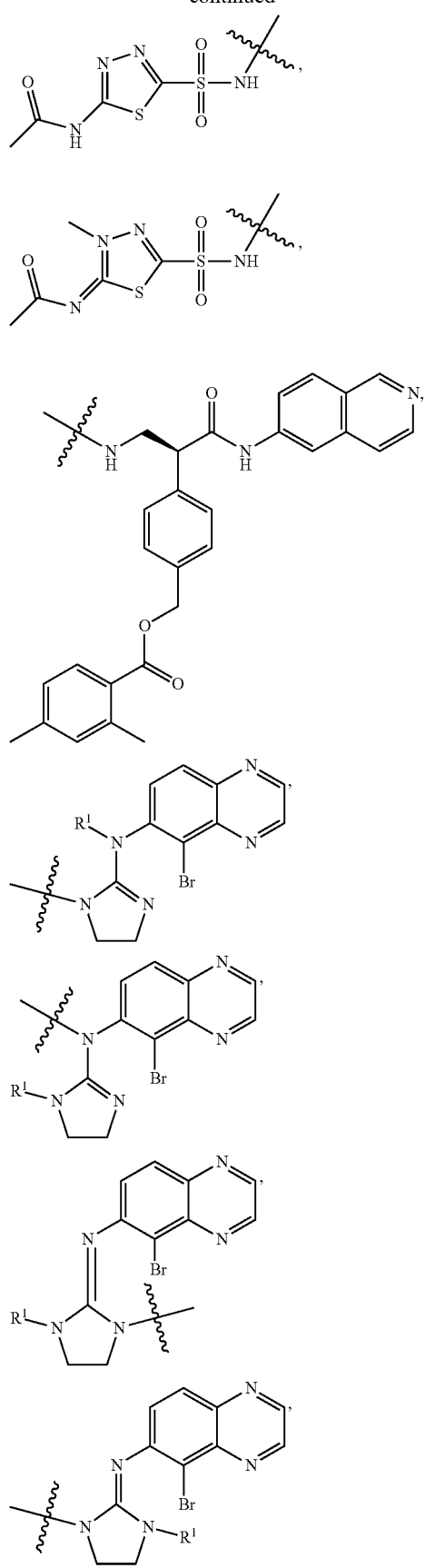
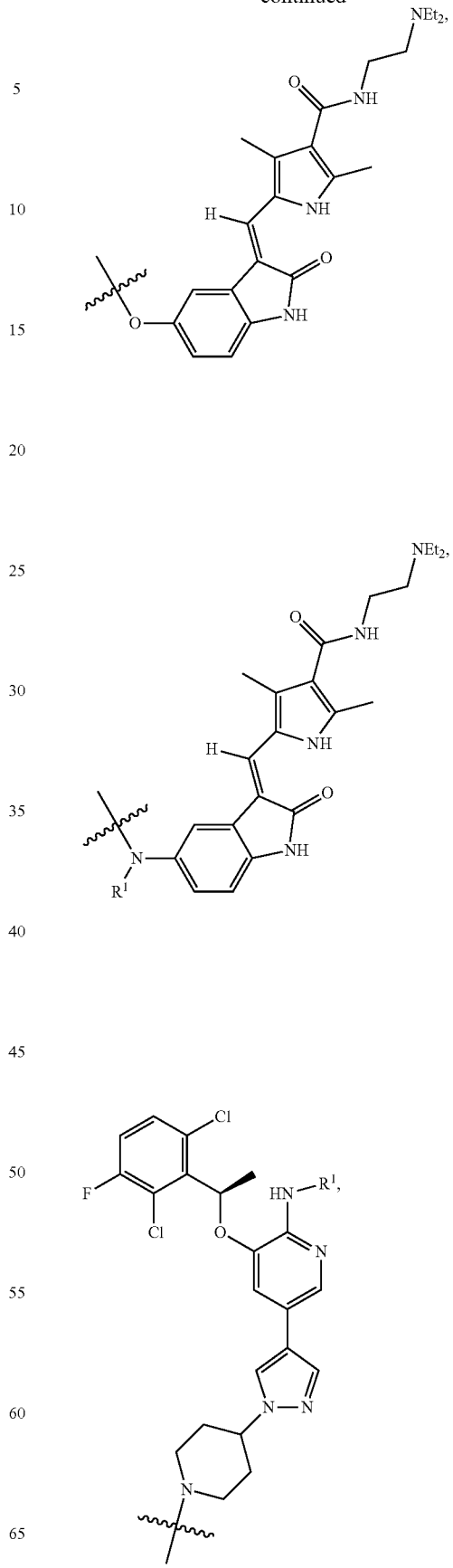

229
-continued
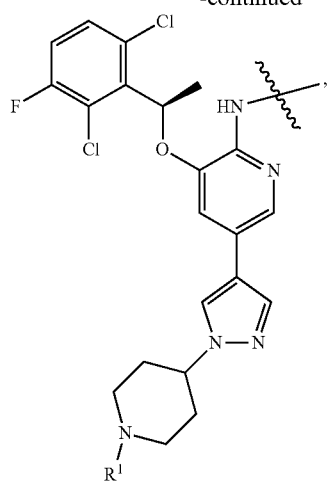
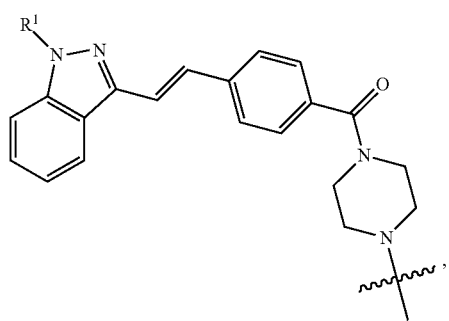
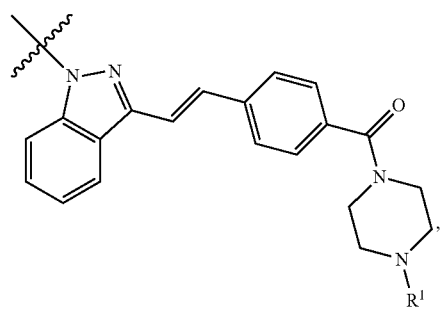
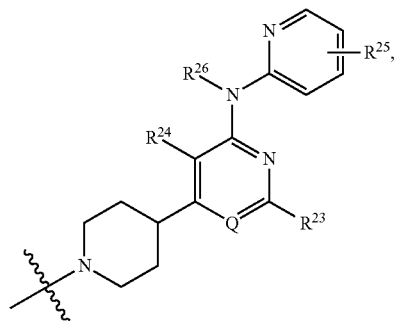
230
-continued
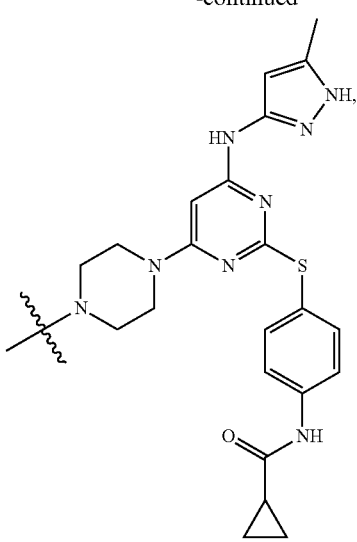
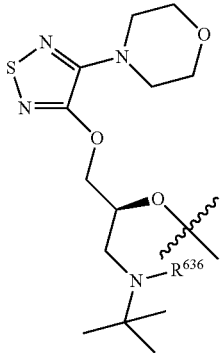
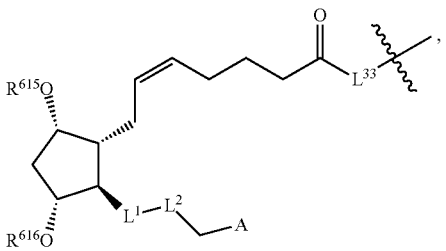
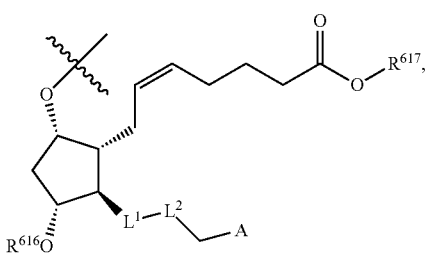
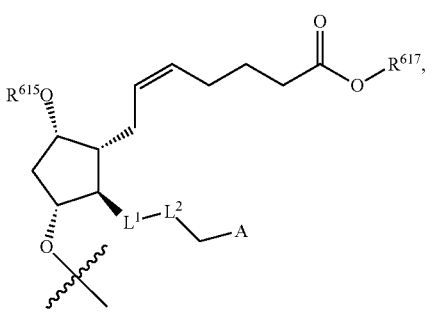

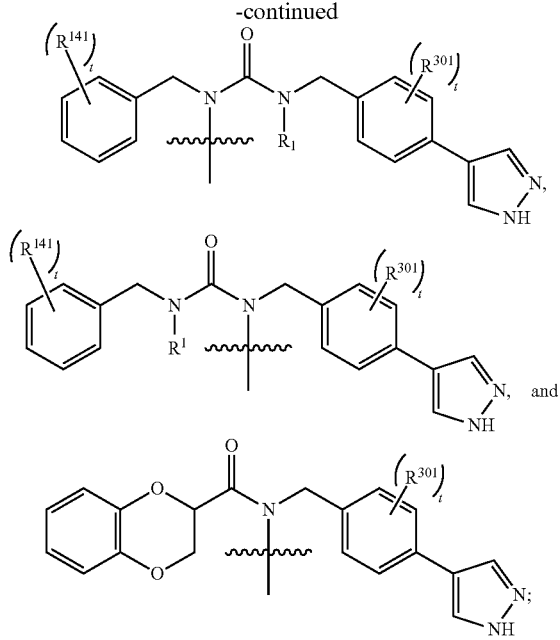
and
wherein all other variables are as defined herein.
Non-limiting examples of $R^{617}$ include:
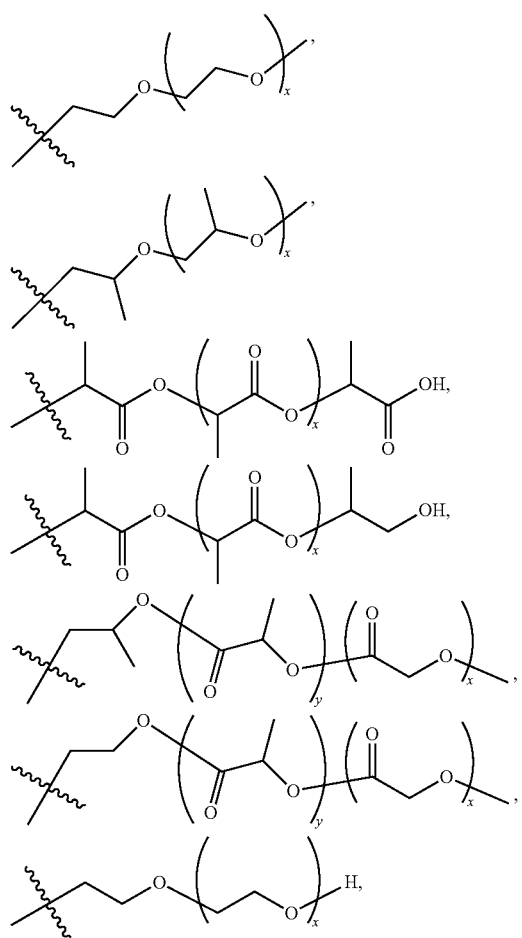
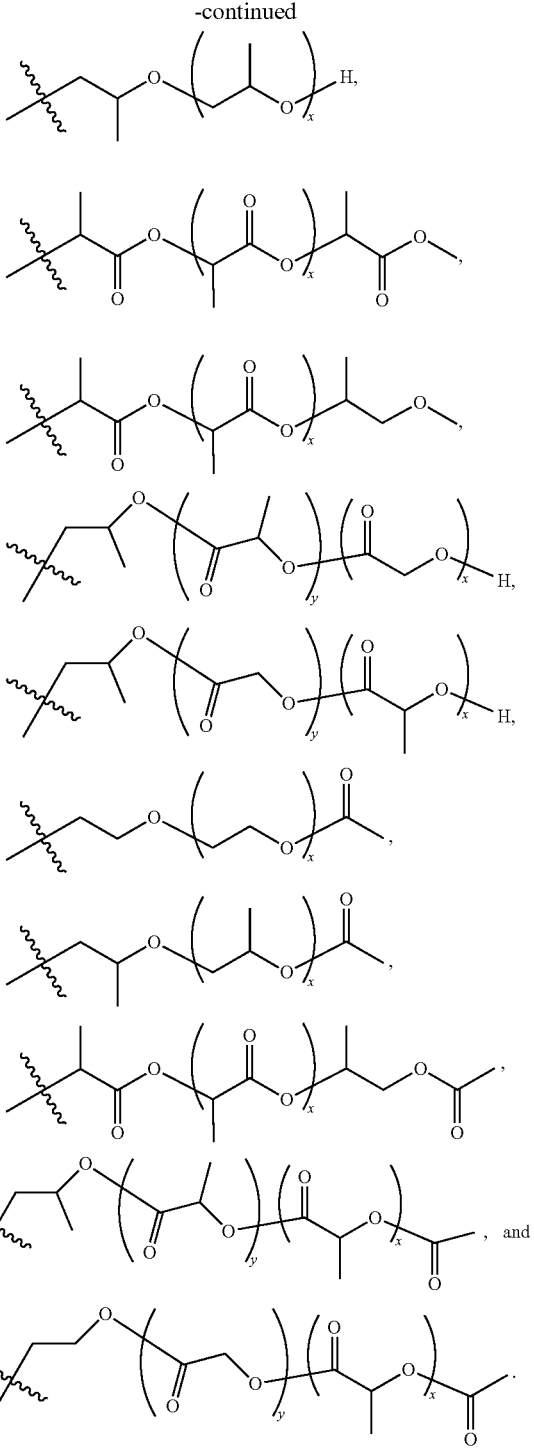
In one embodiment, $R^{360}$ is
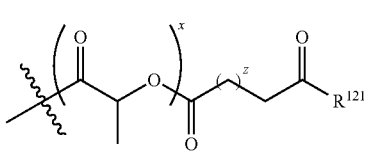

and $R^{366}$ is
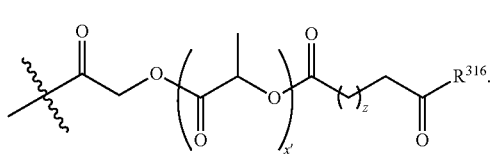
In one embodiment, $R^{360}$ is
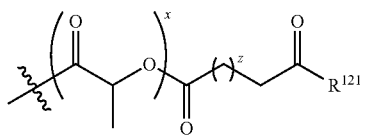
and $R^{366}$ is
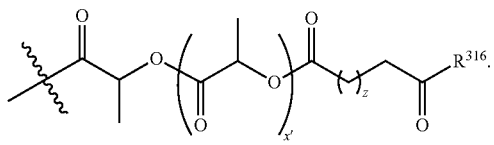
In one embodiment, $R^{360}$ is
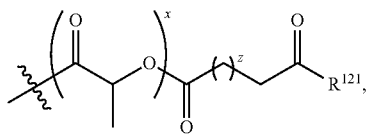
x is 1, 2, 3, or 4, and z is 1, 2, 3, or 4.
In one embodiment, $R^{366}$ is
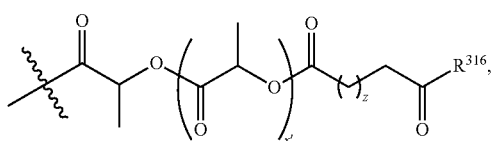
x' an integer between 0 and 4 (0, 1, 2, 3, or 4), and z is an integer between 1 and 4 (1, 2, 3, or 4).
In one embodiment, $R^{360}$ is
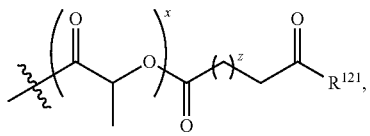
$R^{366}$
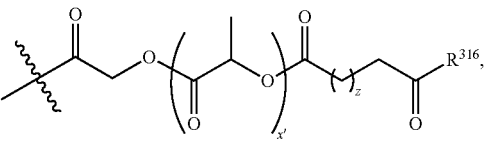
$R^{121}$ is
and $R^{316}$ is
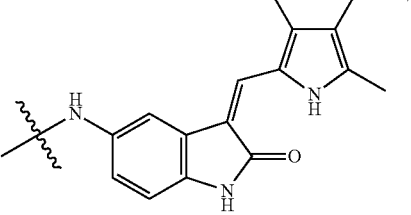
In one embodiment, $R^{360}$ is
$R^{366}$ is
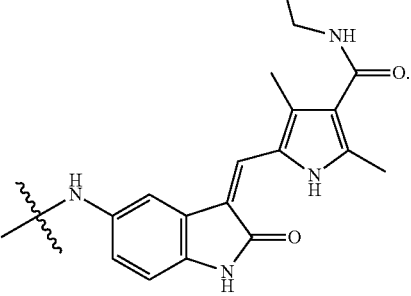
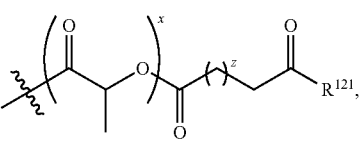
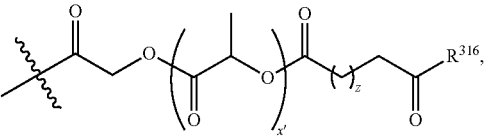

$R^{121}$ is
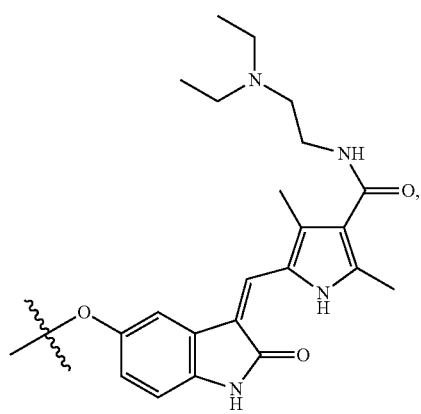 [SMILES: *Oc1ccc2c(c1)/C(=C/c1[nH]c(C)c(C(=O)NCCN(CC)CC)c1C)C(=O)N2]
and $R^{316}$ is
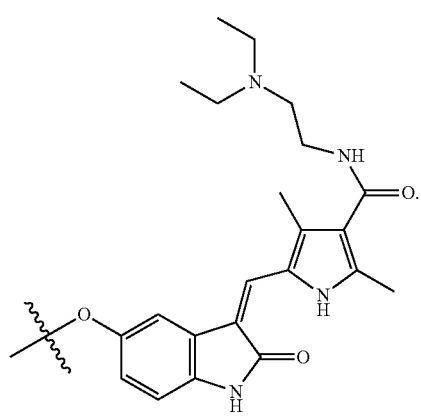 [SMILES: *Oc1ccc2c(c1)/C(=C/c1[nH]c(C)c(C(=O)NCCN(CC)CC)c1C)C(=O)N2]
Non-limiting Examples of Compounds of Formula VIID include:
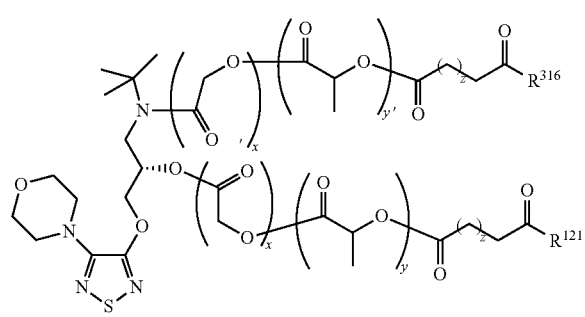
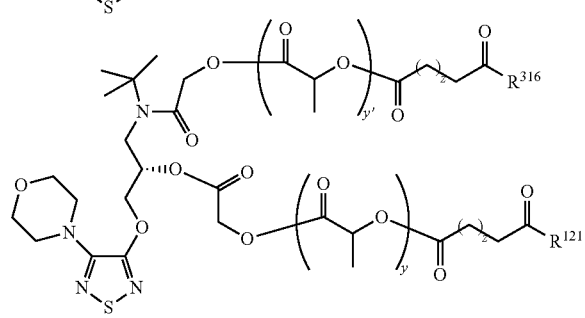
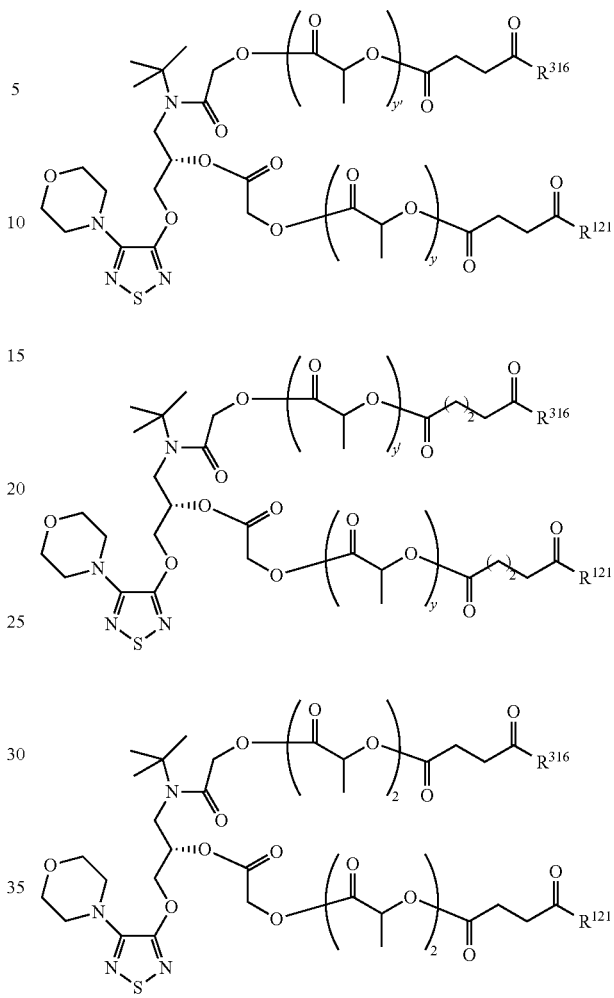

-continued

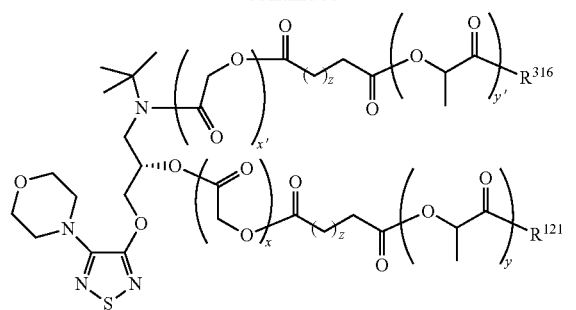

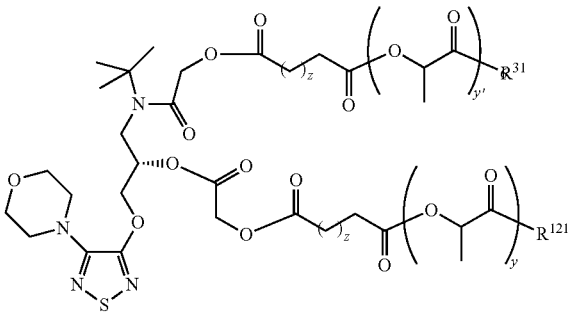

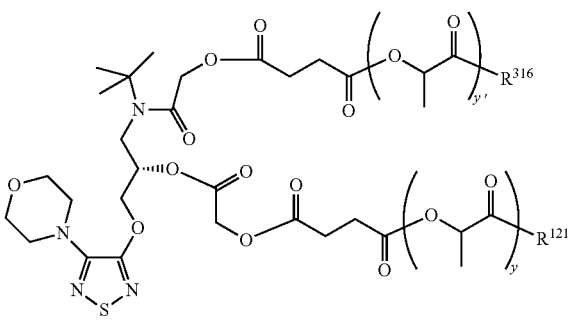

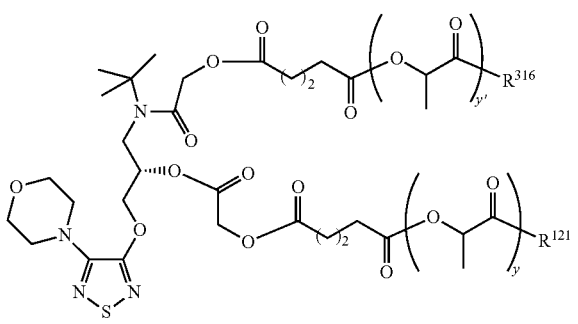

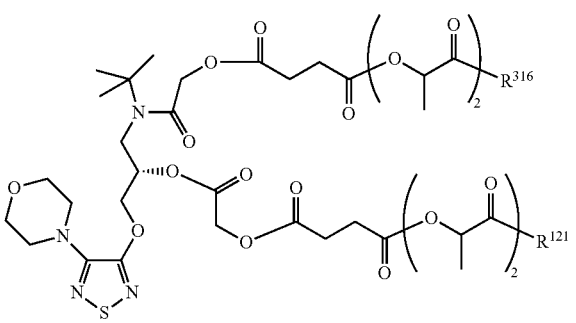

-continued

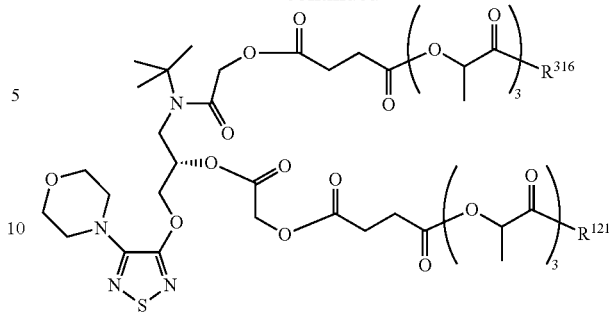

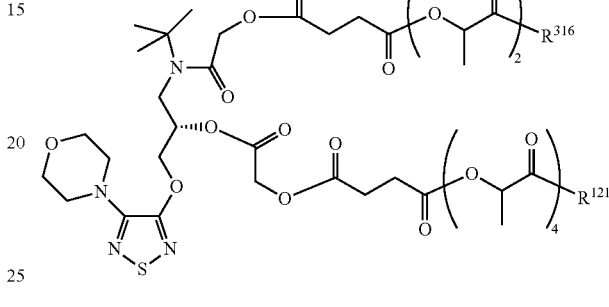

In certain embodiments of Formula VIID, x and x' are independently selected from 1, 2, 3, 4, 5, or 6; y and y' are independently selected from 1, 2, 3, 4, 5, or 6; and z is independently selected at each instance from 1, 2, and 3.

In certain embodiments of Formula VIID, x and x' are independently selected from 1, 2, or 3; y and y' are independently selected from 1, 2, or 3; and z is independently selected at each instance from 1, 2, and 3.

In certain embodiments of Formula VIID, x and x' are independently selected from 1, 2, or 3; y and y' are independently selected from 1, 2, or 3; and z in at least one instance is 1.

In certain embodiments of Formula VIID, x and x' are independently selected from 1, 2, or 3; y and y' are independently selected from 1, 2, or 3; and z in at least one instance is 2.

In certain embodiments of Formula VIID, x and x' are independently selected from 1, 2, or 3; y and y' are independently selected from 1, 2, or 3; and z in at least one instance is 3.

In certain embodiments of Formula VIID, x and x' are 1; y and y' are independently selected from 1, 2, or 3; and z is independently selected at each instance from 1, 2, and 3.

In certain embodiments of Formula VIID, x and x' are 2; y and y' are independently selected from 1, 2, or 3; and z is independently selected at each instance from 1, 2, and 3.

In certain embodiments of Formula VIID, x and x' are 3; y and y' are independently selected from 1, 2, or 3; and z is independently selected at each instance from 1, 2, and 3.

In certain embodiments of Formula VIID, x and x' are independently selected from 1, 2, or 3; y and y' are 1; and z is independently selected at each instance from 1, 2, and 3.

In certain embodiments of Formula VIID, x and x' are independently selected from 1, 2, or 3; y and y' are 2; and z is independently selected at each instance from 1, 2, and 3.

In certain embodiments of Formula VIID, x and x' are independently selected from 1, 2, or 3; y and y' are 3; and z is independently selected at each instance from 1, 2, and 3.

Duel Leucine Zipper Kinase Prodrugs

The disclosure provides duel leucine zipper kinase prodrugs of Formula IE:

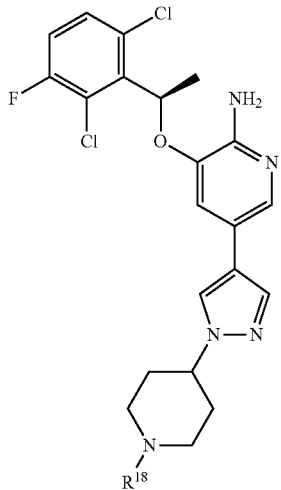

(IE)

or a pharmaceutically acceptable composition, salt, or isotopic derivative thereof.

$R^8$ is selected from: —C(O)CH$_2$CH$_2$C$_{19}$-C$_{30}$alkylR$^5$, —C(O)CH$_2$CH$_2$C$_{19}$-C$_{30}$alkenylR$^5$, —C(O)CH$_2$CH$_2$C$_{19}$-C$_{30}$alkynylR$^5$, —C(O)CH$_2$CH$_2$C$_{19}$-C$_{30}$alkenylalkynylR$^5$, —C(O)CH$_2$CH$_2$C$_{19}$-C$_{30}$alkyl, —C(O)CH$_2$CH$_2$C$_{19}$-C$_{30}$alkenyl, —C(O)CH$_2$CH$_2$C$_{19}$-C$_{30}$alkynyl, —C(O)CH$_2$CH$_2$C$_{19}$-C$_{30}$alkenylalkynyl, and $R^{19}$ wherein $R^{18}$ can be further optionally further substituted with $R^5$ (including for example a second $R^5$) if valence permits, a stable compound is formed, and the resulting compound is pharmaceutically acceptable;

In various different embodiments, —C$_{19}$-C$_{30}$ as used in the definition of $R^{18}$ is —C$_{19}$-C$_{28}$, —C$_{19}$-C$_{26}$, —C$_{19}$-C$_{24}$, —C$_{19}$-C$_{22}$, —C$_{19}$-C$_{20}$, —C$_{20}$-C$_{28}$, —C$_{20}$-C$_{26}$, —C$_{20}$-C$_{24}$, —C$_{20}$-C$_{22}$, —C$_{22}$-C$_{28}$, —C$_{22}$-C$_{26}$, —C$_{22}$-C$_{24}$, or —C$_{26}$-C$_{28}$.

$R^{19}$ is selected from:
(i) an unsaturated fatty acid residue including but not limited to the carbonyl fragment taken from docosahexaenoic acid (—C(O)(CH$_2$)$_2$(CHCHCH$_2$)$_6$CH$_3$)), docosatetraenoic acid, euric acid, or nervonic acid;
(ii) polyethylene glycol, polypropylene glycol, polypropylene oxide, polylactic acid, or poly(lactic-co-glycolic acid) including:

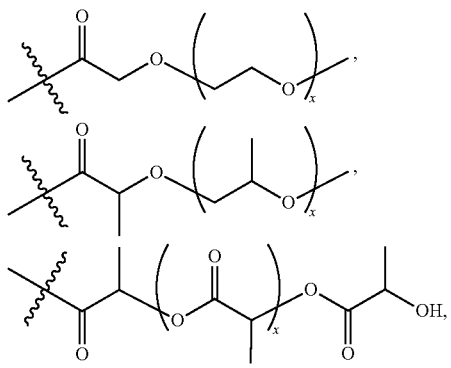

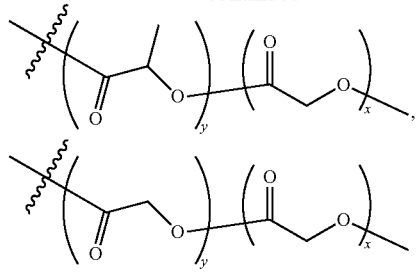

or polyglycolic acid, or a polyester, polyamide, or other biodegradable polymer, each of which can be capped to complete the terminal valence or to create a terminal ether.

The disclosure provides duel leucine zipper kinase prodrugs of Formula IIE:

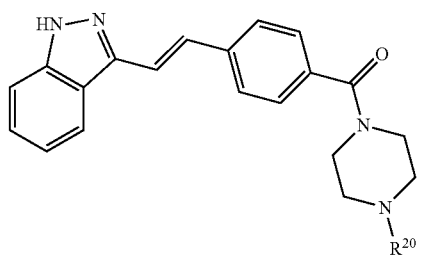

(IIE)

or a pharmaceutically acceptable composition, salt, or isotopic derivative thereof.

$R^{20}$ is selected from: —C(O)CH$_2$CH$_2$C$_9$-C$_{30}$alkylR$^5$, —C(O)CH$_2$CH$_2$C$_9$-C$_{30}$alkenylR$^5$, —C(O)CH$_2$CH$_2$C$_9$-C$_{30}$alkynylR$^5$, —C(O)CH$_2$CH$_2$C$_9$-C$_{30}$alkenylalkynylR$^5$, —C(O)CH$_2$CH$_2$C$_9$-C$_{30}$alkyl, —C(O)CH$_2$CH$_2$C$_9$-C$_{30}$alkenyl, —C(O)CH$_2$CH$_2$C$_9$-C$_{30}$alkynyl, —C(O)CH$_2$CH$_2$C$_9$-C$_{30}$alkenylalkynyl, and $R^{21}$.

In one embodiment, —C$_9$-C$_{30}$ as used in the definition of $R^{20}$ is —C$_{10}$-C$_{28}$, —C$_{11}$-C$_{26}$, —C$_{11}$-C$_{24}$, —C$_{12}$-C$_{22}$, —C$_{12}$-C$_{20}$, —C$_{12}$-C$_{18}$, —C$_{12}$-C$_{16}$, or —C$_{12}$-C$_{14}$ $R^{21}$ is selected from:
(i) an unsaturated fatty acid residue including but not limited the carbonyl fragment taken from linoleic acid (—C(O)(CH$_2$)$_7$(CH)$_2$CH$_2$(CH)$_2$(CH$_2$)$_4$CH$_3$)), docosahexaenoic acid (—C(O)(CH$_2$)$_2$(CHCHCH$_2$)$_6$CH$_3$)), eicosapentaenoic acid (—C(O)(CH$_2$)$_3$(CHCHCH$_2$)$_5$ CH$_3$)), alpha-linolenic acid (—C(O)(CH$_2$)$_7$ (CHCHCH$_2$)$_3$CH$_3$)) stearidonic acid, y-linolenic acid, arachidonic acid, docosatetraenoic acid, palmitoleic acid, vaccenic acid, paullinic acid, oleic acid, elaidic acid, gondoic acid, euric acid, nervonic acid and mead acid, each of which can be further substituted with $R^5$ if valence permits, a stable compound is formed, and the resulting compound is pharmaceutically acceptable;
(ii) polyethylene glycol, polypropylene glycol, polypropylene oxide, polylactic acid, and poly(lactic-co-glycolic acid) including:

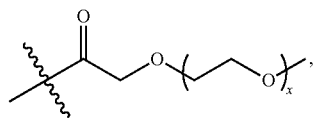

-continued

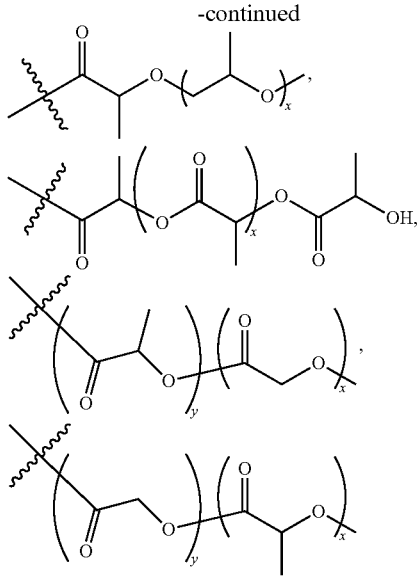

or polyglycolic acid, or a polyester, polyamide, or other biodegradable polymer, each of which can be capped to complete the terminal valence or to create a terminal ether.

(iii) The disclosure provides duel leucine zipper kinase prodrugs of Formula IIIE:

(IIIE)

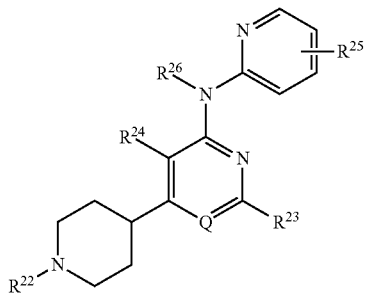

or a pharmaceutically acceptable composition, salt, or isotopic derivative thereof.

Q is selected from: N, CH, and $CR^{23}$.

$R^{22}$ is selected from: —C(O)CH$_2$CH2C$_{11}$-C$_{30}$alkylR$^5$, —C(O)CH$_2$CH$_2$C$_{11}$-C$_{30}$alkenylR$^5$, —C(O)CH$_2$CH$_2$C$_{11}$-C$_{30}$alkynylR$^5$, —C(O)CH$_2$CH$_2$C$_{11}$-C$_{30}$alkenylalkynylR$^5$, —C(O)CH$_2$CH$_2$C$_{11}$-C$_{30}$alkyl, —C(O)CH$_2$CH$_2$C$_{11}$-C$_{30}$alkenyl, —C(O)CH$_2$CH$_2$C$_{11}$-C$_{30}$alkynyl, —C(O)CH$_2$CH$_2$C$_{11}$-C$_{30}$alkenylalkynyl and $R^{21}$ and wherein $R^{22}$ can be further substituted with $R^5$ (including for example a second $R^5$) if valence permits, a stable compound is formed, and the resulting compound is pharmaceutically acceptable.

In one embodiment, —C$_{11}$-C$_{30}$ as used in the definition of $R^{22}$ is —C$_{12}$-C$_{28}$, —C$_{13}$-C$_{26}$, —C$_{13}$-C$_{24}$, —C$_{13}$-C$_{22}$, —C$_{13}$-C$_{20}$, —C$_{13}$-C$_{18}$, —C$_{13}$-C$_{16}$, or —C$_{13}$-C$_{14}$.

$R^{23}$, $R^{24}$, and $R^{25}$ are independently selected from: hydrogen, halogen, hydroxyl, cyano, mercapto, nitro, amino, aryl, alkyl, alkoxy, alkenyl, alkynyl cycloalkyl, cycloalkylalkyl, heterocyclyl, heterocycloalkyl, aryl, arylalkyl, heteroaryl, heteroarylalkyl, aryloxy, —S(O)$_2$alkyl, —S(O)alkyl, —P(O)(Oalkyl)$_2$, B(OH)$_2$, —Si(CH$_3$)$_3$, —COOH, —COOalkyl, —CONH$_2$,

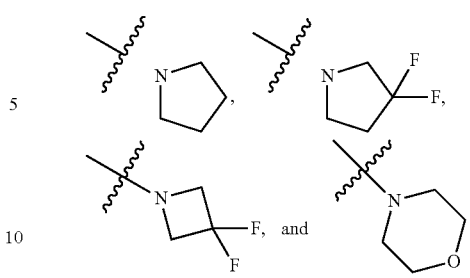

each of which except halogen, nitro, and cyano, may be optionally substituted, for example with halogen, alkyl, aryl, heterocycle or heteroaryl.

$R^{26}$ is selected from H, C(O)A, —C$_0$-C$_{10}$alkylR$^5$, —C$_2$-C$_{10}$alkenylR$^5$, —C$_2$-C$_{10}$alkynylR$^5$, —C$_2$-C$_{10}$alkenyl, and —C$_2$-C$_{10}$alkynyl.

In one embodiment, —C$_2$-C$_{10}$ as used in $R^{26}$ is —C$_4$-C$_{10}$, —C$_6$-C$_{10}$, or —C$_8$-C$_{10}$.

The disclosure also provides a prodrug of Formula IVE:

(IVE)

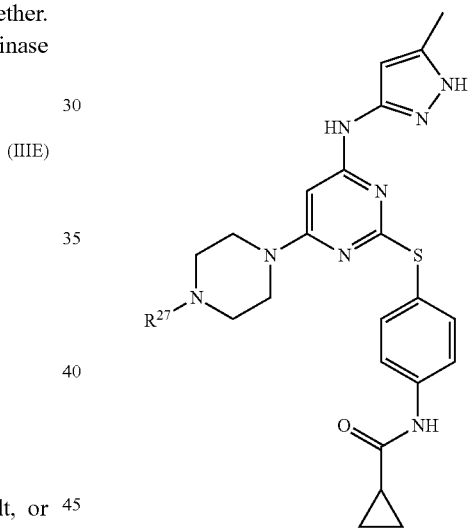

or a pharmaceutically acceptable composition, salt, or isotopic derivative thereof.

$R^{27}$ is selected from: —C(O)CH$_2$CH$_2$C$_0$-C$_{30}$alkylR$^5$, —C(O)CH$_2$CH$_2$C$_0$-C$_{30}$alkenylR$^5$, —C(O)CH$_2$CH$_2$C$_0$-C$_{30}$alkynylR$^5$, —C(O)CH$_2$CH$_2$C$_0$-C$_{30}$alkenylalkynylR$^5$, —C(O)CH$_2$CH$_2$C$_0$-C$_{30}$alkyl, —C(O)CH$_2$CH$_2$C$_0$-C$_{30}$alkenyl, —C(O)CH$_2$CH$_2$C$_0$-C$_{30}$alkynyl, —C(O)CH$_2$CH$_2$C$_0$-C$_{30}$alkenylalkynyl, and $R^{21}$.

In various different embodiments, —C$_0$-C$_{30}$ as used in $R^{27}$ is —C$_0$-C$_{28}$, —C$_0$-C$_{26}$, —C$_0$-C$_{24}$, —C$_0$-C$_{22}$, —C$_0$-C$_{20}$, —C$_0$-C$_{18}$, —C$_0$-C$_{16}$, —C$_0$-C$_{14}$, —C$_0$-C$_{12}$, or —C$_0$-C$_{11}$, —C$_0$-C$_{10}$, —C$_0$-C$_8$, —C$_0$-C$_6$, —C$_0$-C$_4$, —C$_0$-C$_2$, —C$_2$-C$_{28}$, —C$_4$-C$_{26}$, —C$_4$-C$_{24}$, —C$_4$-C$_{22}$, —C$_4$-C$_{20}$, —C$_6$-C$_{18}$, —C$_6$-C$_{16}$, —C$_6$-C$_{14}$, —C$_6$-C$_{12}$, —C$_4$-C$_{11}$, —C$_0$-C$_{10}$, —C$_0$-C$_8$, —C$_0$-C$_6$, —C$_0$-C$_4$, or —C$_0$-C$_2$.

The disclosure also provides a prodrug of Formula VE, Formula VIE, Formula VIIE, Formula VIIIE, Formula IXE, and Formula XE:

(VE)
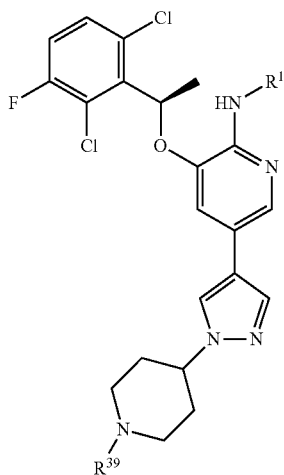
(VIE)
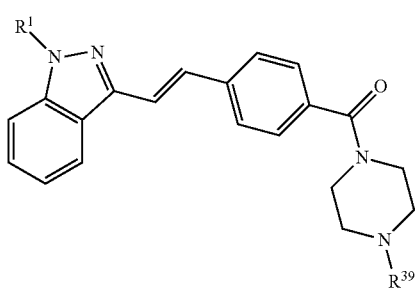
(VIIE)
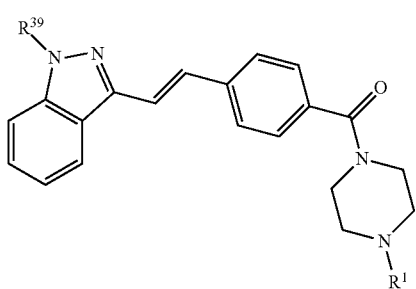
(VIIIE)
(IXE)
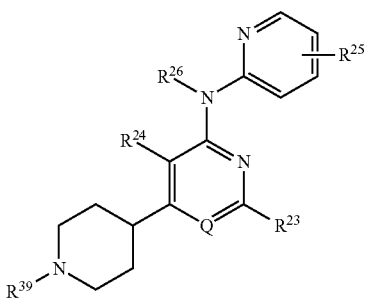
(XE)
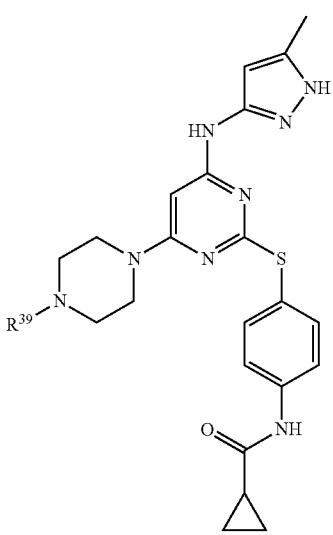
or a pharmaceutically acceptable composition, salt, or isotopic derivative thereof wherein
$R^{39}$ is selected from: $R^{40}$, carbonyl linked polyethylene glycol, carbonyl linked polypropylene glycol, carbonyl linked polypropylene oxide, polylactic acid, and poly(lactic-co-glycolic acid), a polyglycolic acid, a polyester, polyamide,
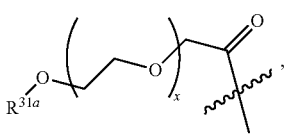
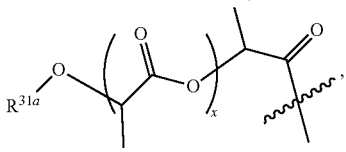
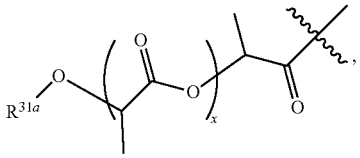
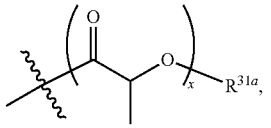

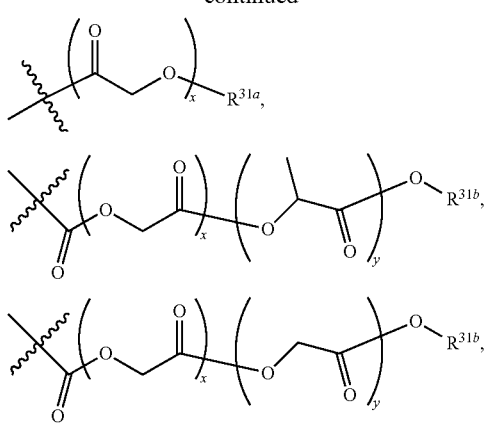
or other biodegradable polymer, wherein each $R^{39}$ other than $R^{40}$ is substituted with at least one $L^4$-$R^{121}$;
$R^{40}$ is selected from:
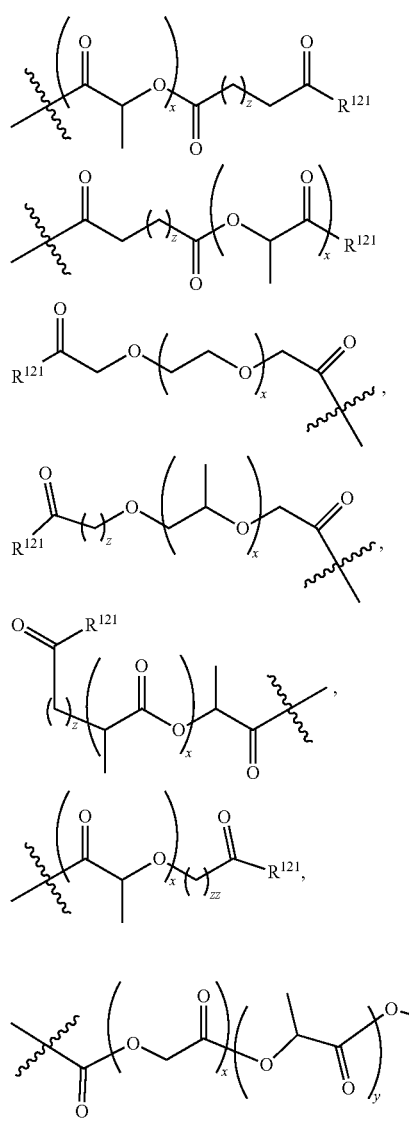
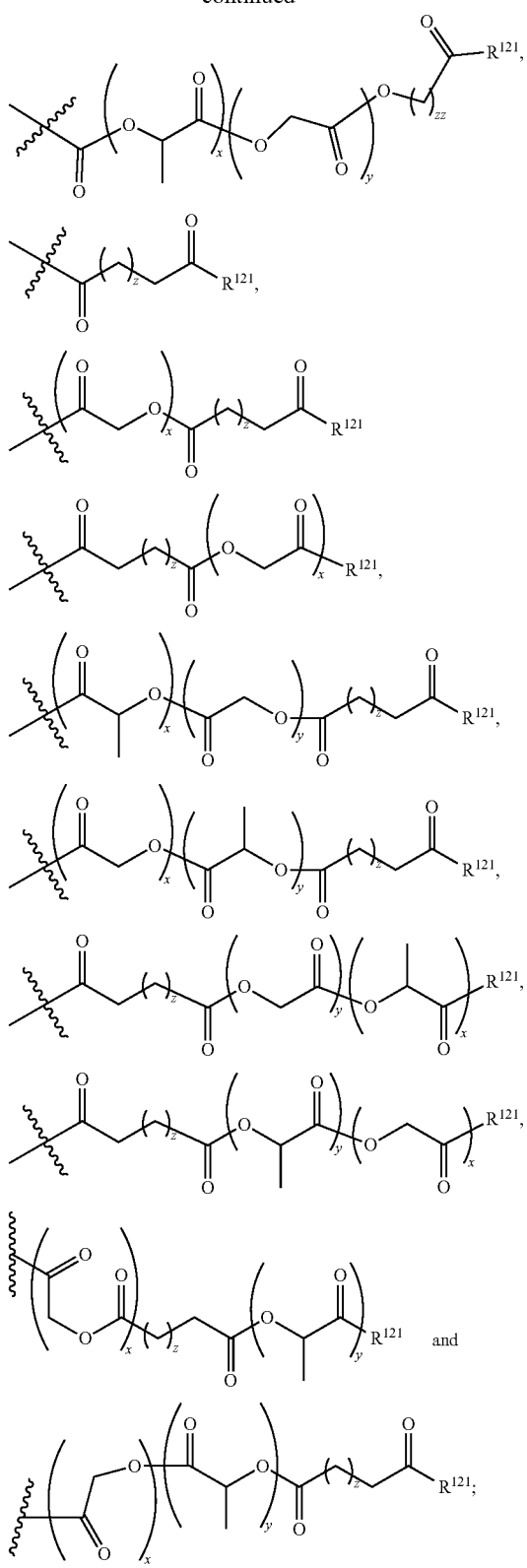
Rho Kinase (ROCK) Inhibitor Prodrugs
The disclosure provides ROCK inhibitor prodrugs of Formula IF, Formula IIF, Formula IIIF, Formula IVF, and Formula VF:

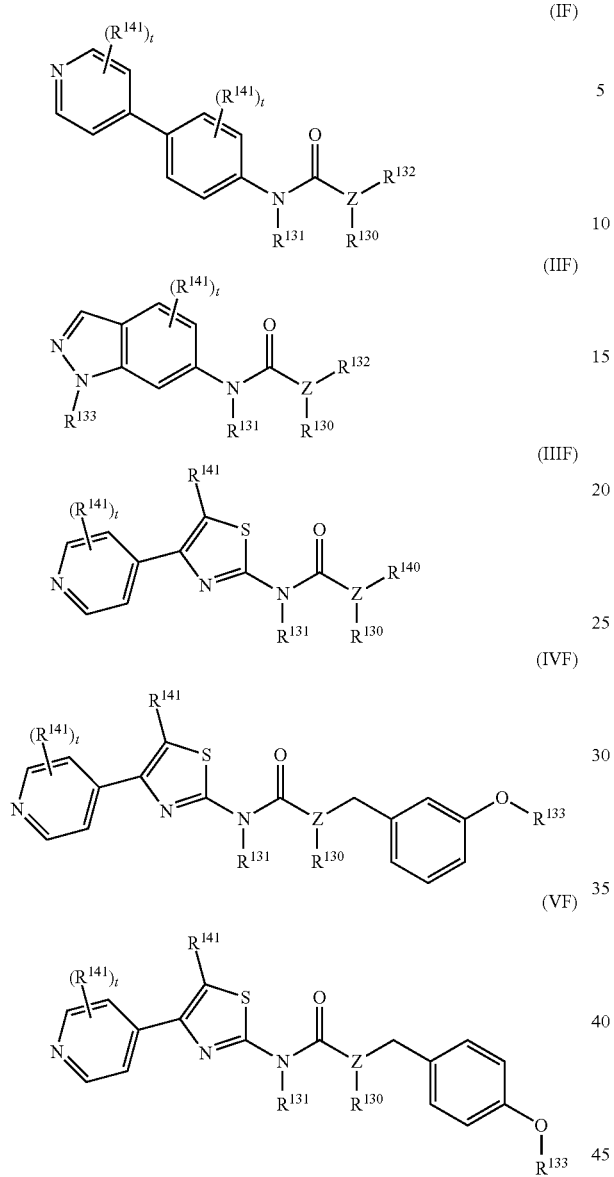

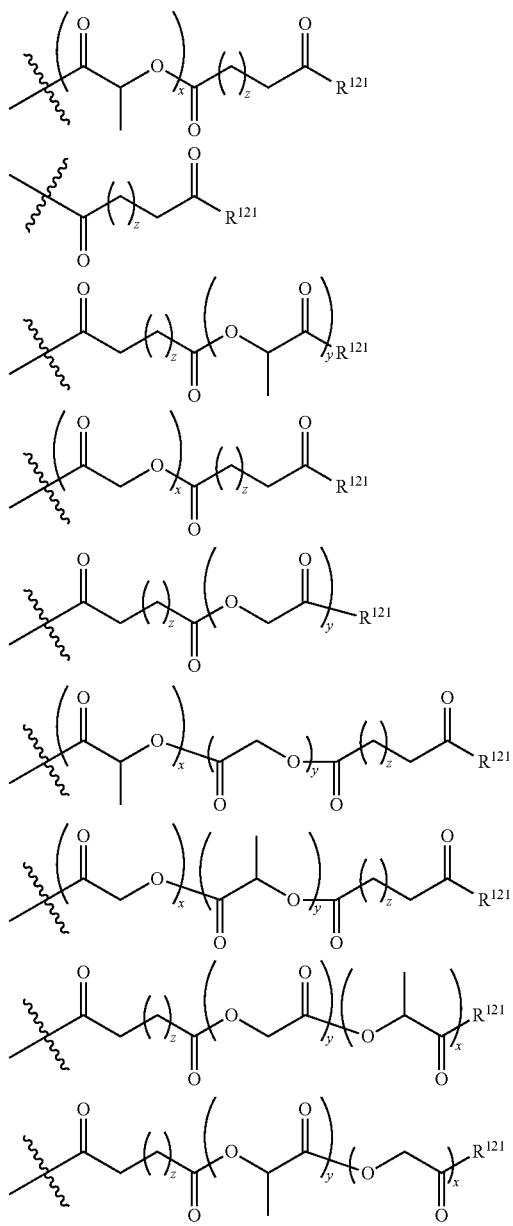

or a pharmaceutically acceptable composition, salt, or isotopic derivative thereof.

Z is $CR^{130}$ or N;

t is independently selected from 0, 1, 2, 3, and 4;

$R^{130}$, $R^{131}$, and $R^{133}$ are independently selected at each occurrence from H, $C_1$-$C_{30}$alkyl, —C(O)$C_1$-$C_{30}$alkyl, $C_1$-$C_{30}$heteroalkyl, and $R^{136}$;

$R^{132}$ is selected from $R^{136}$, $C_1$-$C_{30}$alkyl, $C_1$-$C_{30}$cycloalkyl, heterocycloalkyl, aryl, heteroaryl, and alkylaryl, any of which can be optionally substituted with one or more of hydroxyl, —CH$_2$OH, —C(O)NH$_2$, acetyl, carbonyl, alkyl, cycloalkyl, heterocycloalkyl, aryl, and heteroaryl, any of which can be optionally substituted with one or more of hydroxyl, nitro, amino, —NR$^{134}$R$^{135}$, alkyl, alkoxy, alkylalkoxy, alkoxylalkoxy, haloalkoxy, heteroarylcarbonyl, heteroaryl, —OCH$_3$, —OCF$_3$, —OCHF$_2$, —OCH$_2$F, —OSO$_2$CH$_3$, tosyl, or halogen;

$R^{140}$ is selected from $R^{136}$, hydrogen, alkyl, cycloalkyl, heterocycloalkyl, and aryl, any of which except hydrogen can be optionally substituted with one or more of hydroxyl, —CH$_2$OH, —C(O)NH$_2$, acetyl, carbonyl, alkyl, cycloalkyl, heterocycloalkyl, aryl, and heteroaryl, any of which can be optionally substituted with one or more of hydroxyl, nitro, amino, —NR$^{134}$R$^{135}$, alkyl, alkoxy, alkylalkoxy, alkoxylalkoxy, haloalkoxy, heteroarylcarbonyl, heteroaryl, —OCH$_3$, —OCF$_3$, —OCHF$_2$, —OCH$_2$F, —OSO$_2$CH$_3$, tosyl, or halogen;

$R^{136}$ is selected from: $R^{137}$, acyl, alkyl, alkyloxy, polyethylene glycol, polypropylene glycol, polypropylene oxide, polylactic acid, poly(lactic-co-glycolic acid), a polyglycolic acid, a polyester, polyamide, or other biodegradable polymer, wherein each $R^{136}$ other than $R^{137}$ is substituted with at least one $L^4$-$R^{121}$;

or $R^{136}$ is $L^4$-$R^{121}$ or $R^{121}$;

wherein at least one of $R^{130}$, $R^{131}$, and $R^{133}$ is $R^{136}$; and $R^{137}$ is selected from:

-continued

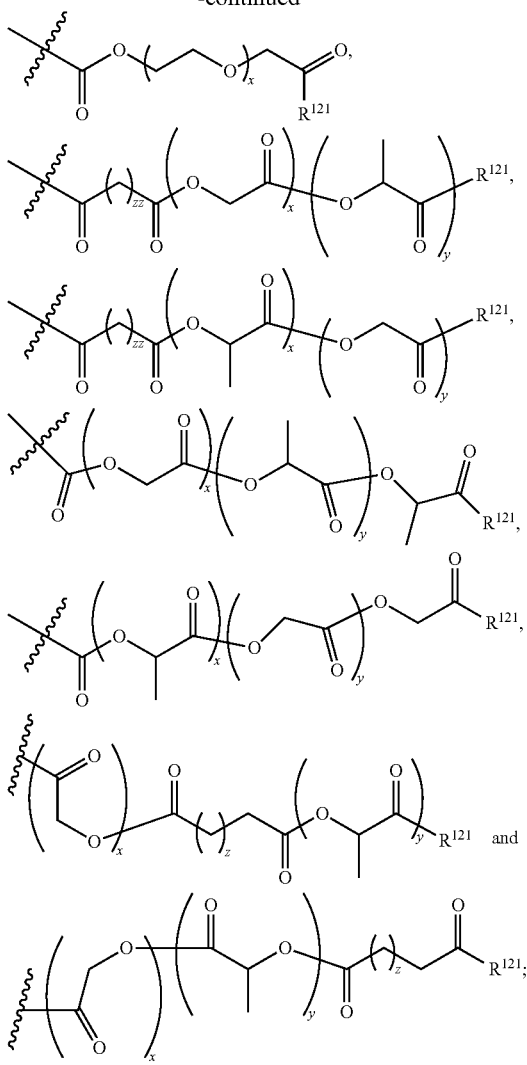

wherein all other variables are as defined herein.
In one embodiment, Formula IF is Formula IFa

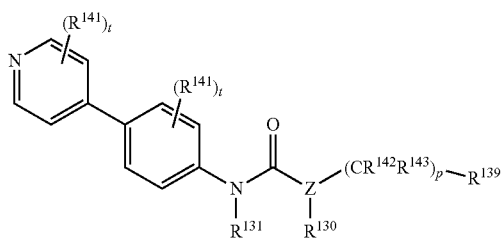

(IFa)

wherein:

$R^{142}$ and $R^{143}$ are independently selected from H, —OH, acetyl, —C(O)NH$_2$, C$_1$-C$_6$alkyl, C$_1$-C$_6$cycloalkyl, heterocycloalkyl, aryl, or heteroaryl, wherein any one of the C$_1$-C$_6$alkyl, C$_1$-C$_6$cycloalkyl, heteroC$_1$-C$_6$cycloalkyl, aryl, or heteroaryl groups is optionally substituted with one or more of hydroxyl, —CH$_2$OH, —C(O)NH$_2$, acetyl, carbonyl, alkyl, cycloalkyl, heterocycloalkyl, aryl, and heteroaryl, any of which can be optionally substituted with one or more of hydroxyl, nitro, amino, —NR$^{134}$R$^{135}$, alkyl, alkyl-O—R$^{136}$, alkoxy, alkylalkoxy, alkoxylalkoxy, heteroarylcarbonyl, heteroaryl, —OCH$_3$, —OCF$_3$, —OCHF$_2$, —OCH$_2$F;

$R^{139}$ is selected from cycloalkyl, heterocycloalkyl, aryl, or heteroaryl, any of which is optionally substituted with one or more of hydroxyl, —CH$_2$OH, —C(O)NH$_2$, acetyl, carbonyl, alkyl, cycloalkyl, heterocycloalkyl, aryl, and heteroaryl, any of which can be optionally substituted with one or more of hydroxyl, nitro, amino, —NR$^{134}$R$^{135}$, alkyl, alkoxy, alkylalkoxy, alkoxylalkoxy, haloalkoxy, heteroarylcarbonyl, heteroaryl, —OCH$_3$, —OCF$_3$, —OCHF$_2$, —OCH$_2$F, —OSO$_2$CH$_3$, tosyl, or halogen;

p is 1, 2, or 3; and wherein all other variables are as defined herein.

In one embodiment, Formula IF is Formula IFb

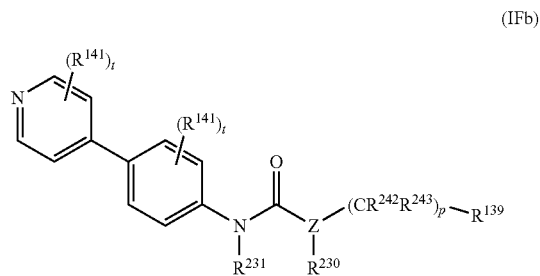

(IFb)

wherein:

$R^{230}$ and $R^{231}$ are independently selected at each occurrence from H, C$_1$-C$_{30}$alkyl, —C(O)C$_1$-C$_{30}$alkyl, C$_1$-C$_{30}$heteroalkyl, and R$^{136}$;

$R^{242}$ and $R^{243}$ are independently selected at each instance from H, —OH, acetyl, —C(O)NH$_2$, C$_1$-C$_6$alkyl, C$_1$-C$_6$cycloalkyl, hereterocycloalkyl, aryl, or heteroaryl, wherein any one of the C$_1$-C$_6$alkyl, C$_1$-C$_6$cycloalkyl, heteroC$_1$-C$_6$cycloalkyl, aryl, or heteroaryl groups is optionally substituted with one or more substituents selected from hydroxyl, nitro, amino, —NR$^{134}$R$^{135}$, alkyl, alkyl-O—R$^{136}$, —O—R$^{136}$, alkoxy, alkylalkoxy, alkoxylalkoxy, heteroarylcarbonyl, heteroaryl, —OCH$_3$, —OCF$_3$, —OCHF$_2$, —OCH$_2$F;

wherein at least one instance of R$^{230}$, R$^{231}$, R$^{242}$, or R$^{243}$ is R$^{136}$ or contains a O—R$^{136}$ substituent; and wherein all other variables are as defined herein.

In one embodiment the compound is:

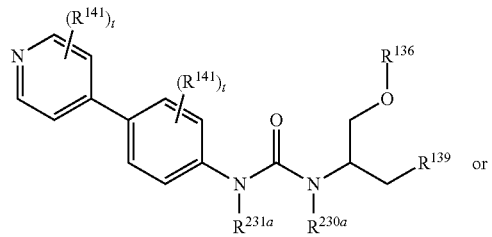

or

-continued

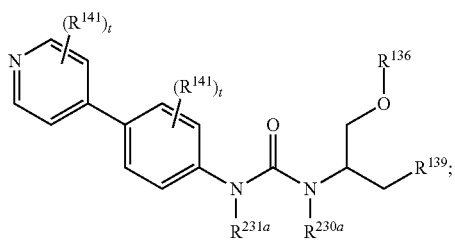

wherein:

$R^{230a}$ and $R^{231a}$ are independently selected at each occurrence from H, $C_1$-$C_{30}$alkyl, —C(O)$C_1$-$C_{30}$alkyl, and $C_1$-$C_{30}$heteroalkyl; and wherein all other variables are as defined herein.

Non-limiting examples of Formula IF include

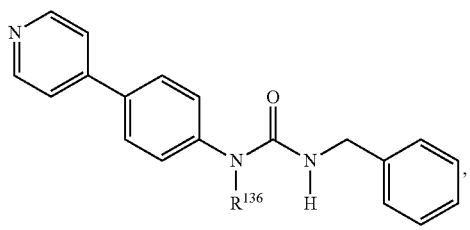

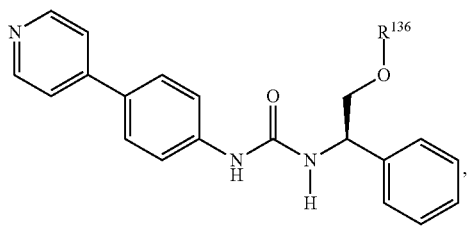

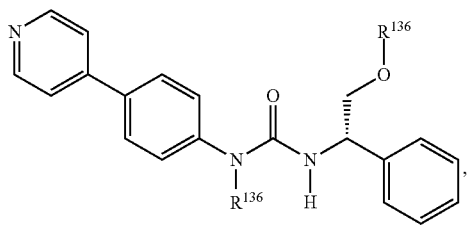

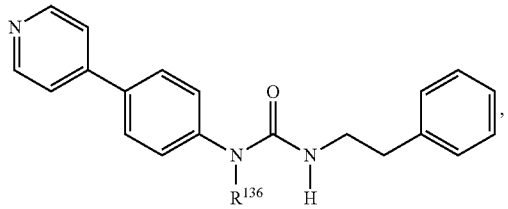

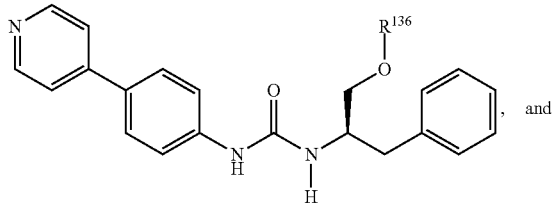

-continued

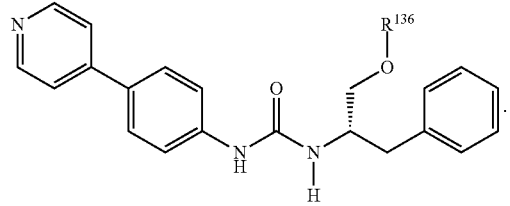

In one embodiment, Formula IIF is Formula IIFa (IIFa)

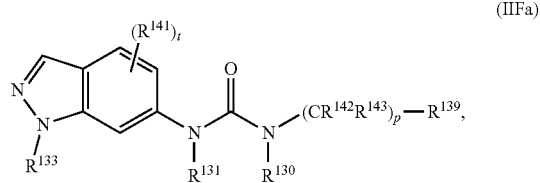

wherein all other variables are as defined herein.

In one embodiment, Formula IIF is Formula IIFb (IIFb)

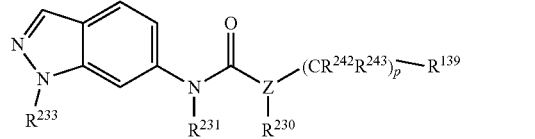

wherein:

$R^{230}$, $R^{231}$, and $R^{233}$ are independently selected at each occurrence from H, $C_1$-$C_{30}$alkyl, —C(O)$C_1$-$C_{30}$alkyl, $C_1$-$C_{30}$heteroalkyl, and $R^{136}$;

wherein at least one instance of $R^{230}$, $R^{231}$, $R^{233}$, $R^{242}$, or $R^{243}$ is $R^{136}$ or contains a O—$R^{136}$ substituent;

wherein all other variables are as defined herein.

Non-limiting examples of Formula IIF include

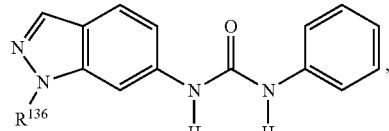

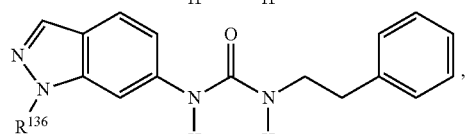

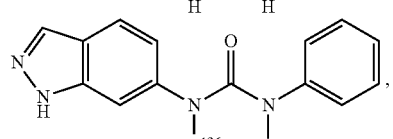

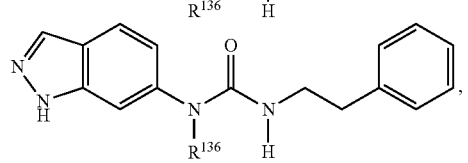

-continued

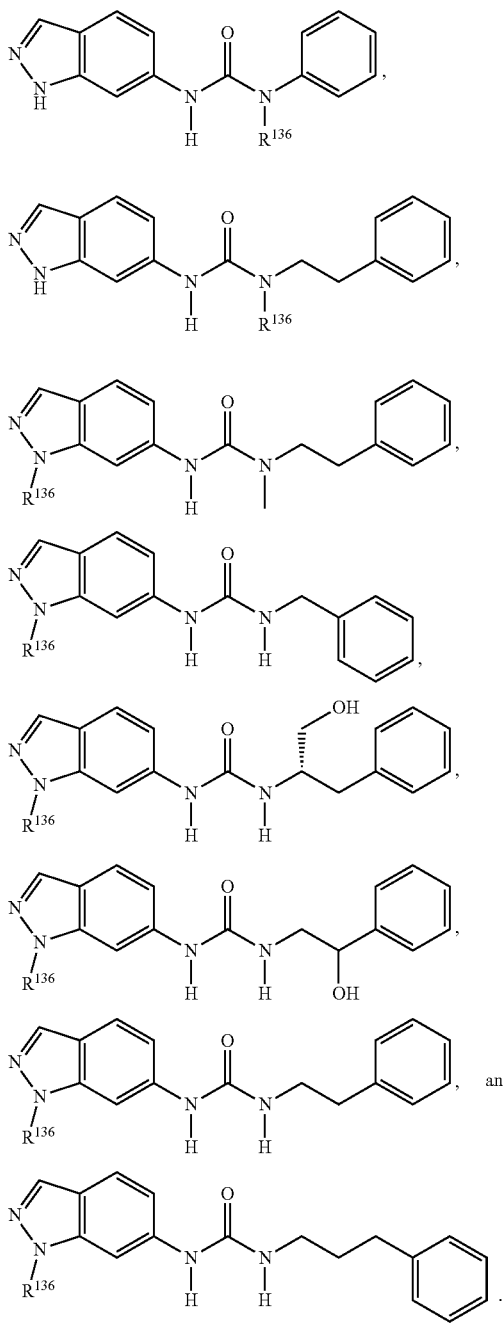

In one embodiment, Formula IIIF is Formula IIIFa

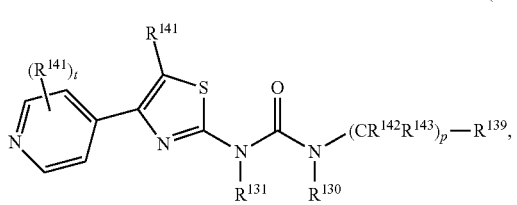

wherein all other variables are as defined herein.

In one embodiment, Formula IIIF is Formula IIIFb

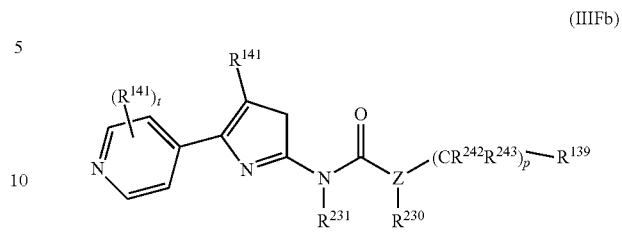

wherein at least one instance of $R^{230}$, $R^{231}$, $R^{242}$, or $R^{243}$ is $R^{136}$ or contains a O—$R^{136}$ substituent; and
wherein all other variables are as defined herein.
In one embodiment the compound is:

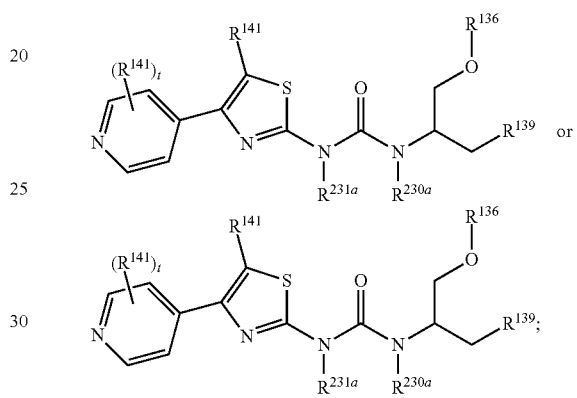

wherein all variables are as defined herein.
Non-limiting examples of Formula IIIF include

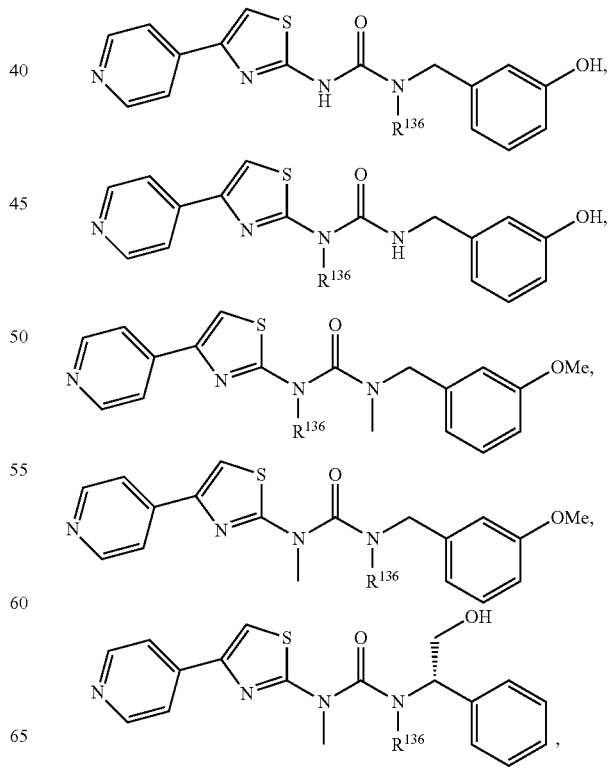

-continued

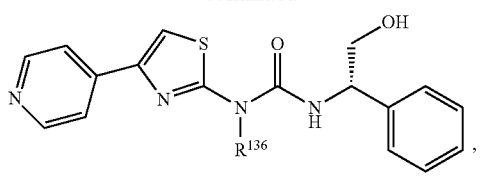

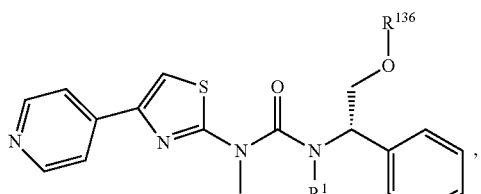

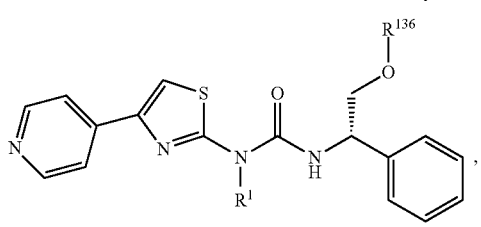

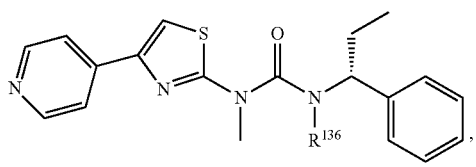

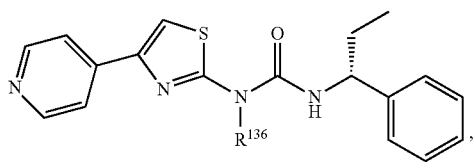

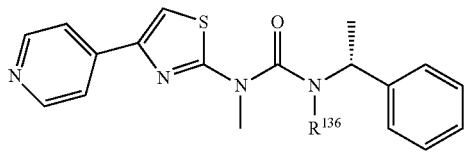

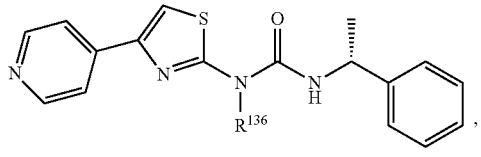

The disclosure provides ROCK inhibitor prodrugs of Formula VIF, Formula VIIF, and Formula VIIIF:

(VIF)

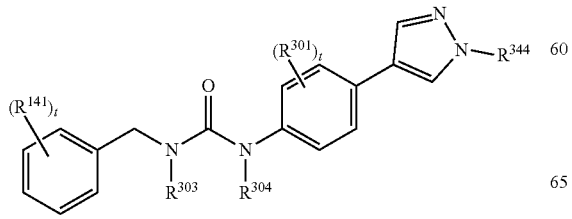

-continued (VIIF)

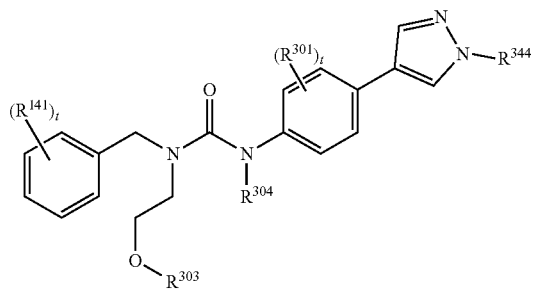

(VIIIF)

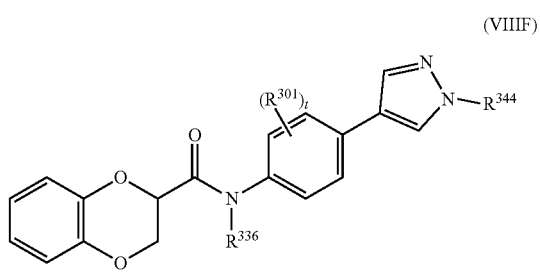

or a pharmaceutically acceptable composition, salt, or isotopic derivative thereof wherein $R^{303}$, $R^{304}$, and $R^{344}$ are independently selected at each occurrence from H, $C_1$-$C_{30}$alkyl, —C(O)$C_1$-$C_{30}$alkyl, $C_2$-$C_{30}$alkenyl, $C_1$-$C_{30}$heteroalkyl, and $R^{336}$;

wherein at least one of $R^{303}$, $R^{304}$, and $R^{344}$ is $R^{336}$;

$R^{336}$ is selected from:

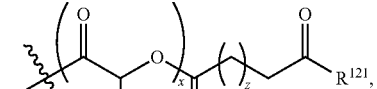

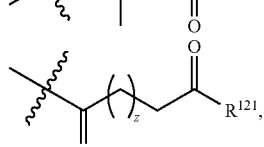

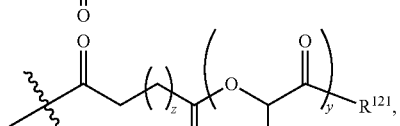

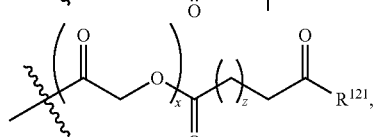

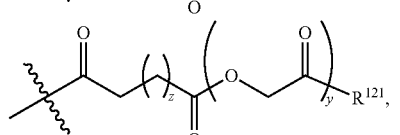

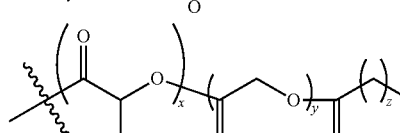

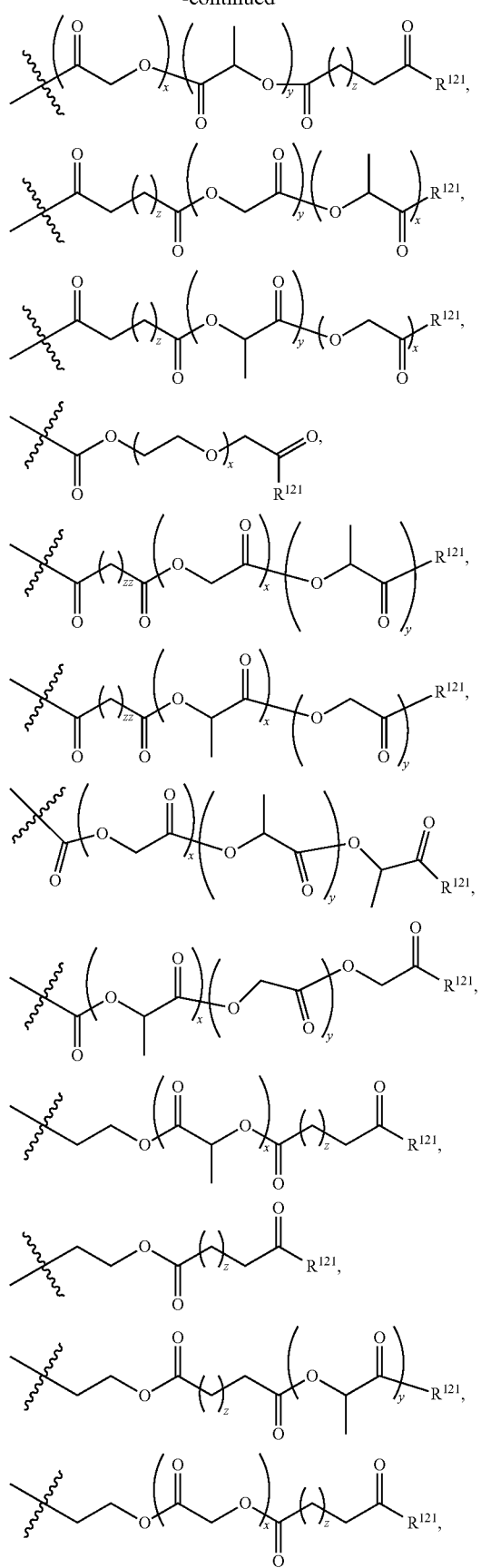
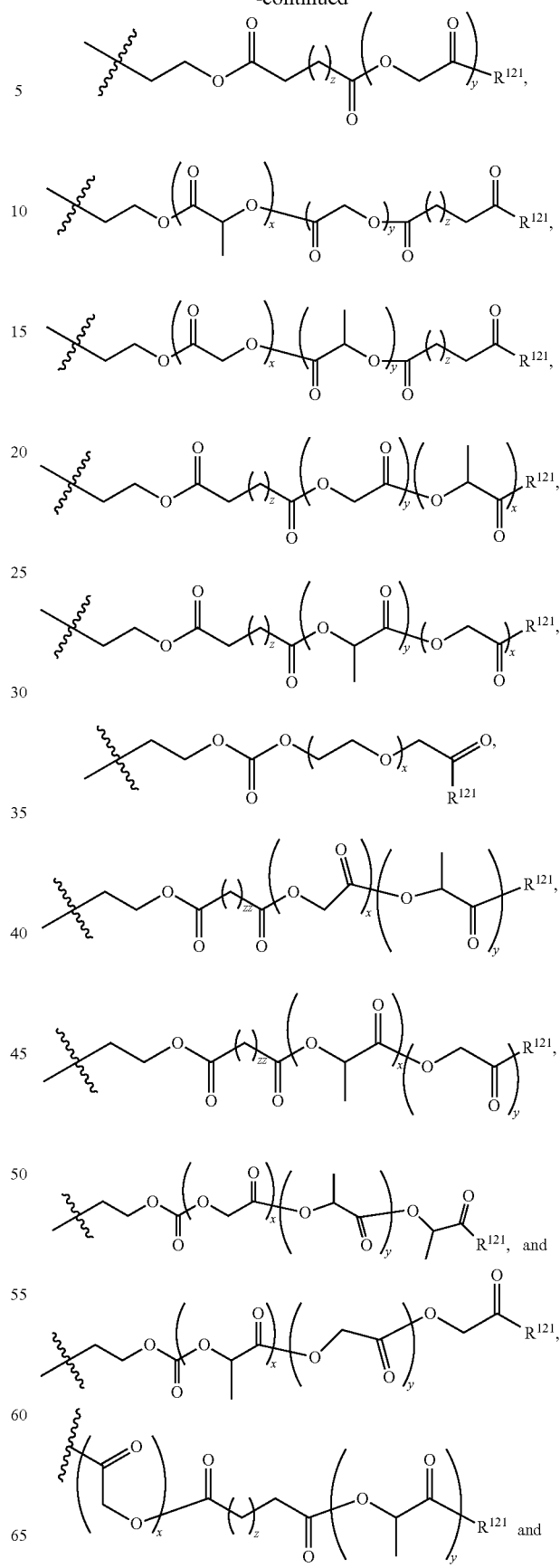

-continued

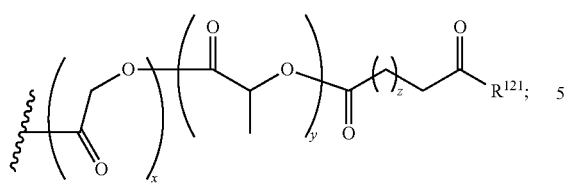

and wherein all other variables are as defined herein.

In one embodiment, $R^{141}$ is $OCH_3$.

In one embodiment, $R^{301}$ is selected from —$N(CH_3)_2$,

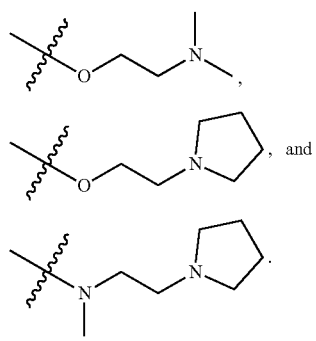

In one embodiment, $R^{301}$ is

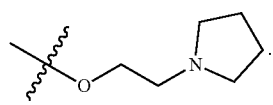 [SMILES: *OCCN1CCCC1]

In one embodiment, $R^{301}$ is —$OCH_3$.

In one embodiment, $R^{301}$ is selected from F and Cl.

In one embodiment, $R^{304}$ is hydrogen.

In one embodiment, $R^{304}$ is $CH_3$.

In one embodiment, $R^{304}$ is $CH_2H_5$.

In one embodiment, $R^{303}$ is

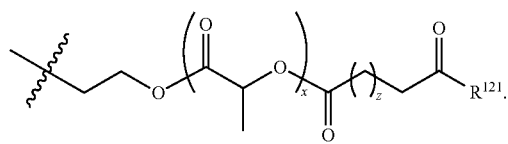

In one embodiment, $R^{303}$ is

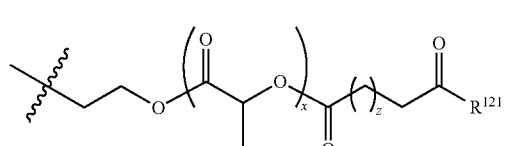

and $R^{121}$ is

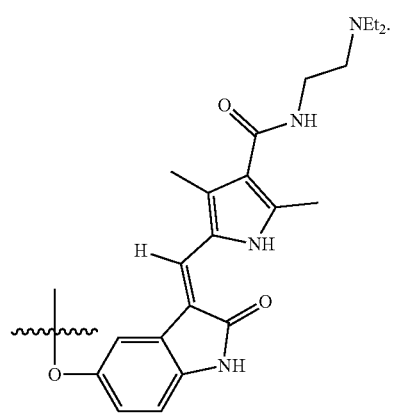

In one embodiment, $R^{303}$ is

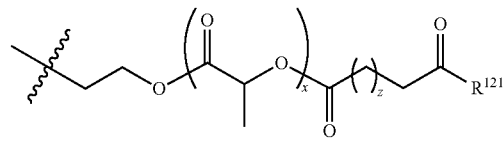

and $R^{121}$ is

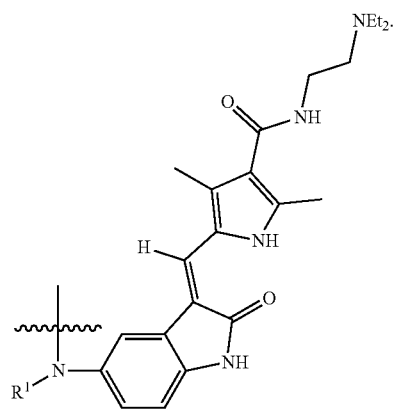

In a further embodiment, x is 2 and z is 2.

Non-limiting Examples of Formula VIF and Formula VIIF include

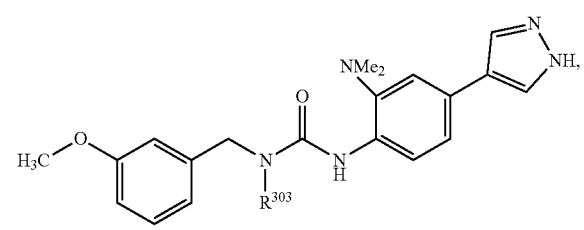

261
-continued

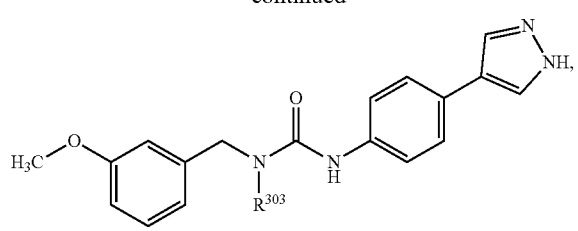
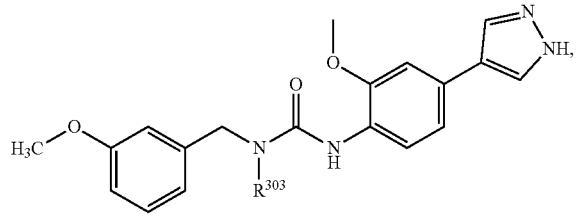
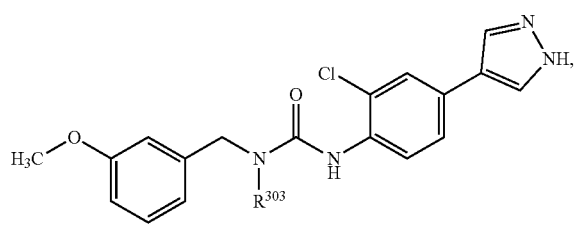
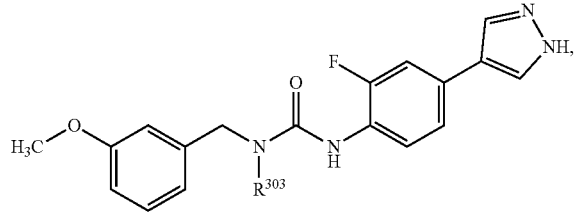
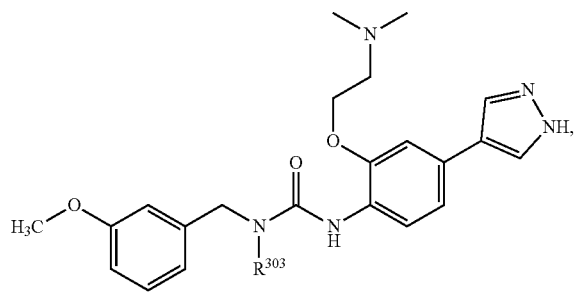
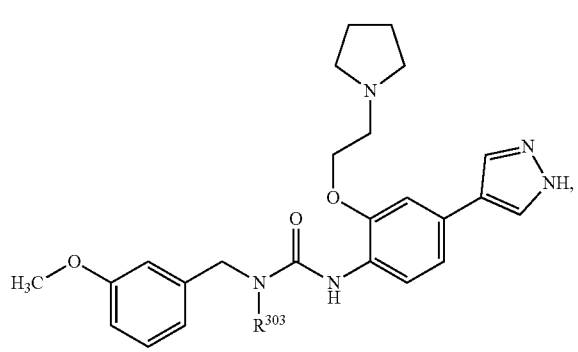

262
-continued

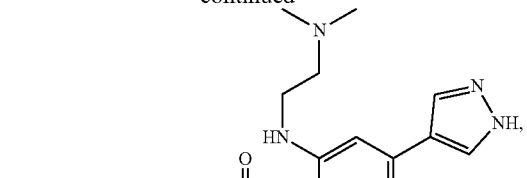
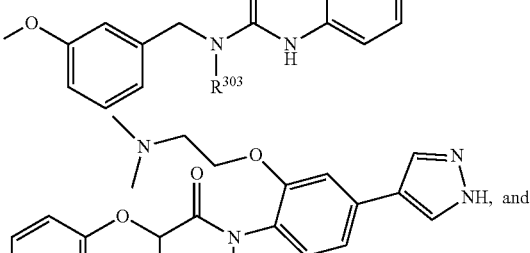
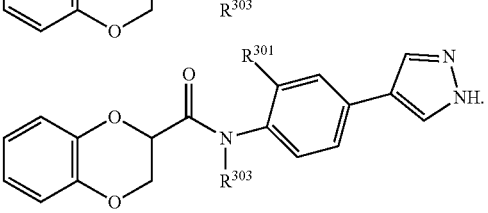

The disclosure provides ROCK inhibitor prodrugs of Formula IXF, Formula XF, and Formula XIF:

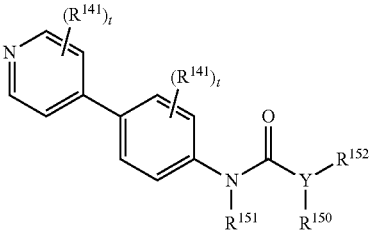

(IXF)

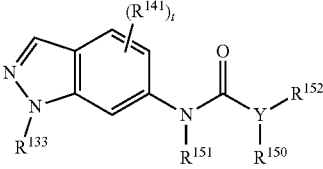

(XF)

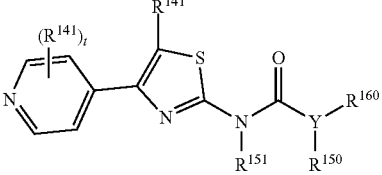

(XIF)

or a pharmaceutically acceptable composition, salt, or isotopic derivative thereof wherein Y is $CR^{150}$ or N;

$R^{150}$ and $R^{151}$ are independently selected at each occurrence from H, $C_1$-$C_{30}$alkyl, —C(O)$C_1$-$C_{30}$alkyl, $C_1$-$C_{30}$heteroalkyl, and $R^{156}$;

$R^{152}$ is selected from $C_1$-$C_{30}$alkyl, $C_1$-$C_{30}$cycloalkyl, heterocycloalkyl, aryl, heteroaryl, or alkylaryl, any of which can be optionally substituted with one or more of hydroxyl, —$CH_2OH$, —C(O)$NH_2$, acetyl, carbonyl, alkyl, cycloalkyl, heterocycloalkyl, aryl, and heteroaryl, any of which can be optionally substituted with one or more of hydroxyl, nitro, amino, —NR$^{134}$R$^{135}$, alkyl, alkoxy, alkylalkoxy, alkoxylalkoxy, haloalkoxy, heteroarylcarbonyl, heteroaryl, —OCH$_3$, —OCF$_3$, —OCHF$_2$, —OCH$_2$F, —OSO$_2$CH$_3$, tosyl, or halogen;

or R$^{151}$ and R$^{152}$ can together form a cycloalkyl or heterocycloalkyl;

R$^{160}$ is selected from H, C$_1$-C$_{30}$alkyl, C$_1$-C$_{30}$cycloalkyl, heterocycloalkyl, and aryl, any of which except hydrogen can be optionally substituted with one or more of hydroxyl, —CH$_2$OH, —C(O)NH$_2$, acetyl, carbonyl, alkyl, cycloalkyl, heterocycloalkyl, aryl, and heteroaryl, any of which can be optionally substituted with one or more of hydroxyl, nitro, amino, —NR$^{134}$R$^{135}$, alkyl, alkoxy, alkylalkoxy, alkoxylalkoxy, haloalkoxy, heteroarylcarbonyl, heteroaryl, —OCH$_3$, —OCF$_3$, —OCHF$_2$, —OCH$_2$F, —OSO$_2$CH$_3$, tosyl, or halogen; or R$^{151}$ and R$^{152}$ can together form a cycloalkyl or heterocycloalkyl;

wherein at least one of R$^{150}$ and R$^{151}$ is R$^{156}$;

R$^{156}$ is selected from:

(i) polyethylene glycol, polypropylene glycol, polypropylene oxide, polylactic acid, poly(lactic-co-glycolic acid) polyglycolic acid, polyester, polyamide, and other biodegradable polymers, each of which can be capped to complete the terminal valence or to create a terminal ether or ester, in one embodiment the capping group is selected from R$^{311}$; and (ii)

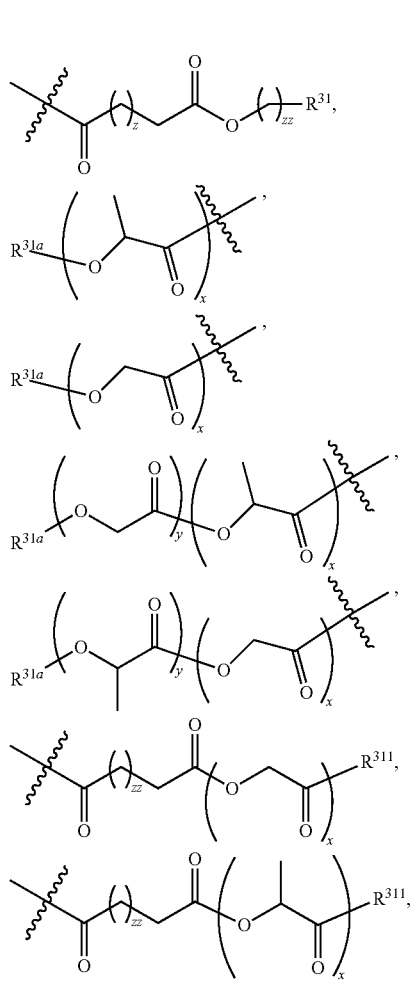

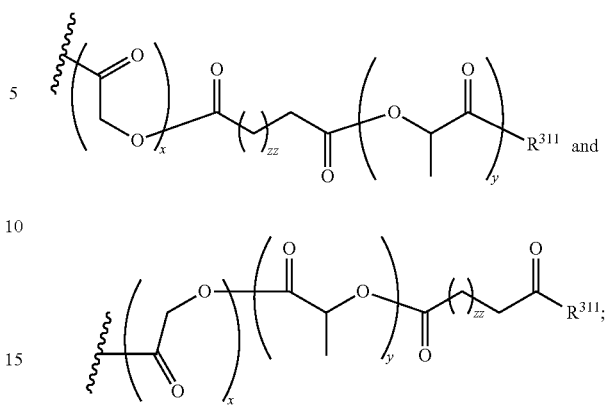

wherein all other variables are as defined herein.

In one embodiment R$^{156}$ is selected from:

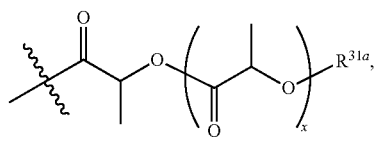

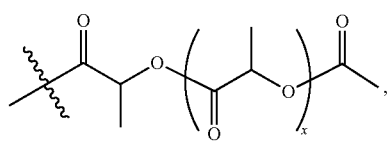

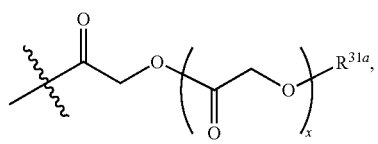

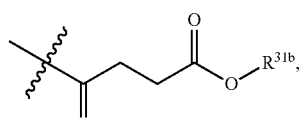

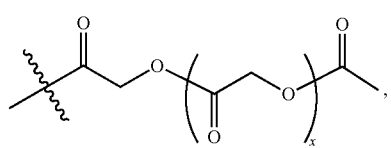

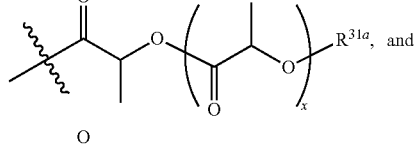

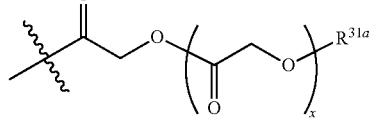

The disclosure provides ROCK inhibitor prodrugs of Formula XIIF, Formula XIIIF, and Formula XIVF:

(XIIF)

(XIIIF)

(XIVF)

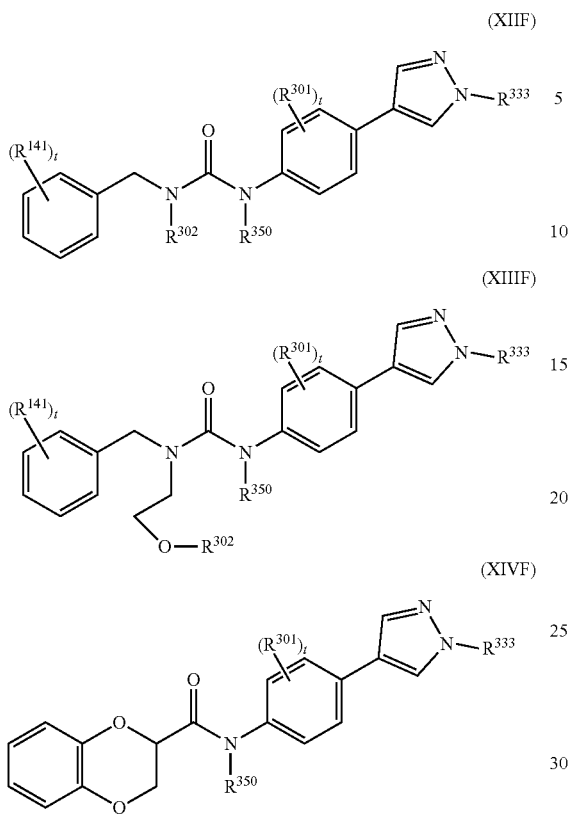

or a pharmaceutically acceptable composition, salt, or isotopic derivative thereof wherein $R^{302}$ and $R^{333}$ are independently selected from H, $C_1$-$C_{30}$alkyl, —C(O)$C_1$-$C_{30}$alkyl, $C_1$-$C_{30}$heteroalkyl, $C_2$-$C_{30}$alkenyl, and $R^{356}$;

$R^{350}$ is selected from H, $C_1$-$C_{30}$alkyl, —C(O)$C_1$-$C_{30}$alkyl, $C_1$-$C_{30}$heteroalkyl, $C_2$-$C_{30}$alkenyl, and $R^{356}$;

$R^{356}$ is selected from (i) polyethylene glycol, polypropylene glycol, polypropylene oxide, polylactic acid, poly(lactic-co-glycolic acid) polyglycolic acid, polyester, polyamide, and other biodegradable polymers, each of which can be capped to complete the terminal valence or to create a terminal ether or ester;

(ii)

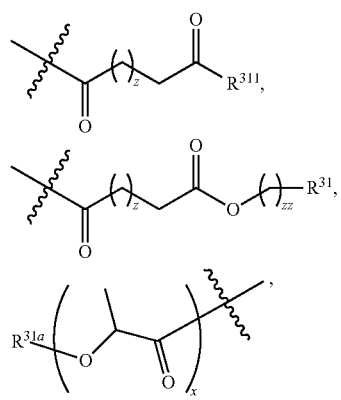

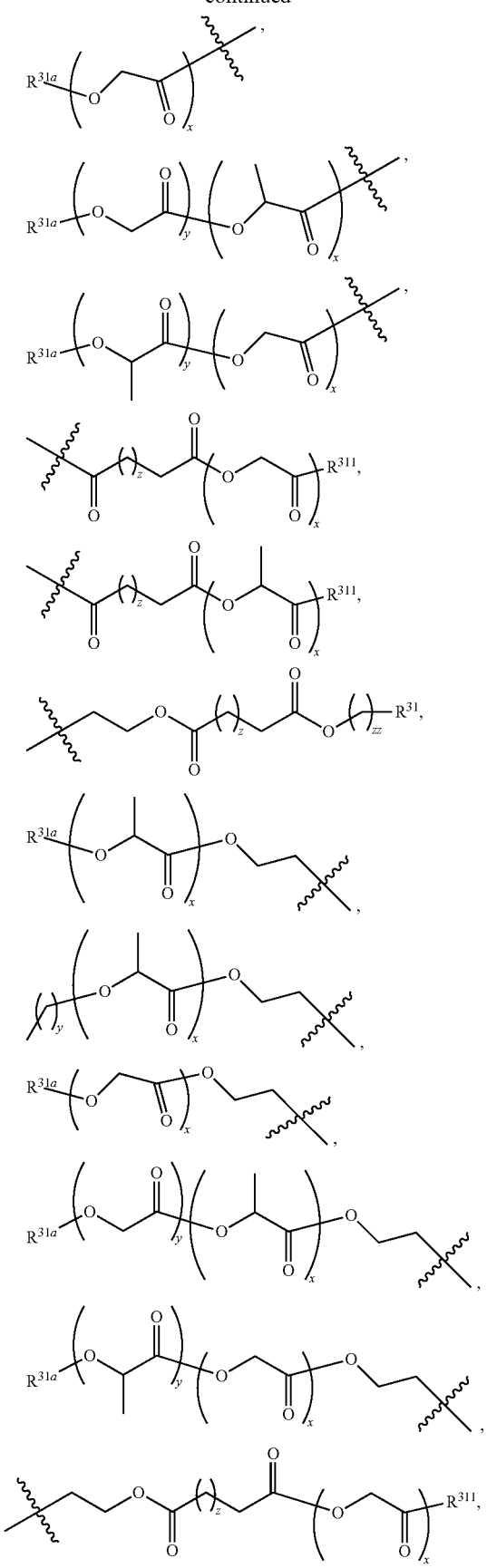

-continued

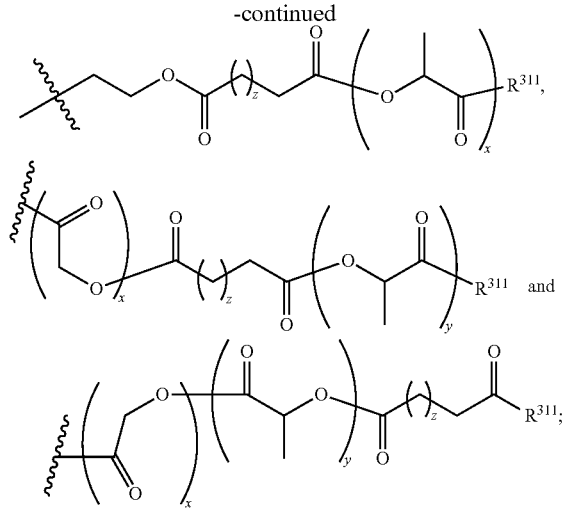

wherein at least one of $R^{302}$ embodiment, $R^{333}$ and $R^{350}$ is $R^{356}$; and
wherein all other variables are as defined herein.
In one embodiment, $R^{141}$ is $OCH_3$.
In one embodiment, $R^{350}$ is selected from $N(CH_3)_2$,

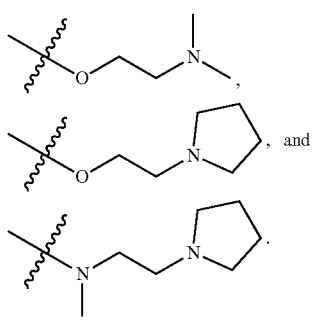

In one embodiment, $R^{301}$ is

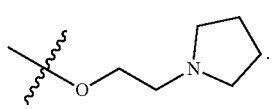 [SMILES: *OCCN1CCCC1]

In one embodiment, $R^{301}$ is —$OCH_3$.
In one embodiment, $R^{31}$ is selected from F and Cl.
In one embodiment, $R^{350}$ is hydrogen.
In one embodiment, $R^{350}$ is $CH_3$.
In one embodiment, $R^{350}$ is $CH_2H_5$.
In one embodiment, $R^{356}$ is

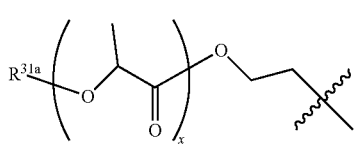

and $R^{31a}$ is —$C(O)CH_3$.

In one embodiment, $R^{356}$ is

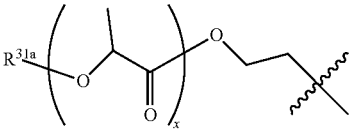

and $R^{31a}$ is stearoyl.
In one embodiment, $R^{356}$ is

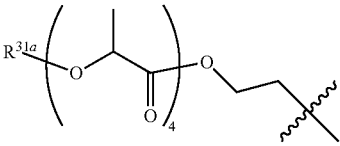

and $R^{31a}$ is —$C(O)CH_3$.
In one embodiment, $R^{356}$ is

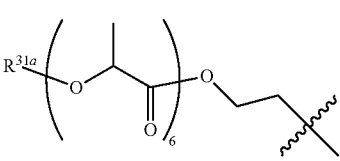

and $R^{31a}$ is —$C(O)CH_3$.
In one embodiment, $R^{356}$ is x

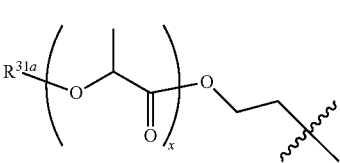

and x is an integer between 1 and 6.
In one embodiment, $R^{356}$ is

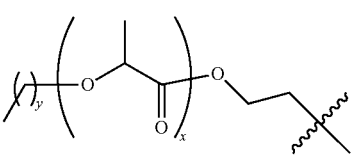

and y is 11.
In one embodiment, $R^{356}$ is

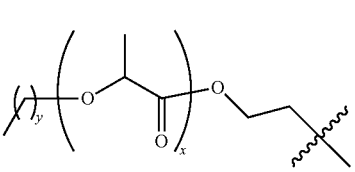

and y is 17.

In one embodiment, $R^{333}$ is
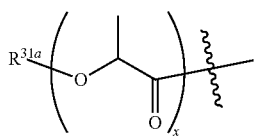
and $R^{31a}$ is —C(O)alkyl.
Non-limiting Examples of Formula XIF and Formula XIIF include
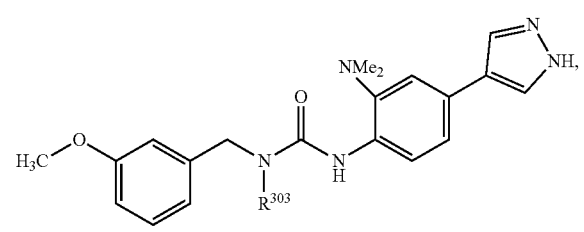
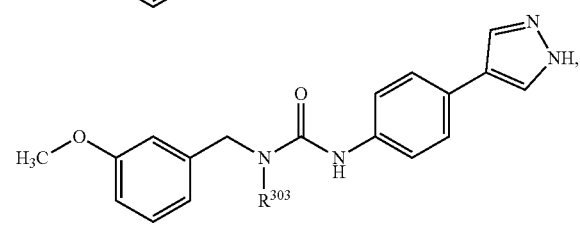
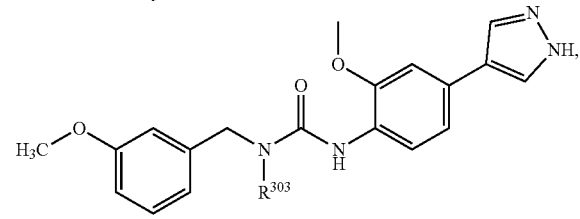
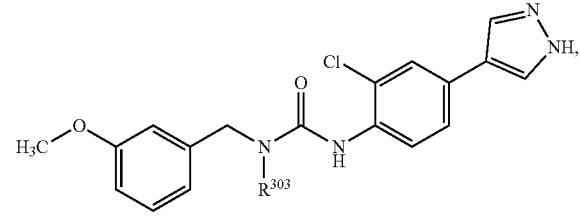
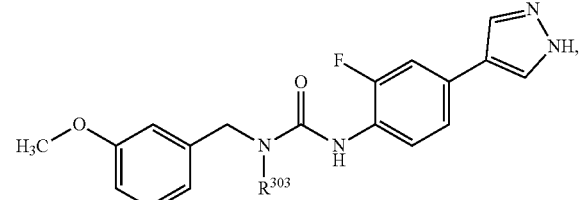
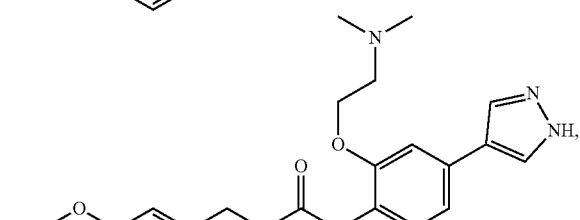
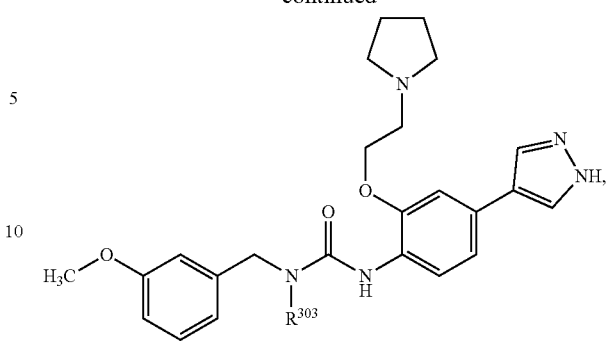
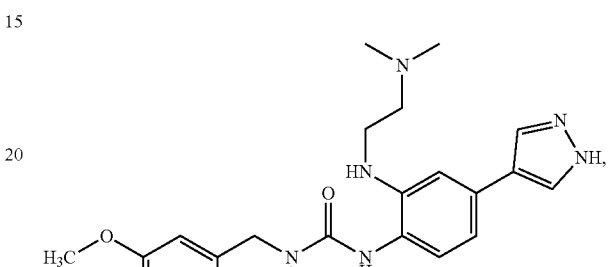
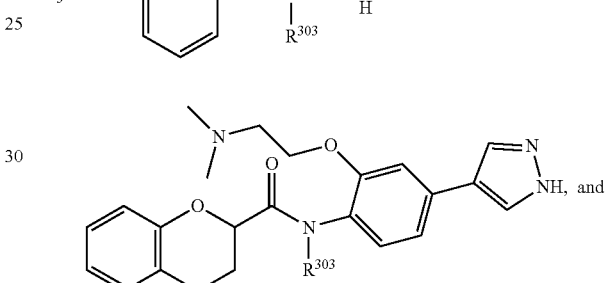
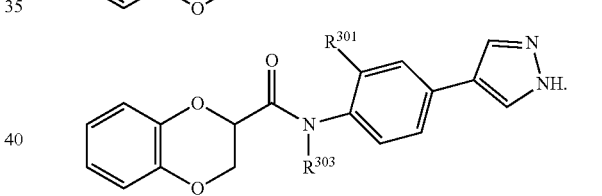
Beta-Blocker Prodrugs
The disclosure provides beta-blocker prodrugs of Formula IG, Formula IIG, Formula IIIG, Formula IVG, Formula VG, Formula VIG, Formula VIIG, and Formula VIIIG:
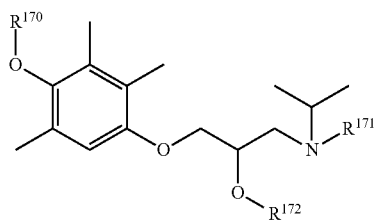
(IG)
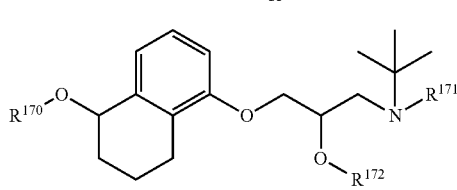
(IIG)

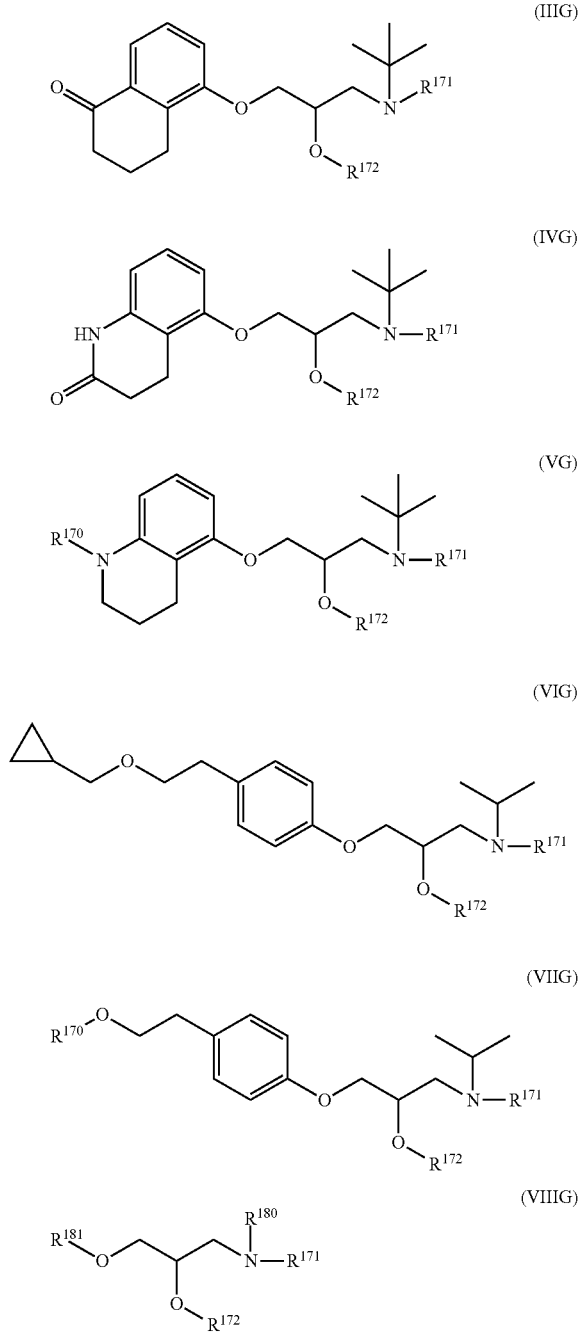

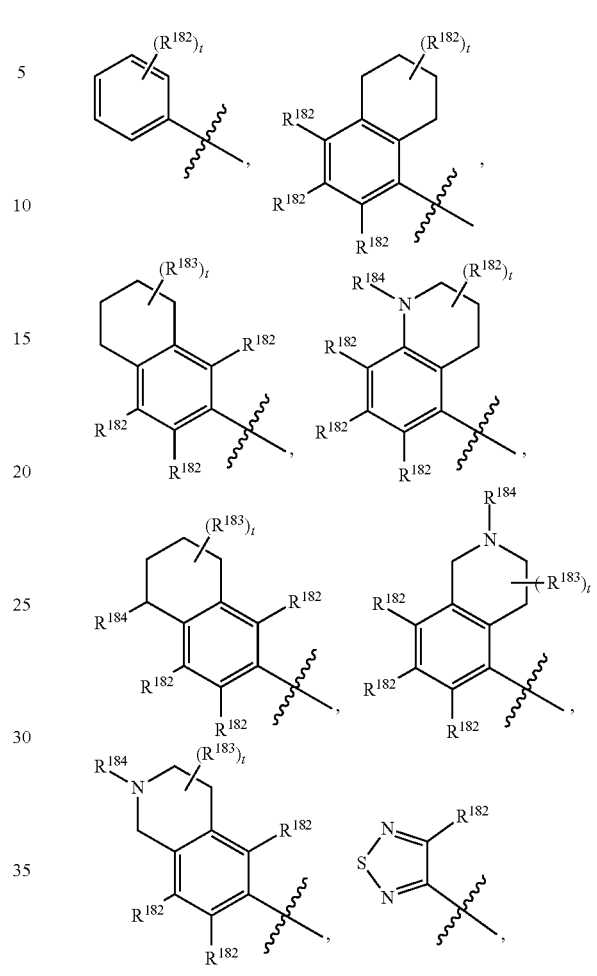

or a pharmaceutically acceptable composition, salt, or isotopic derivative thereof.

$R^{170}$, $R^{171}$, and $R^{172}$ are independently selected from: $R^1$, $R^{173}$, acyl, carbonyl linked polyethylene glycol, carbonyl linked polypropylene glycol, carbonyl linked polypropylene oxide, polylactic acid, poly(lactic-co-glycolic acid), polyglycolic acid, polyester, polyamide, or other biodegradable polymer, each of which $R^{170}$, $R^{171}$, and $R^{172}$ other than $R^{173}$ are optionally substituted with $L^8$-$R^{121}$;

wherein at least one of $R^{170}$, $R^{171}$, and $R^{172}$ is $R^{173}$ or substituted with $L^8$-$R^{121}$ $R^{180}$ is $C_1$-$C_6$ alkyl, acyl, or hydrogen;

$R^{181}$ is selected from:

$R^{182}$ is independently selected from alkyl, cycloalkyl, aryl, heteroaryl, heterocycle, cyano, amino, hydroxyl, and acyl, each of which $R^{182}$ is optionally substituted with a $R^{170}$ group;

$R^{183}$ is independently selected from alkyl, cycloalkyl, aryl, heteroaryl, heterocycle, amino, hydroxyl, and acyl;

or two $R^{183}$ groups with the carbon to which they are linked form a carbonyl group;

or two $R^{183}$ groups with the carbon(s) to which they are linked form a fused or spirocyclic ring;

$R^{184}$ is selected from alkyl, cycloalkyl, $R^{170}$, and acyl;

$R^{185}$ is selected from aryl, heteroaryl, cycloalkyl, and heterocycle, wherein each $R^{185}$ is optionally substituted with 1, 2, 3, or 4 $R^{182}$ groups;

$R^{173}$ is selected from:

(i)

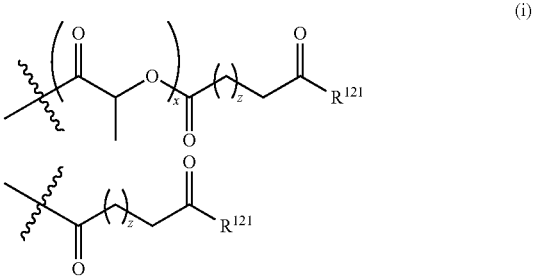

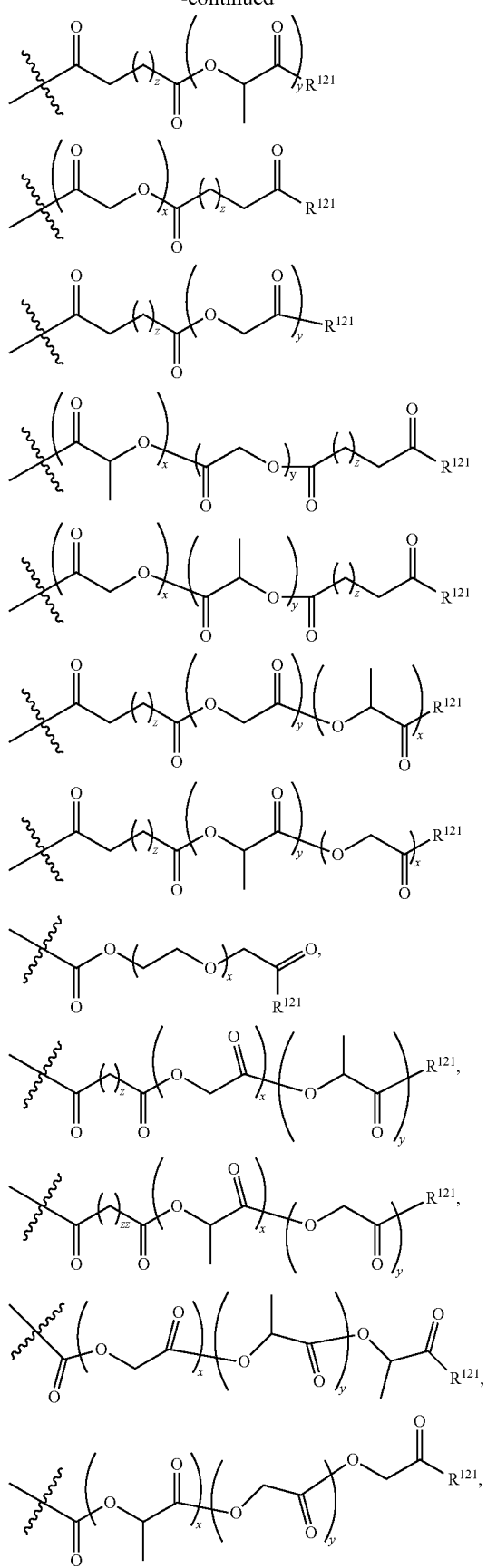
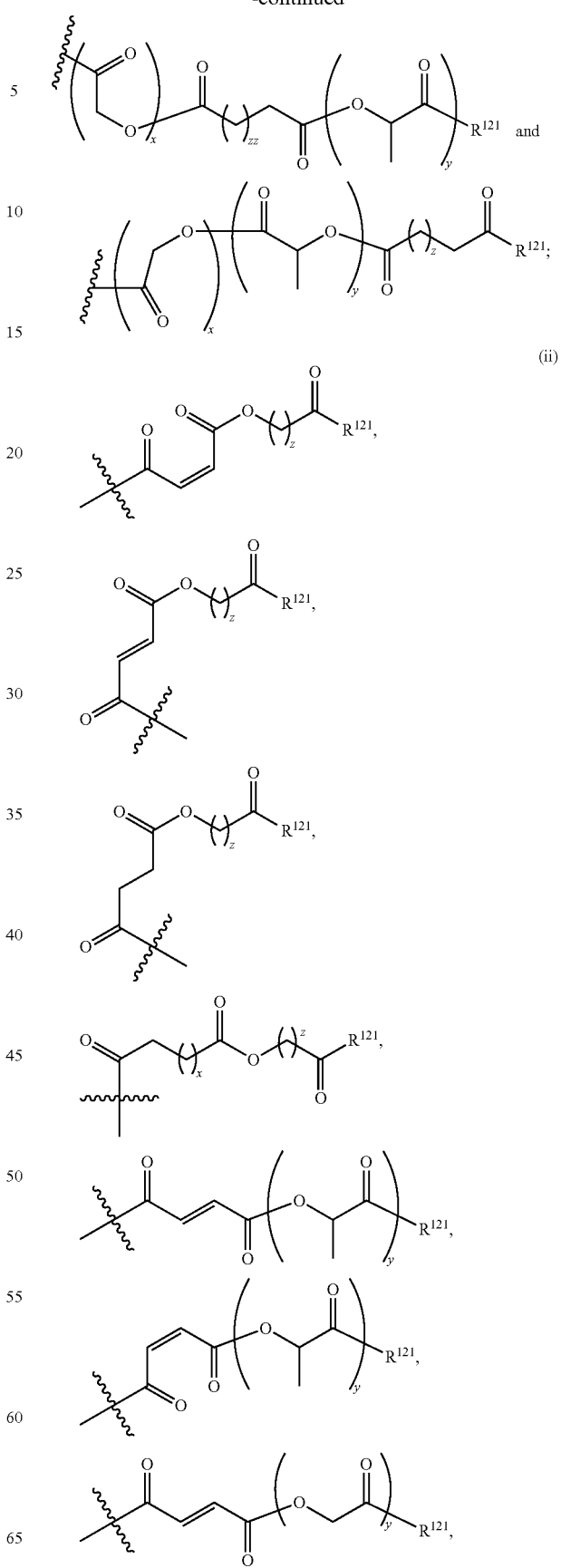

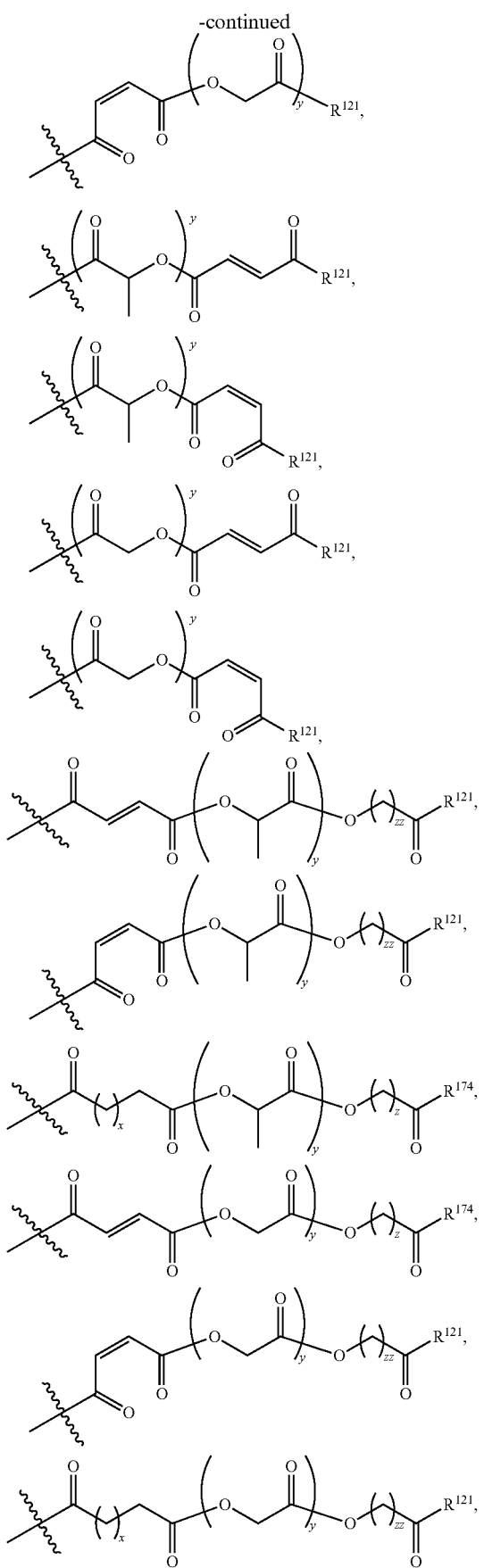
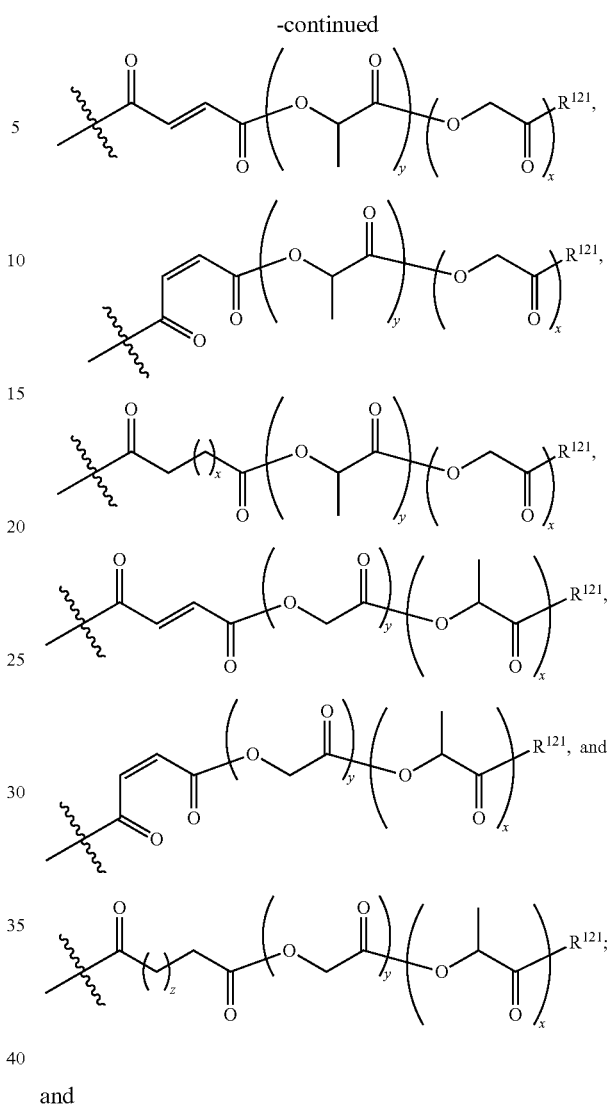
and
wherein all other variables are defined herein.
The disclosure provides beta-blocker prodrugs of Formula IXG, Formula XG, Formula IIIG, Formula XIG, Formula XIIG, Formula XIIIG, Formula XIVG, Formula XVG, and Formula XVIG:
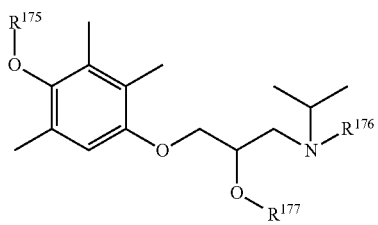
(IXG)
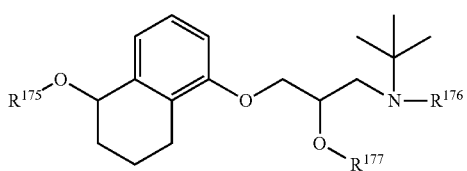
(XG)

(XIG)

(XIIG)

(XIIIG)

(XIVG)

(XVG)

(XVIG)

or a pharmaceutically acceptable composition, salt, or isotopic derivative thereof wherein $R^{175}$, $R^{176}$, and $R^{177}$ are independently selected from: C(O)A, C(O)$R^4$, and $R^{178}$; wherein at least one of $R^{175}$, $R^{176}$, and $R^{177}$ is $R^{178}$; and wherein all other variables are as defined herein.

In some embodiments the compounds of Formula IXG to Formula XVIG can be used in the form of an R enantiomer, an S enantiomer, or a mixture of enantiomers including a racemic mixture.

In some embodiments the compounds of Formula IXG to Formula XVIG have the same stereochemistry as the corresponding commercial drug.

Loop Diuretic Prodrugs, Including Ethacrynic Acid Prodrugs

The disclosure provides ethacrynic acid prodrugs of Formula IH:

(IH)

or a pharmaceutically acceptable composition, salt, or isotopic derivative thereof.

$R^{611}$ is selected from:
- (i) —C(O)OC$_5$-C$_{30}$alkylR$^5$, —C(O)OC$_2$-C$_{30}$alkenylR$^5$, —C(O)OC$_2$-C$_{30}$alkynylR$^5$, —C(O)OC$_4$-C$_{30}$alkenylalkynylR$^5$, —C(O)OC$_5$-C$_{30}$alkyl, —C(O)OC$_2$-C$_{30}$alkenyl, —C(O)OC$_2$-C$_{30}$alkynyl, and —C(O)OC$_4$-C$_{30}$alkenylalkynyl;
- (ii) —C(O)O(C$_{1-30}$alkyl with at least one R$^5$ substituent on the alkyl chain, —C(O)O(C$_{1-30}$alkenyl, with at least one R$^5$ substituent on the alkenyl chain, and —C(O)O(C$_{1-30}$alkynyl, with at least one R$^5$ substituent on the alkynyl chain;
- (iii) —C(O)(OCH$_2$C(O))$_{1-20}$OC$_{1-30}$alkyl, —C(O)(OCH(CH$_3$)C(O))$_{1-20}$OC$_{1-30}$alkyl, —C(O)(OCH$_2$C(O))$_{1-10}$OC$_{1-30}$alkyl, —C(O)(OCH(CH$_3$)C(O))$_{1-10}$OC$_{1-30}$alkyl, —C(O)(OCH$_2$C(O))$_{4-20}$OC$_{1-30}$alkyl, —C(O)(OCH(CH$_3$)C(O))$_{4-20}$OC$_{1-30}$alkyl, —C(O)(OCH$_2$C(O))$_{1-20}$OC$_{1-10}$alkyl, —C(O)(OCH(CH$_3$)C(O))$_{1-20}$OC$_{1-10}$alkyl, —C(O)(OCH$_2$C(O))$_{1-20}$OC$_{4-10}$alkyl, —C(O)(OCH(CH$_3$)C(O))$_{1-20}$OC$_{4-10}$alkyl, —C(O)(OCH$_2$C(O))$_{1-20}$OH, —C(O)(OCH(CH$_3$)C(O))$_{1-20}$OH, —C(O)(OCH$_2$C(O))$_{1-10}$OH, —C(O)(OCH(CH$_3$)C(O))$_{1-10}$OH, —C(O)(OCH$_2$C(O))$_{4-20}$OH, —C(O)(OCH(CH$_3$)C(O))$_{4-20}$OH, —C(O)(OCH$_2$C(O))$_{4-10}$OH, —C(O)(OCH(CH$_3$)C(O))$_{4-10}$OH, —C(O)(OCH(CH$_3$)C(O))$_{4-10}$OC$_{1-10}$alkyl, —C(O)(OCH$_2$C(O))$_{4-10}$OC$_{1-10}$alkyl, —C(O)(OCH(CH$_3$)C(O))$_{1-10}$OC$_{1-10}$alkyl, —C(O)(OCH$_2$C(O))$_{1-10}$OC$_{1-10}$alkyl, —C(O)(OCH(CH$_3$)C(O))$_{1-10}$OC$_{4-10}$alkyl, —C(O)(OCH$_2$C(O))$_{1-10}$OC$_{4-10}$alkyl, —C(O)(OCH$_2$C(O))$_{1-10}$OC$_{4-10}$alkyl, —C(O)(OCH(CH$_3$)C(O))$_{1-10}$OC$_{4-10}$alkyl, —C(O)(OCH$_2$C(O))$_{1-10}$OC$_{4-10}$alkyl, —C(O)(OCH(CH$_3$)C(O))$_{1-10}$OC$_{4-10}$alkyl, —C(O)(OCH$_2$C(O))$_{1-10}$(OCH(CH$_3$)C(O))$_{1-10}$OC$_{1-30}$alkyl, —C(O)(OCH$_2$C(O))$_{2-10}$(OCH(CH$_3$)C(O))$_{2-10}$OC$_{1-30}$alkyl, —C(O)(OCH$_2$C(O))$_{1-10}$(OCH(CH$_3$)C(O))$_{1-10}$OC$_{1-12}$alkyl, —C(O)(OCH$_2$C(O))$_{1-10}$(OCH(CH$_3$)C(O))$_{1-10}$OC$_{4-22}$alkyl, —C(O)(OCH(CH$_3$)C(O))$_{1-10}$(OCH$_2$C(O))$_{1-10}$OC$_{1-30}$alkyl, —C(O)(OCH(CH$_3$)C(O))$_{2-10}$(OCH$_2$C(O))$_{2-10}$OC$_{1-30}$alkyl, —C(O)(OCH(CH$_3$)C(O))$_{1-10}$(OCH$_2$C(O))$_{1-10}$OC$_{1-12}$alkyl, and —C(O)(OCH(CH$_3$)C(O))$_{1-10}$(OCH$_2$C(O))$_{1-10}$OC$_{4-22}$alkyl;
- (iv) polypropylene glycol, polypropylene oxide, polylactic acid, poly(lactic-co-glycolic acid), polyglycolic acid, polyester, polyamide, and other biodegradable polymers, each of which can be capped to complete the terminal valence or to create a terminal ether or ester; and (v)

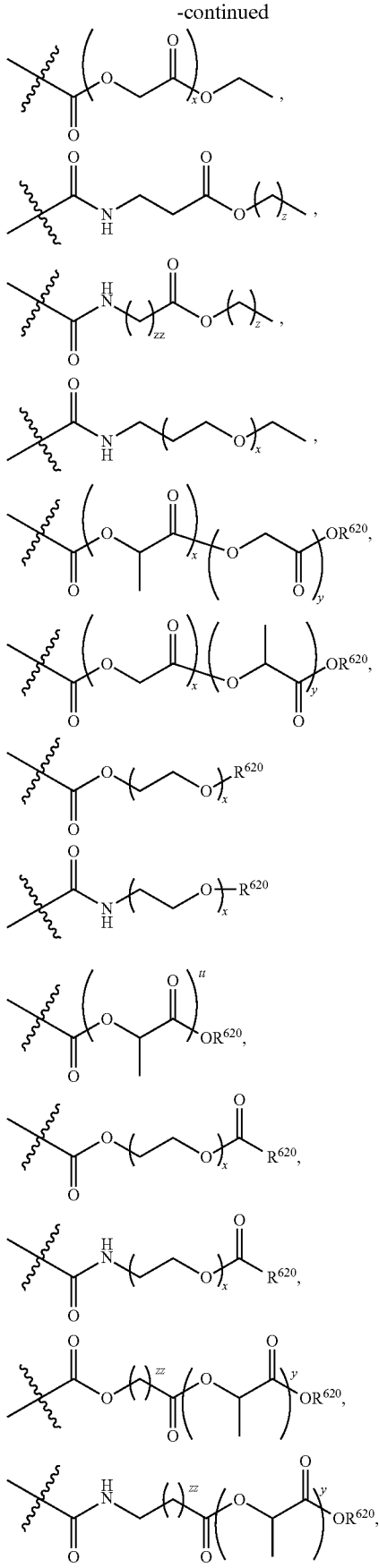
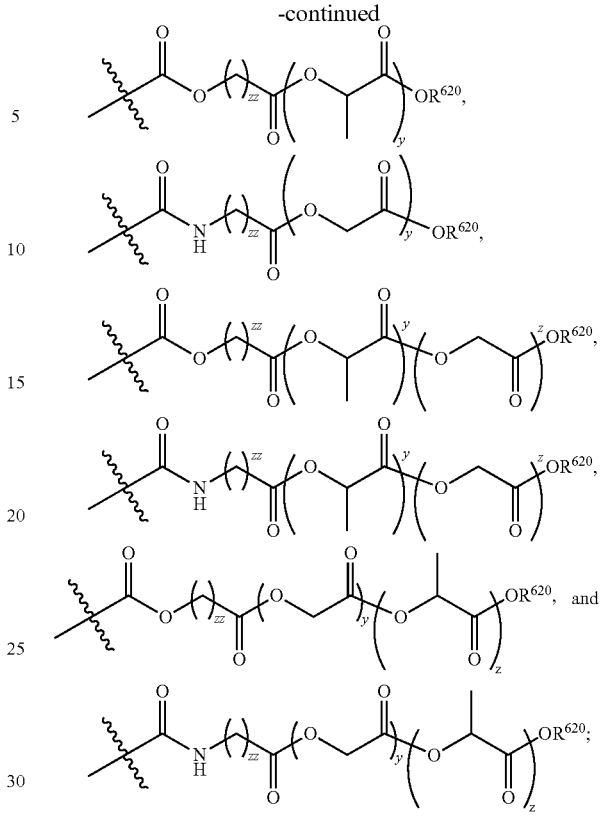

R$^{620}$ is hydrogen, alkyl, alkenyl, alkynyl cycloalkyl, cycloalkylalkyl, heterocyclyl, heterocycloalkyl, aryl, arylalkyl, heteroaryl, or heteroarylalkyl, each of which except hydrogen, may be optionally substituted, for example with halogen, alkyl, aryl, heterocycle or heteroaryl if desired and if the resulting compound is stable and achieves the desired purpose, wherein the group cannot be substituted with itself, for example alkyl would not be substituted with alkyl;

tt is any integer between 4 and 10 (4, 5, 6, 7, 8, 9, or 10); and wherein all other integers are as defined herein.

In one embodiment, x, y, and z are independently an integer between 1 and 12 (1, 2, 3, 4, 5, 6, 7, 8, 9, 10, 11, or 12).

In one embodiment, x, y, and z are independently an integer between 1 and 10 (1, 2, 3, 4, 5, 6, 7, 8, 9, or 10).

In one embodiment, x, y, and z are independently an integer between 1 and 8 (1, 2, 3, 4, 5, 6, 7, or 8).

In one embodiment, x, y, and z are independently an integer between 1 and 6 (1, 2, 3, 4, 5, or 6).

In one embodiment, x, y, and z are independently an integer between 4 and 10 (4, 5, 6, 7, 8, 9, or 10).

In one embodiment, x is an integer between 1 and 12 (1, 2, 3, 4, 5, 6, 7, 8, 9, 10, 11, or 12) and y is an integer between 1 and 6 (1, 2, 3, 4, 5, or 6).

In one embodiment, y is an integer between 1 and 12 (1, 2, 3, 4, 5, 6, 7, 8, 9, 10, 11, or 12) and x is an integer between 1 and 6 (1, 2, 3, 4, 5, or 6).

In one embodiment, x is an integer between 1 and 6 (1, 2, 3, 4, 5, or 6) and y is an integer between 1 and 3 (1, 2, or 3).

In one embodiment, y is an integer between 1 and 6 (1, 2, 3, 4, 5, or 6) and x is an integer between 1 and 3 (1, 2, or 3).

In one embodiment x is 1 and y is 1.
In one embodiment x is 1 and y is 2.
In one embodiment x is 1 and y is 3.
In one embodiment x is 1 and y is 4.
In one embodiment x is 1 and y is 5.
In one embodiment x is 1 and y is 6.
In one embodiment x is 1 and y is 7.
In one embodiment x is 1 and y is 8.
In one embodiment x is 2 and y is 1.
In one embodiment x is 2 and y is 2.
In one embodiment x is 2 and y is 3.
In one embodiment x is 2 and y is 4.
In one embodiment x is 2 and y is 5.
In one embodiment x is 2 and y is 6.
In one embodiment x is 2 and y is 7.
In one embodiment x is 2 and y is 8.
In certain embodiments, x and y are independently selected from 1, 2, 3, 4, 5, or 6, and z is 1.
In certain embodiments, x and y are independently selected from 1, 2, 3, 4, 5, or 6, and z is 2.
In one embodiment, $R^{611}$ is

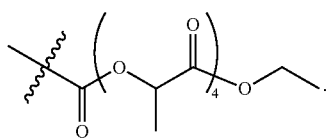

In one embodiment, $R^{611}$ is

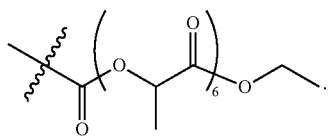

In one embodiment, $R^{611}$ is

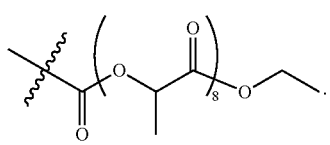

In one embodiment, $R^{611}$ is —$C(O)(OCH(CH_3)C(O))_{4-20}OCH_2CH_3$.
In one embodiment, $R^{611}$ is —$C(O)(OCH(CH_3)C(O))_{4-20}O(CH_2)_{10}CH_3$.
In one embodiment, $R^{611}$ is —$C(O)(OCH(CH_3)C(O))_{4-20}O(CH_2)_{16}CH_3$.
In one embodiment, $R^{611}$ is —$C(O)(OCH(CH_3)C(O))_4OCH_2CH_3$.
In one embodiment, $R^{611}$ is —$C(O)(OCH(CH_3)C(O))_4O(CH_2)_{10}CH_3$.
In one embodiment, $R^{611}$ is —$C(O)(OCH(CH_3)C(O))_4OCH_2)_{16}CH_3$.
In one embodiment, $R^{611}$ is —$C(O)(OCH(CH_3)C(O))_6OCH_2CH_3$.
In one embodiment, $R^{611}$ is —$C(O)(OCH(CH_3)C(O))_6O(CH_2)_{10}CH_3$.
In one embodiment, $R^{611}$ is —$C(O)(OCH(CH_3)C(O))_6O(CH_2)_{16}CH_3$.
In one embodiment, $R^{611}$ is —$C(O)(OCH(CH_3)C(O))_8OOCH_2CH_3$.
In one embodiment, $R^{611}$ is —$C(O)(OCH(CH_3)C(O))_8O(CH_2)_{10}CH_3$.
In one embodiment, $R^{611}$ is —$C(O)(OCH(CH_3)C(O))_8O(CH_2)_{16}CH_3$.
In one embodiment, $R^{611}$ is —$C(O)(OCH(CH_3)C(O))_{4-20}O(CH_2)_{9-17}CH_3$.
In one embodiment, $R^{611}$ is —$C(O)(OCH(CH_3)C(O))_{4-20}O(CH_2)_{11-17}CH_3$.
In one embodiment, $R^{611}$ is —$C(O)(OCH(CH_3)C(O))_{4-20}O(CH_2)_{13-17}CH_3$.
In one embodiment, $R^{611}$ is —$C(O)(OCH(CH_3)C(O))_{4-20}O(CH_2)_{15-17}CH_3$.
In one embodiment, $R^{611}$ is —$C(O)(OCH(CH_3)C(O))_{4-20}O(CH_2)_{11}CH_3$.
In one embodiment, $R^{611}$ is —$C(O)(OCH(CH3)C(O))_{4-20}O(CH2)_{17}CH3$.
In one embodiment, $R^{611}$ is —$C(O)(OCH_2C(O))_{1-2}(OCH(CH_3)C(O))_{4-20}OOCH_2CH_3$.
In one embodiment, $R^{611}$ is —$C(O)(OCH_2C(O))_{1-2}(OCH(CH_3)C(O))_{4-20}O(CH_2)_{11}CH_3$.
In one embodiment, $R^{611}$ is —$C(O)(OCH_2C(O))_{1-2}(OCH(CH_3)C(O))_{4-20}O(CH_2)_{17}CH_3$.
In one embodiment, $R^{611}$ is —$C(O)(OCH_2C(O))_{1-2}(OCH(CH_3)C(O))_{4-20}O(CH_2)_{9-17}CH_3$.
In one embodiment, $R^{611}$ is —$C(O)(OCH_2C(O))_{1-2}(OCH(CH_3)C(O))_{4-20}O(CH_2)_{11-17}CH_3$.
In one embodiment, $R^{611}$ is —$C(O)(OCH_2C(O))_{1-2}(OCH(CH_3)C(O))_{4-20}O(CH_2)_{13-17}CH_3$.
In one embodiment, $R^{611}$ is —$C(O)(OCH_2C(O))_{1-2}(OCH(CH_3)C(O))_{4-20}O(CH_2)_{15-17}CH_3$.
In one embodiment, $C_{1-30}$alkyl as used in the definition of $R^{611}$ is $C_{1-28}$, $C_{1-26}$, $C_{1-24}$, $C_{1-22}$, $C_{1-20}$, $C_{1-18}$, $C_{1-16}$, $C_{1-14}$, $C_{1-12}$, $C_{1-10}$, $C_{1-8}$, $C_{1-6}$, or $C_{1-4}$.

The disclosure provides ECA prodrugs of Formula IIH and Formula IIIH:

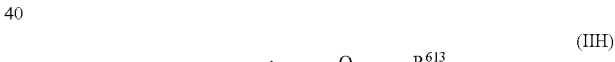 (IIH)

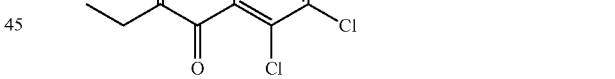 (IIIH)

or a pharmaceutically acceptable composition, salt, or isotopic derivative thereof.

$R^{613}$ is selected from:

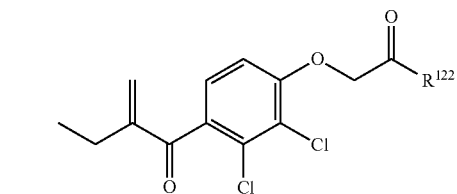

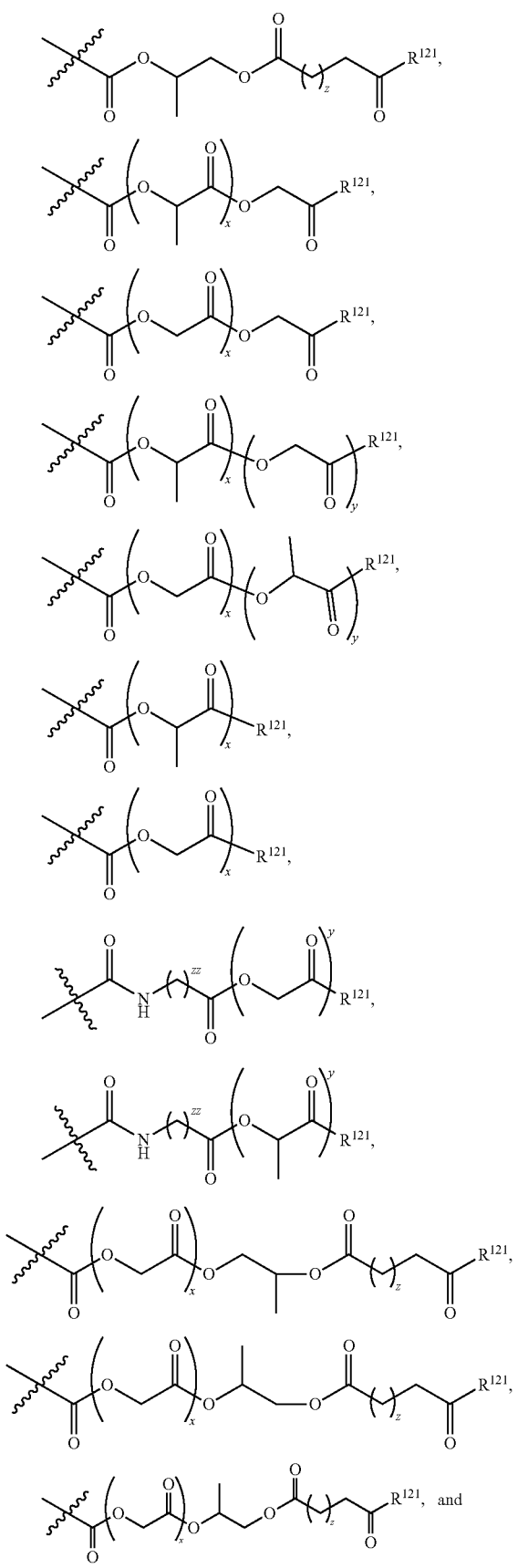
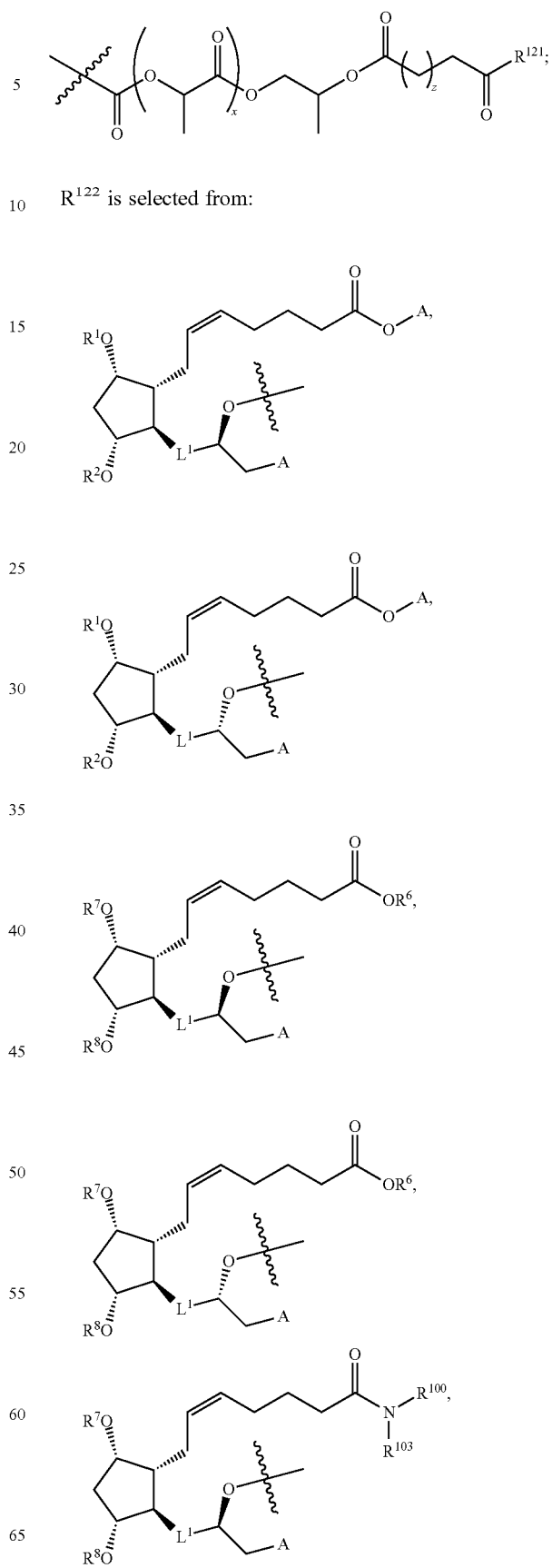
$R^{122}$ is selected from:

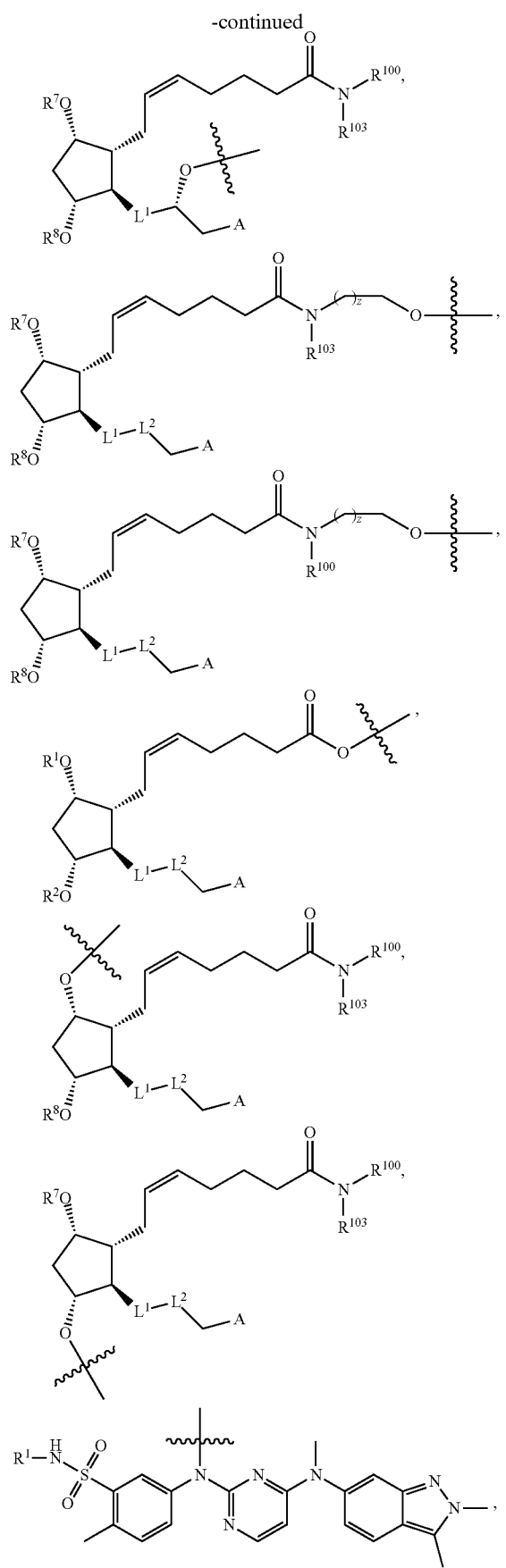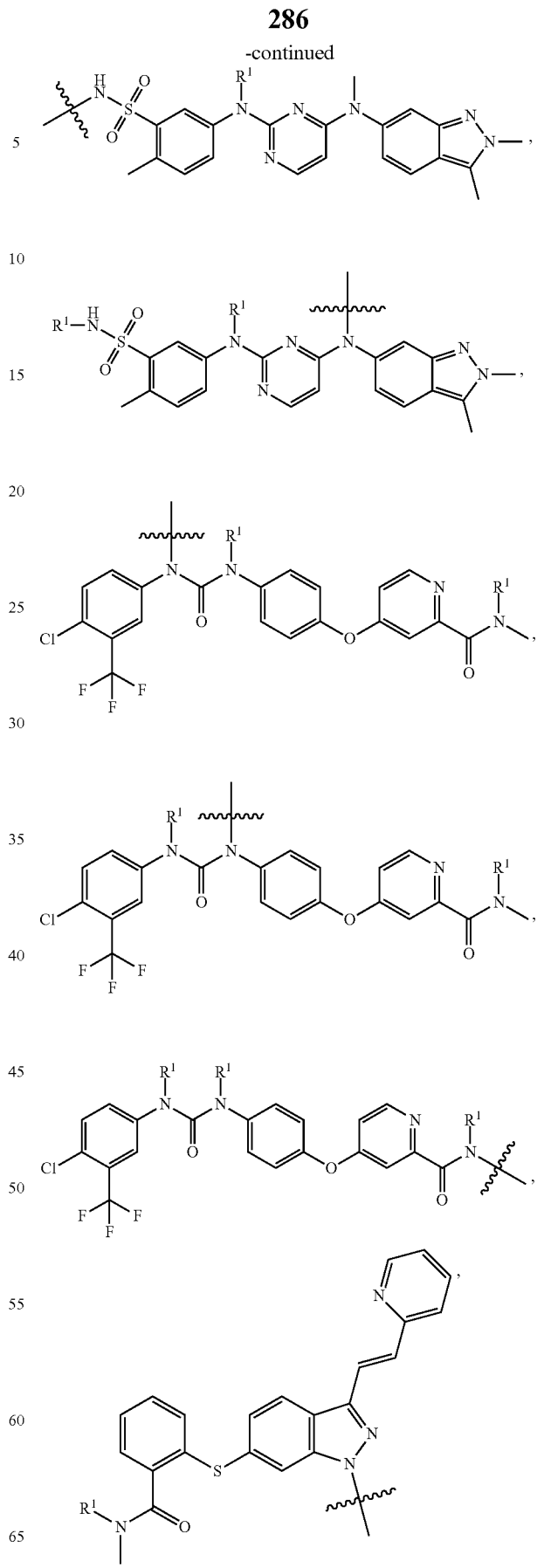

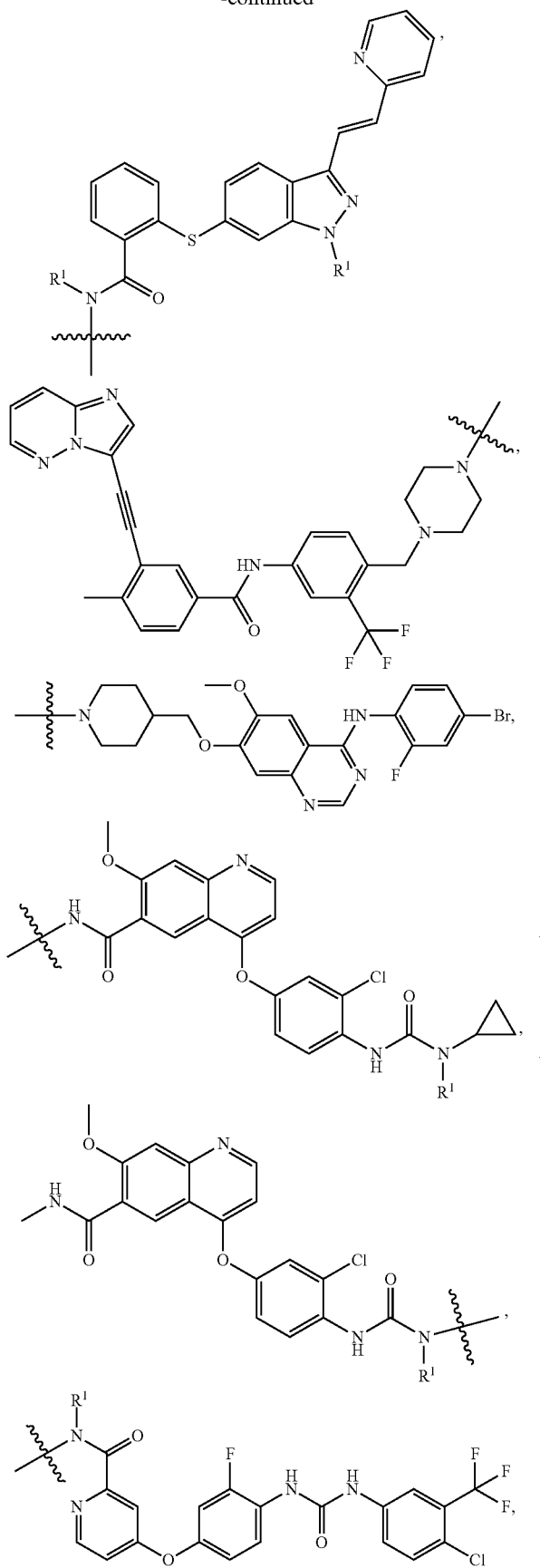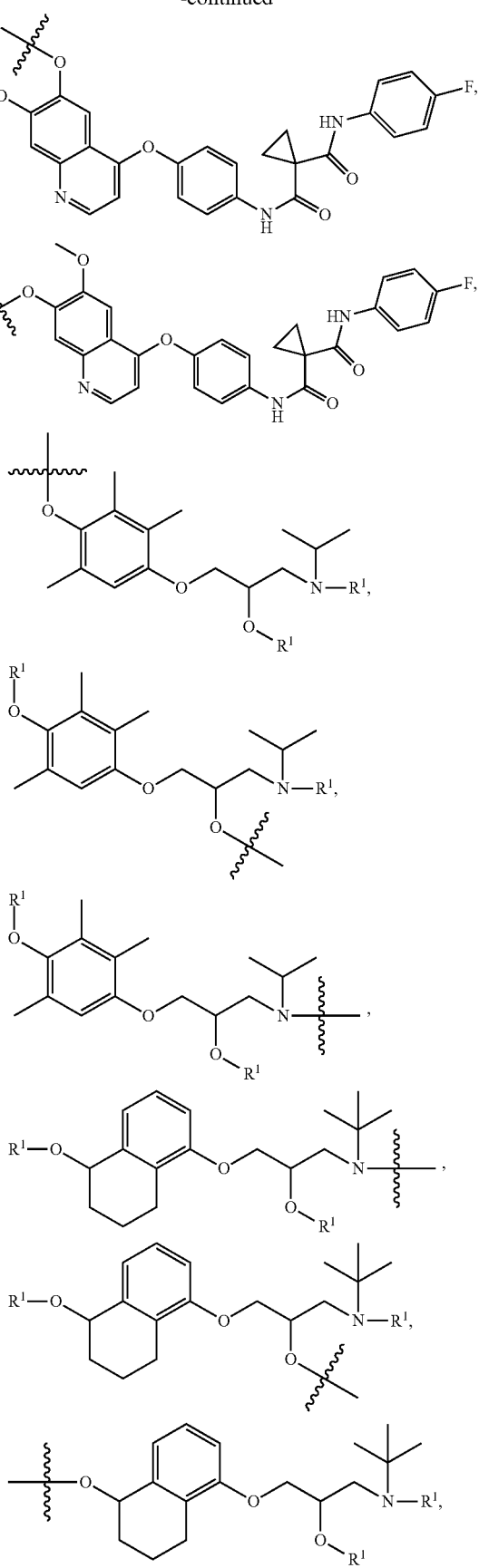

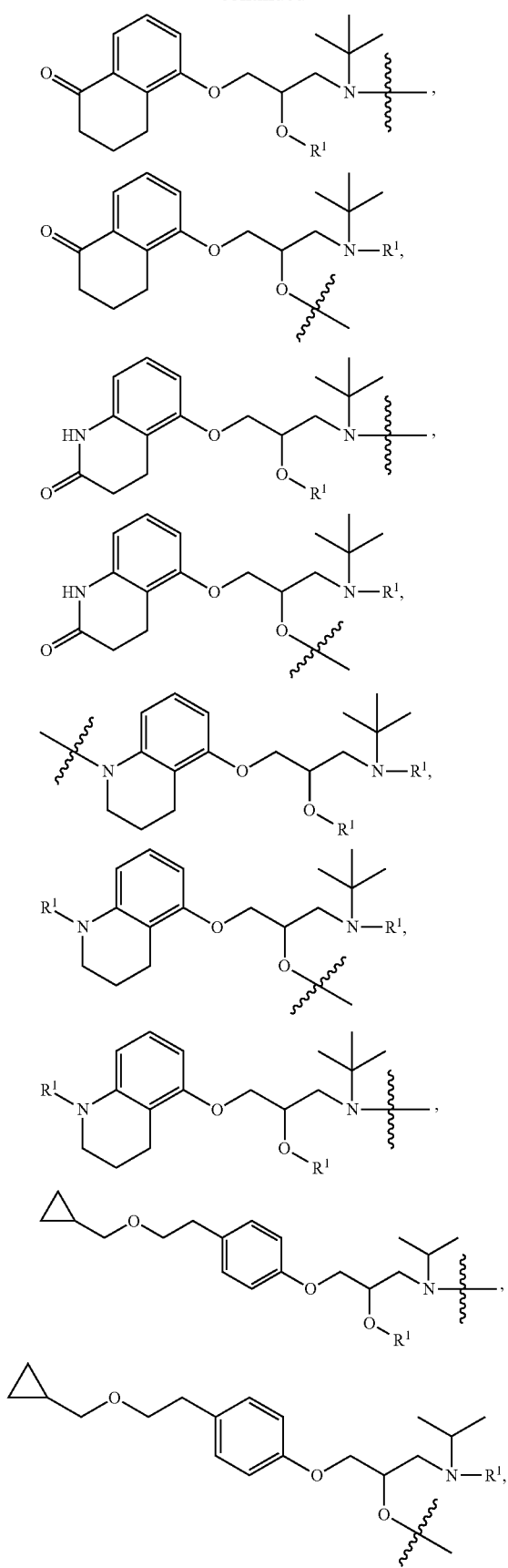
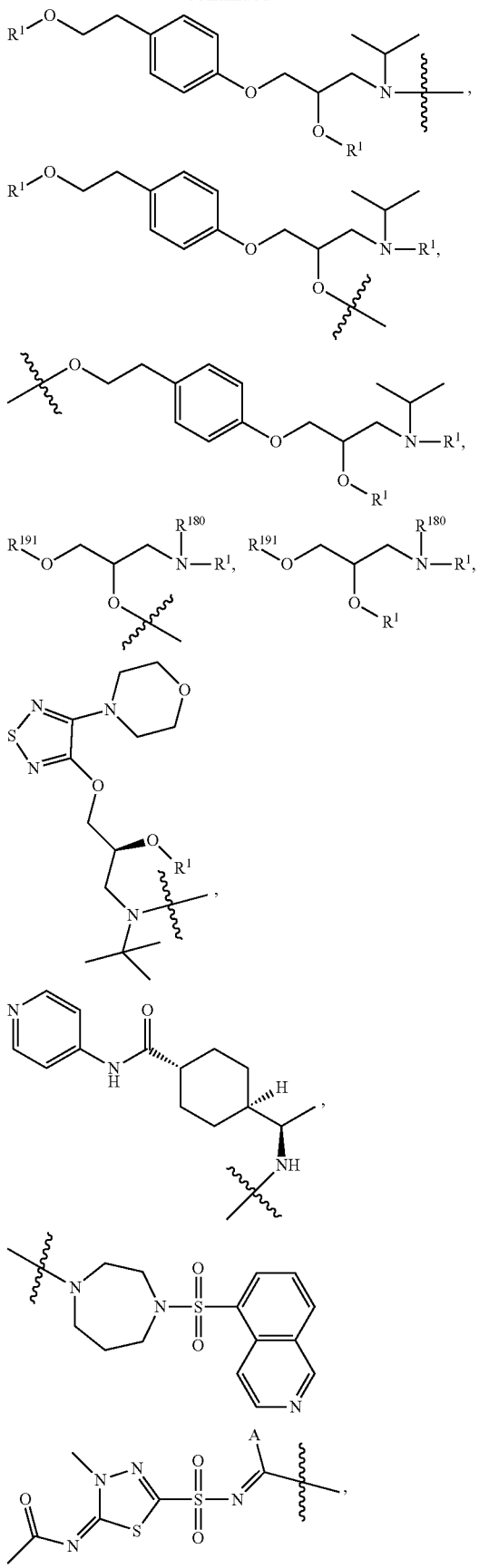

291
-continued
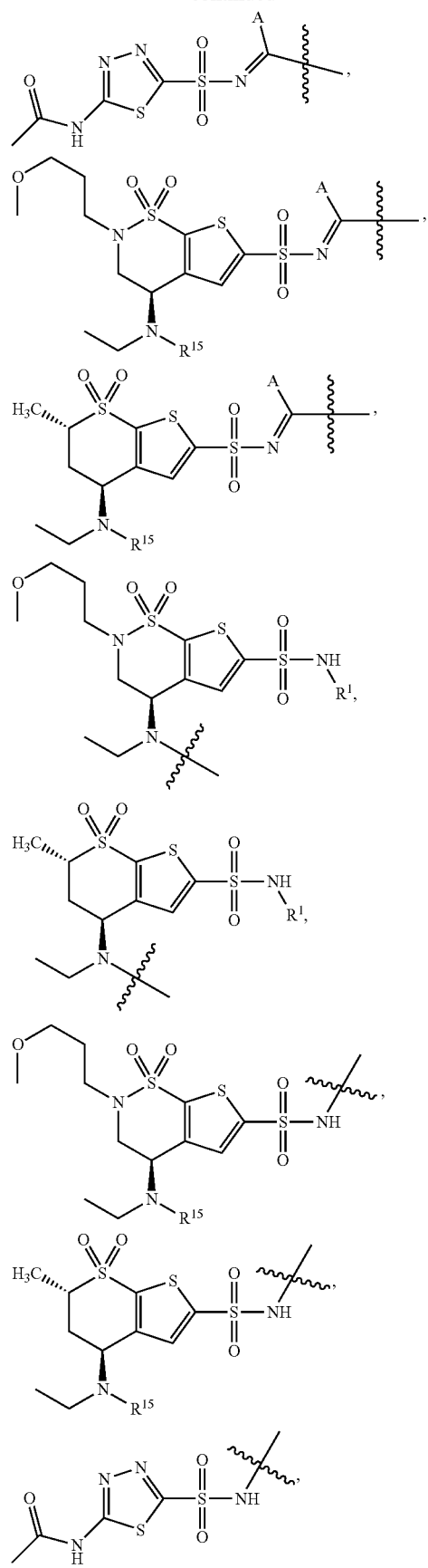
292
-continued
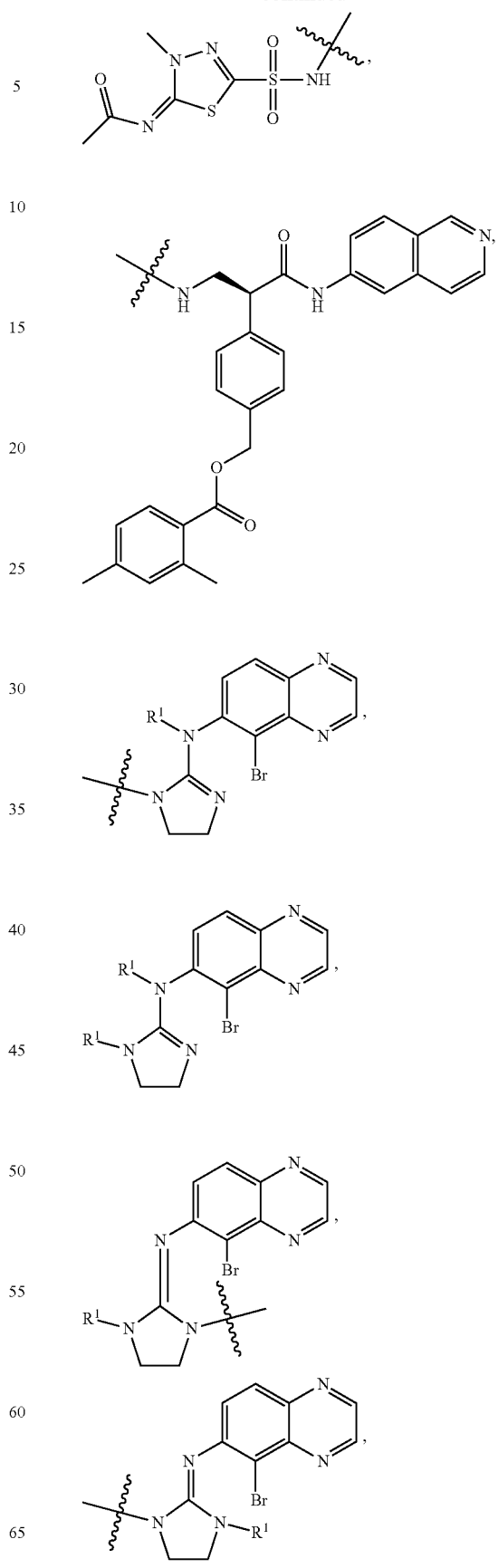

293
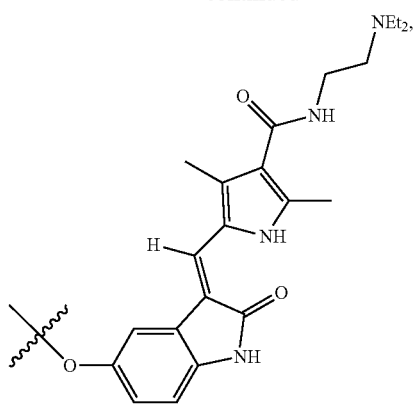
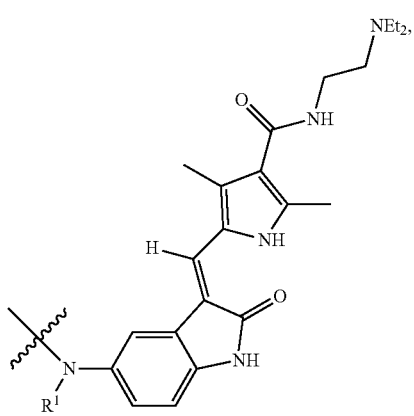
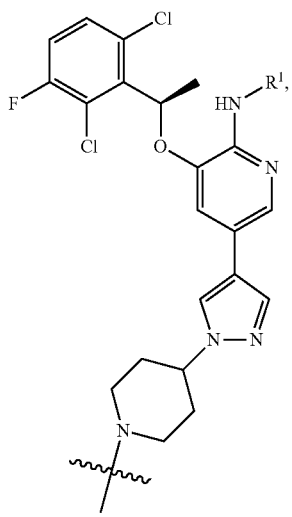
294
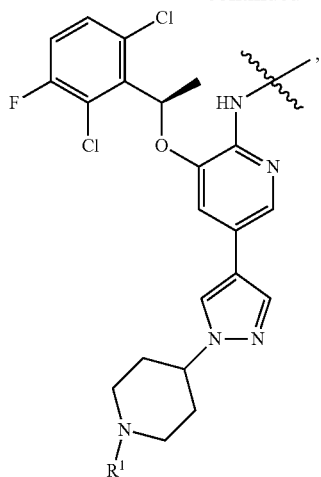
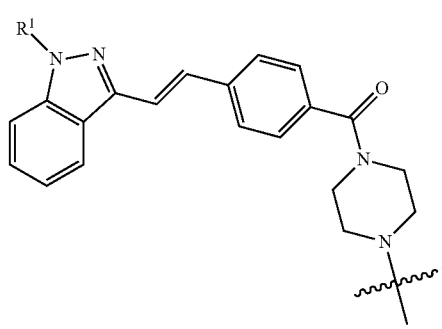
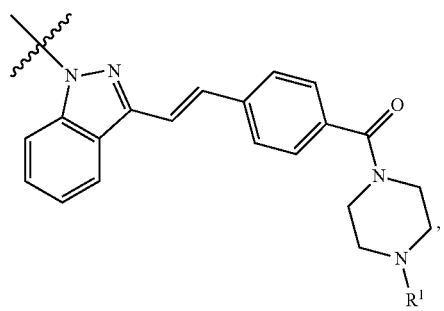
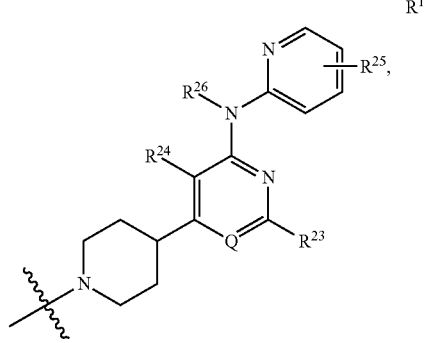

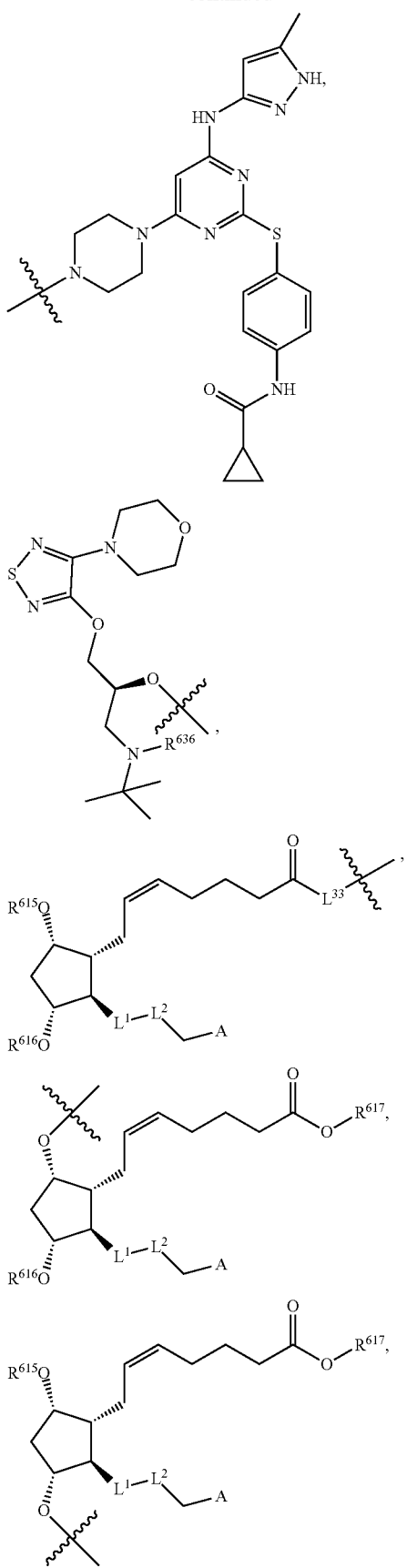
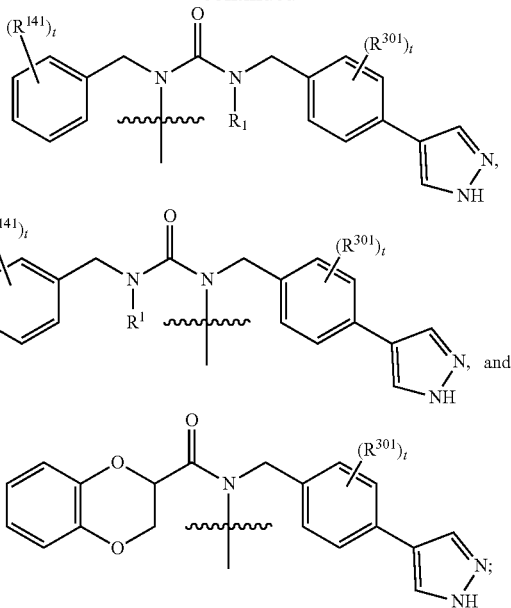
and
wherein all other variables are as defined herein.
In one embodiment of Formula IIH, $R^{613}$ is
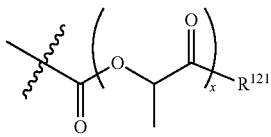
and x is 4.
In one embodiment of Formula IIH, $R^{121}$ is selected from
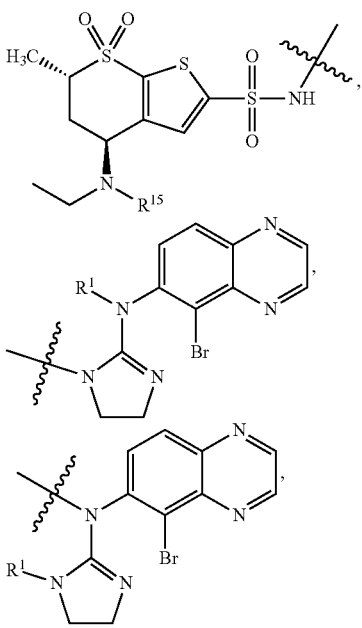

In one embodiment, x is an integer between 1 and 12 (1, 2, 3, 4, 5, 6, 7, 8, 9, 10, 11, or 12) and y is an integer between 1 and 6 (1, 2, 3, 4, 5, or 6).

In one embodiment, y is an integer between 1 and 12 (1, 2, 3, 4, 5, 6, 7, 8, 9, 10, 11, or 12) and x is an integer between 1 and 6 (1, 2, 3, 4, 5, or 6).

In one embodiment, x is an integer between 1 and 6 (1, 2, 3, 4, 5, or 6) and y is an integer between 1 and 3 (1, 2, or 3).

In one embodiment, y is an integer between 1 and 6 (1, 2, 3, 4, 5, or 6) and x is an integer between 1 and 3 (1, 2, or 3).

In one embodiment x is 1 and y is 1.
In one embodiment x is 1 and y is 2.
In one embodiment x is 1 and y is 3.
In one embodiment x is 1 and y is 4.
In one embodiment x is 1 and y is 5.
In one embodiment x is 1 and y is 6.
In one embodiment x is 1 and y is 7.
In one embodiment x is 1 and y is 8.
In one embodiment x is 2 and y is 1.
In one embodiment x is 2 and y is 2.
In one embodiment x is 2 and y is 3.
In one embodiment x is 2 and y is 4.
In one embodiment x is 2 and y is 5.
In one embodiment x is 2 and y is 6.
In one embodiment x is 2 and y is 7.
In one embodiment x is 2 and y is 8.

The disclosure provides loop diuretic prodrugs of Formula IVH, Formula VH, Formula VIH, Formula VIIH, and Formula VIIIH:

In one embodiment, x and y are independently an integer between 1 and 12 (1, 2, 3, 4, 5, 6, 7, 8, 9, 10, 11, or 12).

In one embodiment, x and y are independently an integer between 1 and 10 (1, 2, 3, 4, 5, 6, 7, 8, 9, or 10).

In one embodiment, x and y are independently an integer between 1 and 8 (1, 2, 3, 4, 5, 6, 7, or 8).

In one embodiment, x and y are independently an integer between 1 and 6 (1, 2, 3, 4, 5, or 6).

In one embodiment, x and y are independently an integer between 4 and 10 (4, 5, 6, 7, 8, 9, or 10).

-continued

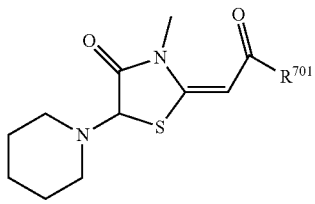
(VIIH)

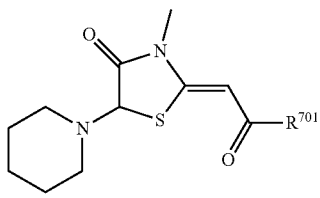
(VIIIH)

or a pharmaceutically acceptable composition, salt, or isotopic derivative thereof.

$R^{70}$ is selected from:
(i) —$OC_{15}$-$C_{30}$alkyl$R^5$, —$OC_2$-$C_{30}$alkenyl$R^5$, —$OC_2$-$C_{30}$alkynyl$R^5$, —$OC_4$-$C_{30}$alkenylalkynyl$R^5$, —$OC_{15}$-$C_{30}$alkyl, —$OC_2$-$C_{30}$alkenyl, —$OC_2$-$C_{30}$alkynyl, and —$OC_4$-$C_{30}$alkenylalkynyl;
(ii) —$OC_{15-30}$alkyl with at least one $R^5$ substituent on the alkyl chain, —$OC_{1-30}$alkenyl with at least one $R^5$ substituent on the alkenyl chain, and —$OC_{1-30}$alkynyl with at least one $R^5$ substituent on the alkynyl chain;
(iii) —$(OCH_2C(O))_{1-20}OC_{1-3}$alkyl, —$(OCH(CH_3)C(O))_{1-20}OC_{1-3}$alkyl, —$(OCH_2C(O))_{1-10}OC_{1-30}$alkyl, —$(OCH(CH_3)C(O))_{1-10}OC_{1-30}$alkyl, —$(OCH_2C(O))_{4-20}OC_{1-30}$alkyl, —$(OCH(CH_3)C(O))_{4-20}OC_{1-30}$alkyl, —$(OCH_2C(O))_{1-20}OC_{1-10}$alkyl, —$(OCH(CH_3)C(O))_{1-20}OC_{1-10}$alkyl, —$(OCH_2C(O))_{1-20}OC_{4-10}$alkyl, —$(OCH(CH_3)C(O))_{1-20}OC_{4-10}$alkyl, —$(OCH_2C(O))_{1-20}OH$, —$(OCH(CH_3)C(O))_{1-20}OH$, —$(OCH_2C(O))_{1-10}OH$, —$(OCH(CH_3)C(O))_{1-10}OH$, —$(OCH_2C(O))_{4-20}OH$, —$(OCH(CH_3)C(O))_{4-20}OH$, —$(OCH_2C(O))_{4-10}OH$, —$(OCH(CH_3)C(O))_{4-10}OH$, —$(OCH(CH_3)C(O))_{4-10}OC_{1-10}$alkyl, —$(OCH_2C(O))_{4-10}OC_{1-10}$alkyl, —$(OCH(CH_3)C(O))_{1-10}OC_{1-10}$alkyl, —$(OCH_2C(O))_{1-10}OC_{1-10}$alkyl, —$(OCH(CH_3)C(O))_{1-10}OC_{4-10}$alkyl, —$(OCH_2C(O))_{1-10}OC_{4-10}$alkyl, —$(OCH_2C(O))_{1-10}OC_{4-10}$alkyl, —$(OCH(CH_3)C(O))_{1-10}OC_{4-10}$alkyl, —$(OCH_2C(O))_{1-10}OC_{4-10}$alkyl, —$(OCH(CH_3)C(O))_{1-10}OC_{4-10}$alkyl, —$(OCH_2C(O))_{1-10}(OCH(CH_3)C(O))_{1-10}OC_{1-30}$alkyl, —$(OCH_2C(O))_{2-10}(OCH(CH_3)C(O))_{2-10}OC_{1-30}$alkyl, —$(OCH_2C(O))_{1-10}(OCH(CH_3)C(O))_{1-10}OC_{1-12}$alkyl, —$(OCH_2C(O))_{1-10}(OCH(CH_3)C(O))_{1-10}OC_{4-22}$alkyl, —$(OCH(CH_3)C(O))_{1-10}(OCH_2C(O))_{1-10}OC_{1-3}$alkyl, —$(OCH(CH_3)C(O))_{2-10}(OCH_2C(O))_{2-10}OC_{1-3}$alkyl, —$(OCH(CH_3)C(O))_{1-10}(OCH_2C(O))_{1-10}OC_{1-12}$alkyl, and —$(OCH(CH_3)C(O))_{1-10}(OCH_2C(O))_{1-10}OC_{4-22}$alkyl;
(iv) polypropylene glycol, polypropylene oxide, polylactic acid, poly(lactic-co-glycolic acid), polyglycolic acid, a polyester, a polyamide, and other biodegradable polymers, each of which can be capped to complete the terminal valence or to create a terminal ether or ester;

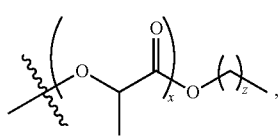

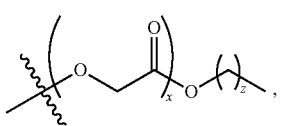

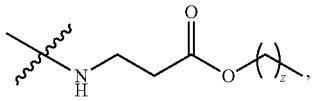

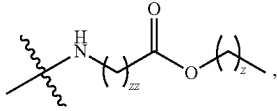

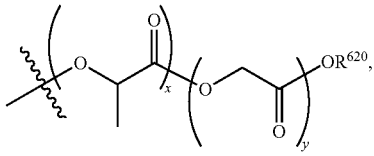

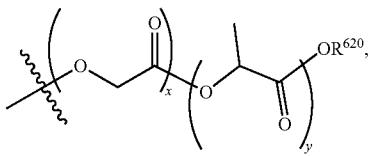

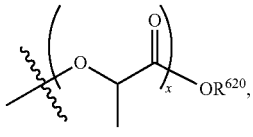

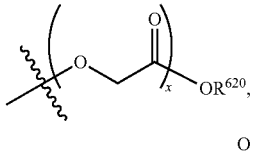

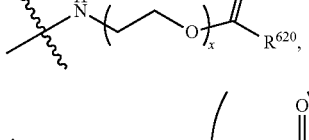

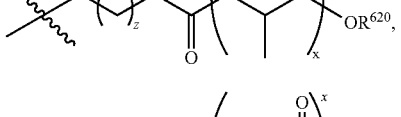

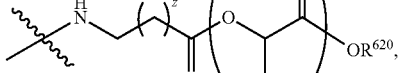

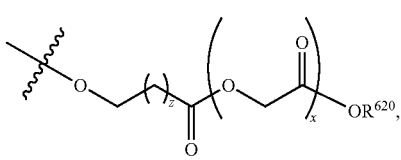

-continued

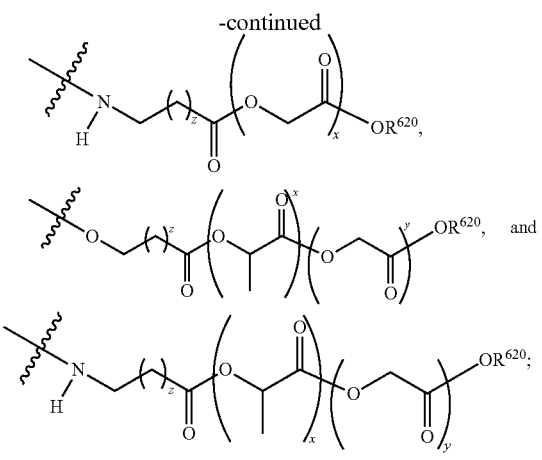

and
(v) —OH;
wherein $R^{701}$ cannot be OH when $R^{751}$ and $R^{752}$ are both hydrogen;
$R^{751}$ and $R^{752}$ are independently selected from hydrogen,

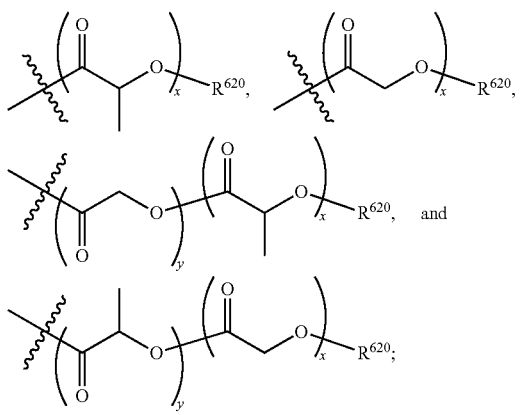

and
wherein all other variables are as defined herein.

In certain embodiments, x and y are independently selected from 1, 2, 3, 4, 5, 6, 7, 8, 9, and 10.

In certain embodiments, x and y are independently selected from 1, 2, 3, 4, 5, and 6.

In certain embodiments, x and y are independently selected from 1, 2, 3, 4, 5, and 6.

In certain embodiments, x and y are independently selected from 1, 2, 3, and 4.

In certain embodiments, x and y are independently selected from 1, 2, and 3.

In certain embodiments, x is selected from 1, 2, 3, 4, 5, and 6 and y is selected from 1, 2, 3, 4, 5, 6, 7, 8, 9, 10, 11, and 12.

In certain embodiments, y is selected from 1, 2, 3, 4, 5, and 6 and x is selected from 1, 2, 3, 4, 5, 6, 7, 8, 9, 10, 11, and 12.

In certain embodiments, x is selected from 1, 2, 3, 4, 5, and 6 and y is selected from 1, 2, 3, 4, 5, 6, 7, 8, 9, 10, 11, and 12.

In certain embodiments, y is selected from 1, 2, 3, 4, 5, and 6 and x is selected from 1, 2, 3, 4, 5, 6, 7, 8, 9, 10, 11, and 12.

In certain embodiments, x is selected from 1, 2, and 3 and y is selected from 1, 2, 3, 4, 5, and 6.

In certain embodiments, x is selected from 1, 2, 3, 4, 5, and 6, and y is selected from 1, 2, and 3.

In certain embodiments, x is selected from 1, 2, 3, 4, 5, 6, 7, 8, 9, 10, 11, and 12 and xx is selected from 1, 2, 3, 4, 5, and 6.

In certain embodiments, x is selected from 1, 2, 3, 4, 5, and 6 and xx is selected from 1, 2, and 3.

In certain embodiments, x is 1, 2, or 3 and xx is 1.
In certain embodiments, x is 1, 2, or 3 and xx is 2.
In certain embodiments, x is 1, 2, or 3 and xx is 3.

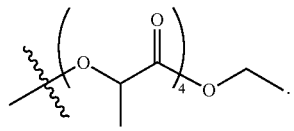

In one embodiment, $R^{701}$ is

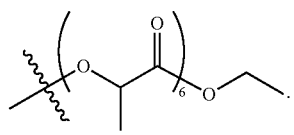

In one embodiment, $R^{701}$ is

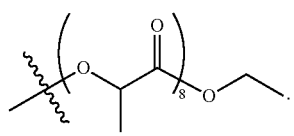

In one embodiment, $R^{701}$ is

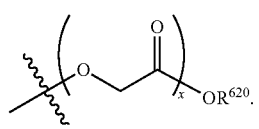

In one embodiment, $R^{701}$ is

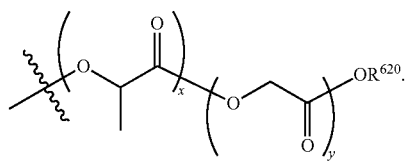

In one embodiment, $R^{701}$ is

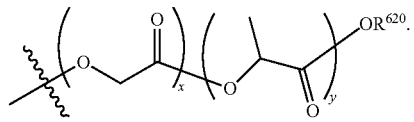

In one embodiment, $R^{701}$ is

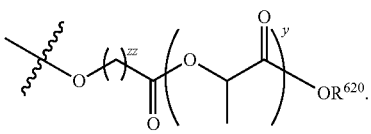

In one embodiment, $R^{701}$ is $-(OCH(CH_3)C(O))_{4-20}OCH_2CH_3$.
In one embodiment, $R^{701}$ is $-(OCH(CH_3)C(O))_{4-20}O(CH_2)_{11}CH_3$.
In one embodiment, $R^{701}$ is $-(OCH(CH_3)C(O))_{4-20}O(CH_2)_{17}CH_3$.
In one embodiment, $R^{701}$ is $-(OCH(CH_3)C(O))_4OCH_2CH_3$.
In one embodiment, $R^{701}$ is $-(OCH(CH_3)C(O))_4O(CH_2)_{11}CH_3$.
In one embodiment, $R^{701}$ is $-(OCH(CH_3)C(O))_4OCH_2)_{17}CH_3$.
In one embodiment, $R^{701}$ is $-(OCH(CH_3)C(O))_6COCH_2CH_3$.
In one embodiment, $R^{701}$ is $-(OCH(CH_3)C(O))_6O(CH_2)_{11}CH_3$.
In one embodiment, $R^{701}$ is $-(OCH(CH_3)C(O))_6O(CH_2)_{17}CH_3$.
In one embodiment, $R^{701}$ is $-(OCH(CH_3)C(O))_8OOCH_2CH_3$.
In one embodiment, $R^{701}$ is $-(OCH(CH_3)C(O))_8O(CH_2)_{11}CH_3$.
In one embodiment, $R^{701}$ is $-(OCH(CH_3)C(O))_8O(CH_2)_{17}CH_3$.
In one embodiment, $R^{701}$ is $-(OCH_2C(O))(OCH(CH_3)C(O))_{4-20}OCH_2CH_3$.
In one embodiment, $R^{701}$ is $-(OCH_2C(O))_2(OCH(CH_3)C(O))_{4-20}OCH_2CH_3$.
In one embodiment, $R^{701}$ is $-(OCH_2C(O))(OCH(CH_3)C(O))_{4-10}OCH_2CH_3$.
In one embodiment, $R^{701}$ is $-(OCH_2C(O))_2(OCH(CH_3)C(O))_{4-10}OCH_2CH_3$.
In one embodiment, $R^{701}$ is $-(OCH_2C(O))(OCH(CH_3)C(O))_6OCH_2CH_3$.
In one embodiment, $R^{701}$ is $-(OCH_2C(O))_2(OCH(CH_3)C(O))_6OCH_2CH_3$.
In one embodiment, $R^{701}$ is $-(OCH(CH_3)C(O))_{4-20}O(CH_2)_{9-17}CH_3$.
In one embodiment, $R^{701}$ is $-(OCH(CH_3)C(O))_{4-20}O(CH_2)_{11-17}CH_3$.
In one embodiment, $R^{701}$ is $-(OCH(CH_3)C(O))_{4-20}O(CH_2)_{13-17}CH_3$.
In one embodiment, $R^{701}$ is $-(OCH(CH_3)C(O))_{4-20}O(CH_2)_{15-17}CH_3$.
In one embodiment, $R^{701}$ is $-(OCH(CH_3)C(O))_{4-20}O(CH_2)_{11}CH_3$.
In one embodiment, $R^{701}$ is $-(OCH(CH_3)C(O))_{4-20}O(CH_2)_{17}CH_3$.
In one embodiment, $R^{701}$ is $-(OCH_2C(O))_{1-2}(OCH(CH_3)C(O))_{4-20}OCH_2CH_3$.
In one embodiment, $R^{701}$ is $-(OCH_2C(O))_{1-2}(OCH(CH_3)C(O))_{4-20}O(CH_2)_{11}CH_3$.
In one embodiment, $R^{701}$ is $-(OCH_2C(O))_{1-2}(OCH(CH_3)C(O))_{4-20}O(CH_2)_{17}CH_3$.
In one embodiment, $R^{701}$ is $-(OCH_2C(O))_{1-2}(OCH(CH_3)C(O))_{4-20}O(CH_2)_{9-17}CH_3$.
In one embodiment, $R^{701}$ is $-(OCH_2C(O))_{1-2}(OCH(CH_3)C(O))_{4-20}O(CH_2)_{11-17}CH_3$.
In one embodiment, $R^{701}$ is $-(OCH_2C(O))_{1-2}(OCH(CH_3)C(O))_{4-20}O(CH_2)_{13-17}CH_3$.
In one embodiment, $R^{701}$ is $-(OCH_2C(O))_{1-2}(OCH(CH_3)C(O))_{4-20}O(CH_2)_{15-17}CH_3$.

In one embodiment, $C_{1-30}$alkyl as used in the definition of $R^{701}$ is $C_{1-28}$, $C_{1-26}$, $C_{1-24}$, $C_{1-22}$, $C_{1-20}$, $C_{1-18}$, $C_{1-16}$, $C_{1-14}$, $C_{1-12}$, $C_{1-10}$, $C_{1-8}$, $C_{1-6}$, or $C_{1-4}$.

In one embodiment the prodrug of Formula IVH, Formula VH, or Formula VIH is selected from:

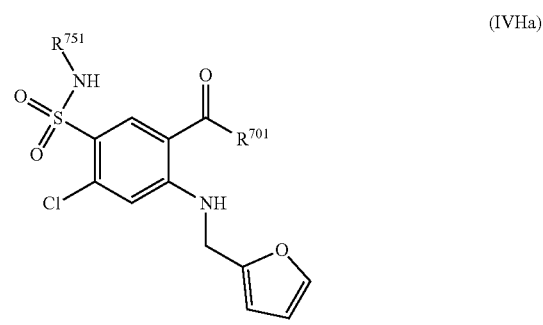

(IVHa)

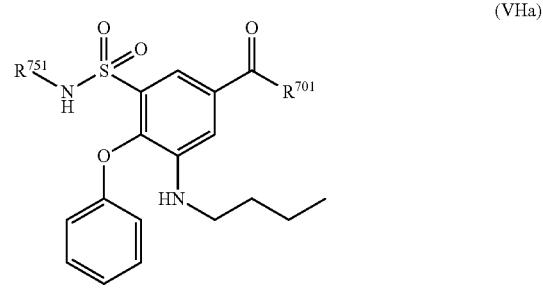

(VHa)

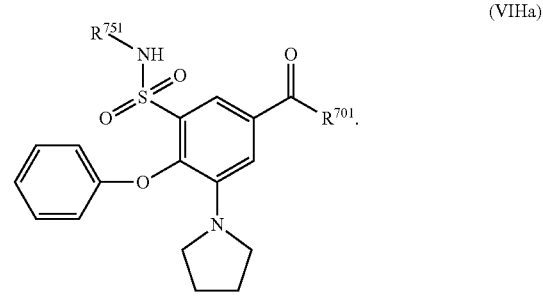

(VIHa)

The disclosure provides loop diuretic prodrugs of Formula IXH, Formula XH, Formula XIH, Formula XIIH, and Formula XIIIH:

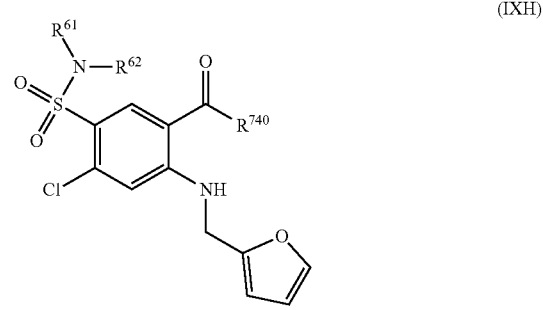

(IXH)

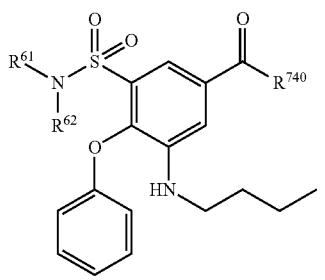
(XH)
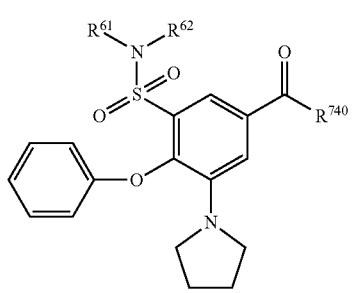
(XIH)
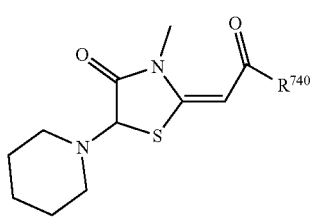
(XIIH)
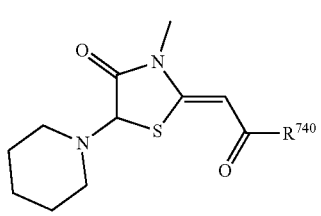
(XIIIH)
or a pharmaceutically acceptable composition, salt, or isotopic derivative thereof.
R$^{740}$ is selected from:
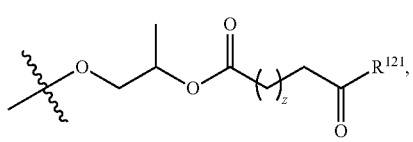
(i)
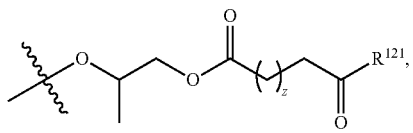
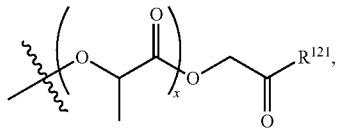
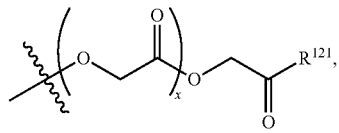
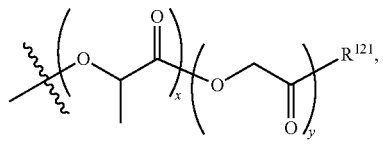
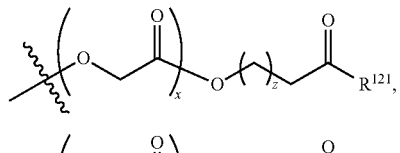
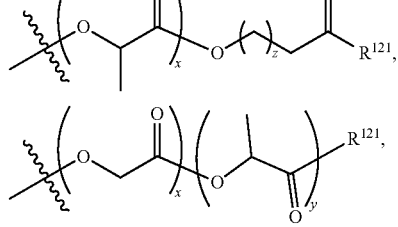
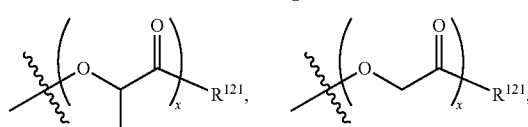
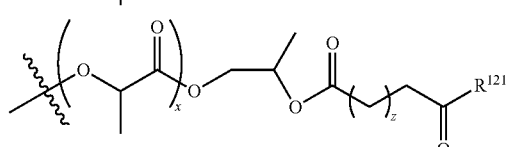
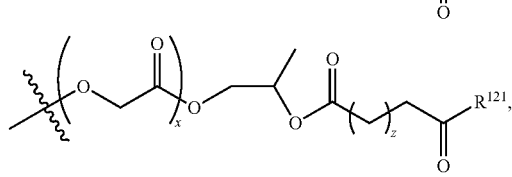
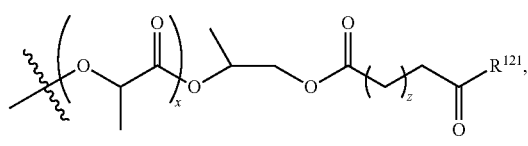
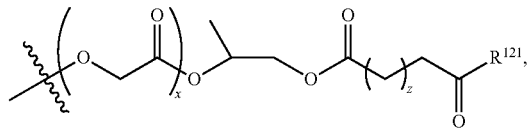
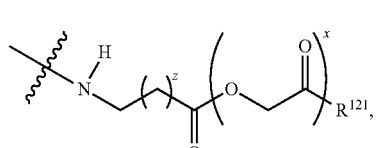
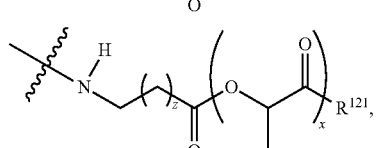
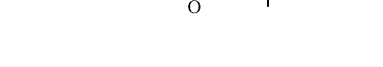

307
-continued
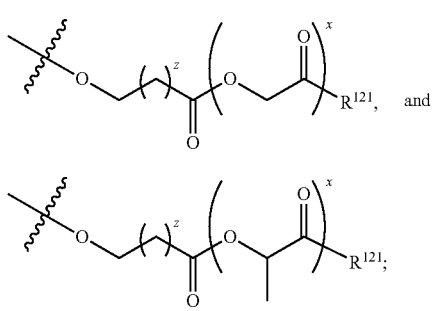
and
(ii) —OH
wherein $R^{740}$ cannot be —OH when $R^{61}$ and $R^{62}$ are both hydrogen;
$R^{61}$ and $R^{62}$ are independently selected from hydrogen.
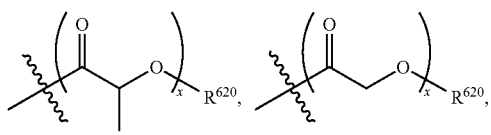
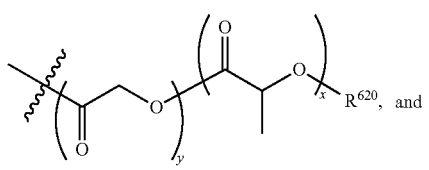
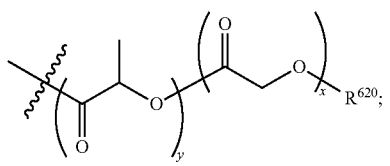
wherein all other variables are as defined herein.
In one embodiment, $R^{740}$ is
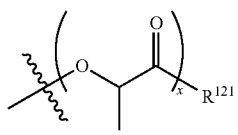
and $R^{121}$ is
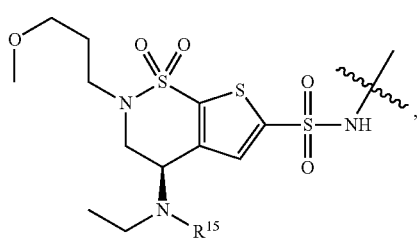
308
-continued
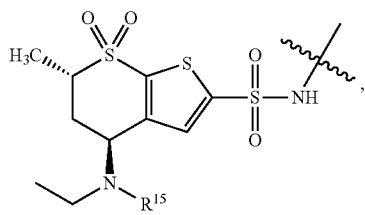
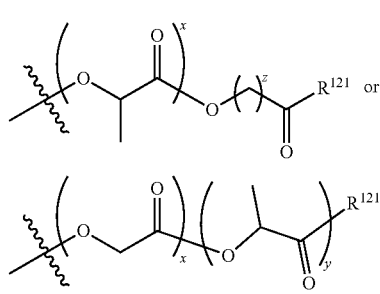
In one embodiment, $R^{740}$ is and R¹²¹ is
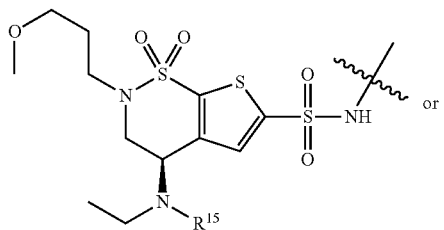
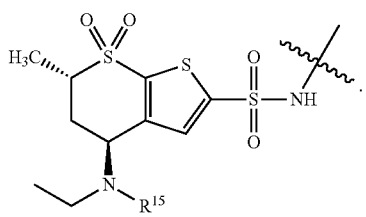
In one embodiment, R⁷⁴⁰ is
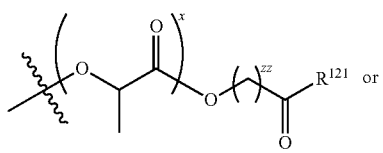
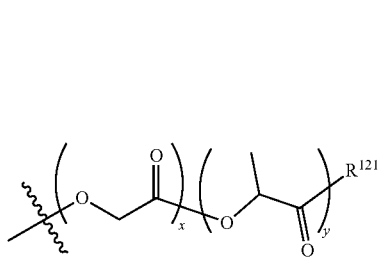
and R¹²¹ is
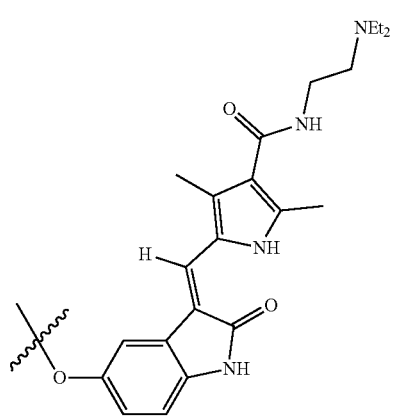
or
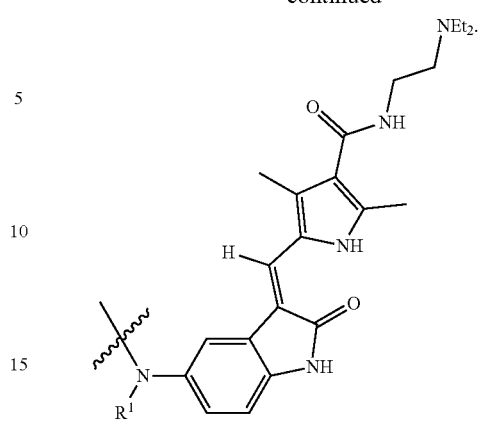
In one embodiment, R⁷⁴⁰ is selected from
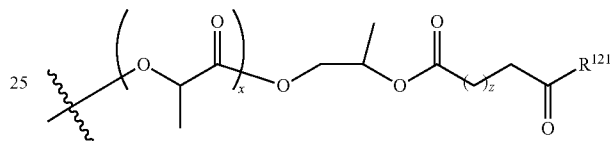
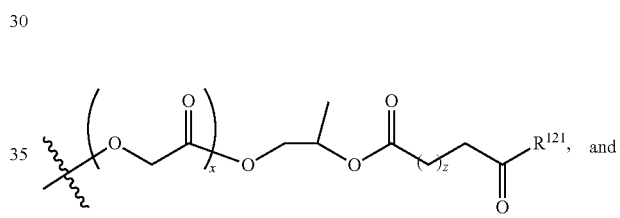
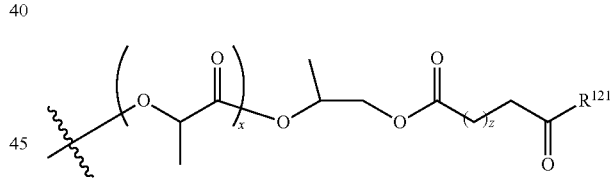
and R¹²¹ is
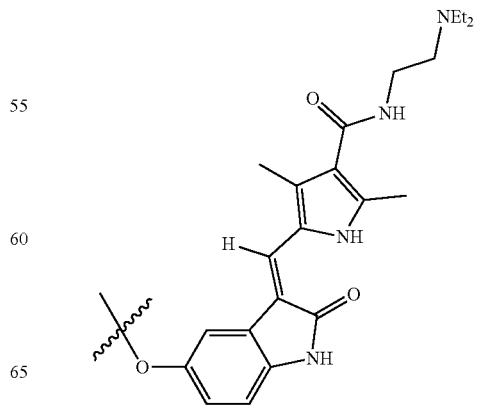
or

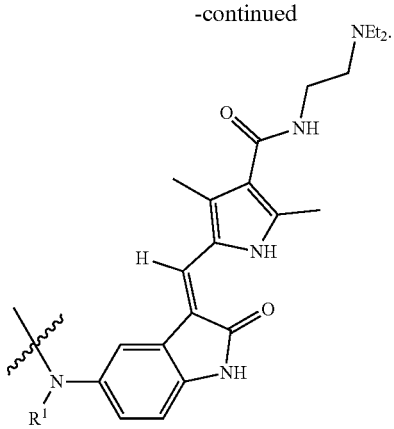

In certain embodiments, x and y are independently selected from 1, 2, 3, 4, 5, and 6.

In certain embodiments, x and y are independently selected from 1, 2, 3, and 4.

In certain embodiments, x and y are independently selected from 1, 2, and 3.

In certain embodiments, x is selected from 1, 2, 3, 4, 5, and 6 and y is selected from 1, 2, 3, 4, 5, 6, 7, 8, 9, 10, 11, and 12.

In certain embodiments, y is selected from 1, 2, 3, 4, 5, and 6 and x is selected from 1, 2, 3, 4, 5, 6, 7, 8, 9, 10, 11, and 12.

In certain embodiments, x is selected from 1, 2, and 3 and y is selected from 1, 2, 3, 4, 5, and 6.

In certain embodiments, x is selected from 1, 2, 3, 4, 5, and 6, and y is selected from 1, 2, and 3.

In certain embodiments, x is selected from 1, 2, 3, 4, 5, 6, 7, 8, 9, 10, 11, and 12 and xx is selected from 1, 2, 3, 4, 5, and 6.

In certain embodiments, x is selected from 1, 2, 3, 4, 5, and 6 and z is selected from 1, 2, and 3.

In certain embodiments, x is 1, 2, or 3 and z is 1.

In certain embodiments, x is 1, 2, or 3 and z is 2.

In certain embodiments, x is 1, 2, or 3 and z is 3.

In one embodiment the prodrug of Formula IXH, Formula XH, or Formula XIH is selected from:

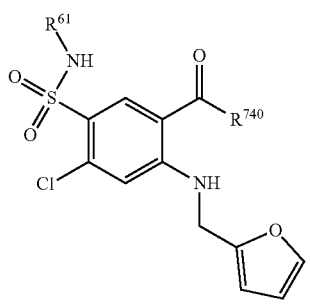
(IXHa)

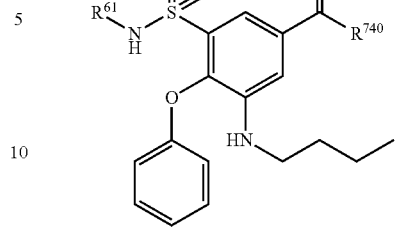
(XHa)

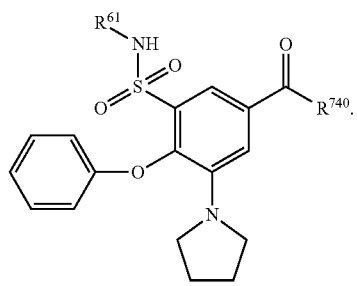
(XIHa)

The disclosure provides loop diuretic prodrugs of Formula XIVH, Formula XVH, Formula XVIH, Formula XVIIH, Formula XVIIIH, and Formula XIXH:

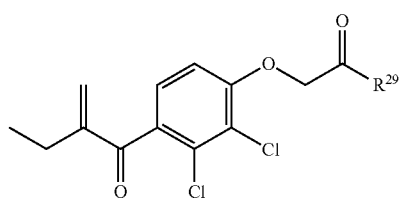
(XIVH)

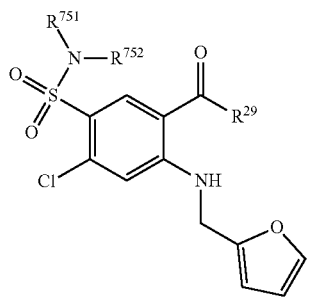
(XVH)

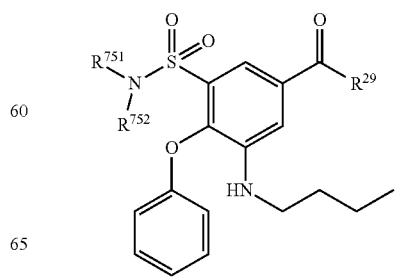
(XVIH)

(XVIIH)
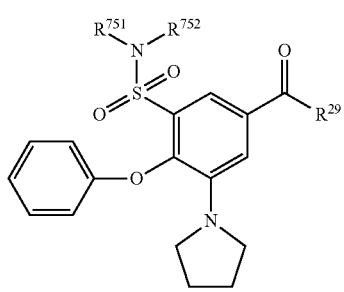
(XVIIIH)
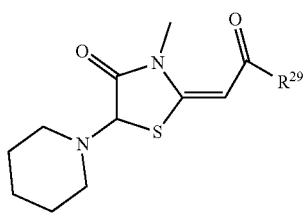
(XIXH)
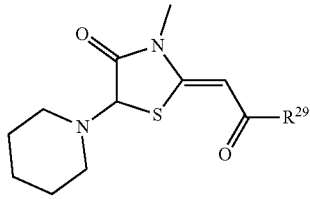
or a pharmaceutically acceptable composition, salt, or isotopic derivative thereof.
wherein:
$R^{29}$ is selected from:
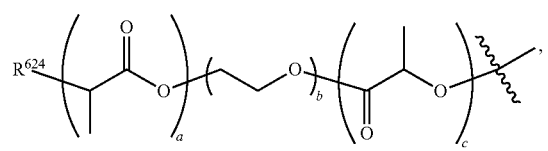
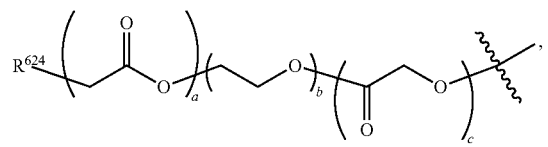
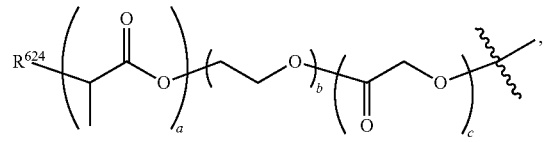
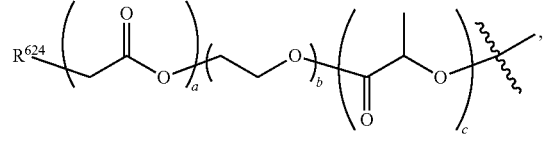
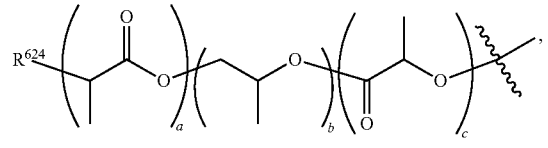
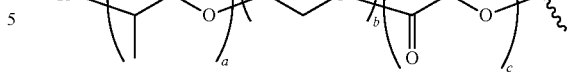,
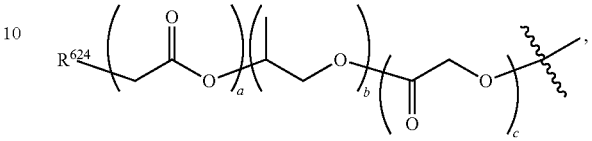,
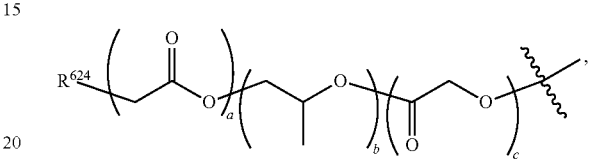,
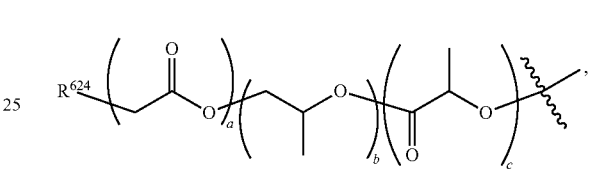,
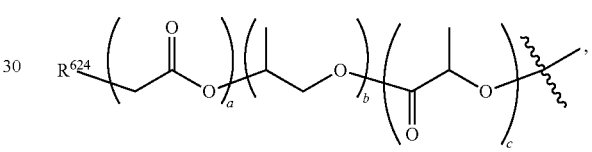,
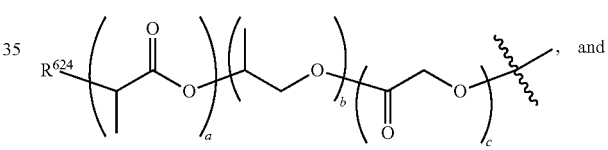, and
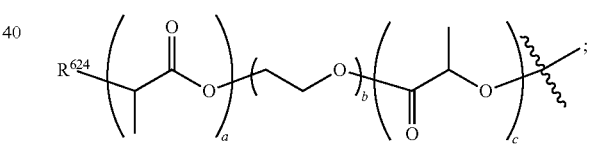;
$R^{624}$ is
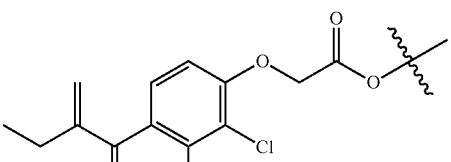,
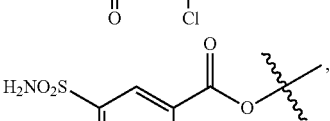,
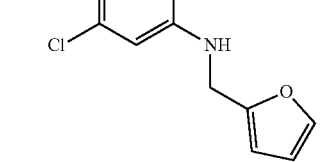

-continued

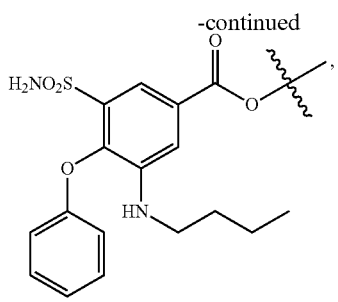

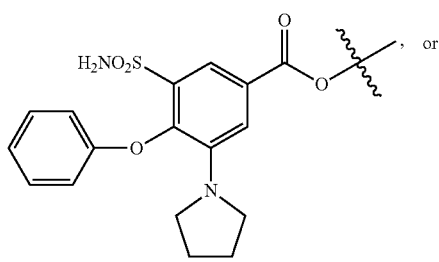, or

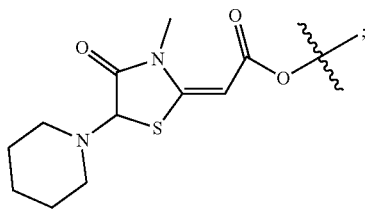;

a, b, and c are independently an integer selected from 0 to 30 (0, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) wherein a and c cannot both be 0; and wherein all other variables are as defined herein.

The polymer moieties described in Formula XIIC, Formula IXD, Formula XD, Formula XID, Formula XIID, and Formula XIID' above are depicted as block copolymers (for example, blocks of "a" followed by blocks of "b" followed by blocks of "c"), but it is intended that the polymer can be a random or alternating copolymer (for example, "a" "b" and "c" are either randomly distributed or alternate).

In one embodiment, a, b, and c are independently selected from an integer between 1 and 12 (1, 2, 3, 4, 5, 6, 7, 8, 9, 10, 11, or 12).

In one embodiment, a, b, and c are independently selected from an integer between 1 and 8 (1, 2, 3, 4, 5, 6, 7, or 8).

In one embodiment, a, b, and c are independently selected from an integer between 1 and 6 (1, 2, 3, 4, 5, or 6).

In one embodiment, a, b, and c are independently selected from an integer between 1 and 3 (1, 2, or 3).

In one embodiment, a and c are independently selected from an integer between 1 and 6 (1, 2, 3, 4, 5, or 6) and b is 1.

In one embodiment, a and c are independently selected from an integer between 1 and 3 (1, 2, or 3) and b is 1.

In one embodiment, a and c are independently selected from an integer between 1 and 12 (1, 2, 3, 4, 5, 6, 7, 8, 9, 10, 11, or 12) and b is selected from an integer between 1 and 6 (1, 2, 3, 4, 5, or 6).

In one embodiment, a and c are independently selected from an integer between 1 and 6 (1, 2, 3, 4, 5, or 6) and b is selected from an integer between 1 and 3 (1, 2, or 3).

In one embodiment, a and c independently selected from an integer between 1, 2, 3, and 4 and b is 1.

In one embodiment, a and c are 2 and b is 1.

In one embodiment, a and c are 3 and b is 1.

In one embodiment, a and c are 4 and b is 1.

In one embodiment the prodrug of Formula XVH, Formula XVIH or Formula XVIIH is selected from:

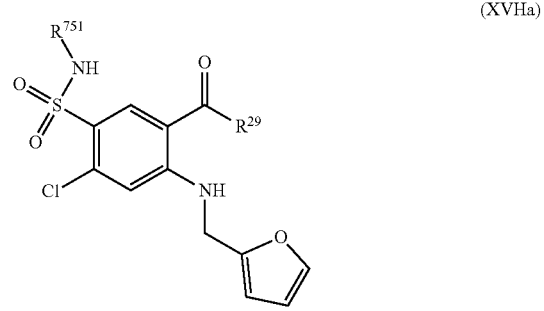

(XVHa)

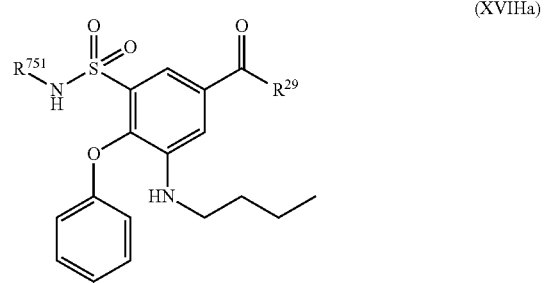

(XVIHa)

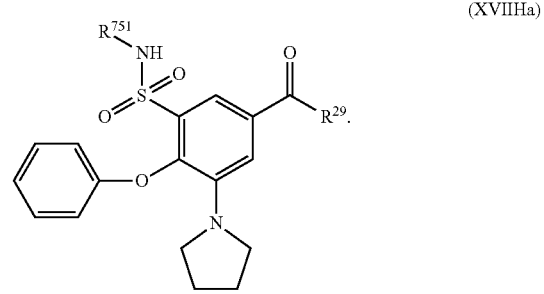

(XVIIHa)

Table A-Table I show illustrative prodrugs encapsulated in the microparticles of the present invention. In one aspect of the invention, a mildly surface-treated microparticle comprising one of more biodegradable polymers and a prodrug selected from Table A-Table I encapsulated in the biodegradable polymer is provided.

An aspect of the invention is a method for the treatment of a disorder, comprising administering to a host in need thereof solid aggregating microparticles comprising an effective amount of a therapeutic agent selected from a prodrug disclosed herein, wherein the therapeutic agent containing solid aggregating microparticles are injected into the body and aggregate in vivo to form at least one pellet of at least 500 µm that provides sustained drug delivery for at least one month.

TABLE A
Non-limiting Examples of Prodrugs
| Comp. # | Structure |
|---|---|
| 1 | 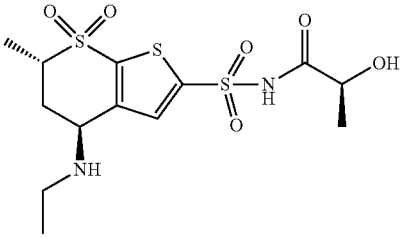 [SMILES: CCN[C@H]1C[C@H](C)S(=O)(=O)c2sc(S(=O)(=O)NC(=O)[C@H](C)O)cc21] |
| 2 | 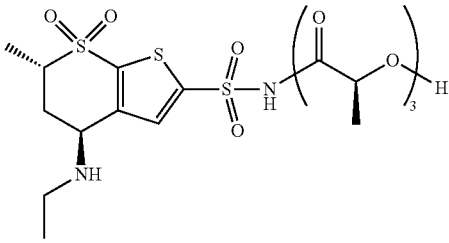 |
| 3 | 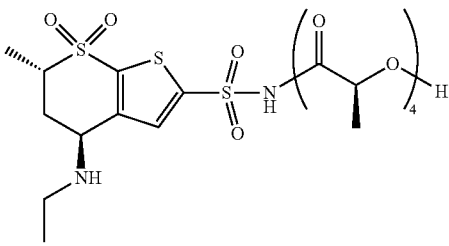 |
| 4 | 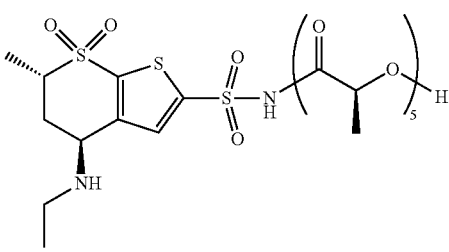 |
| 5 | 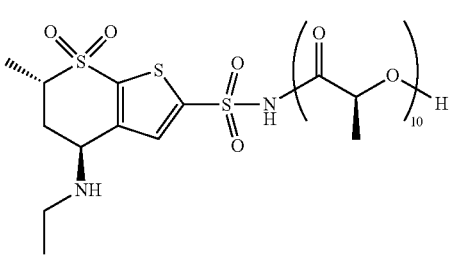 |
| 6 | 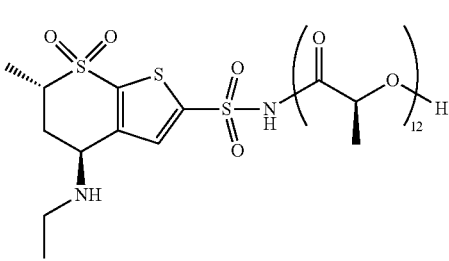 |

TABLE A-continued

Non-limiting Examples of Prodrugs

| Comp. # | Structure |
|---|---|
| 7 | 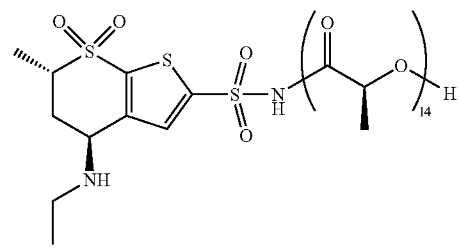 |
| 8 | 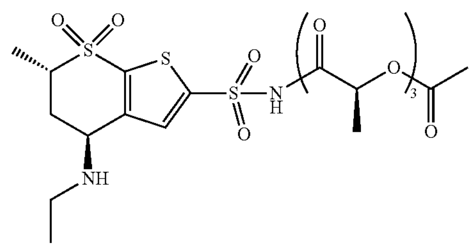 |
| 9 | 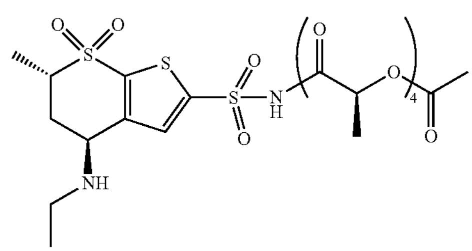 |
| 10 | 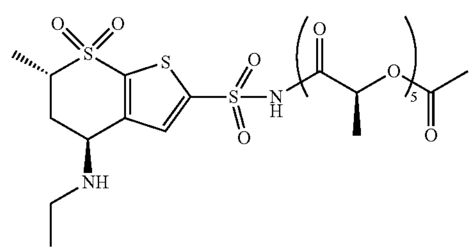 |
| 11 | 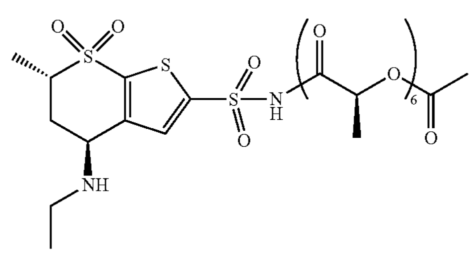 |
| 12 | 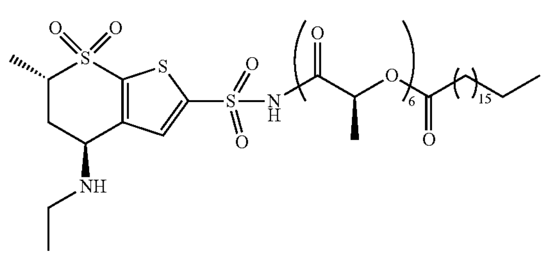 |

TABLE A-continued

Non-limiting Examples of Prodrugs

| Comp. # | Structure |
| --- | --- |
| 13 | 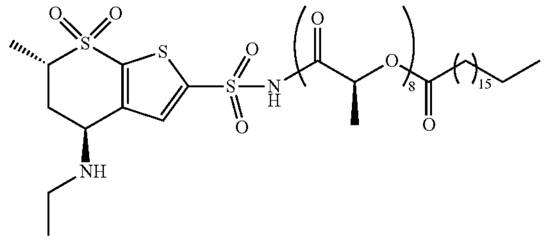 |
| 14 | 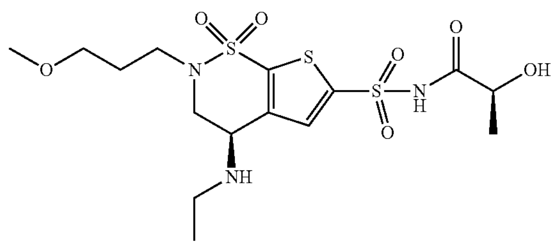 [SMILES: CCN[C@H]1CN(CCCOC)S(=O)(=O)c2sc(S(=O)(=O)NC(=O)[C@H](C)O)cc21] |
| 15 | 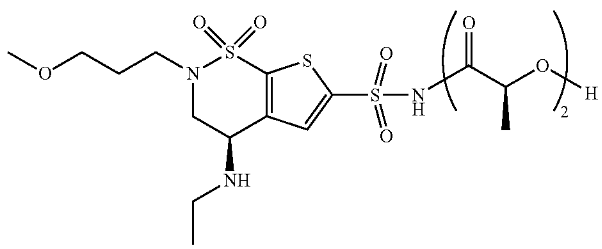 |
| 16 | 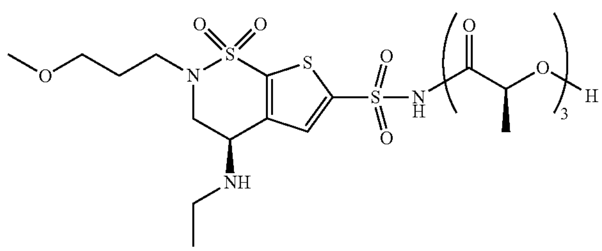 |
| 17 | 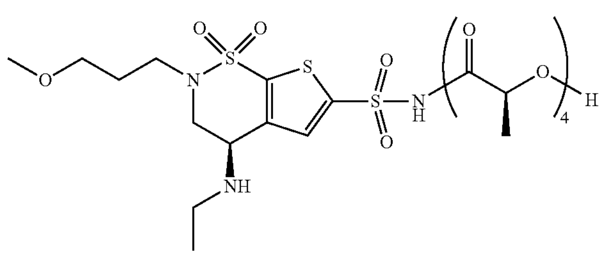 |
| 18 | 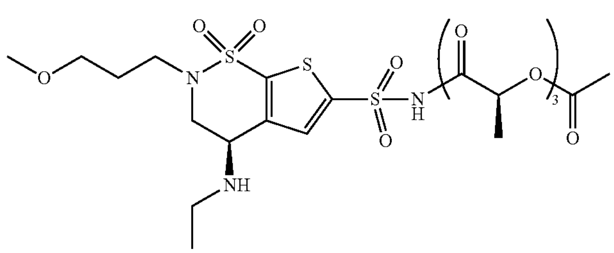 |

TABLE A-continued

Non-limiting Examples of Prodrugs

| Comp. # | Structure |
|---|---|
| 19 | 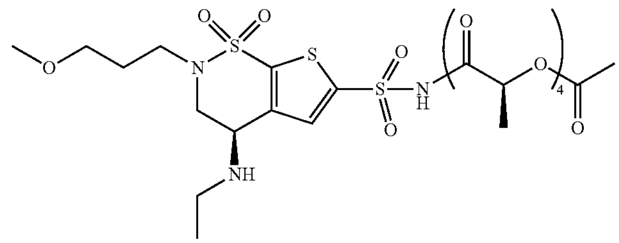 |
| 20 | 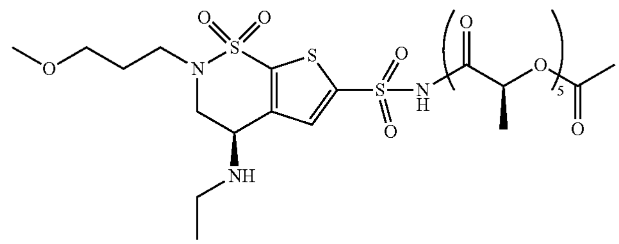 |
| 21 | 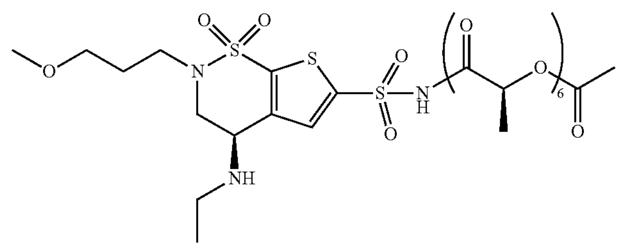 |
| 22 | 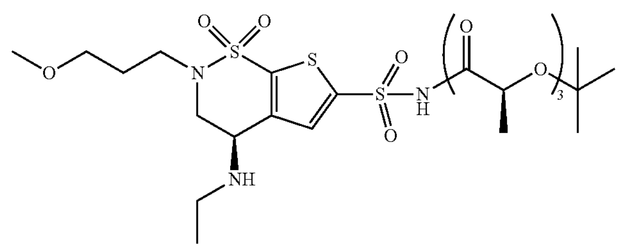 |
| 23 | 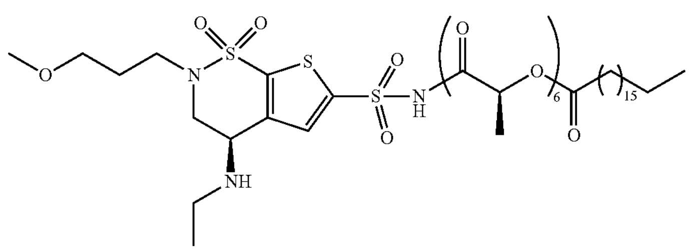 |
| 24 | 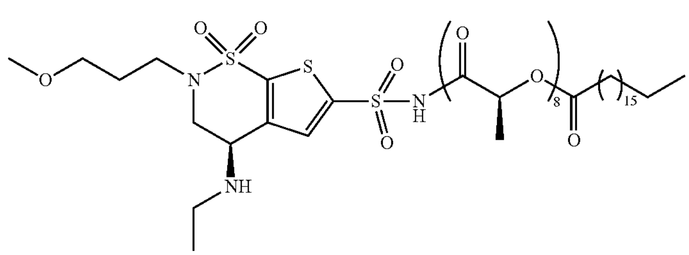 |

TABLE A-continued
Non-limiting Examples of Prodrugs
| Comp. # | Structure |
|---|---|
| 25 | 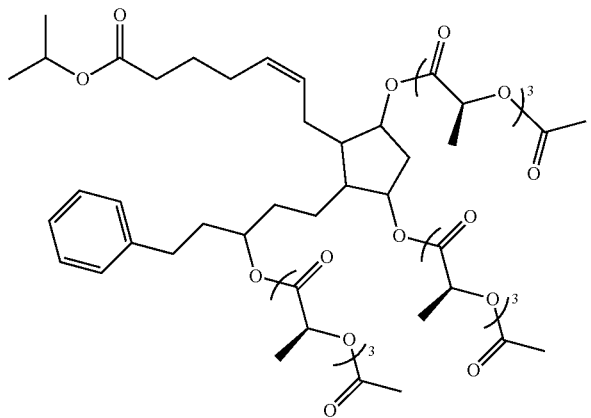 |
| 26 | 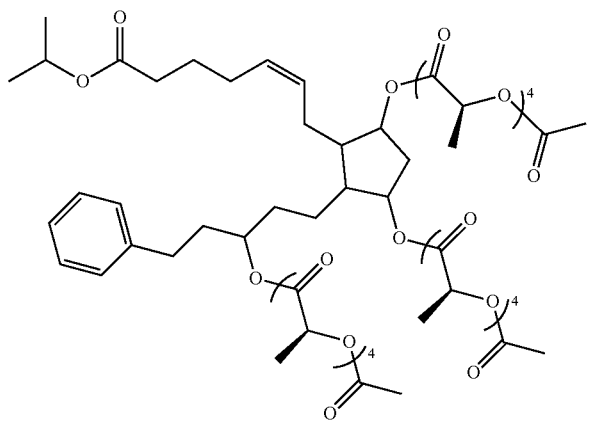 |
| 27 | 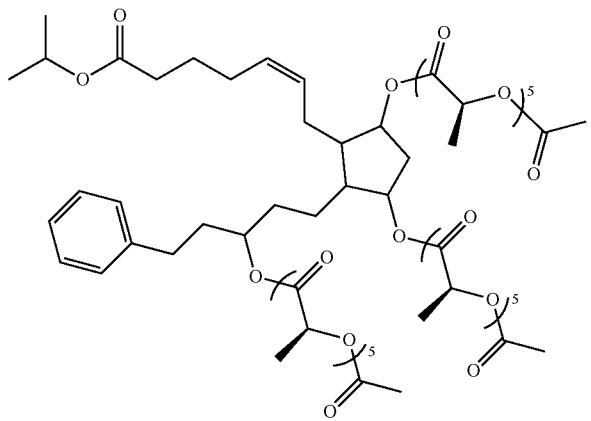 |

TABLE A-continued

Non-limiting Examples of Prodrugs

| Comp. # | Structure |
|---|---|
| 28 | 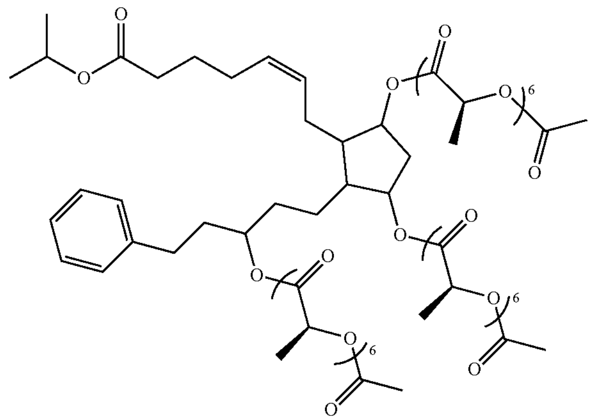 |
| 29 | 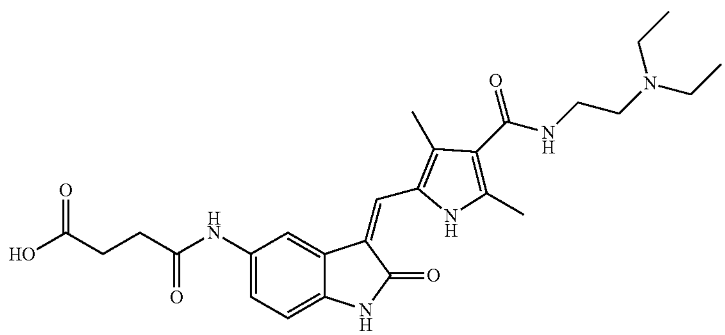 [SMILES: CCN(CC)CCNC(=O)c1c(C)[nH]c(/C=C2\C(=O)Nc3ccc(NC(=O)CCC(=O)O)cc32)c1C] |
| 30 | 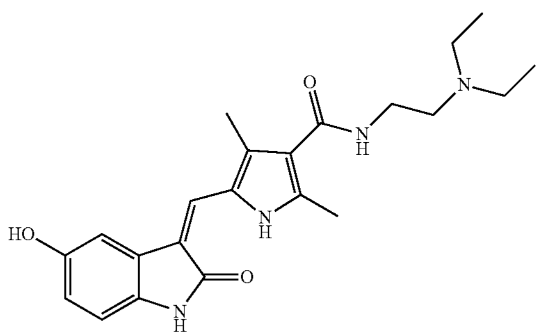 [SMILES: CCN(CC)CCNC(=O)c1c(C)[nH]c(/C=C2\C(=O)Nc3ccc(O)cc32)c1C] |
| 31 | 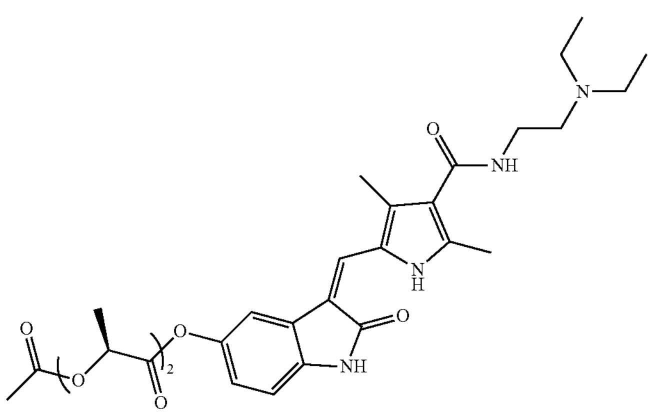 |

US 11,160,870 B2
329                                                                                                              330
TABLE A-continued
Non-limiting Examples of Prodrugs
| Comp. # | Structure |
|---|---|
| 32 | 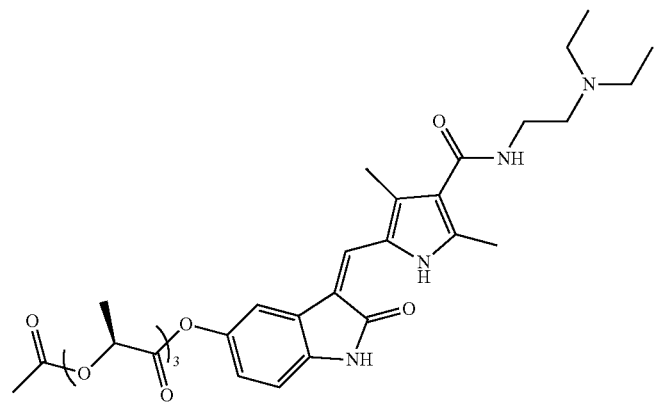 |
| 33 | 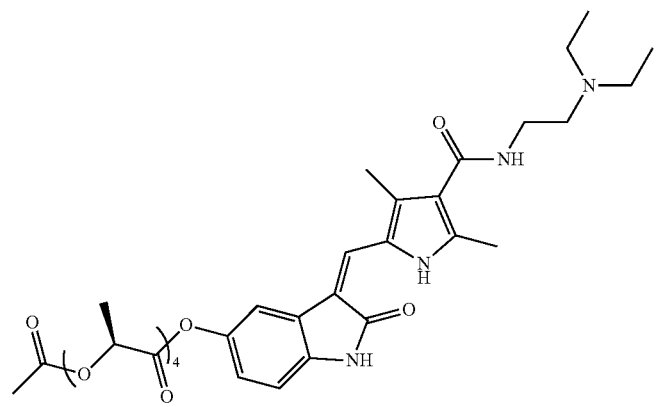 |
| 34 | 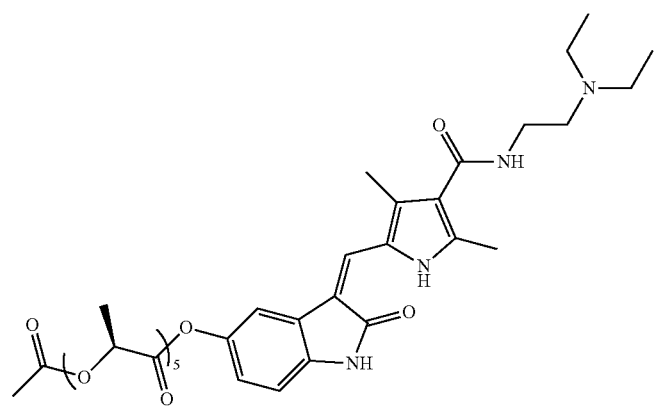 |

TABLE A-continued
Non-limiting Examples of Prodrugs
| Comp. # | Structure |
|---|---|
| 35 | 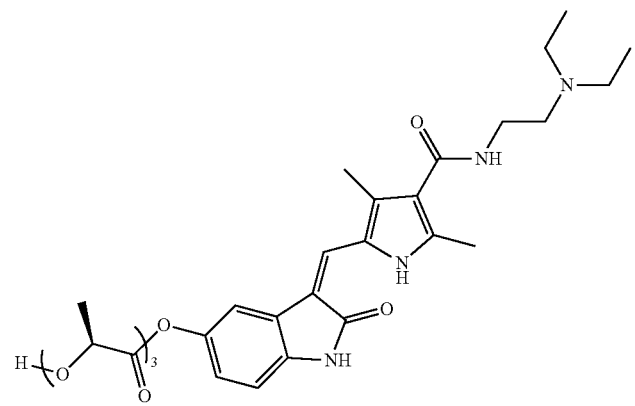 |
| 36 | 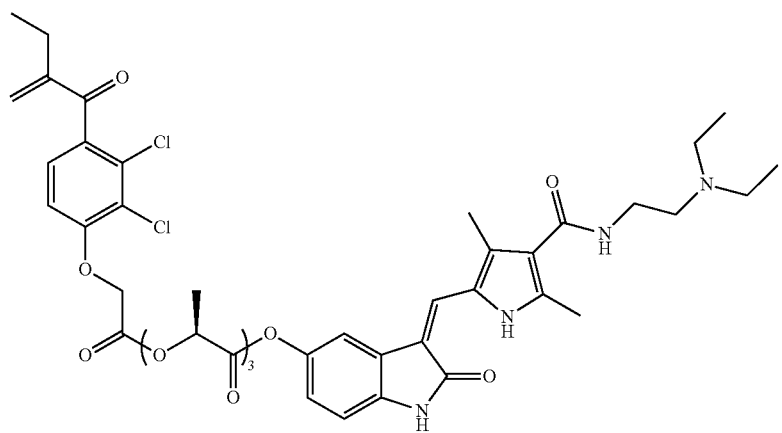 |
| 37 | 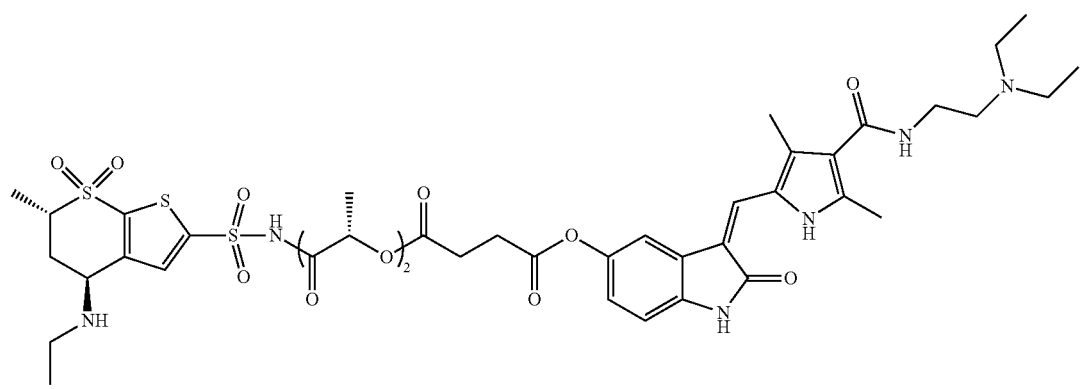 |

TABLE A-continued

Non-limiting Examples of Prodrugs

| Comp. # | Structure |
|---------|-----------|
| 38 | 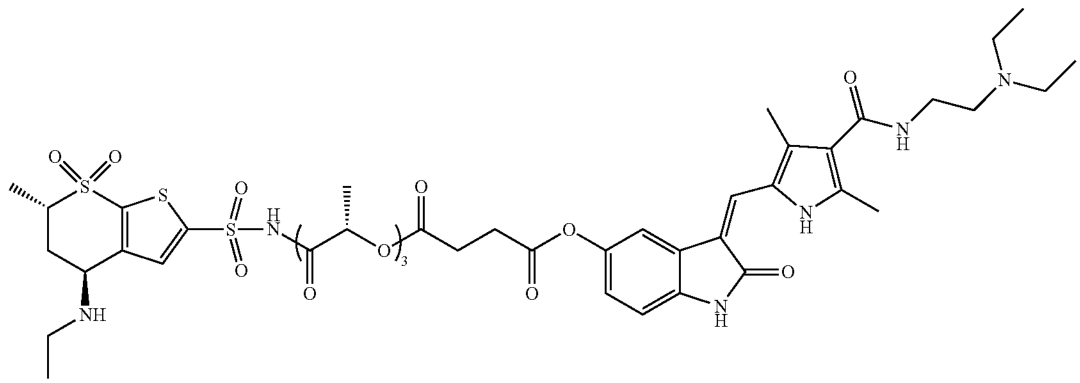 |
| 39 | 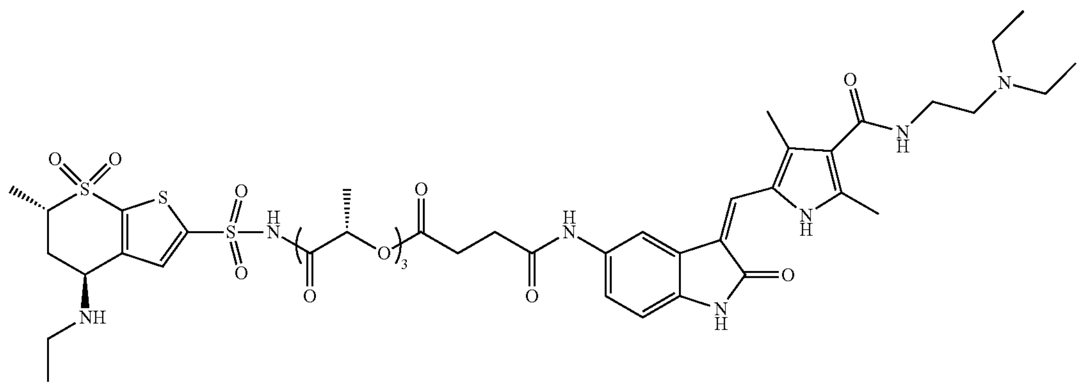 |
| 40 | 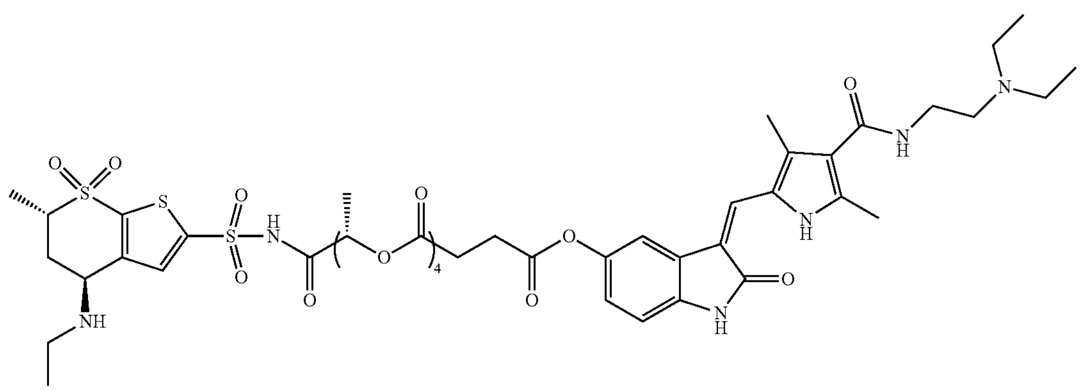 |
| 41 | 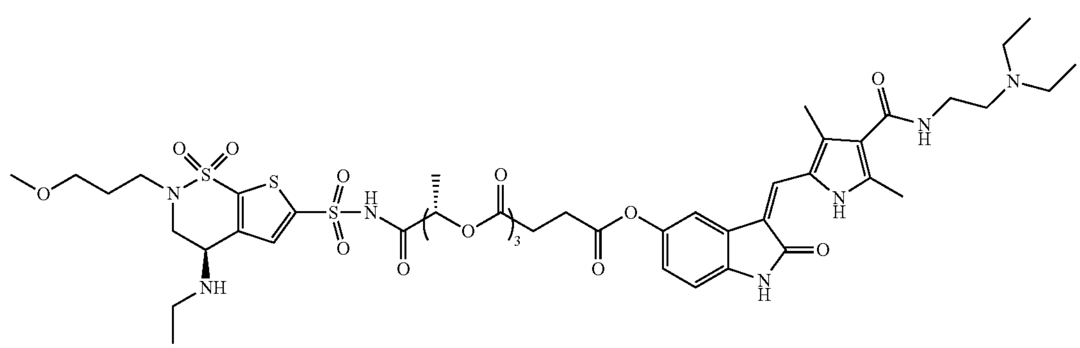 |

TABLE A-continued

Non-limiting Examples of Prodrugs

| Comp. # | Structure |
|---|---|
| 42 | 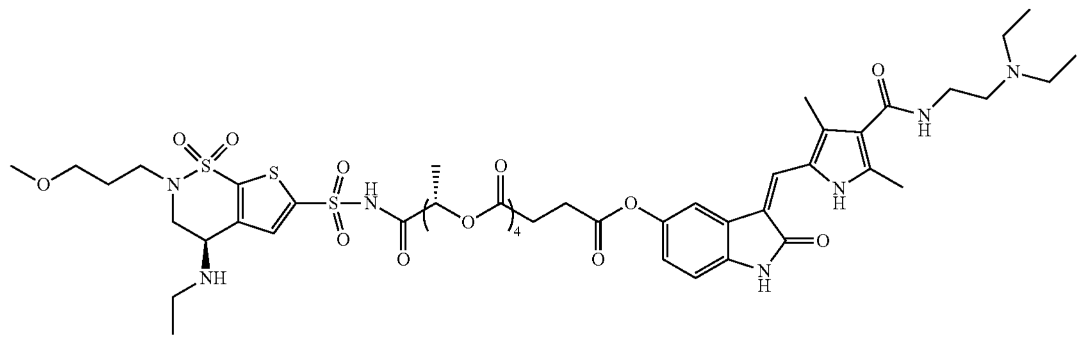 |
| 43 | 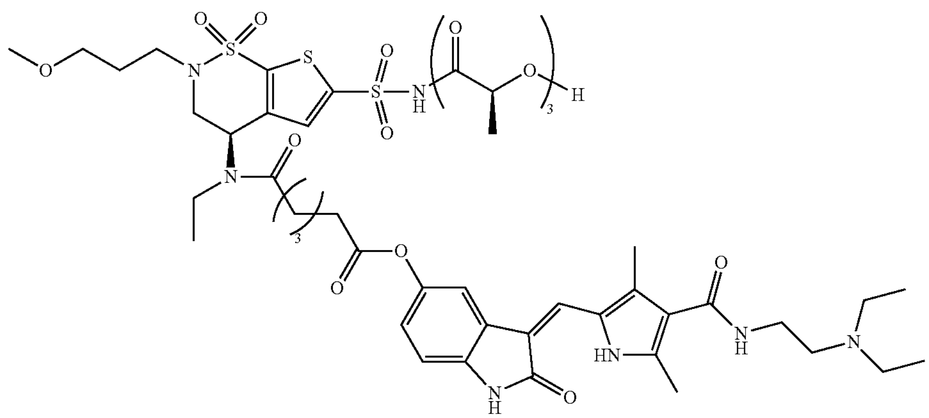 |
| 44 | 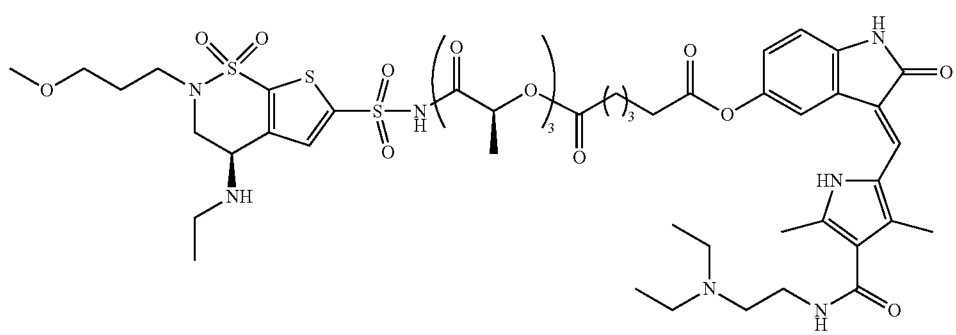 |

TABLE B

Non-limiting Examples of Prodrugs

| 45 | |

TABLE B-continued
Non-limiting Examples of Prodrugs
46 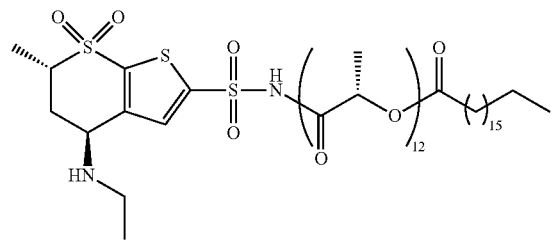
47 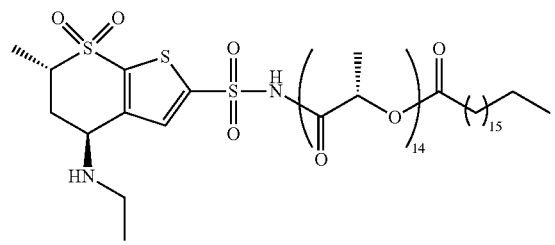
48 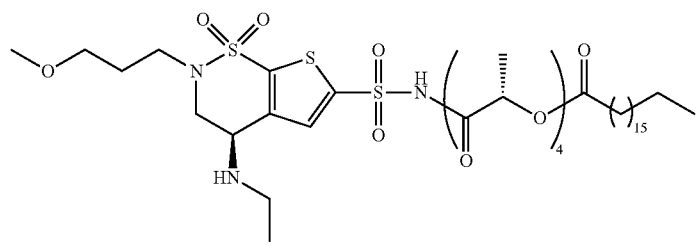
49 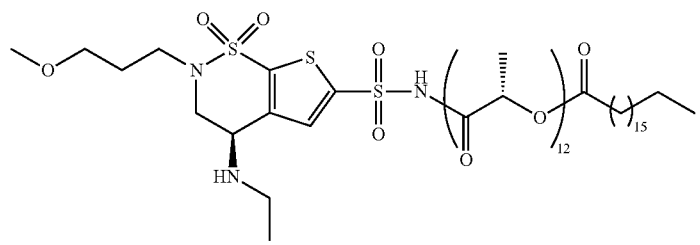
50 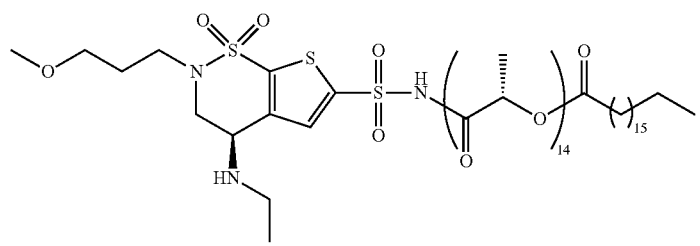
51 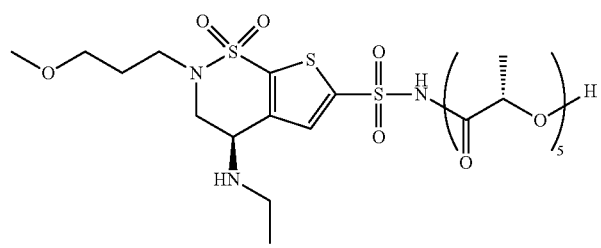

TABLE B-continued
Non-limiting Examples of Prodrugs
52 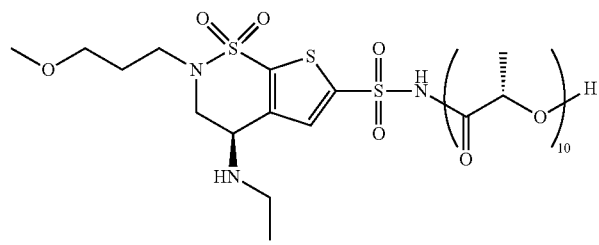
53 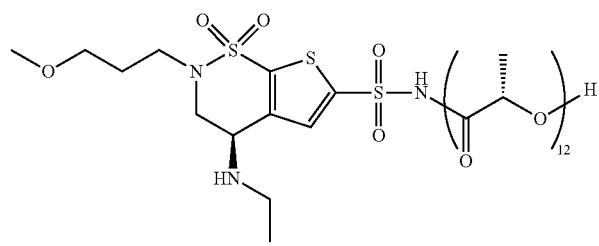
54 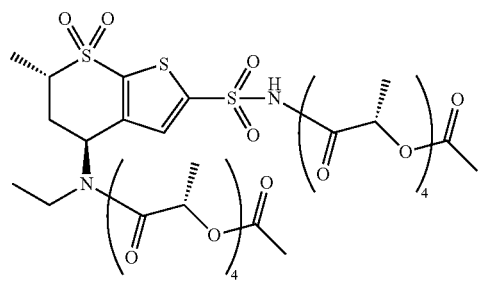
55 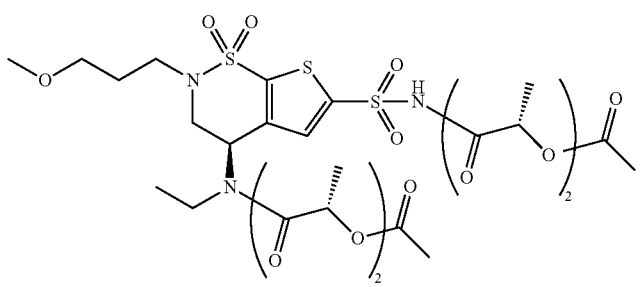
56 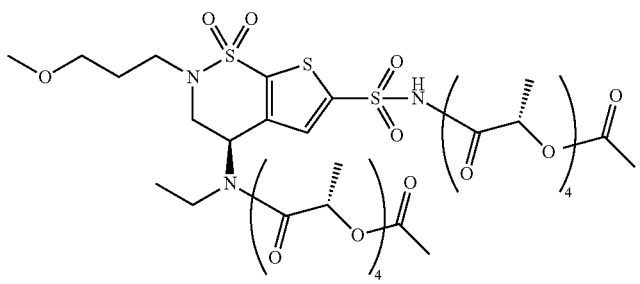
57 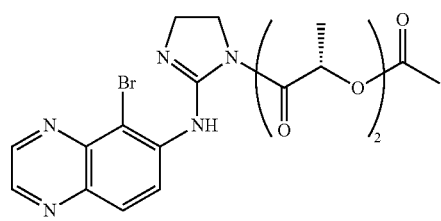

US 11,160,870 B2
TABLE B-continued
Non-limiting Examples of Prodrugs
58 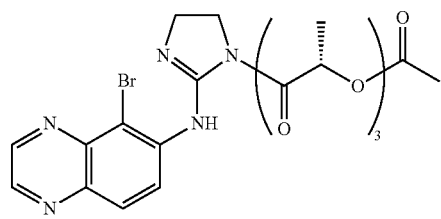
59 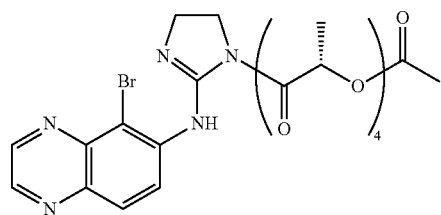
60 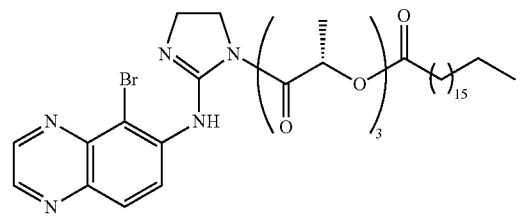
61 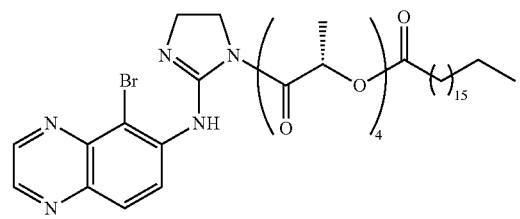
62 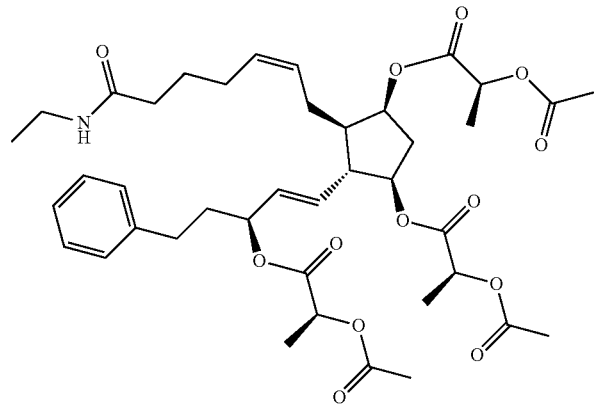 [SMILES: CCNC(=O)CCC/C=C\C[C@@H]1[C@@H](/C=C/[C@H](CCc2ccccc2)OC(=O)[C@H](C)OC(C)=O)[C@H](OC(=O)[C@H](C)OC(C)=O)C[C@@H]1OC(=O)[C@H](C)OC(C)=O]

TABLE B-continued
Non-limiting Examples of Prodrugs
63
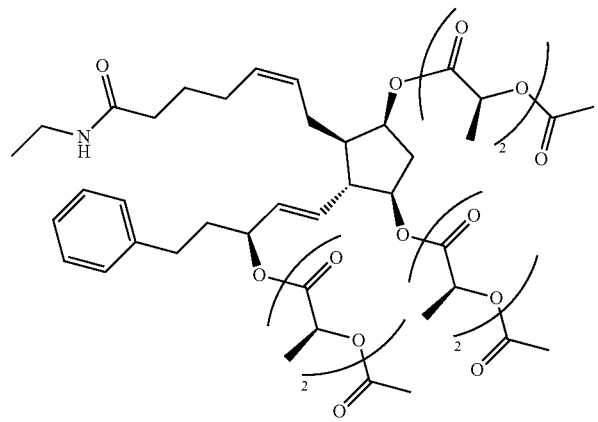
64
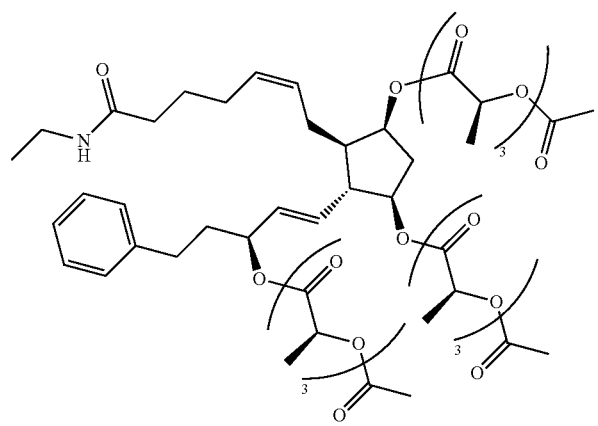
65
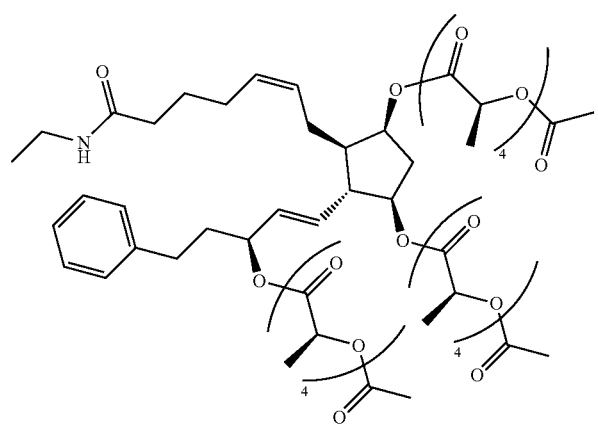

TABLE B-continued
Non-limiting Examples of Prodrugs
| 66 | 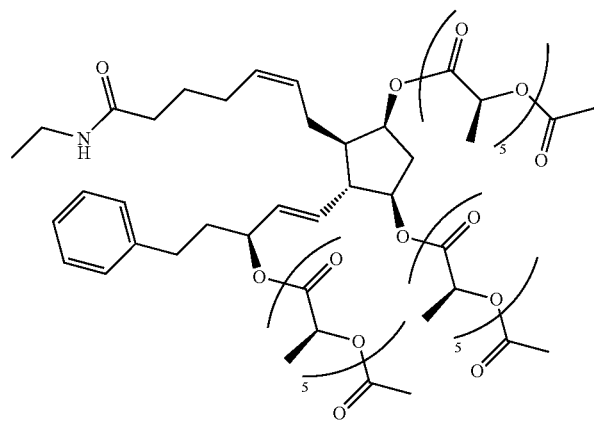 |
| --- | --- |
| 67 | 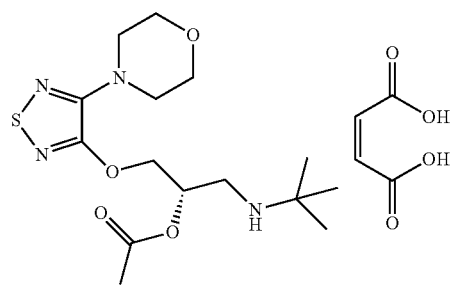 |
| 68 | 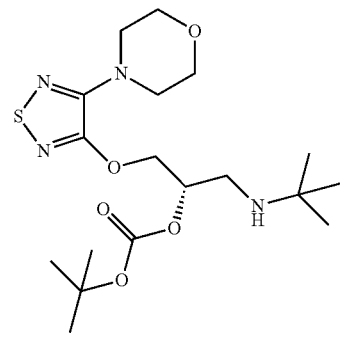 [SMILES: CC(C)(C)NC[C@@H](COc1nsnc1N1CCOCC1)OC(=O)OC(C)(C)C] |
| 69 | 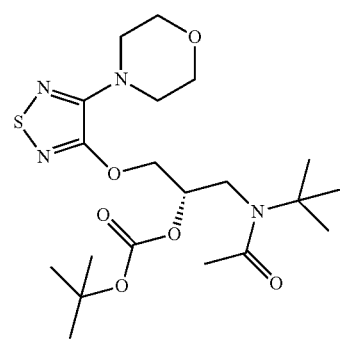 [SMILES: CC(=O)N(C[C@@H](COc1nsnc1N1CCOCC1)OC(=O)OC(C)(C)C)C(C)(C)C] |

TABLE B-continued
Non-limiting Examples of Prodrugs
70 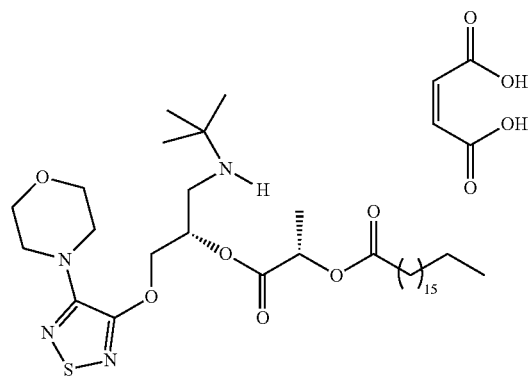
71 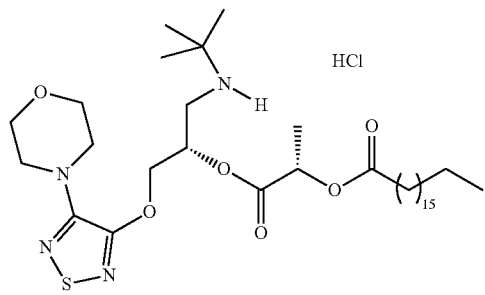
72 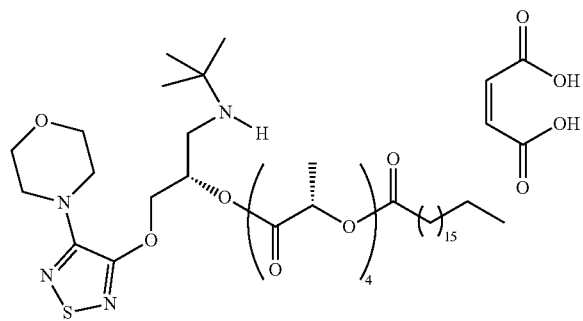
73 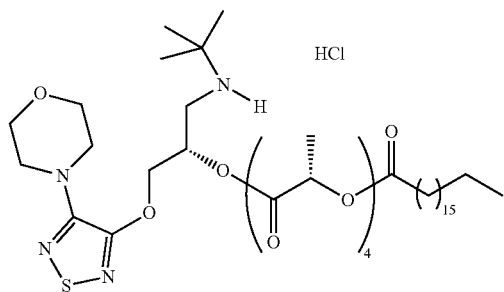

TABLE B-continued
Non-limiting Examples of Prodrugs
74 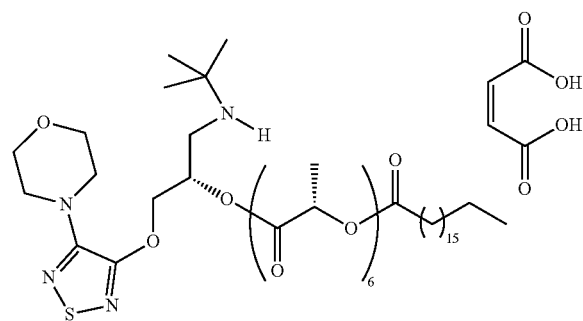
75 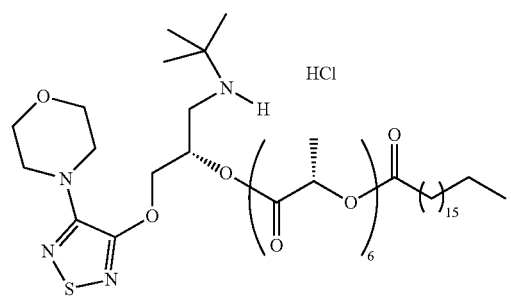
76 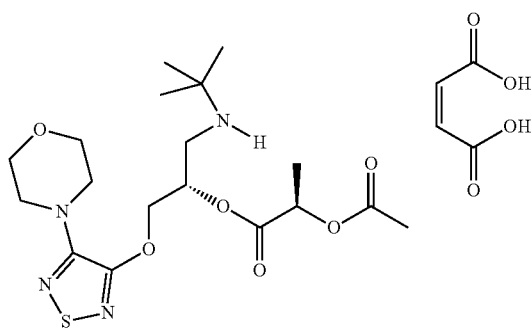 [SMILES: CC(=O)O[C@H](C)C(=O)O[C@@H](CNC(C)(C)C)COc1nsnc1N1CCOCC1 ; O=C(O)/C=C\C(=O)O]
77 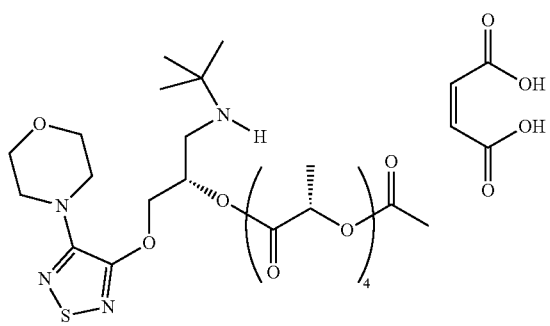
78 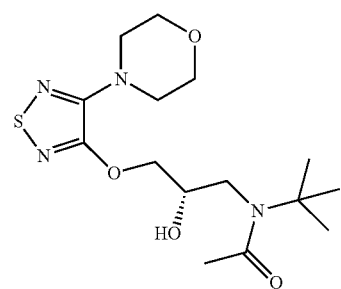 [SMILES: CC(=O)N(C[C@H](O)COc1nsnc1N1CCOCC1)C(C)(C)C]

TABLE B-continued
Non-limiting Examples of Prodrugs
79 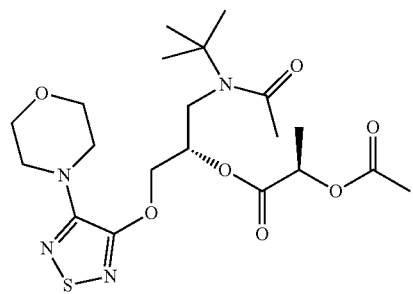 [SMILES: CC(=O)O[C@H](C)C(=O)O[C@H](COc1nsnc1N1CCOCC1)CN(C(C)=O)C(C)(C)C]
80 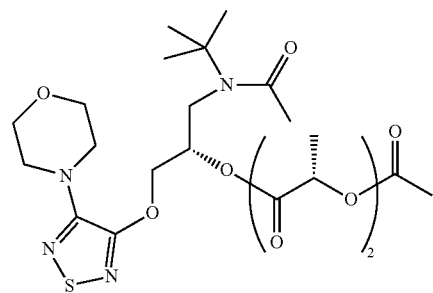
81 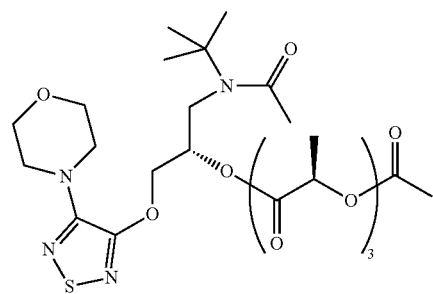
82 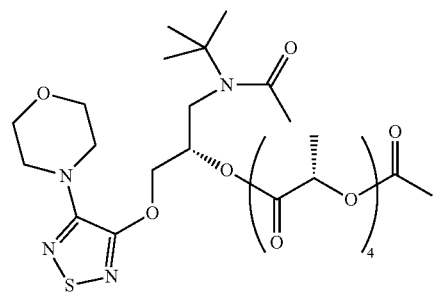
83 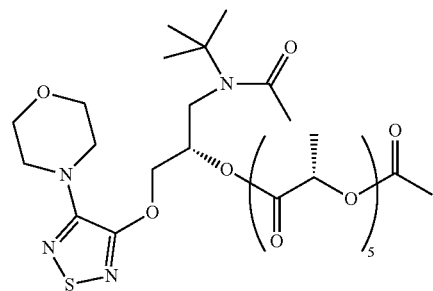

TABLE B-continued
Non-limiting Examples of Prodrugs
84
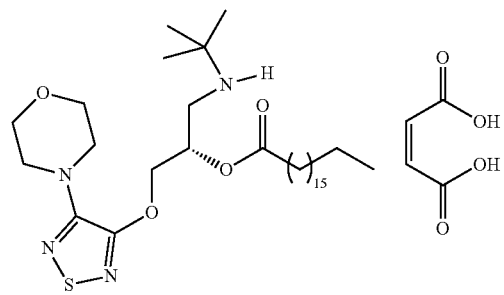
85
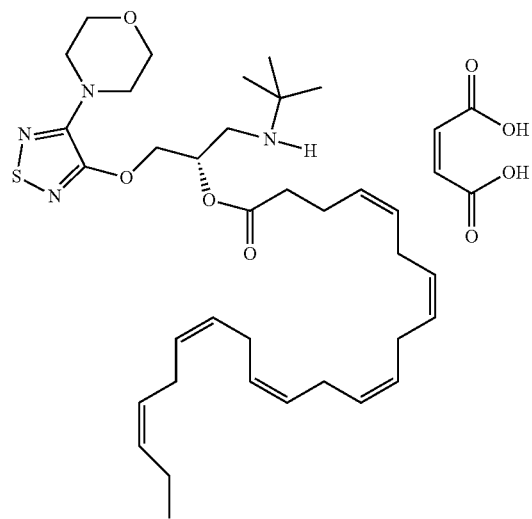
86
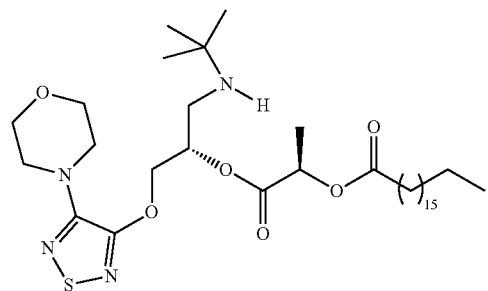
87
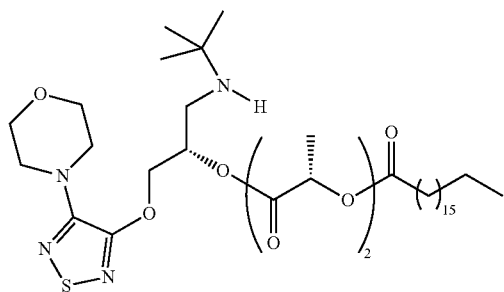

TABLE B-continued
Non-limiting Examples of Prodrugs
88
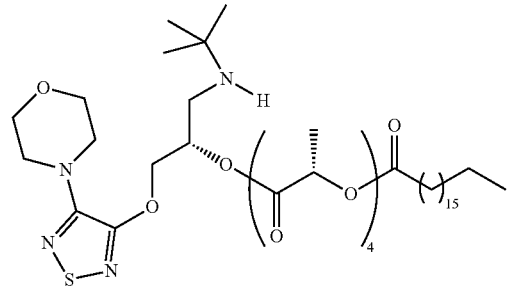
89
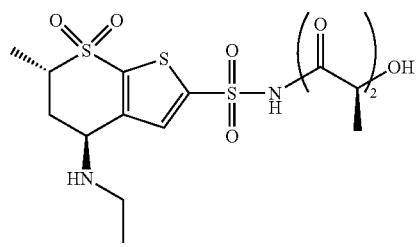
90
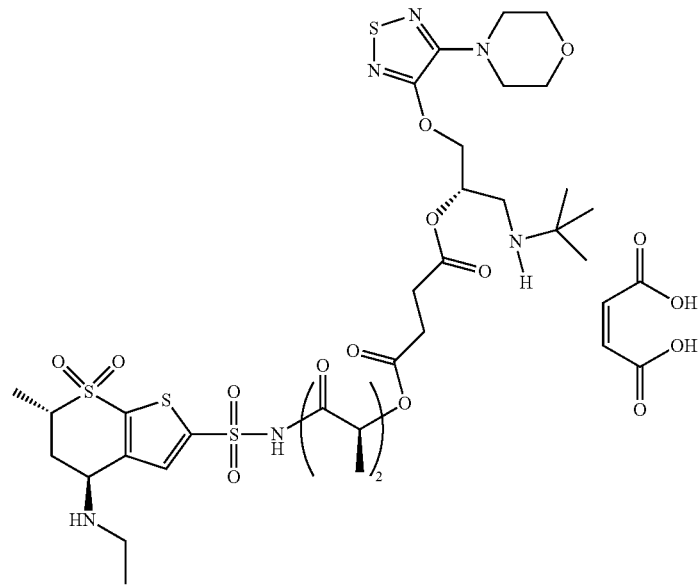

:
| | |
|---|---|
| TABLE B-continued | |
| Non-limiting Examples of Prodrugs | |
| 91 | 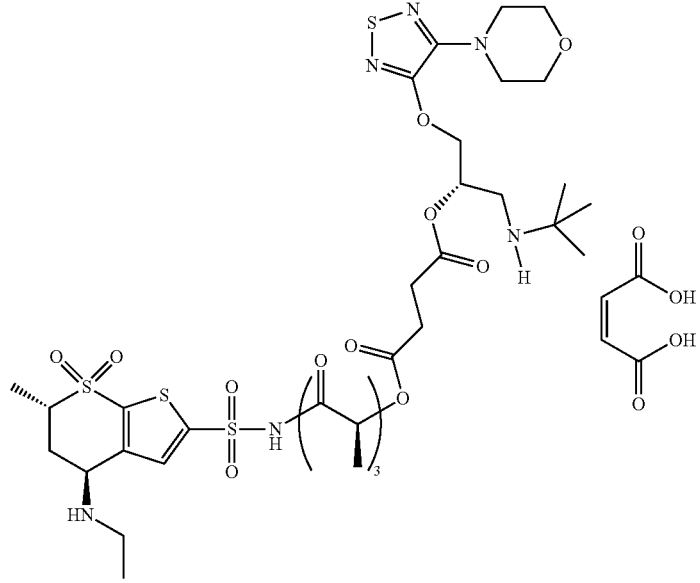 |
| 92 | 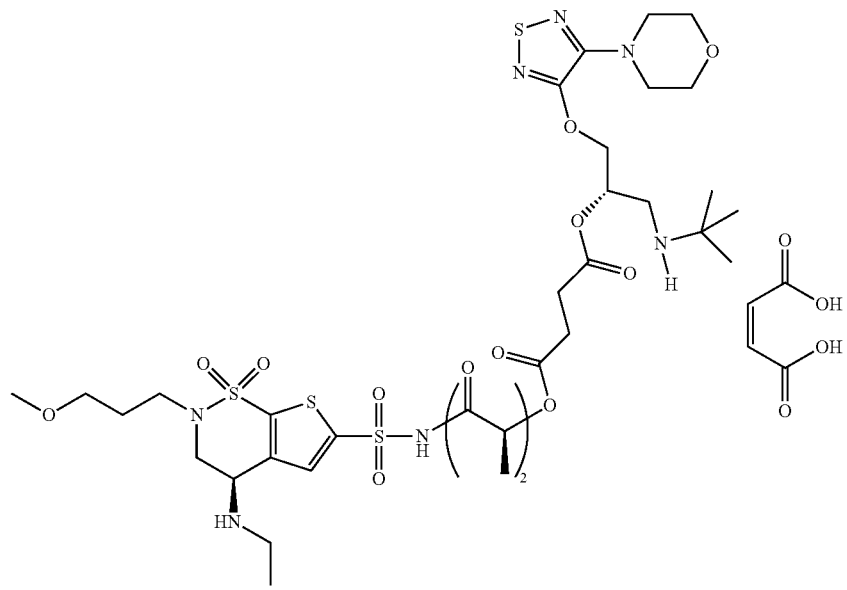 |

TABLE B-continued
Non-limiting Examples of Prodrugs
93
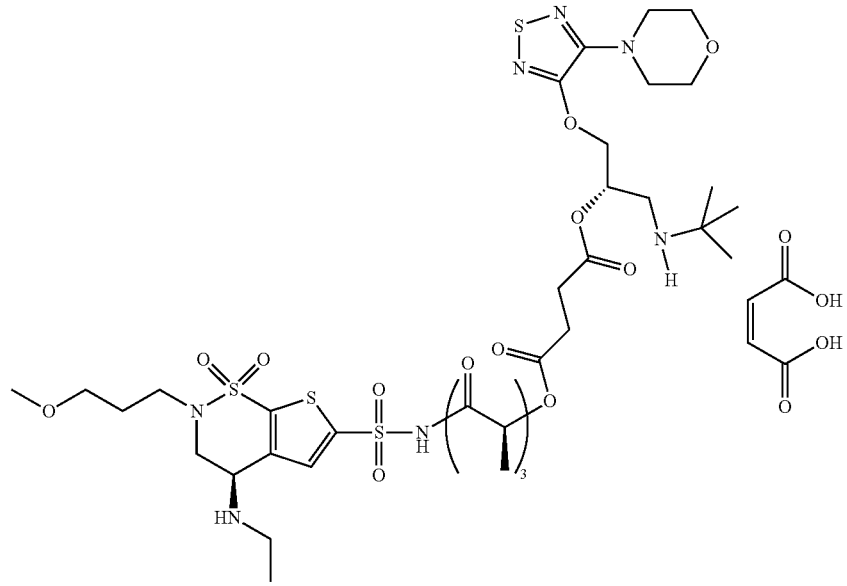
94
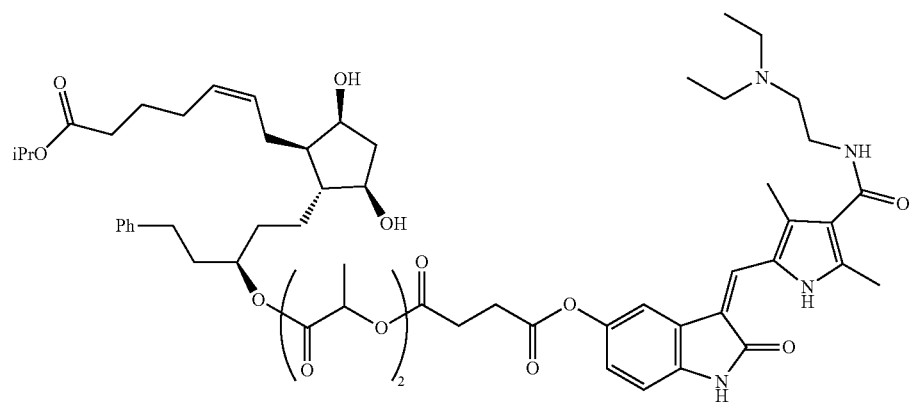
95
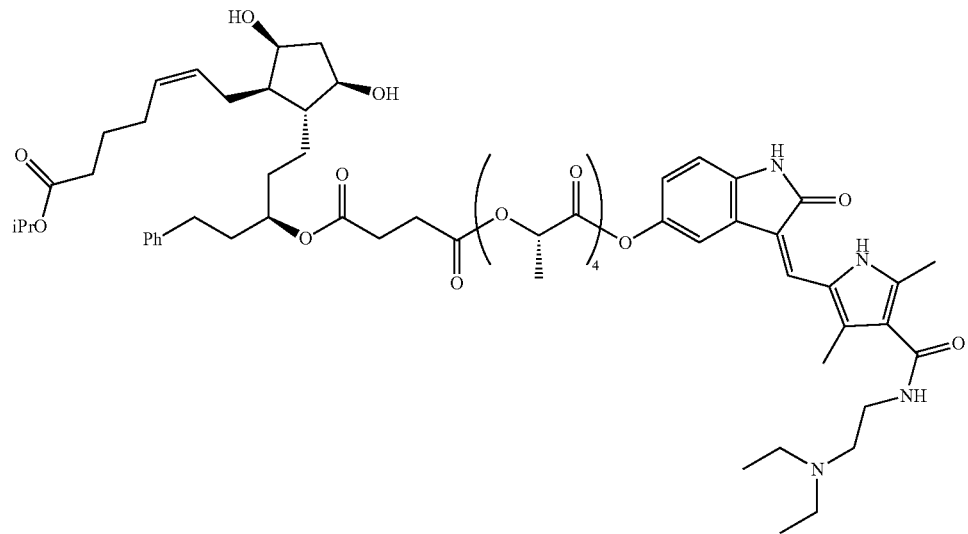

TABLE B-continued
Non-limiting Examples of Prodrugs
96 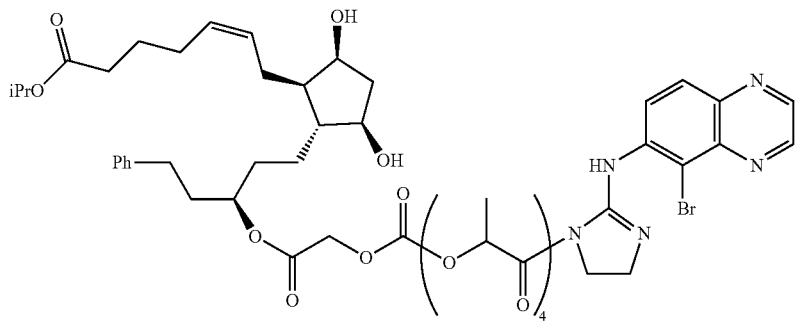
TABLE C
Non-limiting Examples of Prodrugs
97 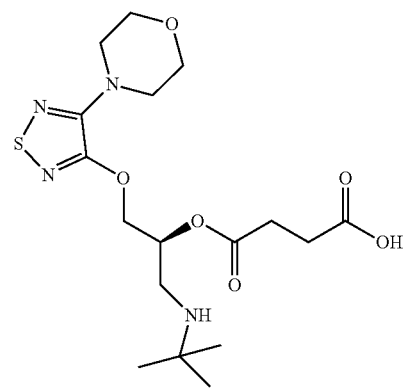 [SMILES: CC(C)(C)NC[C@@H](COc1nsnc1N1CCOCC1)OC(=O)CCC(=O)O]
98 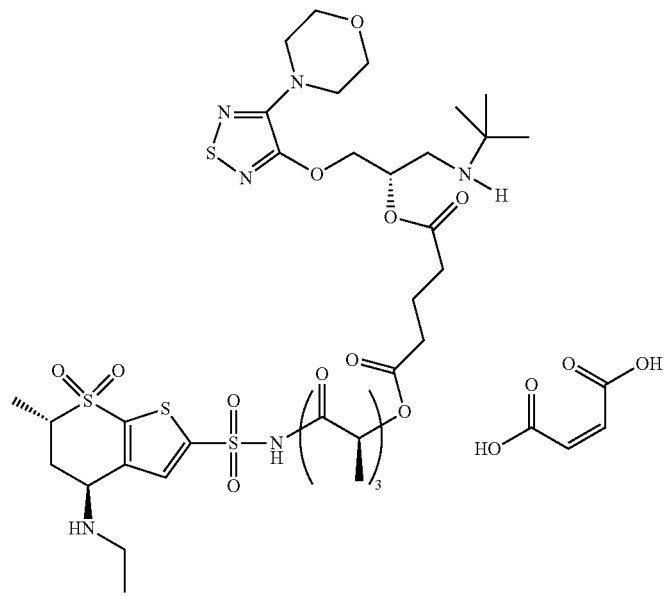

TABLE C-continued
Non-limiting Examples of Prodrugs
99 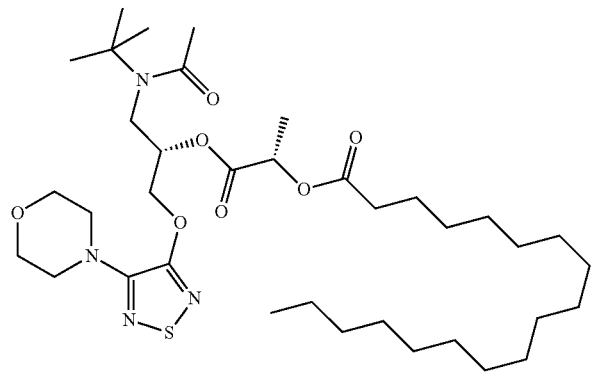 [SMILES: CCCCCCCCCCCCCCCCCC(=O)O[C@@H](C)C(=O)O[C@H](COc1nsnc1N1CCOCC1)CN(C(C)=O)C(C)(C)C]
100 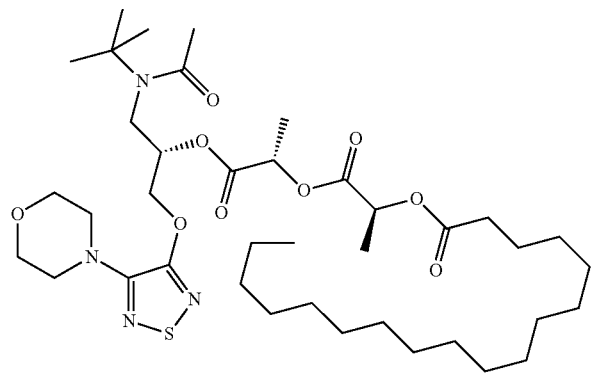 [SMILES: CCCCCCCCCCCCCCCCCC(=O)O[C@@H](C)C(=O)O[C@@H](C)C(=O)O[C@H](COc1nsnc1N1CCOCC1)CN(C(C)=O)C(C)(C)C]
101 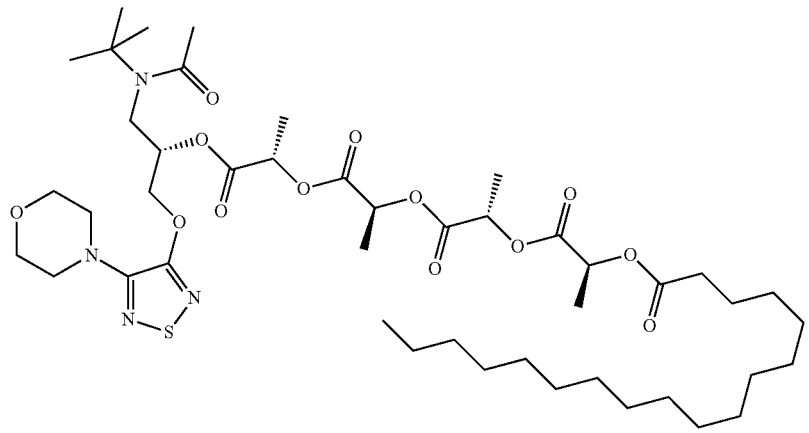 [SMILES: CCCCCCCCCCCCCCCCCC(=O)O[C@@H](C)C(=O)O[C@@H](C)C(=O)O[C@@H](C)C(=O)O[C@@H](C)C(=O)O[C@H](COc1nsnc1N1CCOCC1)CN(C(C)=O)C(C)(C)C]
102 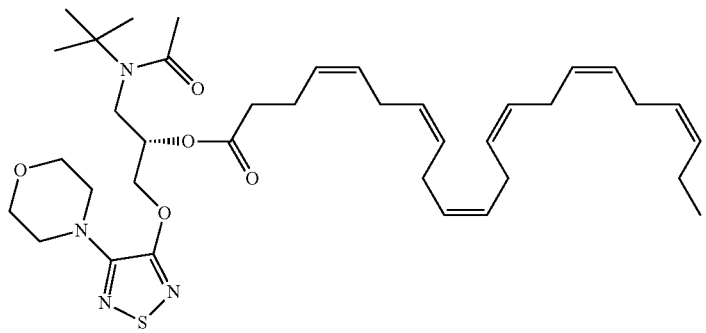 [SMILES: CC/C=C\C/C=C\C/C=C\C/C=C\C/C=C\C/C=C\CCC(=O)O[C@H](COc1nsnc1N1CCOCC1)CN(C(C)=O)C(C)(C)C]

TABLE C-continued
Non-limiting Examples of Prodrugs
103
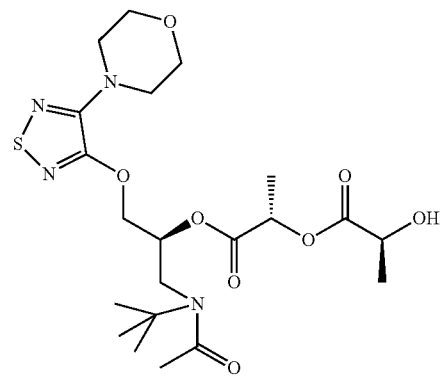 [SMILES: CC(=O)N(C[C@@H](COc1nsnc1N1CCOCC1)OC(=O)[C@H](C)OC(=O)[C@H](C)O)C(C)(C)C]
104
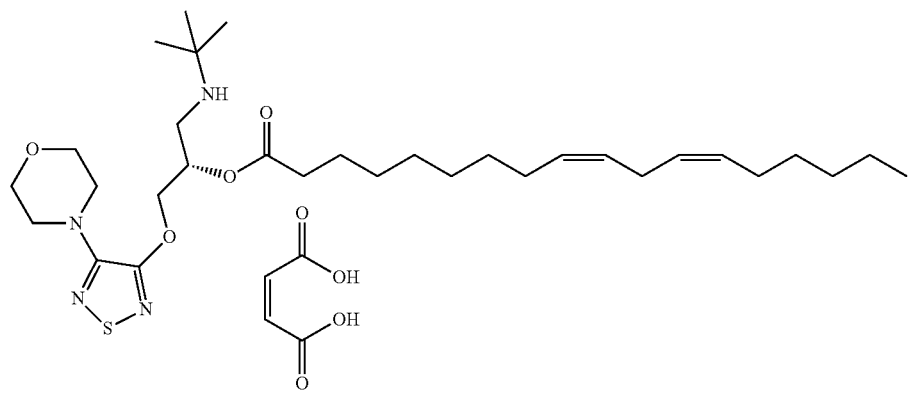
105
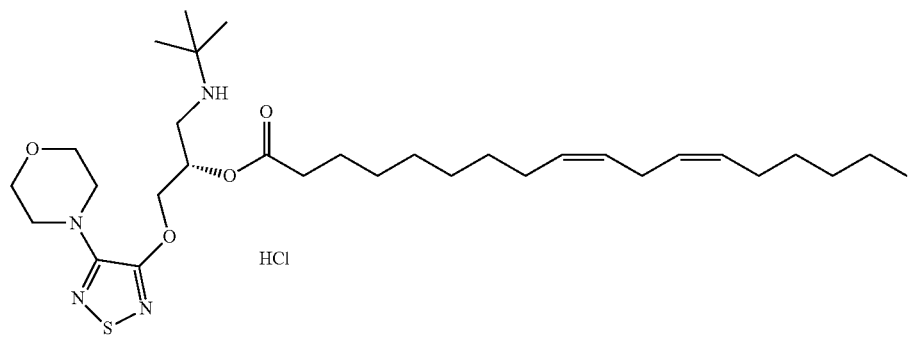 [SMILES: CCCCC/C=C\C/C=C\CCCCCCCC(=O)O[C@@H](CNC(C)(C)C)COc1nsnc1N1CCOCC1 ; Cl]
106
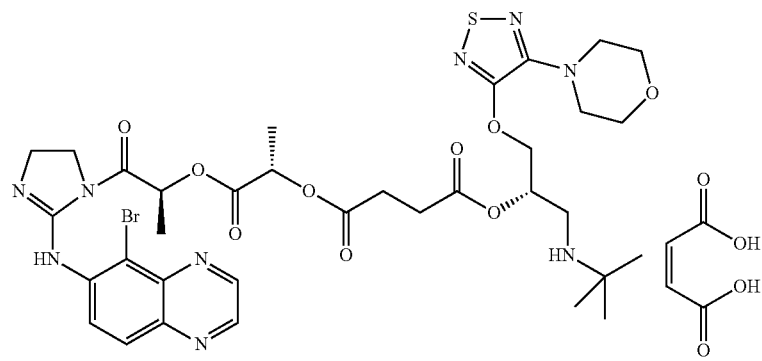

TABLE C-continued
Non-limiting Examples of Prodrugs
107
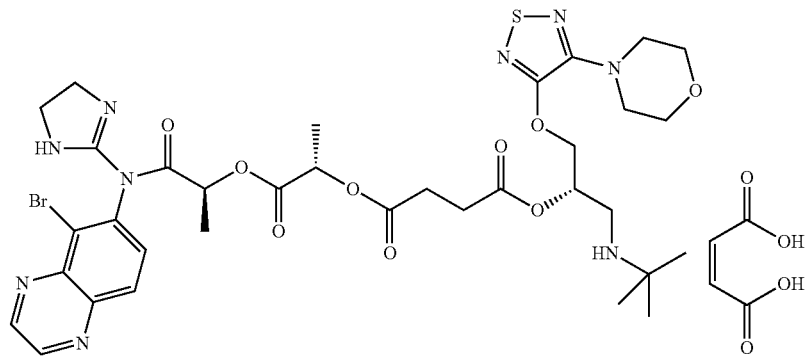
108
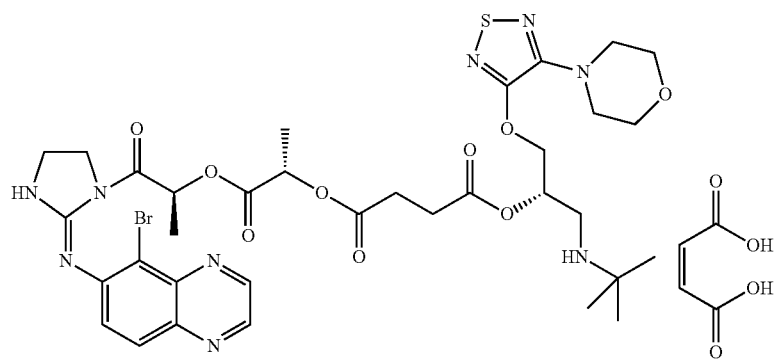
109
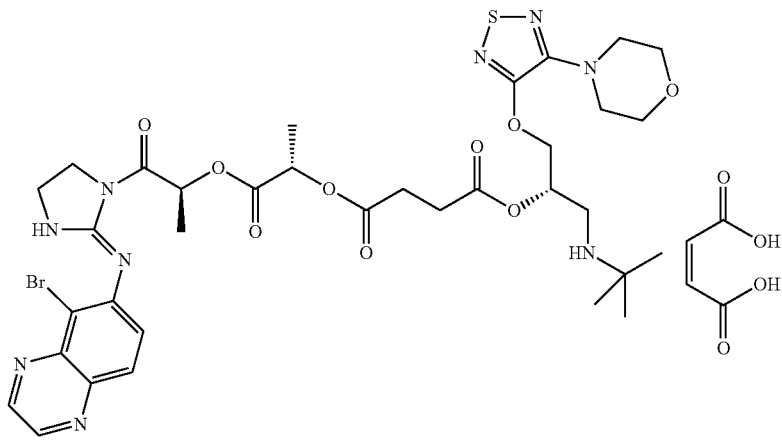
110
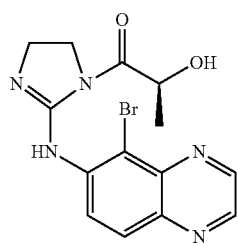 [SMILES: C[C@H](O)C(=O)N1CCN=C1Nc1ccc2nccnc2c1Br]

| | |
|---|---|
| 111 | 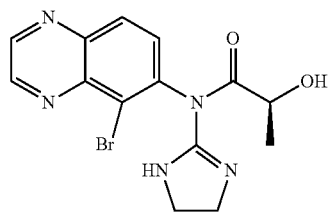 [SMILES: C[C@H](O)C(=O)N(C1=NCCN1)c1ccc2nccnc2c1Br] |
| 112 | 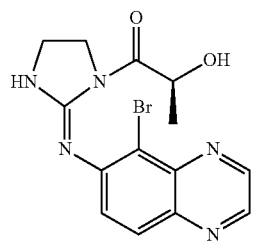 [SMILES: C[C@H](O)C(=O)N1CCN/C1=N/c1ccc2nccnc2c1Br] |
| 113 | 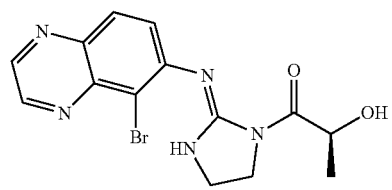 [SMILES: C[C@H](O)C(=O)N1CCN/C1=N\c1ccc2nccnc2c1Br] |
| 114 | 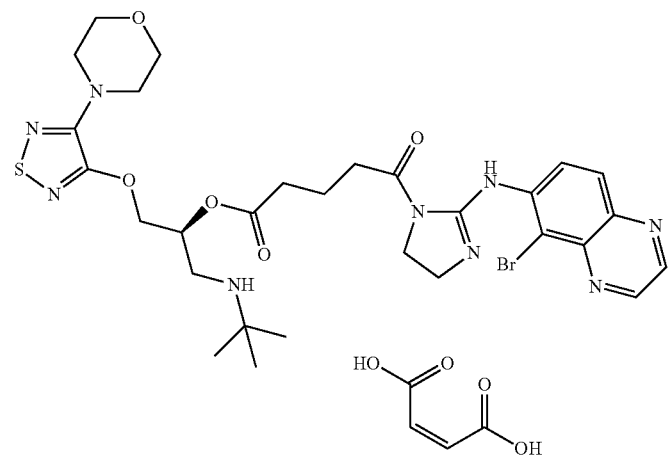 [SMILES: CC(C)(C)NC[C@@H](COc1nsnc1N1CCOCC1)OC(=O)CCCC(=O)N1CCN=C1Nc1ccc2nccnc2c1Br ; O=C(O)/C=C\C(=O)O] |
| 115 | 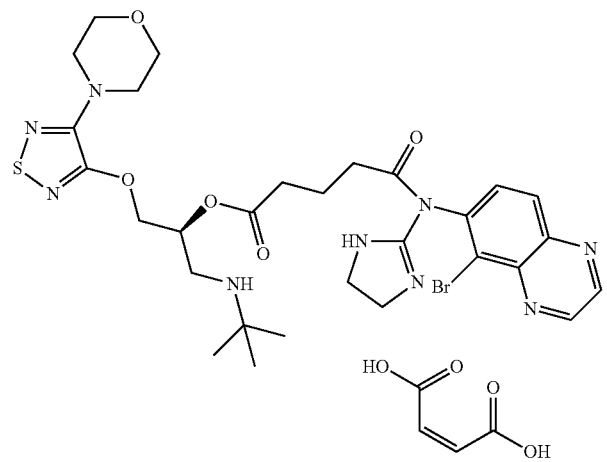 |

TABLE C-continued
Non-limiting Examples of Prodrugs
116
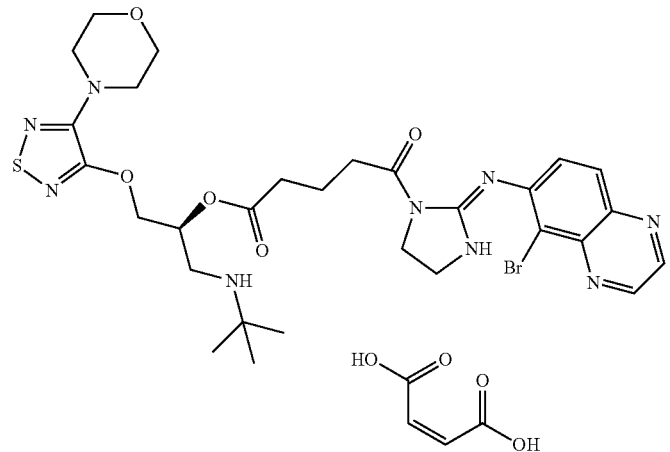 [SMILES: CC(C)(C)NC[C@@H](COc1nsnc1N1CCOCC1)OC(=O)CCCC(=O)N1CCN/C1=N\c1ccc2nccnc2c1Br ; O=C(O)/C=C\C(=O)O]
117
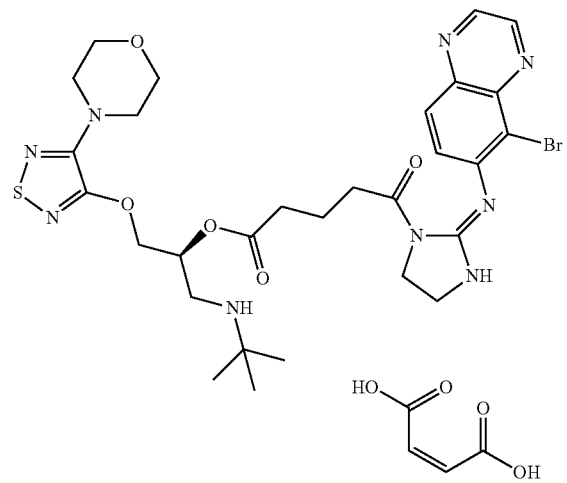 [SMILES: CC(C)(C)NC[C@@H](COc1nsnc1N1CCOCC1)OC(=O)CCCC(=O)N1CCN/C1=N/c1ccc2nccnc2c1Br ; O=C(O)/C=C\C(=O)O]
118
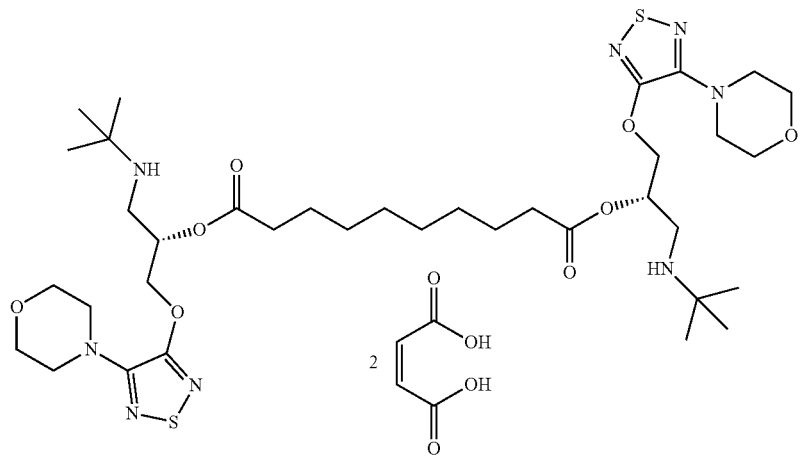

TABLE C-continued
Non-limiting Examples of Prodrugs
119
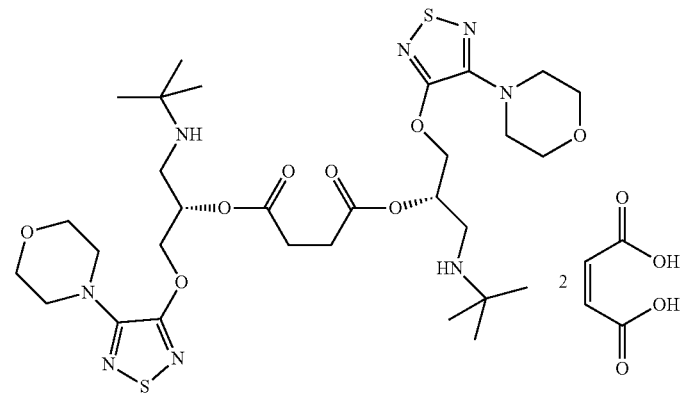 [SMILES: CC(C)(C)NC[C@@H](COc1nsnc1N1CCOCC1)OC(=O)CCC(=O)O[C@@H](CNC(C)(C)C)COc1nsnc1N1CCOCC1 ; O=C(O)/C=C\C(=O)O]
120
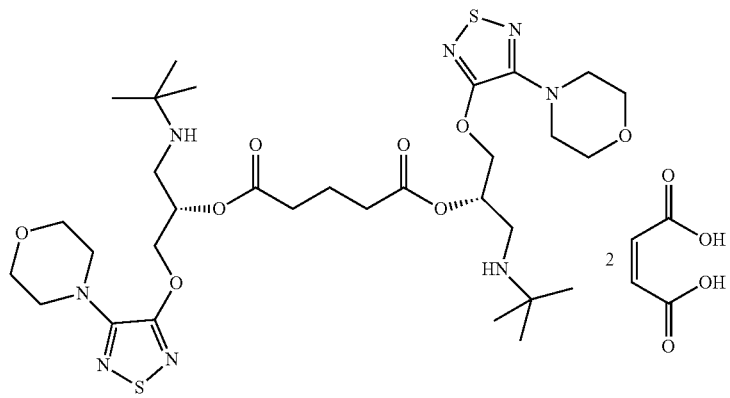
121
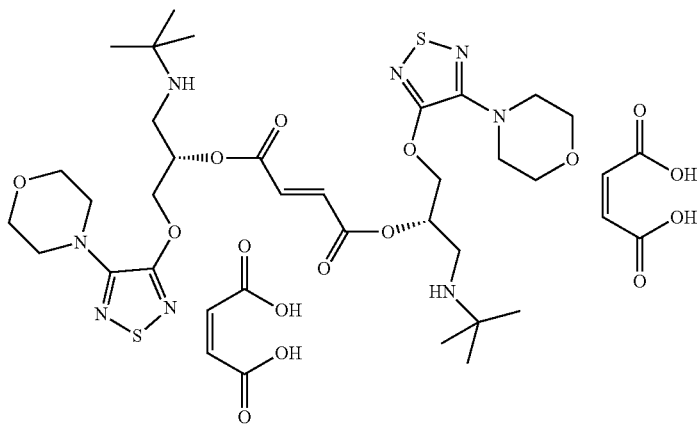
122
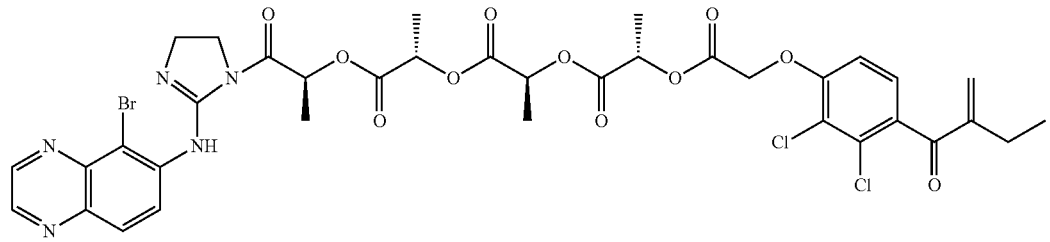 [SMILES: C=C(CC)C(=O)c1ccc(OCC(=O)O[C@@H](C)C(=O)O[C@@H](C)C(=O)O[C@@H](C)C(=O)O[C@@H](C)C(=O)N2CCN=C2Nc2ccc3nccnc3c2Br)c(Cl)c1Cl]

TABLE C-continued
Non-limiting Examples of Prodrugs
123 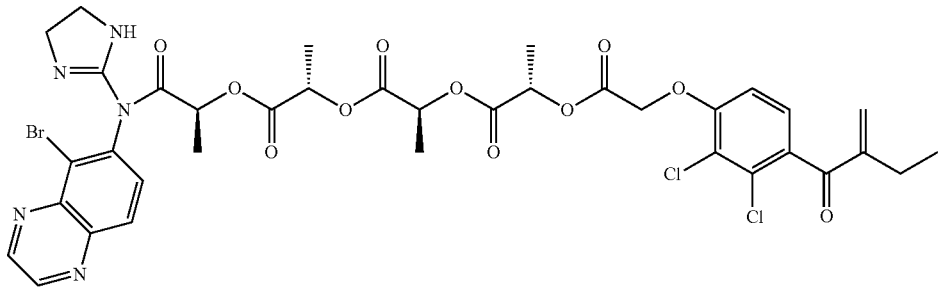 [SMILES: C=C(CC)C(=O)c1ccc(OCC(=O)O[C@@H](C)C(=O)O[C@@H](C)C(=O)O[C@@H](C)C(=O)O[C@@H](C)C(=O)N(C2=NCCN2)c2ccc3nccnc3c2Br)c(Cl)c1Cl]
124 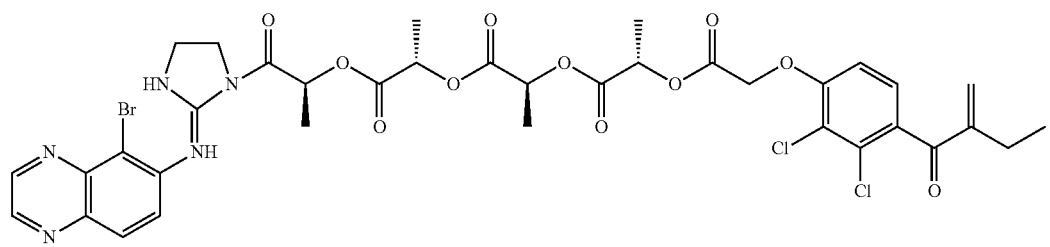 [SMILES: C=C(CC)C(=O)c1ccc(OCC(=O)O[C@@H](C)C(=O)O[C@@H](C)C(=O)O[C@@H](C)C(=O)O[C@@H](C)C(=O)N2CCN/C2=N\c2ccc3nccnc3c2Br)c(Cl)c1Cl]
125 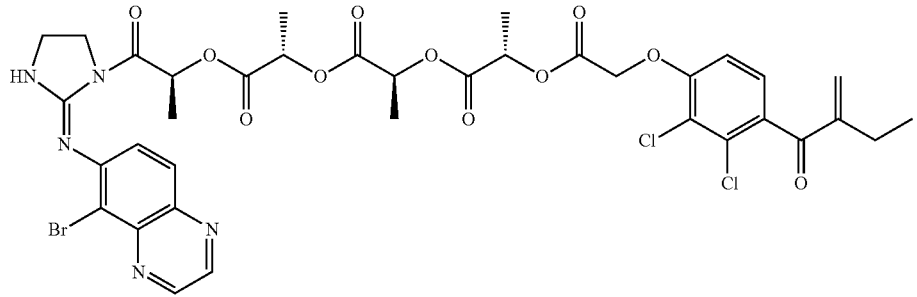 [SMILES: C=C(CC)C(=O)c1ccc(OCC(=O)O[C@@H](C)C(=O)O[C@@H](C)C(=O)O[C@@H](C)C(=O)O[C@@H](C)C(=O)N2CCN/C2=N/c2ccc3nccnc3c2Br)c(Cl)c1Cl]
126 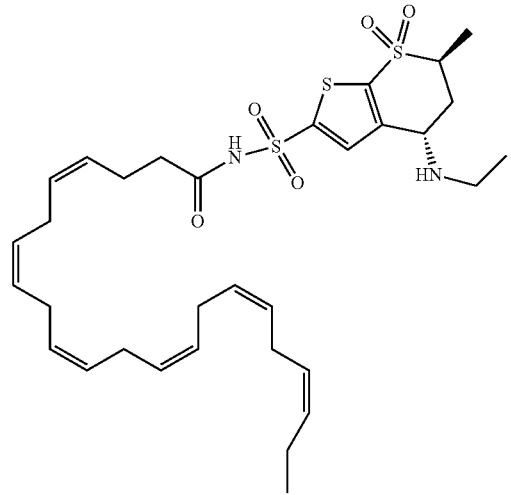 [SMILES: CC/C=C\C/C=C\C/C=C\C/C=C\C/C=C\C/C=C\CCC(=O)NS(=O)(=O)c1cc2c(s1)S(=O)(=O)[C@@H](C)C[C@@H]2NCC]

TABLE C-continued
Non-limiting Examples of Prodrugs
127 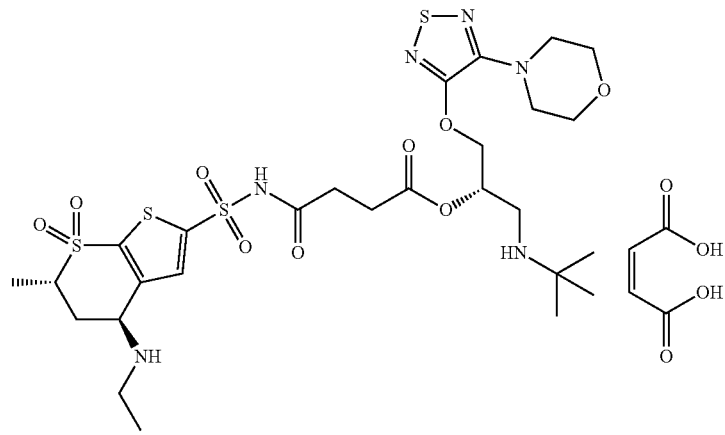
128 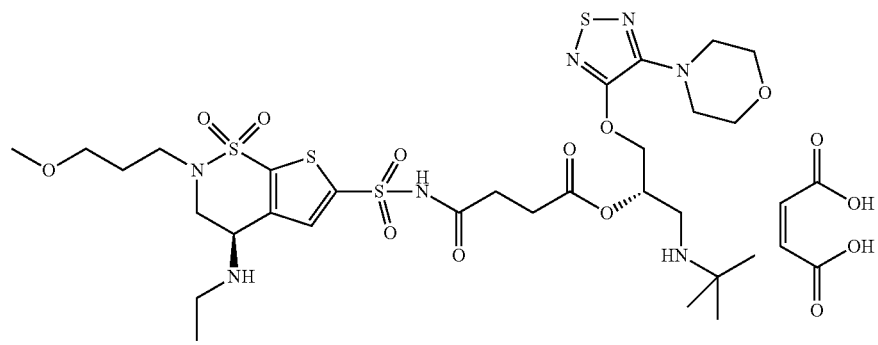
129 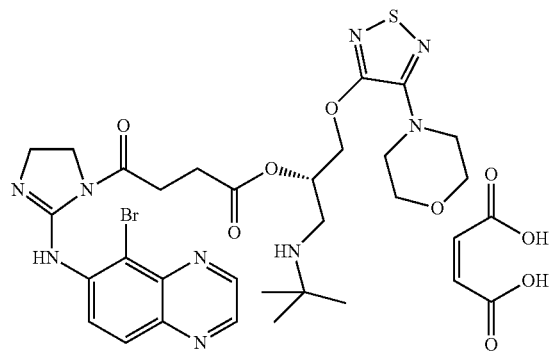
130 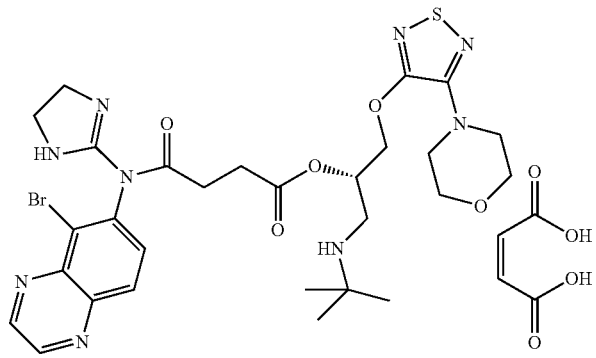

TABLE C-continued
Non-limiting Examples of Prodrugs
131
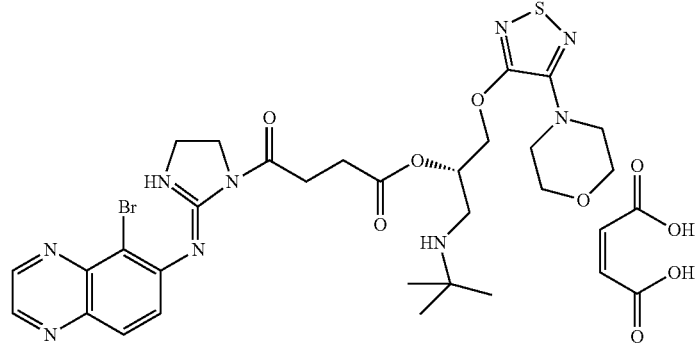
132
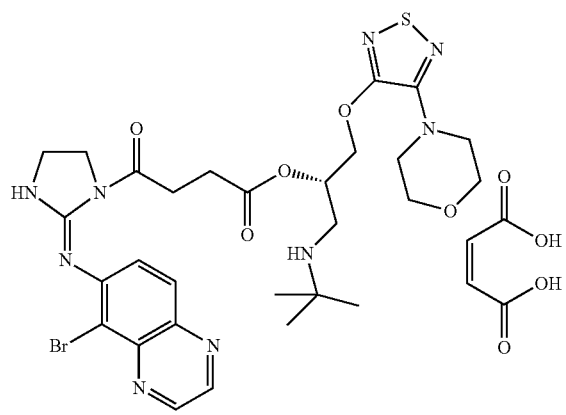
133
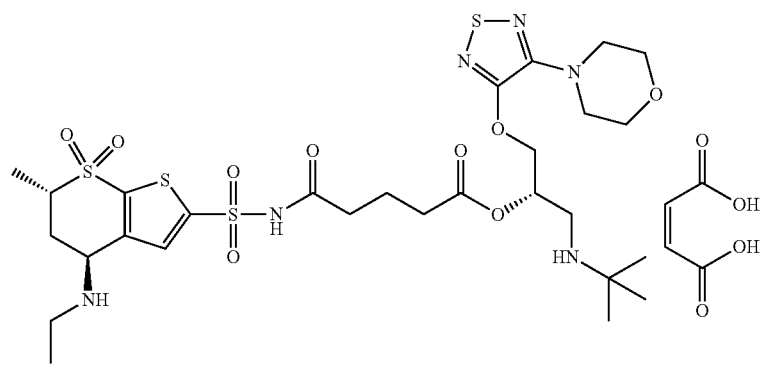
134
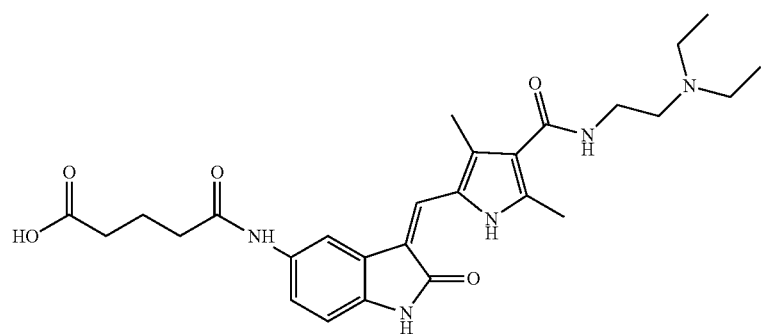 [SMILES: CCN(CC)CCNC(=O)c1c(C)[nH]c(/C=C2\C(=O)Nc3ccc(NC(=O)CCCC(=O)O)cc32)c1C]

TABLE C-continued
Non-limiting Examples of Prodrugs
135
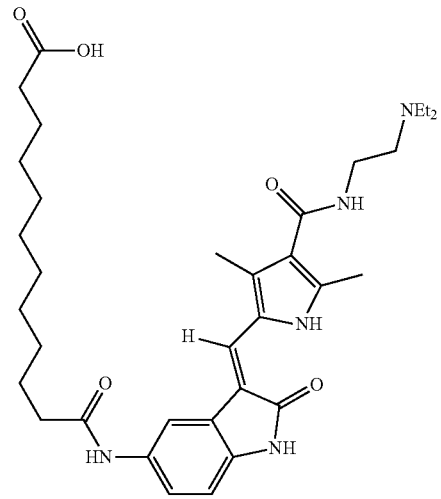
136
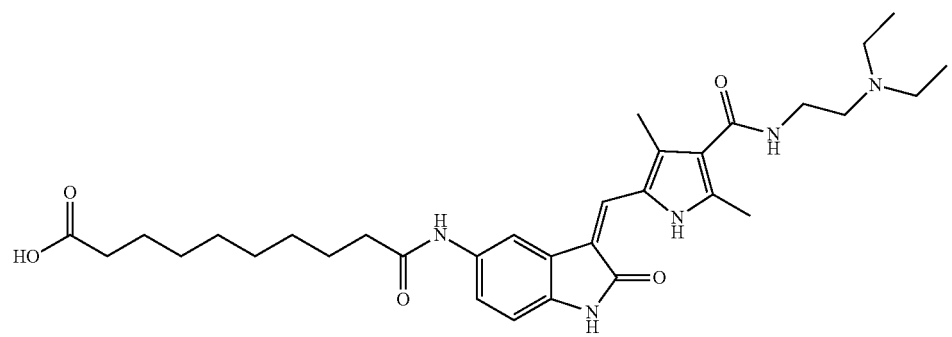 [SMILES: CCN(CC)CCNC(=O)c1c(C)[nH]c(/C=C2\C(=O)Nc3ccc(NC(=O)CCCCCCCCC(=O)O)cc32)c1C]
137
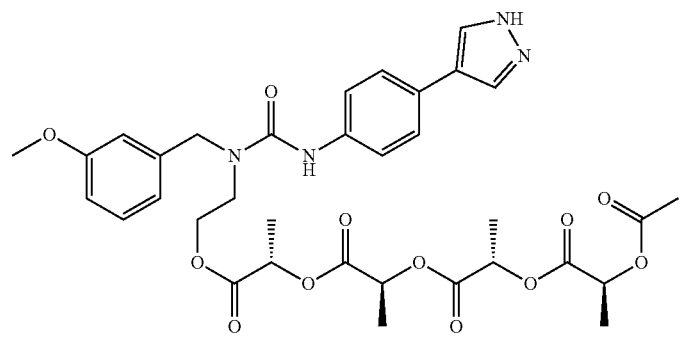 [SMILES: COc1cccc(CN(CCOC(=O)[C@H](C)OC(=O)[C@H](C)OC(=O)[C@H](C)OC(=O)[C@H](C)OC(C)=O)C(=O)Nc2ccc(-c3cn[nH]c3)cc2)c1]
138
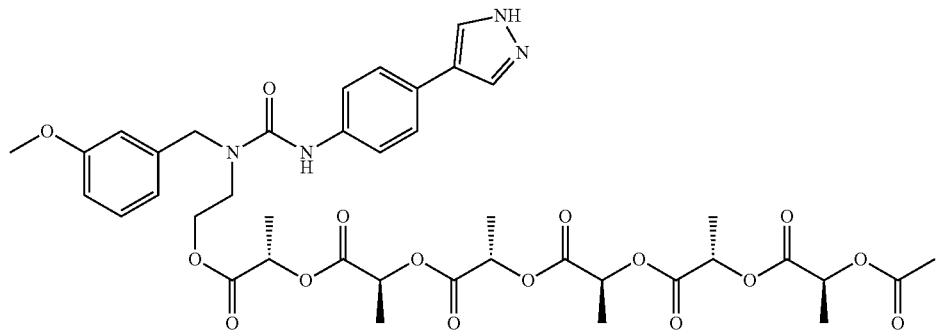 [SMILES: COc1cccc(CN(CCOC(=O)[C@H](C)OC(=O)[C@H](C)OC(=O)[C@H](C)OC(=O)[C@H](C)OC(=O)[C@H](C)OC(=O)[C@H](C)OC(C)=O)C(=O)Nc2ccc(-c3cn[nH]c3)cc2)c1]

TABLE C-continued
Non-limiting Examples of Prodrugs
139
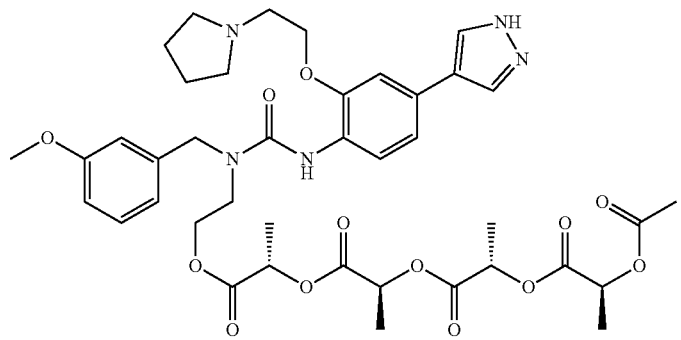 [SMILES: COc1cccc(CN(CCOC(=O)[C@H](C)OC(=O)[C@H](C)OC(=O)[C@H](C)OC(=O)[C@H](C)OC(C)=O)C(=O)Nc2ccc(-c3cn[nH]c3)cc2OCCN2CCCC2)c1]
140
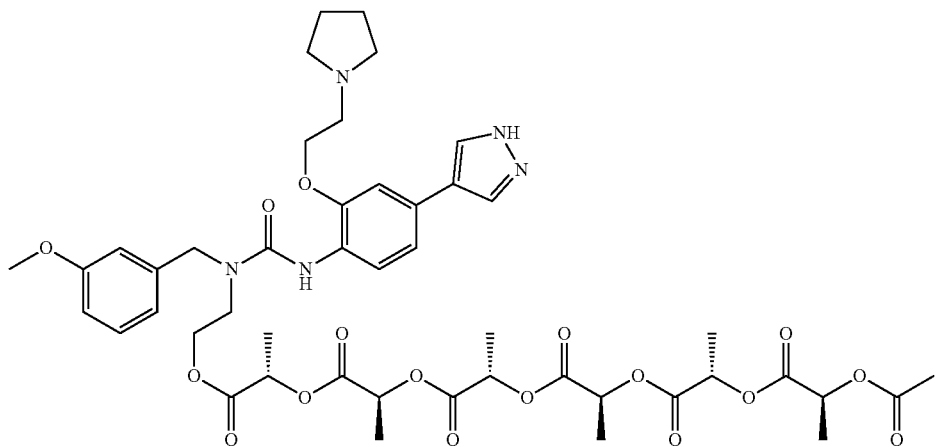 [SMILES: COc1cccc(CN(CCOC(=O)[C@H](C)OC(=O)[C@H](C)OC(=O)[C@H](C)OC(=O)[C@H](C)OC(=O)[C@H](C)OC(=O)[C@H](C)OC(C)=O)C(=O)Nc2ccc(-c3cn[nH]c3)cc2OCCN2CCCC2)c1]
141
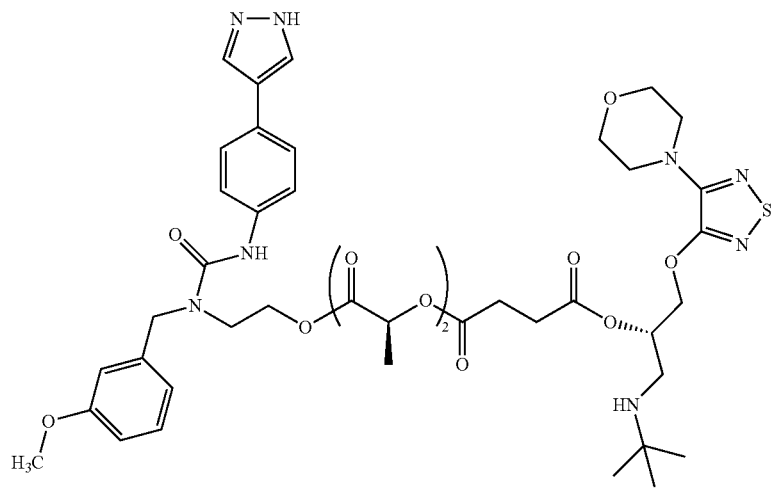

TABLE C-continued
Non-limiting Examples of Prodrugs
142 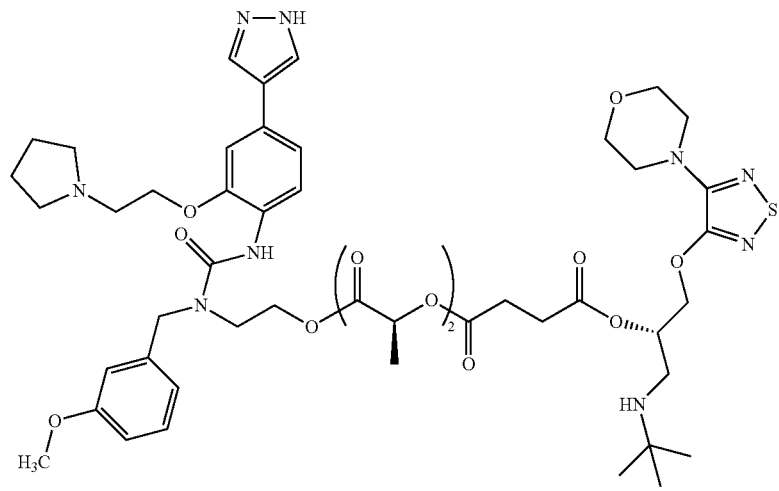
143 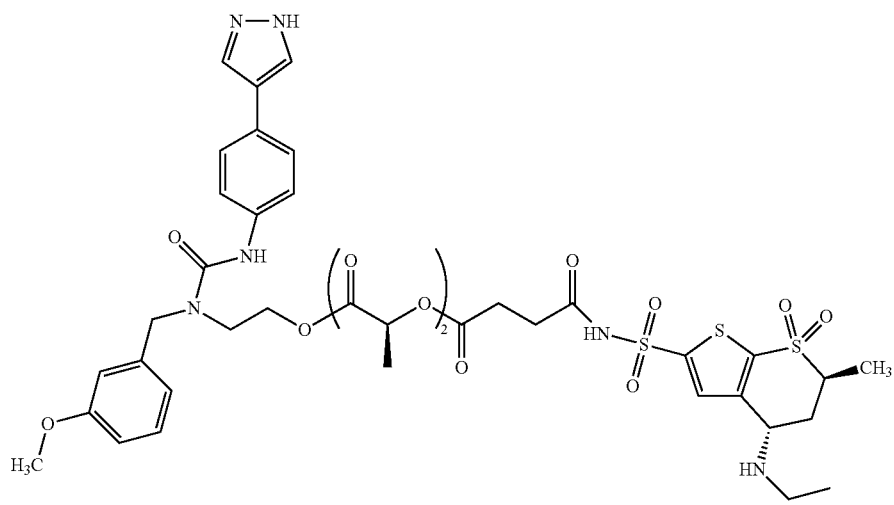
144 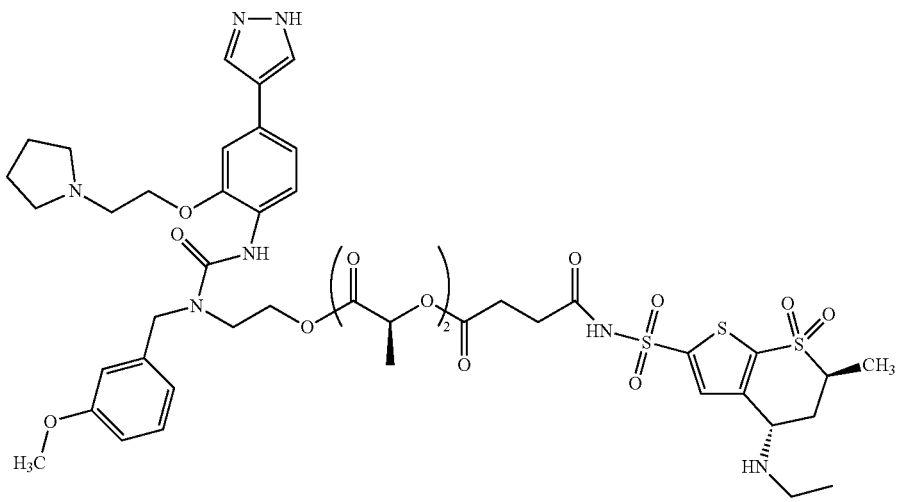

TABLE C-continued
Non-limiting Examples of Prodrugs
145
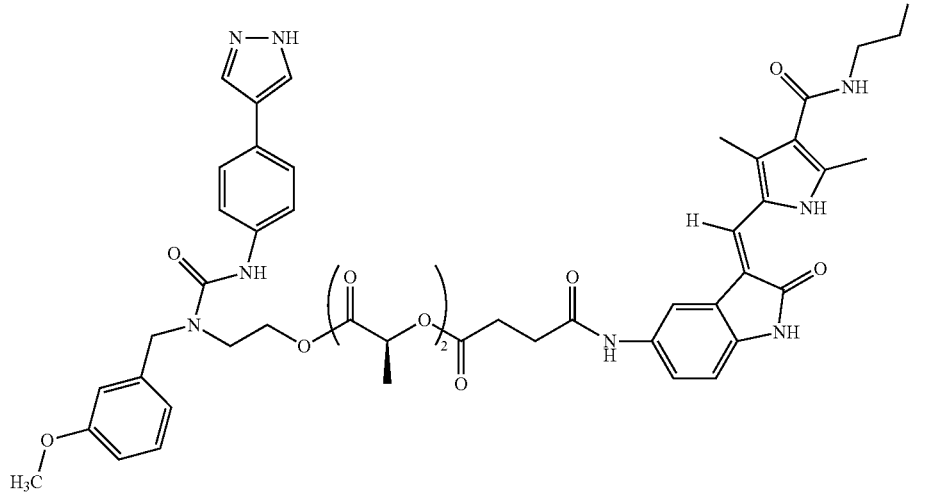
146
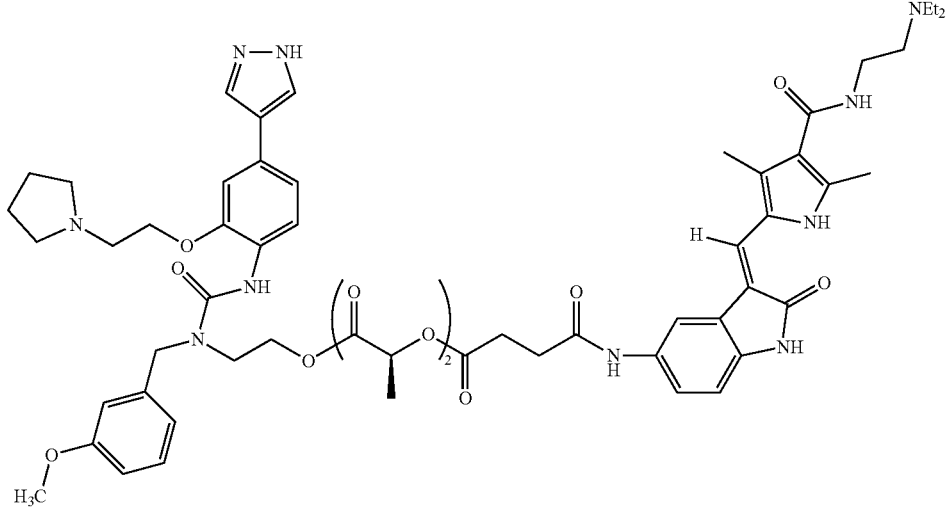
147
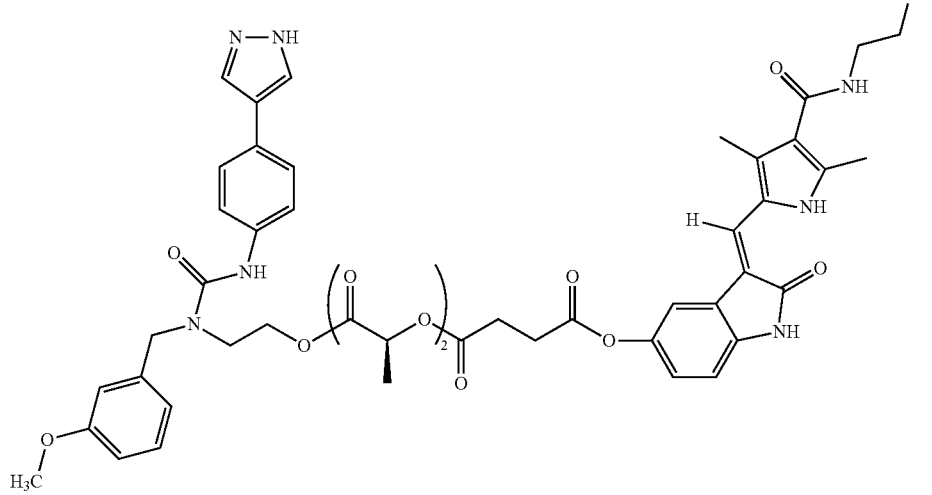

TABLE C-continued
Non-limiting Examples of Prodrugs
148
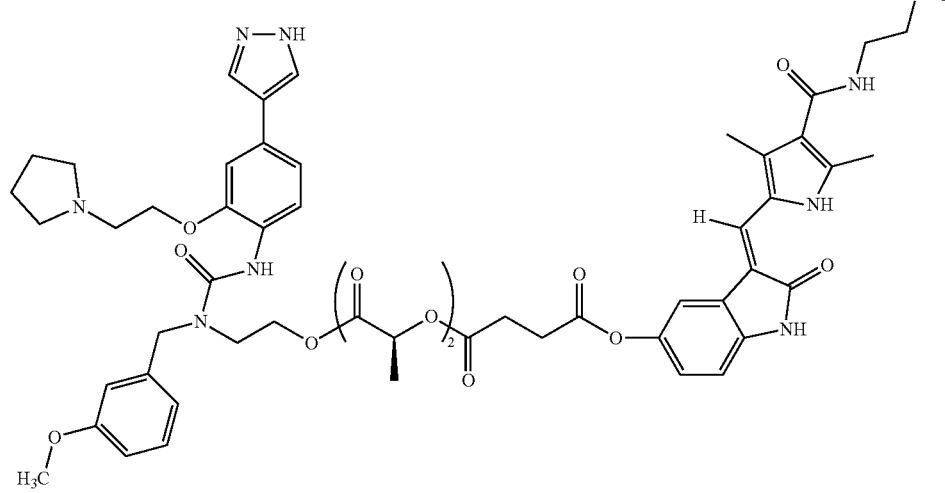
149
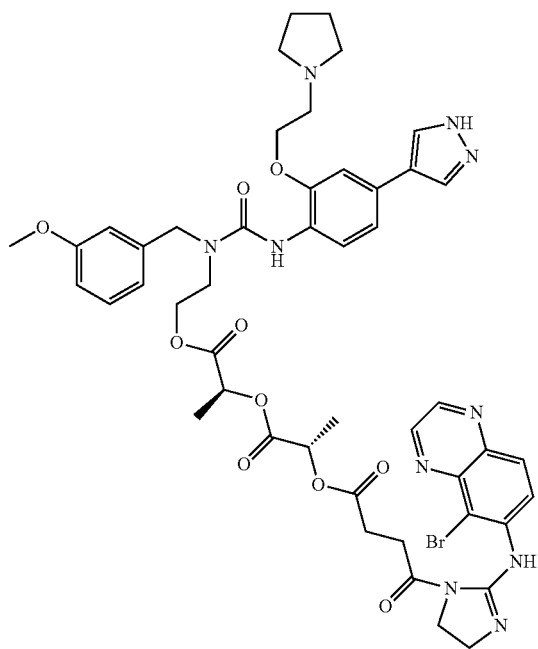 [SMILES: COc1cccc(CN(CCOC(=O)[C@H](C)OC(=O)[C@H](C)OC(=O)CCC(=O)N2CCN=C2Nc2ccc3nccnc3c2Br)C(=O)Nc2ccc(-c3cn[nH]c3)cc2OCCN2CCCC2)c1]

TABLE C-continued
Non-limiting Examples of Prodrugs
150
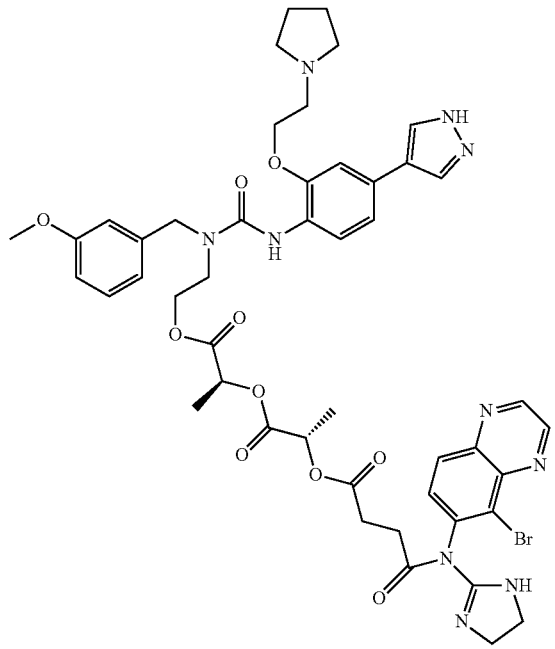 [SMILES: COc1cccc(CN(CCOC(=O)[C@H](C)OC(=O)[C@H](C)OC(=O)CCC(=O)N(C2=NCCN2)c2ccc3nccnc3c2Br)C(=O)Nc2ccc(-c3cn[nH]c3)cc2OCCN2CCCC2)c1]
151
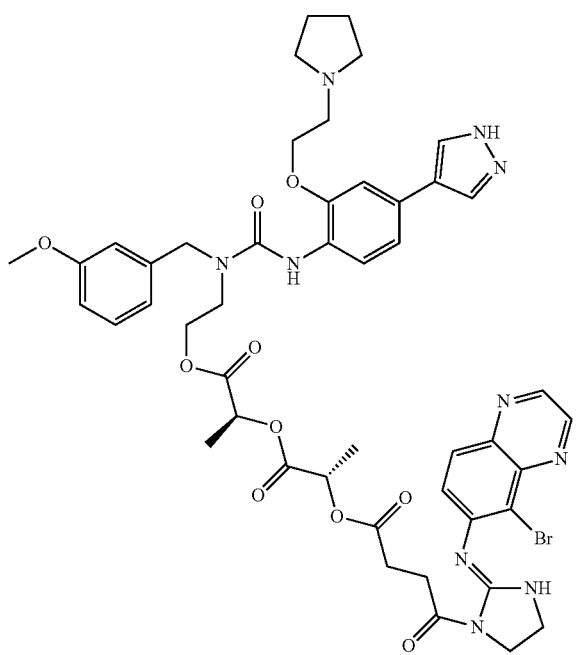 [SMILES: COc1cccc(CN(CCOC(=O)[C@H](C)OC(=O)[C@H](C)OC(=O)CCC(=O)N2CCN/C2=N\c2ccc3nccnc3c2Br)C(=O)Nc2ccc(-c3cn[nH]c3)cc2OCCN2CCCC2)c1]

TABLE C-continued
Non-limiting Examples of Prodrugs
152
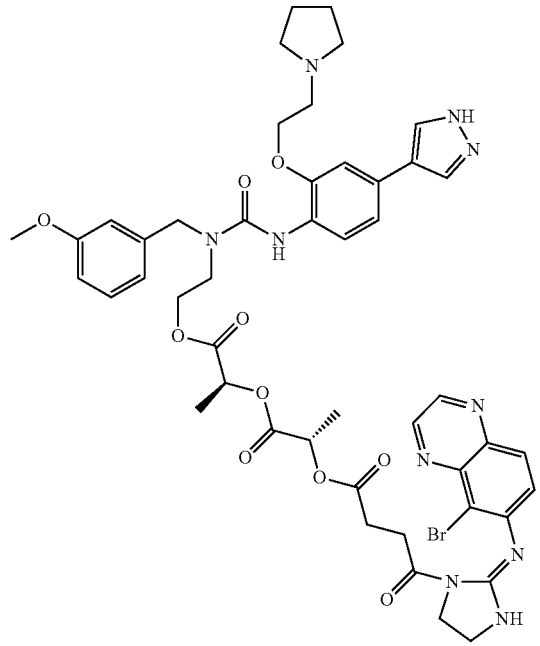 [SMILES: COc1cccc(CN(CCOC(=O)[C@H](C)OC(=O)[C@H](C)OC(=O)CCC(=O)N2CCN/C2=N/c2ccc3nccnc3c2Br)C(=O)Nc2ccc(-c3cn[nH]c3)cc2OCCN2CCCC2)c1]
153
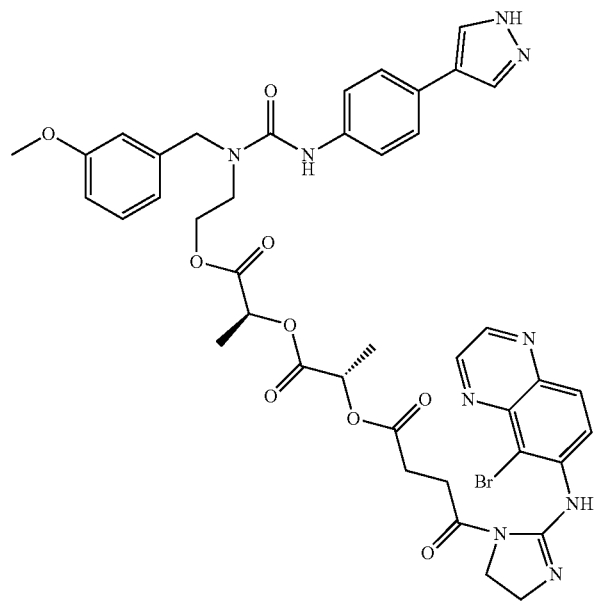 [SMILES: COc1cccc(CN(CCOC(=O)[C@H](C)OC(=O)[C@H](C)OC(=O)CCC(=O)N2CCN=C2Nc2ccc3nccnc3c2Br)C(=O)Nc2ccc(-c3cn[nH]c3)cc2)c1]

TABLE C-continued
Non-limiting Examples of Prodrugs
154
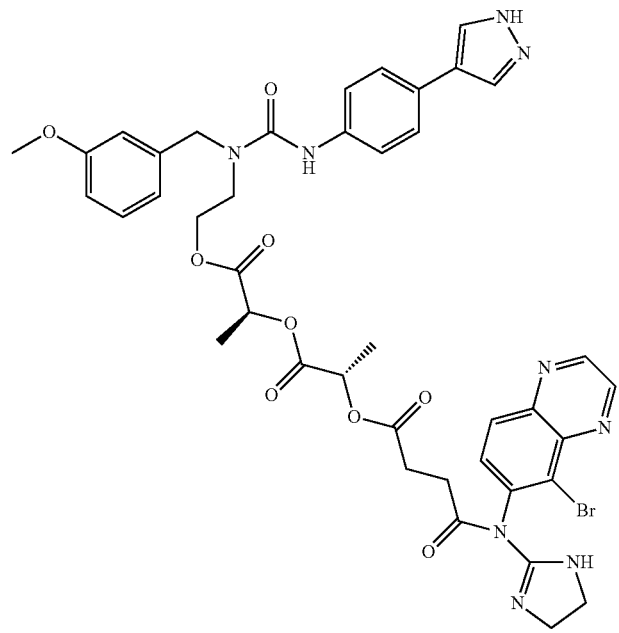 [SMILES: COc1cccc(CN(CCOC(=O)[C@H](C)OC(=O)[C@H](C)OC(=O)CCC(=O)N(C2=NCCN2)c2ccc3nccnc3c2Br)C(=O)Nc2ccc(-c3cn[nH]c3)cc2)c1]
155
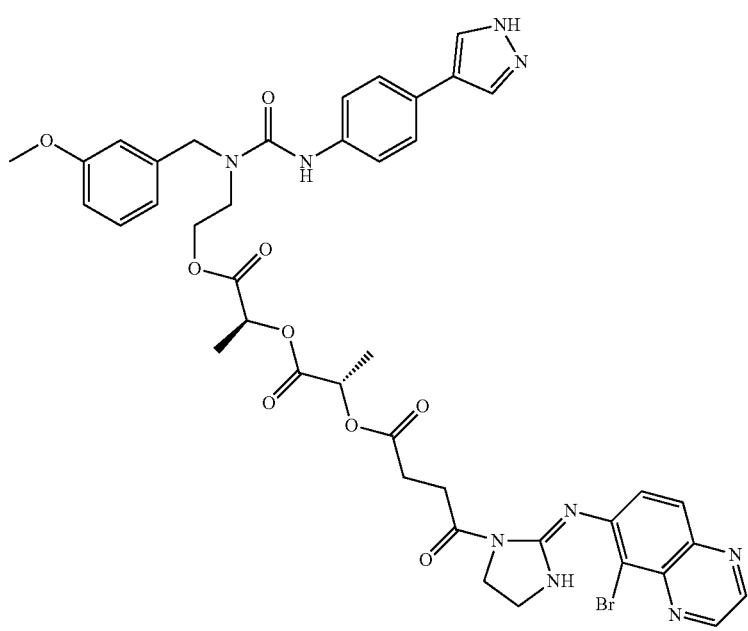 [SMILES: COc1cccc(CN(CCOC(=O)[C@H](C)OC(=O)[C@H](C)OC(=O)CCC(=O)N2CCN/C2=N\c2ccc3nccnc3c2Br)C(=O)Nc2ccc(-c3cn[nH]c3)cc2)c1]

TABLE C-continued
Non-limiting Examples of Prodrugs
156
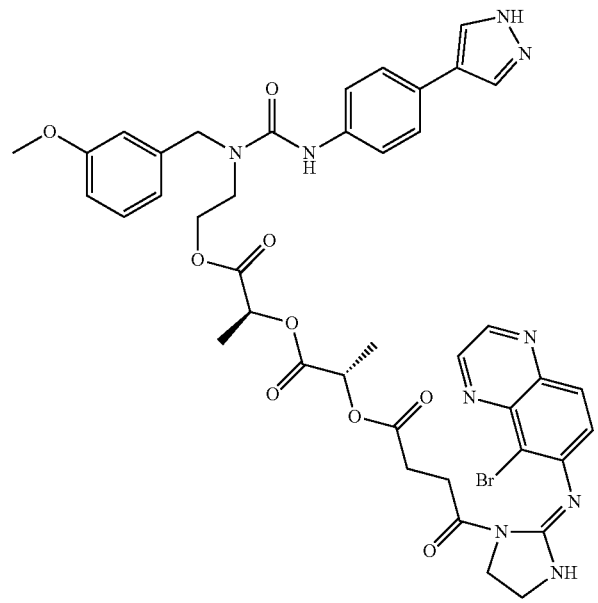 [SMILES: COc1cccc(CN(CCOC(=O)[C@H](C)OC(=O)[C@H](C)OC(=O)CCC(=O)N2CCN/C2=N/c2ccc3nccnc3c2Br)C(=O)Nc2ccc(-c3cn[nH]c3)cc2)c1]
157
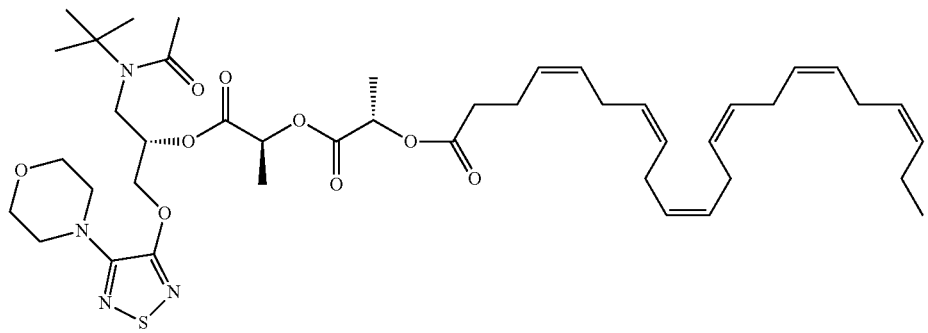 [SMILES: CC/C=C\C/C=C\C/C=C\C/C=C\C/C=C\C/C=C\CCC(=O)O[C@@H](C)C(=O)O[C@@H](C)C(=O)O[C@H](COc1nsnc1N1CCOCC1)CN(C(C)=O)C(C)(C)C]
158
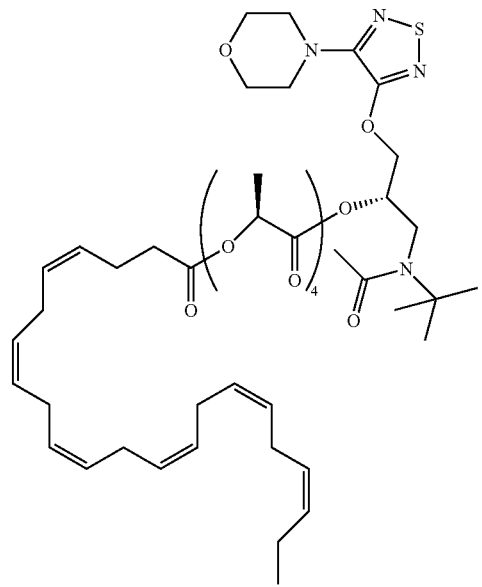

TABLE C-continued
Non-limiting Examples of Prodrugs
159
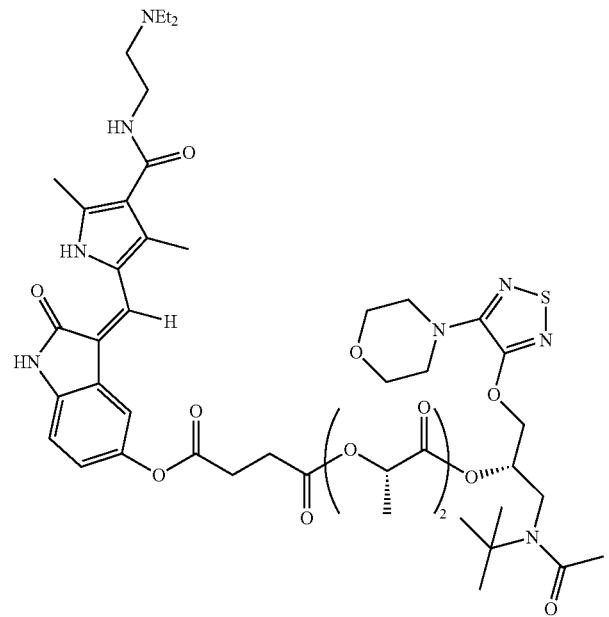
160
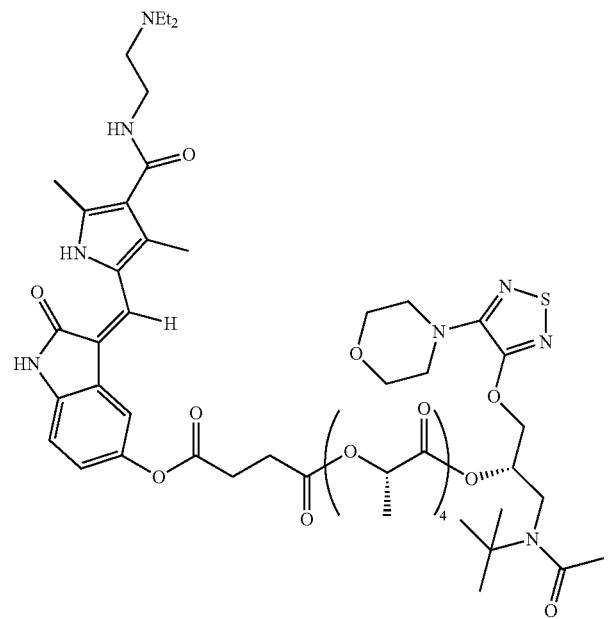

TABLE C-continued
Non-limiting Examples of Prodrugs
161
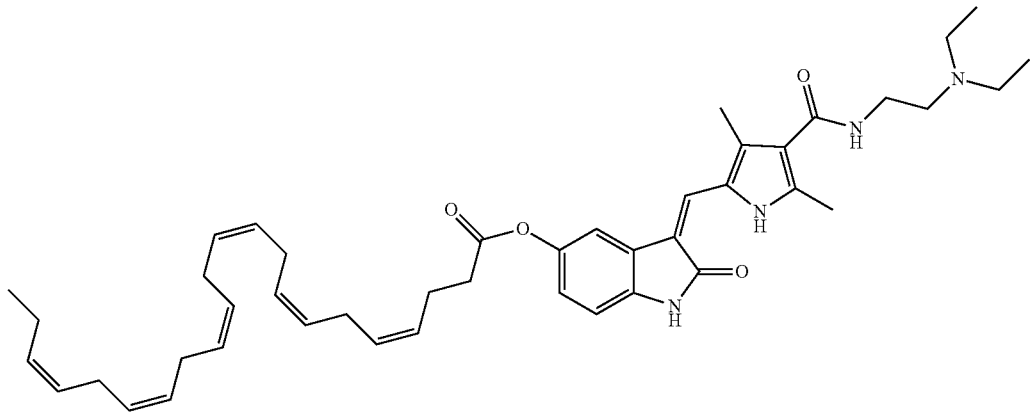 [SMILES: CC/C=C\C/C=C\C/C=C\C/C=C\C/C=C\C/C=C\CCC(=O)Oc1ccc2c(c1)/C(=C/c1[nH]c(C)c(C(=O)NCCN(CC)CC)c1C)C(=O)N2]
162
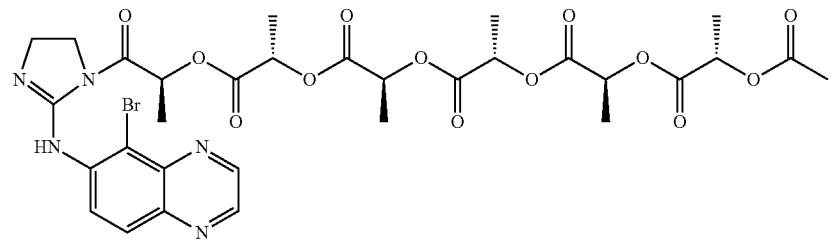 [SMILES: CC(=O)O[C@@H](C)C(=O)O[C@@H](C)C(=O)O[C@@H](C)C(=O)O[C@@H](C)C(=O)O[C@@H](C)C(=O)O[C@@H](C)C(=O)N1CCN=C1Nc1ccc2nccnc2c1Br]
163
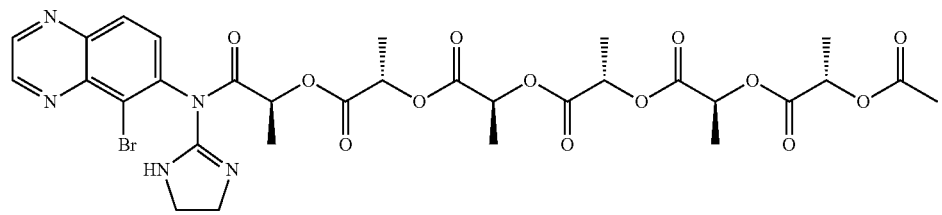 [SMILES: CC(=O)O[C@@H](C)C(=O)O[C@@H](C)C(=O)O[C@@H](C)C(=O)O[C@@H](C)C(=O)O[C@@H](C)C(=O)O[C@@H](C)C(=O)N(C1=NCCN1)c1ccc2nccnc2c1Br]
164
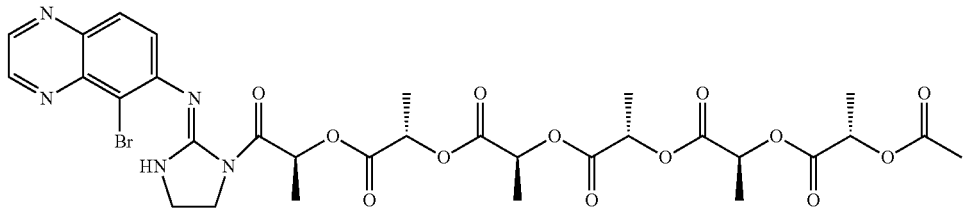 [SMILES: CC(=O)O[C@@H](C)C(=O)O[C@@H](C)C(=O)O[C@@H](C)C(=O)O[C@@H](C)C(=O)O[C@@H](C)C(=O)O[C@@H](C)C(=O)N1CCN/C1=N\c1ccc2nccnc2c1Br]
165
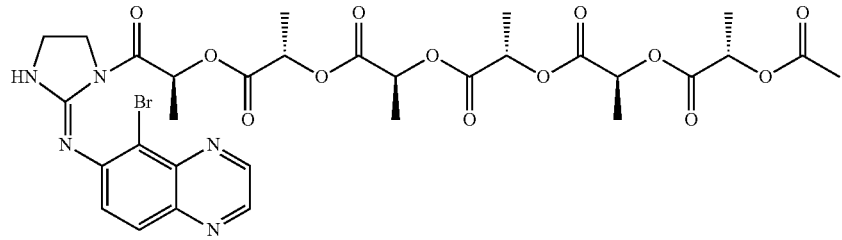 [SMILES: CC(=O)O[C@@H](C)C(=O)O[C@@H](C)C(=O)O[C@@H](C)C(=O)O[C@@H](C)C(=O)O[C@@H](C)C(=O)O[C@@H](C)C(=O)N1CCN/C1=N/c1ccc2nccnc2c1Br]

TABLE C-continued
Non-limiting Examples of Prodrugs
166 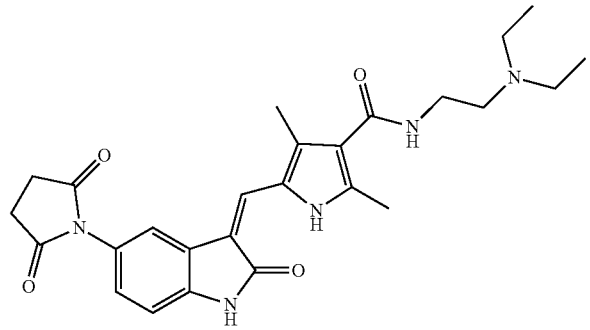 [SMILES: CCN(CC)CCNC(=O)c1c(C)[nH]c(/C=C2\C(=O)Nc3ccc(N4C(=O)CCC4=O)cc32)c1C]
167 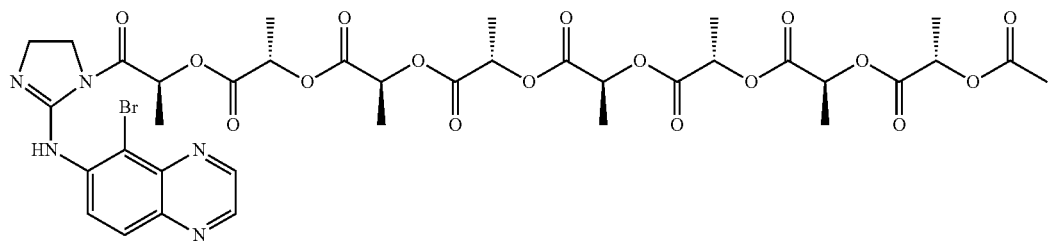 [SMILES: CC(=O)O[C@@H](C)C(=O)O[C@@H](C)C(=O)O[C@@H](C)C(=O)O[C@@H](C)C(=O)O[C@@H](C)C(=O)O[C@@H](C)C(=O)O[C@@H](C)C(=O)O[C@@H](C)C(=O)N1CCN=C1Nc1ccc2nccnc2c1Br]
168 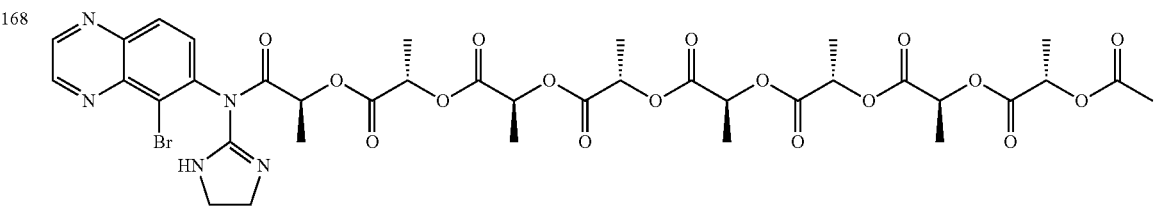
169 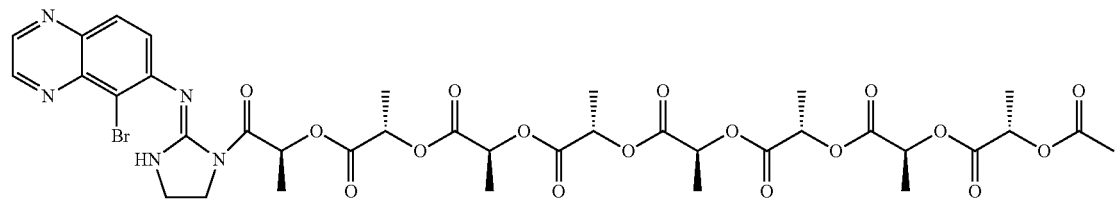 [SMILES: CC(=O)O[C@@H](C)C(=O)O[C@@H](C)C(=O)O[C@@H](C)C(=O)O[C@@H](C)C(=O)O[C@@H](C)C(=O)O[C@@H](C)C(=O)O[C@@H](C)C(=O)O[C@@H](C)C(=O)N1CCN/C1=N\c1ccc2nccnc2c1Br]
170 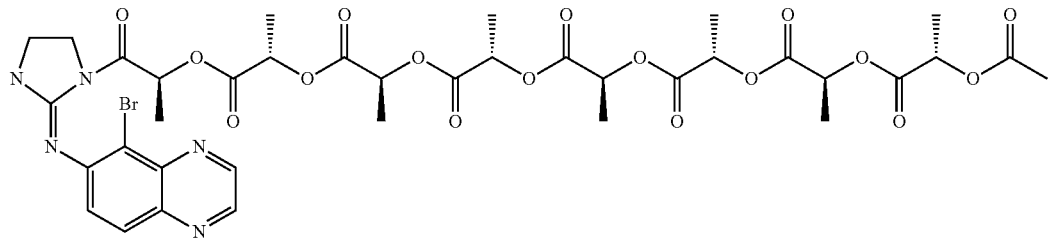 [SMILES: CC(=O)O[C@@H](C)C(=O)O[C@@H](C)C(=O)O[C@@H](C)C(=O)O[C@@H](C)C(=O)O[C@@H](C)C(=O)O[C@@H](C)C(=O)O[C@@H](C)C(=O)O[C@@H](C)C(=O)N1CCN/C1=N/c1ccc2nccnc2c1Br]
171 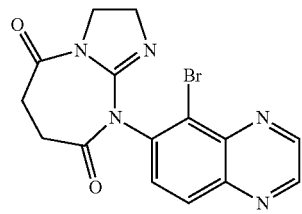 [SMILES: O=C1CCC(=O)N(c2ccc3nccnc3c2Br)C2=NCCN12]

TABLE C-continued
Non-limiting Examples of Prodrugs
172
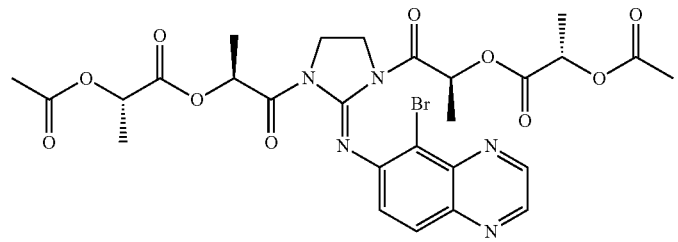 [SMILES: CC(=O)O[C@@H](C)C(=O)O[C@@H](C)C(=O)N1CCN(C(=O)[C@H](C)OC(=O)[C@H](C)OC(C)=O)C1=Nc1ccc2nccnc2c1Br]
173
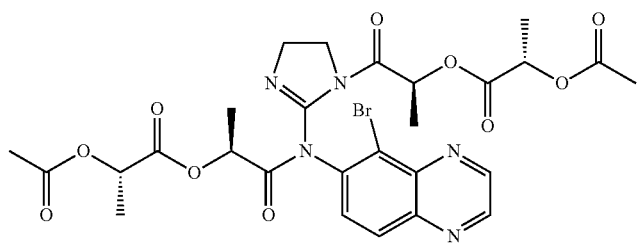 [SMILES: CC(=O)O[C@@H](C)C(=O)O[C@@H](C)C(=O)N1CCN=C1N(C(=O)[C@H](C)OC(=O)[C@H](C)OC(C)=O)c1ccc2nccnc2c1Br]
174
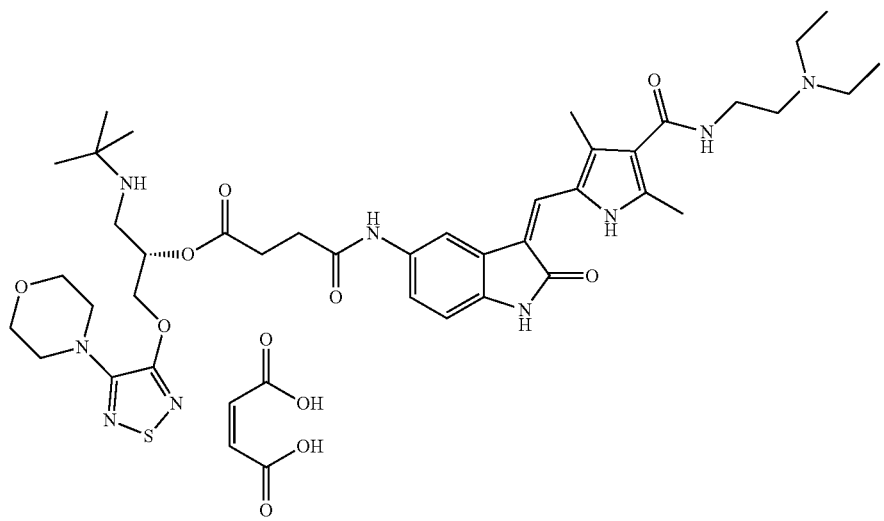
175
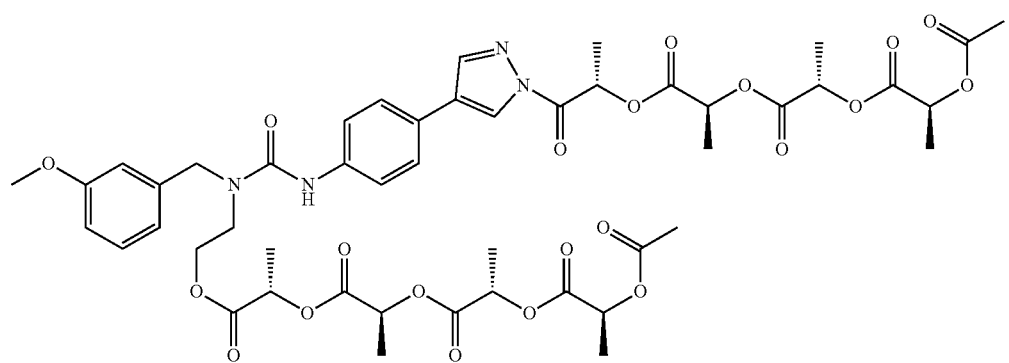 [SMILES: COc1cccc(CN(CCOC(=O)[C@H](C)OC(=O)[C@H](C)OC(=O)[C@H](C)OC(=O)[C@H](C)OC(C)=O)C(=O)Nc2ccc(-c3cnn(C(=O)[C@H](C)OC(=O)[C@H](C)OC(=O)[C@H](C)OC(=O)[C@H](C)OC(C)=O)c3)cc2)c1]

TABLE C-continued
Non-limiting Examples of Prodrugs
176 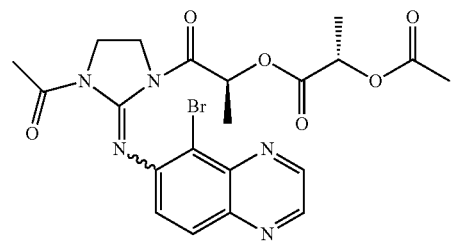
177 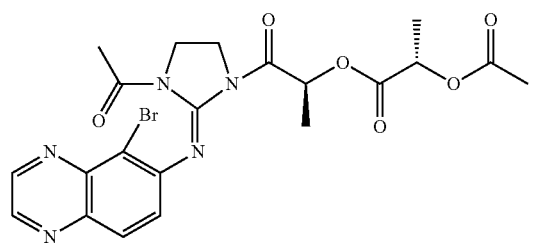 [SMILES: CC(=O)O[C@@H](C)C(=O)O[C@@H](C)C(=O)N1CCN(C(C)=O)/C1=N\c1ccc2nccnc2c1Br]
178 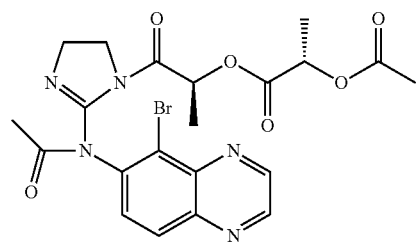 [SMILES: CC(=O)O[C@@H](C)C(=O)O[C@@H](C)C(=O)N1CCN=C1N(C(C)=O)c1ccc2nccnc2c1Br]
179 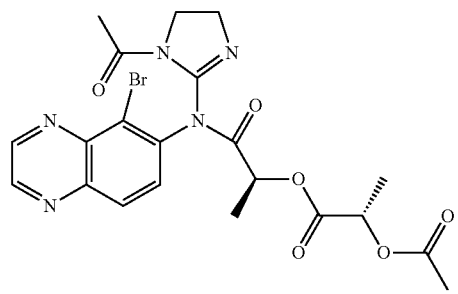 [SMILES: CC(=O)O[C@@H](C)C(=O)O[C@@H](C)C(=O)N(C1=NCCN1C(C)=O)c1ccc2nccnc2c1Br]
180 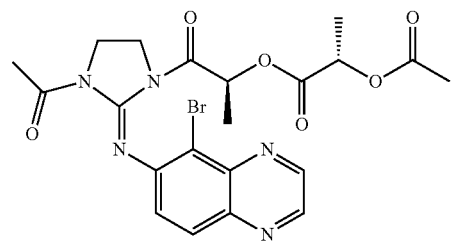
181 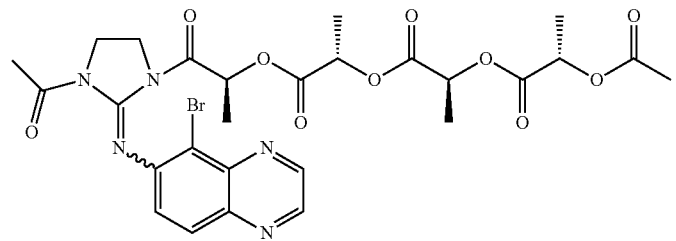 [SMILES: CC(=O)O[C@@H](C)C(=O)O[C@@H](C)C(=O)O[C@@H](C)C(=O)O[C@@H](C)C(=O)N1CCN(C(C)=O)C1=Nc1ccc2nccnc2c1Br]

TABLE C-continued
Non-limiting Examples of Prodrugs
182 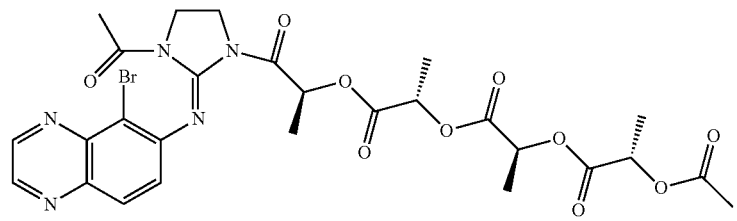 [SMILES: CC(=O)O[C@@H](C)C(=O)O[C@@H](C)C(=O)O[C@@H](C)C(=O)O[C@@H](C)C(=O)N1CCN(C(C)=O)/C1=N\c1ccc2nccnc2c1Br]
183 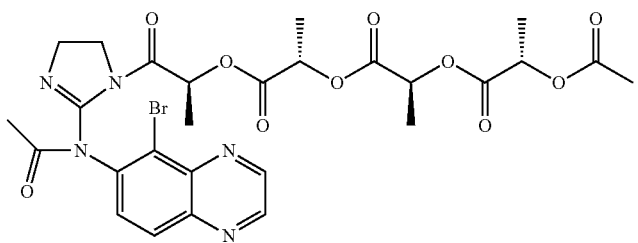 [SMILES: CC(=O)O[C@@H](C)C(=O)O[C@@H](C)C(=O)O[C@@H](C)C(=O)O[C@@H](C)C(=O)N1CCN=C1N(C(C)=O)c1ccc2nccnc2c1Br]
184 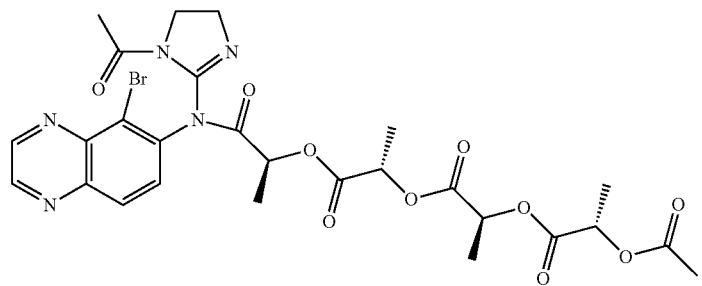 [SMILES: CC(=O)O[C@@H](C)C(=O)O[C@@H](C)C(=O)O[C@@H](C)C(=O)O[C@@H](C)C(=O)N(C1=NCCN1C(C)=O)c1ccc2nccnc2c1Br]
185 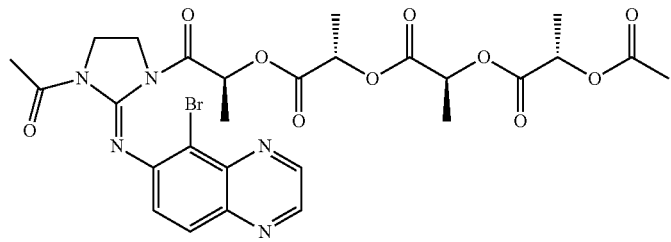 [SMILES: CC(=O)O[C@@H](C)C(=O)O[C@@H](C)C(=O)O[C@@H](C)C(=O)O[C@@H](C)C(=O)N1CCN(C(C)=O)/C1=N/c1ccc2nccnc2c1Br]
186 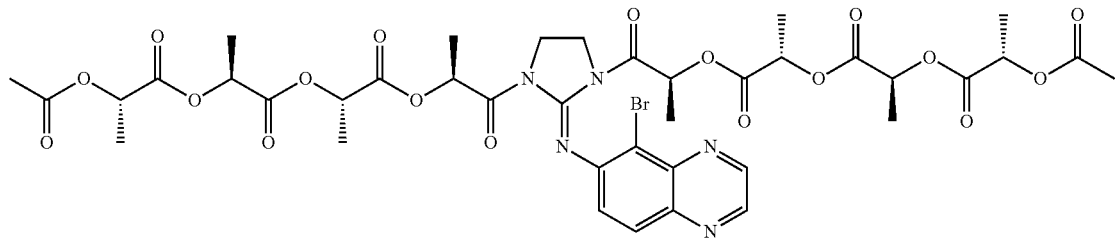 [SMILES: CC(=O)O[C@@H](C)C(=O)O[C@@H](C)C(=O)O[C@@H](C)C(=O)O[C@@H](C)C(=O)N1CCN(C(=O)[C@H](C)OC(=O)[C@H](C)OC(=O)[C@H](C)OC(=O)[C@H](C)OC(C)=O)C1=Nc1ccc2nccnc2c1Br]
187 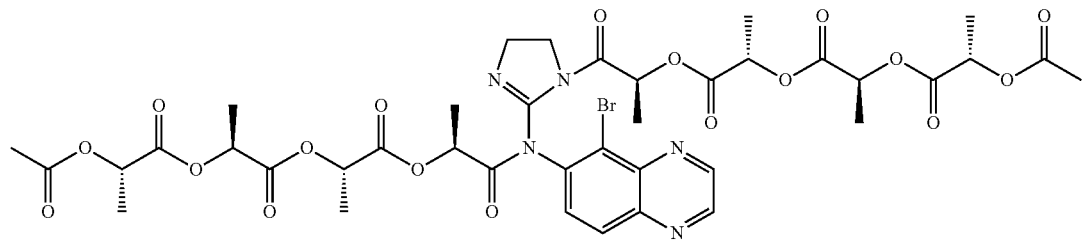 [SMILES: CC(=O)O[C@@H](C)C(=O)O[C@@H](C)C(=O)O[C@@H](C)C(=O)O[C@@H](C)C(=O)N1CCN=C1N(C(=O)[C@H](C)OC(=O)[C@H](C)OC(=O)[C@H](C)OC(=O)[C@H](C)OC(C)=O)c1ccc2nccnc2c1Br]

TABLE C-continued
Non-limiting Examples of Prodrugs
188 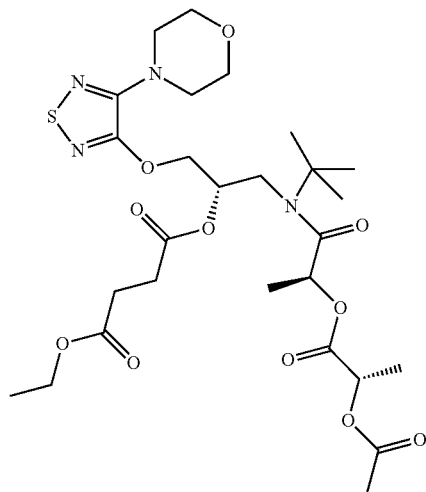 [SMILES: CCOC(=O)CCC(=O)O[C@H](COc1nsnc1N1CCOCC1)CN(C(=O)[C@H](C)OC(=O)[C@H](C)OC(C)=O)C(C)(C)C]
189 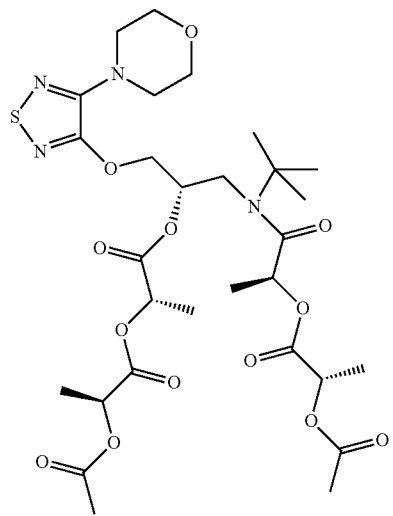 [SMILES: CC(=O)O[C@@H](C)C(=O)O[C@@H](C)C(=O)O[C@H](COc1nsnc1N1CCOCC1)CN(C(=O)[C@H](C)OC(=O)[C@H](C)OC(C)=O)C(C)(C)C]

TABLE C-continued
Non-limiting Examples of Prodrugs
190
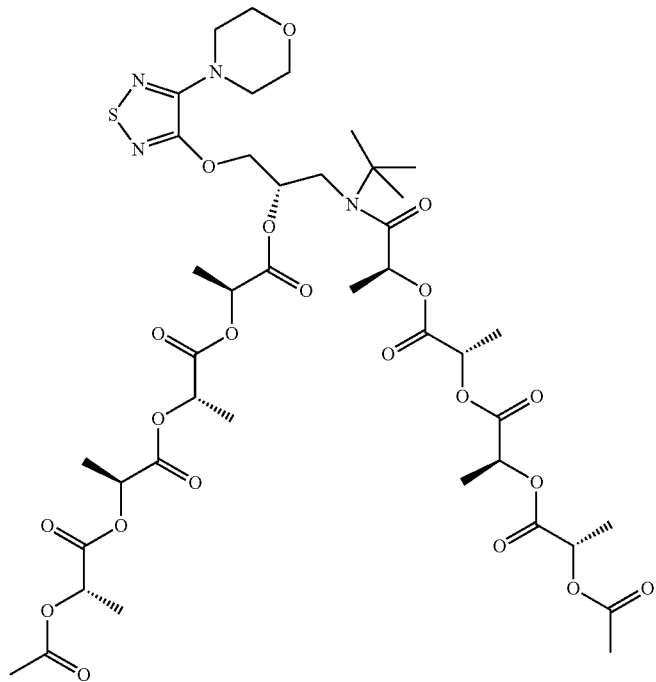 [SMILES: CC(=O)O[C@@H](C)C(=O)O[C@@H](C)C(=O)O[C@@H](C)C(=O)O[C@@H](C)C(=O)O[C@H](COc1nsnc1N1CCOCC1)CN(C(=O)[C@H](C)OC(=O)[C@H](C)OC(=O)[C@H](C)OC(=O)[C@H](C)OC(C)=O)C(C)(C)C]
191
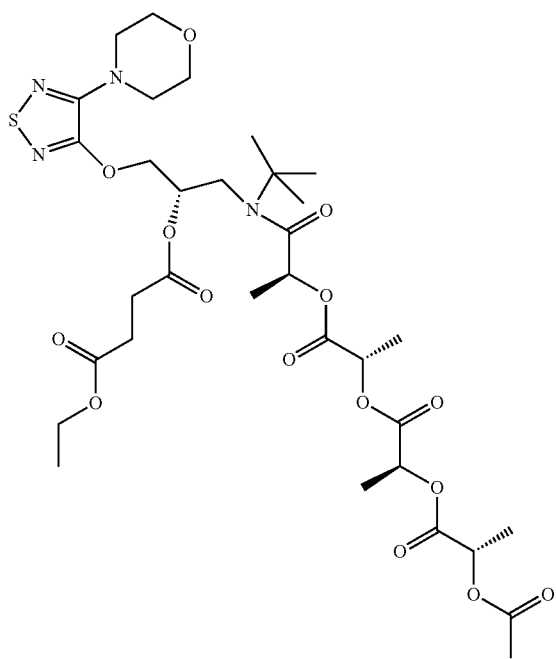 [SMILES: CCOC(=O)CCC(=O)O[C@H](COc1nsnc1N1CCOCC1)CN(C(=O)[C@H](C)OC(=O)[C@H](C)OC(=O)[C@H](C)OC(=O)[C@H](C)OC(C)=O)C(C)(C)C]

TABLE C-continued
Non-limiting Examples of Prodrugs
192
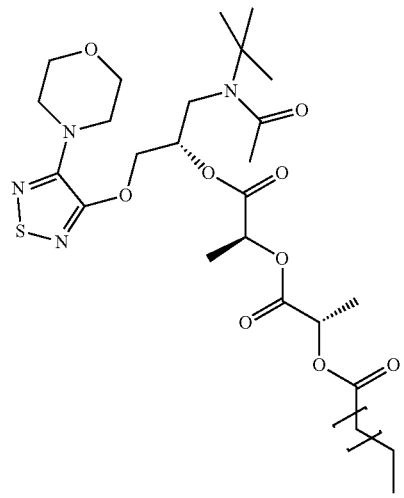
n = 15
193
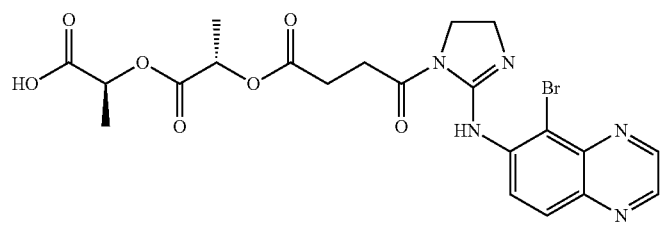 [SMILES: C[C@H](OC(=O)[C@H](C)OC(=O)CCC(=O)N1CCN=C1Nc1ccc2nccnc2c1Br)C(=O)O]
194
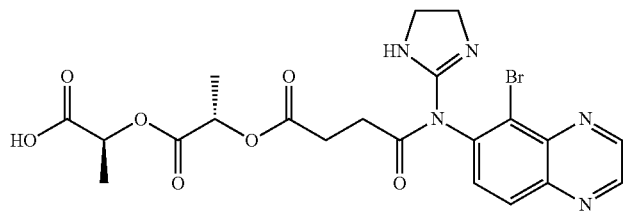 [SMILES: C[C@H](OC(=O)[C@H](C)OC(=O)CCC(=O)N(C1=NCCN1)c1ccc2nccnc2c1Br)C(=O)O]
195
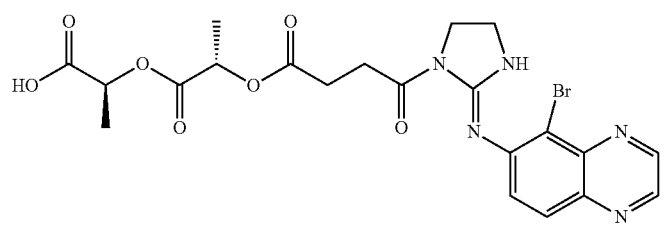 [SMILES: C[C@H](OC(=O)[C@H](C)OC(=O)CCC(=O)N1CCN/C1=N\c1ccc2nccnc2c1Br)C(=O)O]

417 418
TABLE C-continued
Non-limiting Examples of Prodrugs
196 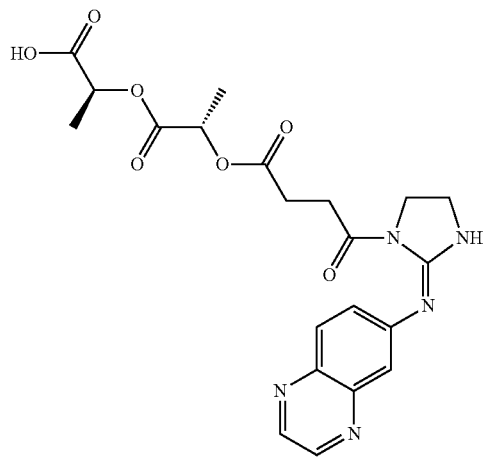 [SMILES: C[C@H](OC(=O)[C@H](C)OC(=O)CCC(=O)N1CCN/C1=N/c1ccc2nccnc2c1)C(=O)O]
197 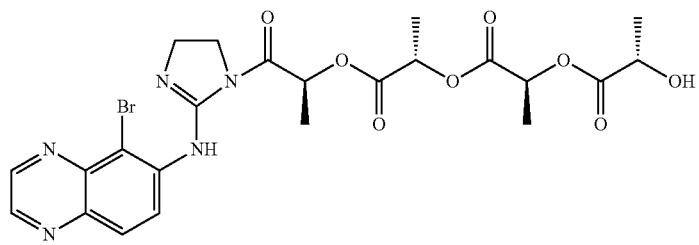 [SMILES: C[C@H](O)C(=O)O[C@@H](C)C(=O)O[C@@H](C)C(=O)O[C@@H](C)C(=O)N1CCN=C1Nc1ccc2nccnc2c1Br]
198 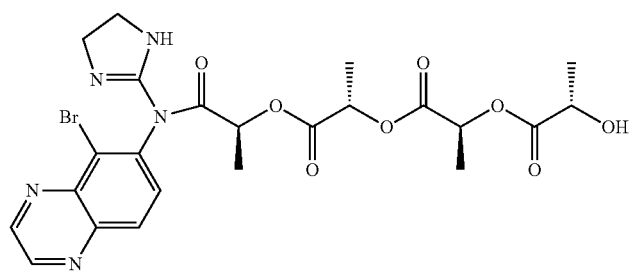 [SMILES: C[C@H](O)C(=O)O[C@@H](C)C(=O)O[C@@H](C)C(=O)O[C@@H](C)C(=O)N(C1=NCCN1)c1ccc2nccnc2c1Br]
199 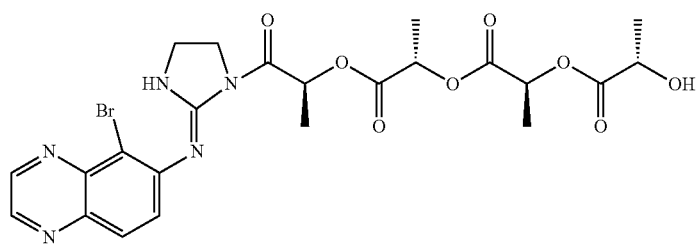 [SMILES: C[C@H](O)C(=O)O[C@@H](C)C(=O)O[C@@H](C)C(=O)O[C@@H](C)C(=O)N1CCN/C1=N\c1ccc2nccnc2c1Br]
200 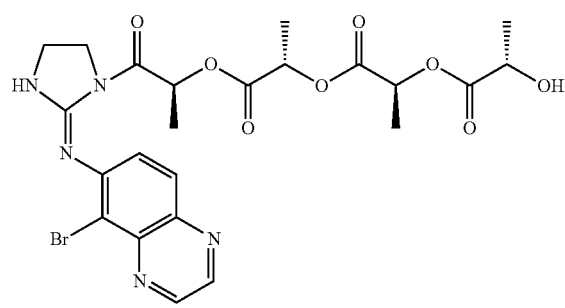 [SMILES: C[C@H](O)C(=O)O[C@@H](C)C(=O)O[C@@H](C)C(=O)O[C@@H](C)C(=O)N1CCN/C1=N/c1ccc2nccnc2c1Br]

TABLE C-continued
Non-limiting Examples of Prodrugs
201 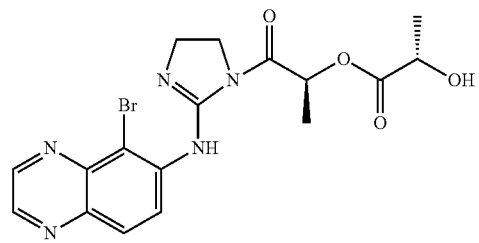 [SMILES: C[C@H](O)C(=O)O[C@@H](C)C(=O)N1CCN=C1Nc1ccc2nccnc2c1Br]
202 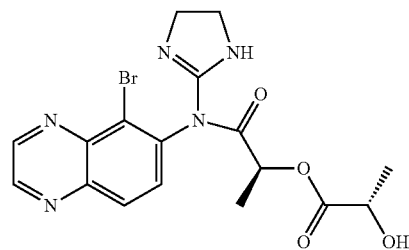 [SMILES: C[C@H](O)C(=O)O[C@@H](C)C(=O)N(C1=NCCN1)c1ccc2nccnc2c1Br]
203 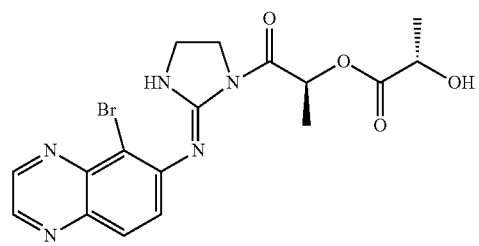 [SMILES: C[C@H](O)C(=O)O[C@@H](C)C(=O)N1CCN/C1=N\c1ccc2nccnc2c1Br]
204 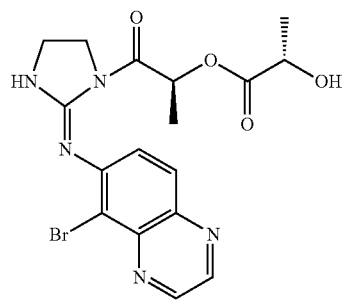 [SMILES: C[C@H](O)C(=O)O[C@@H](C)C(=O)N1CCN/C1=N/c1ccc2nccnc2c1Br]

TABLE D
Non-limiting Examples of Prodrugs
205
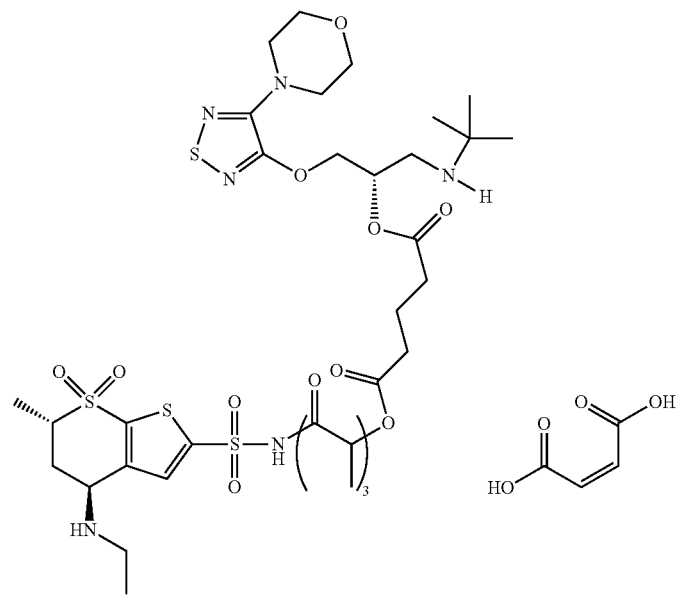
206
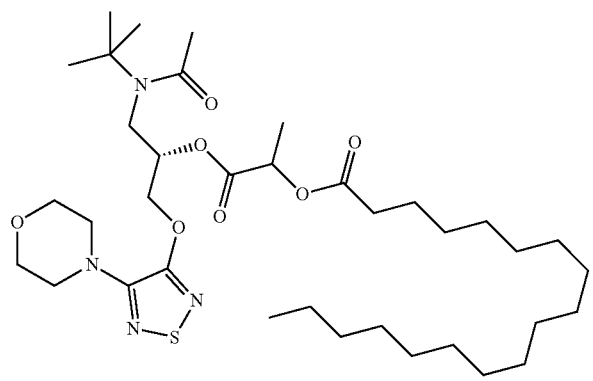 [SMILES: CCCCCCCCCCCCCCCCCC(=O)OC(C)C(=O)O[C@H](COc1nsnc1N1CCOCC1)CN(C(C)=O)C(C)(C)C]
207
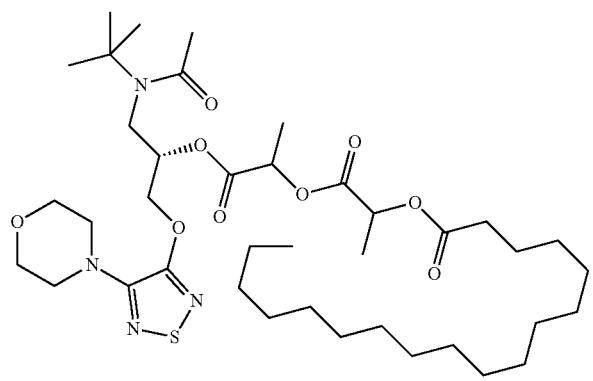 [SMILES: CCCCCCCCCCCCCCCCCC(=O)OC(C)C(=O)OC(C)C(=O)O[C@H](COc1nsnc1N1CCOCC1)CN(C(C)=O)C(C)(C)C]

TABLE D-continued
Non-limiting Examples of Prodrugs
208
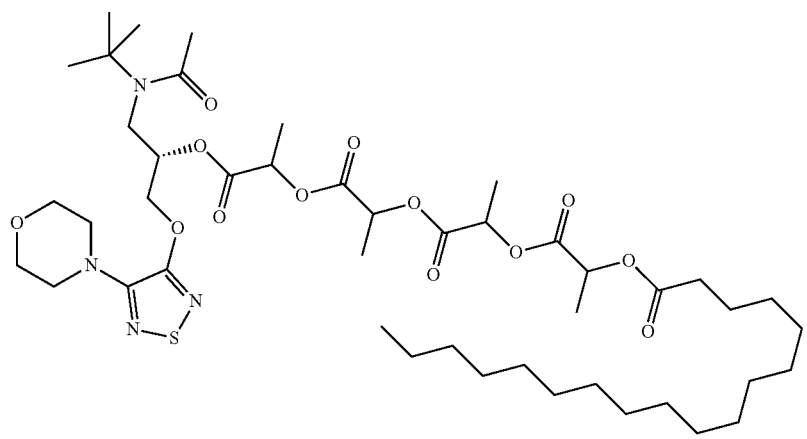 [SMILES: CCCCCCCCCCCCCCCCCC(=O)OC(C)C(=O)OC(C)C(=O)OC(C)C(=O)OC(C)C(=O)O[C@H](COc1nsnc1N1CCOCC1)CN(C(C)=O)C(C)(C)C]
209
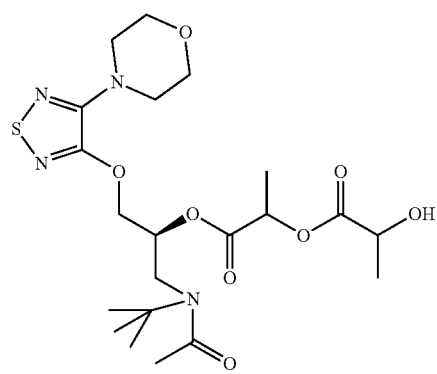 [SMILES: CC(=O)N(C[C@@H](COc1nsnc1N1CCOCC1)OC(=O)C(C)OC(=O)C(C)O)C(C)(C)C]
210
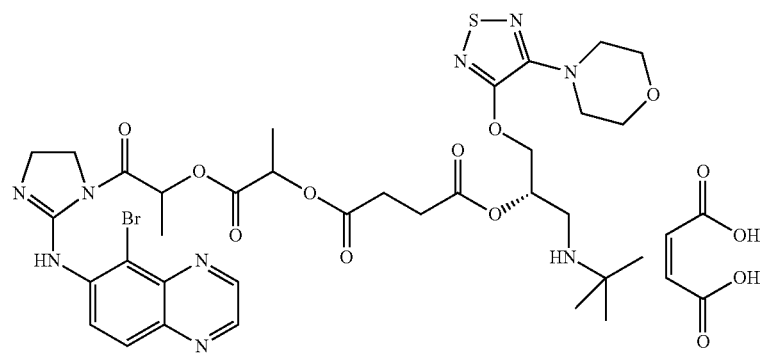
211
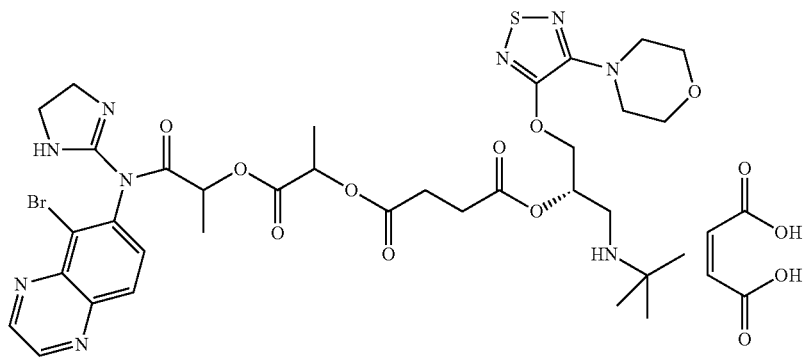

US 11,160,870 B2
425                                                                                                    426
TABLE D-continued
Non-limiting Examples of Prodrugs
212
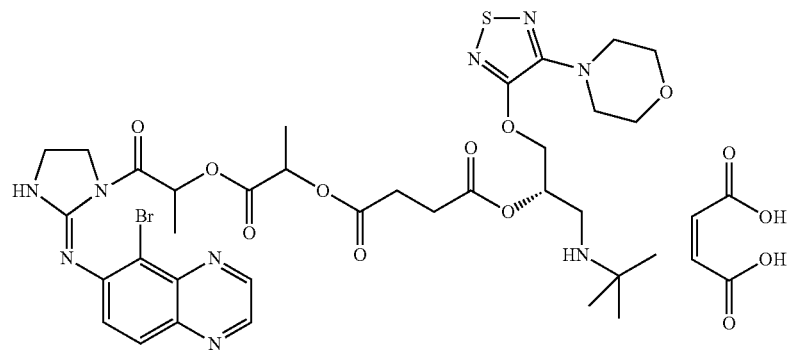
213
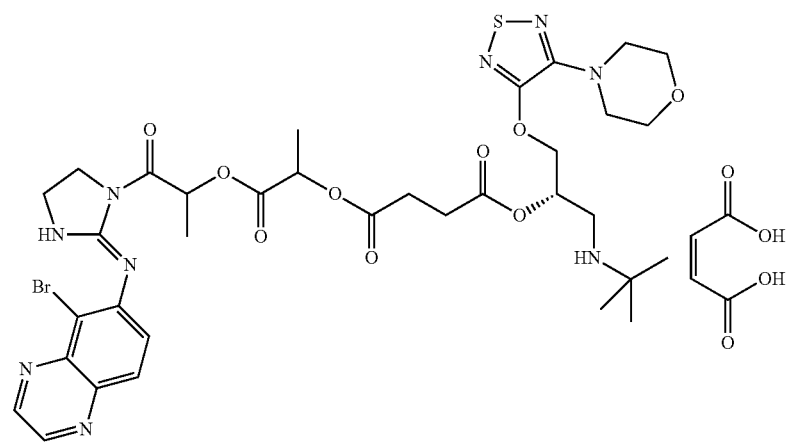
214
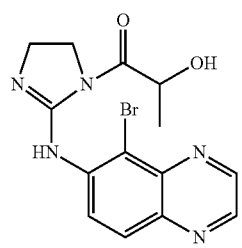
215
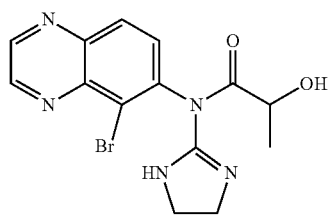 [SMILES: CC(O)C(=O)N(C1=NCCN1)c1ccc2nccnc2c1Br]
216
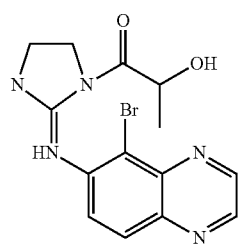 [SMILES: CC(O)C(=O)N1CCN/C1=N/c1ccc2nccnc2c1Br]

TABLE D-continued
Non-limiting Examples of Prodrugs
217 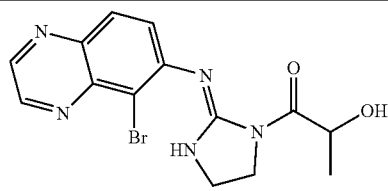
218 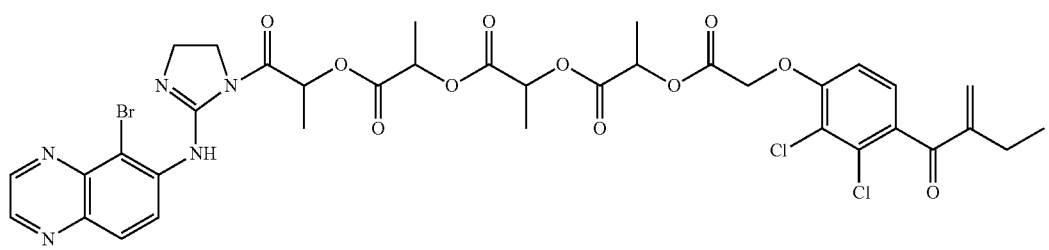 [SMILES: C=C(CC)C(=O)c1ccc(OCC(=O)OC(C)C(=O)OC(C)C(=O)OC(C)C(=O)OC(C)C(=O)N2CCN=C2Nc2ccc3nccnc3c2Br)c(Cl)c1Cl]
219 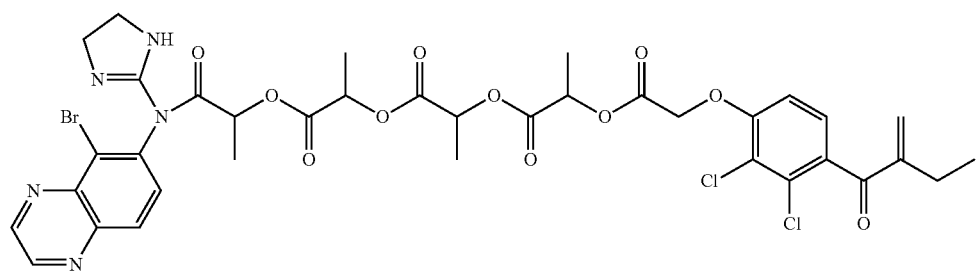 [SMILES: C=C(CC)C(=O)c1ccc(OCC(=O)OC(C)C(=O)OC(C)C(=O)OC(C)C(=O)OC(C)C(=O)N(C2=NCCN2)c2ccc3nccnc3c2Br)c(Cl)c1Cl]
220 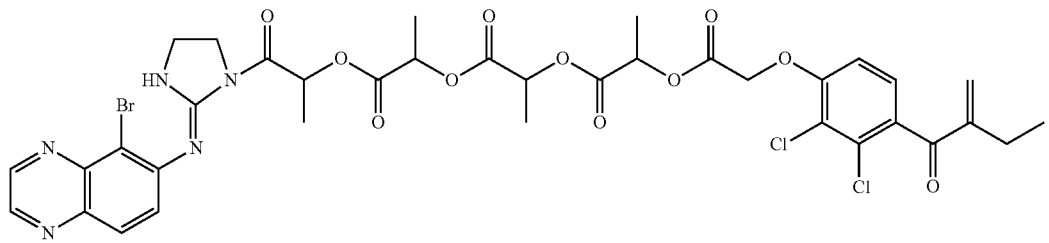 [SMILES: C=C(CC)C(=O)c1ccc(OCC(=O)OC(C)C(=O)OC(C)C(=O)OC(C)C(=O)OC(C)C(=O)N2CCN/C2=N\c2ccc3nccnc3c2Br)c(Cl)c1Cl]
221 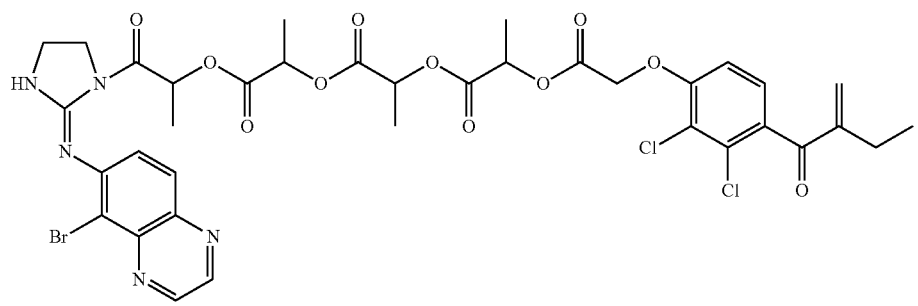 [SMILES: C=C(CC)C(=O)c1ccc(OCC(=O)OC(C)C(=O)OC(C)C(=O)OC(C)C(=O)OC(C)C(=O)N2CCN/C2=N/c2ccc3nccnc3c2Br)c(Cl)c1Cl]
222 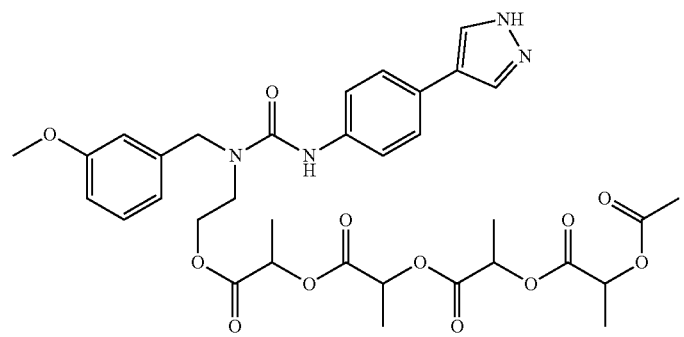 [SMILES: COc1cccc(CN(CCOC(=O)C(C)OC(=O)C(C)OC(=O)C(C)OC(=O)C(C)OC(C)=O)C(=O)Nc2ccc(-c3cn[nH]c3)cc2)c1]

TABLE D-continued
Non-limiting Examples of Prodrugs
223
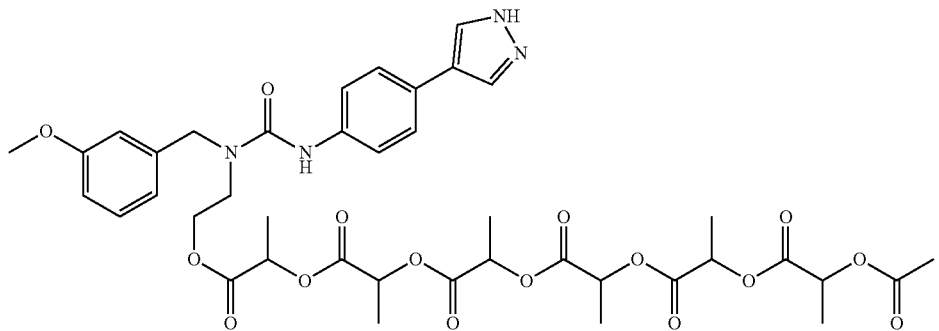 [SMILES: COc1cccc(CN(CCOC(=O)C(C)OC(=O)C(C)OC(=O)C(C)OC(=O)C(C)OC(=O)C(C)OC(=O)C(C)OC(C)=O)C(=O)Nc2ccc(-c3cn[nH]c3)cc2)c1]
224
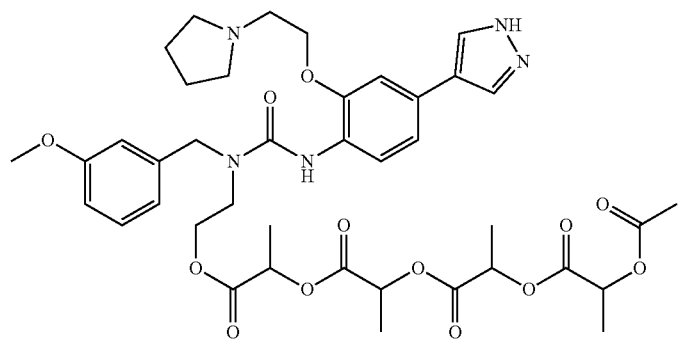 [SMILES: COc1cccc(CN(CCOC(=O)C(C)OC(=O)C(C)OC(=O)C(C)OC(=O)C(C)OC(C)=O)C(=O)Nc2ccc(-c3cn[nH]c3)cc2OCCN2CCCC2)c1]
225
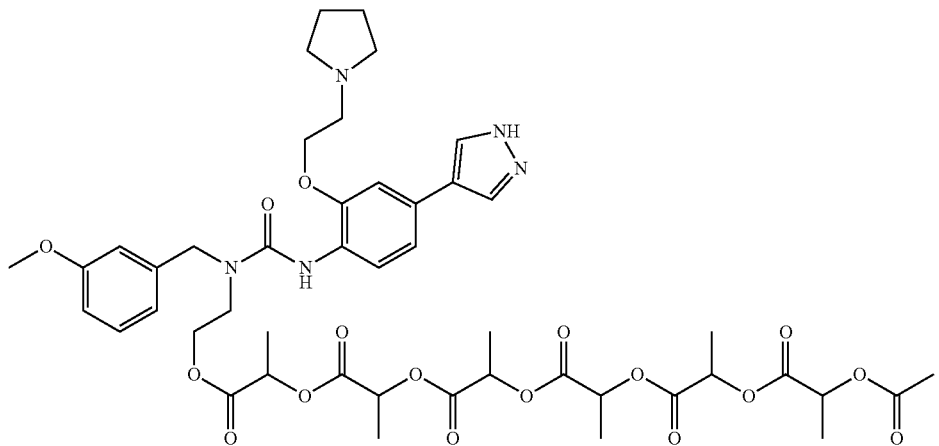 [SMILES: COc1cccc(CN(CCOC(=O)C(C)OC(=O)C(C)OC(=O)C(C)OC(=O)C(C)OC(=O)C(C)OC(=O)C(C)OC(C)=O)C(=O)Nc2ccc(-c3cn[nH]c3)cc2OCCN2CCCC2)c1]

TABLE D-continued
Non-limiting Examples of Prodrugs
226
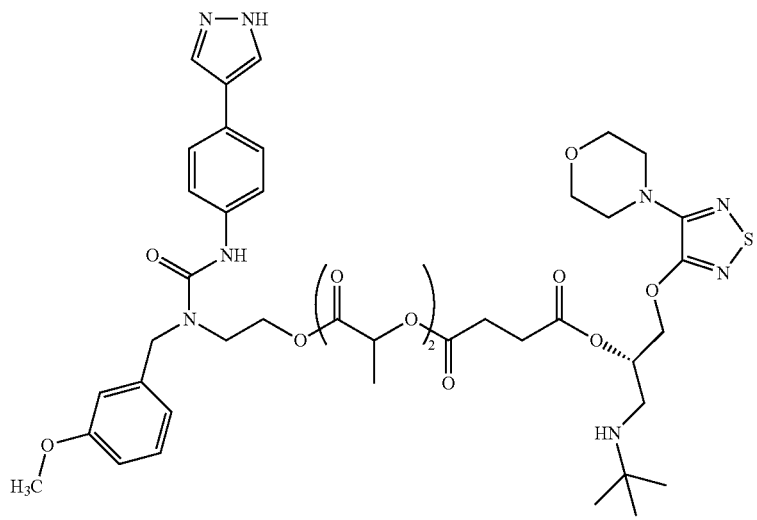
227
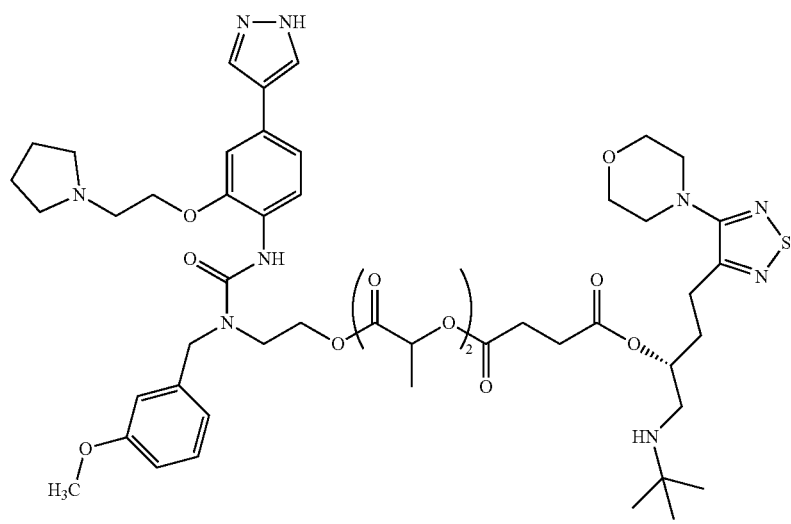
228
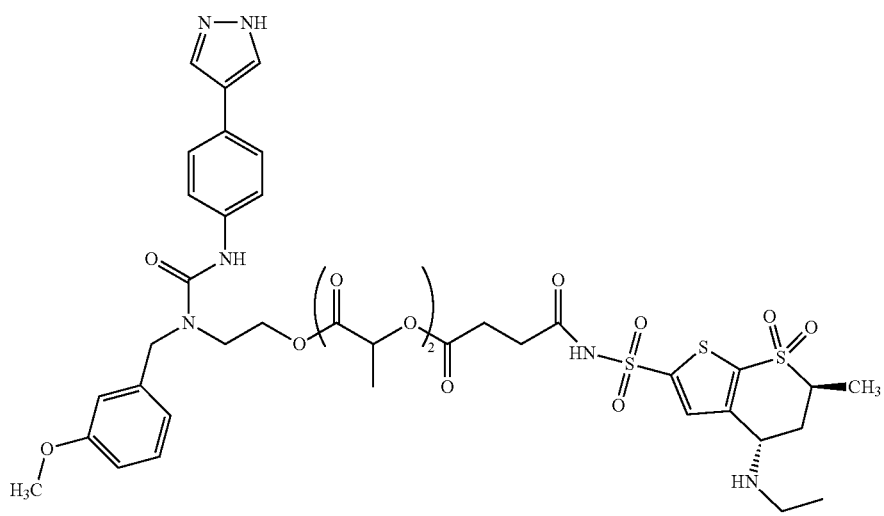

TABLE D-continued
Non-limiting Examples of Prodrugs
229
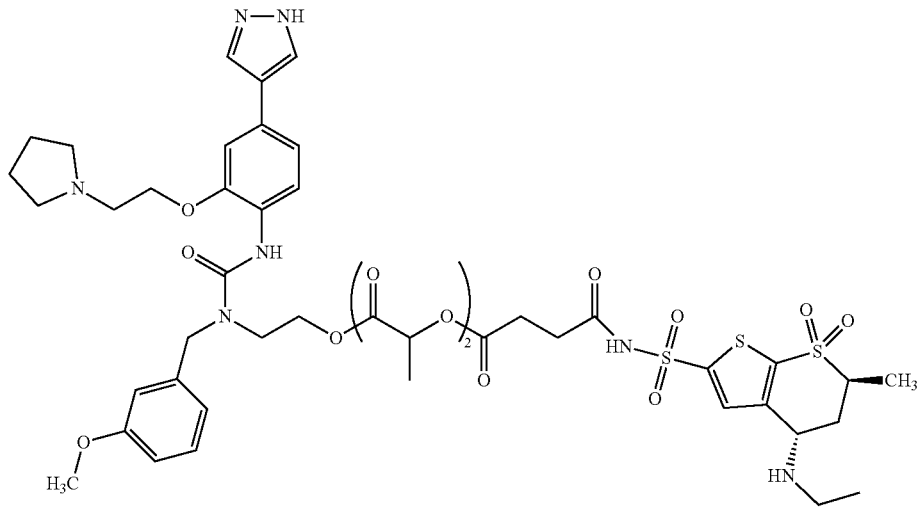
230
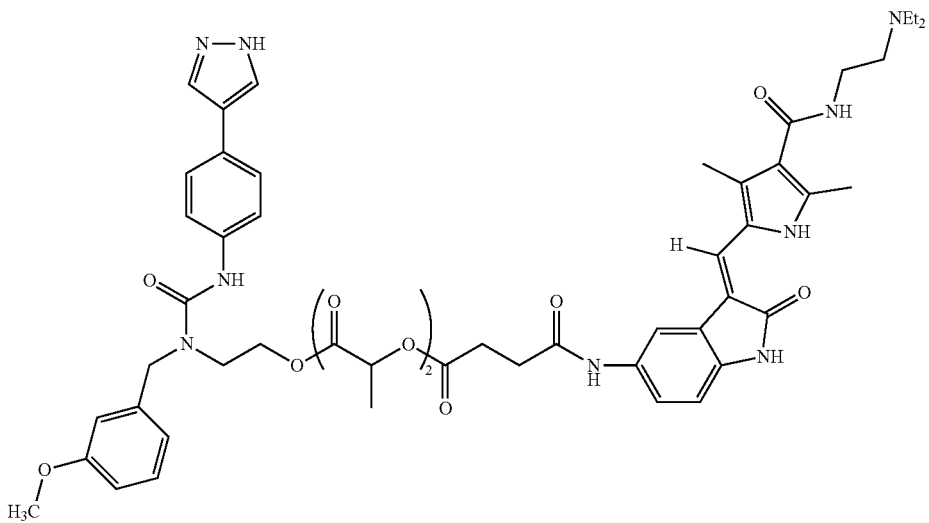
231
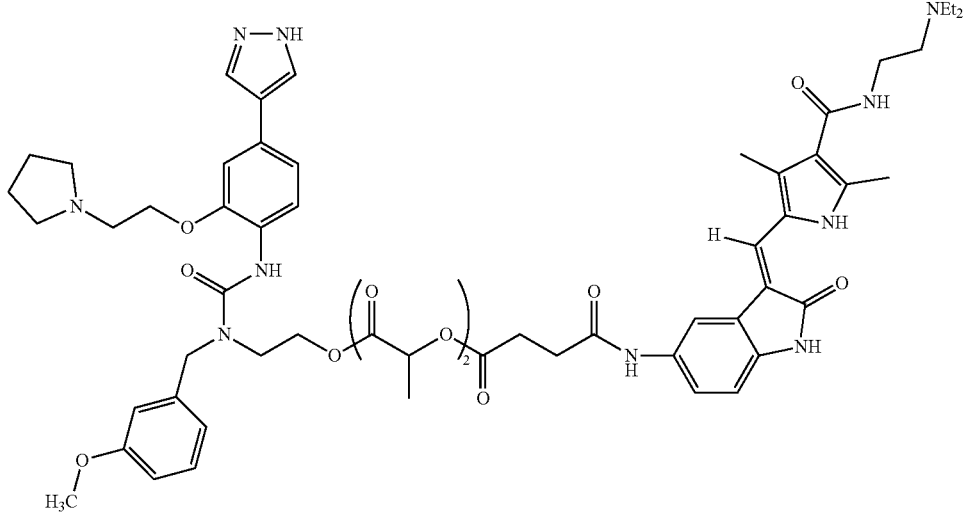

TABLE D-continued
Non-limiting Examples of Prodrugs
232
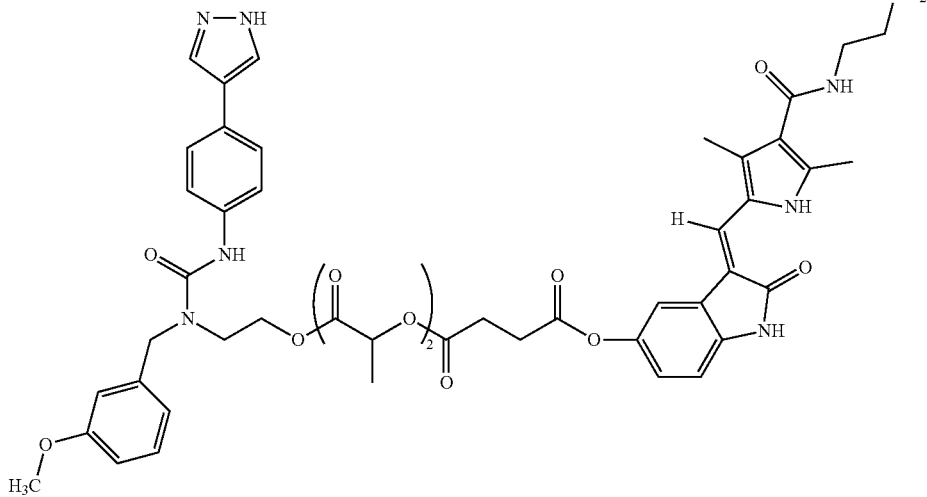
233
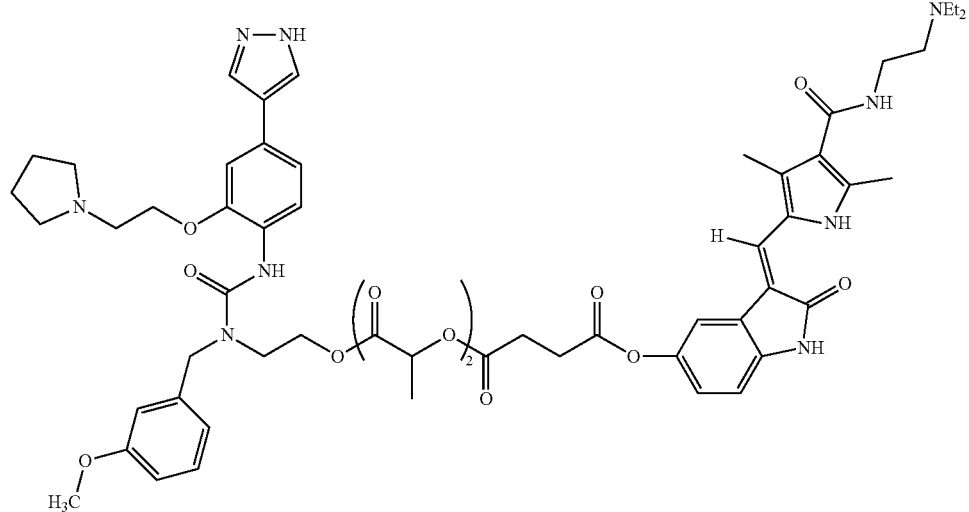

TABLE D-continued
Non-limiting Examples of Prodrugs
234
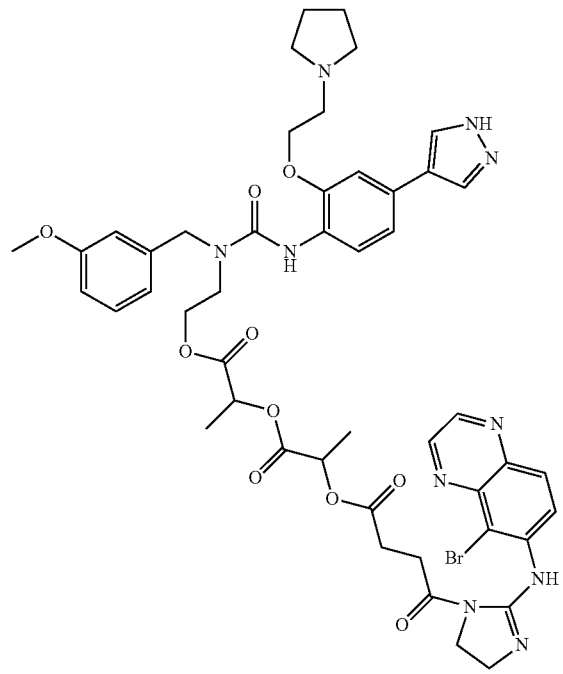 [SMILES: COc1cccc(CN(CCOC(=O)C(C)OC(=O)C(C)OC(=O)CCC(=O)N2CCN=C2Nc2ccc3nccnc3c2Br)C(=O)Nc2ccc(-c3cn[nH]c3)cc2OCCN2CCCC2)c1]
235
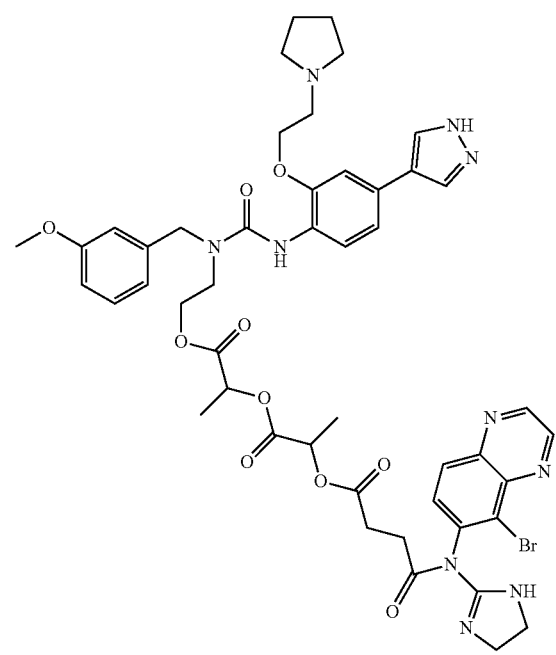 [SMILES: COc1cccc(CN(CCOC(=O)C(C)OC(=O)C(C)OC(=O)CCC(=O)N(C2=NCCN2)c2ccc3nccnc3c2Br)C(=O)Nc2ccc(-c3cn[nH]c3)cc2OCCN2CCCC2)c1]

TABLE D-continued
Non-limiting Examples of Prodrugs
236
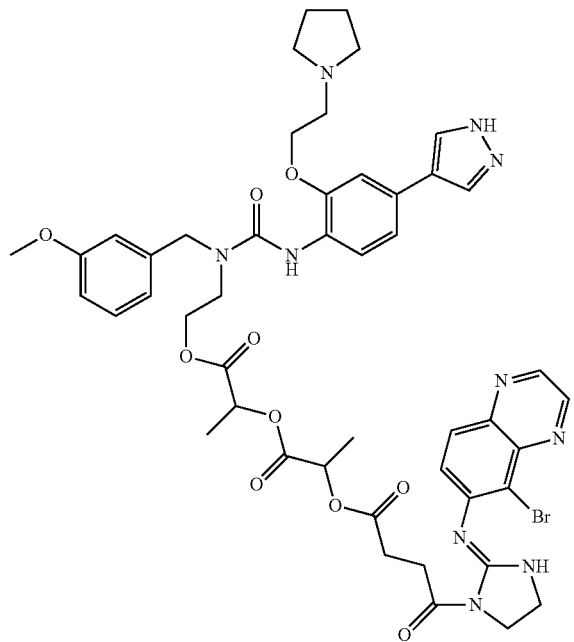 [SMILES: COc1cccc(CN(CCOC(=O)C(C)OC(=O)C(C)OC(=O)CCC(=O)N2CCN/C2=N\c2ccc3nccnc3c2Br)C(=O)Nc2ccc(-c3cn[nH]c3)cc2OCCN2CCCC2)c1]
237
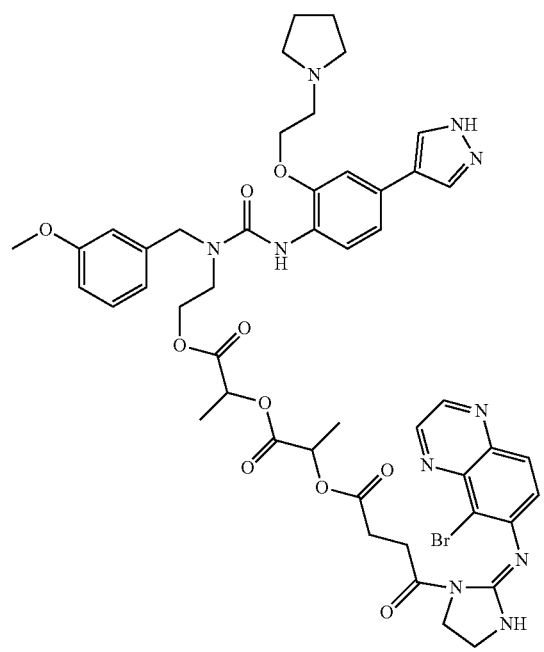 [SMILES: COc1cccc(CN(CCOC(=O)C(C)OC(=O)C(C)OC(=O)CCC(=O)N2CCN/C2=N/c2ccc3nccnc3c2Br)C(=O)Nc2ccc(-c3cn[nH]c3)cc2OCCN2CCCC2)c1]

TABLE D-continued
Non-limiting Examples of Prodrugs
238
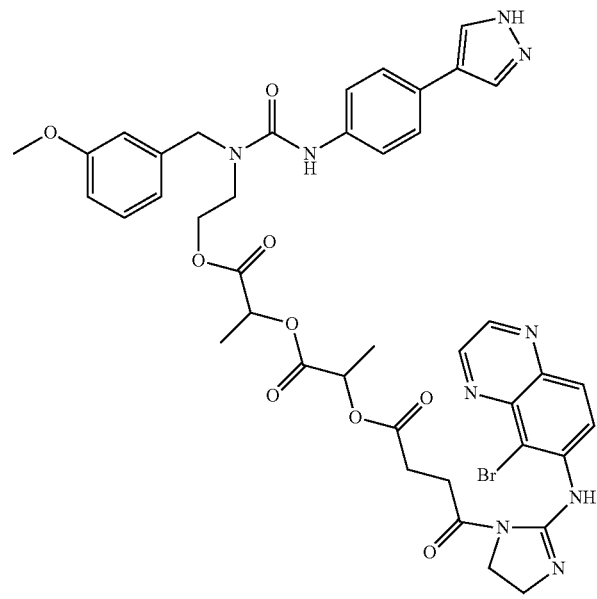 [SMILES: COc1cccc(CN(CCOC(=O)C(C)OC(=O)C(C)OC(=O)CCC(=O)N2CCN=C2Nc2ccc3nccnc3c2Br)C(=O)Nc2ccc(-c3cn[nH]c3)cc2)c1]
239
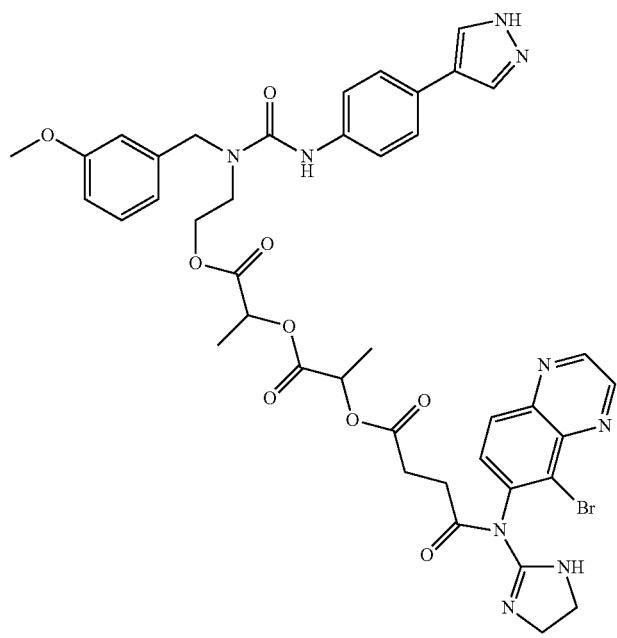 [SMILES: COc1cccc(CN(CCOC(=O)C(C)OC(=O)C(C)OC(=O)CCC(=O)N(C2=NCCN2)c2ccc3nccnc3c2Br)C(=O)Nc2ccc(-c3cn[nH]c3)cc2)c1]

TABLE D-continued
Non-limiting Examples of Prodrugs
240
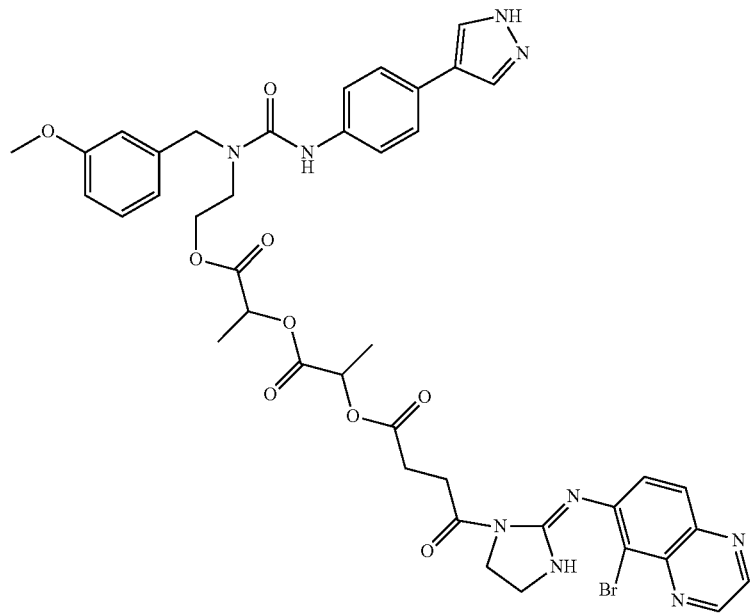 [SMILES: COc1cccc(CN(CCOC(=O)C(C)OC(=O)C(C)OC(=O)CCC(=O)N2CCN/C2=N\c2ccc3nccnc3c2Br)C(=O)Nc2ccc(-c3cn[nH]c3)cc2)c1]
241
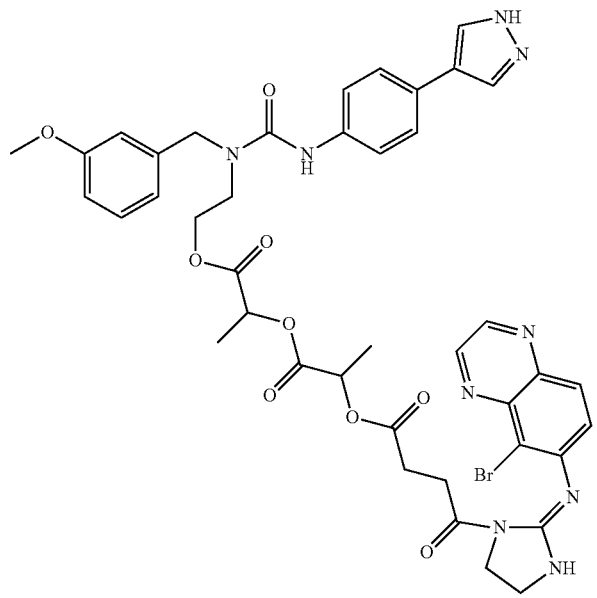 [SMILES: COc1cccc(CN(CCOC(=O)C(C)OC(=O)C(C)OC(=O)CCC(=O)N2CCN/C2=N/c2ccc3nccnc3c2Br)C(=O)Nc2ccc(-c3cn[nH]c3)cc2)c1]
242
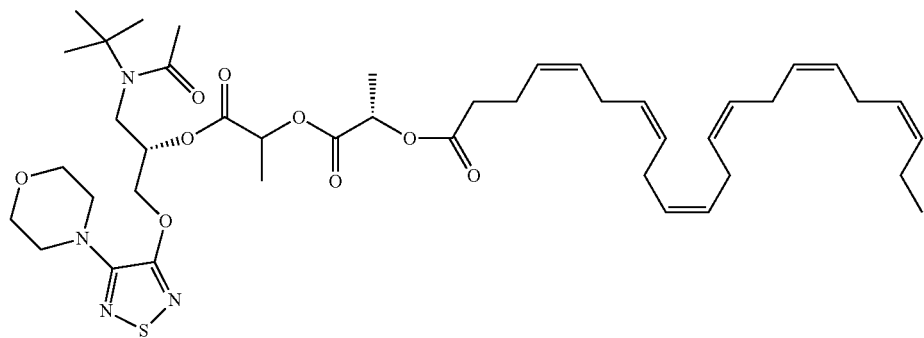 [SMILES: CC/C=C\C/C=C\C/C=C\C/C=C\C/C=C\C/C=C\CCC(=O)O[C@@H](C)C(=O)OC(C)C(=O)O[C@H](COc1nsnc1N1CCOCC1)CN(C(C)=O)C(C)(C)C]

US 11,160,870 B2
445	446
TABLE D-continued
Non-limiting Examples of Prodrugs
243
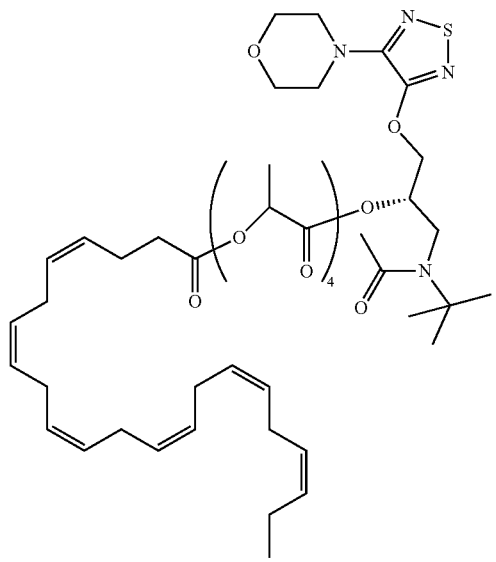
244
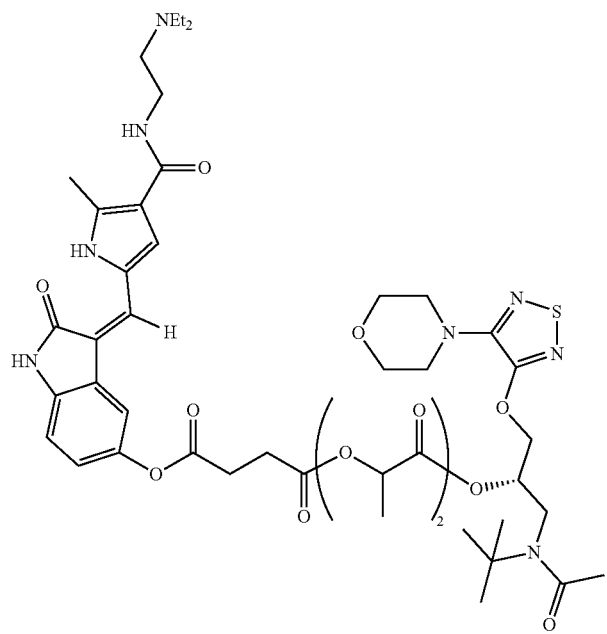

TABLE D-continued
Non-limiting Examples of Prodrugs
245 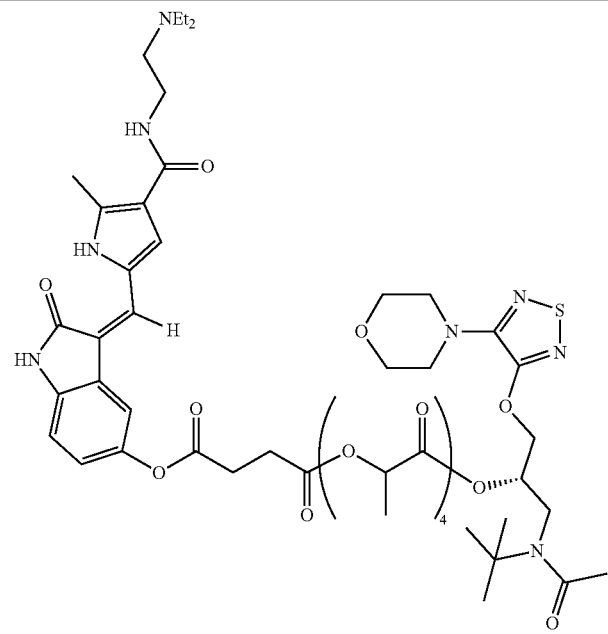
246 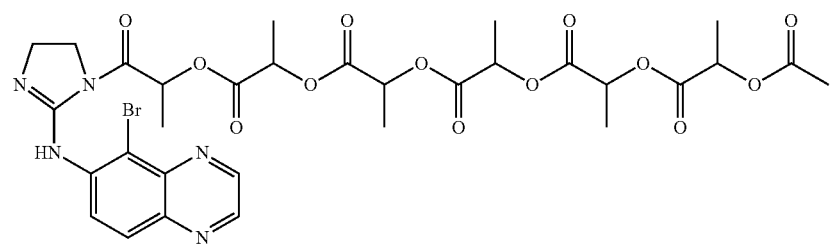 [SMILES: CC(=O)OC(C)C(=O)OC(C)C(=O)OC(C)C(=O)OC(C)C(=O)OC(C)C(=O)OC(C)C(=O)N1CCN=C1Nc1ccc2nccnc2c1Br]
247 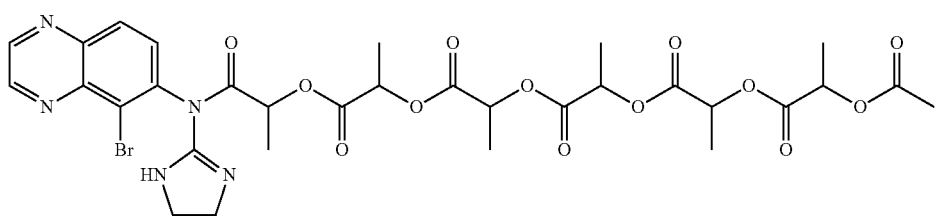 [SMILES: CC(=O)OC(C)C(=O)OC(C)C(=O)OC(C)C(=O)OC(C)C(=O)OC(C)C(=O)OC(C)C(=O)N(C1=NCCN1)c1ccc2nccnc2c1Br]
248 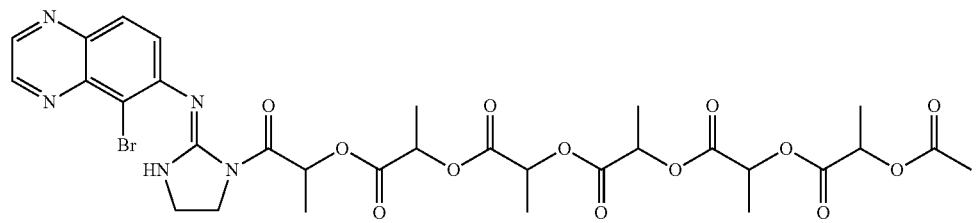 [SMILES: CC(=O)OC(C)C(=O)OC(C)C(=O)OC(C)C(=O)OC(C)C(=O)OC(C)C(=O)OC(C)C(=O)N1CCN/C1=N\c1ccc2nccnc2c1Br]
249 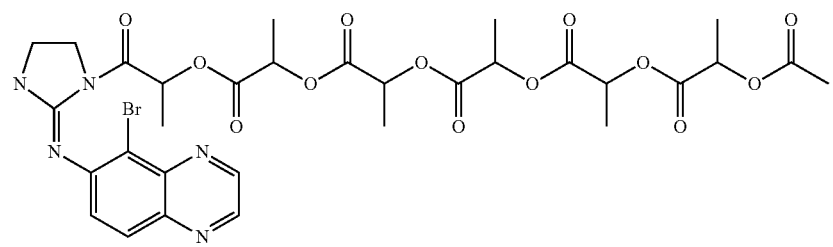 [SMILES: CC(=O)OC(C)C(=O)OC(C)C(=O)OC(C)C(=O)OC(C)C(=O)OC(C)C(=O)OC(C)C(=O)N1CCN/C1=N/c1ccc2nccnc2c1Br]

TABLE D-continued
Non-limiting Examples of Prodrugs
250 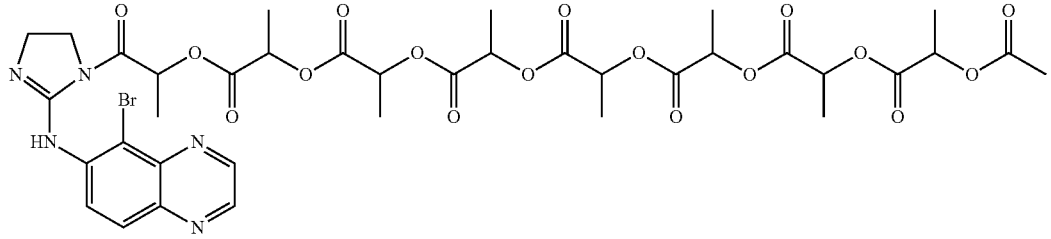 [SMILES: CC(=O)OC(C)C(=O)OC(C)C(=O)OC(C)C(=O)OC(C)C(=O)OC(C)C(=O)OC(C)C(=O)OC(C)C(=O)OC(C)C(=O)N1CCN=C1Nc1ccc2nccnc2c1Br]
251 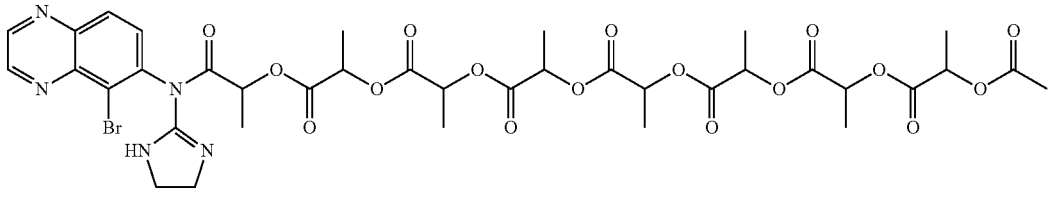 [SMILES: CC(=O)OC(C)C(=O)OC(C)C(=O)OC(C)C(=O)OC(C)C(=O)OC(C)C(=O)OC(C)C(=O)OC(C)C(=O)OC(C)C(=O)N(C1=NCCN1)c1ccc2nccnc2c1Br]
252 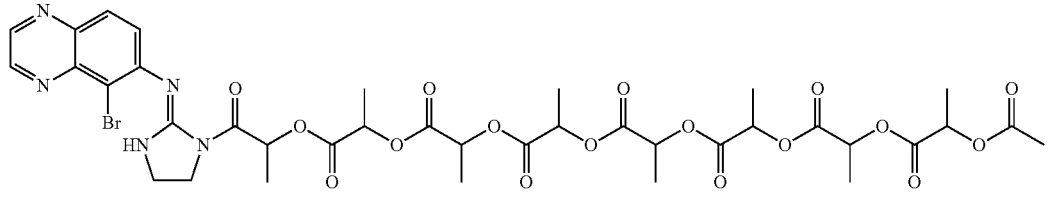 [SMILES: CC(=O)OC(C)C(=O)OC(C)C(=O)OC(C)C(=O)OC(C)C(=O)OC(C)C(=O)OC(C)C(=O)OC(C)C(=O)OC(C)C(=O)N1CCN/C1=N\c1ccc2nccnc2c1Br]
253 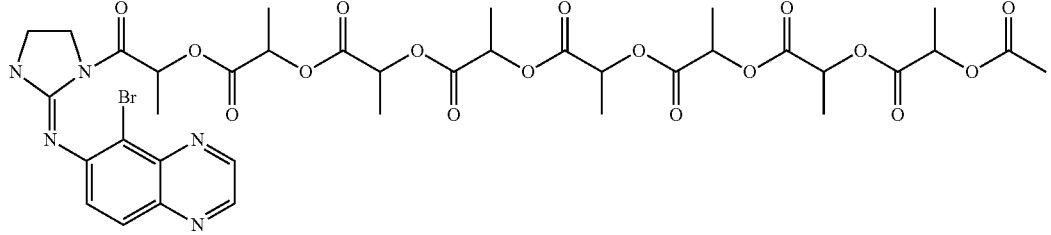 [SMILES: CC(=O)OC(C)C(=O)OC(C)C(=O)OC(C)C(=O)OC(C)C(=O)OC(C)C(=O)OC(C)C(=O)OC(C)C(=O)OC(C)C(=O)N1CCN/C1=N/c1ccc2nccnc2c1Br]
254 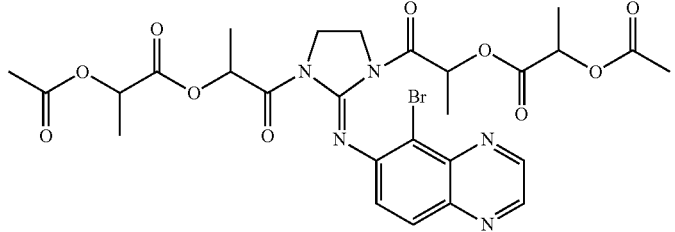 [SMILES: CC(=O)OC(C)C(=O)OC(C)C(=O)N1CCN(C(=O)C(C)OC(=O)C(C)OC(C)=O)C1=Nc1ccc2nccnc2c1Br]
255 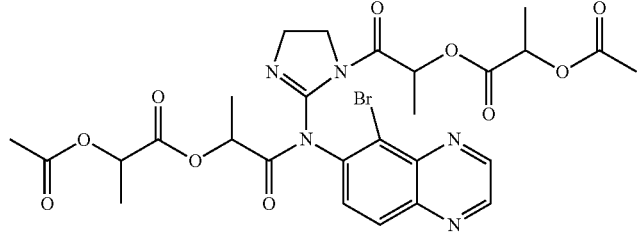 [SMILES: CC(=O)OC(C)C(=O)OC(C)C(=O)N1CCN=C1N(C(=O)C(C)OC(=O)C(C)OC(C)=O)c1ccc2nccnc2c1Br]

TABLE D-continued
Non-limiting Examples of Prodrugs
256 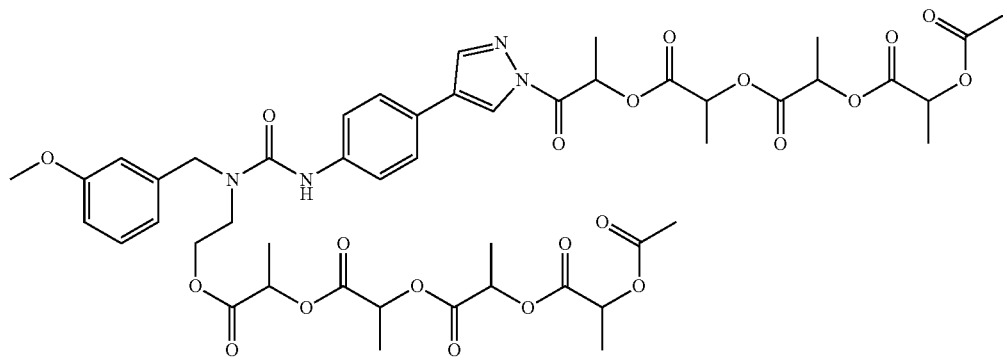 [SMILES: COc1cccc(CN(CCOC(=O)C(C)OC(=O)C(C)OC(=O)C(C)OC(=O)C(C)OC(C)=O)C(=O)Nc2ccc(-c3cnn(C(=O)C(C)OC(=O)C(C)OC(=O)C(C)OC(=O)C(C)OC(C)=O)c3)cc2)c1]
257 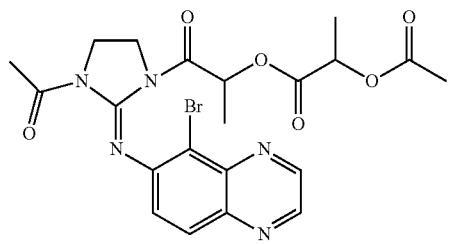 [SMILES: CC(=O)OC(C)C(=O)OC(C)C(=O)N1CCN(C(C)=O)/C1=N/c1ccc2nccnc2c1Br]
258 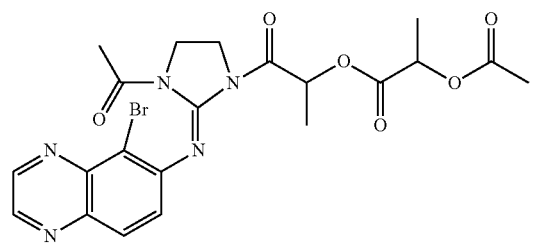 [SMILES: CC(=O)OC(C)C(=O)OC(C)C(=O)N1CCN(C(C)=O)/C1=N\c1ccc2nccnc2c1Br]
259 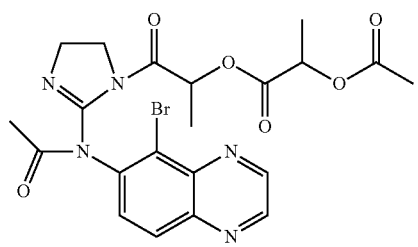 [SMILES: CC(=O)OC(C)C(=O)OC(C)C(=O)N1CCN=C1N(C(C)=O)c1ccc2nccnc2c1Br]
260 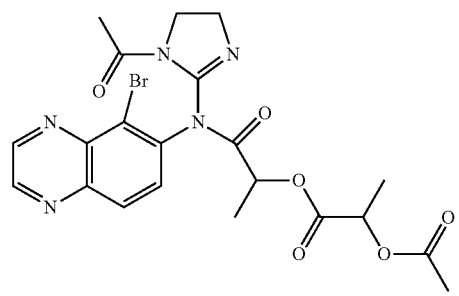 [SMILES: CC(=O)OC(C)C(=O)OC(C)C(=O)N(C1=NCCN1C(C)=O)c1ccc2nccnc2c1Br]

TABLE D-continued
Non-limiting Examples of Prodrugs
261 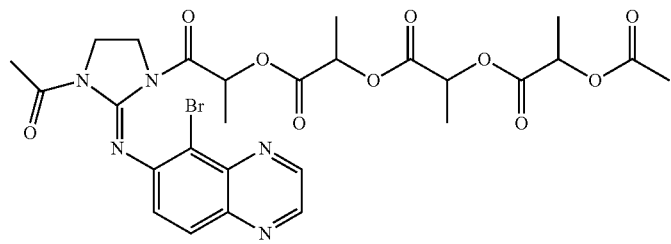 [SMILES: CC(=O)OC(C)C(=O)OC(C)C(=O)OC(C)C(=O)OC(C)C(=O)N1CCN(C(C)=O)/C1=N/c1ccc2nccnc2c1Br]
262 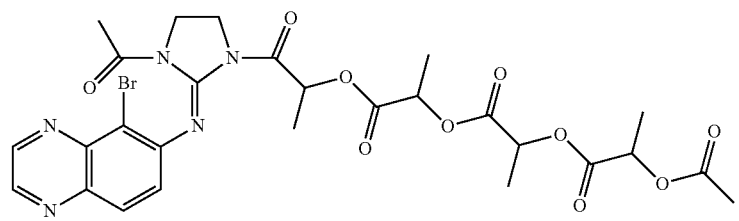 [SMILES: CC(=O)OC(C)C(=O)OC(C)C(=O)OC(C)C(=O)OC(C)C(=O)N1CCN(C(C)=O)/C1=N\c1ccc2nccnc2c1Br]
263 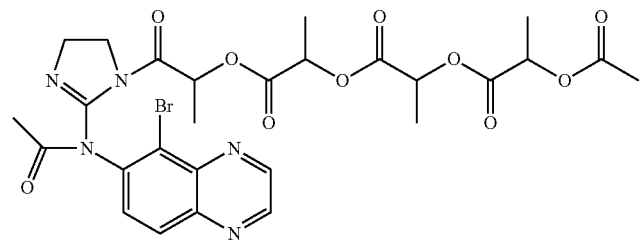 [SMILES: CC(=O)OC(C)C(=O)OC(C)C(=O)OC(C)C(=O)OC(C)C(=O)N1CCN=C1N(C(C)=O)c1ccc2nccnc2c1Br]
264 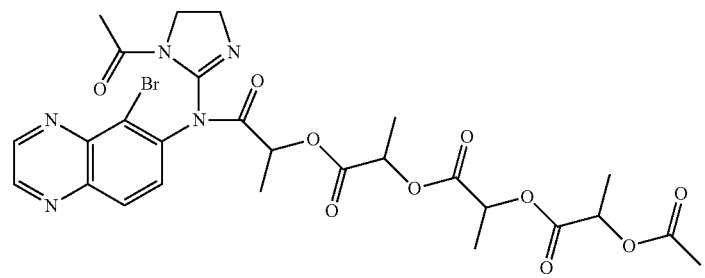 [SMILES: CC(=O)OC(C)C(=O)OC(C)C(=O)OC(C)C(=O)OC(C)C(=O)N(C1=NCCN1C(C)=O)c1ccc2nccnc2c1Br]
265 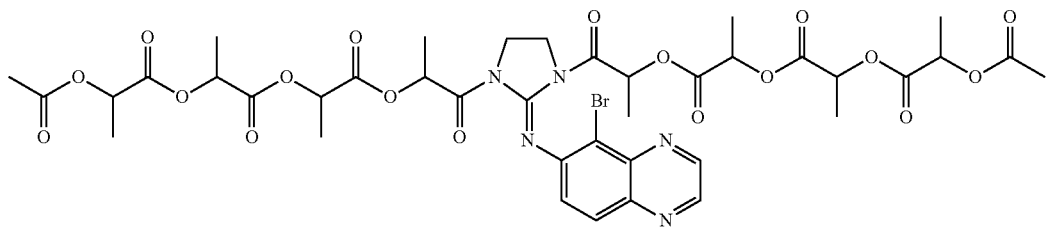 [SMILES: CC(=O)OC(C)C(=O)OC(C)C(=O)OC(C)C(=O)OC(C)C(=O)N1CCN(C(=O)C(C)OC(=O)C(C)OC(=O)C(C)OC(=O)C(C)OC(C)=O)C1=Nc1ccc2nccnc2c1Br]
266 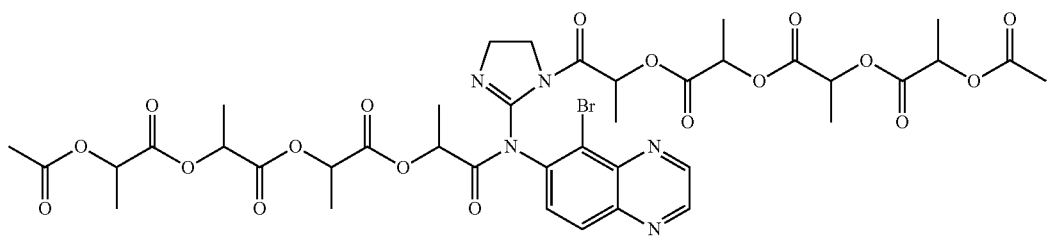 [SMILES: CC(=O)OC(C)C(=O)OC(C)C(=O)OC(C)C(=O)OC(C)C(=O)N1CCN=C1N(C(=O)C(C)OC(=O)C(C)OC(=O)C(C)OC(=O)C(C)OC(C)=O)c1ccc2nccnc2c1Br]

TABLE D-continued
Non-limiting Examples of Prodrugs
267
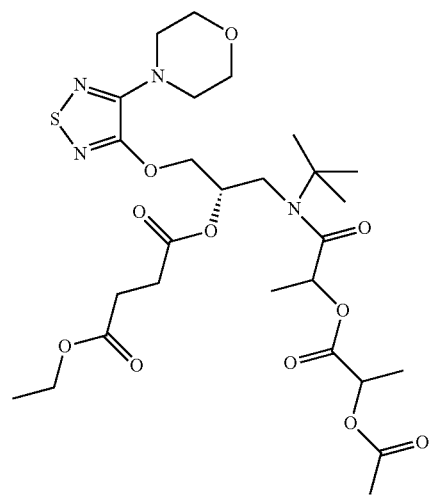 [SMILES: CCOC(=O)CCC(=O)O[C@H](COc1nsnc1N1CCOCC1)CN(C(=O)C(C)OC(=O)C(C)OC(C)=O)C(C)(C)C]
268
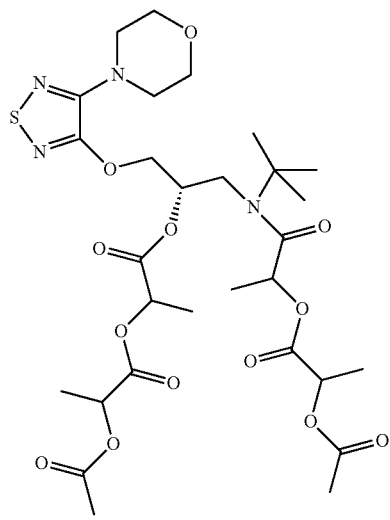 [SMILES: CC(=O)OC(C)C(=O)OC(C)C(=O)O[C@H](COc1nsnc1N1CCOCC1)CN(C(=O)C(C)OC(=O)C(C)OC(C)=O)C(C)(C)C]

TABLE D-continued
Non-limiting Examples of Prodrugs
269
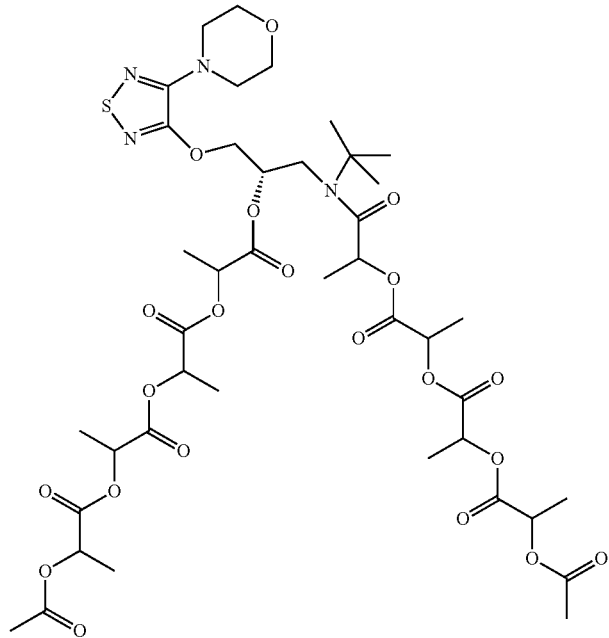 [SMILES: CC(=O)OC(C)C(=O)OC(C)C(=O)OC(C)C(=O)OC(C)C(=O)O[C@H](COc1nsnc1N1CCOCC1)CN(C(=O)C(C)OC(=O)C(C)OC(=O)C(C)OC(=O)C(C)OC(C)=O)C(C)(C)C]
270
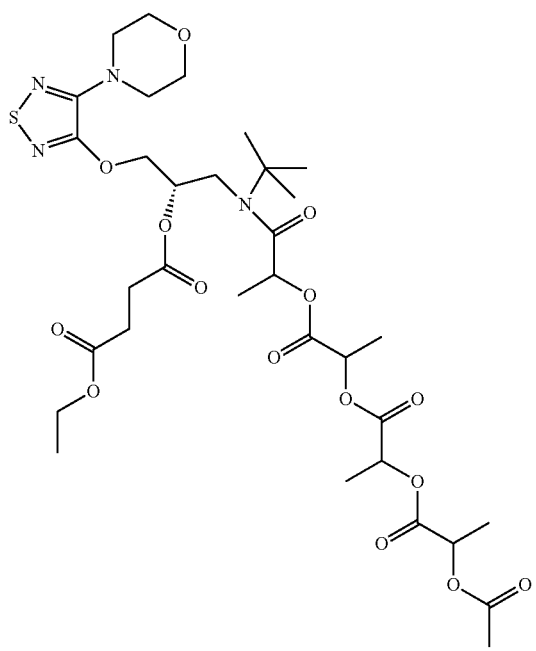 [SMILES: CCOC(=O)CCC(=O)O[C@H](COc1nsnc1N1CCOCC1)CN(C(=O)C(C)OC(=O)C(C)OC(=O)C(C)OC(=O)C(C)OC(C)=O)C(C)(C)C]

460
TABLE D-continued
Non-limiting Examples of Prodrugs
271 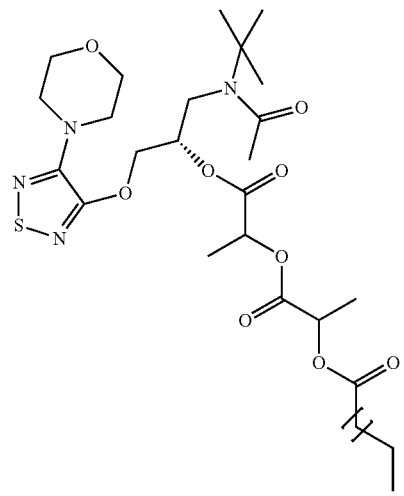
n = 15
272 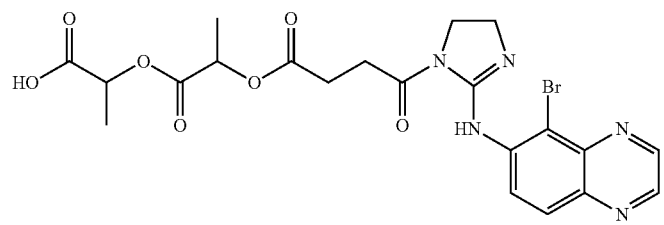 [SMILES: CC(OC(=O)C(C)OC(=O)CCC(=O)N1CCN=C1Nc1ccc2nccnc2c1Br)C(=O)O]
273 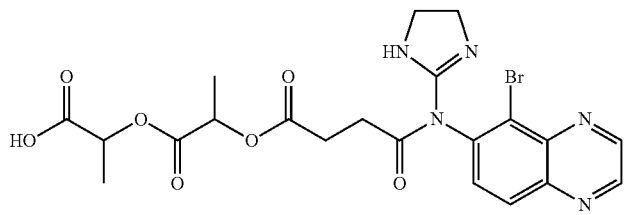 [SMILES: CC(OC(=O)C(C)OC(=O)CCC(=O)N(C1=NCCN1)c1ccc2nccnc2c1Br)C(=O)O]
274 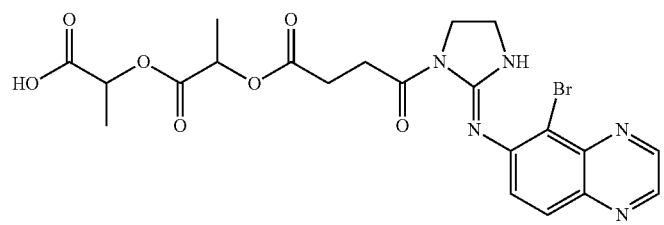 [SMILES: CC(OC(=O)C(C)OC(=O)CCC(=O)N1CCN/C1=N\c1ccc2nccnc2c1Br)C(=O)O]

TABLE D-continued
Non-limiting Examples of Prodrugs
275 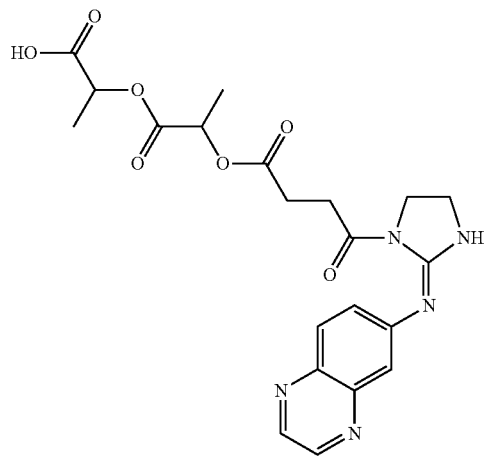 [SMILES: CC(OC(=O)C(C)OC(=O)CCC(=O)N1CCN/C1=N/c1ccc2nccnc2c1)C(=O)O]
276 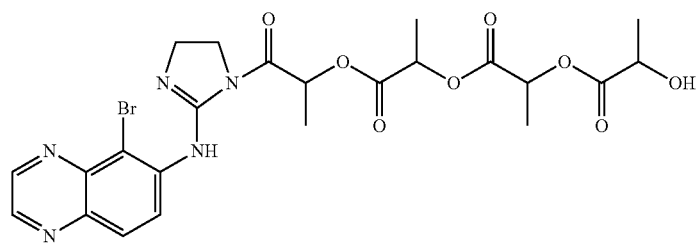 [SMILES: CC(O)C(=O)OC(C)C(=O)OC(C)C(=O)OC(C)C(=O)N1CCN=C1Nc1ccc2nccnc2c1Br]
277 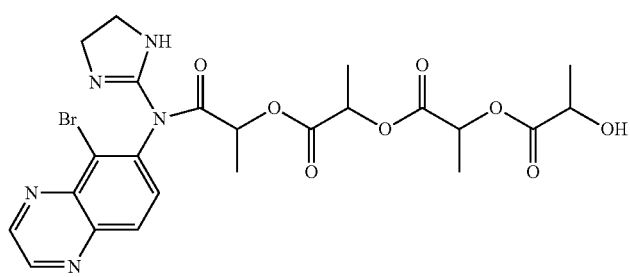 [SMILES: CC(O)C(=O)OC(C)C(=O)OC(C)C(=O)OC(C)C(=O)N(C1=NCCN1)c1ccc2nccnc2c1Br]
278 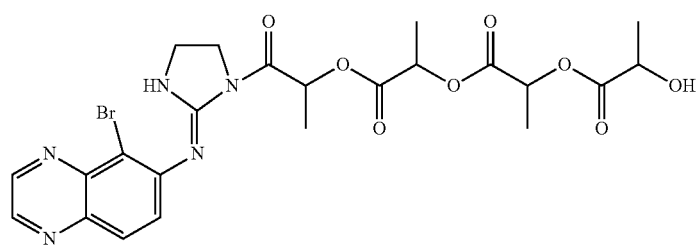 [SMILES: CC(O)C(=O)OC(C)C(=O)OC(C)C(=O)OC(C)C(=O)N1CCN/C1=N\c1ccc2nccnc2c1Br]
279 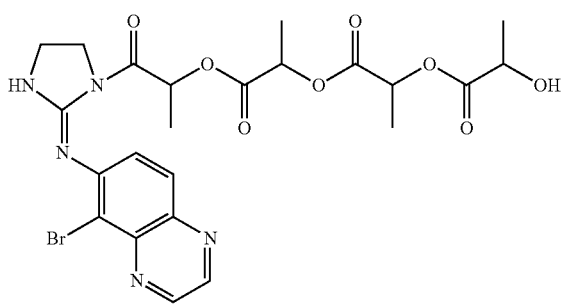 [SMILES: CC(O)C(=O)OC(C)C(=O)OC(C)C(=O)OC(C)C(=O)N1CCN/C1=N/c1ccc2nccnc2c1Br]

TABLE D-continued
Non-limiting Examples of Prodrugs
280
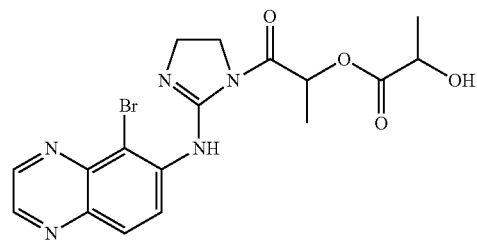 [SMILES: CC(O)C(=O)OC(C)C(=O)N1CCN=C1Nc1ccc2nccnc2c1Br]
281
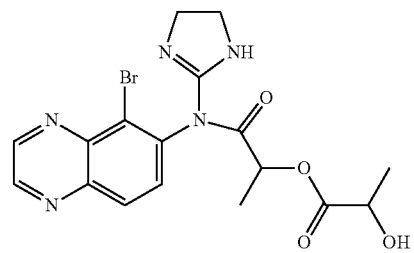 [SMILES: CC(O)C(=O)OC(C)C(=O)N(C1=NCCN1)c1ccc2nccnc2c1Br]
282
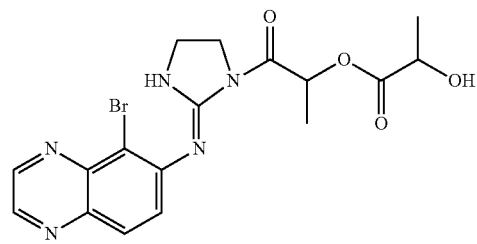 [SMILES: CC(O)C(=O)OC(C)C(=O)N1CCN/C1=N\c1ccc2nccnc2c1Br]
283
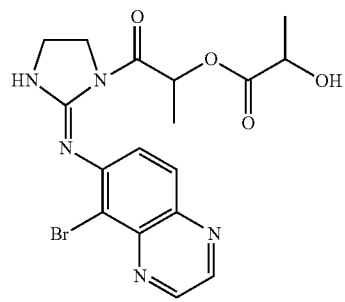 [SMILES: CC(O)C(=O)OC(C)C(=O)N1CCN/C1=N/c1ccc2nccnc2c1Br]

TABLE E
Select Compounds of the Present Invention
284
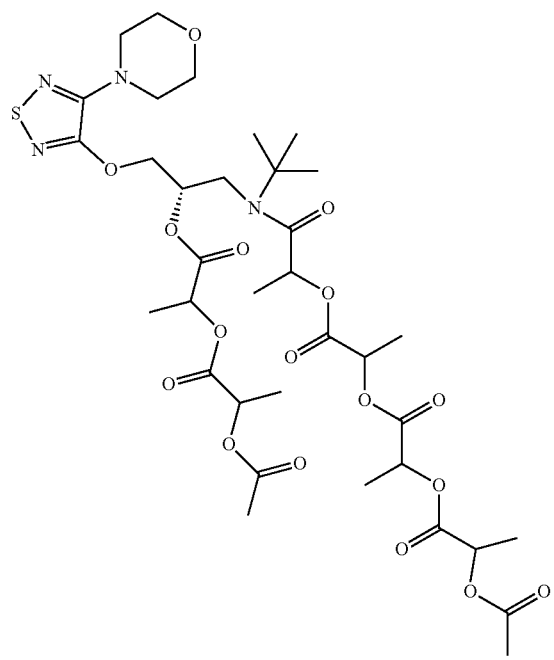 [SMILES: CC(=O)OC(C)C(=O)OC(C)C(=O)OC(C)C(=O)OC(C)C(=O)N(C[C@@H](COc1nsnc1N1CCOCC1)OC(=O)C(C)OC(=O)C(C)OC(C)=O)C(C)(C)C]
285
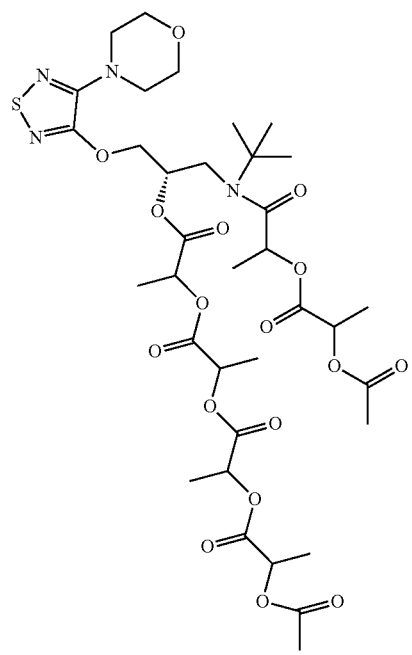 [SMILES: CC(=O)OC(C)C(=O)OC(C)C(=O)OC(C)C(=O)OC(C)C(=O)O[C@H](COc1nsnc1N1CCOCC1)CN(C(=O)C(C)OC(=O)C(C)OC(C)=O)C(C)(C)C]
286
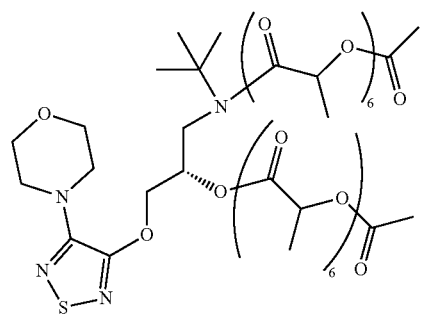

US 11,160,870 B2
467                                                                468
TABLE E-continued
Select Compounds of the Present Invention
287
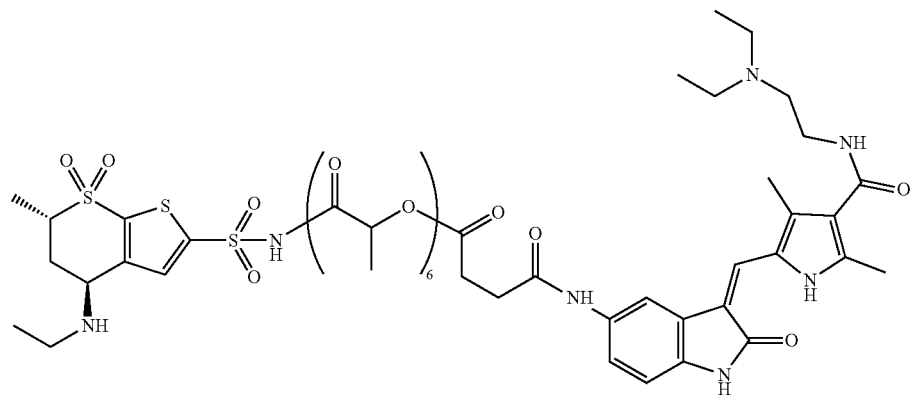
288
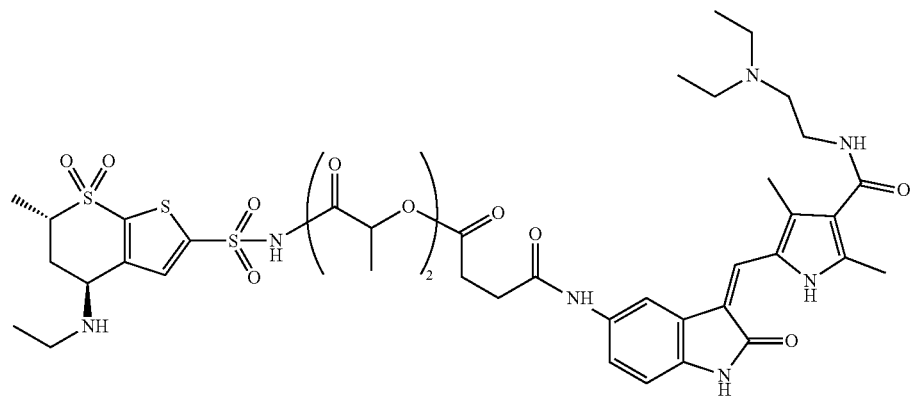
289
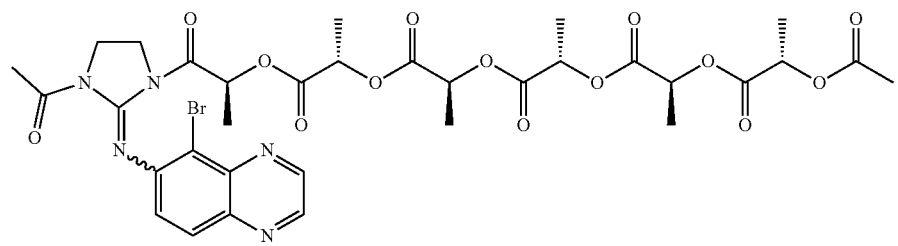 [SMILES: CC(=O)O[C@@H](C)C(=O)O[C@@H](C)C(=O)O[C@@H](C)C(=O)O[C@@H](C)C(=O)O[C@@H](C)C(=O)O[C@@H](C)C(=O)N1CCN(C(C)=O)C1=Nc1ccc2nccnc2c1Br]
290
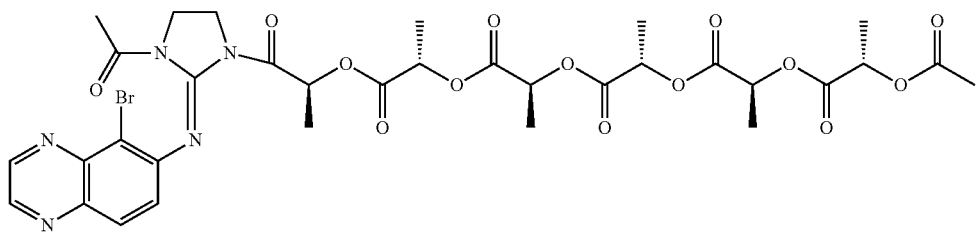 [SMILES: CC(=O)O[C@@H](C)C(=O)O[C@@H](C)C(=O)O[C@@H](C)C(=O)O[C@@H](C)C(=O)O[C@@H](C)C(=O)O[C@@H](C)C(=O)N1CCN(C(C)=O)/C1=N\c1ccc2nccnc2c1Br]
291
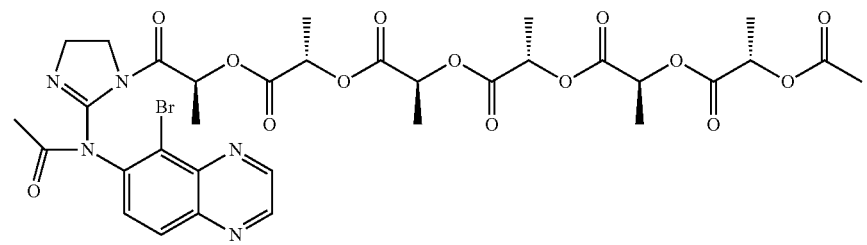 [SMILES: CC(=O)O[C@@H](C)C(=O)O[C@@H](C)C(=O)O[C@@H](C)C(=O)O[C@@H](C)C(=O)O[C@@H](C)C(=O)O[C@@H](C)C(=O)N1CCN=C1N(C(C)=O)c1ccc2nccnc2c1Br]

TABLE E-continued
Select Compounds of the Present Invention
292 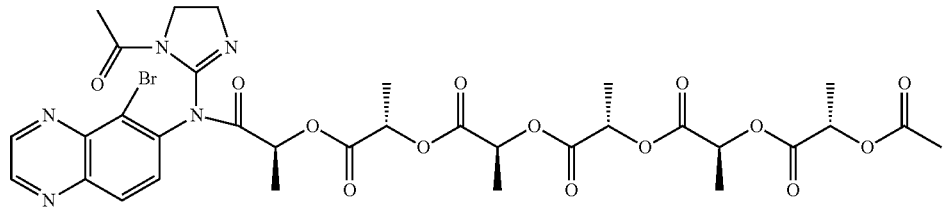 [SMILES: CC(=O)O[C@@H](C)C(=O)O[C@@H](C)C(=O)O[C@@H](C)C(=O)O[C@@H](C)C(=O)O[C@@H](C)C(=O)O[C@@H](C)C(=O)N(C1=NCCN1C(C)=O)c1ccc2nccnc2c1Br]
293 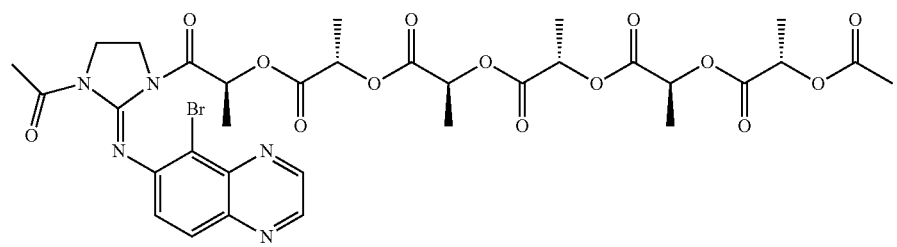 [SMILES: CC(=O)O[C@@H](C)C(=O)O[C@@H](C)C(=O)O[C@@H](C)C(=O)O[C@@H](C)C(=O)O[C@@H](C)C(=O)O[C@@H](C)C(=O)N1CCN(C(C)=O)/C1=N/c1ccc2nccnc2c1Br]
294 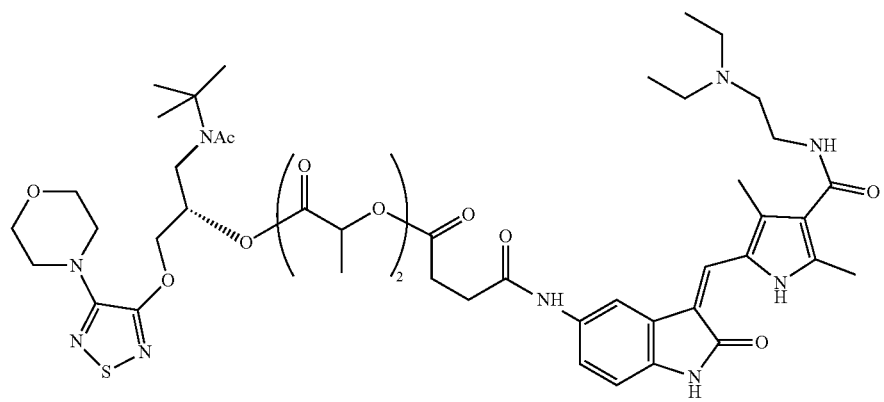
295 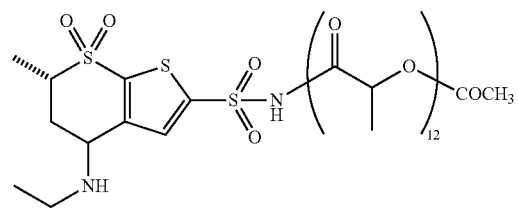
296 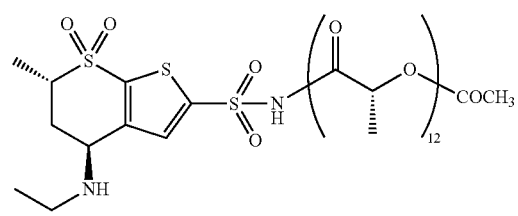
297 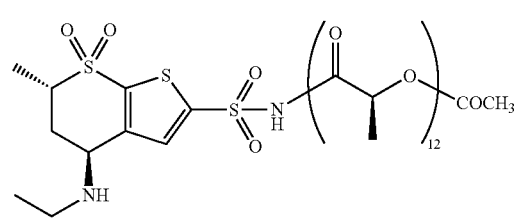

TABLE E-continued
Select Compounds of the Present Invention
298
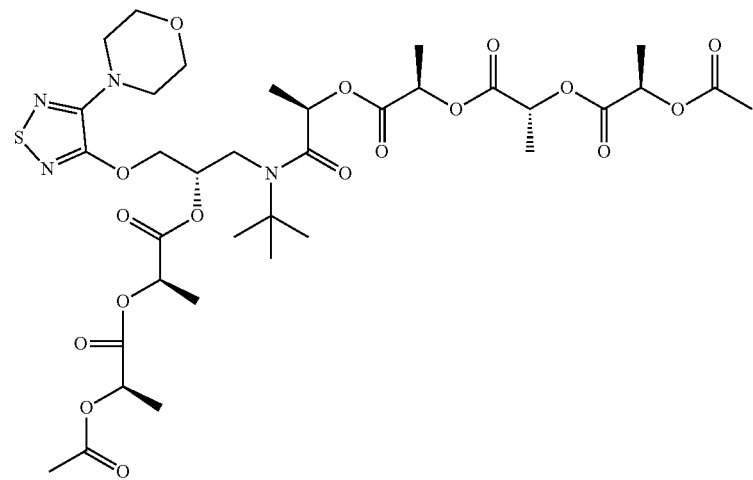 [SMILES: CC(=O)O[C@H](C)C(=O)O[C@H](C)C(=O)O[C@H](COc1nsnc1N1CCOCC1)CN(C(=O)[C@@H](C)OC(=O)[C@@H](C)OC(=O)[C@@H](C)OC(=O)[C@@H](C)OC(C)=O)C(C)(C)C]
299
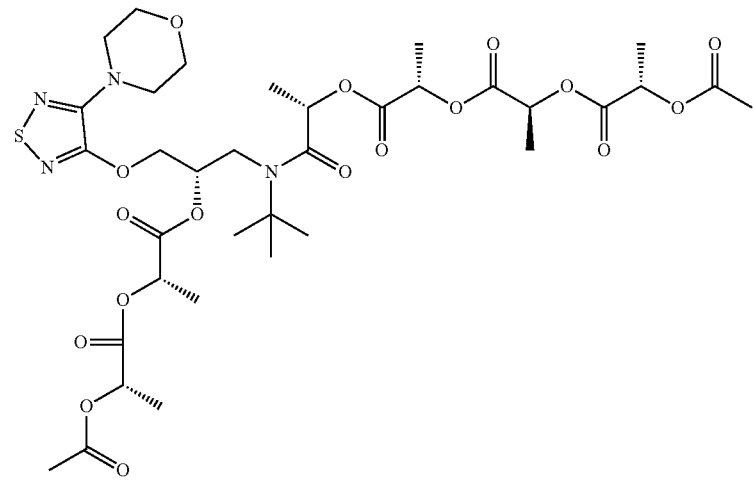 [SMILES: CC(=O)O[C@@H](C)C(=O)O[C@@H](C)C(=O)O[C@H](COc1nsnc1N1CCOCC1)CN(C(=O)[C@H](C)OC(=O)[C@H](C)OC(=O)[C@H](C)OC(=O)[C@H](C)OC(C)=O)C(C)(C)C]
300
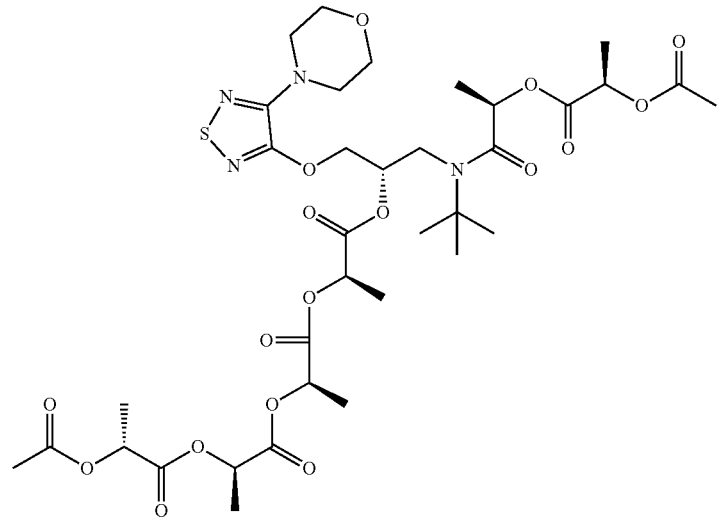 [SMILES: CC(=O)O[C@H](C)C(=O)O[C@H](C)C(=O)O[C@H](C)C(=O)O[C@H](C)C(=O)O[C@H](COc1nsnc1N1CCOCC1)CN(C(=O)[C@@H](C)OC(=O)[C@@H](C)OC(C)=O)C(C)(C)C]

TABLE E-continued
Select Compounds of the Present Invention
301 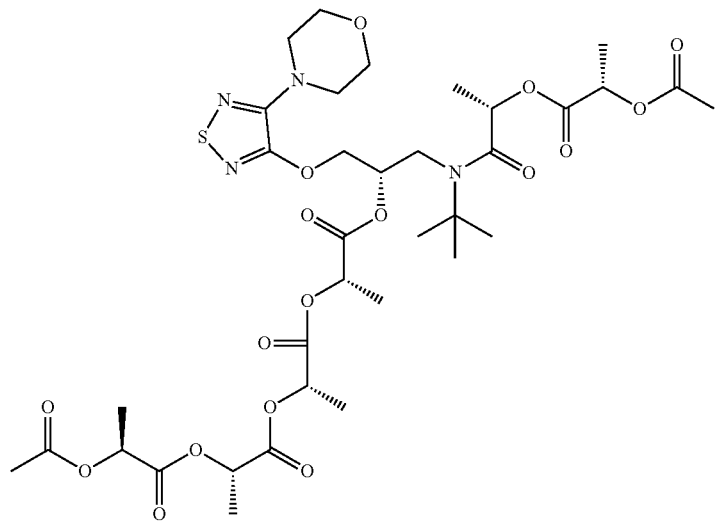 [SMILES: CC(=O)O[C@@H](C)C(=O)O[C@@H](C)C(=O)O[C@@H](C)C(=O)O[C@@H](C)C(=O)O[C@H](COc1nsnc1N1CCOCC1)CN(C(=O)[C@H](C)OC(=O)[C@H](C)OC(C)=O)C(C)(C)C]
302 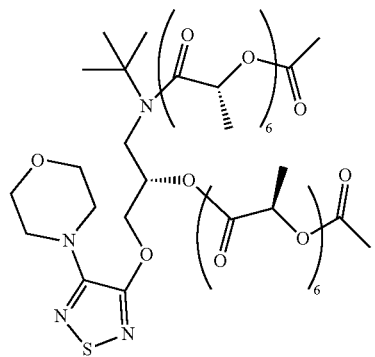
303 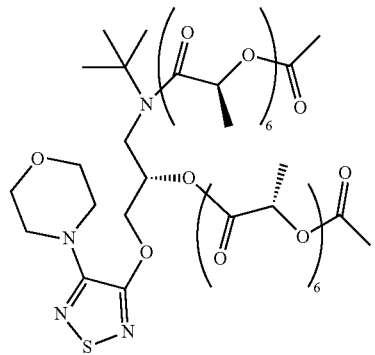

TABLE E-continued
Select Compounds of the Present Invention
304 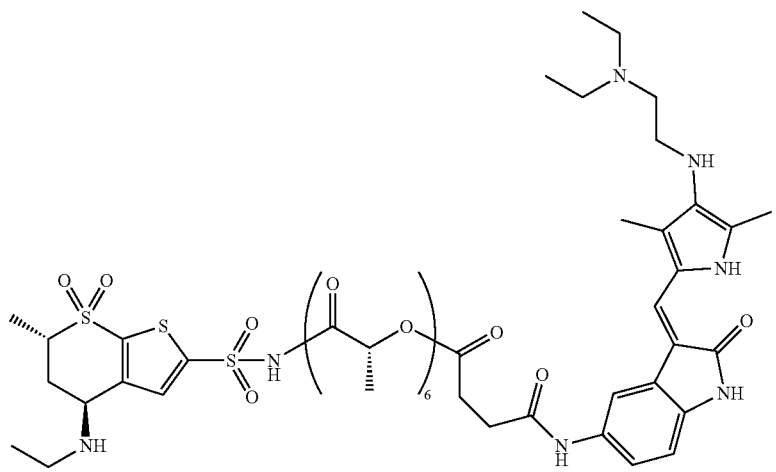
305 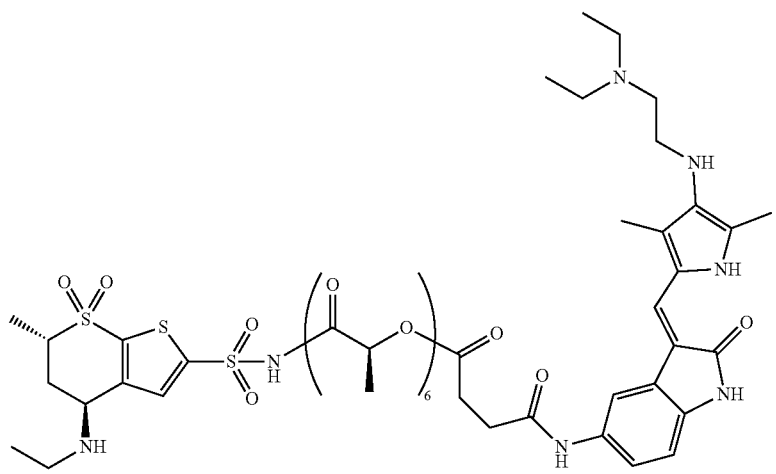
306 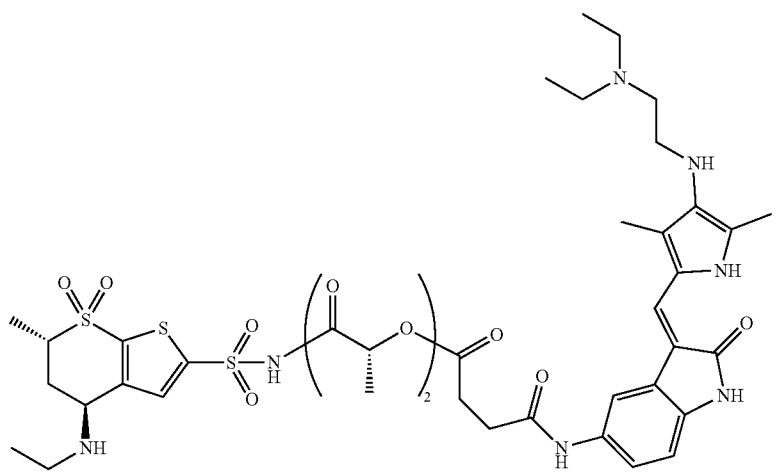

TABLE E-continued
Select Compounds of the Present Invention
307
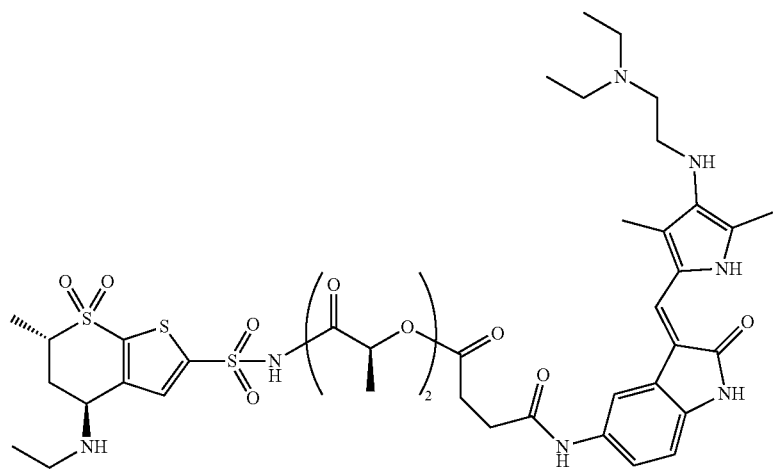
308
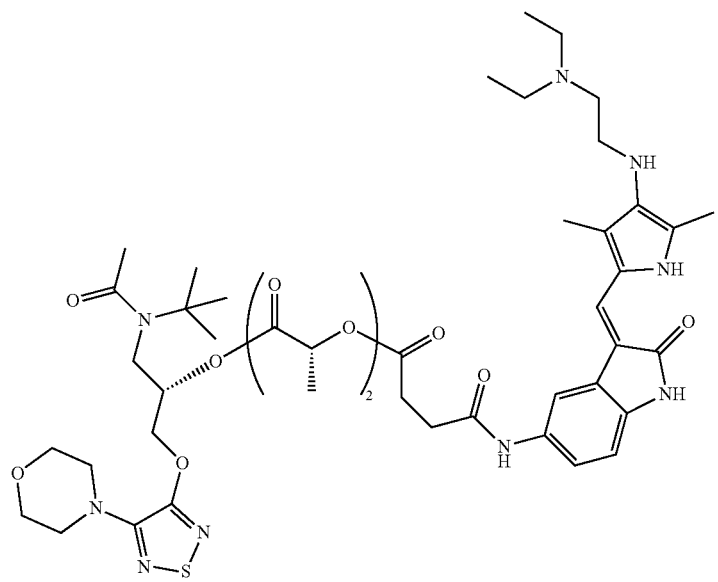
309
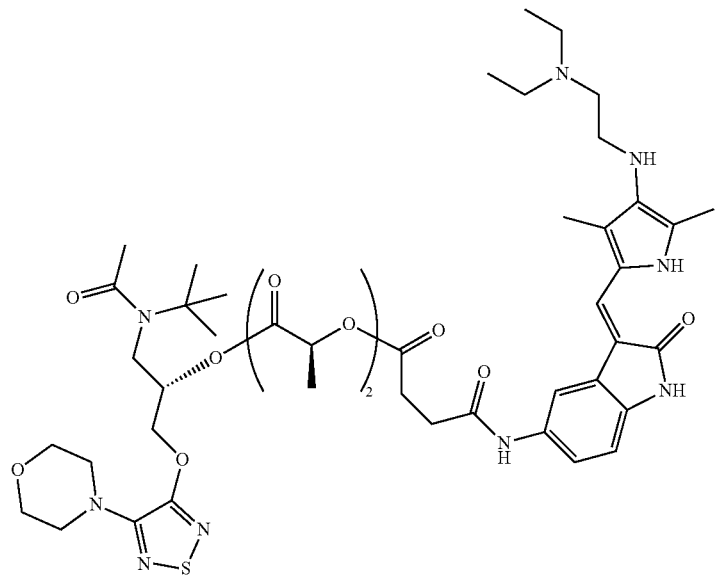

US 11,160,870 B2
479                                                                 480
TABLE E-continued
Select Compounds of the Present Invention
310 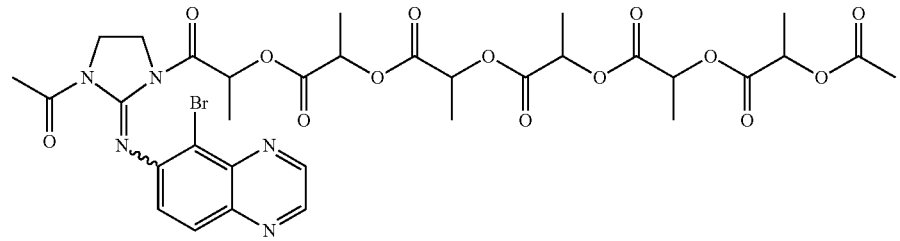 [SMILES: CC(=O)OC(C)C(=O)OC(C)C(=O)OC(C)C(=O)OC(C)C(=O)OC(C)C(=O)OC(C)C(=O)N1CCN(C(C)=O)C1=Nc1ccc2nccnc2c1Br]
311 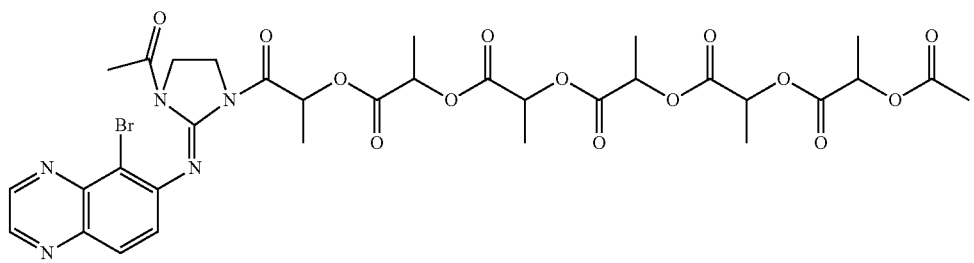 [SMILES: CC(=O)OC(C)C(=O)OC(C)C(=O)OC(C)C(=O)OC(C)C(=O)OC(C)C(=O)OC(C)C(=O)N1CCN(C(C)=O)/C1=N\c1ccc2nccnc2c1Br]
312 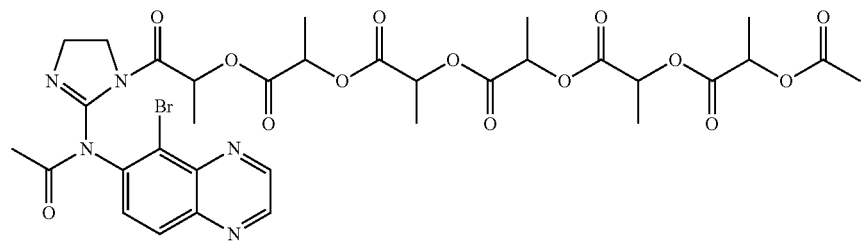 [SMILES: CC(=O)OC(C)C(=O)OC(C)C(=O)OC(C)C(=O)OC(C)C(=O)OC(C)C(=O)OC(C)C(=O)N1CCN=C1N(C(C)=O)c1ccc2nccnc2c1Br]
313 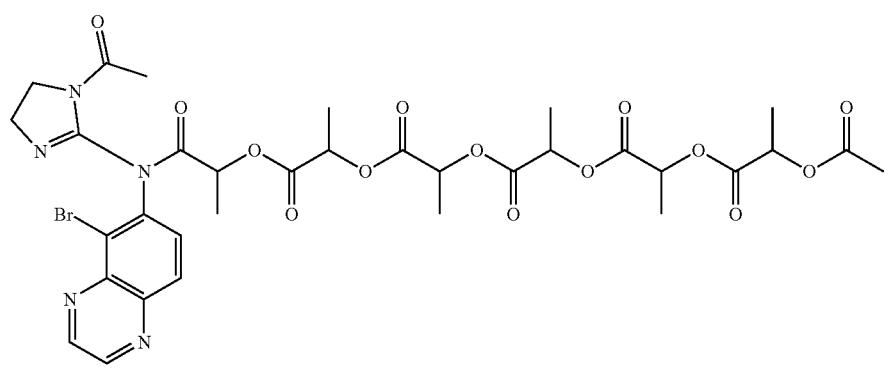 [SMILES: CC(=O)OC(C)C(=O)OC(C)C(=O)OC(C)C(=O)OC(C)C(=O)OC(C)C(=O)OC(C)C(=O)N(C1=NCCN1C(C)=O)c1ccc2nccnc2c1Br]
314 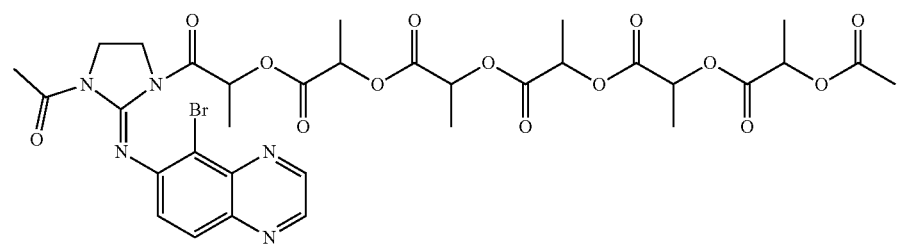 [SMILES: CC(=O)OC(C)C(=O)OC(C)C(=O)OC(C)C(=O)OC(C)C(=O)OC(C)C(=O)OC(C)C(=O)N1CCN(C(C)=O)/C1=N/c1ccc2nccnc2c1Br]

US 11,160,870 B2
481                                                                                                                482
TABLE E-continued
Select Compounds of the Present Invention
315 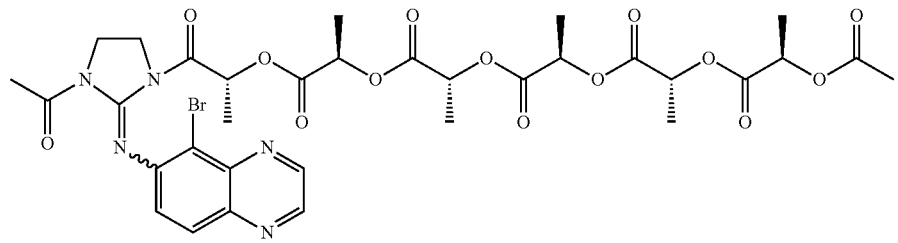 [SMILES: CC(=O)O[C@H](C)C(=O)O[C@H](C)C(=O)O[C@H](C)C(=O)O[C@H](C)C(=O)O[C@H](C)C(=O)O[C@H](C)C(=O)N1CCN(C(C)=O)C1=Nc1ccc2nccnc2c1Br]
316 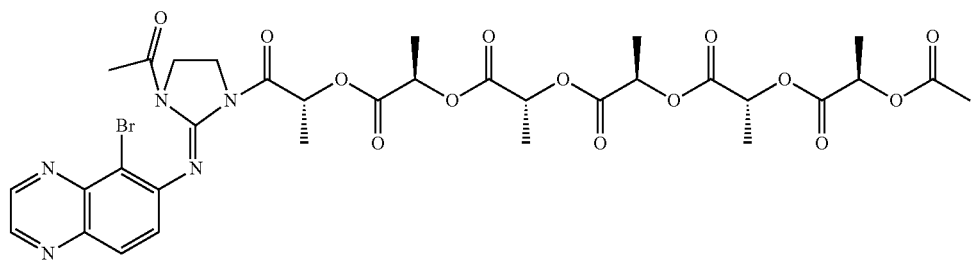 [SMILES: CC(=O)O[C@H](C)C(=O)O[C@H](C)C(=O)O[C@H](C)C(=O)O[C@H](C)C(=O)O[C@H](C)C(=O)O[C@H](C)C(=O)N1CCN(C(C)=O)/C1=N\c1ccc2nccnc2c1Br]
317 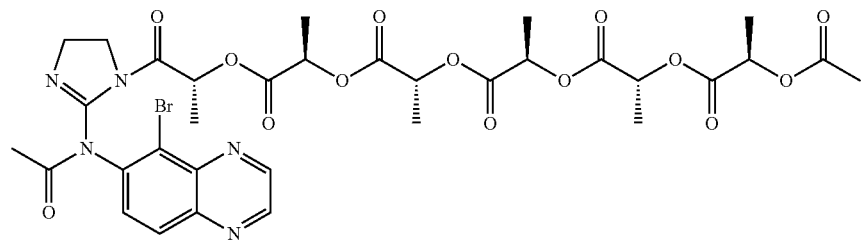 [SMILES: CC(=O)O[C@H](C)C(=O)O[C@H](C)C(=O)O[C@H](C)C(=O)O[C@H](C)C(=O)O[C@H](C)C(=O)O[C@H](C)C(=O)N1CCN=C1N(C(C)=O)c1ccc2nccnc2c1Br]
318 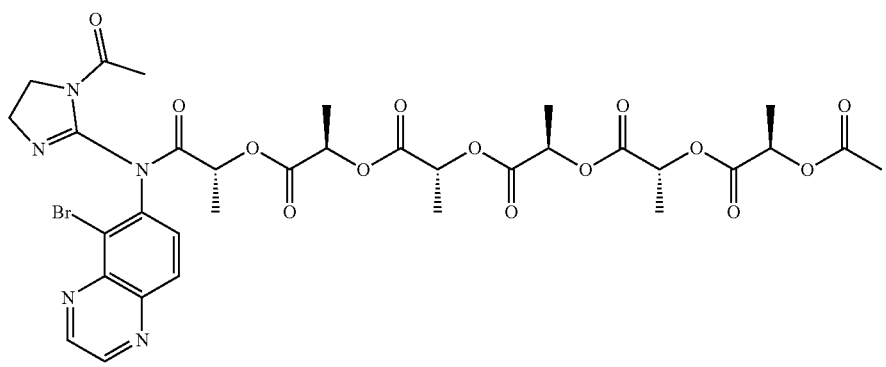 [SMILES: CC(=O)O[C@H](C)C(=O)O[C@H](C)C(=O)O[C@H](C)C(=O)O[C@H](C)C(=O)O[C@H](C)C(=O)O[C@H](C)C(=O)N(C1=NCCN1C(C)=O)c1ccc2nccnc2c1Br]
319 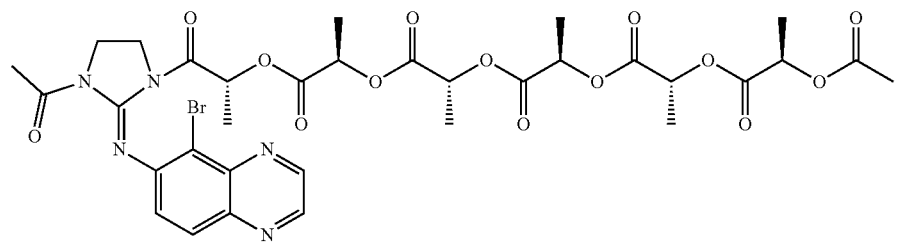 [SMILES: CC(=O)O[C@H](C)C(=O)O[C@H](C)C(=O)O[C@H](C)C(=O)O[C@H](C)C(=O)O[C@H](C)C(=O)O[C@H](C)C(=O)N1CCN(C(C)=O)/C1=N/c1ccc2nccnc2c1Br]

TABLE E-continued
Select Compounds of the Present Invention
320
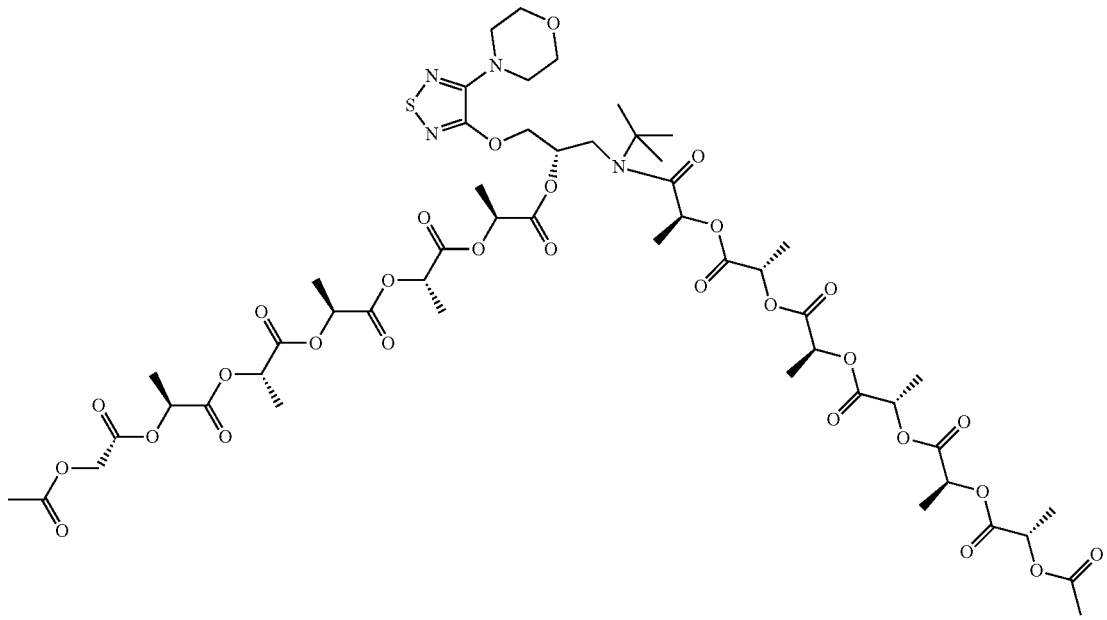
TABLE F
Compounds of the Present Invention
| Compd No. | Structure |
|---|---|
| 321 | 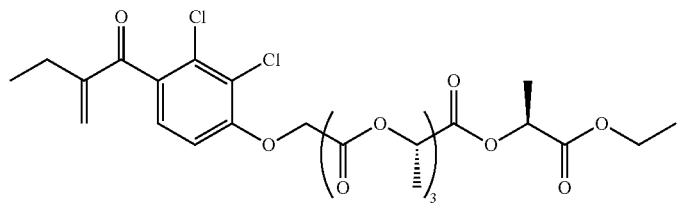 |
| 322 | 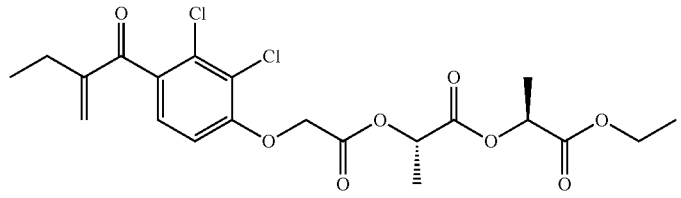 [SMILES: C=C(CC)C(=O)c1ccc(OCC(=O)O[C@@H](C)C(=O)O[C@@H](C)C(=O)OCC)c(Cl)c1Cl] |
| 323 | 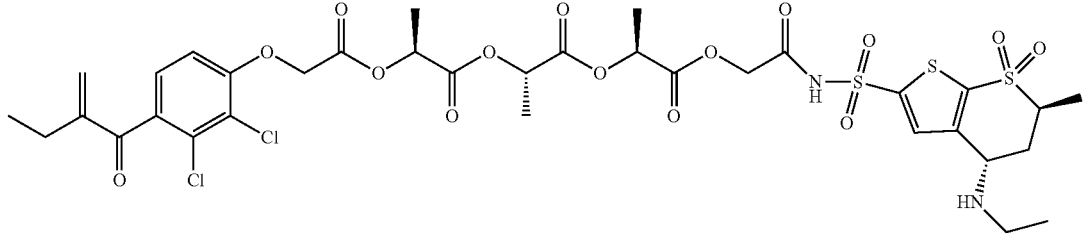 [SMILES: C=C(CC)C(=O)c1ccc(OCC(=O)O[C@@H](C)C(=O)O[C@@H](C)C(=O)O[C@@H](C)C(=O)OCC(=O)NS(=O)(=O)c2cc3c(s2)S(=O)(=O)[C@@H](C)C[C@@H]3NCC)c(Cl)c1Cl] |

TABLE F-continued

Compounds of the Present Invention

| Compd No. | Structure |
|---|---|
| 324 | 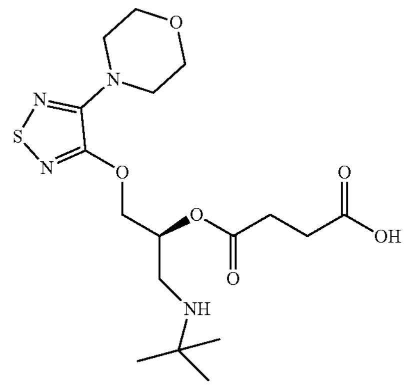 [SMILES: CC(C)(C)NC[C@@H](COc1nsnc1N1CCOCC1)OC(=O)CCC(=O)O] |
| 325 | 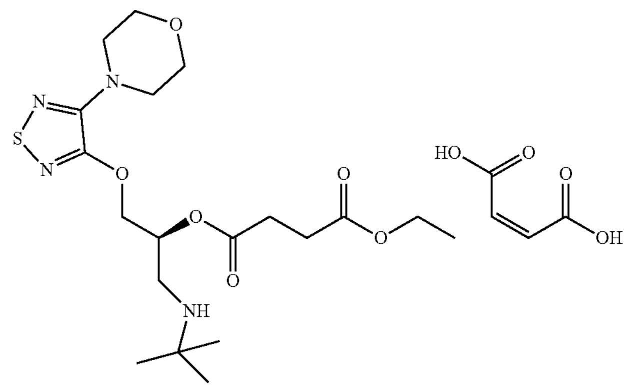 |
| 326 | 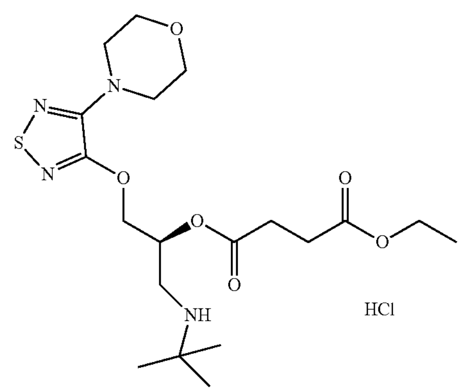 [SMILES: CCOC(=O)CCC(=O)O[C@@H](CNC(C)(C)C)COc1nsnc1N1CCOCC1 ; Cl] |
| 327 | 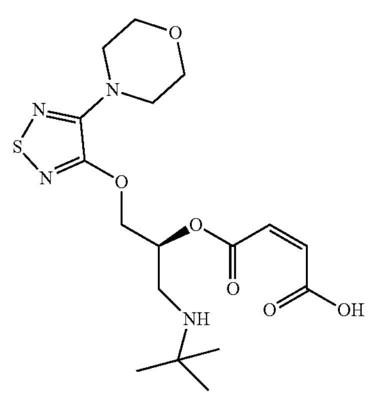 [SMILES: CC(C)(C)NC[C@@H](COc1nsnc1N1CCOCC1)OC(=O)/C=C\C(=O)O] |

TABLE F-continued

Compounds of the Present Invention

| Compd No. | Structure |
|---|---|
| 328 | 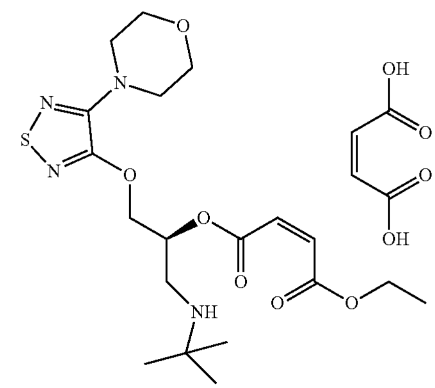 |
| 329 | 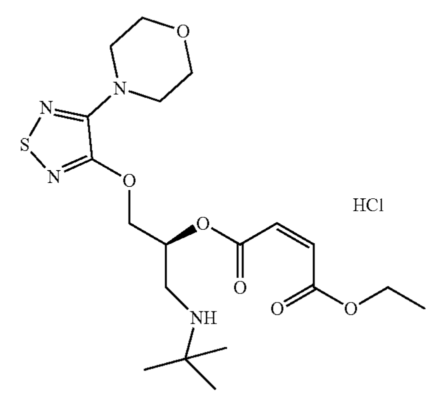 [SMILES: CCOC(=O)/C=C\C(=O)O[C@@H](CNC(C)(C)C)COc1nsnc1N1CCOCC1 ; Cl] |
| 330 | 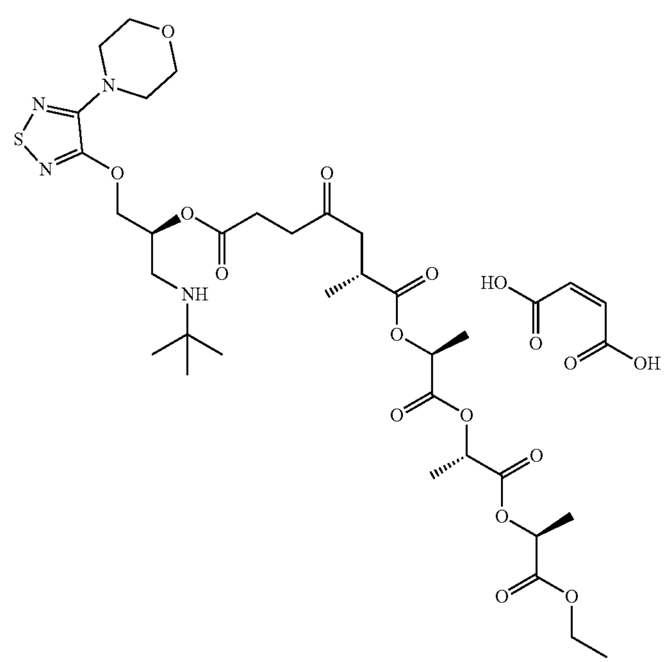 [SMILES: CCOC(=O)[C@H](C)OC(=O)[C@H](C)OC(=O)[C@H](C)OC(=O)[C@H](C)CC(=O)CCC(=O)O[C@@H](CNC(C)(C)C)COc1nsnc1N1CCOCC1 ; O=C(O)/C=C\C(=O)O] |

TABLE F-continued

Compounds of the Present Invention

| Compd No. | Structure |
|---|---|
| 331 | (timolol-morpholine-thiadiazole core with ethyl fumarate ester, HCl salt) |
| 332 | (timolol-morpholine-thiadiazole core with fumarate ester, -(CH₂)₁₁- chain) |
| 333 | (timolol-morpholine-thiadiazole core with fumarate ester, -(CH₂)₁₆- chain) |
| 334 | (dorzolamide sulfonamide linked to ethyl fumarate) |

TABLE F-continued
Compounds of the Present Invention
| Compd No. | Structure |
|---|---|
| 335 | 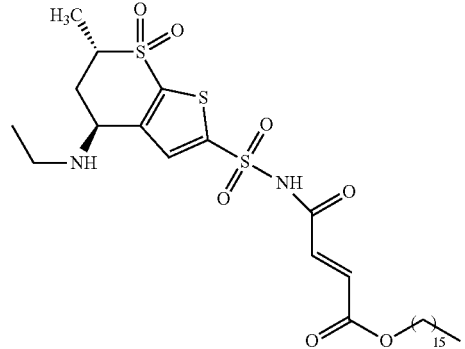 |
| 336 | 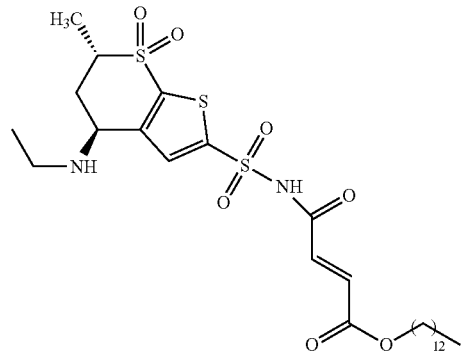 |
| 337 | 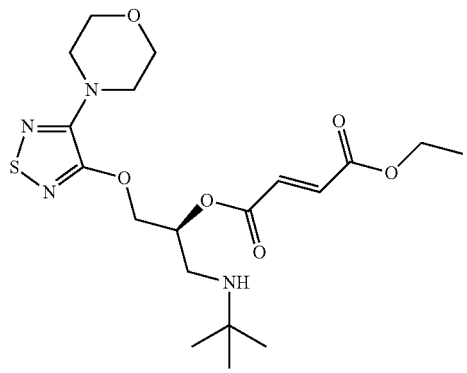 [SMILES: CCOC(=O)/C=C/C(=O)O[C@@H](CNC(C)(C)C)COc1nsnc1N1CCOCC1] |
| 338 | 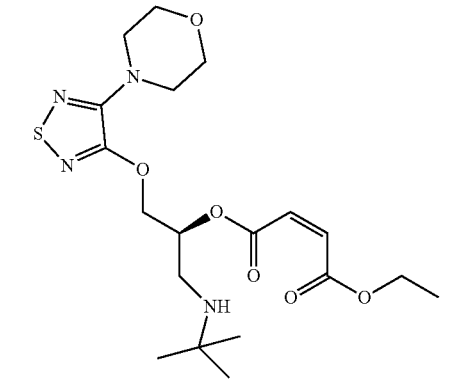 [SMILES: CCOC(=O)/C=C\C(=O)O[C@@H](CNC(C)(C)C)COc1nsnc1N1CCOCC1] |

TABLE F-continued
Compounds of the Present Invention
| Compd No. | Structure |
|---|---|
| 339 | 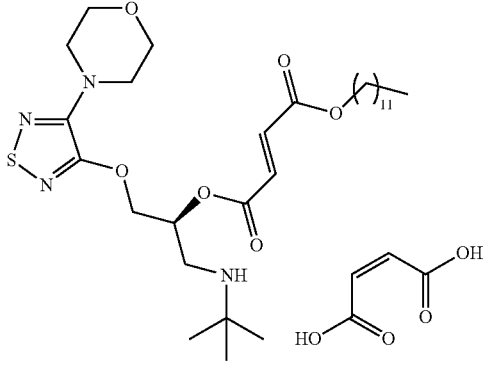 |
| 340 | 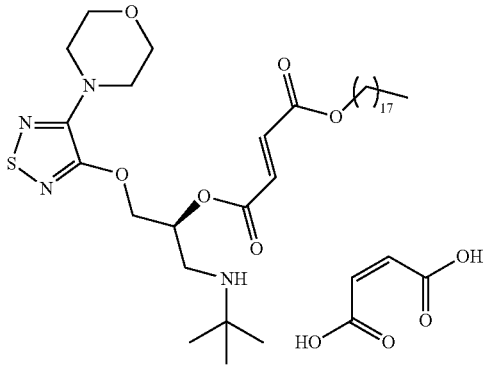 |
| 341 | 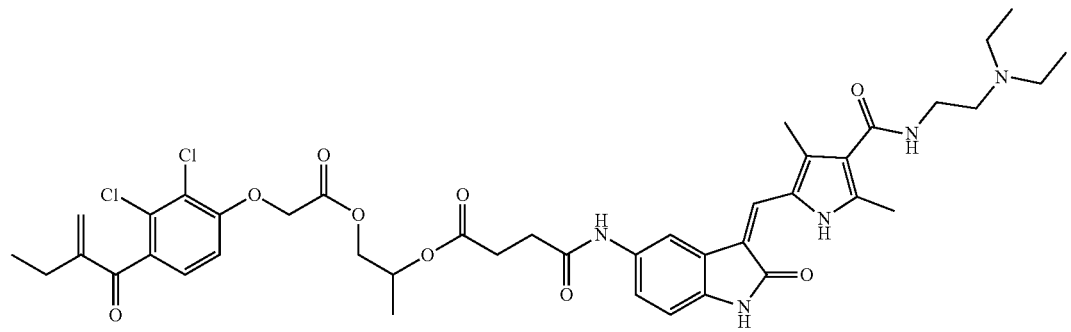 [SMILES: C=C(CC)C(=O)c1ccc(OCC(=O)OCC(C)OC(=O)CCC(=O)Nc2ccc3c(c2)/C(=C/c2[nH]c(C)c(C(=O)NCCN(CC)CC)c2C)C(=O)N3)c(Cl)c1Cl] |
| 342 | 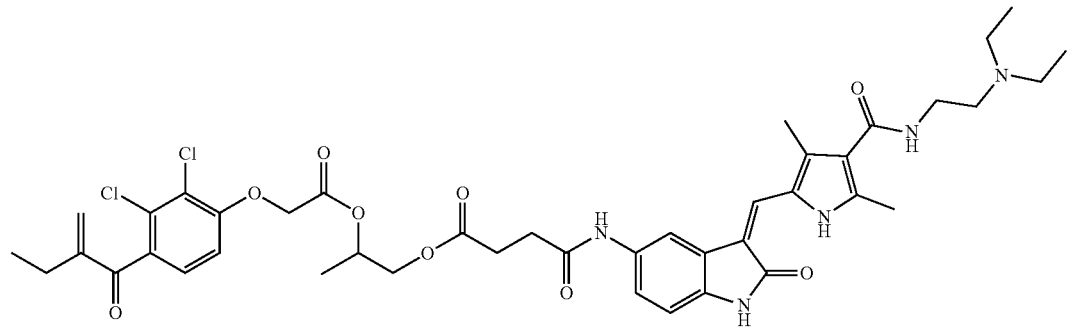 [SMILES: C=C(CC)C(=O)c1ccc(OCC(=O)OC(C)COC(=O)CCC(=O)Nc2ccc3c(c2)/C(=C/c2[nH]c(C)c(C(=O)NCCN(CC)CC)c2C)C(=O)N3)c(Cl)c1Cl] |

TABLE F-continued

Compounds of the Present Invention

| Compd No. | Structure |
|---|---|
| 343 | 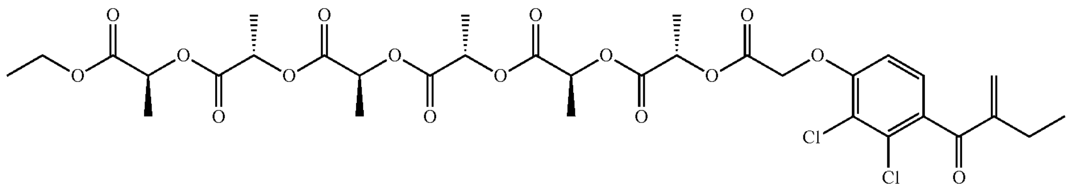 [SMILES: C=C(CC)C(=O)c1ccc(OCC(=O)O[C@@H](C)C(=O)O[C@@H](C)C(=O)O[C@@H](C)C(=O)O[C@@H](C)C(=O)O[C@@H](C)C(=O)O[C@@H](C)C(=O)OCC)c(Cl)c1Cl] |
| 344 | 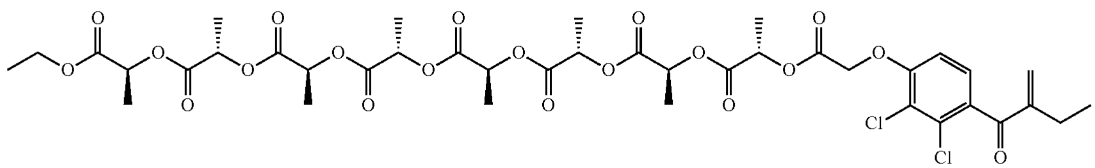 [SMILES: C=C(CC)C(=O)c1ccc(OCC(=O)O[C@@H](C)C(=O)O[C@@H](C)C(=O)O[C@@H](C)C(=O)O[C@@H](C)C(=O)O[C@@H](C)C(=O)O[C@@H](C)C(=O)O[C@@H](C)C(=O)O[C@@H](C)C(=O)OCC)c(Cl)c1Cl] |
| 345 | 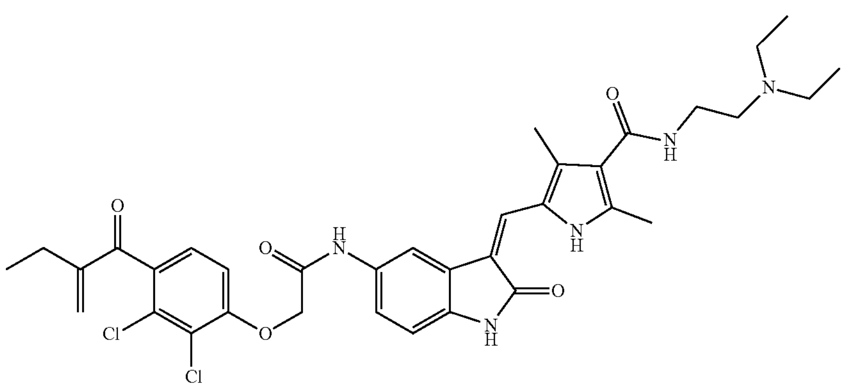 [SMILES: C=C(CC)C(=O)c1ccc(OCC(=O)Nc2ccc3c(c2)/C(=C/c2[nH]c(C)c(C(=O)NCCN(CC)CC)c2C)C(=O)N3)c(Cl)c1Cl] |
| 346 | 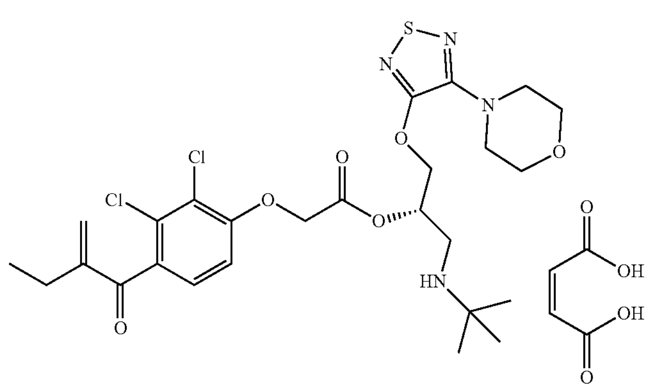 |

TABLE F-continued
Compounds of the Present Invention
| Compd No. | Structure |
|---|---|
| 347 | 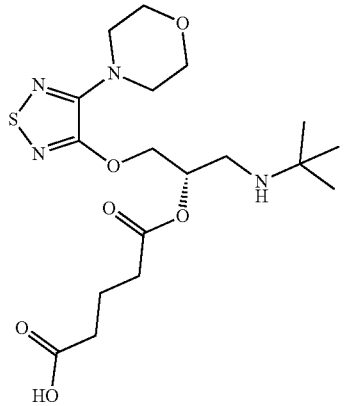 [SMILES: CC(C)(C)NC[C@@H](COc1nsnc1N1CCOCC1)OC(=O)CCCC(=O)O] |
TABLE G
Compounds of the Present Invention
| | |
|---|---|
| 348 | 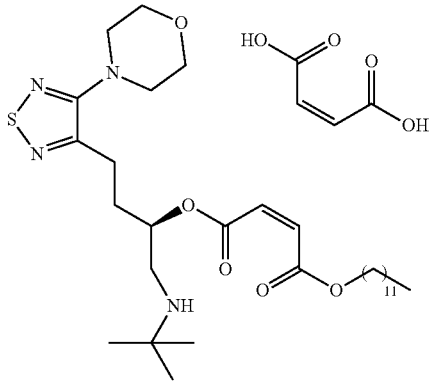 |
| 349 | 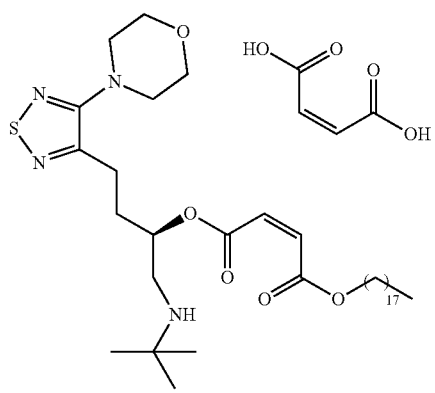 |

TABLE G-continued
Compounds of the Present Invention
350
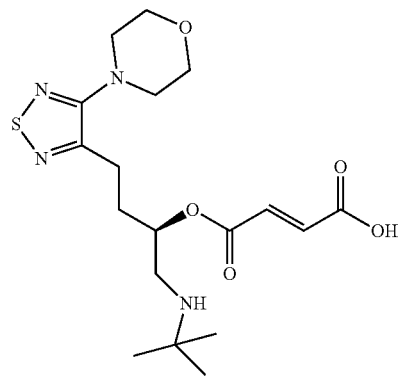 [SMILES: CC(C)(C)NC[C@@H](CCc1nsnc1N1CCOCC1)OC(=O)/C=C/C(=O)O]
351
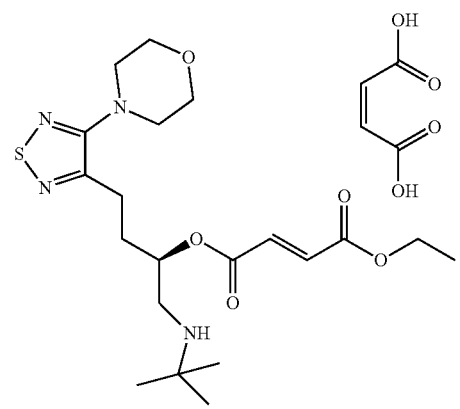
352
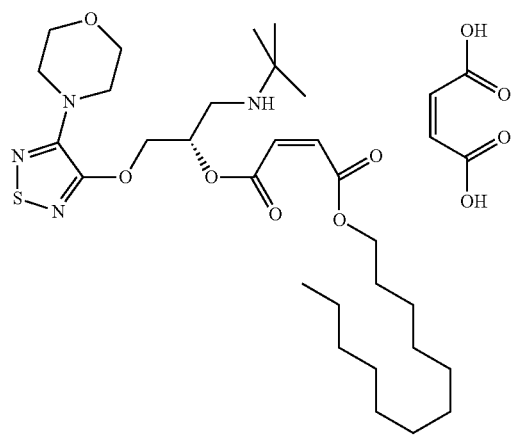

TABLE G-continued
Compounds of the Present Invention
353 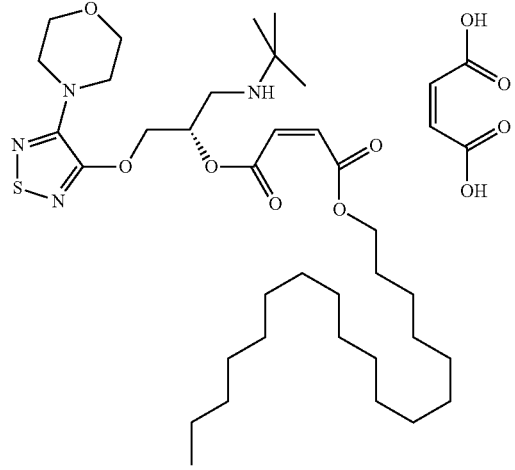
354 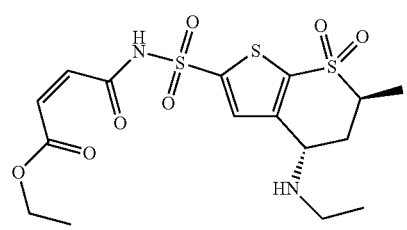 [SMILES: CCN[C@H]1C[C@H](C)S(=O)(=O)c2sc(S(=O)(=O)NC(=O)/C=C\C(=O)OCC)cc21]
355 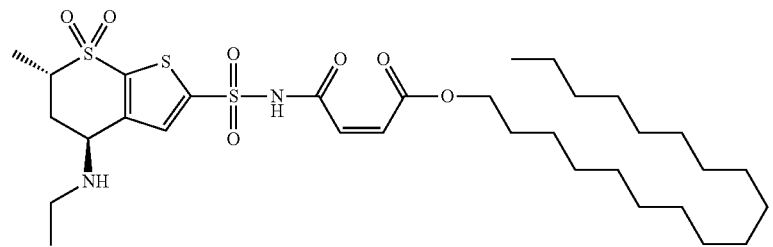 [SMILES: CCCCCCCCCCCCCCCCCCOC(=O)/C=C\C(=O)NS(=O)(=O)c1cc2c(s1)S(=O)(=O)[C@@H](C)C[C@@H]2NCC]
356 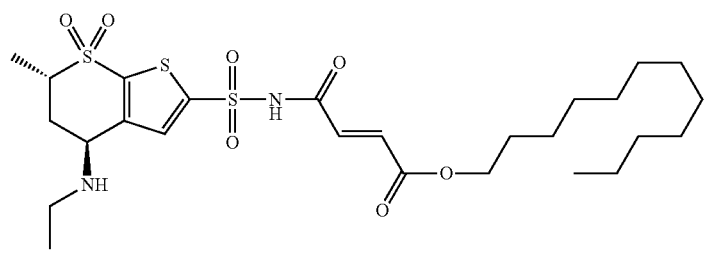 [SMILES: CCCCCCCCCCCCOC(=O)/C=C/C(=O)NS(=O)(=O)c1cc2c(s1)S(=O)(=O)[C@@H](C)C[C@@H]2NCC]
357 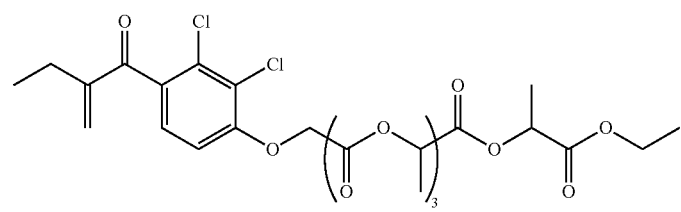

503 504
TABLE G-continued
Compounds of the Present Invention
358 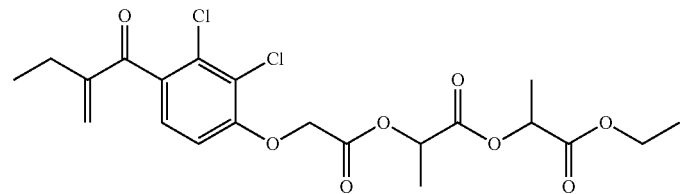 [SMILES: C=C(CC)C(=O)c1ccc(OCC(=O)OC(C)C(=O)OC(C)C(=O)OCC)c(Cl)c1Cl]
359 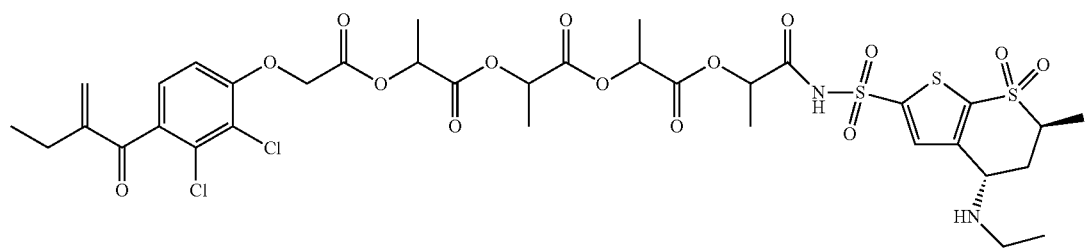 [SMILES: C=C(CC)C(=O)c1ccc(OCC(=O)OC(C)C(=O)OC(C)C(=O)OC(C)C(=O)OC(C)C(=O)NS(=O)(=O)c2cc3c(s2)S(=O)(=O)[C@@H](C)C[C@@H]3NCC)c(Cl)c1Cl]
360 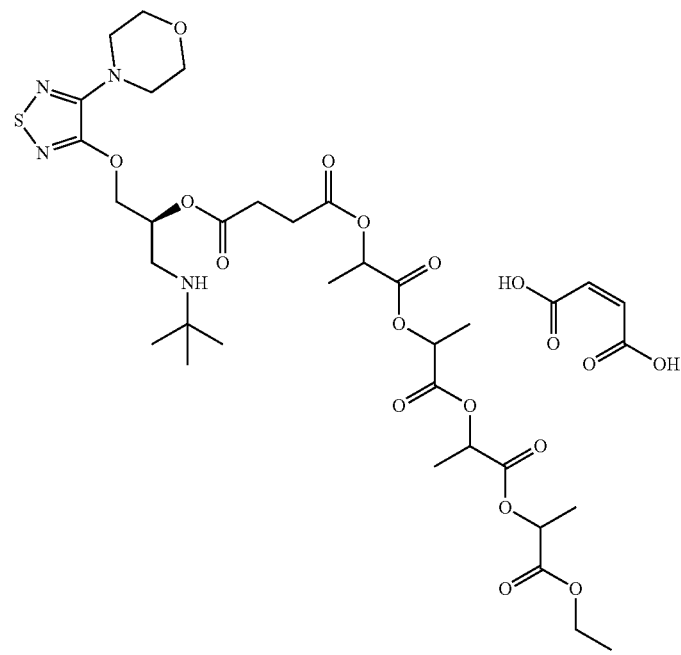 [SMILES: CCOC(=O)C(C)OC(=O)C(C)OC(=O)C(C)OC(=O)C(C)OC(=O)CCC(=O)O[C@@H](CNC(C)(C)C)COc1nsnc1N1CCOCC1 ; O=C(O)/C=C\C(=O)O]
361 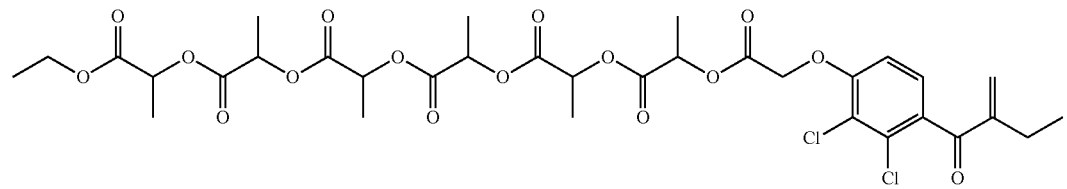 [SMILES: C=C(CC)C(=O)c1ccc(OCC(=O)OC(C)C(=O)OC(C)C(=O)OC(C)C(=O)OC(C)C(=O)OC(C)C(=O)OC(C)C(=O)OCC)c(Cl)c1Cl]
362 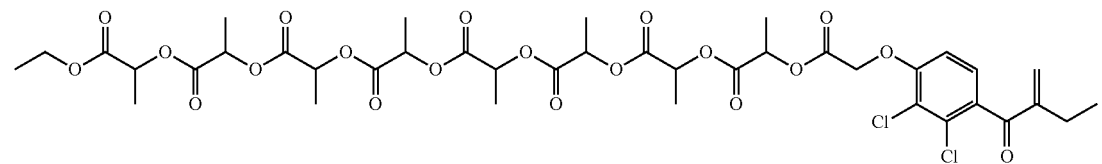 [SMILES: C=C(CC)C(=O)c1ccc(OCC(=O)OC(C)C(=O)OC(C)C(=O)OC(C)C(=O)OC(C)C(=O)OC(C)C(=O)OC(C)C(=O)OC(C)C(=O)OC(C)C(=O)OCC)c(Cl)c1Cl]

TABLE H
Additional Compounds of the Present Invention
363 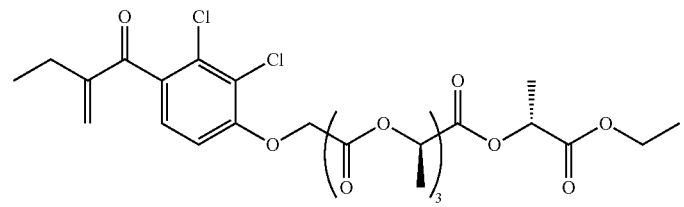
364 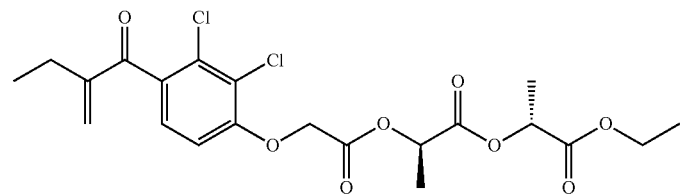 [SMILES: C=C(CC)C(=O)c1ccc(OCC(=O)O[C@H](C)C(=O)O[C@H](C)C(=O)OCC)c(Cl)c1Cl]
365 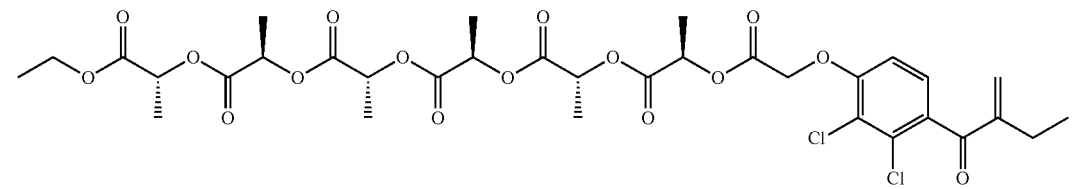 [SMILES: C=C(CC)C(=O)c1ccc(OCC(=O)O[C@H](C)C(=O)O[C@H](C)C(=O)O[C@H](C)C(=O)O[C@H](C)C(=O)O[C@H](C)C(=O)O[C@H](C)C(=O)OCC)c(Cl)c1Cl]
366 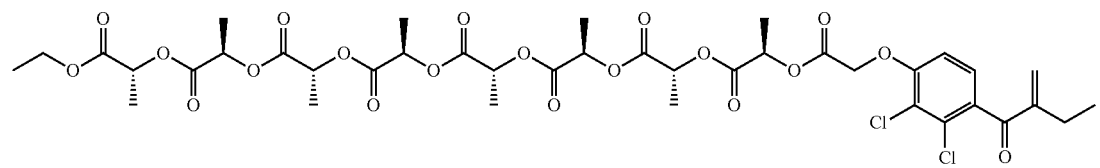 [SMILES: C=C(CC)C(=O)c1ccc(OCC(=O)O[C@H](C)C(=O)O[C@H](C)C(=O)O[C@H](C)C(=O)O[C@H](C)C(=O)O[C@H](C)C(=O)O[C@H](C)C(=O)O[C@H](C)C(=O)O[C@H](C)C(=O)OCC)c(Cl)c1Cl]
367 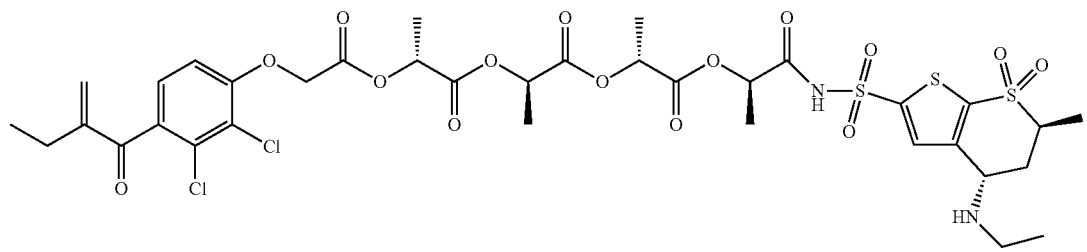 [SMILES: C=C(CC)C(=O)c1ccc(OCC(=O)O[C@H](C)C(=O)O[C@H](C)C(=O)O[C@H](C)C(=O)O[C@H](C)C(=O)NS(=O)(=O)c2cc3c(s2)S(=O)(=O)[C@@H](C)C[C@@H]3NCC)c(Cl)c1Cl]
TABLE I
Additional Compounds of the Present Invention
368 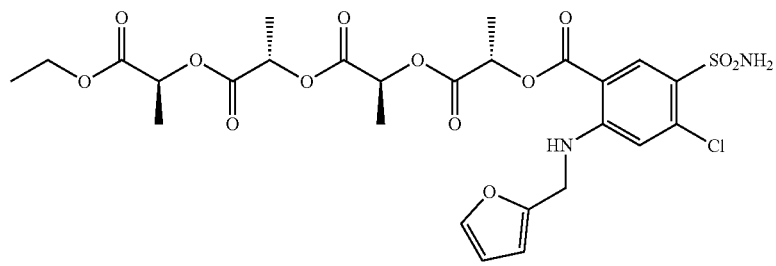 [SMILES: CCOC(=O)[C@H](C)OC(=O)[C@H](C)OC(=O)[C@H](C)OC(=O)[C@H](C)OC(=O)c1cc(S(N)(=O)=O)c(Cl)cc1NCc1ccco1]

TABLE I-continued
Additional Compounds of the Present Invention
369 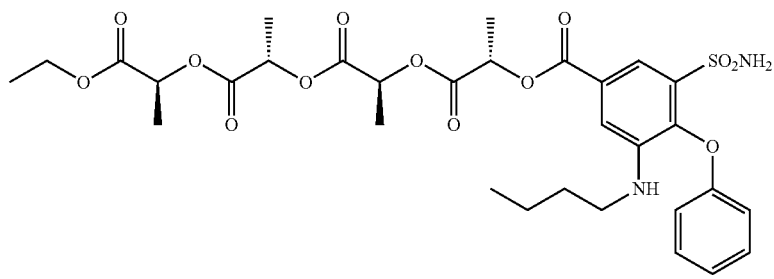 [SMILES: CCCCNc1cc(C(=O)O[C@@H](C)C(=O)O[C@@H](C)C(=O)O[C@@H](C)C(=O)O[C@@H](C)C(=O)OCC)cc(S(N)(=O)=O)c1Oc1ccccc1]
370 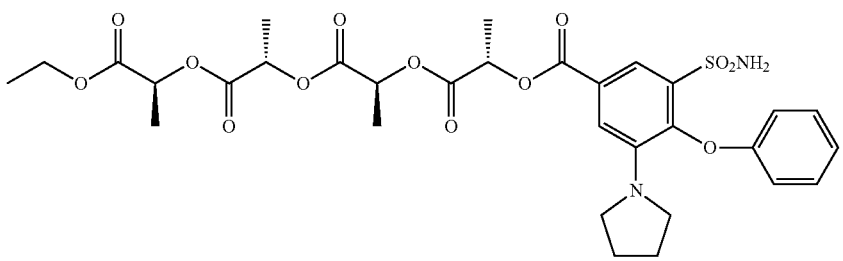 [SMILES: CCOC(=O)[C@H](C)OC(=O)[C@H](C)OC(=O)[C@H](C)OC(=O)[C@H](C)OC(=O)c1cc(N2CCCC2)c(Oc2ccccc2)c(S(N)(=O)=O)c1]
371 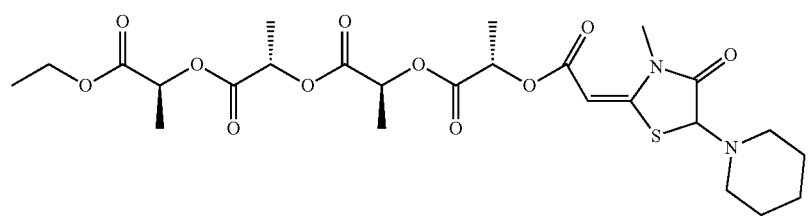 [SMILES: CCOC(=O)[C@H](C)OC(=O)[C@H](C)OC(=O)[C@H](C)OC(=O)[C@H](C)OC(=O)/C=C1/SC(N2CCCCC2)C(=O)N1C]
372 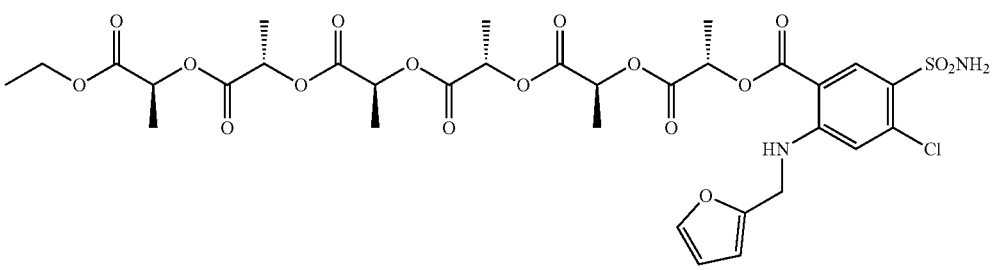 [SMILES: CCOC(=O)[C@H](C)OC(=O)[C@H](C)OC(=O)[C@H](C)OC(=O)[C@H](C)OC(=O)[C@H](C)OC(=O)[C@H](C)OC(=O)c1cc(S(N)(=O)=O)c(Cl)cc1NCc1ccco1]
373 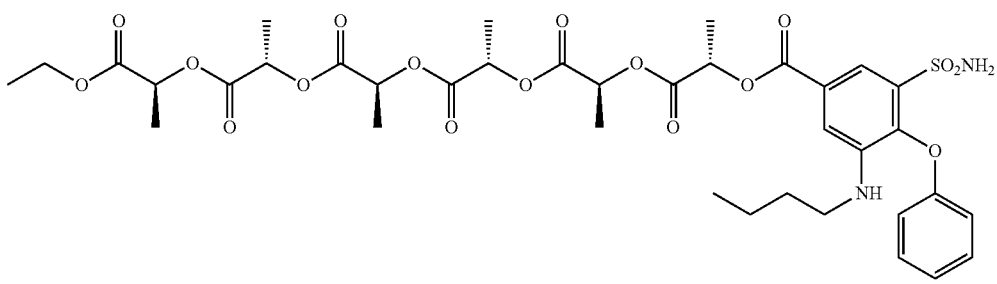 [SMILES: CCCCNc1cc(C(=O)O[C@@H](C)C(=O)O[C@@H](C)C(=O)O[C@@H](C)C(=O)O[C@@H](C)C(=O)O[C@@H](C)C(=O)O[C@@H](C)C(=O)OCC)cc(S(N)(=O)=O)c1Oc1ccccc1]
374 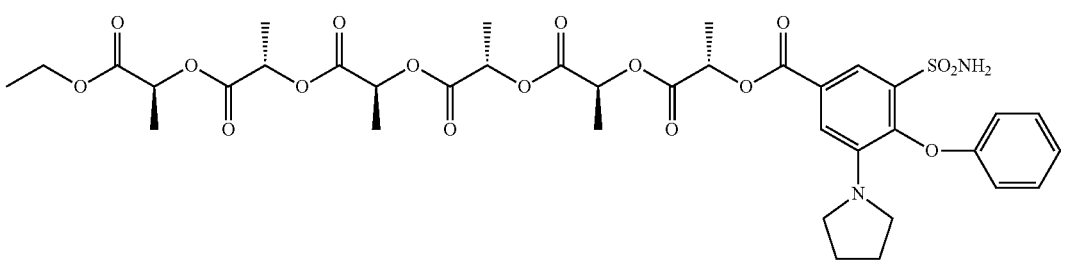 [SMILES: CCOC(=O)[C@H](C)OC(=O)[C@H](C)OC(=O)[C@H](C)OC(=O)[C@H](C)OC(=O)[C@H](C)OC(=O)[C@H](C)OC(=O)c1cc(N2CCCC2)c(Oc2ccccc2)c(S(N)(=O)=O)c1]

TABLE I-continued

Additional Compounds of the Present Invention

375

In one embodiment, a mildly surface-treated microparticle comprising one or more biodegradable polymers and a compound of formula:

encapsulated in the biodegradable polymer is provided.

In one embodiment, a mildly surface-treated microparticle comprising one or more biodegradable polymers and a compound of formula:

encapsulated in the biodegradable polymer is provided.

In one embodiment, a mildly surface-treated microparticle comprising one or more biodegradable polymers and a compound selected from:

encapsulated in the biodegradable polymer is provided.

In one embodiment, a mildly surface-treated microparticle comprising one or more biodegradable polymers and a compound selected from:

and

-continued

[Chemical structure: timolol-morpholine thiadiazole derivative with maleate ester linked to -(O-CH₂)₁₁- chain] and

[Chemical structure: timolol-morpholine thiadiazole derivative with maleate ester linked to -(O-CH₂)₁₇- chain]

encapsulated in the biodegradable polymer is provided.

In one embodiment, a mildly surface-treated microparticle comprising one or more biodegradable polymers and a compound selected from:

[Chemical structure: PLA oligomer ethyl ester terminated with dichlorophenoxy methacryloyl ketone group]

[Chemical structure: shorter PLA oligomer ethyl ester terminated with dichlorophenoxy methacryloyl ketone group], and

[Chemical structure: dichlorophenyl methacryloyl ketone with phenoxy-(CH₂-C(=O)-O)₃ -lactate ethyl ester]

encapsulated in the biodegradable polymer is provided.

In one embodiment, a mildly surface-treated microparticle comprising one or more biodegradable polymers and a compound selected from:

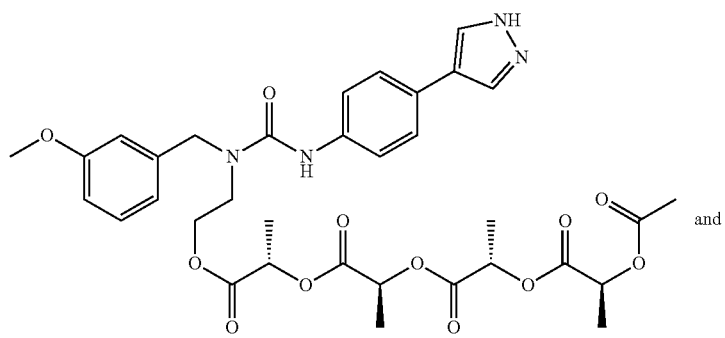
and
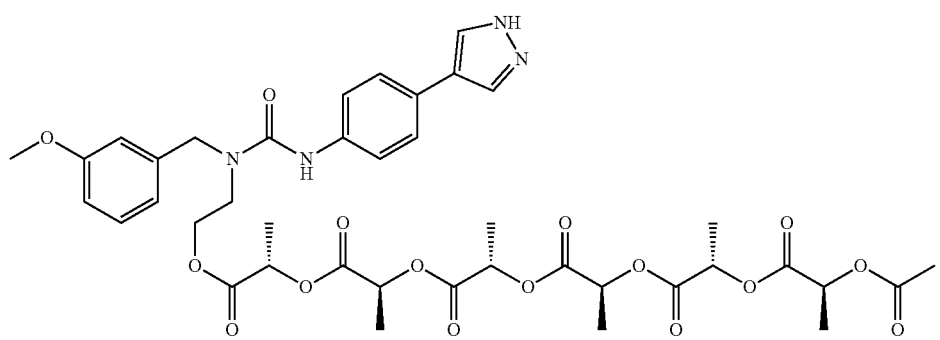

encapsulated in the biodegradable polymer is provided.

In one embodiment, a mildly surface-treated microparticle comprising one of more biodegradable polymers and a compound of formula:

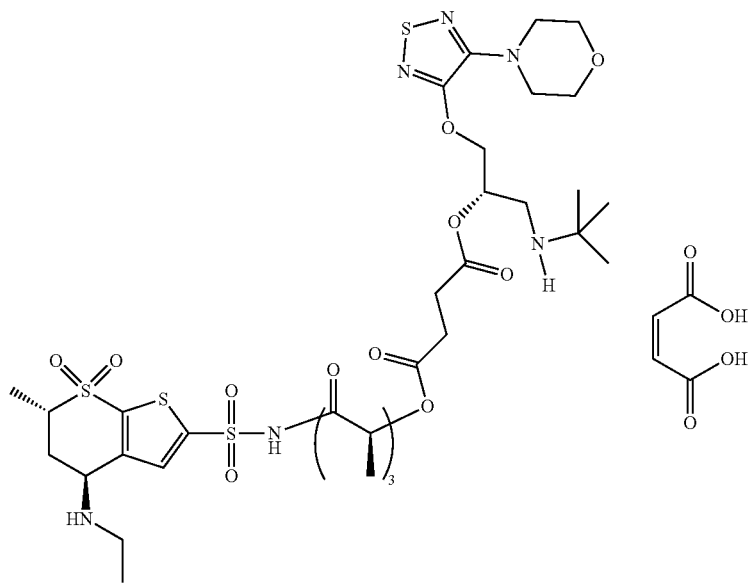

encapsulated in the biodegradable polymer is provided.

In one embodiment, a mildly surface-treated microparticle comprising one or more biodegradable polymers and a compound selected from:

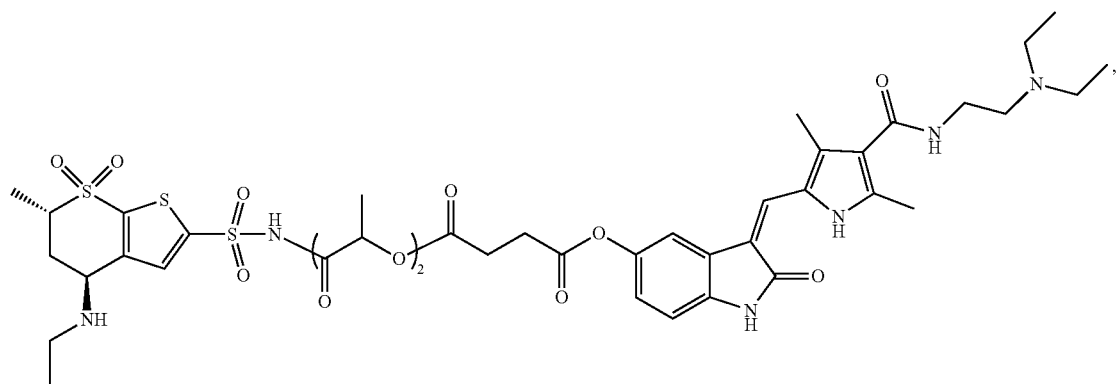
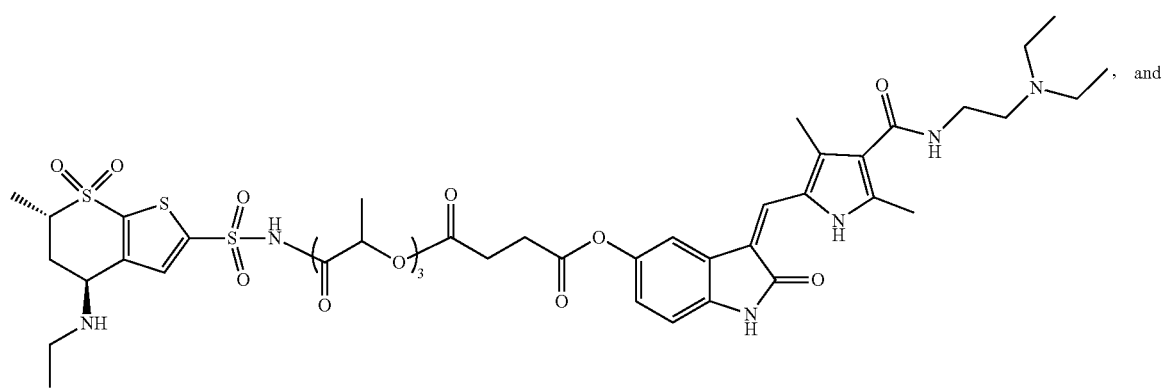
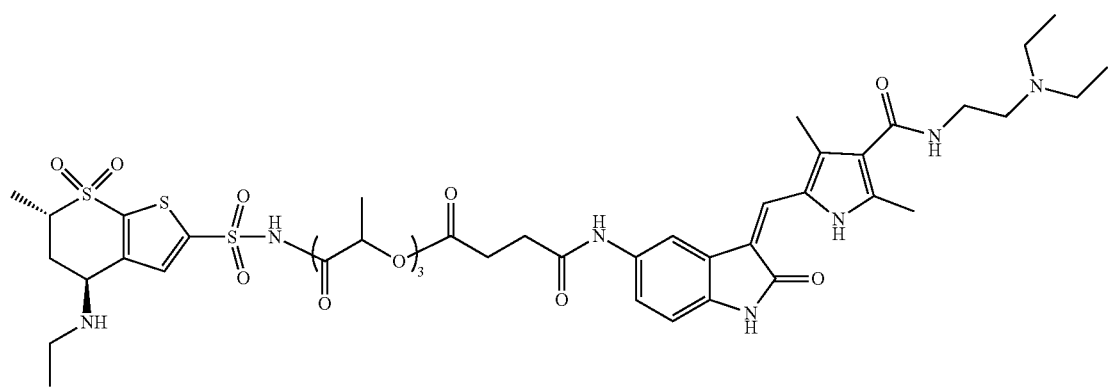
encapsulated in the biodegradable polymer is provided.
In one embodiment, a mildly surface-treated microparticle comprising one or more biodegradable polymers and a compound selected from:

517
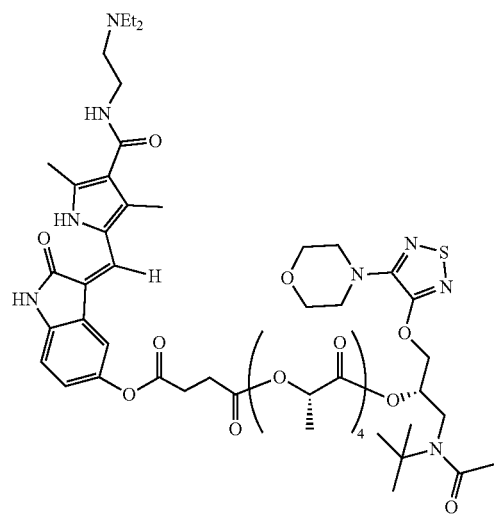
and
518
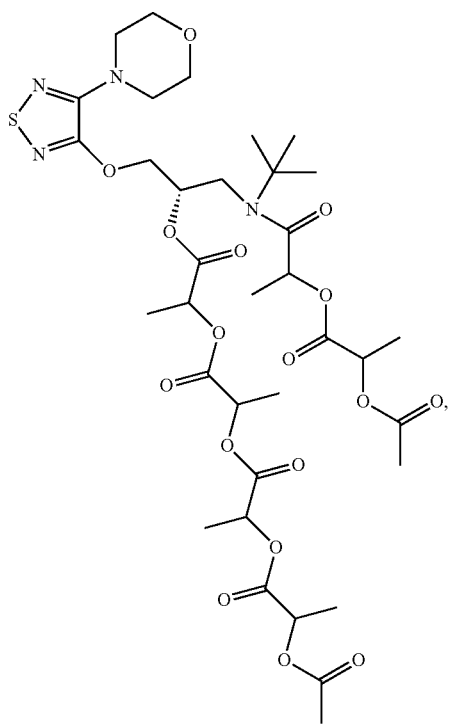
encapsulated in the biodegradable polymer is provided.
In one embodiment, a mildly surface-treated microparticle comprising one or more biodegradable polymers and a compound selected from:

519
-continued

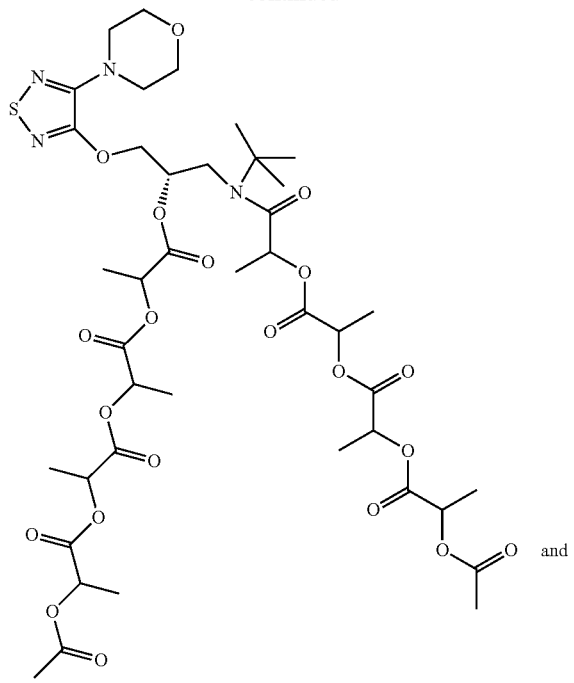

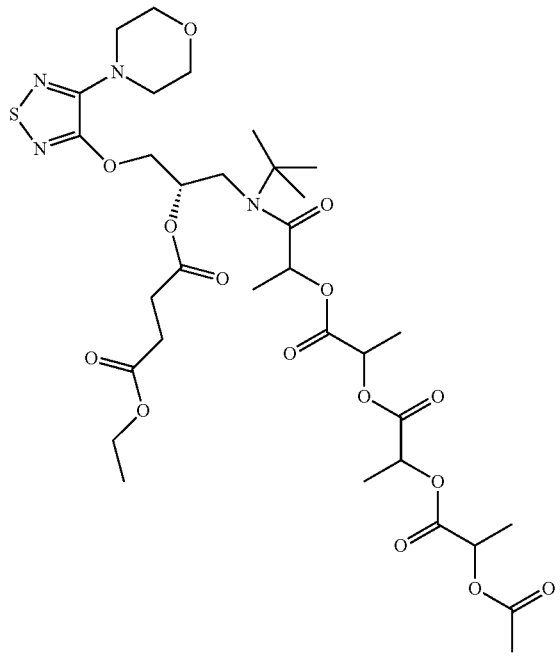

encapsulated in the biodegradable polymer is provided.

In one embodiment, a mildly surface-treated microparticle comprising one or more biodegradable polymers and a compound selected from:

520

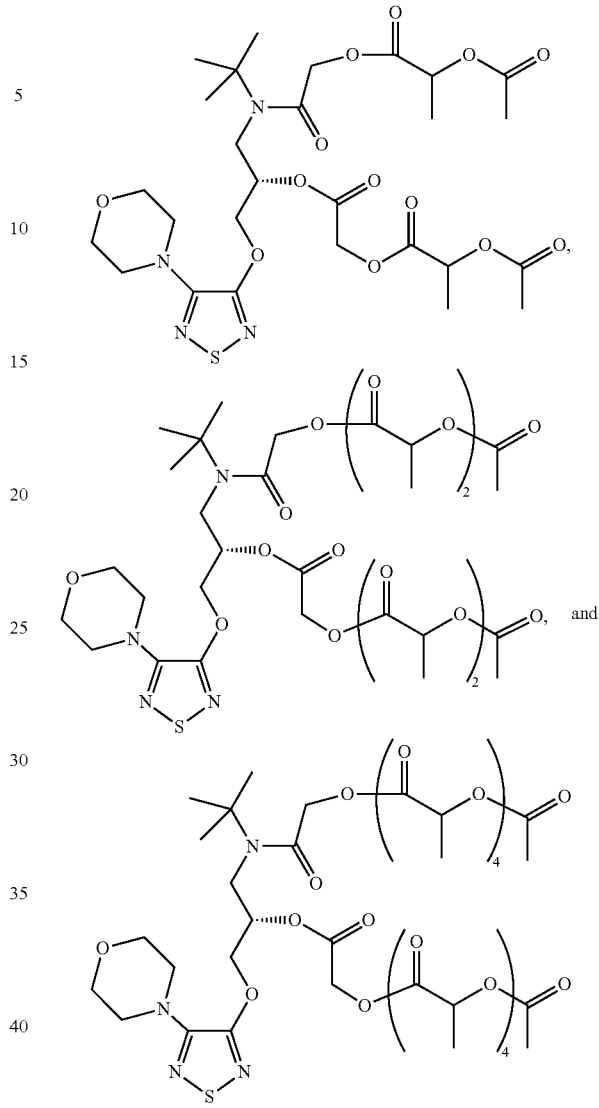

encapsulated in the biodegradable polymer is provided.

VII. Pharmaceutically Acceptable Carriers

Any suitable pharmaceutically acceptable carrier, for example, ophthalmically acceptable viscous carrier, may be employed in accordance with the invention. The carrier is present in an amount effective in providing the desired viscosity to the drug delivery system. Advantageously, the viscous carrier is present in an amount in a range of from about 0.5 wt percent to about 95 wt percent of the drug delivery particles. The specific amount of the viscous carrier used depends upon a number of factors including, for example and without limitation, the specific viscous carrier used, the molecular weight of the viscous carrier used, the viscosity desired for the present drug delivery system being produced and/or used and like factors. Examples of useful viscous carriers include, but are not limited to, hyaluronic acid, sodium hyaluronate, carbomers, polyacrylic acid, cellulosic derivatives, polycarbophil, polyvinylpyrrolidone, gelatin, dextrin, polysaccharides, polyacrylamide, polyvinyl alcohol (which can be partially hydrolyzed polyvinyl acetate), polyvinyl acetate, derivatives thereof and mixtures thereof.

The carrier can also be an aqueous carrier. Example of aqueous carriers include, but are not limited to, an aqueous solution or suspension, such as saline, plasma, bone marrow aspirate, buffers, such as Hank's Buffered Salt Solution (HBSS), HEPES (4-(2-hydroxyethyl)-1-piperazineethane-sulfonic acid), Ringers buffer, ProVisc®, diluted ProVisc®, ProVisc® diluted with PBS, Krebs buffer, Dulbecco's PBS, normal PBS; sodium hyaluronate solution (HA, 5 mg/mL in PBS), simulated body fluids, plasma platelet concentrate and tissue culture medium or an aqueous solution or suspension comprising an organic solvent.

In one embodiment, the carrier is PBS.

In one embodiment, the carrier is HA, 5 mg/mL in PBS.

In one embodiment, the carrier is ProVisc® diluted with water.

In one embodiment, the carrier is ProVisc® dilution in PBS.

In one embodiment, the carrier is ProVisc® 5-fold diluted with water.

In one embodiment, the carrier is ProVisc® 5-fold dilution in PBS.

In one embodiment, the carrier is ProVisc® 10-fold diluted with water.

In one embodiment, the carrier is ProVisc® 10-fold dilution in PBS.

In one embodiment, the carrier is ProVisc® 20-fold dilution with water.

In one embodiment, the carrier is ProVisc® 20-fold dilution in PBS.

In one embodiment, the carrier is HA, 1.25 mg/mL in an isotonic buffer solution with neutral pH.

In one embodiment, the carrier is HA, 0.625 mg/mL in an isotonic buffer solution with neutral pH.

In one embodiment, the carrier is HA, 0.1-5.0 mg/mL in PBS.

In one embodiment, the carrier is HA, 0.5-4.5 mg/mL in PBS.

In one embodiment, the carrier is HA, 1.0-4.0 mg/mL in PBS.

In one embodiment, the carrier is HA, 1.5-3.5 mg/mL in PBS.

In one embodiment, the carrier is HA, 2.0-3.0 mg/mL in PBS.

In one embodiment, the carrier is HA, 2.5-3.0 mg/mL in PBS.

The carrier may, optionally, contain one or more suspending agent. The suspending agent may be selected from carboxy methylcellulose (CMC), mannitol, polysorbate, poly propylene glycol, poly ethylene glycol, gelatin, albumin, alginate, hydroxyl propyl methyl cellulose (HPMC), hydroxyl ethyl methyl cellulose (HEMC), bentonite, tragacanth, dextrin, sesame oil, almond oil, sucrose, acacia gum and xanthan gum and combinations thereof.

The carrier may, optionally, contain one or more plasticizers. Thus the carrier may also include a plasticizer. The plasticizer may, for example, be polyethylene glycol (PEG), polypropylene glycol, poly (lactic acid) or poly (glycolic acid) or a copolymer thereof, polycaprolactone, and low molecule weight oligomers of these polymers, or conventional plasticizers, such as, adipates, phosphates, phthalates, sabacates, azelates and citrates. The carrier can also include other known pharmaceutical excipients in order to improve the stability of the agent.

In one embodiment, one or more additional excipients or delivery enhancing agents may also be included e.g., surfactants and/or hydrogels, in order to further influence release rate.

VIII. Sustained Release of Pharmaceutically Active Compound

The rate of release of the pharmaceutically active compound can be related to the concentration of pharmaceutically active compound dissolved in the surface treated microparticle. In some embodiments, the polymeric composition of the surface treated microparticle includes non-therapeutic agents that are selected to provide a desired solubility of the pharmaceutically active compound. The selection of the polymeric composition can be made to provide the desired solubility of the pharmaceutically active compound in the surface treated microparticle, for example, a hydrogel may promote solubility of a hydrophilic material. In some embodiments, functional groups can be added to the polymer to increase the desired solubility of the pharmaceutically active compound in the surface treated microparticle. In some embodiments, additives may be used to control the release kinetics of the pharmaceutically active compound, for example, the additives may be used to control the concentration of the pharmaceutically active compound by increasing or decreasing the solubility of the pharmaceutically active compound in the polymer so as to control the release kinetics of the pharmaceutically active compound. The solubility may be controlled by including appropriate molecules and/or substances that increase and/or decrease the solubility of the dissolved form of the pharmaceutically active compound in the surface treated microparticle. The solubility of the pharmaceutically active compound may be related to the hydrophobic and/or hydrophilic properties of the surface treated microparticle and the pharmaceutically active compound. Oils and hydrophobic molecules can be added to the polymer(s) to increase the solubility of a pharmaceutically active compound in the surface treated microparticle.

Instead of, or in addition to, controlling the rate of migration based on the concentration of the pharmaceutically active compound dissolved in the surface treated microparticle, the surface area of the polymeric composition can be controlled to attain the desired rate of drug migration out of the surface treated microparticle comprising a pharmaceutically active compound. For example, a larger exposed surface area will increase the rate of migration of the pharmaceutically active compound to the surface, and a smaller exposed surface area will decrease the rate of migration of the pharmaceutically active compound to the surface. The exposed surface area can be increased in any number of ways, for example, by castellation of the exposed surface, a porous surface having exposed channels connected with the tear or tear film, indentation of the exposed surface, or protrusion of the exposed surface. The exposed surface can be made porous by the addition of salts that dissolve and leave a porous cavity once the salt dissolves. In the present invention, these trends can be used to decrease the release rate of the active material from the polymeric composition by avoiding these paths to quicker release. For example, the surface area can be minimized, or channels can be avoided.

Where more than one type of polymer is used, each surface treated microparticle may have a different solidifying or setting property. For example, the surface treated microparticles may be made from similar polymers but may have different gelling pHs or different melting temperatures or glass transition points.

In order for the surface treated microparticles to form a consolidated aggregate, the temperature around the particles, for example in the human or non-human animal where the composition is administered, is approximately equal to, or greater than, the glass transition temperature ($T_g$) of the polymer particles. At such temperatures the polymer particles will cross-link to one or more other polymer particles to form a consolidated aggregate. By cross-link it is meant that adjacent polymer particles become joined together. For example, the particles may cross-link due to entanglement of the polymer chains at the surface of one particle with polymer chains at the surface of another particle. There may be adhesion, cohesion or fusion between adjacent particles.

Typically, the injectable surface treated microparticles which are formed of a polymer or a polymer blend have a glass transition temperature ($T_g$) either close to or just above body temperature (such as from about 30° C. to 45° C., e.g., from about 35° C. to 40° C., for example, from about 37° C. to 40° C.). Accordingly, at room temperature the surface treated microparticles are below their $T_g$ and behave as discrete particles, but in the body the surface treated microparticles soften and interact/stick to themselves. Typically, agglomeration begins within 20 seconds to about 15 minutes of the raise in temperature from room to body temperature.

The surface treated microparticles may be formed from a polymer which has a $T_g$ from about 35° C. to 40° C., for example from about 37° C. to 40° C., wherein the polymer is a poly(α-hydroxyacid) (such as PLA, PGA, PLGA, or PDLLA or a combination thereof), or a blend thereof with PLGA-PEG. Typically, these particles will agglomerate at body temperature. The injectable surface treated microparticles may comprise only poly(α-hydroxyacid) particles or other particle types may be included. The microparticles can be formed from a blend of poly(D,L-lactide-co-glycolide) (PLGA), PLGA-PEG and PVA which has a $T_g$ at or above body temperature. In one embodiment, at body temperature the surface treated microparticles will interact to form a consolidated aggregate. The injectable microparticle may comprise only PLGA/PLGA-PEG/PVA surface treated microparticles or other particle types may be included.

The composition may comprise a mixture of temperature sensitive surface treated microparticles and non-temperature sensitive surface treated microparticles. Non-temperature sensitive surface treated microparticles are particles with a glass transition temperature which is above the temperature at which the composition is intended to be used. Typically, in a composition comprising a mixture of temperature sensitive surface treated microparticles and non-temperature sensitive particles the ratio of temperature sensitive to non-temperature sensitive surface treated microparticles is about 3:1, or lower, for example, 4:3. The temperature sensitive surface treated microparticles are advantageously capable of crosslinking to each other when the temperature of the composition is raised to or above the glass transition of these microparticles. By controlling the ratio of temperature sensitive surface treated microparticles to non-temperature sensitive surface treated microparticles it may be possible to manipulate the porosity of the resulting consolidated aggregate. The surface treated microparticles may be solid, that is with a solid outer surface, or they may be porous. The particles may be irregular or substantially spherical in shape.

The surface treated microparticles can have a size in their longest dimension, or their diameter if they are substantially spherical, of less than about 100 μm and more than about 1 μm.

The surface treated microparticles can have a size in their longest dimension, or their diameter, of less than about 100 μm. The surface treated microparticles can have a size in their longest dimension, or their diameter, of between about 1 μm and about 40 μm, more typically, between about 20 μm and about 40 μm. Polymer particles of the desired size will pass through a sieve or filter with a pore size of about 40 μm.

Formation of the consolidated aggregate from the composition, once administered to a human or non-human animal, typically takes from about 20 seconds to about 24 hours, for example, between about 1 minute and about 5 hours, between about 1 minute and about 1 hour, less than about 30 minutes, less than about 20 minutes. Typically, the solidification occurs in between about 1 minute and about 20 minutes from administration.

Typically, the composition comprises from about 20 percent to about 80 percent injectable surface treated microparticle material and from about 20 percent to about 80 percent carrier; from about 30 percent to about 70 percent injectable surface treated microparticle material and from about 30 percent to about 70 percent carrier; e.g., the composition may comprise from about 40 percent to about 60 percent injectable surface treated microparticle material and from about 40 percent to about 60 percent carrier; the composition may comprise about 50 percent injectable surface treated microparticle material and about 50 percent carrier. The aforementioned percentages all refer to percentage by weight.

The surface treated microparticles are loaded, for example, in the surface treated microparticle or as a coating on the surface treated microparticle, with a pharmaceutically active compound.

The system of the invention can allow for the pharmaceutically active compound release to be sustained for some time, for example, release can be sustained for at least about 2 hours, at least about 4 hours, at least about 6 hours, at least about 10 hours, at least about 12 hours, at least about 24 hours, at least 48 hours, at least a week, more than one week, at least a month, at least two months, at least three months, at least four months, at least five months, at least six months, at least seven months, at least eight months, at least nine months, at least ten months, at least eleven months, at least twelve months, or more.

In one embodiment, the solid aggregating microparticles that produce a pellet in vivo release the therapeutic agent without a burst of more than about 1 percent to about 5 percent of total payload over a 24 hour period.

In one embodiment, the solid aggregating microparticles that produce a pellet in vivo release the therapeutic agent without a burst of more than about 10 percent of total payload over a 24 hour period.

In one embodiment, the solid aggregating microparticles that produce a pellet in vivo release the therapeutic agent without a burst of more than about 15 percent of total payload over a 24 hour period.

In one embodiment, the solid aggregating microparticles that produce a pellet in vivo release the therapeutic agent without a burst of more than about 20 percent of total payload over a 24 hour period.

In one embodiment, the solid aggregating microparticles that produce a pellet in vivo release the therapeutic agent without a burst of more than about 1 percent to about 5 percent of total payload over a 12 hour period.

In one embodiment, the solid aggregating microparticles that produce a pellet in vivo release the therapeutic agent without a burst of more than about 5 percent to about 10 percent of total payload over a 12 hour period.

In one embodiment, the solid aggregating microparticles that produce a pellet in vivo release the therapeutic agent without a burst of more than about 10 percent of total payload over a 12 hour period.

In one embodiment, the solid aggregating microparticles that produce a pellet in vivo release the therapeutic agent without a burst of more than about 15 percent of total payload over a 12 hour period.

In one embodiment, the solid aggregating microparticles that produce a pellet in vivo release the therapeutic agent without a burst of more than about 20 percent of total payload over a 12 hour period.

In one embodiment, the pharmaceutically active compound is released in an amount effective to have a desired local or systemic physiological or pharmacologically effect.

In one embodiment, delivery of a pharmaceutically active compound means that the pharmaceutically active compound is released from the consolidated aggregate into the environment around the consolidated aggregate, for example, the vitreal fluid.

In one embodiment, a microparticle comprising a pharmaceutically active compound of the invention allows a substantially zero or first order release rate of the pharmaceutically active compound from the consolidated aggregate once the consolidated aggregate has formed. A zero order release rate is a constant release of the pharmaceutically active compound over a defined time; such release is difficult to achieve using known delivery methods.

IX. Manufacture of Microparticles

Microparticle Formation

Microparticles can be formed using any suitable method for the formation of polymer microparticles known in the art. The method employed for particle formation will depend on a variety of factors, including the characteristics of the polymers present in the drug or polymer matrix, as well as the desired particle size and size distribution. The type of drug(s) being incorporated in the microparticles may also be a factor as some drugs are unstable in the presence of certain solvents, in certain temperature ranges, and/or in certain pH ranges.

Particles having an average particle size of between 1 micron and 100 microns are useful in the compositions described herein. In typical embodiments, the particles have an average particle size of between 1 micron and 40 microns, more typically between about 10 micron and about 40 microns, more typically between about 20 micron and about 40 microns. The particles can have any shape but are generally spherical in shape.

In circumstances where a monodisperse population of particles is desired, the particles may be formed using a method which produces a monodisperse population of microparticles. Alternatively, methods producing polydispersed microparticle distributions can be used, and the particles can be separated using methods known in the art, such as sieving, following particle formation to provide a population of particles having the desired average particle size and particle size distribution.

Common techniques for preparing microparticles include, but are not limited to, solvent evaporation, hot melt particle formation, solvent removal, spray drying, phase inversion, coacervation, and low temperature casting. Suitable methods of particle formulation are briefly described below. Pharmaceutically acceptable excipients, including pH modifying agents, disintegrants, preservatives, and antioxidants, can optionally be incorporated into the particles during particle formation.

In one embodiment, surface treated microparticles are prepared using continuous chemistry manufacturing processes. In one embodiment, surface treated microparticles are prepared using step-wise manufacturing processes.

In one embodiment, microparticles containing a therapeutic agent can be prepared as described in PCT/US2015/065894. In one embodiment, the microparticles are prepared by:
(i) dissolving or dispersing the therapeutic agent or its salt in an organic solvent optionally with an alkaline agent;
(ii) mixing the solution/dispersion of step (i) with a polymer solution that has a viscosity of at least about 300 cPs (or perhaps at least about 350, 400, 500, 600, 700 or 800 or more cPs);
(iii) mixing the therapeutic agent polymer solution/dispersion of step (ii) with an aqueous non-acidic or alkaline solution (for example at least approximately a pH of 7, 8, or 9 and typically not higher than about 10) optionally with a surfactant or emulsifier, to form a solvent-laden therapeutic agent encapsulated microparticle,
(iv) isolating the microparticles.

In one embodiment, the therapeutic agent is sunitinib.

It has been found that it may be useful to include the alkaline agent in the organic solvent. However, as described in PCT/US2015/065894, it has been found that adding an acid to the organic solvent can improve drug loading of the microparticle. Examples demonstrate that polyesters such as PLGA, PEG-PLGA(PLA) and PEG-PLGA/PLGA blend microparticles display sustained release of the therapeutic agent or its pharmaceutically acceptable salt. Polymer microparticles composed of PLGA and PEG covalently conjugated to PLGA (Mw 45 kDa) (PLGA45k-PEG5k) loaded with the therapeutic agent were prepared using a single emulsion solvent evaporation method. The therapeutic agent loading was further increased by increasing the pH of the aqueous solution. Still further significant increases in therapeutic agent loading in the microparticles was achieved by increasing polymer concentration or viscosity. In one embodiment, the therapeutic agent is sunitinib.

Solvent Evaporation

In this method, the drug (or polymer matrix and drug) is dissolved in a volatile organic solvent, such as methylene chloride, acetone, acetonitrile, 2-butanol, 2-butanone, t-butyl alcohol, benzene, chloroform, cyclohexane, 1,2-dichloroethane, diethyl ether, ethanol, ethyl acetate, heptane, hexane, methanol, methyl tert-butyl ether, pentane, petroleum ether, iso-propanol, n-propanol, tetrahydrofuran, or mixtures thereof. The organic solution containing the drug is then suspended in an aqueous solution that contains a surface active agent such as poly(vinyl alcohol). The resulting emulsion is stirred until most of the organic solvent is evaporated, leaving solid microparticles. The resulting microparticles are washed with water and dried overnight in a lyophilizer. Microparticles with different sizes and morphologies can be obtained by this method.

Microparticles which contain labile polymers, such as certain polyanhydrides, may degrade during the fabrication process due to the presence of water. For these polymers, the following two methods, which are performed in completely anhydrous organic solvents, can be used.

Oil-in-Oil Emulsion Technique

Solvent removal can also be used to prepare particles from drugs that are hydrolytically unstable. In this method, the drug (or polymer matrix and drug) is dispersed or dissolved in a volatile organic solvent such as methylene chloride, acetone, acetonitrile, benzene, 2-butanol, 2-butanone, t-butyl alcohol, chloroform, cyclohexane, 1,2-dichloroethane, diethyl ether, ethanol, ethyl acetate, heptane, hexane, methanol, methyl tert-butyl ether, pentane, petroleum ether, iso-propanol, n-propanol, tetrahydrofuran, or mixtures thereof. This mixture is then suspended by stirring in an organic oil (such as silicon oil, castor oil, paraffin oil, or mineral oil) to form an emulsion. Solid particles form from the emulsion, which can subsequently be isolated from the supernatant. The external morphology of spheres produced with this technique is highly dependent on the identity of the drug.

Oil-in-Water Emulsion Technique

In this method, the drug (or polymer matrix and drug) is dispersed or dissolved in a volatile organic solvent such as methylene chloride, acetone, acetonitrile, benzene, 2-butanol, 2-butanone, t-butyl alcohol, chloroform, cyclohexane, 1,2-dichloroethane, diethyl ether, ethanol, ethyl acetate, heptane, hexane, methanol, methyl tert-butyl ether, pentane, petroleum ether, iso-propanol, n-propanol, tetrahydrofuran, or mixtures thereof. This mixture is then suspended by stirring in an aqueous solution of surface active agent, such as poly(vinyl alcohol), to form an emulsion. Solid particles form from the emulsion, which can subsequently be isolated from the supernatant. The external morphology of spheres produced with this technique is highly dependent on the identity of the drug.

As described in PCT/US2015/065894, microparticles with a therapeutic agent can be prepared using the oil-in-water emulsion method. In one example, sunitinib microparticles were prepared by dissolving 100 mg PEG-PLGA (5K, 45) in 1 mL methylene chloride, and dissolving 20 mg sunitinib malate in 0.5 mL DMSO and triethylamine. The solutions were then mixed together, homogenized at 5000 rpm, 1 minute into an aqueous solution containing 1% polyvinyl alcohol (PVA) and stirred for 2 hours. The particles were collected, washed with double distilled water, and freeze dried. In another example, sunitinib microparticles were also prepared according to PCT/US2015/065894 by dissolving 200 mg PLGA (2A, Alkermers) in 3 mL methylene chloride, and 40 mg sunitinib malate in 0.5 mL DMSO and triethylamine. The solutions were then mixed together and homogenized at 5000 rpm, 1 minute in 1% PVA and stirred for 2 hours. The particles were collected, washed with double distilled water, and freeze dried.

Spray Drying

In this method, the drug (or polymer matrix and drug) is dissolved in an organic solvent such as methylene chloride, acetone, acetonitrile, 2-butanol, 2-butanone, t-butyl alcohol, benzene, chloroform, cyclohexane, 1,2-dichloroethane, diethyl ether, ethanol, ethyl acetate, heptane, hexane, methanol, methyl tert-butyl ether, pentane, petroleum ether, iso-propanol, n-propanol, tetrahydrofuran, or mixtures thereof. The solution is pumped through a micronizing nozzle driven by a flow of compressed gas, and the resulting aerosol is suspended in a heated cyclone of air, allowing the solvent to evaporate from the microdroplets, forming particles. Particles ranging between 0.1-10 microns can be obtained using this method.

Phase Inversion

Particles can be formed from drugs using a phase inversion method. In this method, the drug (or polymer matrix and drug) is dissolved in a solvent, and the solution is poured into a strong non solvent for the drug to spontaneously produce, under favorable conditions, microparticles or nanoparticles. The method can be used to produce nanoparticles in a wide range of sizes, including, for example, about 100 nanometers to about 10 microns, typically possessing a narrow particle size distribution.

Coacervation

Techniques for particle formation using coacervation are known in the art, for example, in GB-B-929 406; GB-B-929 40 1; and U.S. Pat. Nos. 3,266,987, 4,794,000, and 4,460,563. Coacervation involves the separation of a drug (or polymer matrix and drug) solution into two immiscible liquid phases. One phase is a dense coacervate phase, which contains a high concentration of the drug, while the second phase contains a low concentration of the drug. Within the dense coacervate phase, the drug forms nanoscale or microscale droplets, which harden into particles. Coacervation may be induced by a temperature change, addition of a non-solvent or addition of a micro-salt (simple coacervation), or by the addition of another polymer thereby forming an interpolymer complex (complex coacervation).

Low Temperature Casting

Methods for very low temperature casting of controlled release microspheres are described in U.S. Pat. No. 5,019,400 to Gombotz et al. In this method, the drug (or polymer matrix and sunitinib) is dissolved in a solvent. The mixture is then atomized into a vessel containing a liquid non-solvent at a temperature below the freezing point of the drug solution which freezes the drug droplets. As the droplets and non-solvent for the drug are warmed, the solvent in the droplets thaws and is extracted into the non-solvent, hardening the microspheres.

Scale Up

The processes for producing microparticles described in the Examples are amenable to scale up by methods known in the art. Examples of such methods include U.S. Pat. Nos. 4,822,534; 5,271,961; 5,945,126; 6,270,802; 6,361,798; 8,708,159; and U.S. publication 2010/0143479. U.S. Pat. No. 4,822,534 describes a method of manufacture to provide solid microspheres that involves the use of dispersions. These dispersions could be produced industrially and allowed for scale up. U.S. Pat. No. 5,271,961 disclosed the production of protein microspheres which involved the use of low temperatures, usually less than 45° C. U.S. Pat. No. 5,945,126 describes the method of manufacture to produce microparticles on full production scale while maintaining size uniformity observed in laboratory scale. U.S. Pat. Nos. 6,270,802 and 6,361,798 describe the large scale method of manufacture of polymeric microparticles whilst maintaining a sterile field. U.S. Pat. No. 8,708,159 describes the processing of microparticles on scale using a hydrocyclone apparatus. U.S. publication 2010/0143479 describes the method of manufacture of microparticles on large scale specifically for slow release microparticles.

XSpray has disclosed a device and the use of supercritical fluids to produce particles of a size below 10 µM (U.S. Pat. No. 8,167,279). Additional patents to XSpray include U.S. Pat. Nos. 8,585,942 and 8,585,943. Sun Pharmaceuticals has disclosed a process for the manufacture of microspheres or microcapsules, WO 2006/123,359, herein incorporated by reference. As an example, Process A involves five steps that include 1) the preparation of a first dispersed phase comprising a therapeutically active ingredient, a biodegradable polymer and an organic solvent 2) mixing the first dispersed phase with an aqueous phase to form an emulsion 3) spraying the emulsion into a vessel equipped to remove an organic solvent and 4) passing the resulting microspheres or microcapsules through a first and second screen thereby collecting a fractionated size of the microspheres or microcapsules and 5) drying the microspheres or microcapsules.

Xu, Q. et al. have disclosed the preparation of monodispersed biodegradable polymer microparticles using a microfluidic flow-focusing device (Xu, Q., et al "Preparation of Monodispersed Biodegradable Polymer Microparticles Using a Microfluidic Flow-Focusing Device for Controlled Drug Delivery", Small, Vol 5(13): 1575-1581, 2009).

Duncanson, W. J. et al. have disclosed the use of microfluidic devices to generate microspheres (Duncanson, W. J. et al. "Microfluidic Synthesis of Monodisperse Porous Microspheres with Size-tunable Pores", Soft Matter, Vol 8, 10636-10640, 2012).

U.S. Pat. No. 8,916,196 to Evonik describes an apparatus and method for the production of emulsion based microparticles that can be used in connection with the present invention.

X. Process of Preparation of Surface Treated Microparticles

Abbreviations

DCM, $CH_2Cl_2$ Dichloromethane
DL Drug loading
DMSO Dimethyl sulfoxide
EtOH Ethanol
HA Sodium hyaluronate
hr, h Hour
min Minute
NaOH Sodium hydroxide
NSTMP Non-surface treated microparticles
PBS Dulbecco's phosphate-buffered saline
PCL Polycaprolactone
PEG Polyethylene glycol
PLA Poly(lactic acid)
PLGA Poly(lactic-co-glycolic acid)
PVA Polyvinyl alcohol
Rpm Revolutions per minute
RT, r.t. Room temperature
SD Standard deviation
STMP Surface treated microparticles
UV Ultraviolet Examples 1-30 and FIGS. 1-19 were first presented in U.S. Ser. No. 15/349,985 and PCT/US16/61706 and are provided again herein for background information for the improved invention described herein.

General Methods

All non-aqueous reactions were performed under an atmosphere of dry argon or nitrogen gas using anhydrous solvents. The structure of starting materials, intermediates, and final products was confirmed by standard analytical techniques, including NMR spectroscopy and mass spectrometry.

Materials

Sodium hydroxide (NaOH, catalog #: S318-1, Fisher Chemical), ethanol (EtOH, catalog #: A405-20, Fisher Chemical), Dulbecco's phosphate-buffered saline (PBS, catalog #: SH3085003, GE Healthcare HyClone™), sodium hyaluronate (HA, catalog #: AC251770010, Acros Organics) and Tween 20 (catalog #: BP337-100, Fisher BioReagents) were purchased from Fisher Scientific. Polyvinyl alcohol (PVA) (88 percent hydrolyzed, MW approximately 25 kD) (catalog #: 02975) was purchased from Polysciences, Inc. Sunitinib malate was purchased from LC Laboratories (catalog #: S-8803). ProVisc® (10 mg/mL, 0.85 mL, catalog #: 21989, Alcon) was purchased from Besse Medical. Poly (lactic-co-glycolic acid) (PLGA) polymer, poly(lactic-acid) (PLA) polymer, and diblock co-polymers of PLGA and polyethylene glycol (PLGA-PEG) were purchased from the Evonik Corporation (RESOMER Select 5050 DLG mPEG 5000 (10 wt percent PEG)). A FreeZone 4.5 liter benchtop freeze dry system was used for lyophilization.

ProVisc® OVD (Ophthalmic Viscosurgical Device) is a sterile, non-pyrogenic, high molecular weight, non-inflammatory highly purified fraction of sodium hyaluronate dissolved in physiological sodium chloride phosphate buffer. It is FDA approved and indicated for use as an ophthalmic surgical aid. Sodium hyaluronate is a derivative of hyaluronan for clinical use. Hyaluronan, also known as hyaluronic acid, is a naturally occurring glycosaminoglycan found throughout the body including in the aqueous and vitreous humors of the eye.

Example 1

Preparation of Biodegradable Non-Surface Treated Microparticles (NSTMP) Containing PLGA Polymer microparticles comprising PLGA and diblock copolymer of PLGA and PEG with or without sunitinib malate were prepared using a single emulsion solvent evaporation method. Briefly, PLGA (560 mg) and PLGA-PEG (5.6 mg) were co-dissolved in dichloromethane (DCM) (4 mL). Sunitinib malate (90 mg) was dissolved in dimethyl sulfoxide (DMSO) (2 mL). The polymer solution and the drug solution were mixed to form a homogeneous solution (organic phase). For empty NSTMP, DMSO (2 mL) without drug was used. For drug-loaded NSTMP, the organic phase was added to an aqueous 1% PVA solution in PBS (200 mL) and homogenized at 5,000 rpm for 1 minute using an L5M-A laboratory mixer (Silverson Machines Inc., East Longmeadow, Mass.) to obtain an emulsion. For empty NSTMP, 1 percent PVA solution in water (200 mL) was used.

The emulsion (solvent-laden microparticles) was then hardened by stirring at room temperature for more than 2 hours to allow the DCM to evaporate. The microparticles were collected by sedimentation and centrifugation, washed three times in water, and filtered through a 40-μm sterile Falcon® cell strainer (Corning Inc., Corning, N.Y.). The non-surface treated microparticles (NSTMP) were either used directly in the surface treatment process or dried by lyophilization and stored as a dry powder at −20° C. until used.

Example 2

Surface Treatment of Non-Surface Treated Microparticles (NSTMP) Using NaOH(Aq)/EtOH A pre-chilled solution containing 0.25 M NaOH (aq) and ethanol at a predetermined ratio was added to microparticles in a glass vial under stirring in an ice bath at approximately 4° C. to form a suspension at 100 mg/mL. The suspension was then stirred for a predetermined time (e.g., 3, 6 or 10 minutes) on ice and poured into a pre-chilled filtration apparatus to remove the NaOH (aq)/EtOH solution. The microparticles were further rinsed with pre-chilled water and transferred to a 50-mL centrifuge tube. The particles were then suspended in pre-chilled water and kept in a refrigerator for 30 minutes to allow the particles to settle. Following removal of the supernatant, the particles were resuspended and filtered through a 40-μm cell strainer to remove large aggregates. Subsequently, the particles were washed twice with water at room temperature and freeze-dried overnight. Detailed formulation information and conditions of NaOH (aq)/EtOH surface treatment experiments are listed in Table 1.

TABLE 1

Detailed batch information on NaOH(aq)/EtOH surface treated microparticles

| Microparticles before surface treatment | Batch size (mg) | Ratio of 0.25M NaOH (aq) to EtOH (v/v) | Treatment Time (min) | STMP ID |
|---|---|---|---|---|
| S-1 (99% PLGA 7525 4A, 1% PLGA-PEG) DL = 18.0% | 200 | 30/70 | 3 | S-2 |
|  | 200 |  | 6 | S-3 |
|  | 200 |  | 10 | S-4 |
| S-5 (90% PLGA 7525 4A, 10% PLGA-PEG) DL = 18.9% | 200 | 50/50 | 3 | S-6 |
|  | 200 |  | 6 | S-7 |
|  | 200 | 30/70 | 6 | S-8 |
| S-9 (99% PLGA 7525 4A, 1% PLGA-PEG) DL = 18.3% | 1000 | 30/70 | 3 | S-10 |
| S-11 (99% PLGA 7525 4A, 1% PLGA-PEG) DL = 11.1% | 2300 | 30/70 | 3 | S-12 |
| S-13 (99% PLGA 7525 4A, 1% PLGA-PEG) DL = 11.9% | 3600 | 30/70 | 3 | S-14 |
| S-15 (99% PLGA 7525 4A, 1% PLGA-PEG) DL = 2.15% | 2000 | 30/70 | 3 | S-16 |
| S-17 (99% PLGA 7525 4A, 1% PLGA-PEG) DL = 2.21% | 2000 | 30/70 | 3 | S-18 |

DL = Drug loading.

Example 3

In Vitro Assessment of Particle Aggregability

Surface treated microparticles (STMP) were suspended in phosphate buffered saline (PBS) at a concentration of 200 mg/mL. Thirty or fifty microliters of the suspension were injected into 1.5-2.0 mL of PBS or sodium hyaluronate solution (HA, 5 mg/mL in PBS) pre-warmed at 37° C. in a 2 mL microcentrifuge tube using a 0.5 mL insulin syringe with a permanent 27-gauge needle (Terumo or Easy Touch brand). The microcentrifuge tube was then incubated in a water bath at 37° C. for 2 hours. The aggregability of the microparticles was assessed by visual observation and/or imaging under gentle agitation by inverting and/or tapping and flicking the tubes containing the microparticles. Non-surface treated microparticles (NSTMP) were used as a control.

A successful surface treatment process is expected to result in STMP that maintain good suspendability, syringe-ability and injectability. Most importantly, after the injection into PBS or sodium hyaluronate and the 2-hour incubation at 37° C., the STMP are expected to form consolidated aggregate(s) that do not break into smaller aggregates or free-floating particles under gentle agitation, a key feature that differentiates STMP from NSTMP and STMP with low aggregability.

Example 4

Effect of Temperature During Surface Treatment on Microparticle Properties

The effect of temperature on surface treatment was studied by comparing particles treated at room temperature vs. treated at 4° C. The procedure for surface treatment at room temperature was identical to the procedure described in Example 2 except that it was conducted at room temperature instead of at 4° C.

When the surface treatment process was carried out at room temperature in a mixture of 0.25 M NaOH and EtOH (v/v: 30/70 or 70/30), the particles aggregated quickly and irreversibly during surface treatment. In contrast, particles treated at 4° C. in a mixture of NaOH/EtOH at the same volume ratio did not aggregate during the surface treatment process and maintained good suspendability and injectability upon reconstitution. For surface treatment at room temperature in 0.25 M NaOH without EtOH, the particles did not aggregate during the 1-hour surface treatment. In addition, STMP treated in NaOH failed to aggregate following incubation at 37° C. In contrast, STMP treated around 4 OC did not aggregate during surface treatment, but aggregated following incubation at 37° C. After lyophilization and reconstitution in a particle diluent, the STMP were easily loaded into syringes through a 27-gauge needle and injected without needle blockage.

Example 5

Effect of PEG Content on the Aggregability of Surface Treated Microparticles

TABLE 2

NSTMP and STMP containing different percentages of PLGA:PLGA-PEG

| Formulation # | PLGA (wt %) | PLGA-PEG (wt %) | Surface Treatment Condition |
|---|---|---|---|
| S-1 | 99% | 1% | None |
| S-3 | 99% | 1% | 0.25M NaOH/EtOH (30/70, v/v), 6 min |
| S-5 | 90% | 10% | None |
| S-8 | 90% | 10% | 0.25M NaOH/EtOH (30/70, v/v), 6 min |

Two batches of NSTMP (S-1 and S-5) and two batches of STMP (S-3 and S-8) containing different weight percentages of PLGA/PLGA-PEG were surface treated following the procedure described below and their aggregability in both PBS and HA gel were evaluated.

As listed in Table 2 above, formulation S-3 contained 1% PLGA-PEG and S-8 contained 10% of PLGA-PEG. Samples S-3 and S-8 were individually treated in a mixture of 0.25M NaOH and EtOH at a volume ratio of 30/70 at 4° C. for 6 minutes. Following injection in PBS and incubation at 37° C. for 2 hours, the microcentrifuge tubes were inverted and the aggregability of the particles was assessed by visual inspection. As illustrated in FIG. 1, the NSTMP S-1 and S-5 started to disperse immediately after the tubes were inverted, while the STMP, S-3 and S-8, remained aggregated at the bottom of the tubes without dispersion throughout the entire period of observation (about 10 minutes).

A similar second experiment was conducted by injecting the same particle suspensions into HA solutions and incubating the samples at 37° C. for 2 hours. Immediately after the tubes were inverted, none of the particles became dispersed, including NSTMP; refer to FIG. 2. This is likely due to the higher viscosity of HA that prevents particles from diffusing rapidly in the gel solution. Different from S-1 which remained aggregated throughout the experiment, S-5 started to become dispersed in HA 2 minutes after the tube was inverted. Without wishing to be bound to any one theory, this may be related to the higher PEG content in S-1 that affects the interaction between particles and between the particle surfaces and HA, and thus the diffusion of S-5 in HA was less hindered than that of S-1. Though S-8 remained aggregated after injection and incubation in PBS, it appeared more dispersive in HA solution. In contrast, S-3, which contains less PEG than S-8, was able to aggregate in both PBS and HA solution. These data indicate that the aggregation and dispersion of STMP can be affected by both the particle composition and properties of the medium where the STMP are injected.

Figure 3:
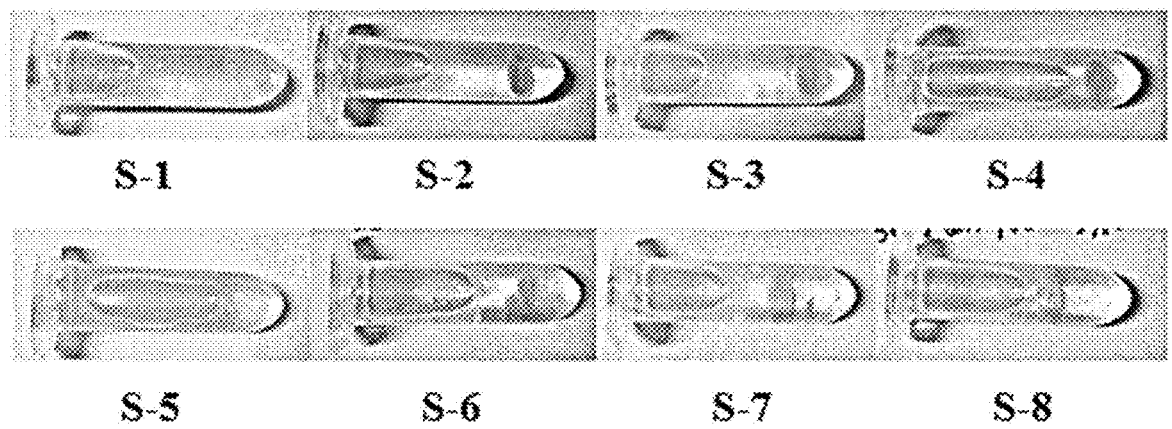
FIG. 3 illustrates the result of in vitro aggregation and dispersion of particles after a 2-hour incubation in PBS at 37° C. followed by agitation to detach the aggregates from the bottom of the tubes. Top row from left to right samples: S-1, S-2, S-3, S-4; Bottom row from left to right samples: S-5, S-6, S-7 and S-8 (Example 5).
Figure 4:
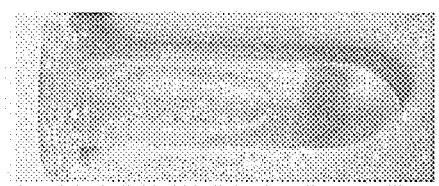
FIG. 4 illustrates in vitro aggregation of representative surface treated microparticles (STMP) treated with PBS/EtOH (sample S-21) after a 2-hour incubation in PBS at 37° C. followed by agitation by tapping and flicking the tube (Example 6).

In a third experiment, samples containing S-1, S-2, S-3, S-4, S-5, S-6, S-7 and S-8 were incubated in PBS at 37° C. for 2 hours. After assessing the aggregability by inverting the tubes, stronger agitation was applied by tapping the tubes on the bench, which caused the particle aggregates to detach from the bottom of the tubes. The integrity of the aggregates was then examined and compared among different formulations. As shown in FIG. 3, S-3 (1 percent PLGA-PEG) remained as an integrated single aggregate after detachment from the bottom of the tube. In comparison, though most particles in S-8 (10% PLGA-PEG) remained as one large aggregate, many dispersed small aggregates or particles were visible in the tube. The assay with stronger agitation allowed further differentiation of the aggregability of different particle formulations. Overall, the data suggest that STMP with lower PEG content generally form stronger and more consolidated aggregates than STMP with higher PEG content.

Example 6

Effect of Surface Treatment with PBS/EtOH on Microparticles

Since NaOH is a strong base that may cause partial degradation of polymers and lead to rapid modification of the surface properties of particles, a neutral phosphate buffered saline (PBS) solution at pH 7.4 was evaluated as an alternative to NaOH and the effect of surface treatment using PBS/EtOH on microparticles was studied. The surface treatment procedure was identical to that described in Example 2, except that the NaOH solution was replaced with PBS (pH 7.4). The experiment was performed in an ice bath at approximately 4° C. Detailed formulation composition and surface treatment conditions are listed in Table 3. The aggregability of the surface treated microparticles (STMP) was tested following the procedure described in Example 3.

TABLE 3

Formulation composition and conditions of surface treatment with PBS/EtOH

| Particle ID before treatment | Composition | Drug Loading | Batch size (mg) | PBS/EtOH (v/v) | Treatment Time (min) | STMP ID |
|---|---|---|---|---|---|---|
| S-11 | 99% PLGA 7525 4A, 1% PLGA-PEG | 11.1% | 200 | 30/70 | 3 | S-21 |
| S-19 | | 11.8% | 500 | | | S-22 |
| | | | 500 | | | S-23 |
| | | | 500 | | 6 | S-24 |
| S-20 | | 0% | 200 | | 6 | S-25 |
| | | | 200 | | 12 | S-26 |

The results of the aggregability test demonstrated that similar to surface treatment with NaOH/EtOH, all of the STMP treated with PBS/EtOH were able to form an aggregate after injection into PBS and incubation for 2 hours at 37° C. The aggregates appeared stable and resistant to gentle agitation; refer to FIG. 4, a photo of S-21. There was no apparent difference in particle aggregability under in vitro aggregation assay (procedure was conducted as described in Example 3) between these STMP and the STMP generated by treatment in NaOH/EtOH. Both drug-loaded STMP and empty STMP were able to aggregate in PBS, suggesting the surface treatment process likely has good compatibility with various particle formulations with or without drug.

Example 7

Modification of the Surface Treatment Conditions Using NaOH(Aq)/EtOH

To further optimize the surface treatment conditions with NaOH(aq)/EtOH, the impact of various parameters, such as NaOH concentration, aqueous/EtOH ratio, and treatment time, on surface treatment were studied (Table 4). It is worth noting that in this Example, the overall molar concentration of NaOH in the entire aqueous/EtOH mixture was used as a variable independent of the ratio of aqueous solution to EtOH instead of using the molarity of NaOH in the aqueous phase only as in Example 2. For example, 0.25M NaOH (aq)/EtOH (v/v: 30/70) in Example 2 is equivalent to 0.075M of NaOH in an aqueous/EtOH (v/v: 30/70) mixture. Thus, the volume ratio of aqueous to EtOH was modified from 30/70 to 50/50 and 70/30 with the same total amount of NaOH in the mixture. In addition, the amount of NaOH was decreased by 10- or 100-fold without changing the ratio of aqueous solution to EtOH. The different treatment time was chosen to achieve comparable effectiveness of surface treatment. The procedure for surface treatment on microparticles was the same as Example 2.

TABLE 4

Detailed batch information on modified NaOH(aq)/EtOH STMP

| Microparticles before surface treatment | Batch size (mg) | NaOH concentration in H$_2$O/EtOH mixture (M) | H$_2$O/EtOH ratio (v/v) | Treatment Time (min) | STMP ID |
|---|---|---|---|---|---|
| S-27 (99% PLGA 7525 4A, 1% PLGA-PEG) DL = 11.3% | 200 | 0.075 | 50/50 | 10 | S-28 |
| | 200 | | 50/50 | 20 | S-29 |
| | 200 | | 70/30 | 15 | S-30 |
| | 200 | | 70/30 | 30 | S-31 |
| | 200 | 0.0075 | 30/70 | 3 | S-32 |
| | 200 | | 30/70 | 10 | S-33 |
| | 200 | 0.00075 | 30/70 | 3 | S-34 |
| | 200 | | 30/70 | 10 | S-35 |

Example 8

Effect of Surface Treatment Using HCl/EtOH on Microparticles

As surface treatment using an aqueous solution of basic pH (Example 2 and Example 7) or neutral pH (Example 6) had been tested previously, the effect of aqueous solution of acidic pH was evaluated in Example 8. HCl was selected as a representative acid. As shown in Table 5, microparticles were treated for 3 minutes in 0.075 M or 0.0075 M of HCl in $H_2O$/EtOH (v/v: 30/70) mixture, respectively. The procedure for HCl/EtOH surface treatment was the same as in Example 2 except that HCl (aq) was used to replace NaOH (aq).

TABLE 5

Detailed batch information of HCl/EtOH treated STMP

| Microparticles before surface treatment | Batch size (mg) | HCl concentration in $H_2O$/EtOH mixture (M) | $H_2O$/EtOH ratio (v/v) | Treatment Time (min) | Final surface treated particles |
|---|---|---|---|---|---|
| S-27 (99% PLGA 7525 4A, 1% PLGA-PEG) DL = 11.3% | 200 | 0.075 | 30/70 | 3 | S-36 |
|  | 200 | 0.0075 | 30/70 | 3 | S-37 |

Example 9

Surface Treatment on Wet Microparticles

In addition to conducting surface treatment on NSTMP by first re-suspending NSTMP dry powder in an aqueous solution as illustrated in the previous examples, the feasibility of surface treatment on NSTMP prior to drying (i.e., "wet" microparticles) was also evaluated. It is expected to be easier to integrate a surface treatment step using "wet" NSTMP into the entire process of scale-up production of STMP than a step using dry powder of NSTMP. After obtaining "wet" NSTMP prior to lyophilization as shown in Example 1, an aliquot of the suspension was lyophilized to determine the particle mass per volume. The particle suspension was then concentrated or diluted accordingly to reach desired concentration and cooled down to desired temperature. Other reagents needed for surface treatment were then added to the suspension to reach desired conditions (e.g., concentration of each chemical reagent) as described in Table 6 to start the surface treatment process. The rest of the surface treatment process is the same as described on dry particles in Example 2. The detailed batch information and experimental conditions are listed in Table 6.

TABLE 6

Detailed batch information and experimental conditions of surface treatment on "wet" microparticles

| Microparticles before surface treatment | Batch size (mg) | Final surface treatment solvent | | | Treatment Time (min) | STMP ID |
|---|---|---|---|---|---|---|
| | | Solute (base, acid or salt) | Solute concentration in $H_2O$/EtOH mixture (M) | $H_2O$/EtOH ratio (v/v) | | |
| S-38 (99% PLGA 7525 4A, 1% PLGA-PEG) DL = 11.6% | 450 | NaOH | 0.075 | 30/70 | 3 | S-39 |
| | 450 | | 0.0075 | 30/70 | 10 | S-40 |
| | 450 | | 0.075 | 70/30 | 15 | S-41 |
| | 450 | | 0.00075 | 70/30 | 30 | S-42 |
| | 450 | HCl | 0.0075 | 30/70 | 3 | S-43 |
| | 450 | KCl | 0.075 | 30/70 | 20 | S-44 |
| | 450 | | 0.35 | 30/70 | 20 | S-45 |

Example 10

Optimized Method for Assessing Particle Aggregability In Vitro

To improve the method for assessing particle aggregability in vitro, an orbital shaker was used to replace the manual agitation used in Example 3.

Fifty microliters of STMP suspension in PBS at 200 mg/mL was injected in 2 mL of PBS pre-warmed at 37° C. in a 16-mm round-bottom glass test tube using a 1 mL insulin syringe with a permanent 27-gauge needle (Terumo or Easy Touch brand). The test tube was then incubated in a water bath at 37° C. for 2 hours. The aggregability of the microparticles was assessed by visual inspection and/or imaging after shaking for 30 seconds at 400 rpm on an orbital shaker (Thermo Scientific™ Multi-Platform Shakers: Catalog No. 13-687-700). The test tube containing particles/aggregates was then turned horizontally for visual assessment of the particle aggregability. NSTMP were used as a control.

Figure 17:
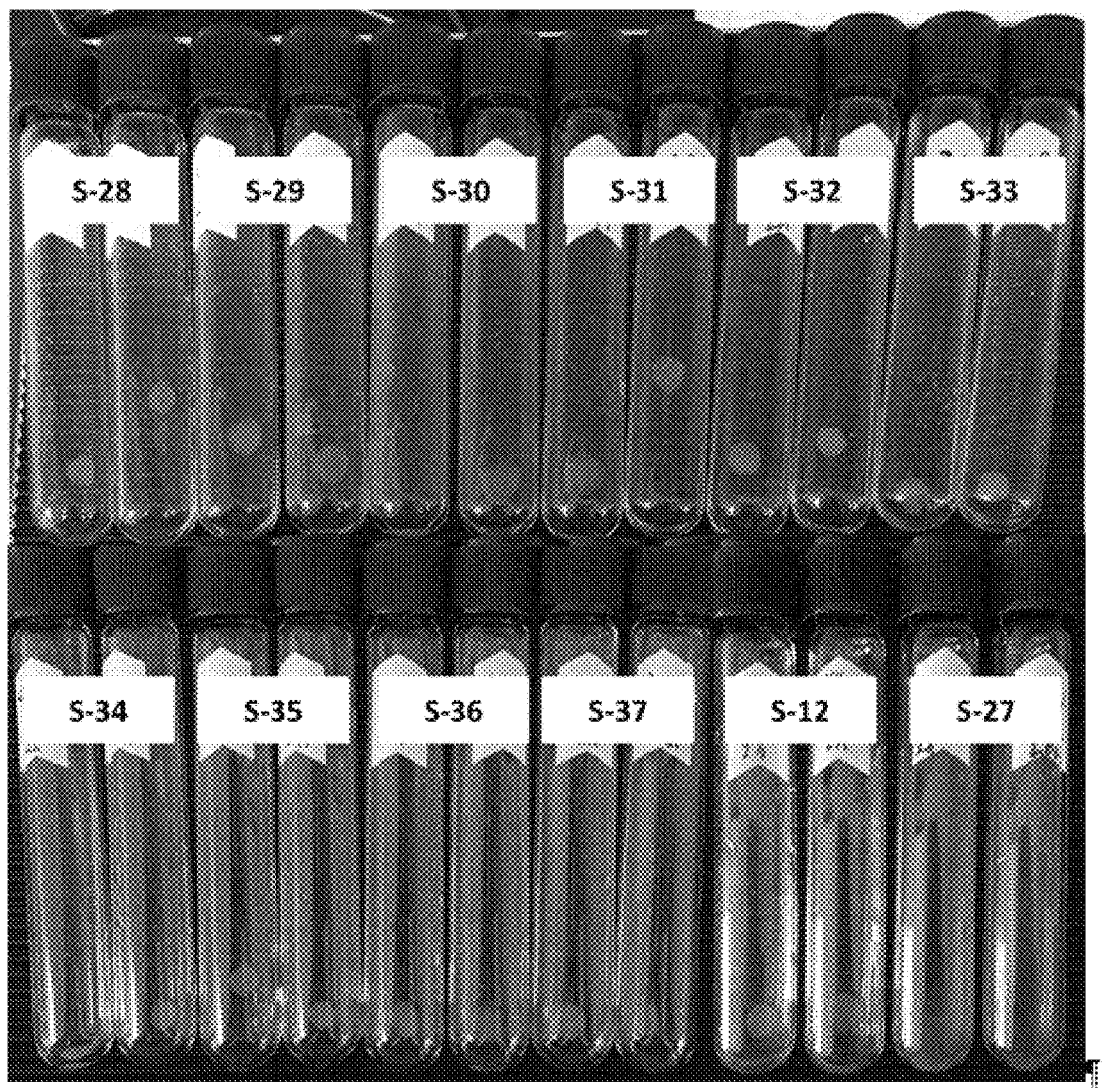
FIG. 17 illustrates the aggregation of surface treated microparticles (STMP) (S-28 to S-37 and S-12) after injection into PBS and incubation at 37° C. for 2 hours. After the 2 hour-incubation, the non-surface treated microparticles (NSTMP), S-27, became dispersed when the test tube was placed on an orbital shaker at 400 rpm for 30 seconds, while the surface treated microparticles (STMP), S-28 to S-37 and S-12, remained aggregated under the same agitation condition. Samples from left to right, top row to bottom row are S-28, S-29, S-30, S-31, S-32, S-33, S-34, S-35, S-36, S-37, S-12 and S-27 (Example 10).

As shown in FIG. 17, all the STMP in Examples 7 and 8 formed an aggregate after the 2-hour incubation and the aggregates remained mostly intact following 30-second shaking on an orbital shaker. In contrast, NSTMP in S-27 became fully dispersed following the same agitation. S-12 described in Example 2 was also included in this assessment to compare the aggregability of microparticles treated under different conditions. The results suggest all the modified surface treatment conditions in Examples 7 and 8 resulted in STMP with aggregability similar to that of S-12.

Figure 18:
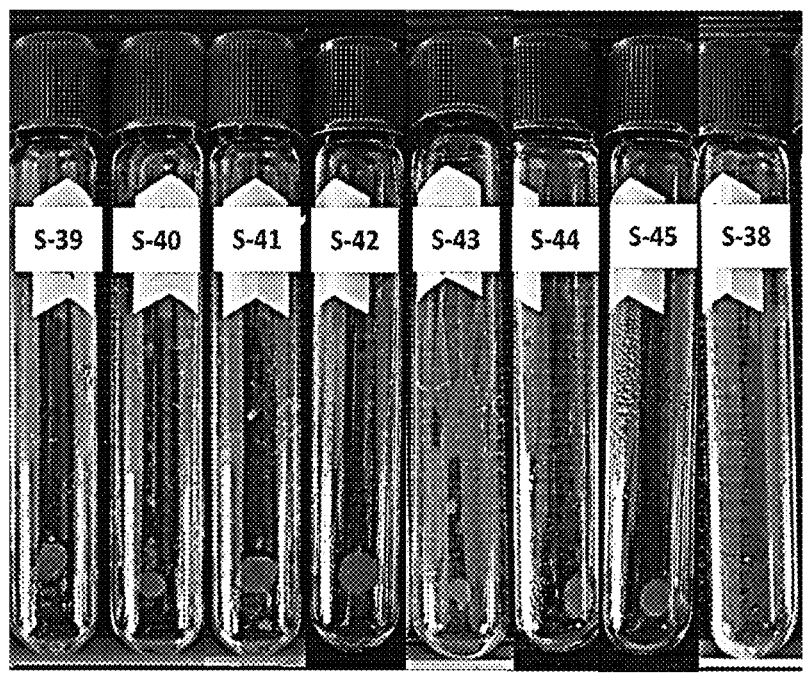
FIG. 18 illustrates the aggregation of surface treated microparticles (STMP) (S-39 to S-45) after injection into PBS and incubation at 37° C. for 2 hours. After the 2 hour-incubation, the non-surface treated microparticles (NSTMP), S-38, became dispersed when the test tube was placed on an orbital shaker at 400 rpm for 30 seconds, while the surface treated microparticles (STMP), S-39 to S-45, remained aggregated under the same agitation condition. Samples from left to right, top row to bottom row are S-39, S-40, S-41, S-42, S-43, S-44 and S-45 (Example 10).

As shown in FIG. 18, all the STMP (S-39, S-40, S-41, S-42, S-43, S-44, S-45) in Example 9 formed an aggregate after the 2-hour incubation and the aggregates remained mostly intact following 30-second shaking on an orbital shaker, while NSTMP (S-38) became fully dispersed following the same agitation. S-42, S-44 and S-45 appeared to aggregate better than other STMP samples in FIG. 18 and as well as surface treatment on dry particle in FIG. 17. The results demonstrate the success and feasibility of surface treatment on wet microparticles.

Example 11

Determination of Drug Loading

Drug loading was determined by UV-Vis spectrophotometry. Microparticles containing sunitinib (10 mg total weight) were dissolved in anhydrous DMSO (1 mL) and further diluted until the concentration of drug was in the linear range of the standard curve of UV absorbance of the drug. The concentration of the drug was determined by comparing the UV absorbance to a standard curve. Drug loading is defined as the weight ratio of drug to microparticles.

Example 12

In Vitro Drug Release Study

Figure 5:
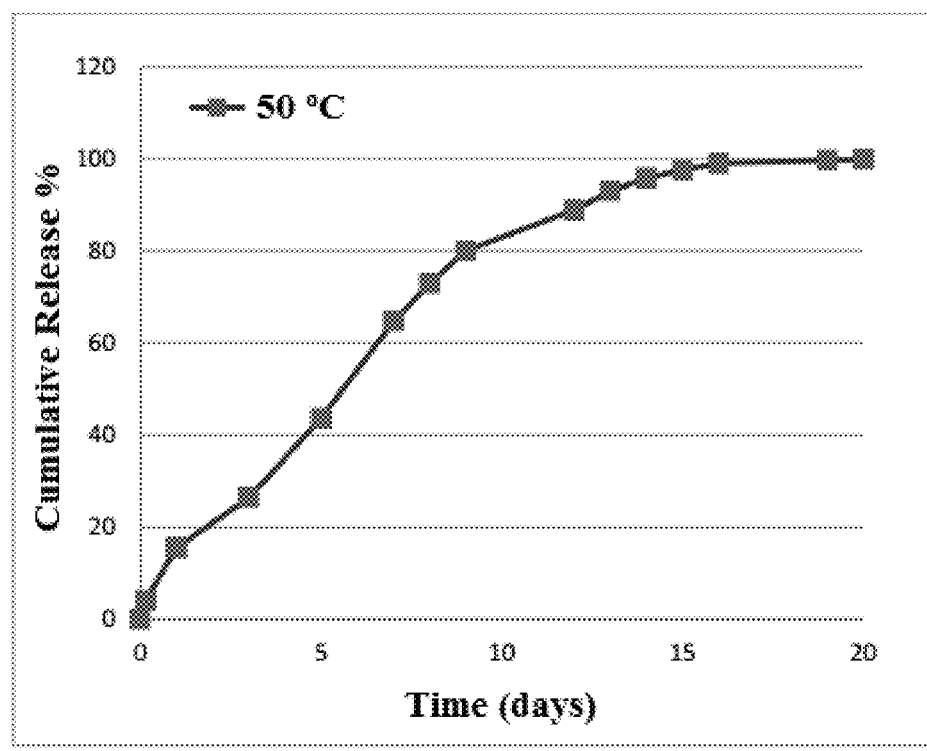
FIG. 5 illustrates the in vitro accelerated drug release profile of a representative batch of surface treated microparticles (STMP) (S-12) (Example 12). The x-axis is time measured in days and the y-axis is cumulative release percent.

Microparticles containing sunitinib (10 mg total weight) were suspended in PBS (4 mL) containing 1% Tween 20 in a 6-mL glass vial and incubated at 37° C. under shaking at 150 rpm. At predetermined time points, 3 mL of the supernatant was withdrawn after particles settled to the bottom of the vial and replaced with 3 mL of fresh release medium. The drug content in the supernatant was determined by UV-Vis spectrophotometry or HPLC. Alternatively, the above procedure can be run at 50° C. to determine an accelerated in vitro drug release rate as shown in FIG. 5.

Example 13

Studies on the Effects of Surface Treatment on Microparticles

Besides aggregability, the effect of surface treatment on other properties of microparticles was also studied to fully evaluate the feasibility of surface treatment. As shown in Table 7, in general, the yield and drug loading of STMP (in Example 2) treated for longer periods of time were slightly lower than those treated for shorter period of time, suggesting that at 0.25M NaOH/EtOH (v/v: 3:7), the time window for producing STMP with high yield and loading is narrow (on the order of minutes). However, under the modified conditions presented in Example 7, the treatment time can be further extended to tens of minutes without reducing DL and yield (Table 7) as well as aggregability (Example 10). STMP treated with HCl(aq)/EtOH in Example 8 maintained the DL prior to surface treatment with relatively high yield (S-36 and S-37). In addition, STMP (S-42, S-44 and S-45) produced by surface treatment on wet microparticles in Example 9 also maintained the DL prior to surface treatment with comparable yield as STMP produced by surface treatment on dry particles in Example 7 and 8.

TABLE 7

Yield and drug loading of STMP

| Sample | Yield | Drug loading (DL) prior to surface treatment | Drug loading after surface treatment |
|---|---|---|---|
| S-2 | 51% | 18.0% | 14.2% |
| S-3 | 50% | 18.0% | 15.3% |
| S-4 | 36% | 18.0% | 6.3% |
| S-6 | 30% | 18.9% | 15.0% |
| S-7 | 35% | 18.9% | 14.7% |
| S-8 | 28% | 18.9% | 11.6% |
| S-10 | 67% | 18.3% | 18.6% |
| S-12 | 68% | 11.1% | 11.6% |
| S-14 | 70% | 11.9% | 12.0% |
| S-16 | 56% | 2.15% | 2.11% |
| S-28 | 43% | 11.3% | 11.8% |
| S-29 | 49% | 11.3% | 11.0% |
| S-30 | 60% | 11.3% | 10.1% |
| S-31 | 61% | 11.3% | 10.6% |
| S-32 | 44% | 11.3% | 12.0% |
| S-33 | 48% | 11.3% | 11.5% |
| S-34 | 49% | 11.3% | 11.5% |
| S-35 | 58% | 11.3% | 12.0% |
| S-36 | 61% | 11.3% | 10.3% |
| S-37 | 69% | 11.3% | 11.6% |
| S-42 | 44% | 11.6% | 11.2% |
| S-44 | 50% | 11.6% | 12.0% |
| S-45 | 43% | 11.6% | 12.1% |

Figure 6:
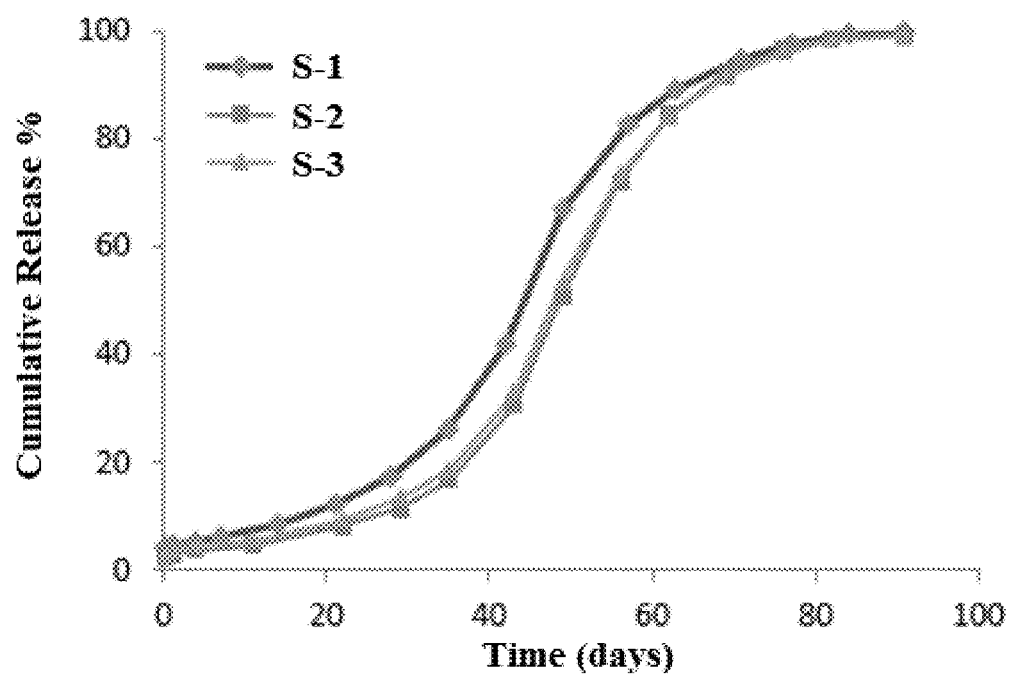
FIG. 6 illustrates the in vitro drug release profiles for samples S-1, S-2, and S-3 in PBS with 1% Tween 20 at 37° C. (Example 13). The x-axis is time measured in days and the y-axis is cumulative release percent.

FIG. 6 illustrates representative in vitro drug release profiles of NSTMP (S-1) and the corresponding STMP (S-2 and S-3) generated from the same batch of NSTMP. Overall, the release profiles are similar for microparticles before and after surface treatment except that the initial release rate of STMP was lower than that of NSTMP. This suggests that under the surface treatment conditions drug molecules that are bound to or near the microparticle surface may have been removed during the surface treatment process.

Example 14

Wettability of Surface Treated Microparticles

The wettability of representative batches of STMP and NSTMP was characterized using the Washburn method. Briefly, two glass capillary tubes with filter bases were separately filled with equivalent masses of STMP and NSTMP dry powder. The bottom of the capillary tubes was then inserted into a beaker with water and water was drawn into the tubes over time due to capillary action. The increase in mass of the tube and the height of water in the tubes were determined as a function of time. The rate of water absorption was relatively rapid in the tube containing NSTMP, but relatively slow for STMP. Similarly, at the end of the test, the mass increase of the tubes was much higher for NSTMP than for STMP, indicating that the surface modification leads to reduction of wettability of the microparticles likely due to removal of surfactant or both surfactant and polymer from particle surface.

Example 15

Figure 7:
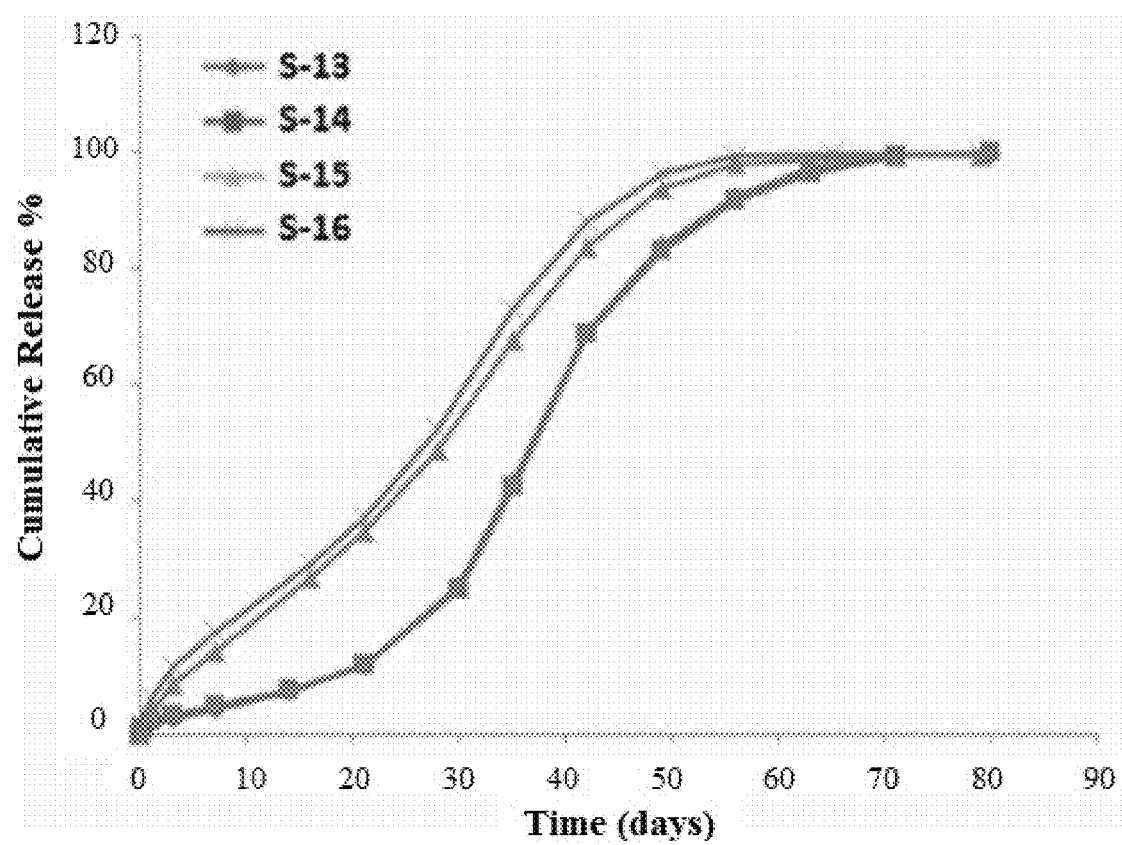
FIG. 7 illustrates the in vitro drug release profile of S-13, S-14, S-15 and S-16 in PBS with 1% Tween 20 at 37° C. (Example 15). The x-axis is time measured in days and the y-axis is cumulative release percent.
Figure 10A:
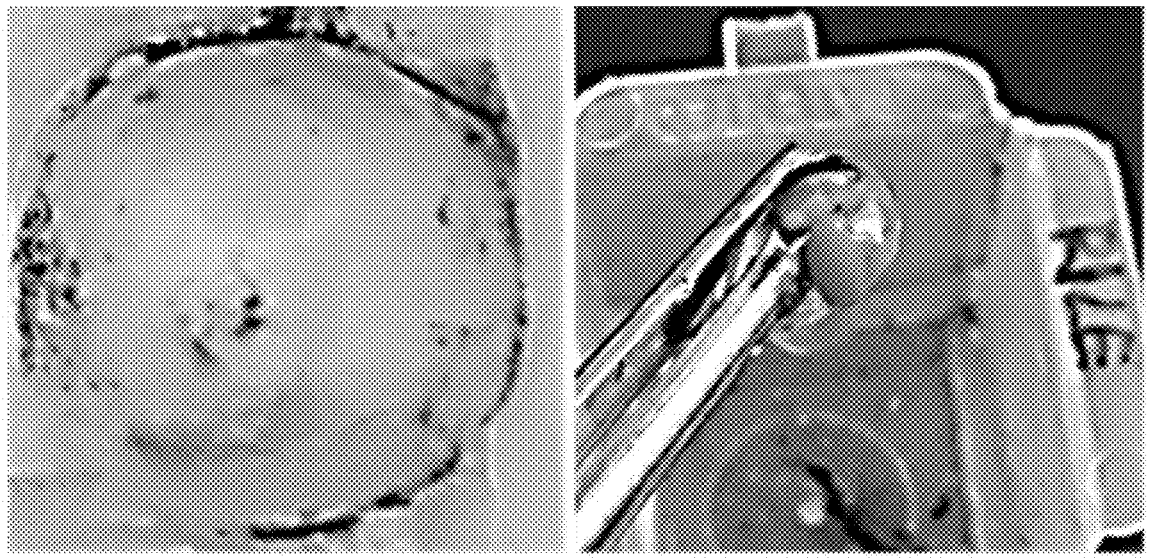
FIG. 10A are photos of particle aggregates in the vitreous (left) and out of the vitreous (right) following injection of STMP, S-10, suspended in PBS into the central vitreous of rabbit eyes (Example 19).
Figure 10B:
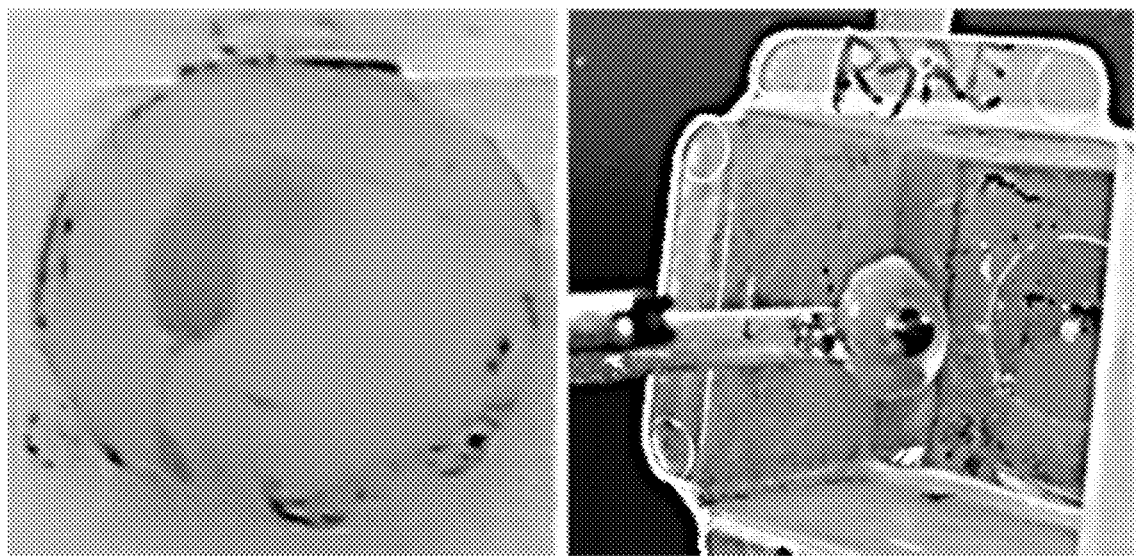
FIG. 10B are photos of particle aggregates in the vitreous (left) and out of the vitreous (right) following injection of STMP, S-10, suspended in 5-fold diluted ProVisc into the central vitreous of rabbit eyes (Example 19).

Preparation of Samples S-10, S-12, S-14, S-16, and S-18 and the Study of their Drug Release Profiles Samples S-10 to S-16 and S-18 were prepared at a larger scale of 1 to 3.6 grams. The yield and drug loading of these batches are shown in Table 6 above. It is worth noting that the drug loading was not significantly changed by surface treatment. The average particle size of these STMP samples was similar to that of the corresponding NSTMP prior to surface treatment (data not shown). As shown in FIG. 7, the release profiles of the STMP prepared at a larger scale (S-14 and S-16) were similar to the corresponding NSTMP as well, indicating that the surface treatment process had minimal effect on the overall drug release.

Example 16

Injectability and Dosing Consistency of Surface Treated Microparticles (STMP)

A suspension of STMP (ST-1-5, approximately 10 percent drug loading) at approximately 200 mg/mL was prepared by suspending the microparticles in 5-fold diluted ProVisc® solution containing 2 mg/mL of HA. After an incubation period of 2 hours at room temperature, 10 µL of the STMP suspension was loaded into a 50 µL Hamilton syringe with an attached 27-gauge needle. Following brief vortexing to fully suspend the STMP, the syringe was held horizontally for 2 minutes and vertically for 2 minutes prior to injection into a microcentrifuge tube. The injection was repeated using 3 different syringes and each syringe was tested 3 times. The STMP in each tube was then dissolved in DMSO and the dose of drug was determined by UV-Vis spectrophotometry. As shown in Table 8, excellent dosing consistency between injections using the same syringe and between different syringes was observed, suggesting that the STMP suspension in diluted ProVisc® remained stable at room temperature for a sufficient amount of time to allow consistent dosing of the relatively small volume of injection (e.g., 10 µL).

between STMP and slow down the aggregation process. On the other hand, due to its viscoelastic properties, HA may help keep particles localized and allow sufficient time for STMP to form an aggregate. The particle aggregates formed in HA also appeared to have a more spherical morphology than those formed in PBS, suggesting that if a viscoelastic solution is used as the particle diluent, an optimal range of diluent concentration needs to be identified to improve the overall performance of STMP aggregation.

After the 2-hour incubation, the strength of the aggregates was tested by shaking the test tubes at 250 rpm on an orbital shaker. As illustrated in the bottom panel of FIG. 8C and FIG. 8D, the aggregates were able to endure the shear stress generated by shaking with no or limited dispersion of microparticles.

In comparison, even though the STMP of 100 mg/mL appeared to form an aggregate in PBS (top panel, FIG. 8A), the aggregate appeared less dense than that of the 200 mg/mL STMP in PBS (top panel, FIG. 8C) and tended to disaggregate into individual microparticles under agitation (bottom panel, FIG. 8A). In addition, the STMP of 100 mg/mL was not able to form one consolidated aggregate in

TABLE 8

Injectability and dosing consistency of STMP

| Sample Name | UV Reading | Dose (mg) | Average dose per syringe n = 3 (mg) | Standard deviation (mg) | Standard deviation (%) | Average dose n = 9 (mg) | Standard deviation (mg) | Standard deviation (%) |
|---|---|---|---|---|---|---|---|---|
| Syringe 1-a | 1.019 | .1966 | .1974 | .0140 | 7.0942 | | | |
| Syringe 1-b | .953 | .1838 | | | | | | |
| Syringe 1-c | 1.098 | .2118 | | | | | | |
| Syringe 2-a | 1.136 | .2191 | .2058 | .0122 | 5.9332 | .2031 | .0129 | 6.3345 |
| Syringe 2-b | 1.052 | .2029 | | | | | | |
| Syringe 2-c | 1.012 | .1952 | | | | | | |
| Syringe 3-a | 1.052 | .2029 | .2062 | .0156 | 7.5633 | | | |
| Syringe 3-b | 1.157 | .2232 | | | | | | |
| Syringe 3-c | .998 | .1925 | | | | | | |

Example 17

Impact of Microparticle Concentration and Particle Diluent on the Aggregation of Surface Treated Microparticles (STMP)

To investigate the effect of particle concentration and diluent on the aggregation of STMP, STMP suspensions (50 µL) in 5-fold diluted ProVisc® at 2 different microparticle concentrations (100 mg/mL and 200 mg/mL) were injected into 4 mL of PBS or HA solution and incubated at 37° C. for 2 hours.

As illustrated in the top panel of FIG. 8C and FIG. 3D, the STMP at 200 mg/mL in diluted ProVisc® were able to form a consolidated aggregate in both PBS and HA following a 2-hour incubation at 37° C. Compared to 200 mg/mL STMP suspended in PBS, the aggregation of 200 mg/mL STMP in diluted ProVisc® appeared slower, but the aggregate became more consolidated over time, suggesting the HA molecules in the particle diluent may hinder the contact HA at the end of the 2-hour incubation period (top panel, FIG. 8B) and many STMP became dispersed in HA upon shaking at 250 rpm (bottom panel, FIG. 8B). Similar to HA molecules in particle diluent, the HA molecules in the test medium may further decrease particle-particle contact and reduce the chance of forming a consolidated aggregate. The results suggest that the aggregability of STMP decreases at lower microparticle concentration, possibly due to increased average particle-particle distance and decreased chance of direct contact between particles. The aggregation may also be further hindered by other molecules, such as HA, in the test medium.

In summary, the aggregation of STMP can be affected by particle concentration, particle diluent and the environment into which the particles are delivered. Overall the data demonstrate that under appropriate conditions, the STMP have good aggregability in different particle diluents and test media.

Example 18

Aggregation of Surface Treated Microparticles (STMP) in Cow Eyes Ex Vivo

To evaluate the aggregability of STMP following intravitreal injection ex vivo, enucleated cow eyes (J.W. Treuth & Sons, Catonsville, Md.) were utilized. The eyes were kept on ice prior to use. Briefly, 30 µL of 200 mg/mL STMP, S-10, suspended in 5-fold diluted ProVisc® was injected into the central vitreous of cow eyes using a 0.5 mL insulin syringe (Terumo) with a 27-gauge needle and three injections were performed in each cow eye at different locations. After a 2-hour incubation at 37° C., the eyes were cut open and the aggregates of STMP were examined using a dissecting microscope. As shown in FIG. 9, the injected STMP formed consolidated aggregates in cow vitreous and no apparent particle dispersion was observed.

Example 19

Aggregation of Surface Treated Microparticles (STMP) in Rabbit Eyes In Vivo

To study the aggregation of surface treated microparticles in rabbit eyes in vivo, 50 µL of 200 mg/mL STMP S-10 suspended in PBS (FIG. 10A) or 5-fold diluted ProVisc® (FIG. 10B) were injected to the central vitreous of Dutch Belted rabbit eyes using a 0.5 mL insulin syringe (Terumo) with a 27-gauge needle. Four days after the dosing, the rabbits were sacrificed and the eyes were nucleated and frozen immediately. The frozen eyes were cut into halves and the posterior half of the eye was thawed at room temperature for 3 minutes to allow isolation of the vitreous from the eye cup, as shown in the left photo of FIG. 10A and FIG. 10B. The frozen vitreous containing particles was placed in a cassette to allow the vitreous to thoroughly thaw. The aggregates of STMP in the vitreous could be easily separated from vitreous using forceps, proving the formation of consolidated STMP aggregates in rabbit eyes.

Example 20

Distribution, Tolerability and Pharmacokinetics of Sunitinib-Encapsulated Surface Treated Microparticles (STMP) Following an Intravitreal (IVT) Injection in Rabbits The distribution and tolerability of STMP and NSTMP were studied in pigmented New Zealand rabbits (F1) following an intravitreal injection of the microparticles. ProVisc® was diluted 5-fold in PBS and used as a diluent to prepare particle suspensions of about 200 mg/mL for injection. Detailed study groups and conditions are presented in Table 9.

Figure 11A:
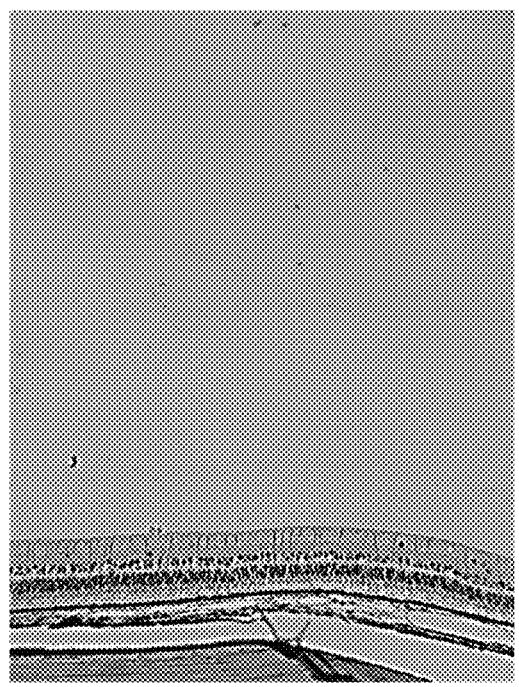
FIG. 11A illustrates representative 1-month histology images of rabbit eyes injected with surface treated microparticles (STMP) (Example 20).
Figure 11B:
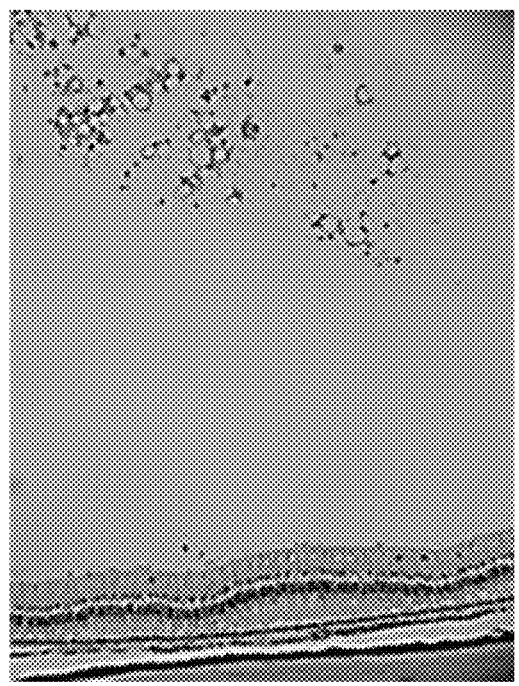
FIG. 11B illustrates representative 1-month histology images of rabbit eyes injected with non-surface treated microparticles (NSTMP) (Example 20).
Figure 12:
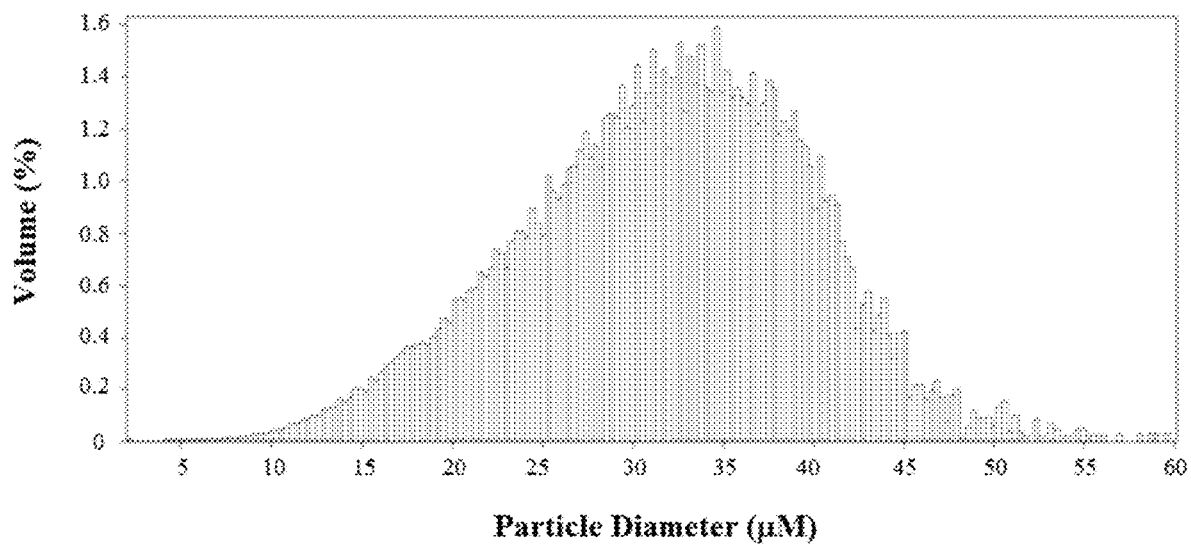
FIG. 12 illustrates the size distribution of a representative batch of surface treated microparticles (STMP) (S-12) (Example 22). The x-axis represents particle diameter measured in micrometers and the y-axis represents volume percent.

Complete ocular examinations were performed for up to 7 months after the dosing, using a slit lamp biomicroscope and an indirect ophthalmoscope, to evaluate ocular surface morphology, anterior segment and posterior segment inflammation, cataract formation, and retinal changes. A retinal lens was used to examine the location, morphology and distribution of the microspheres in vitreous. Histological analysis was also performed on enucleated and fixed eyes for up to 7 months. At pre-determined time points for up to 7 months, the drug levels of sunitinib (ng/g) in various ocular tissues (e.g. vitreous, retina, and RPE/choroid) and plasma were also analyzed. FIG. 11A illustrates a representative 1-month histology image following injection with surface treated microparticles (STMP) and FIG. 11B illustrates a representative 1-month histology images following injection with non-surface treated microparticles (NSTMP).

TABLE 9

Detailed information on rabbit study groups and dosing conditions

| Microsphere Type | | Group # | Microsphere Mass | *SM Dose | Microsphere Drug Loading | Injection Volume |
|---|---|---|---|---|---|---|
| With surface treatment | Drug-loaded | #1 | 2 mg | 0.2 mg | 10% | 10 uL |
| | | #2 | 10 mg | 1.0 mg | 10% | 50 uL |
| | | #3 | 10 mg | 0.2 mg | 2% | 50 uL |
| | Empty | #7 | 2 and 10 mg | None | None | 10 uL (Left eye) 50 uL (Right eye) |
| Without surface treatment | Drug-loaded | #4 | 2 mg | 0.2 mg | 10% | 10 uL |
| | | #5 | 10 mg | 1.0 mg | 10% | 50 uL |
| | | #6 | 10 mg | 0.2 mg | 2% | 50 uL |
| | Empty | #8 | 2 and 10 mg | None | None | 10 uL (Left eye) 50 uL (Right eye) |

*SM = Sunitinib Malate Dose

Immediately following dosing, the microspheres remained localized at the site of injection in the vitreous as a depot for all the injections. At 1 and 2 months, fundus examination using a retina lens showed that in the eyes injected with STMP, most particle injections remained consolidated in the vitreous without dispersion and no vision impairment or disturbance was observed. In contrast, particle dispersion was more commonly observed in the eyes injected with NSTMP.

Histological analysis for up to 7 months showed that overall the injections were well tolerated with minimal evidence of ocular inflammation or toxicity. No evidence of retinal toxicity (thinning and degeneration, etc.) was observed with any treatment. With STMP, the only eyes with observed inflammation were those with injection-related lens trauma/cataract and associated secondary lens-induced uveitis, which is believed to be associated with the injection procedure and not the STMP; no other evidence of inflammation in eyes dosed with surface treated microspheres was observed (FIG. 11, left). In some of the eyes dosed with NSTMP, very mild, but present, inflammation in the vitreous that may be associated with the NSTMP was observed (FIG. 11, right). The results suggest that surface treatment not only reduces the chance of particle dispersion in the vitreous that can cause visual impairment or disturbance, but it may also reduce potential intraocular inflammation associated with microspheres and improve the overall safety of the treatment.

Figure 14:
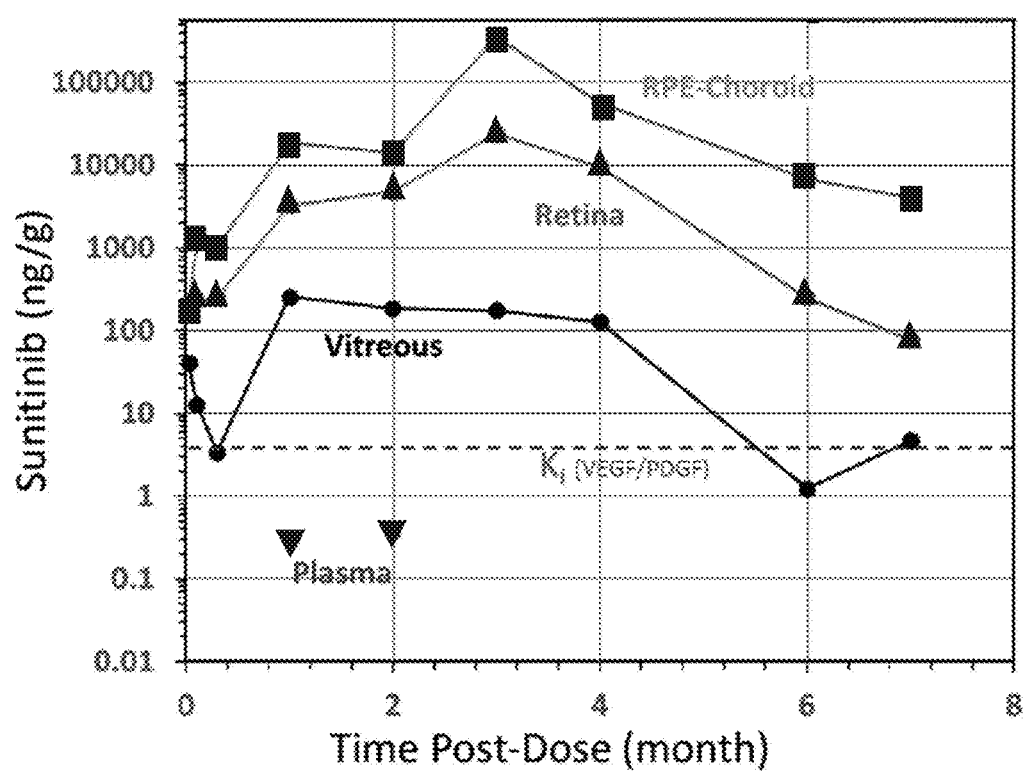
FIG. 14 illustrates sunitinib levels (ng/g) in rabbits injected with 10 mg of STMP containing 1 mg sunitinib for 7-months post-dose. The rabbits were sacrificed at 7 months and sunitinib levels (ng/g) were determined in the vitreous, retina, plasma, and RPE-Choroid. Sunitinib levels were above the $K_i$ for sunitinib against VEGFR and PDGFR (Example 20). The x-axis represents time post-dose in month and the y-axis represents the concentration of sunitinib measured in ng/g.
Figure 15:
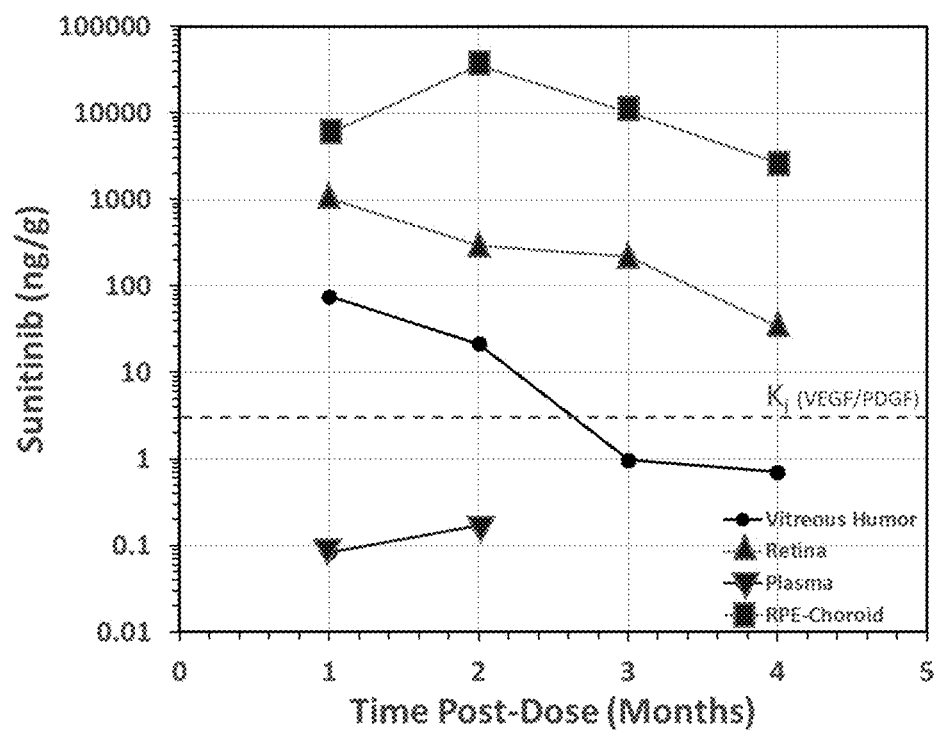
FIG. 15 illustrates sunitinib levels (ng/g) in rabbits injected with 2 mg of STMP containing 0.2 mg sunitinib (10% w/w STMP) for 4-months post-dose. The rabbits were sacrificed at 4 months and sunitinib levels (ng/g) were determined in the vitreous, retina, plasma, and RPE-Choroid. Sunitinib levels were above the $K_i$ for sunitinib against VEGFR and PDGFR in the RPE-Choroid and retina (Example 20). The x-axis represents time post-dose in months and the y-axis represents the concentration of sunitinib measured in ng/g.
Figure 16:
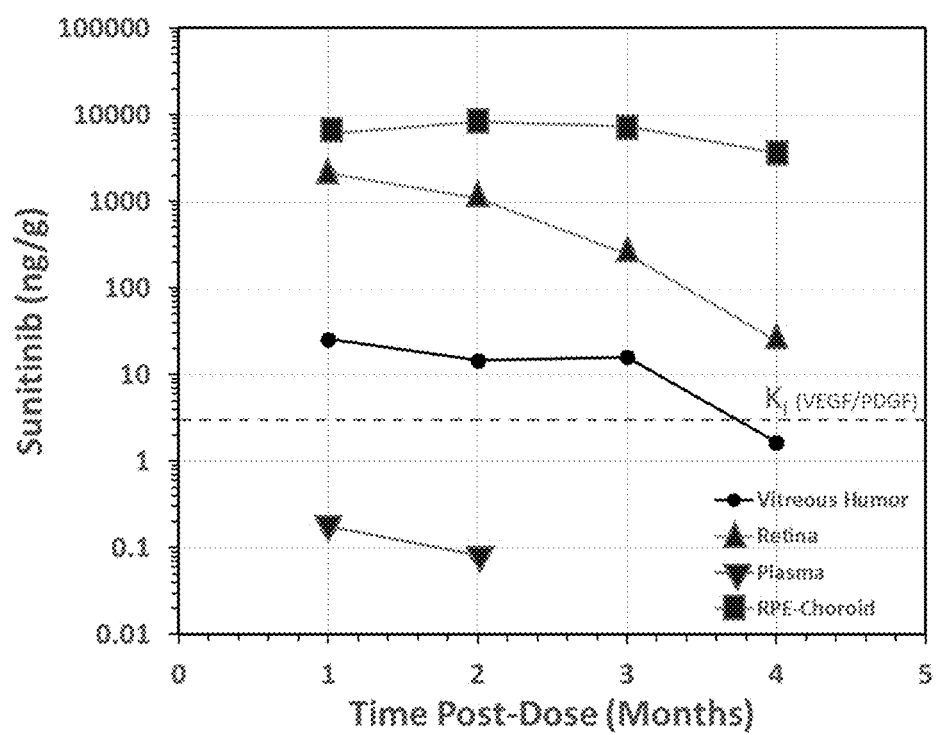
FIG. 16 illustrates sunitinib levels (ng/g) in rabbits injected with 10 mg of STMP containing 0.2 mg sunitinib (2% w/w STMP). The rabbits were sacrificed at 4 months and sunitinib levels (ng/g) were determined in the vitreous, retina, plasma, and RPE-Choroid. Sunitinib levels were above the $K_i$ for sunitinib against VEGFR and PDGFR in the RPE-Choroid and retina (Example 20). The x-axis represents time post-dose in month and the y-axis represents the concentration of sunitinib measured in ng/g.

As shown in FIGS. 14, 15, and 16, the sunitinib levels in the retina or RPE/choroid of rabbits receiving STMP containing 1 or 0.2 mg of sunitinib malate were above the $K_i$ for sunitinib against VEGFR and PDGFR at 1, 2, and 4 months, respectively. Low levels of sunitinib were detected in plasma only at 1 and 2 months.

Example 21

Determination of Drug Purity and Impurities in Particles

Sample S-12 (10.5 mg) was measured into an amber vial. N,N-dimethylacetamide (0.3 mL) and acetonitrile (0.6 mL) were added to dissolve the particles. Water (2.1 mL) was added and the mixture was thoroughly mixed. The final concentration of particles in the N,N-dimethylacetamide/ acetonitrile/water (v/v 1:2:7) mixture was 3.5 mg/mL. The purity of active compound in STMP S-12 was determined by HPLC and is reported in Table 10. The results suggest that the surface treatment did not affect the purity of encapsulated drug.

TABLE 10

HPLC analysis of drug purity in STMP

| Peak Number | Retention time | Area (%) |
|---|---|---|
| 1 | 0.24 | 0.157 |
| 2 | 0.78 | 0.283 |
| 3 | 0.82 | 0.044 |
| 4 | 1.00 | 99.39 |
| 5 | 1.12 | 0.046 |
| 6 | 1.41 | 0.084 |

Example 22

Measurement of Average Size and Size Distribution of Surface Treated Microparticles (STMP)

Several milligrams of S-12 were suspended in water. The mean particle size and distributions were determined using a Coulter Multisizer IV (Beckman Coulter, Inc., Brea, Calif.). The distribution shown in FIG. 12 has the following statistics: D10 of 20.98 µm, D50 of 32.32 m, D90 of 41.50 µm, mean of 31.84 µm, and standard deviation of 8.07 µm.

Example 23

Determination of Endotoxin Level in Particle Suspension

Microparticles (5-10 mg, S-12) were added to a sterile vial in a biosafety cabinet. The particles were suspended in endotoxin-free PBS. Using a ToxinSensor™ chromogenic LAL endotoxin assay kit (GenScript USA Inc., Piscataway, N.J.) and the instructions provided by the manufacture, the sample's total level of endotoxin was measured. S-12 had a low endotoxin level of less than 10 EU/mg.

Example 24

Toxicity Studies

An acute, non-GLP IVT study was conducted to evaluate the ocular tolerability and toxicity of sunitinib malate (free drug) for up to 7 days following a single IVT injection. Sunitinib malate was formulated in phosphate buffered saline and injected bilaterally (0.1 mL) at 0.125 or 1.25 mg per eye. At the 1.25 mg/eye dose, histologically significant findings related to sunitinib included residual test article, lenticular vacuoles/degeneration, mild to minimal inflammatory cell infiltration in vitreous, retinal degeneration, detachment, and necrosis. No toxicologically significant findings were observed at the 0.125 mg/eye dose, which is considered the no-observed-adverse-effect-level (NOAEL) dose.

Figure 13A:
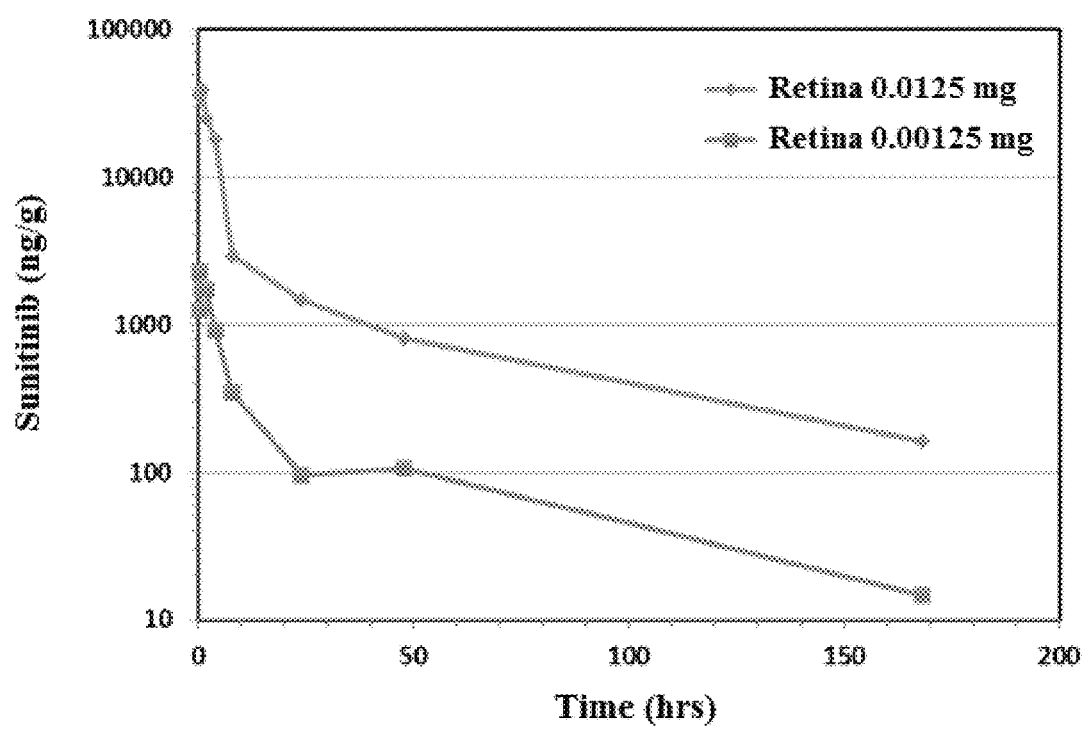
FIG. 13A illustrates select PK profiles for sunitinib in the retina following a bilateral injection of sunitinib malate (free drug) at a dose of 0.0125 mg/eye or 0.00125 mg/eye in pigmented rabbits (Example 24). The x-axis is time measured in hours and the y-axis is the concentration of sunitinib in ng/g.
Figure 13B:
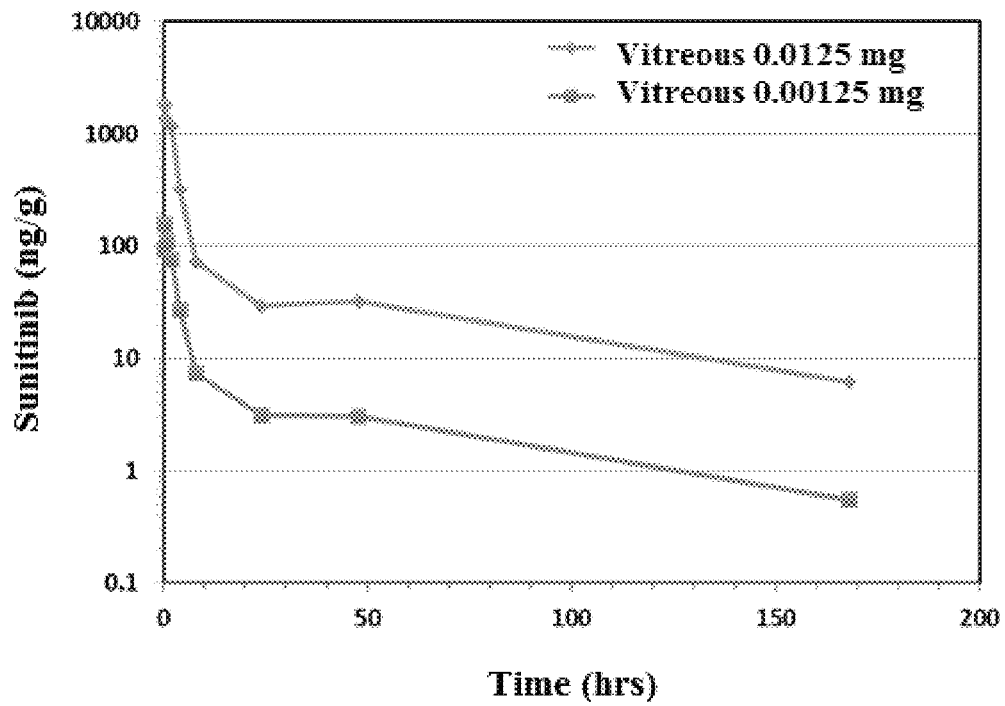
FIG. 13B illustrates select PK profiles for sunitinib in the vitreous following a bilateral injection of sunitinib malate (free drug) at a dose of 0.0125 mg/eye or 0.00125 mg/eye in pigmented rabbits (Example 24). The x-axis is time measured in hours and the y-axis is the concentration of sunitinib in ng/g.
Figure 13C:
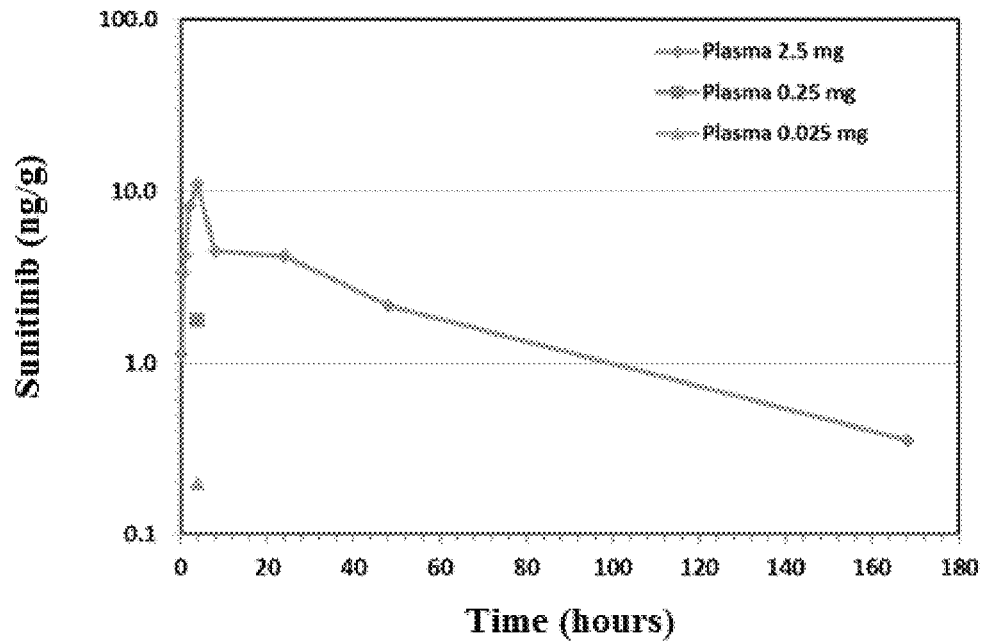
FIG. 13C illustrates select PK profiles for sunitinib in the plasma following a bilateral injection of sunitinib malate (free drug) at a dose of 2.5 mg/eye, 0.25 mg/eye, or 0.025 mg/eye in pigmented rabbits (Example 24). The x-axis is time measured in hours and the y-axis is the concentration of sunitinib in ng/g.

FIG. 13A, FIG. 13B, and FIG. 13C illustrate select PK profiles for sunitinib malate in the retina, vitreous, and plasma, respectively, from pigmented rabbits.

Example 25

Preparation of Sunitinib Microparticles (not Surface Treated)

PLGA (555 mg) and PLGA-PEG5K (5.6 mg) were dissolved in DCM (4 mL). Sunitinib malate (90 mg) was dissolved in DMSO (2 mL). The polymer and drug solutions were then mixed. The resulting reaction mixture was filtered through a 0.22 µm PTFE syringe filter. The resulting reaction mixture was diluted with 1% PVA in PBS (200 mL) in a 250 mL beaker and then homogenized at 5,000 rpm for 1 minute. (The polymer/drug solution was poured into the aqueous phase using homogenization conditions and homogenized at 5,000 rpm for 1 minute) The reaction was next stirred at 800 rpm at room temperature for 3 hours in a biosafety cabinet. The particles were allowed to settle in the beaker for 30 minutes and approximately 150 mL of the supernatant was decanted off. The microparticle suspension underwent centrifugation at 56×g for 4.5 minutes, the solvent was removed, and the microparticles were then washed three times with water. The microparticle size and size distribution was determined using a Coulter Multisizer IV prior to lyophilization. The microparticles were lyophilized using a FreeZone 4.5-liter benchtop lyophilizer. Light exposure was avoided throughout the entire process.

Example 26

General Procedure for the Preparation of Surface Treated Sunitinib Microparticles Microparticle dry powder was weighed and placed in a small beaker and a stirring bar was added. The beaker was placed in an ice bath and cooled to about 4° C. A NaOH/ EtOH solution was prepared by mixing NaOH in water (0.25M) with EtOH at 3:7 (v/v) and cooling to about 4° C. The cold NaOH/EtOH solution was added with stirring to the beaker containing the microparticles to afford a particle suspension of 100 mg/mL. The suspension was stirred for 3 minutes at about 4° C. and poured into a filtration apparatus to quickly remove the NaOH/EtOH solution. (The filtration apparatus needed to be pre-chilled in a −20° C. freezer prior to use.) Following filtration, the microparticles were rinsed in the filtration apparatus with ice cold deionized water and transferred to 50 mL centrifuge tubes. Each 50 mL centrifuge tube with filled with cold water to afford a 40 mL particle suspension at a concentration of 5-10 mg/mL. The centrifuge tubes were placed in a regenerator and the particles were allowed to settle for 30 minutes. The supernatant was then decanted. The particles were resuspended in cold water and filtered through a 40 µm cell strainer to remove any large aggregates. The particles were collected by centrifugation (56×g for 4.5 minutes) and washed twice with water. The product was lyophilized using a FreeZone 4.5 liter benchtop lyophilizer. The surface treatment process was conducted at approximately 4° C. and light exposure was avoided throughout the entire process.

Example 27

Method for Determining Accelerating In Vitro Drug Release at 50° C.

Microparticles (10 mg) were added to glass scintillation vials. Four milliliters of the release medium (1% Tween 20 in 1×PBS at pH 7.4) was added into the vials and the mixtures were vortexed. The vials were shaken on an orbital shaker at 150 rpm in a Fisher general-purpose incubator at 50° C. At pre-determined time points, the appropriate vial was cooled and the particles were allowed to settle for 10 minutes. Release medium (3 mL) was then carefully removed from the top of the vial and replaced with fresh release medium (3 mL). The vial was then returned to the orbital shaker and the amount of drug in the release medium was measured by UV spectroscopy. The concentration of drug was determined by comparing to a standard curve for the drug.

Example 28

Preparation of Biodegradable Surface-Treated Microparticles (STMP) Comprising PLA NSTMP were first produced similarly as described in Example 1. Briefly, PLA and PLGA-PEG were co-dissolved in dichloromethane (DCM) and sunitinib malate was dissolved in dimethyl sulfoxide (DMSO). The polymer solution and the drug solution were mixed to form a homogeneous solution (organic phase). For empty microparticles, DMSO without drug was used. The organic phase was added to an aqueous 1% PVA solution and homogenized at 5,000 rpm for 1 minute using an L5M-A laboratory mixer (Silverson Machines Inc., East Longmeadow, Mass.) to obtain an emulsion. The emulsion (solvent-laden microparticles) was then hardened by stirring at room temperature for more than 2 hours to allow the DCM to evaporate. The microparticles were collected by sedimentation and centrifugation, washed three times in water, and filtered through a 40-μm sterile Falcon® cell strainer (Corning Inc., Corning, N.Y.). The non-surface-treated microparticles (NSTMP) were either used directly in the surface treatment process or dried by lyophilization and stored as a dry powder at −20° C. until used.

A pre-chilled solution containing NaOH and ethanol was added to microparticles in a glass vial under stirring in an ice bath at approximately 4° C. to form a suspension. The suspension was then stirred for a predetermined time on ice and poured into a pre-chilled filtration apparatus to remove the NaOH (aq)/EtOH solution. The microparticles were further rinsed with pre-chilled water and transferred to a 50-mL centrifuge tube. The STMP were then suspended in pre-chilled water and kept in a refrigerator for 30 minutes to allow the particles to settle. Following removal of the supernatant, the particles were resuspended and filtered through a 40-μm cell strainer to remove large aggregates. Subsequently, the particles were washed twice with water at room temperature and freeze-dried overnight.

TABLE 11

Detailed formulation information of STMP comprising PLA

| STMP ID | NSTMP | | | | Surface Treatment | | |
|---|---|---|---|---|---|---|---|
| | Polymer | Drug | Aqueous Phase | Mixing | Solution | Particle Conc. | Treatment Time |
| S-46 | 800 mg PLA 100 4A and 8 mg PLGA-PEG in 4 mL DCM | 100 mg sunitinib malate in 1 mL DMSO | 200 mL of 1% PVA in PBS | 5000 rpm 1 min | 0.075M NaOH and 50% EtOH | 200 mg/mL | 3 min |
| S-47 | 800 mg PLA 100 4A and 8 mg PLGA-PEG in 4 mL DCM | 1 mL DMSO | 200 mL of 1% PVA in water | 5000 rpm 1 min | 0.075M NaOH and 50% EtOH | 200 mg/mL | 3 min |
| S-48 | 640 mg PLA 100 4A and 6.4 mg PLGA-PEG in 4 mL DCM | 2 mL DMSO | 200 mL of 1% PVA in water | 5000 rpm 1 min | 0.075M NaOH and 50% EtOH | 200 mg/mL | 3 min |

The in vitro aggregability of the STMP was characterized similarly as described in Example 3. Briefly, STMP were suspended in PBS at 200 mg/mL and 30-50 uL of the suspension was injected into 1.5-2.0 mL of PBS pre-warmed at 37° C. After incubation at 37° C. for 2 hours, the aggregability of the microparticles was assessed by visual observation and/or imaging following gentle mechanical agitation. Overall all STMP described in Table 11 were able to aggregate upon incubation at 37° C. for 2 hours.

Example 29

Figure 19:
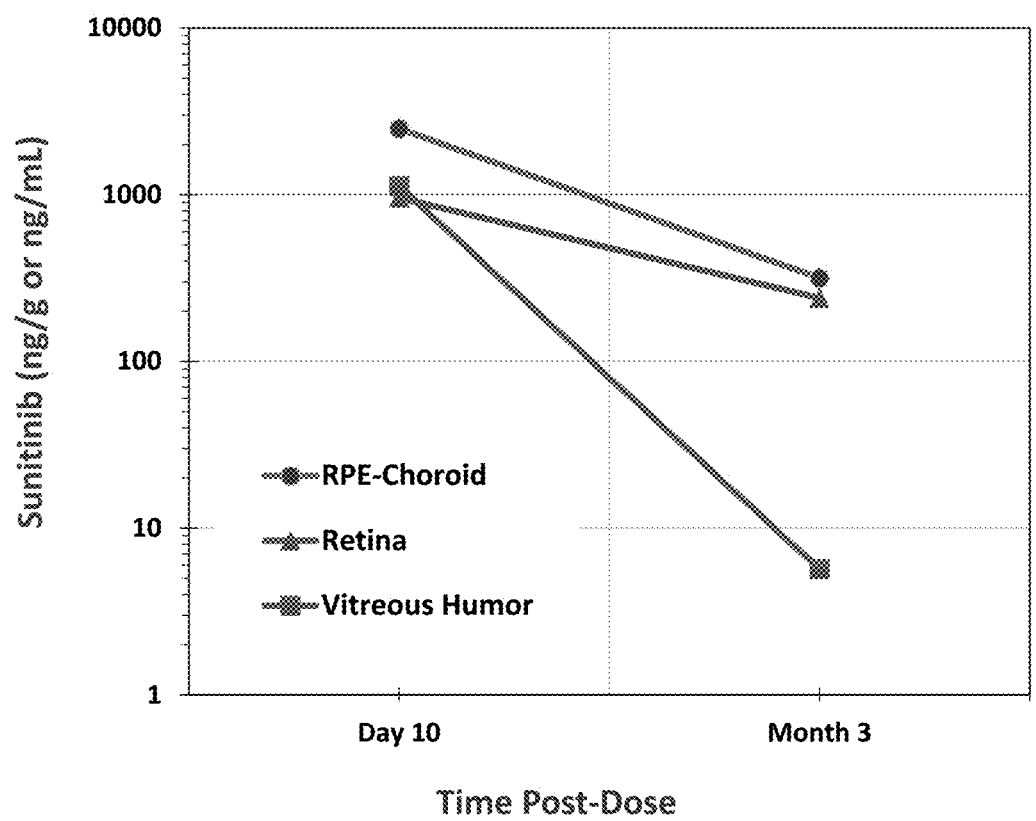
FIG. 19 is a graph depicting PK after a single IVT injection of STMP containing 1 mg sunitinib malate in rabbits. The rabbits were sacrificed at 10 days and 3 months and sunitinib levels (ng/g) were determined in the vitreous, retina, and RPE-Choroid. Sunitinib levels were above the $K_i$ for sunitinib against VEGFR and PDGFR in the RPE-Choroid and retina (Example 29). The x-axis represents time post-dose in moths and the y-axis represents the concentration of sunitinib measured in ng/g.

Distribution, Tolerability and Pharmacokinetics of Sunitinib-Encapsulated STMP Comprising PLA Following an Intravitreal (IVT) Injection in Rabbits Sunitinib-encapsulated STMP comprising PLA were suspended in ProVisc® diluted 5-fold in PBS to achieve a target dose of 1 mg sunitinib malate in a 50 uL particle suspension. The tolerability and pharmacokinetics were studied in pigmented New Zealand rabbits (F1) following an intravitreal injection of the STMP suspension. At pre-determined time points after the dosing, complete ocular examinations were performed and the drug levels of sunitinib (ng/g) in various ocular tissues (e.g. vitreous, retina, and RPE/choroid) were also analyzed (FIG. 19).

Ocular examinations for up to 6 months showed that the STMP were well tolerated in rabbit eyes and remained consolidated in the vitreous without dispersion and no vision impairment or disturbance was observed. As shown in FIG. 19, the sunitinib levels in retina or RPE/choroid of rabbits receiving STMP containing 1 mg of sunitinib malate were above the $K_i$ for sunitinib against VEGFR and PDGFR at 10 days and 3 months.

Example 30

Production of Surface-Treated Microparticles (STMP) on a Larger Scale (100 g and Higher)

NSTMP were produced using a continuous flow, oil-in-water emulsification method. The scale of the pilot batches was 100-200 g. A dispersed phase (DP) and a continuous phase (CP) were first prepared. For placebo microparticles, the DP was prepared by co-dissolving PLGA and PLGA-PEG polymers in DCM. The CP was a 0.25% PVA solution in water. For drug-loaded microparticles, the DP was prepared by dissolving sunitinib malate in DMSO and mixing with the polymer solution in DCM. The CP was a 0.25% PVA solution in PBS (pH approximately 7). Detailed formulation parameters are listed in Table 12. An emulsion was produced by mixing the DP and the CP using a high shear inline mixer. The solvents in the DP were diluted by the CP, causing the emulsion droplets to solidify and become polymer microparticles. The microparticles were then washed with water using the volume exchange principle with the addition of fresh water and removal of solvent-containing water with a hollow fiber filter. The washed microparticles were subsequently suspended in a solution containing NaOH and ethanol for surface modification of the NSTMP. This step was performed in a jacketed vessel and the temperature of the suspension was maintained around 8° C. Several surface treatment conditions have been tested as shown in Table 12. Following additional washing in water and analysis of the microparticle and drug concentration of in-process samples, the STMP suspension was adjusted to target concentration prior to filling of glass vials. In some batches, mannitol was added to the final suspension. The vials were then lyophilized and sealed. The manufacturing process can be completed aseptically and the final product in vials may also be terminally sterilized by E-Beam or gamma irradiation.

The in vitro aggregability of the STMP was characterized by a similar method to that in Example 3. Briefly, STMP was suspended in PBS at 200 mg/mL and 30-50 uL of the suspension was injected into 1.5-2.0 mL of PBS pre-warmed to 37° C. After incubation at 37° C. for 2 hours, the aggregability of the microparticles was assessed by visual observation and/or imaging following gentle mechanical agitation. In general, all STMP treated with a solution containing 0.75 mM NaOH and EtOH of 40% or higher were able to aggregate upon incubation at 37° C. Following suspension in hyaluronate solution and injection in PBS, STMP treated with a higher concentration of EtOH showed a higher tendency of floatation in PBS, suggesting reduced wettability as a result of the surface treatment.

Example 31A

Particle Vacuum Treatment Procedure

Particles were machine-filled into 2 mL glass vials and sealed with rubber septum. A vial adapter with a luer-lock opening (source) was attached to the vial and diluents (e.g., hyaluronic solution (HA)) were injected into the vial through the vial adapter. Particles were mixed with the diluent in the vial by manual tapping or vortex to yield a homogeneous suspension. A 60 mL VacLok syringe (Merit Medical, South Jordan, Utah) was attached to the vial adapter and its plunger was pulled to a predetermined volume and locked by turning the plunger per the manufacturer's instruction (FIG. 20A, FIG. 20C, and FIG. 21). This creates a negative pressure in the vial containing particle suspension as low as approximately 30 Torr depending on the plunger locking position. This negative pressure pulls air bubbles away from the particles and the suspension and thus

TABLE 12

Formulation and process parameters of STMP produced on larger scale

| NSTMP | | | | | | | | | |
|---|---|---|---|---|---|---|---|---|---|
| DP | | | | | Mixing | Surface Treatment | | | |
| PLGA 7525 4A (g) | PLGA-PEG5k (g) | DCM (g) | Sunitinib Malate (g) | DMSO (g) | speed (rpm) | Time (min) | EtOH | NaOH (mM) | Excipient |
| 86 | 0.86 | 640 | 16.5 | 260 | 4000 | 30 | 30% | 0.53 | |
| 86 | 0.86 | 640 | 16.5 | 260 | 4000 | 60 | 30% | 75 | |
| 86 | 0.86 | 640 | 15.3 | 260 | 4000 | 30 | 40% | 0.075 | |
| 86 | 0.86 | 640 | 15.3 | 260 | 4000 | 30 | 40% | 0.75 | |
| 86 | 0.86 | 640 | 15.3 | 260 | 4000 | 30 | 40% | 0.75 | |
| 86 | 0.86 | 640 | 15.3 | 260 | 4000 | 30 | 40% | 0.75 | |
| 86 | 0.86 | 640 | | | 3600 | 30 | 50% | 0.75 | |
| 86 | 0.86 | 640 | | | 3600 | 30 | 40% | 0.75 | |
| 86 | 0.86 | 640 | | 260 | 3300 | 30 | 50% | 0.75 | |
| 86 | 0.86 | 640 | 15.3 | 260 | 4000 | 30 | 40% | 0.75 | |
| 86 | 0.86 | 640 | | | 3600 | 30 | 60% | 0.75 | |
| 86 | 0.86 | 640 | 15.3 | 260 | 4000 | 30 | 40% | 0.75 | |
| 86 | 0.86 | 640 | | | 3600 | 30 | 70% | 0.75 | |
| 86 | 0.86 | 640 | 15.3 | 260 | 4000 | 30 | 50% | 0.75 | Mannitol |
| 86 | 0.86 | 640 | 15.3 | 260 | 4000 | 30 | 60% | 0.75 | Mannitol |
| 86 | 0.86 | 640 | 15.3 | 260 | 4000 | 30 | 70% | 0.75 | Mannitol |
| 172 | 1.72 | 1280 | 30.6 | 520 | 4000 | 30 | 70% | 0.75 | Mannitol |
| 172 | 1.72 | 1280 | | | 3600 | 30 | 70% | 0.75 | |
| 172 | 1.72 | 1280 | | | 3600 | 25 | 70% | 0.75 | |
| 172 | 1.72 | 1280 | 30.6 | 520 | 4000 | 30 | 60% | 0.75 | Mannitol |
| 172 | 1.72 | 1280 | 30.6 | 520 | 4000 | 30 | 60% | 0.75 | Mannitol |
| 172 | 1.72 | 1280 | | | 3600 | 25 | 70% | 0.75 | Mannitol |
| 172 | 1.72 | 1280 | 30.6 | 520 | 3800 | 30 | 60% | 0.75 | Mannitol |
| 172 | 1.72 | 1280 | 30.6 | 520 | 4000 | 30 | 60% | 0.75 | |
| 172 | 1.72 | 1280 | 30.6 | 520 | 4000 | 30 | 60% | 0.75 | | reduces particle floatation upon injection later. The vial was then rested in an upright position for a predetermined period (i.e., 10-30 minutes) to allow most of the air to be removed. After the vacuuming procedure, the 60 mL syringe plunger was released and the syringe was detached from the vial adapter. The suspension was remixed by gentle tapping and loaded into syringe for injection.

Example 31B

Optimized Particle Vacuum Treatment Procedure

The vacuuming step described in Example 31A was optimized. In the method described in Example 31B, particles were mixed after negative pressure was created in the vial and the particles were allowed to rest for a period of 10-60 minutes. In the method described in Example 31A, a negative pressure was created in the vial prior to mixing and particles were allowed to rest for 10-30 minutes.

Particles were filled into 2 mL glass vial with rubber septum. A vial adapter with a luer-lock opening was attached to the vial and diluent (e.g., hyaluronic solution (HA)) was injected into the vial through the vial adapter. A 60 mL VacLok syringe (Merit Medical, South Jordan, Utah) was attached to the vial adapter and its plunger was pulled to a predetermined volume and locked by turning the plunger per the manufacturer's instruction (FIG. 20A, FIG. 20C, and FIG. 21).

This created a negative pressure in the vials as low as approximately 30 Torr depending on the plunger locking position. Particles were mixed with the diluent in the vial by manual tapping or vortexing under the vacuum created by the VacLok syringe to yield a homogeneous suspension. Due to the vacuum, less air bubbles were generated in the suspension upon mixing. The vial was then rested in an upright position for a predetermined period (i.e., 10-60 minutes). This further allowed formed air bubbles to be pulled out of the suspension, thus reducing particle floatation upon injection later. After the vacuuming step, the plunger of the 60 mL syringe was released and the syringe was detached from the vial adapter. The suspension was remixed by gentle tapping and loaded into a dosing syringe for injection.

Figure 22A:
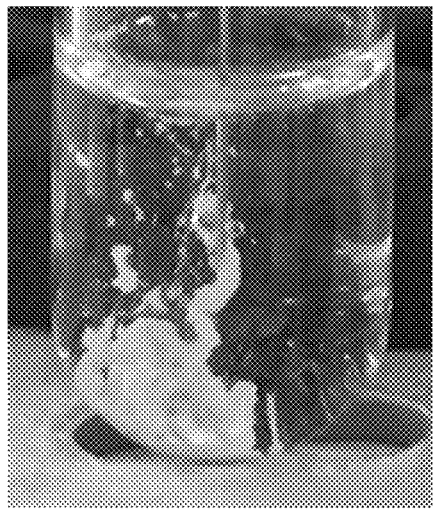
FIG. 22A is an image depicting the effect of vacuum treatment as described in Example 31A. The image was taken following the injection of particles into 37° C. phosphate buffered saline solution (PBS). Compared to the FIG. 22B, the microparticles floated following injection.
Figure 22B:
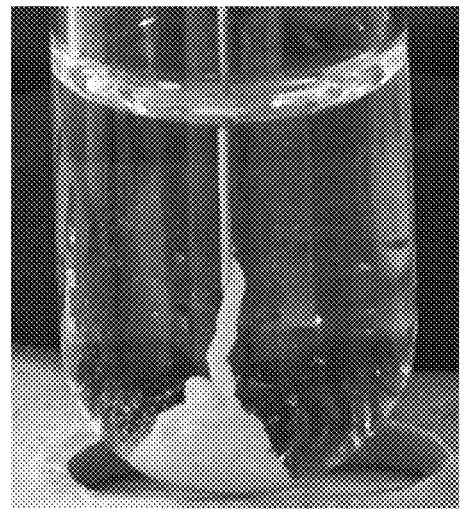
FIG. 22B is an image depicting the effect of vacuum treatment as described in the optimized procedure of Example 31B. The image was taken following the injection of particles into 37° C. phosphate buffered saline solution (PBS). Compared to FIG. 22A, microparticle floatation was reduced.
Figure 22C:
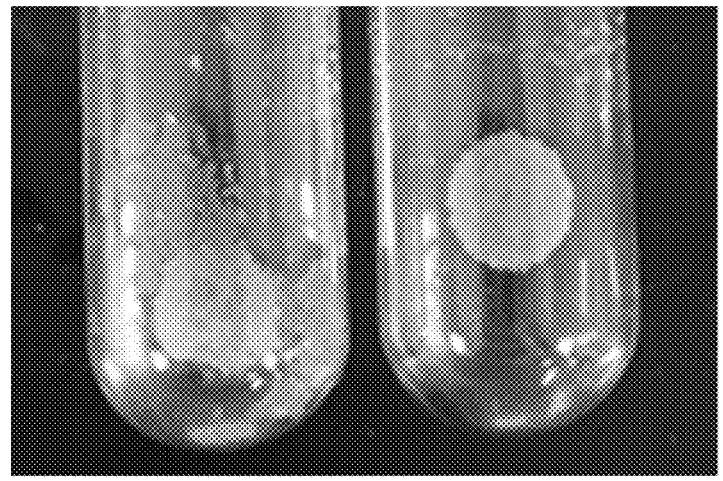
FIG. 22C is a comparison of microparticles subjected to the vacuum procedure of Example 31A (left) and the optimized vacuum procedure of Example 31B (right). The images were taken following the injection of particles into 37° C. phosphate buffered saline solution (PBS). Microparticles subjected to the optimized procedure were less dispersed compared to the particles subjected to the procedure in Example 31A.

With the optimized reconstitution procedure, microparticle floatation during injection was further reduced as compared to the procedure in Example 31A, especially when the viscosity of the suspension was high (e.g. particle concentration higher than 200 mg/mL). (FIGS. 22A and 22B are images comparing microparticles that were exposed to the vacuum treatment of Example 31A (FIG. 22A) and Example 31B (FIG. 22B). As a result, a more consolidated aggregate/depot was formed by the microparticles and less particle dispersion was observed as shown in FIG. 22C comparing microparticles exposed to the vacuum treatment of Example 31A (left) and Example 31B (right).

Example 32

Effect of Vacuum Strength During Vacuum Treatment on Particle Floatation and Aggregation Particles were suspended in 10× ProVisc (0.125% HA in PBS) to afford a final concentration of 200 mg/mL. The particle suspensions were vacuumed for 10 minutes at different strengths of approximately 550 Torr, 143 Torr, 87 Torr, and 32 Torr. Following vacuum treatment, the suspension was injected into a 37° C. phosphate buffered saline (PBS) in glass tubes and the particle floatation during and after injection was monitored. Particles were incubated in the glass tubes at 37° C. for 2 hours after injection to assess degree of aggregation. After the 2-hour incubation, the particle aggregate was detached from the bottom of glass tubes by gentle tapping and rotation.

Vacuuming strength inversely correlated with the degree of particle floatation (FIG. 23A-23L). At 32 Torr, almost no particle floatation was observed after injection (FIG. 23H) and the resulting aggregation (FIG. 23L) was very good with one large aggregate and minimal free flowing particles. When no vacuum was pulled, most of the particles floated after injection (FIG. 23A) and the aggregation was poor (FIG. 23I). The intermediate vacuum strengths yielded floatation (FIGS. 23B, 23C, 23F, and 23G) and aggregation (FIGS. 23K and 23L) results in between the two extreme cases.

Example 33

Impact of Particle Concentration on Vacuuming Outcome

Figure 24A:
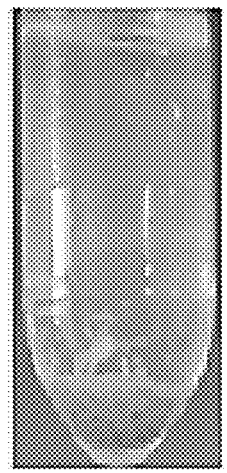
FIG. 24A is an image depicting the effect of particle concentration on vacuuming outcome as described in Example 33. The image was taken after particles (200 mg/mL) were injected into a glass tube containing 37° C. phosphate buffered saline solution (PBS) following vacuuming treatment for 20 minutes at approximately 30 Torr. In the image, as measured by visual assessment, less than 5% of the particles floated.
Figure 24B:
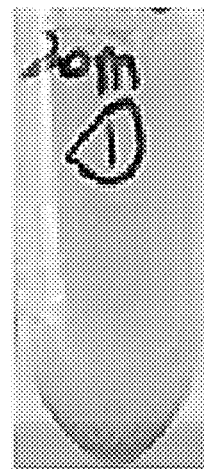
FIG. 24B is an image depicting the effect of particle concentration on vacuuming outcome as described in Example 33. The image was taken after particles (400 mg/mL) were injected into a plastic tube containing 37° C. phosphate buffered saline solution (PBS) following vacuuming treatment for 20 minutes at approximately 30 Torr. In the image, as measured by visual assessment, approximately 40% of the particles floated.

Particle suspensions with concentrations of 200 mg/mL and 400 mg/mL were prepared by dissolving particles in a 10× ProVisc solution (0.125% HA in PBS) and a 20× ProVisc solution (0.063% HA in PBS), respectively. The particles were vacuumed as described in Example 31. Under the same conditions (vacuum treatment for 20 minutes at approximately 30 Torr), the suspension with 400 mg/mL particles had significantly more floatation compared to the 200 mg/mL particles (FIG. 24A and FIG. 24B). Without wishing to be bound by any particular one theory, this could be because more particles were present in the 400 mg/mL suspension and trapped more air, rendering a longer time and/or higher vacuuming strength needed to remove the air. Higher particle concentration also increased the suspension viscosity and slowed down the traveling speed of air out of the suspension.

Example 34

Effect of Vacuum Time on Particle Floatation

Figure 25A:
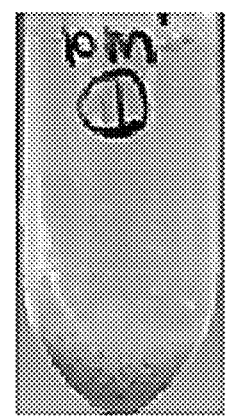
FIG. 25A is an image depicting the effect of vacuum treatment time on particle floatation as described in Example 34. The image was taken after particles (400 mg/mL) were injected into a plastic tube containing 37° C. phosphate buffered saline solution (PBS) following vacuuming treatment for 10 minutes at approximately 30 Torr. In the image, as measured by visual assessment, approximately 20% of the particles floated.
Figure 25B:
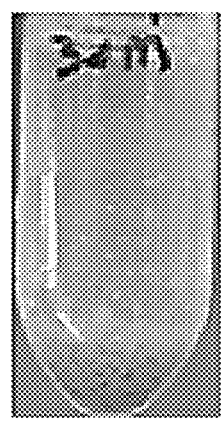
FIG. 25B is an image depicting the effect of vacuum treatment time on particle floatation as described in Example 34. The image was taken after particles (400 mg/mL) were injected into a plastic tube containing 37° C. phosphate buffered saline solution (PBS) following vacuuming treatment for 30 minutes at approximately 30 Torr. In the image, as measured by visual assessment, approximately 8% of the particles floated.

Particle suspensions with concentrations of 400 mg/mL were prepared by dissolving particles in a 40× ProVisc solution (0.031% HA in PBS). The particles were vacuumed as described in Example 31. Under the same vacuuming strength of approximately 0 Torr and the same particle concentration of 400 mg/mL, the longer the vacuuming time, the less floatation was observed. As shown in FIG. 25A, floatation percentage was approximately 20% after 10 minutes of vacuuming treatment compared to approximately 8% floatation after 30 minutes of vacuuming treatment (FIG. 25B). Without wishing to be bound by any particular one theory, this is because more air was removed after a longer vacuuming time.

Example 35

Figure 26A:
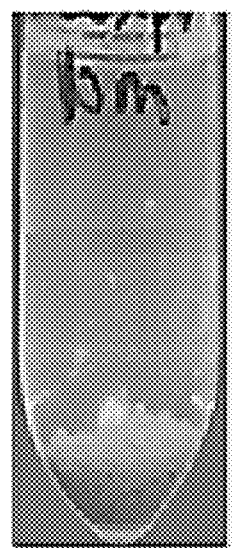
FIG. 26A is an image depicting the effect of vacuum treatment on particle floatation as described in Example 35. The image was taken after particles (400 mg/mL) were injected into a plastic tube containing 37° C. phosphate buffered saline solution (PBS) following high vacuuming treatment for 10 minutes at approximately 35 Torr.
Figure 26B:
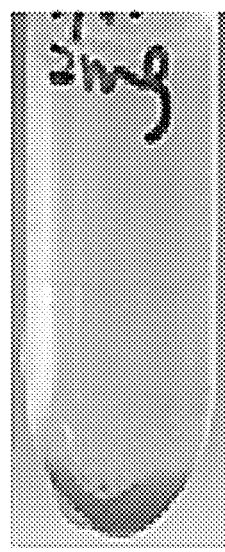
FIG. 26B is an image depicting the effect of vacuum treatment on particle floatation as described in Example 35. The image was taken after particles (400 mg/mL) were injected into a plastic tube containing 37° C. phosphate buffered saline solution (PBS) following low vacuuming treatment for 10 minutes at approximately 550 Torr.

Effect of High Vacuum Pre-Treatment Compared to Low Vacuum Pre-Treatment on Particle Floatation Particle suspensions with concentrations of 400 mg/mL were prepared by dissolving particles in a 20× ProVisc solution (0.063% HA in PBS). Particle vials were sealed under a high vacuum of approximately 35 Torr and the suspensions were vacuumed as described in Example 31. Compared to particles sealed under a low vacuum of approximately 550 Torr (FIG. 26B), the particles subjected to high vacuum treatment (FIG. 26A) exhibited less floatation especially when the suspension was concentrated (e.g., 400 mg/mL). FIG. 26A and FIG. 26B show the degree of particle floatation after injection from suspensions with 400 mg/mL particles vacuumed at approximately 35 Torr and 550 Torr for 10 minutes. The suspension prepared in the vial sealed under approximately 35 Torr had significantly less floatation than the suspension sealed at approximately 550 Torr. Without being bound to any one theory, this is because less air was present in the vial sealed under high vacuum, resulting in less air associated with the particles.

Example 36

Effects of Excipient Type Concentration on Floatation

Particles were suspended in solutions of 1% or 10% sucrose, mannitol, or trehalose to afford solutions with concentrations of approximately 60 mg/mL. The particles were then sonicated for a few minutes, flash frozen in −80° C. ethanol and lyophilized overnight. The lyophilized particles were then suspended in water and injected into 37° C. PBS or hyaluronic acid (HA) solution (5 mg/mL) to assess floatation and aggregation. Control particles had no excipients added.

Figure 27A:
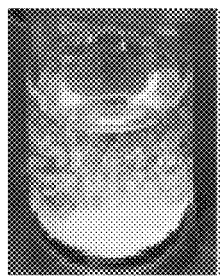
FIG. 27A is an image depicting the effects of excipient type and concentration on particle floatation as described in Example 36. The image was taken after particles were injected into a glass tube containing phosphate buffered saline solution (PBS) following lyophilization in 1% sucrose.
Figure 27B:
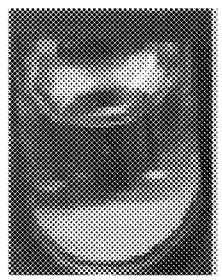
FIG. 27B is an image depicting the effects of excipient type and concentration on particle floatation as described in Example 36. The image was taken after particles were injected into a glass tube containing phosphate buffered saline solution (PBS) following lyophilization in 10% sucrose.
Figure 27C:
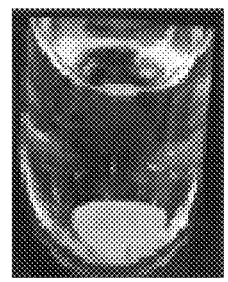
FIG. 27C is an image depicting the effects of excipient type and concentration on particle floatation as described in Example 36. The image was taken after particles were injected into a glass tube containing HA solution (5 mg/mL) following lyophilization in 1% sucrose.
Figure 27D:
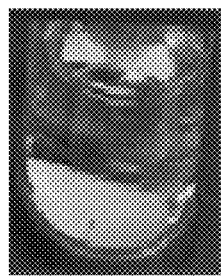
FIG. 27D is an image depicting the effects of excipient type and concentration on particle floatation as described in Example 36. The image was taken after particles were injected into a glass tube containing HA solution (5 mg/mL) following lyophilization in 10% sucrose.
Figure 27E:
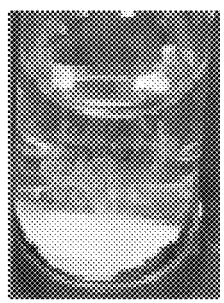
FIG. 27E is an image depicting the effects of excipient type and concentration on particle floatation as described in Example 36. The image was taken after particles were injected into a glass tube containing phosphate buffered saline solution (PBS) following lyophilization in 1% mannitol.
Figure 27F:
FIG. 27F is an image depicting the effects of excipient type and concentration on particle floatation as described in Example 36. The image was taken after particles were injected into a glass tube containing phosphate buffered saline solution (PBS) following lyophilization in 10% mannitol.
Figure 27G:
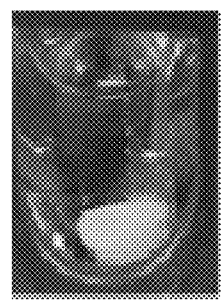
FIG. 27G is an image depicting the effects of excipient type and concentration on particle floatation as described in Example 36. The image was taken after particles were injected into a glass tube containing HA solution (5 mg/mL) following lyophilization in 1% mannitol.
Figure 27H:
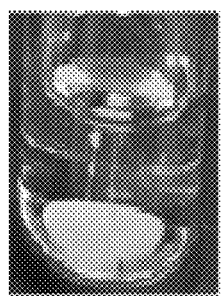
FIG. 27H is an image depicting the effects of excipient type and concentration on particle floatation as described in Example 36. The image was taken after particles were injected into a glass tube containing HA solution (5 mg/mL) following lyophilization in 10% mannitol.
Figure 27I:
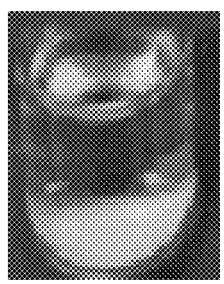
FIG. 27I is an image depicting the effects of excipient type and concentration on particle floatation as described in Example 36. The image was taken after particles were injected into a glass tube containing HA solution (5 mg/mL) following lyophilization in 1% trehalose.
Figure 27J:
FIG. 27J is an image depicting the effects of excipient type and concentration on particle floatation as described in Example 36. The image was taken after particles were injected into a glass tube containing HA solution (5 mg/mL) following lyophilization in 10% trehalose.
Figure 27K:
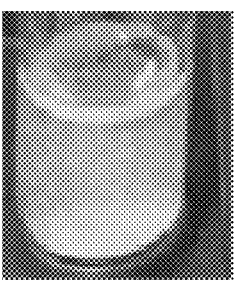
FIG. 27K is an image depicting the effects of excipient type and concentration on particle floatation as described in Example 36. The image was taken after particles were injected into a glass tube containing phosphate buffered saline solution (PBS) without any lyophilization pre-treatment.
Figure 27L:
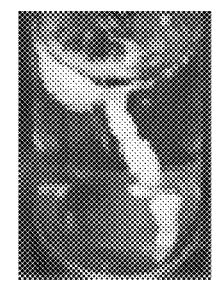
FIG. 27L is an image depicting the effects of excipient type and concentration on particle floatation as described in Example 36. The image was taken after particles were injected into a glass tube containing HA solution (5 mg/mL) without any lyophilization pre-treatment.

Upon injection into PBS and HA solution, particles with excipients (FIGS. 27A-27J) had less floatation compared to controls (FIGS. 27K and 27L). Particle sonicated in 10% sucrose excipient (FIGS. 27B and 27D) yielded less floatation than 1% sucrose (FIGS. 27A and 27C), while 1% and 10% mannitol (FIGS. 27E-27H) or trehalose (FIGS. 27I and 27J) yielded similar degree of floatation.

Particles were incubated in the glass tubes at 37° C. for 2 hours after injection to assess degree of aggregation. After the 2-hour incubation, the particle aggregate was detached from the bottom of glass tubes by gentle tapping and rotation. Particles with excipients exhibited aggregation whereas particles without excipients had poor aggregation (FIG. 28).

Example 37

The Effect of Sonication on Particle Floatation and Aggregation

Particles were suspended in HA solution, sonicated for a few minutes, and injected into 37° C. PBS. The sonicated particles had less floatation and better aggregation compared to the control (FIGS. 29A and 29B). Without wishing to be bound to any one theory, this is because sonication introduces high frequency agitation and can remove the air associated with the particles, reduce floatation, and improve aggregation as shown in FIG. 30.

Example 38

Longer-Lasting Sunitinib-Encapsulated Polymer Microparticles
Preparation of Sunitinib Particles Polymer microparticles comprising PLA, PLGA and/or diblock copolymer of PLGA and PEG encapsulating sunitinib malate were prepared using a single emulsion solvent evaporation method. PLA, PLGA and PLGA-PEG were purchased from Evonik Corporation (Birmingham, Ala.). Sunitinib malate (SM) was purchased from Teva Pharmaceutical Industries Ltd. (Parsippany, N.J.) or LC Laboratory (Woburn, Mass.).

Briefly, PLA, PLGA and PLGA-PEG of selected ratios were weighed and co-dissolved in dichloromethane (DCM) at pre-determined concentration. Sunitinib malate was dissolved in an organic solvent such as dimethyl sulfoxide (DMSO) at pre-determined concentration. After mixing the polymer solution and the drug solution to form a homogeneous solution (organic phase), the organic phase was homogenized in an aqueous solution of polyvinyl alcohol (PVA) (Mw 25 kD, 88% hydrolyzed) in a phosphate buffer saline (PBS) solution with a pH~7.4 using an L5M-A laboratory mixer or a Verso laboratory in-line mixer (Silverson Machines Inc., East Longmeadow, Mass.) to form particles. Detailed formulation and process parameters are presented in Table 13.

Particles were hardened by stirring at room temperature for >2 hr to allow DCM to evaporate, and then collected by centrifugation and washed prior to drying by lyophilization. Mean particle sizes and particle size distributions were determined using a Coulter Multisizer IV (Beckman Coulter, Inc., Brea, Calif.). Lyophilized particles were stored at −20° C. until use.

Determination of Drug Loading and Encapsulation Efficiency

Drug loading was determined by UV absorbance. 10 mg of particles containing sunitinib malate were dissolved in 1 mL of anhydrous DMSO. Appropriate dilutions of this solution were made in DMSO until the concentration of drug was in the linear range of the standard curve of UV absorbance for the drug. The concentration of the drug was determined by comparison to the standard curve.

In Vitro Drug Release at Body Temperature 5 mg of dried particles were suspended in 1 mL of PBS (pH 7.4) and incubated at 37° C. on a rotating platform (140 rpm). At selected time points, supernatant was collected by centrifugation and particles were resuspended in 1 mL of fresh PBS. The UV absorbance of the collected release medium was measured and the concentration of drug at each time point was determined by comparison to a standard curve for the drug.

Influence of Polymer Composition on the Release Kinetics of Sunitinib

Particles composed of a polymer blend including PLA, PLGA, and PLGA5050-PEG5k (10% PEG) were made as described above. Polymers with different hydrophobicity (LA/GA ratio) and MW were tested. The drug loading and encapsulation efficiency were characterized. The polymer composition, formulation parameters, and in vitro characterization data of select formulations are shown in Table 13, Table 14, Table 15, Table 16, and Table 17.

TABLE 13

Polymer Composition, Formulation Parameters, and In Vitro Characterization of Sunitinib-encapsulated Microparticles.

| ID | Polymer Composition | Ratio and conc. of polymer composition | Polymer conc. in DCM (mg/mL) | Sunitinib Malate in DMSO (mg/mL) | DCM to DMSO ratio | Drug loading (wt %) | Mean Size (μm) | In Vitro burst % |
|---|---|---|---|---|---|---|---|---|
| SM 72 | PLGA 75:25[a] 4A/PLGA-PEG | 100/1 (99% PLGA and 1% PLGA-PEG) | 140 | 45 | 2:1 | 12.0 | 31 | 0.92 |
| SM 60 | PLA 4A/PLGA-PEG | 100/1 (99% PLA and 1% PLGA-PEG) | 200 | 100 | 4:1 | 13.3 | 26 | 0.41 |
| SM 61 | PLA 4A/PLGA-PEG | 100/1 (99% PLA and 1% PLGA-PEG) | 200 | 100 | 2:1 | 18.5 | 40 | 2.08 |
| SM 62 | PLA 4A/PLGA/PLGA-PEG | 90/10/1 (99% PLA, PLGA blend and 1% PLGA-PEG) | 200 | 100 | 2:1 | 18.6 | 40 | 1.81 |
| SM 63 | PLA 4A/PLGA/PLGA-PEG | 70/30/1 (99% PLA, PLGA blend and 1% PLGA-PEG) | 200 | 100 | 2:1 | 18.5 | 38 | 2.23 |
| SM 64 | PLA 4A/PLGA/PLGA-PEG | 50/50/1 (49.5% PLA, 49.5% PLGA and 1% PLGA-PEG) | 200 | 100 | 2:1 | 17.6 | 38 | 1.92 |

[a] PLGA 75:25 is a PLGA polymer where the ratio of lactide units to glycolide units is 75 to 25

TABLE 14

Polymer Composition, Formulation Parameters, and In Vitro Characterization of Sunitinib-encapsulated Microparticles.

| ID | Polymer Composition | Ratio and conc. of polymer composition | Polymer conc. in DCM (mg/mL) | Sunitinib Malate in DMSO (mg/mL) | DCM to DMSO ratio | Drug loading (wt %) | Mean Size (μm) | In Vitro burst % |
|---|---|---|---|---|---|---|---|---|
| SM 65 | PLA 4A/PLGA 5050[a] 4A/PLGA-PEG = 95/5/1 | 95/5/1 (99% PLA, PLGA blend and 1% PLGA-PEG) | 200 | 100 | 2:1 | 18.2 | 26 | 2.16 |
| SM 66 | PLA 4A/PLGA 5050[a] 4A/PLGA-PEG = 90/10/1 | 90/10/1 (99% PLA, PLGA blend and 1% PLGA-PEG) | 200 | 100 | 2:1 | 20.3 | 22 | 2.49 |
| SM 67 | PLA 4A/PLGA 5050[a] 5A/PLGA-PEG = 95/5/1 | 95/5/1 (99% PLA, PLGA blend and 1% PLGA-PEG) | 200 | 100 | 2:1 | 17.4 | 25 | 1.75 |

TABLE 14-continued

Polymer Composition, Formulation Parameters, and In Vitro Characterization of Sunitinib-encapsulated Microparticles.

| ID | Polymer Composition | Ratio and conc. of polymer composition | Polymer conc. in DCM (mg/mL) | Sunitinib Malate in DMSO (mg/mL) | DCM to DMSO ratio | Drug loading (wt %) | Mean Size (μm) | In Vitro burst % |
|---|---|---|---|---|---|---|---|---|
| SM 68 | PLA 4A/PLGA 5050[a] 5E/PLGA-PEG = 70/30/1 | 70/30/1 (99% PLA, PLGA blend and 1% PLGA-PEG) | 200 | 100 | 2:1 | 18.1 | 25 | 2.03 |
| SM 69 | PLA 4A/PLGA 5050[a] 5E/PLGA-PEG = 90/10/1 | 90/10/1 (99% PLA, PLGA blend and 1% PLGA-PEG) | 200 | 100 | 2:1 | 16.5 | 27 | 1.07 |
| SM 70 | PLA 4A/PLGA 7525[b] 3A/PLGA-PEG = 70/30/1 | 70/30/1 (99% PLA, PLGA blend and 1% PLGA-PEG) | 200 | 100 | 2:1 | 15.2 | 24 | 6.61 |
| SM 71 | PLA 4A/PLGA 7525[b] 3A/PLGA-PEG = 90/10/1 | 90/10/1 (99% PLA, PLGA blend and 1% PLGA-PEG) | 200 | 100 | 2:1 | 18.1 | 25 | 3.78 |

[a] PLGA 50:50 is a PLGA polymer where the ratio of lactide units to glycolide units is 50 to 50
[b] PLGA 75:25 is a PLGA polymer where the ratio of lactide units to glycolide units is 75 to 25

TABLE 15

Polymer Composition, Formulation Parameters, and In Vitro Characterization of Sunitinib-encapsulated Microparticles.

| ID | Polymer Composition | Ratio and conc. of polymer composition | Polymer conc. in DCM (mg/mL) | Sunitinib Malate in DMSO (mg/mL) | DCM to DMSO ratio | Drug loading (wt %) | Mean Size (μm) | In Vitro burst % |
|---|---|---|---|---|---|---|---|---|
| SM 74 | PLA 4A/PLGA 75:25[a] 4A/PLGA-PEG | 90/10/1 (99% PLA, PLGA blend and 1% PLGA-PEG) | 200 | 110 | 2:1 | 19.0 | 26 | 0.87 |
| SM 75 | PLA 4A/PLGA 75:25[a] 4A/PLGA-PEG | 70/30/1 (99% PLA, PLGA blend and 1% PLGA-PEG) | 200 | 110 | 2:1 | 18.8 | 25 | 1.78 |
| SM 76 | PLA 4A/PLGA 75:25[a] 4A/PLGA-PEG | 50/50/1 (49.5% PLA, 49.5% PLGA and 1% PLGA-PEG) | 200 | 110 | 2:1 | 18.1 | 28 | 3.03 |
| SM 77 | PLA 4A/PLGA-PEG | 100/1 (99% PLA and 1% PLGA-PEG) | 200 | 110 | 2:1 | 18.8 | 28 | 1.52 |

[a] PLGA 75:25 is a PLGA polymer where the ratio of lactide units to glycolide units is 75 to 25

TABLE 16

Polymer Composition, Formulation Parameters, and In Vitro Characterization of Sunitinib-encapsulated Microparticles.

| ID | Polymer Composition | Ratio and conc. of polymer composition | Polymer conc. in DCM (mg/mL) | Sunitinib Malate in DMSO (mg/mL) | DCM to DMSO ratio | Drug loading (wt %) | Mean Size (μm) | In Vitro burst % |
|---|---|---|---|---|---|---|---|---|
| SM 78 | PLGA 75:25[a] 4A/PLGA-PEG | 100/1 (99% PLGA and 1% PLGA-PEG) | 140 | 45 | 2:1 | 13.3 | 28 | n/a |
| SM 79 | PLA 4A/PLGA-PEG | 100/1 (99% PLA and 1% PLGA-PEG) | 200 | 100 | 4:1 | 12.0 | 24 | n/a |

[a]PLGA 75:25 is a PLGA polymer where the ratio of lactide units to glycolide units is 75 to 25

Figure 31:
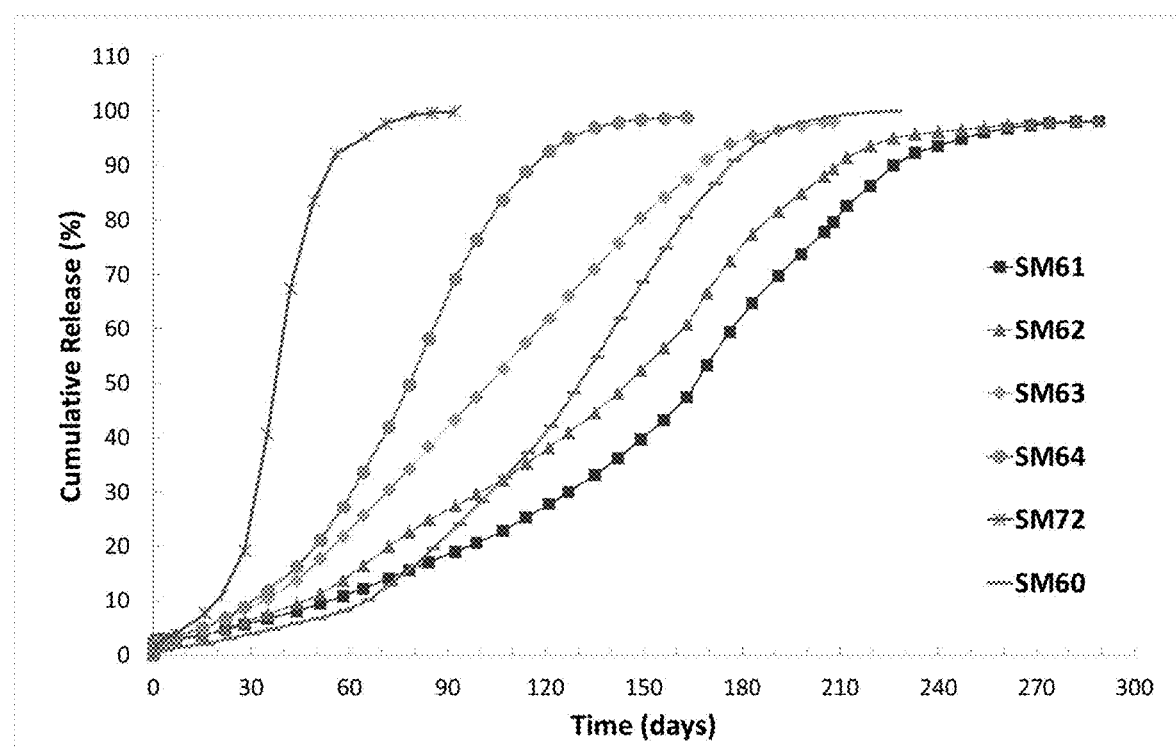
FIG. 31 is a graft depicting the in vitro drug release profile determined at 37° C. of the compounds of Table 13 in Example 38. The x-axis is time measured in days and the y-axis is cumulative release percent.
Figure 32:
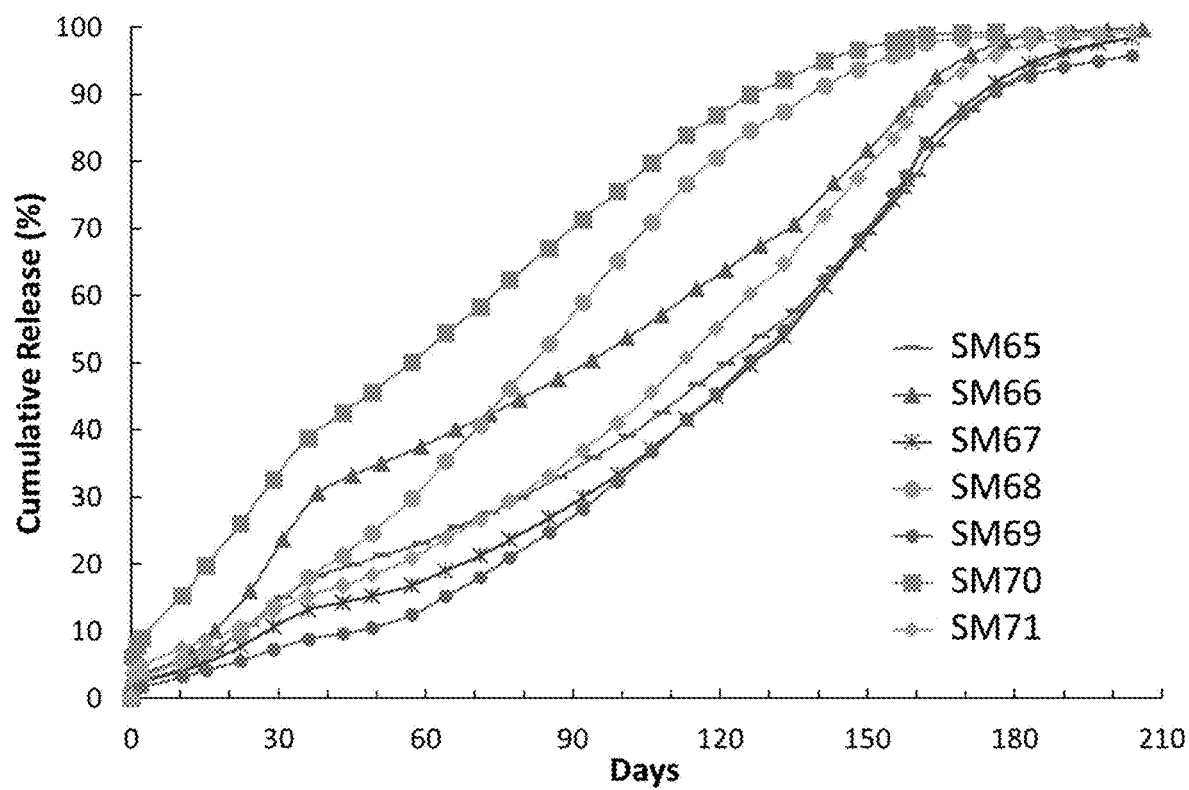
FIG. 32 is a graft depicting the in vitro drug release profile of the microparticles Table 14 at 37° C. as described in Example 38. The x-axis is time measured in days and the y-axis is cumulative release percent.
Figure 33:
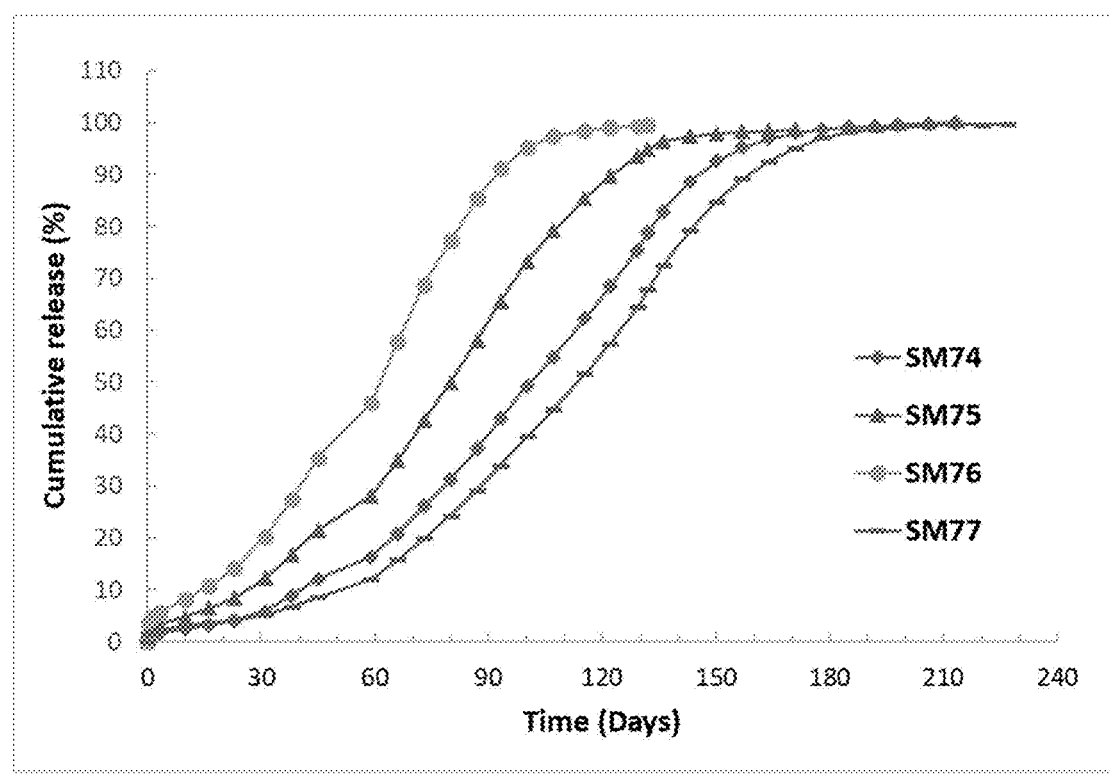
FIG. 33 is a graft depicting the in vitro drug release profile of the microparticles Table 15 at 37° C. as described in Example 38. The x-axis is time measured in days and the y-axis is cumulative release percent.
Figure 34:
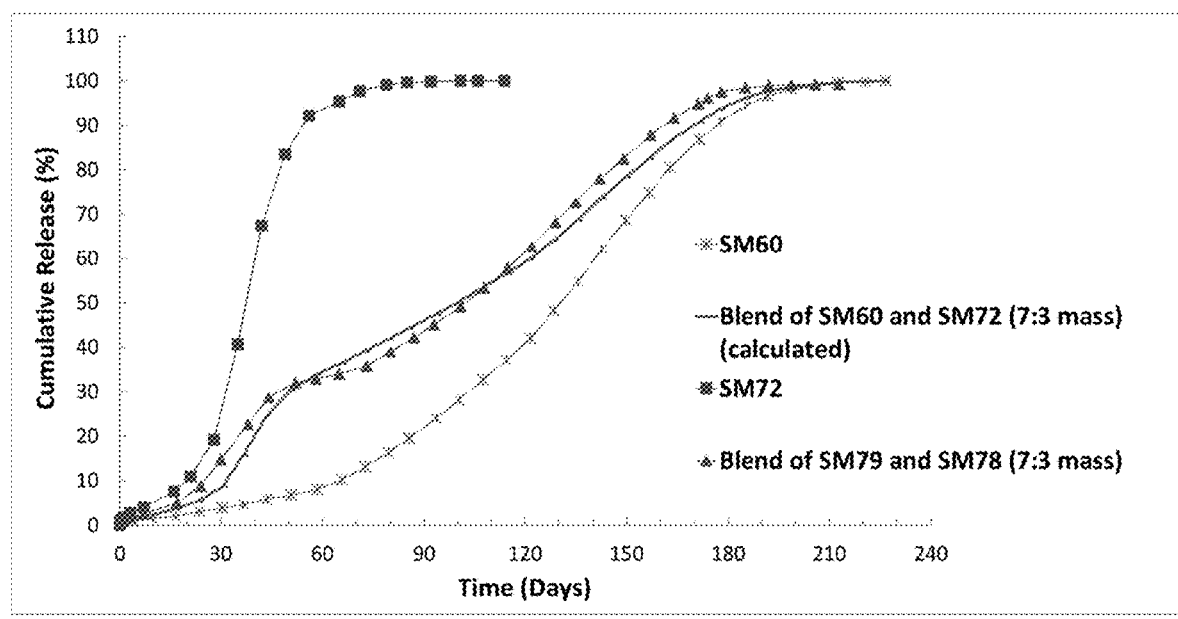
FIG. 34 is a graft depicting the in vitro drug release profile at 37° C. of the microparticles SM60, SM72, a 7:3 blend of SM60 and SM72, and a 7:3 blend of SM79 and SM78 as described in Example 38. The x-axis is time measured in days and the y-axis is cumulative release percent.

The in vitro release kinetics of the formulations in Table 13 are presented in FIG. 31. SM62 and SM63 exhibit release kinetics that are relatively linear over 180 days. The in vitro release kinetics of the formulations in Table 14 are presented in FIG. 32. SM65 exhibits release kinetics that are relatively linear by 100 days with a slight increase in release rate beyond 120 days. SM 66 exhibits relatively linear release by 100 days and faster release in the first 40 days. There is also a slight increase in release rate beyond 120 days. SM71 exhibits relative higher burst and relatively linear release by 100 days with a slight increase in release rate past 100 days. A previously developed formulation (SM72) that does not contain PLA was included for comparison. The in vitro release kinetics of the formulations in Table 15 are presented in FIG. 33. The in vitro release kinetics of the formulations of SM60, SM72, and a 7:3 mass ratio blend of SM79/SM78 described in Table 16 are presented in FIG. 34. As shown in FIG. 31, all formulations containing PLA have substantially longer duration of release than SM72 which does not contain PLA. As shown in FIG. 31, FIG. 32, and FIG. 33, by changing the composition of the polymer blend including the choice of PLGA and/or varying the ratio between polymers, the release kinetics can be fine-tuned to improve the linearity of drug release. Alternatively, a more linear release profile may also be obtained by blending different particle formulations that have different release kinetics, as demonstrated in FIG. 34.

To further improve the drug loading and extend the release duration of microparticle formulations shown in Tables 13-16, formulations described in Table 17 were made using different polymers with longer MW. The digit in the name of polymer, such as 4A, 6E, or 8E, indicates the viscosity rank of these polymers. Therefore, the larger the number, the higher the viscosity and larger the molecular weight.

Polymer utilized in the formulations described in Table 17 have viscosity ranks of 6E and 8E, while the polymer formulations described in Tables 13-16 have viscosity ranks of 3A, 4A, 5A, and 5E. Formulations SM81, SM82, SM83, and SM84 contain PLGA 75:25 8E, which has an approximate Mw (weight-average molecular weight) of 141 KDa and an Mn (number-average molecular weight) of 84 KDa. As shown in Table 17, drug loading of these formulations was significantly improved from approximately 20% as shown in Tables 13-16 to approximately 30-40% as shown in Table 17.

TABLE 17

Polymer Composition, Formulation Parameters, and In Vitro Characterization of Sunitinib-encapsulated Microparticles.

| ID | Polymer Composition | Polymer conc. in DCM (mg/mL) | Sunitinib Malate in DMSO (mg/mL) | DCM to DMSO ratio | Drug loading (wt %) | Mean Size (μm) |
|---|---|---|---|---|---|---|
| SM 80 | PLA 6E/PLGA-PEG = 100/1 (99% PLA and 1% PLGA-PEG) | 100 | 105 | 2:1 | 27.0 | 28.1 |
| SM 81 | PLGA 7525 8E/PLGA-PEG = 100/1 (99% PLGA and 1% PLGA-PEG) | 80 | 105 | 2:1 | 30.1 | 24.5 |
| SM 82 | PLGA 7525 8E/PLGA-PEG = 100/1 (99% PLGA and 1% PLGA-PEG) | 100 | 105 | 2:1 | 27.9 | 32.7 |
| SM 83 | PLGA 7525 8E/PLGA-PEG = 100/1 (99% PLGA and 1% PLGA-PEG) | 50 | 75 | 2:1 | 31.0 | 22.9 |
| SM 84 | PLGA 7525 8E/PLGA-PEG = 100/1 (99% PLGA and 1% PLGA-PEG) | 50 | 105 | 2:1 | 37.2 | 25.0 |

Four additional lots of sterile longer-lasting formulations are described in Tables 18A.

Figure 35:
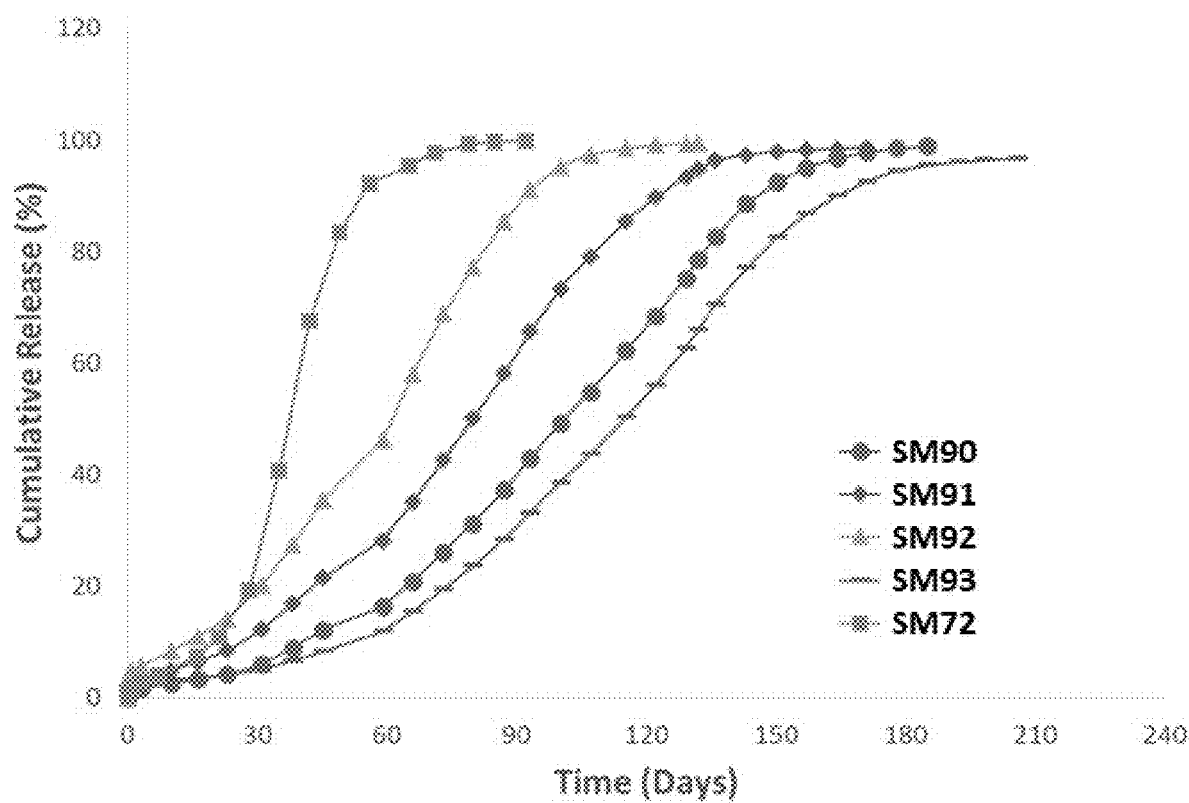
FIG. 35 is a graft depicting the in vitro drug release profile of the microparticles SM90, SM91, SM92, and SM93 as described in Table 18A and Table 18B as described in Example 38. SM 72 is also shown for comparison. The x-axis is time measured in days and the y-axis is cumulative release percent.

The mean, median, standard deviation, d10, d50, and d90 of the microparticles are give in Table 18B. All microparticles were formulated with different ratios of PLA 4A/PLGA 7525 4A/PLGA-PEG. All four lots exhibited good aggregation in vitro and exhibited release rates of approximately 20%. The in vitro release data following dosing in rabbits of the four lots characterized in Table 18A and 18B is shown in FIG. 35. The release rate of microparticles formulated without PLA (SM 72) is shown for comparison. The formulations shown in Tables 18A and 18B were produced by an in-line mixer, sterilized, and surface-treated.

TABLE 18A

Characterization of PLA/PLGA/PLGA-PLA Blended Microparticles

| ID | Composition (PLA 4A/PLGA 7525 4A/PLGA-PEG) | DL (%) | Endotoxin (surface) | In vitro aggregation (PBS/PBS) | In vitro aggregation (10X PV/PBS) | In vitro burst at 37° C. (~3 h) | Yield (g) | Yield (%) | Mean size (um) |
|---|---|---|---|---|---|---|---|---|---|
| SM 90 | 90/10/1 (99% PLA, PLGA blend and 1% PLGA-PEG) | 19.02 | 0.000055 | Good | Good | 0.87 | 4.55 | 34.7 | 25.17 |
| SM 91 | 70/30/1 (99% PLA, PLGA blend and 1% PLGA-PEG) | 18.78 | 0.000034 | Good | Good | 1.88 | 6.01 | 46.6 | 25.33 |
| SM 92 | 50/50/1 (99% PLA, PLGA blend and 1% PLGA-PEG) | 18.09 | 0.00022 | Good | Good | 3.28 | 3.58 | 27.6 | 27.84 |
| SM 93 | 100/0/1 (99% PLA and 1% PLGA-PEG) | 18.76 | 0.00023 | Good | Good | 1.59 | 4.24 | 32.9 | 28.15 |

TABLE 18B

Characterization of PLA/PLGA/PLGA-PLA Blended Microparticles

| ID | Composition (PLA 4A/PLGA 7525 4A/PLGA-PEG) | Mean (μm) | Median (μm) | S.D. (μm) | d10 (μm) | d50 (μm) | d90 (μm) |
|---|---|---|---|---|---|---|---|
| SM90 | 90/10/1 (99% PLA, PLGA blend and 1% PLGA-PEG) | 25.17 | 25.69 | 6.685 | 16.33 | 25.69 | 32.84 |
| SM91 | 70/30/1 (99% PLA, PLGA blend and 1% PLGA-PEG) | 25.33 | 25.87 | 7.866 | 14.48 | 25.87 | 34.92 |
| SM92 | 50/50/1 (99% PLA, PLGA blend and 1% PLGA-PEG) | 27.84 | 27.82 | 8.6 | 16.81 | 27.82 | 38.98 |
| SM93 | 100/0/1 (99% PLA and 1% PLGA-PEG) | 28.15 | 28.15 | 8.704 | 16.8 | 28.15 | 39.37 |

Figure 36:
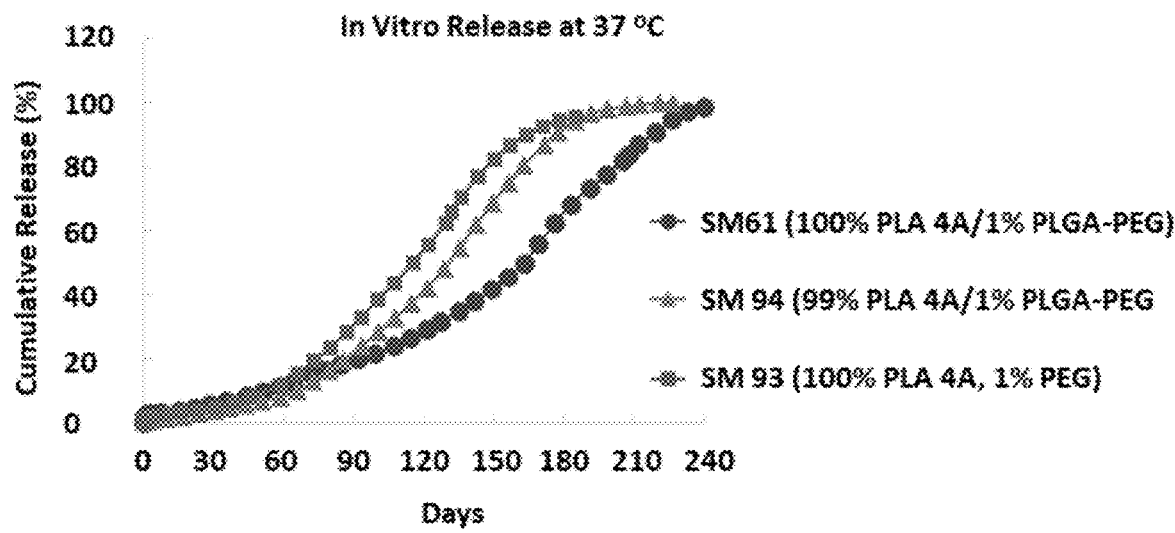
FIG. 36 is a graft depicting the in vitro drug release profile of the microparticles SM94, SM61, and SM93 as described in Table 19A and Table 19B as described in Example 38. The x-axis is time measured in days and the y-axis is cumulative release percent.

A comparison of the in vitro release of three lots of PLA 4A particles is shown in FIG. 36. Two of the microparticle lots (SM 94 and SM 61) were homogenized via a small probe, while one lot (SM 93) was homogenized via an in-line mixer. SM 94 and SM 61 were not surface-treated, while SM 93 was surface-treated. Further characterization details for the three lots are shown in Tables 19A and 19B.

TABLE 19A

Characterization of Microparticles formulated with PLA

| ID | Composition | Homogenizer type | Surface treated (Y/N) | Polymer conc. in DCM (mg/mL) | API conc. in DMSO (mg/mL) | DCM to DMSO ratio |
|---|---|---|---|---|---|---|
| SM 94 | 99% PLA 4A/1% PLGA-PEG | Small probe | N | 200 | 100 | 4:1 |
| SM 61 | 100% PLA 4A/1% PLGA-PEG | Small probe | N | 200 | 100 | 2:1 |
| SM 93 | 100% PLA 4A/1% PLGA-PEG | In-line mixer | Y | 200 | 110 | |

TABLE 19B

Drug loading, mean size, and in vitro burst percent of microparticles formulated with PLA

| ID | Composition | Drug loading (wt %) | Mean Size (μm) | In vitro burst % |
|---|---|---|---|---|
| SM 94 | 99% PLA 4A/1% PLGA-PEG | 13.3 | 26 | 0.41 |
| SM 61 | 100% PLA 4A/1% PLGA-PEG | 18.5 | 40 | 2.08 |
| SM 93 | 100% PLA 4A/1% PLGA-PEG | 18.8 | 28 | 1.59 |

Example 39

In Vitro Release of Particle Blending

Figure 37:
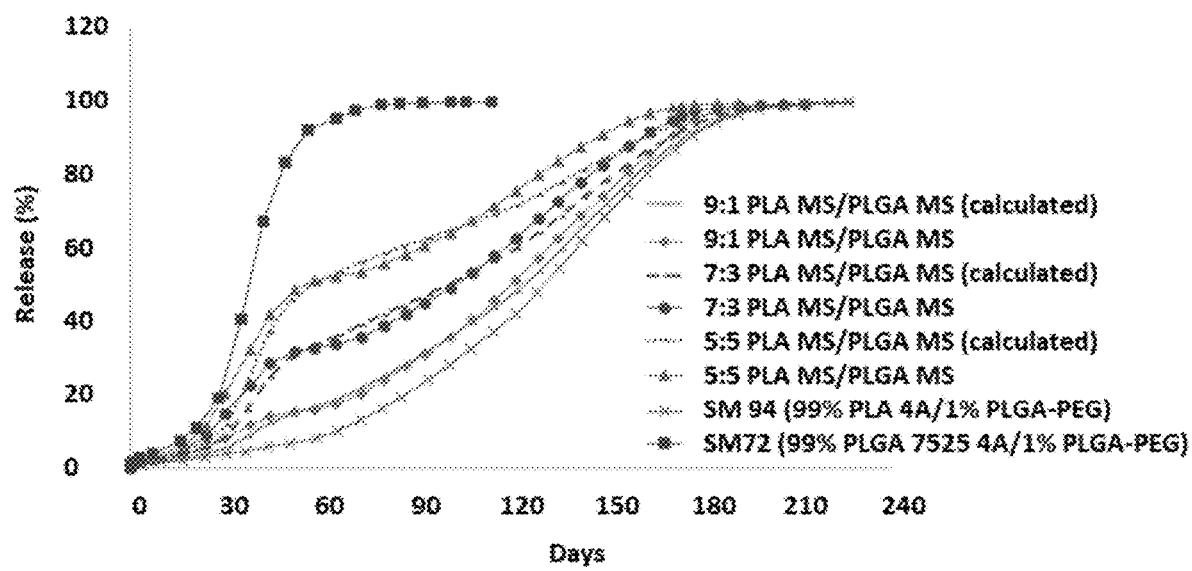
FIG. 37 is a graft depicting the in vitro drug release profile of microparticle blends as described in Example 39. The x-axis is time measured in days and the y-axis is cumulative release percent.

The in vitro release of particle blending is shown in FIG. 37. The release rate of blends of different formulations of microspheres (9:1 PLA:PLGA, 7:3 PLA:PLGA, and 5:5 PLA:PLGA) are shown and compared to formulations SM 94 and SM 72. The calculated release rate and the actual release rate is shown for each of the blends.

Example 40

In Vivo Injection of Sunitinib Encapsulated Microparticles Ocular Drug Levels after an Intravitreal Injection Drug-containing microparticles (1 mg sunitinib) were injected (0.05 mL) into the vitreous of pigmented New Zealand rabbits using a 27G needle and the ocular levels of sunitinib were assessed for 9 months. Complete ocular examinations were performed 10 days after dosing and monthly thereafter for 9 months, using a slit lamp biomicroscope and an indirect opthalmoscope, to evaluate ocular surface morphology, anterior segment and posterior segment inflammation, cataract formation, and retinal changes. A retinal lens was used to examine the location, morphology and distribution of the microspheres in vitreous. At time points of 3, 6, and 9 months, the drug levels of sunitinib (ng/g) in various ocular tissues (e.g. vitreous, retina, and RPE/choroid) and plasma were also analyzed.

After injection, microparticles were shown to coalesce in the inferior vitreous into an immobile, implant-like depot that remains outside of the visual axis. Slit-lamp and fundus examinations showed no OE findings in any of the eyes dosed with the formulations or with the placebo formulation for the entire in-life portion (9-months post dose).

Figure 38:
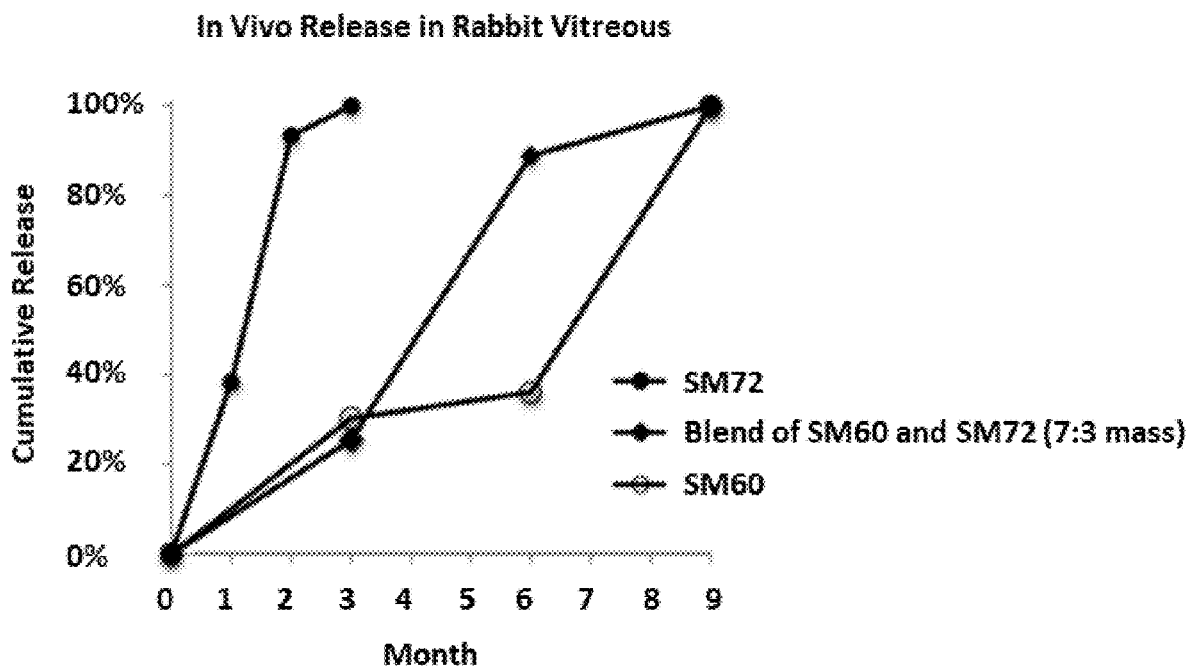
FIG. 38 is a graph depicting the in vivo release of the microparticles SM72, SM60, and a 7:3 mass ratio blend of SM60 and SM72 in a rabbit vitreous after a single intravitreal injection as described in Example 40. The x-axis is time measured in months and the y-axis is cumulative release percent.

Both SM60 and a blend of SM60 and SM72 at a 7:3 mass ratio were evaluated. The in vivo release profiles of the formulations are shown in FIG. 38. The data show that the duration of release of both SM60 and the blend of SM60 and SM72 was significantly longer than that of SM72. The release profile of the blend of SM60 and SM72 is also more linear than that of SM60. In addition, as shown in FIGS. 39A and 39B, relatively high drug levels were maintained in the rabbit eyes injected with SM60 or the blend of SM60 and SM72 for at least 9 months.

Figure 39A:
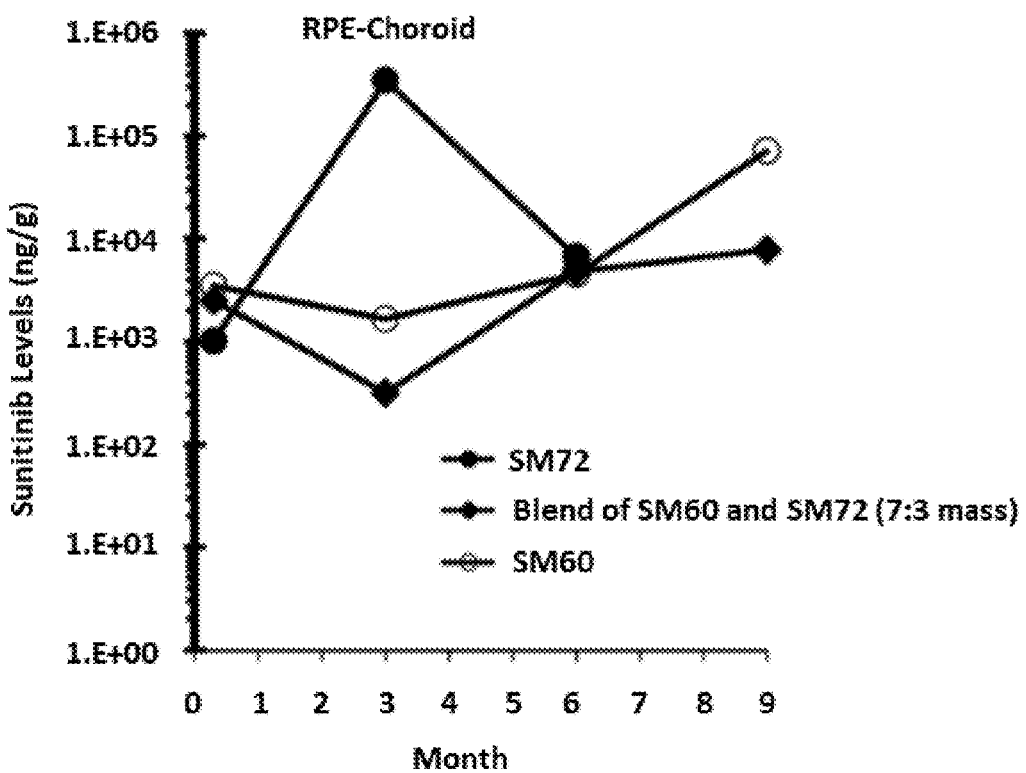
FIG. 39A is a graph depicting the in vivo release profile of the microparticles SM72, SM60, and a 7:3 mass ratio blend of SM60 and SM72 in a rabbit RPE-Choroid as described in Example 40. The x-axis is time measured in months and the y-axis is the level of sunitinib (ng/g).
Figure 39B:
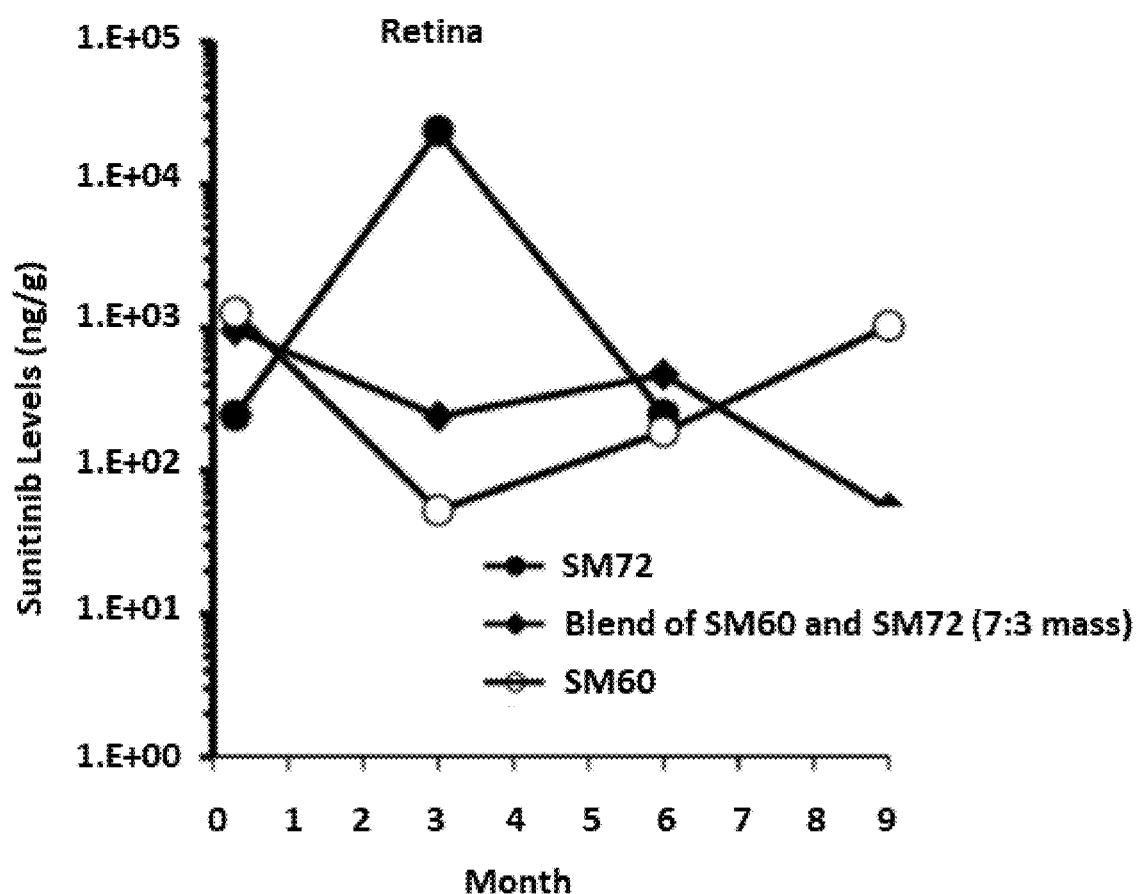
FIG. 39B is a graph depicting in vivo release profile of the microparticles SM72, SM60, and a 7:3 mass ratio blend of SM60 and SM72 in a rabbit retina as described in Example 40. The x-axis is time measured in months and the y-axis is the level of sunitinib (ng/g).

As shown in FIGS. 38, 39A, and 39B (in vitro and in vivo drug release kinetics), the inclusion of PLA in the formulation extends the duration of drug release by up to 6 months with a good correlation seen between in vitro and in vivo release kinetics. In addition, the PLA-based formulations maintain pharmacologically active levels in retina/RPE choroid for at least 9-months post-dose.

Figure 40A:
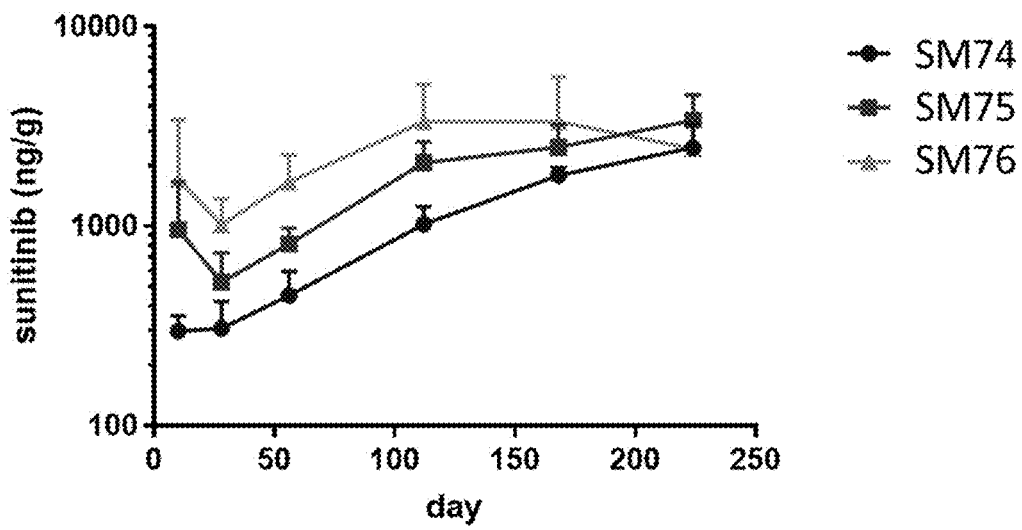
FIG. 40A is a graph depicting the sunitinib levels in the central retina and the RPE/choroid area following dosing with SM74, SM75, and SM76 as described in Example 40. The x-axis is time measured in days and the y-axis is the level of sunitinib (ng/g).
Figure 40B:
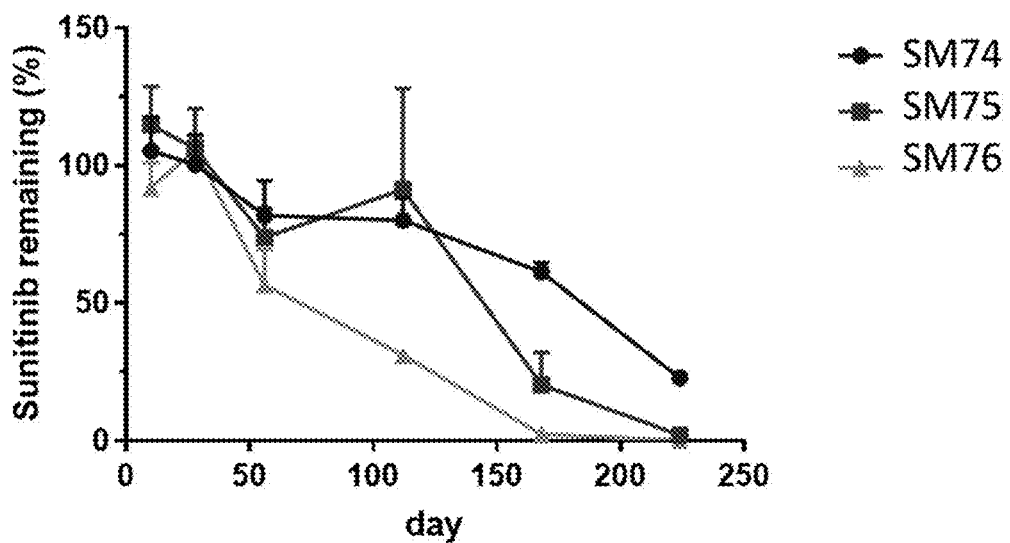
FIG. 40B is a graph depicting the remaining sunitinib encapsulated in particles after dosing with SM74, SM75, and SM76 as described in Example 40. The x-axis is time measured in days and the y-axis is sunitinib remaining measured in percent.

Pharmacokinetics (PK) and Toxicity Study for Longer-Lasting Sunitinib-Encapsulated Polymer Microparticles Drug-containing microparticles (~0.75 mg sunitinib) (SM74, 75 and 76) were injected (0.02 mL) into the vitreous of pigmented Dutch Belted rabbits using a 27G needle and the ocular levels of sunitinib were assessed for up to 8 months. To evaluate ocular surface morphology, anterior segment and posterior segment inflammation, cataract formation, and retinal changes, ocular examinations were performed 10 days and 1, 2, 4, 6 and 8 months post-injection using a slit lamp biomicroscope and fundus examination A retinal lens was used to examine the location, morphology and distribution of the microspheres in vitreous. At time points of 10 days and 1, 2, 4, 6 and 8 months the drug levels of sunitinib (ng/g) in various ocular tissues (e.g. retina and RPE/choroid) were also analyzed. FIG. 40A illustrates the remaining drug in the central retina and RPE/choroid area and FIG. 40B illustrates the remaining drug in the eye. The in vivo data indicate that these formulations can safely and effectively last at least 8 months in rabbit eyes.

After injection, microparticles were shown to coalesce in the inferior vitreous into an immobile, implant-like depot that remains outside of the visual axis. Slit-lamp and fundus examinations showed no OE findings in any of the eyes dosed with the formulations or with the placebo formulation for the partial in-life portion (8-months post dose).

As shown in FIG. 40A and FIG. 40B, increasing the PLA ratio in the formulation extends the duration of drug release in vivo. SM76 with a ratio of PLA:PLGA:PLGA-PEG of 50:50:1 exhibited drug release of 6 months, while SM75 (ratio of 70:30:1) exhibited a drug release of 8 months. SM74, which was formulated with a PLA:PLGA:PLGA-PEG ratio of 90:10:1 exhibited a drug release rate of greater than >8 months.

This specification has been described with reference to embodiments of the invention. However, one of ordinary skill in the art appreciates that various modifications and changes can be made without departing from the scope of the invention as set forth herein. Accordingly, the specification is to be regarded in an illustrative rather than a restrictive sense, and all such modifications are intended to be included within the scope of invention.

We claim:

1. A solid aggregating biodegradable microparticle comprising a prodrug of a therapeutically active compound, encapsulated in (a) poly(lactic-co-glycolic acid) (PLGA) and/or polylactic acid (PLA) and (b) poly(lactic-co-glycolic acid) (PLGA) covalently bound to polyethylene glycol (PEG) and/or polylactic acid (PLA) covalently bound to polyethylene glycol (PEG), and a surfactant, wherein the microparticle (i) has a mean diameter between 20 μm and 40 μm;

(ii) has been surface-modified with a surface-treatment agent to partially degrade surface polymer at a temperature less than about 18° C. wherein the surface-treatment agent is selected from (a) an aqueous base/alcohol, (b) an aqueous acid/alcohol, (c) phosphate buffered saline/alcohol, or (d) water/alcohol;

(iii) aggregates in vivo to form at least one pellet of at least 500 μm in vivo that provides sustained drug delivery in vivo for at least three months; and (v) wherein the prodrug is of the formula:

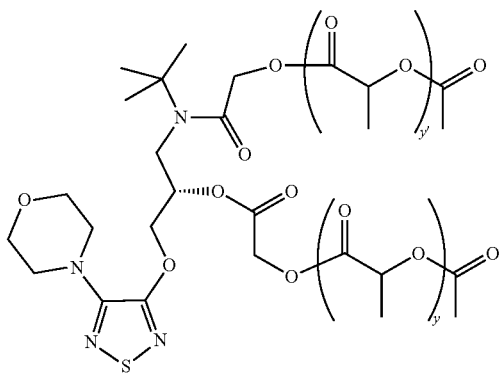

or a pharmaceutically acceptable salt thereof wherein y is 1, 2, 3, 4, 5, 6, 7, 8, 9, or 10; and y' is 1, 2, 3, 4, 5, 6, 7, 8, 9, or 10.

2. The solid aggregating microparticle of claim 1, wherein the prodrug is selected from

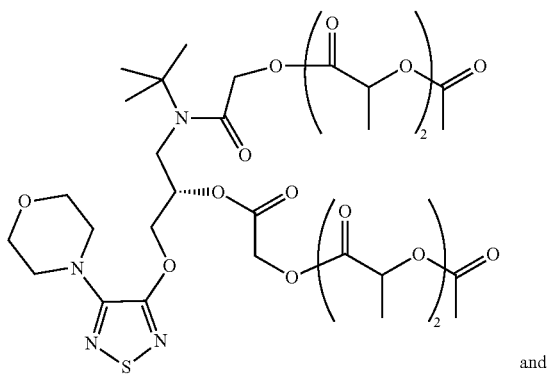

and

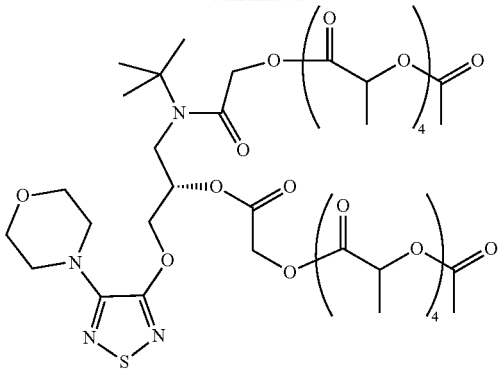

or a pharmaceutically acceptable salt thereof.

3. The solid aggregating microparticle of claim 1 in a dosage form for a delivery route selected from the group consisting of intravitreal, intrastromal, intracameral, sub-tenon, sub-retinal, retrobulbar, peribulbar, suprachoroidal, subchoroidal, conjunctival, subconjunctival, epi scleral, posterior juxtascleral, circumcorneal, and tear duct injections.

4. The solid aggregating microparticle of claim 1, wherein the at least one pellet provides sustained drug delivery for at least 4 months.

5. The solid aggregating microparticle of claim 1, wherein the microparticle comprises PLGA and PLGA-PEG.

6. The solid aggregating microparticle of claim 5, wherein the ratio of PLGA/PLGA-PEG is about 99/1.

7. The solid aggregating microparticle of claim 1, wherein the microparticle comprises PLA and PLGA-PEG.

8. The solid aggregating microparticle of claim 7, wherein the ratio of PLA/PLGA-PEG is about 99/1.

9. The solid aggregating microparticle of claim 1, wherein the microparticle comprises PLGA, PLA, and PLGA-PEG.

10. The solid aggregating microparticle of claim 9, wherein the PLGA-PEG is in an amount from about 0.5 percent to about 10 percent.

11. The solid aggregating microparticle of claim 1, wherein the microparticle comprises (i) PLGA; (ii) PLGA wherein the PLGA in (ii) has a different ratio of lactide to glycolide than the PLGA in (i); and, (iii) PLGA-PEG.

12. The solid aggregating microparticle of claim 7, wherein the PLA is acid end-capped.

13. The solid aggregating microparticle of claim 7, wherein the PLA is ester end-capped.

14. The solid aggregating microparticle of claim 5, wherein the PLGA-PEG is PLGA45k-PEG5k.

15. The solid aggregating microparticle of claim 1, wherein y is selected from 1, 2, 3, 4, 5, and 6.

16. The solid aggregating microparticle of claim 1, wherein y is 1, 2, 3, 4, 5, or 6 and y' is 1, 2, 3, 4, 5, or 6.

17. The solid aggregating microparticle of claim 16, wherein y is 2, 3, or 4 and y' is 2, 3, or 4.

18. The solid aggregating microparticle of claim 1, wherein the alcohol is selected from ethanol, propanol, and 2-propanol.

19. The solid aggregating microparticle of claim 18, wherein the alcohol is ethanol.

20. The solid aggregating microparticle of claim 1, wherein the surface-treatment agent is an aqueous acid/alcohol and the aqueous acid is selected from hydrochloric acid, hydrobromic acid, and sulfuric acid.

21. The solid aggregating microparticle of claim 1, wherein the surface-treatment agent is an aqueous base/alcohol.

22. The solid aggregating microparticle of claim 21, wherein the aqueous base is a hydroxide base.

23. The solid aggregating microparticle of claim 22, wherein the hydroxide base is selected from sodium hydroxide and potassium hydroxide.

24. The solid aggregating microparticle of claim 21, wherein the alcohol is ethanol.

25. The solid aggregating microparticle of claim 21, wherein the surface-treatment agent is ethanol and sodium hydroxide.

26. The solid aggregating microparticle of claim 1, wherein at least one pellet provides sustained drug delivery for at least 5 months.

27. The solid aggregating microparticle of claim 1, wherein at least one pellet provides sustained drug delivery for at least 6 months.

28. The solid aggregating microparticle of claim 2, wherein the prodrug is

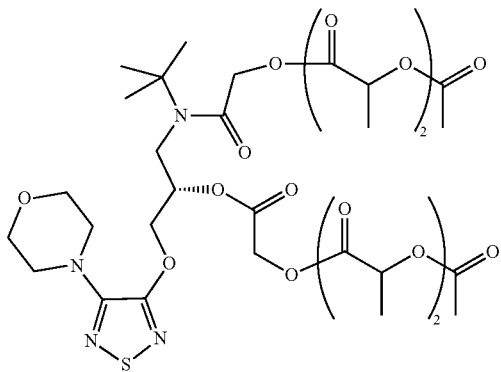

or a pharmaceutically acceptable salt thereof.

29. The solid aggregating microparticle of claim 2, wherein the prodrug is

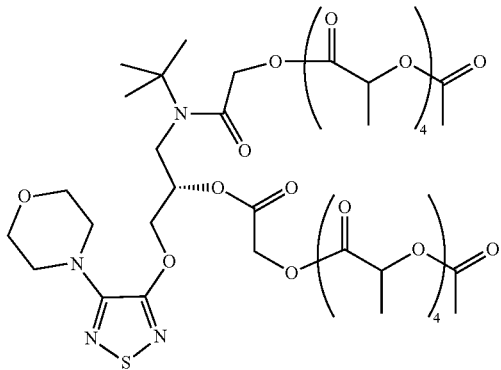

or a pharmaceutically acceptable salt thereof.

30. The solid aggregating microparticle of claim 1, wherein the prodrug is

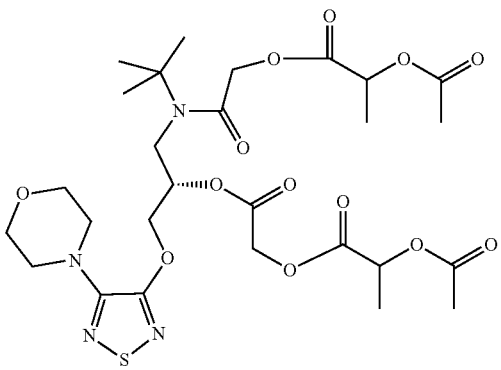 [SMILES: CC(=O)OC(C)C(=O)OCC(=O)O[C@H](COc1nsnc1N1CCOCC1)CN(C(=O)COC(=O)C(C)OC(C)=O)C(C)(C)C]

or a pharmaceutically acceptable salt thereof.

31. The solid aggregating microparticle of claim 1 with a mean diameter between 25 μm and 40 μm.

32. The solid aggregating microparticle of claim 28 with a mean diameter between 25 μm and 40 μm.

33. The solid aggregating microparticle of claim 29 with a mean diameter between 25 μm and 40 μm.

34. The solid aggregating microparticle of claim 30 with a mean diameter between 25 μm and 40 μm.

35. The solid aggregating microparticle of claim 28, wherein the microparticle comprises PLGA and PLGA-PEG.

36. The solid aggregating microparticle of claim 29, wherein the microparticle comprises PLGA and PLGA-PEG.

37. The solid aggregating microparticle of claim 30, wherein the microparticle comprises PLGA and PLGA-PEG.

38. The solid aggregating microparticle of claim 35, wherein the ratio of PLGA/PLGA-PEG is about 99/1.

39. The solid aggregating microparticle of claim 36, wherein the ratio of PLGA/PLGA-PEG is about 99/1.

40. The solid aggregating microparticle of claim 35, wherein the PLGA-PEG is PLGA45k-PEG5k.

41. The solid aggregating microparticle of claim 36, wherein the PLGA-PEG is PLGA45k-PEG5k.

42. The solid aggregating microparticle of claim 28, wherein the at least one pellet provides sustained drug delivery for at least 4 months.

43. The solid aggregating microparticle of claim 29, wherein the at least one pellet provides sustained drug delivery for at least 4 months.

44. The solid aggregating microparticle of claim 30, wherein at least one pellet provides sustained drug delivery for at least 4 months.

45. The solid aggregating microparticle of claim 28, wherein the surface-treatment agent is an aqueous base/alcohol.

46. The solid aggregating microparticle of claim 29, wherein the surface-treatment agent is an aqueous base/alcohol.

47. The solid aggregating microparticle of claim 30, wherein the surface-treatment agent is an aqueous base/alcohol.

48. The solid aggregating microparticle of claim 45, wherein the alcohol is selected from ethanol, propanol, and 2-propanol.

49. The solid aggregating microparticle of claim 46, wherein the alcohol is selected from ethanol, propanol, and 2-propanol.

50. The solid aggregating microparticle of claim 48, wherein the alcohol is ethanol.

51. The solid aggregating microparticle of claim 49, wherein the alcohol is ethanol.

52. The solid aggregating microparticle of claim 45, wherein the aqueous base is a hydroxide base.

53. The solid aggregating microparticle of claim 46, wherein the aqueous base is a hydroxide base.

54. The solid aggregating microparticle of claim 52, wherein the hydroxide base is selected from sodium hydroxide and potassium hydroxide.

55. The solid aggregating microparticle of claim 53, wherein the hydroxide base is selected from sodium hydroxide and potassium hydroxide.

56. The solid aggregating microparticle of claim 45, wherein the surface-treatment agent is ethanol and sodium hydroxide.

57. The solid aggregating microparticle of claim 46, wherein the surface-treatment agent is ethanol and sodium hydroxide.

\* \* \* \* \*